(12) United States Patent
Deonarain et al.

(10) Patent No.: US 11,202,837 B2
(45) Date of Patent: Dec. 21, 2021

(54) BIOLOGICAL MATERIALS AND USES THEREOF

(71) Applicant: Antikor Biopharma Limited, Stevenage (GB)

(72) Inventors: Mahendra Persaud Deonarain, Wallington (GB); Gokhan Yahioglu, London (GB); Ioanna Stamati, London (GB); Savvas Saouros, London (GB); Prashant Bhimrao Kapadnis, Harlow (GB)

(73) Assignee: ANTIKOR BIOPHARMA LIMITED, Stevenage (GB)

( * ) Notice: Subject to any disclaimer, the term of this patent is extended or adjusted under 35 U.S.C. 154(b) by 0 days.

(21) Appl. No.: 15/513,393

(22) PCT Filed: Sep. 25, 2015

(86) PCT No.: PCT/GB2015/052800
§ 371 (c)(1),
(2) Date: Mar. 22, 2017

(87) PCT Pub. No.: WO2016/046574
PCT Pub. Date: Mar. 31, 2016

(65) Prior Publication Data
US 2017/0360951 A1 Dec. 21, 2017

(30) Foreign Application Priority Data
Sep. 25, 2014 (GB) ..................... 1416960

(51) Int. Cl.
| A61K 47/64 | (2017.01) |
| A61K 47/68 | (2017.01) |
| A61K 47/00 | (2006.01) |
| C07K 16/00 | (2006.01) |

(52) U.S. Cl.
CPC ...... *A61K 47/6803* (2017.08); *A61K 47/6809* (2017.08); *A61K 47/6855* (2017.08); *A61K 47/00* (2013.01); *C07K 16/00* (2013.01); *C07K 2317/92* (2013.01)

(58) Field of Classification Search
CPC .............. C07K 2317/92; A61K 47/64; A61K 47/6809; A61K 47/6803
USPC .................................................... 424/133.1
See application file for complete search history.

(56) References Cited

U.S. PATENT DOCUMENTS

| 5,208,020 | A | 5/1993 | Chari et al. |
| 5,416,064 | A | 5/1995 | Chari et al. |
| 7,276,497 | B2 | 10/2007 | Chari et al. |
| 7,276,499 | B2 | 10/2007 | Chari et al. |
| 8,227,580 | B2 | 7/2012 | Jakobovits et al. |
| 8,680,293 | B2 | 3/2014 | Beusker et al. |
| 8,703,427 | B2* | 4/2014 | Deonarain ............... A61P 25/00 435/7.1 |
| 8,808,679 | B2 | 8/2014 | Yurkovetskiy et al. |
| 2006/0074008 | A1 | 4/2006 | Senter et al. |
| 2010/0136033 | A1 | 6/2010 | Erickson et al. |
| 2011/0070428 | A1 | 3/2011 | Skoog et al. |
| 2012/0070377 | A1* | 3/2012 | Yahioglu ............... A61K 31/409 424/9.1 |
| 2013/0101546 | A1 | 4/2013 | Yurkovetskiy et al. |
| 2014/0227295 | A1 | 8/2014 | Cong et al. |
| 2014/0227299 | A1 | 8/2014 | Cohen et al. |
| 2014/0234346 | A1 | 8/2014 | Howard |
| 2015/0133653 | A1* | 5/2015 | Yahioglu ............... A61K 31/409 540/145 |

FOREIGN PATENT DOCUMENTS

| WO | WO-2003/015825 | 2/2003 |
| WO | WO 2007/042775 A2 | 4/2007 |
| WO | WO 2010/093395 A1 | 8/2010 |
| WO | WO 2010/106341 A1 | 9/2010 |
| WO | WO 2010/141566 A1 | 12/2010 |
| WO | WO 2011/001052 A1 | 1/2011 |
| WO | WO 2012/024223 A2 | 2/2012 |
| WO | WO 2012/041504 A1 | 4/2012 |
| WO | WO 2012/104344 A1 | 8/2012 |
| WO | WO 2013/082254 A1 | 6/2013 |
| WO | WO 2014/031566 A1 | 2/2014 |
| WO | WO 2014/068443 A1 | 5/2014 |
| WO | WO 2014/124227 A1 | 8/2014 |
| WO | WO 2014/134457 A2 | 9/2014 |

OTHER PUBLICATIONS

Ward et al. (Nature 341:544-546 (1989)).*
Butt et al. (Oncotarget, vol. 8, (No. 15), pp. 25080-25096 (2017)).*
Pye et al. (Oncotarget, vol. 9, (No. 33), pp. 22945-22959 (2018)).*
Kim et al. (Bioconjugate Chem. 25, 1223-1232 (2014)).*
Deonarain et al. (Expert Opin. Drug Discov. (2015) 10(5):463-481).*
Sun et al. (Bioconjugate Chem. 2011, 22, 728-735).*
Bhatti et al. Targeted photodynamic therapy with multiply-loaded recombinant antibody fragments. Int J Cancer. Mar. 1, 2008;122(5):1155-63.
Chari et al. Antibody-drug conjugates: an emerging concept in cancer therapy. Angew Chem Int Ed Engl. Apr. 7, 2014;53(15):3796-827.

(Continued)

*Primary Examiner* — Lynn A Bristol
(74) *Attorney, Agent, or Firm* — Marshall, Gerstein & Borun LLP

(57) ABSTRACT

The invention provides compounds comprising a therapeutic agent coupled to a carrier molecule, with a minimum coupling ratio of 5:1; wherein the carrier molecule is (i) an antibody fragment or derivative thereof or (ii) an antibody mimetic or derivative thereof; and wherein the therapeutic agents are coupled onto a lysine amino acid residue; and further wherein the therapeutic agent is not a photosensitising agent. There is also provided uses, methods relating to such compounds, as well as processes for their manufacture.

Figure 1:
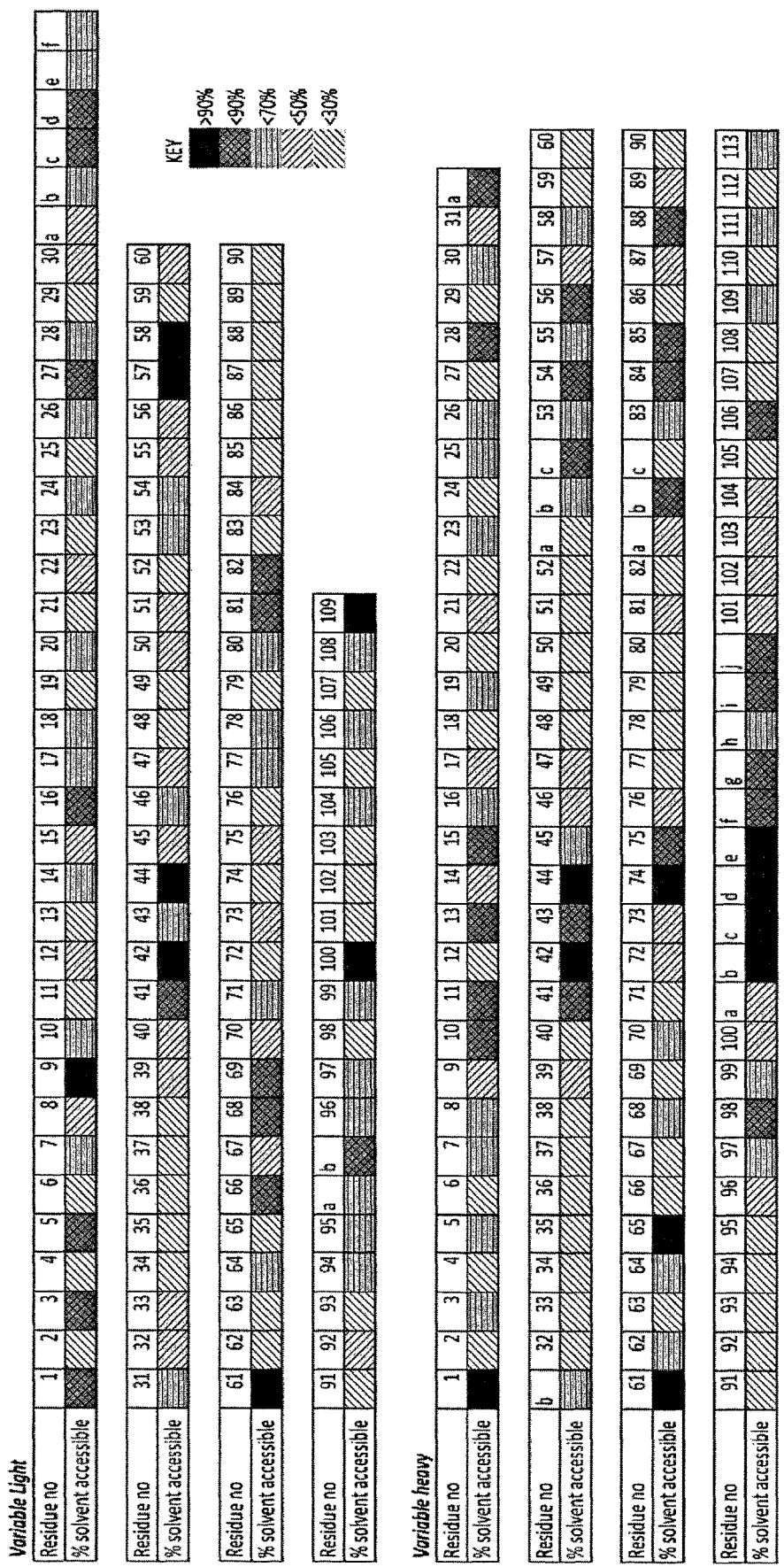

22 Claims, 166 Drawing Sheets
Specification includes a Sequence Listing.

(56) References Cited

OTHER PUBLICATIONS

Deonarain et al. Emerging formats for next-generation antibody drug conjugates. Expert Opin Drug Discov. May 2015;10(5):463-81.
Gianolio et al. Targeting HER2-positive cancer with dolastatin 15 derivatives conjugated to trastuzumab, novel antibody-drug conjugates. Cancer Chemother Pharmacol. Sep. 2012;70(3):439-49.
Adair et al. Antibody-drug conjugates—a perfect synergy. Expert Opin Biol Ther. Sep. 2012;12(9):1191-206.
Adams et al. High affinity restricts the localization and tumor penetration of single-chain fv antibody molecules. Cancer Res. Jun. 15, 2001;61(12):4750-5.
Alley et al. The pharmacologic basis for antibody-auristatin conjugate activity. J Pharmacol Exp Ther. Sep. 2009;330(3):932-8.
Alzari et al. Three-dimensional structure of antibodies. Annu Rev Immunol. 1988;6:555-80.
Amiri-Kordestani et al. FDA approval: ado-trastuzumab emtansine for the treatment of patients with HER2-positive metastatic breast cancer. Clin Cancer Res. Sep. 1, 2014;20(17):4436-41.
Avendaño & Menéndez. Medicinal Chemistry of Anticancer Drugs. $1^{st}$ ed. 2008. Elsevier Press, Amsterdam, The Netherlands.
Badescu et al. Bridging disulfides for stable and defined antibody drug conjugates. Bioconjug Chem. Jun. 18, 2014;25(6):1124-36.
Ban et al. Facile and stabile linkages through tyrosine: bioconjugation strategies with the tyrosine-click reaction. Bioconjug Chem. Apr. 17, 2013;24(4):520-32.
Barok et al. Trastuzumab-DM1 causes tumour growth inhibition by mitotic catastrophe in trastuzumab-resistant breast cancer cells in vivo. Breast Cancer Res. Apr. 21, 2011;13(2):R46.
Baron et al. Ado-trastuzumab emtansine (T-DM1): a novel antibody-drug conjugate for the treatment of HER2-positive metastatic breast cancer. J Oncol Pharm Pract. Apr. 2015;21(2):132-42. Epub Mar. 27, 2014.
Batra et al. Pharmacokinetics and biodistribution of genetically engineered antibodies. Curr Opin Biotechnol. Dec. 2002;13(6):603-8.
Behrens & Liu. Methods for site-specific drug conjugation to antibodies. MAbs. Jan. 2014-Feb. 2014;6(1):46-53.
Blackman et al. Tetrazine ligation: fast bioconjugation based on inverse-electron-demand Diels-Alder reactivity. J Am Chem Soc. Oct. 15, 2008;130(41):13518-9.
Borsi et al. Selective targeted delivery of TNFalpha to tumor blood vessels. Blood. Dec. 15, 2003;102(13):4384-92.
Boxer et al. Localisation of monoclonal antibodies reacting with different epitopes on carcinoembryonic antigen (CEA)-implications for targeted therapy. Br J Cancer. Feb. 1994;69(2):307-14.
Brand et al. Molecular mechanisms of resistance to the EGFR monoclonal antibody cetuximab. Cancer Biol Ther. May 1, 2011;11(9):777-92.
Burke et al. Design, synthesis, and biological evaluation of antibody-drug conjugates comprised of potent camptothecin analogues. Bioconjug Chem. Jun. 2009;20(6):1242-50.
Burkhart et al. Syntheses and Evaluation of Simplified Pretubulysin Analogues. Eur J Org Chem. Jun. 2011;2011(16):3050-9.
Carlson. Antibody-Drug Conjugates: Where the Action Is: ADCs—The New Frontier. Biotechnol Healthc. 2012 Winter;9(4):28-31.
Carter. Potent antibody therapeutics by design. Nat Rev Immunol. May 2006;6(5):343-57.
Castañeda et al. Acid-cleavable thiomaleamic acid linker for homogeneous antibody-drug conjugation. Chem Commun (Camb). Sep. 25, 2013;49(74):8187-9.
Chames (Ed.). Antibody Engineering: Methods and Protocols. $2^{nd}$ ed. 2012. Humana Press, NY.
Lefranc et al. Use of IMGT(@) databases and tools for antibody engineering and humanization. Methods Mol Biol. 2012;907:3-37, in, CHAMES (Ed.). Antibody Engineering: Methods and Protocols. $2^{nd}$ ed. 2012. Humana Press, NY.
Katsuda et al. Production of antibody fragments in *Escherichia coli*. Methods Mol Biol. 2012;907:305-24, in, CHAMES (Ed.). Antibody Engineering: Methods and Protocols. $2^{nd}$ ed. 2012. Humana Press, NY.
Schoonooghe et al. Production of antibody derivatives in the methylotrophic yeast *Pichia pastoris*. Methods Mol Biol. 2012;907:325-40, in, CHAMES (Ed.). Antibody Engineering: Methods and Protocols. $2^{nd}$ ed. 2012. Humana Press, NY.
Zhang & Shen, Monoclonal antibody expression in mammalian cells. Methods Mol Biol. 2012;907:341-58, in, CHAMES (Ed.). Antibody Engineering: Methods and Protocols. $2^{nd}$ ed. 2012. Humana Press, NY.
Johansson et al. Production of recombinant antibodies in *Drosophila melanogaster* S2 cells. Methods Mol Biol. 2012;908:359-70, in, CHAMES (Ed.). Antibody Engineering: Methods and Protocols. $2^{nd}$ ed. 2012. Humana Press, NY.
Furuta et al. Production of antibody fragments using the baculovirus-insect cell system. Methods Mol Biol. 2012;907:371-87, in, CHAMES (Ed.). Antibody Engineering: Methods and Protocols. $2^{nd}$ ed. 2012. Humana Press, NY.
Garabagi et al. Transient and stable expression of antibodies in Nicotiana species. Methods Mol Biol. 2012;907:389-408, in, CHAMES (Ed.). Antibody Engineering: Methods and Protocols. $2^{nd}$ ed. 2012. Humana Press, NY.
Chan & Carter. Therapeutic antibodies for autoimmunity and inflammation. Nat Rev Immunol. May 2010;10(5):301-16.
Chari et al. Enhancement of the selectivity and antitumor efficacy of a CC-1065 analogue through immunoconjugate formation. Cancer Res. Sep. 15, 1995;55(18):4079-84.
Constantinou et al. Site-specific polysialylation of an antitumor single-chain Fv fragment. Bioconjug Chem. May 20, 2009;20(5):924-31.
Davies & Metzger. Structural basis of antibody function. Annu Rev Immunol. 1983;1:87-117.
De Marco. Strategies for successful recombinant expression of disulfide bond-dependent proteins in *Escherichia coli*. Microb Cell Fact. May 14, 2009;8:26.
De Vries et al. The novel calicheamicin-conjugated CD22 antibody inotuzumab ozogamicin (CMC-544) effectively kills primary pediatric acute lymphoblastic leukemia cells. Leukemia. Feb. 2012;26(2):255-64.
Dennis et al. Imaging tumors with an albumin-binding Fab, a novel tumor-targeting agent. Cancer Res. Jan. 1, 2007;67(1):254-61.
Deonarain & Epenetos. Design, characterization and anti-tumour cytotoxicity of a panel of recombinant, mammalian ribonuclease-based immunotoxins. Br J Cancer. Feb. 1998;77(4):537-46.
Deonarain et al. Redesigned anti-human placental alkaline phosphatase single-chain Fv: soluble expression, characterization and in vivo tumour targeting. Protein Eng. Jan. 1997;10(1):89-98.
Doppalapudi et al. Chemical generation of bispecific antibodies. Proc Natl Acad Sci USA. Dec. 28, 2010;107(52):22611-6.
Doronina et al. Development of potent monoclonal antibody auristatin conjugates for cancer therapy. Nat Biotechnol. Jul. 2003;21(7):778-84.
Dubowchik et al. Cathepsin B-labile dipeptide linkers for lysosomal release of doxorubicin from internalizing immunoconjugates: model studies of enzymatic drug release and antigen-specific in vitro anticancer activity. Bioconjug Chem. Jul. 2002-Aug. 2002;13(4):855-69.
Ducry (Ed.). Antibody-Drug Conjugates. 2013. Humana Press, NY.
Stefano et al. Micro- and mid-scale maleimide-based conjugation of cytotoxic drugs to antibody hinge region thiols for tumor targeting. Methods Mol Biol. 2013;1045:145-71, in, DUCRY (Ed.). Antibody-Drug Conjugates. 2013. Humana Press, NY.
Brun & Gauzy-Lazo. Protocols for lysine conjugation. Methods Mol Biol. 2013;1045:173-87, in, DUCRY (Ed.). Antibody-Drug Conjugates. 2013. Humana Press, NY.
Bhakta et al. Engineering THIOMABs for site-specific conjugation of thiol-reactive Linkers. Methods Mol Biol. 2013;1045:189-203, in, DUCRY (Ed.). Antibody-Drug Conjugates. 2013. Humana Press, NY.
Dennler et al. Enzymatic antibody modification by bacterial transglutaminase. Methods Mol Biol. 2013;1045:205-15, in, DUCRY (Ed.). Antibody-Drug Conjugates. 2013. Humana Press, NY.

(56) References Cited

OTHER PUBLICATIONS

EMBL-EBI. Multiple Sequence Alignment. www.ebi.ac.uk/Tools/msa/. Wayback machine version Sep. 14, 2014.

Epenetos et al. Limitations of radiolabeled monoclonal antibodies for localization of human neoplasms. Cancer Res. Jun. 1986;46(6):3183-91.

Erickson et al. Antibody-maytansinoid conjugates are activated in targeted cancer cells by lysosomal degradation and linker-dependent intracellular processing. Cancer Res. Apr. 15, 2006;66(8):4426-33.

Fauvel & Yasri. Antibodies directed against receptor tyrosine kinases: current and future strategies to fight cancer. MAbs. Jul. 2014-Aug. 2014;6(4):838-51.

FDA—U.S. Food and Drug Administration. Inactive Ingredient Search for Approved Drug Products. www.accessdata.fda.gov/scripts/cder/iig/index.Cfm. Wayback machine version Jul. 12, 2014.

Fernandez-Fernandez et al. Theranostic applications of nanomaterials in cancer: drug delivery, image-guided therapy, and multifunctional platforms. Appl Biochem Biotechnol. Dec. 2011;165(7-8):1628-51.

Firestone et al. Synthesis and antitumor activity of the immunoconjugate BR96-Dox. J Control Release. May 1996;39(2-3):251-9.

Flygare et al. Antibody-drug conjugates for the treatment of cancer. Chem Biol Drug Des. Jan. 2013;81(1):113-21.

Gallardo et al. Increased signalling of EGFR and IGF1R, and deregulation of PTEN/PI3K/Akt pathway are related with trastuzumab resistance in HER2 breast carcinomas. Br J Cancer. Apr. 10, 2012;106(8):1367-73.

Gangopadhyay et al. Modification of antibody isoelectric point affects biodistribution of 111-indium-labeled antibody. Nucl Med Biol. Apr. 1996;23(3):257-61.

Govindan et al. Milatuzumab-SN-38 conjugates for the treatment of CD74+ cancers. Mol Cancer Ther. Jun. 2013;12(6):968-78.

Hackenberger & Schwarzer. Chemoselective ligation and modification strategies for peptides and proteins. Angew Chem Int Ed Engl. 2008;47(52):10030-74.

Hamblett et al. Effects of drug loading on the antitumor activity of a monoclonal antibody drug conjugate. Clin Cancer Res. Oct. 15, 2004;10(20):7063-70.

Harlow & Lane. Antibodies: A Laboratory Manual. 1$^{st}$ ed. 1988. Cold Spring Harbor Laboratory Press, Cold Spring Harbor, NY. [Chapter 6].

Harlow & Lane. Using Antibodies: A Laboratory Manual. 1998. Cold Spring Harbor Laboratory Press, Cold Spring Harbor, NY.

Hermanson. Bioconjugate Techniques. 2$^{nd}$ ed. 2008. Academic Press, London, UK.

Hermanson. Bioconjugate Techniques. 3$^{rd}$ ed. 2013. Academic Press, London, UK. [Chapters 2-6].

Hollander et al. Selection of reaction additives used in the preparation of monomeric antibody-calicheamicin conjugates. Bioconjug Chem. Jan. 2008;19(1):358-61.

Honegger & Plückthun. Yet another numbering scheme for immunoglobulin variable domains: an automatic modeling and analysis tool. J Mol Biol. Jun. 8, 2001;309(3):657-70.

Hoogenboom. Selecting and screening recombinant antibody libraries. Nat Biotechnol. Sep. 2005;23(9):1105-16.

Hopper. Photodynamic therapy: a clinical reality in the treatment of cancer. Lancet Oncol. Dec. 2000;1:212-9.

Hudson. Recombinant antibodies: a novel approach to cancer diagnosis and therapy. Expert Opin Investig Drugs. Jun. 2000;9(6):1231-42.

Jain. Delivery of molecular and cellular medicine to solid tumors. Adv Drug Deliv Rev. Dec. 1, 2012;64(Suppl):353-365.

Jeffrey et al. A potent anti-CD70 antibody-drug conjugate combining a dimeric pyrrolobenzodiazepine drug with site-specific conjugation technology. Bioconjug Chem. Jul. 17, 2013;24(7):1256-63.

Jeffrey et al. Dipeptide-based highly potent doxorubicin antibody conjugates. Bioorg Med Chem Lett. Jan. 15, 2006;16(2):358-62.

Jones et al. Replacing the complementarity-determining regions in a human antibody with those from a mouse. Nature. May 29, 1986-Jun. 4, 1986;321(6069):522-5.

Jordan & Wilson. Microtubules as a target for anticancer drugs. Nat Rev Cancer. Apr. 2004;4(4):253-65.

Kaur et al. Bioanalytical assay strategies for the development of antibody-drug conjugate biotherapeutics. Bioanalysis. Jan. 2013;5(2):201-26.

Kelley & Sternberg. Protein structure prediction on the Web: a case study using the Phyre server. Nat Protoc. 2009;4(3):363-71.

Kellogg et al. Disulfide-linked antibody-maytansinoid conjugates: optimization of in vivo activity by varying the steric hindrance at carbon atoms adjacent to the disulfide linkage. Bioconjug Chem. Apr. 20, 2011;22(4):717-27.

Kim et al. Anti-CD30 diabody-drug conjugates with potent antitumor activity. Mol Cancer Ther. Aug. 2008;7(8):2486-97.

King et al. Monoclonal antibody conjugates of doxorubicin prepared with branched linkers: A novel method for increasing the potency of doxorubicin immunoconjugates. Bioconjug Chem. Mar. 1999-Apr. 1999;10(2):279-88.

Knappik et al. Fully synthetic human combinatorial antibody libraries (HuCAL) based on modular consensus frameworks and CDRs randomized with trinucleotides. J Mol Biol. Feb. 11, 2000;296(1):57-86.

Korbelik. Cellular delivery and retention of photofrin: III. Role of plasma proteins in photosensitizer clearance from cells. Photochem Photobiol. May 1993;57(5):846-50.

Kostron. Photodynamic Diagnosis and Therapy and the Brain. Methods Mol Biol. 2010;635:261-80.

Kung Sutherland et al. SGN-CD33A: a novel CD33-targeting antibody-drug conjugate using a pyrrolobenzodiazepine dimer is active in models of drug-resistant AML. Blood. Aug. 22, 2013;122(8):1455-63.

Lang & Chin. Cellular incorporation of unnatural amino acids and bioorthogonal labeling of proteins. Chem Rev. May 14, 2014;114(9):4764-806.

Lazar et al. Engineered antibody Fc variants with enhanced effector function. Proc Natl Acad Sci U S A. Mar. 14, 2006;103(11):4005-10.

Lee & Swain. Peripheral neuropathy induced by microtubule-stabilizing agents. J Clin Oncol. Apr. 1, 2006;24(10):1633-42.

Lin & Tibbitts. Pharmacokinetic considerations for antibody drug conjugates. Pharm Res. Sep. 2012;29(9):2354-66.

Litvak-Greenfeld & Benhar. Risks and untoward toxicities of antibody-based immunoconjugates. Adv Drug Deliv Rev. Dec. 2012;64(15):1782-99.

Lobstein et al. SHuffle, a novel *Escherichia coli* protein expression strain capable of correctly folding disulfide bonded proteins in its cytoplasm. Microb Cell Fact. May 8, 2012;11:56.

Lorusso et al. Trastuzumab emtansine: a unique antibody-drug conjugate in development for human epidermal growth factor receptor 2-positive cancer. Clin Cancer Res. Oct. 15, 2011;17(20):6437-47.

Lu et al. Population pharmacokinetics of trastuzumab emtansine (T-DM1), a HER2-targeted antibody-drug conjugate, in patients with HER2-positive metastatic breast cancer: clinical implications of the effect of covariates. Cancer Chemother Pharmacol. Aug. 2014;74(2):399-410.

Mariuzza et al. The structural basis of antigen-antibody recognition. Annu Rev Biophys Biophys Chem. 1987;16:139-59.

Ménard et al. Biologic and therapeutic role of HER2 in cancer. Oncogene. Sep. 29, 2003;22(42):6570-8.

Monjanel et al. Brentuximab vedotin in heavily treated Hodgkin and anaplastic large-cell lymphoma, a single centre study on 45 patients. Br J Haematol. Jul. 2014;166(2):306-8.

Moon et al. Antibody conjugates of 7-ethyl-10-hydroxycamptothecin (SN-38) for targeted cancer chemotherapy. J Med Chem. Nov. 13, 2008;51(21):6916-26.

Nahta et al. Mechanisms of disease: understanding resistance to HER2-targeted therapy in human breast cancer. Nat Clin Pract Oncol. May 2006;3(5):269-80.

Ojima et al. Tumor-specific novel taxoid-monoclonal antibody conjugates. J Med Chem. Dec. 19, 2002;45(26):5620-3.

(56) References Cited

OTHER PUBLICATIONS

Ojima. Guided molecular missiles for tumor-targeting chemotherapy-case studies using the second-generation taxoids as warheads. Acc Chem Res. Jan. 2008;41(1):108-19.

Palumbo et al. A chemically modified antibody mediates complete eradication of tumours by selective disruption of tumour blood vessels. Br J Cancer. Mar. 29, 2011;104(7):1106-15.

Pardoll. The blockade of immune checkpoints in cancer immunotherapy. Nat Rev Cancer. Mar. 22, 2012;12(4):252-64.

Parikh et al. The potential roles of hepatocyte growth factor (HGF)-MET pathway inhibitors in cancer treatment. Onco Targets Ther. Jun. 11, 2014;7:969-83.

Patapoff & Esue. Polysorbate 20 prevents the precipitation of a monoclonal antibody during shear. Pharm Dev Technol. 2009;14(6):659-64.

Patterson et al. Improving the serum stability of site-specific antibody conjugates with sulfone linkers. Bioconjug Chem. Aug. 20, 2014;25(8):1402-7.

Pimm et al. Biodistribution and tumour localization of a methotrexate-monoclonal-antibody 791T/36 conjugate in nude mice with human tumour xenografts. Int J Cancer. Jun. 15, 1988;41(6):886-91.

Presta. Antibody engineering. Curr Opin Struct Biol. Aug. 1992;2(4):593-6.

Ranganathan et al. Notch signalling in solid tumours: a little bit of everything but not all the time. Nat Rev Cancer. May 2011;11(5):338-51.

Reichmann et al. Reshaping human antibodies for therapy. Nature. Mar. 24, 1988;332(6162):323-7.

Robak & Robak. Current Phase II antibody-drug conjugates for the treatment of lymphoid malignancies. Expert Opin Investig Drugs. Jul. 2014;23(7):911-24.

Sambrook & Russell. Molecular Cloning: A Laboratory Manual. 3rd ed. 2001. Cold Spring Harbor Laboratory Press, New York.

Savellano & Hasan. Photochemical targeting of epidermal growth factor receptor: a mechanistic study. Clin Cancer Res. Feb. 15, 2005;11(4):1658-68.

Schaefer & Plückthun. Transfer of engineered biophysical properties between different antibody formats and expression systems. Protein Eng Des Sel. Oct. 2012;25(10):485-506.

Schrödinger. PyMOL. www.pymol.org. Wayback machine version Sep. 24, 2014.

Scopes. Protein Purification: Principles and Practice. $3^{rd}$ ed. 1993. Springer, NY.

Scott et al. Antibody therapy of cancer. Nat Rev Cancer. Mar. 22, 2012;12(4):278-87.

Shen et al. Conjugation site modulates the in vivo stability and therapeutic activity of antibody-drug conjugates. Nat Biotechnol. Jan. 22, 2012;30(2):184-9.

SIB (Swiss Institute of Bioinformatics). ExPASy Bioinformatics Resource Portal. www.expasy.org. Wayback machine version Sep. 24, 2014.

Sievers & Senter. Antibody-drug conjugates in cancer therapy. Annu Rev Med. 2013;64:15-29.

Sievers et al. Efficacy and safety of gemtuzumab ozogamicin in patients with CD33-positive acute myeloid leukemia in first relapse. J Clin Oncol. Jul. 1, 2001;19(13):3244-54.

Sliwkowski & Mellman. Antibody therapeutics in cancer. Science. Sep. 13, 2013;341(6151):1192-8.

Sonoda et al. Functional expression of single-chain Fv antibody in the cytoplasm of *Escherichia coli* by thioredoxin fusion and co-expression of molecular chaperones. Protein Expr Purif. Apr. 2010;70(2):248-53.

Spadiut et al. Microbials for the production of monoclonal antibodies and antibody fragments. Trends Biotechnol. Jan. 2014;32(1):54-60.

Teicher & Chari. Antibody conjugate therapeutics: challenges and potential. Clin Cancer Res. Oct. 15, 2011;17(20):6389-97.

Van Regenmortel et al. Measurement of antigen-antibody interactions with biosensors. J Mol Recognit. 1998 Winter;11(1-6):163-7.

Vanneman & Dranoff. Combining immunotherapy and targeted therapies in cancer treatment. Nat Rev Cancer. Mar. 22, 2012;12(4):237-51.

Verhoeyen et al. Reshaping human antibodies: grafting an antilysozyme activity. Science. Mar. 25, 1988;239(4847):1534-6.

Wang et al. In vitro and in vivo responses of advanced prostate tumors to PSMA ADC, an auristatin-conjugated antibody to prostate-specific membrane antigen. Mol Cancer Ther. Sep. 2011;10(9):1728-39.

Weroha & Haluska. The insulin-like growth factor system in cancer. Endocrinol Metab Clin North Am. Jun. 2012;41(2):335-50.

Widdison et al. Semisynthetic maytansine analogues for the targeted treatment of cancer. J Med Chem. Jul. 13, 2006;49(14):4392-408.

Wörn & Plückthun. Stability engineering of antibody single-chain Fv fragments. J Mol Biol. Feb. 2, 2001;305(5):989-1010.

Wozniak-Knopp et al. Introducing antigen-binding sites in structural loops of immunoglobulin constant domains: Fc fragments with engineered HER2/neu-binding sites and antibody properties. Protein Eng Des Sel. Apr. 2010;23(4):289-97.

Wu & Senter. Arming antibodies: prospects and challenges for immunoconjugates. Nat Biotechnol. Sep. 2005;23(9):1137-46.

Wurch et al. Novel protein scaffolds as emerging therapeutic proteins: from discovery to clinical proof-of-concept. Trends Biotechnol. Nov. 2012;30(11):575-82.

Zhao et al. Synthesis and evaluation of hydrophilic linkers for antibody-maytansinoid conjugates. J Med Chem. May 26, 2011;54(10):3606-23.

Brockhoff et al. Differential impact of Cetuximab, Pertuzumab and Trastuzumab on BT474 and SK-BR-3 breast cancer cell proliferation. Cell Prolif. Aug. 2007;40(4):488-507.

Constantinou et al. Modulating the pharmacokinetics of therapeutic antibodies. Biotechnol Lett. May 2010;32(5):609-22.

Schier et al. Isolation of picomolar affinity anti-c-erbB-2 single-chain Fv by molecular evolution of the complementarity determining regions in the center of the antibody binding site. J Mol Biol. Nov. 8, 1996;263(4):551-67.

Yamashita-Kashima et al. Enhanced antitumor activity of trastuzumab emtansine (T-DM1) in combination with pertuzumab in a HER2-positive gastric cancer model. Oncol Rep. Sep. 2013;30(3):1087-93.

Zimmerman et al. Production of site-specific antibody-drug conjugates using optimized non-natural amino acids in a cell-free expression system. Bioconjug Chem. Feb. 19, 2014;25(2):351-61.

Zitron et al. Targeting and killing of glioblastoma with activated T cells armed with bispecific antibodies. BMC Cancer. Feb. 22, 2013;13:83.

Bernardes et al. A traceless vascular-targeting antibody-drug conjugate for cancer therapy. Angew Chem Int Ed Engl. Jan. 23, 2012;51(4):941-4.

Casi et al. Site-specific traceless coupling of potent cytotoxic drugs to recombinant antibodies for pharmacodelivery. J Am Chem Soc. Apr. 4, 2012;134(13):5887-92.

Chen et al. A human anti-c-Met Fab fragment conjugated with doxorubicin as targeted chemotherapy for hepatocellular carcinoma. PLoS One. May 13, 2013;8(5):e63093.

Chen et al. Anti-hepatoma human single-chain Fv antibody and adriamycin conjugates with potent antitumor activity. Int Immunopharmacol. Jan. 2014;18(1):20-6.

Junutula et al. Site-specific conjugation of a cytotoxic drug to an antibody improves the therapeutic index. Nat Biotechnol. Aug. 2008;26(8):925-32.

Lillo et al. A human single-chain antibody specific for integrin alpha3beta1 capable of cell internalization and delivery of antitumor agents. Chem Biol. Jul. 2004;11(7):897-906.

Steiner et al. Spacer length shapes drug release and therapeutic efficacy of traceless disulfide-linked ADCs targeting the tumor neovasculature. Chem Sci. 2013;4:297-302.

Stamati. OptiLinked Antibody Fragments for ADCs. PEGS 2015, Protein and Antibody Engineering Conference. Oral Presentation, May 7, 2015.

Beckley et al. Investigation into Temperature-Induced Aggregation of an Antibody Drug Conjugate. Bioconjug Chem. Sep. 2013; 24: 1674-1683.

(56) References Cited

OTHER PUBLICATIONS

Dere et al. PK assays for antibody-drug conjugates: case study with ado-trastuzumab emtansine. Bioanalysis. 2013; 5(9): 1025-1040.
Erickson et al. The Effect of Different Linkers on Target Cell Catabolism and Pharmacokinetics/Pharmacodynamics of Trastuzumab Maytansinoid Conjugates. Mol Cancer Ther. 2012; 11:1133-1142.
Gorovits et al. Bioanalysis of antibody-drug conjugates: American Association of Pharmaceutical Scientists Antibody-Drug Conjugate Working Group position paper. Bioanalysis. 2013; 5(9):997-1006.
Gowder et al. Prediction and Analysis of Surface Hydrophobic Residues in Tertiary Structure of Proteins. The Scientific World Journal. 2014; 971258.
Harper et al. Selecting an Optimal Antibody for Antibody-Drug Conjugate Therapy: Internalization and Intracellular Localization. Methods in Molecular Biology. 2013; 1045:41-49.
Lins et al. Analysis of accessible surface of residues in proteins. Protein Science. 2003; 12:1406-1417.
Masuko et al. Anti-Tumor Effect against Human Cancer Xenografts by a Fully Human Monoclonal Antibody to a Variant 8-Epitope of CD44R1 Expressed on Cancer Stem Cells. PLoS ONE. 2012; 7(1): e29728.
Olson & Markwell. Assays for Determination of Protein Concentration. Current Protocols in Protein Science. 2007; 3.4.1-3.4.29.
Sun et al. Design of Antibody-Maytansinoid Conjugates Allows for Efficient Detoxification via Liver Metabolism. Bioconjugate Chem. 2011; 22: 728-735.
Tanious et al. Biosensor-Surface Plasmon Resonance Methods for Quantitative Analysis of Biomolecular Interactions. Methods in Cell Biology. 2008; 84: 53-77.
Thakkar et al. An Application of Ultraviolet Spectroscopy to Study Interactions in Proteins Solutions at High Concentrations. Journal of Pharmaceutical Sciences. 2012; 101(9): 3051-3061.
Vaughan et al. Human Antibodies with Sub-nanomolar Affinities Isolated from a Large Non-immunized Phage Display Library. Nature Biotechnology. 1996; 14:309-314.
Wakankar et al. Analytical methods for physicochemical characterization of antibody drug conjugates. mAbs. 2011; 3(2): 161-172.
SIB (Swiss Institute of Bioinformatics). Swiss-Pdb viewer, https://spdbv.vital-it.ch/.
Structural Bioinformatics Group, Imperial College London. The Phyre2 web portal for protein modeling, prediction and analysis. http://www.sbg.bio.ic.ac.uk/phyre2/html/page.cgi?id=index.
The European Bioinformatics Institute. EMBL-EBI. https://www.ebi.ac.uk/.
IMGT®, The International ImMunoGeneTics Information System®, http://www.imgt.org.
Thermofisher Scientific. Amine-Reactive Crosslinker Chemistry. https://www.thermofisher.com/uk/en/home/life-science/protein-biology/protein-biology-learning-center/protein-biology-resource-library/pierce-protein-methods/amine-reactive-crosslinker-chemistry.html.
GE Healthcare. Biacore Life Sciences, https://www.biacore.com/lifesciences/index.html.
Cragg et al (eds.). Anticancer agents from natural products. 2nd ed. 2012. CRC Press, Boca Raton, FL.
"Inactive Ingredient Search for Approved Drug Products," FDA Inactive Ingredient Database, https://www.fda.gov/Drugs/InformationOnDrugs/ucm080123.htm.
Bai et al., Binding of dolastatin 10 to tubulin at a distinct site for peptide antimitotic agents near the exchangeable nucleotide and vinca alkaloid sites, *J. Biol. Chem*. 265:17141-9 (1990).
Chakravarty et al., Nanobody: the "magic bullet" for molecular imaging? *Theranostics*. 4:386-98 (2014).
De Marco, Biotechnological applications of recombinant single-domain antibody fragments, *Microb. Cell. Fact*. 10:44 (2011).
Deng et al., Brentuximab Vedotin, *Clin. Cancer Res*. 19:22-27 (2013).
Dumontet et al., Microtubule-binding agents: a dynamic field of cancer therapeutics, *Nat. Rev. Drug Discov*. 9:790-803 (2010).

Gerber et al., The antibody-drug conjugate: an enabling modality for natural product-based cancer therapeutics, *Nat. Prod. Rep*. 30:625-639 (2013).
Kelley et al., The Phyre2 web portal for protein modeling, prediction and analysis, *Nat. Protoc*. 10:845-58 (2015).
Klinguer-Hamour et al., World Antibody-Drug Conjugate Summit, Oct. 15-16, 2013, San Francisco, CA, *MAbs*. 6:18-29 (2014).
Lipovsek, Adnectins: engineered target-binding protein therapeutics, *Protein Eng. Des. Sel*. 24:3-9 (2011).
Lopus, Antibody-DM1 conjugates as cancer therapeutics, *Cancer Lett*. 307:113-8 (2011).
Mersana Therapeutics, Creating Next Generation ADCs—Diverse Payloads, Higher Drug Loading, & Alternative Targeting Moieties, European Antibody Congress. Nov. 2012.
Siontorou, Nanobodies as novel agents for disease diagnosis and therapy, *Int. J. Nanomedicine*. 8:4215-27 (2013).
Trail, Antibody drug conjugates as cancer therapeutics, *Antibodies*. 2:113-29 (2013).
Vanlandschoot et al., Nanobodies®: new ammunition to battle viruses, *Antiviral Res*. 92:389-407 (2011).
Yurkovetskiy et al., A Polymer-Based Antibody-Vinca Drug Conjugate Platform: Characterization and Preclinical Efficacy, *Cancer Res*. 75:3365-72 (2015).
Brady et al., Crystal Structure of a Chimeric Fab' Fragment of an Antibody Binding Tumour Cells, *J. Mol. Biol.*, 227:253-64 (1992).
Chames et al., Bispecific antibodies for cancer therapy, The light at the end of the tunnel., *mAbs*, 1(6):539-47 (2009).
Dooley et al., Stabilization of antibody fragments in adverse enviroments, *Biotechnol. Appl. Biochem.*, 28:77-83 (1998).
Janeway, Chapter 3, Section 3: The structure of a typical antibody molecule, Janeway's Immunobiology textbook (2001).
Kontermann, Dual targeting strategies with bispecific antibodies, 4(2):182-97 (2012).
Kortt et al., Recombinant anti-sialidase single-chain variable fragment antibody, *Eur. J. Biochem*. 221:151-7 (1994).
May et al., Advances in bispecific biotherapies for the treatment of cancer, *Biochem., Pharmacol.*, 84:1105-12 (2012).
Perisic et al., Crystal structure of a diabody, a bivalent antibody fragment, *Structure*, 2(12):1217-26 (1994).
Burmester et al., Selection, Characterization and X-ray Structure of Anti-ampicillin Single-chain Fv Fragments from Phage-displayed Murine Antibody Libraries, *J. Mol. Biol.*, 309:671-85 (2001).
Sokalingam et al., A Study on the Effect of Surface Lysine to Arginine Mutagenesis on Protein Stability and Structure Using Green Fluorescent Protein, *PLoS One*, 7(7):e40410 (2012).
Rotenberg et al., Deuteroporphyrin-albumin binding equilibrium. The effects of porphyrin self-aggregation studied for the human and the bovine proteins, *Biochem. J*. 229:197-203 (1985).
Staneloudi et al., Development and characterization of novel photosensitizer: scFv conjugates for use in photodynamic therapy of cancer, *Immunol*. 120:512-7 (2007).
Yokota et al., Rapid tumor penetration of a single-chain Fv and comparison with other immunoglobulin forms, *Cancer Research*. 52:3402-8 (1992).
Kontermann et al., Bispecific antibodies, Drug Discovery Today. 20:838-47 (2015).
Weidle et al., The intriguing options of multispecific antibody formats for treatment of cancer, Cancer Genomics & Proteomics. 10:1-18 (2013).
Xiong et al., Development of tumor targeting anti-MUC-1 multimer: effects of di-scFv unpaired cysteine location on PEGylation and tumor binding, Protein Engineering, Design & Selection. 19:359-67 (2006).
Berman et al., Protein Data Bank, Nuc. Acids Res., 28(1):235-42 (2000).
Canul-Tec et. al., Structural Basis of Neutralization of the Major Toxic Component from the Scorpion *Centruroides noxius* Hoffmann by a Human-derived Single-chain Antibody Fragment, J. Biol. Chem., 286, 20892 (2011).
Clark et al., Crystal structure of a 3B3 variant—A broadly neutralizing HIV-1 scFv antibody, Protein Sci., 18, 2429 (2009).

(56) References Cited

OTHER PUBLICATIONS

Garcia-Rodriguez C et. al., Molecular evolution of antibody cross-reactivity for two subtypes of type A botulinum neurotoxin, Nat. Biotechnol., 25:107 (2007).

Gilmartin et al., High-level secretion of recombinant monomeric murine and human single-chain Fv antibodies from *Drosphila* S2 cells, Prot. Eng. Des. Sel., 25, 59 (2012).

Honegger et. al., A mutation designed to alter crystal packing permits structural analysis of tight-binding fluorescein-scFv complex, Protein Sci., 14:2537 (2005).

Hwang et. al., Structural Basis of Neutralization by a Human Anti-severe Acute Respiratory Syndrome Spike protein Antibody, 80R, J. Biol. Chem., 281(45):34610 (2006).

Kelley et al., Protein structure prediction on the Web: a case study using the Phyre Server, Nat. Protocols., 4:363 (2009).

Levin et al., Human IgE against the major allergen Bet v 1—defining an epitope with limited cross reactivity between different PR-10 family proteins, (2014) Clin Exp Allergy 44:288-99 (2013).

Lill et al., Comupter Aided Drug Design platform using PyMOL, J. Comp. Aided Mol. Dess., 25:13-19 (2011).

Ouyang et al., Structural insigns into a human anti-IFN antibody exerting therapeutic potential for systemic lupus erythematosus, J. Mol. Med., 90:837 (2012).

Sabin et. al., Crystal Structure and Size—Dependent Neutralization Properties of HK20, a Human Monoclonal Antibody Binding to the Highly Conserved Heptad Repeat 1 of gp41, PLoS One, 6(11):e1001195 (2010).

Sui et al., Structural and functional bases for broad-spectrum neutralization of avian and human influenza A viruses, Nat. Struct. Biol., 16(3):265 (2009).

* cited by examiner

Fluorescent image of same Gel

Coomassie-stained SDS PAGE Gel

Left: fluorescent imaging of gel and right Coomassie stained gels.

B

B

B

C

D

E

B

C

B

A

B

C

D

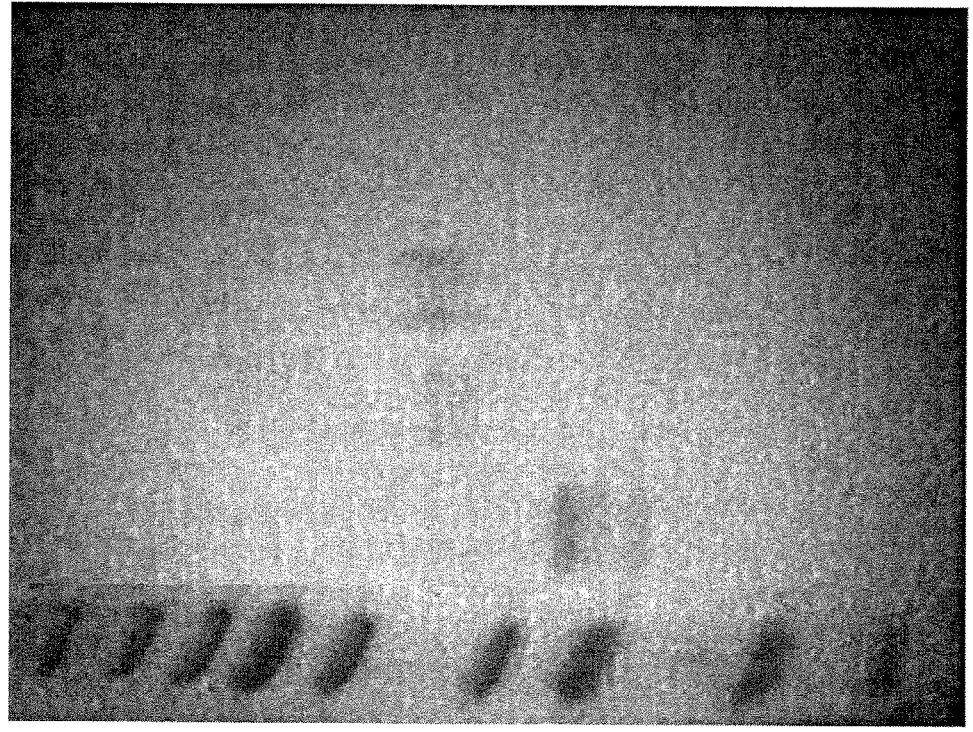
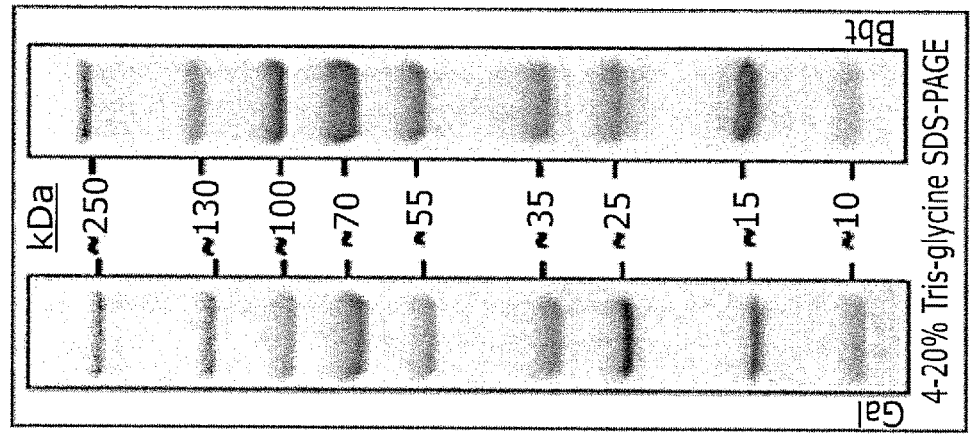
Figure 69A
Figure 69B

- scFv (TCT1067) (Total protein)
- scFv (TCT1067)-AF-C5 (Total protein)
- scFv (TCT1067)-AF-C5 (Total drug)

A

BIOLOGICAL MATERIALS AND USES THEREOF

REFERENCE TO RELATED APPLICATIONS

This application is a U.S. national stage application filed under 35 U.S.C. § 371, based on International Application No. PCT/GB2015/052800, filed on Sep. 25, 2015, which claims priority to United Kingdom Patent Application No. 1416960.1, filed on Sep. 25, 2014. The entire contents of both applications are incorporated herein by reference.

BACKGROUND OF THE INVENTION

The invention relates to optimised targeted therapeutic compounds comprising a carrier molecule and an active therapeutic agent, thereby providing more effective clinical treatments for various diseases requiring targeted therapeutic action.

Current treatment of disease is predominantly non-targeted. Drugs are administered systemically or orally which exposes many other tissues as well as the tissues which are diseased. In cancer therapy, for example, chemotherapeutic drugs act on mechanisms which are of particular significance in cancer cells (commonly DNA or cellular replication related). However, other non-cancerous cells can also take up the chemotherapeutic drug and be affected, such as rapidly dividing bone marrow stem cells, resulting in immunosuppression and sickness (common side effects of chemotherapeutic treatments). In infectious diseases, an antibacterial drug is introduced into the blood (orally or by injection) and typically interferes with a particular bacterial metabolic pathway. Exposure of other tissues to the drug can result in side effects as well as the major problem of drug resistance. Virally-infected cells are also difficult to treat as their metabolism is generally practically identical to uninfected human cells.

It is widely hypothesised that future advances in medicine are likely to be in the tailoring of drugs to the disease. This means, delivering the therapeutic to the correct target tissue or organism, rather than the non-selective hit and miss approach of most of the conventional drugs used today. This will result in lower doses administered, lower side effects and toxicities, and overall better clinical response for patients.

There are many drugs used clinically today that are very good at treating specific diseases, once the drug has accumulated in the correct tissue. Therefore, the problem is with the specific targeting of drugs rather than their mechanism of action. Targeting drugs or other effectors to the desired cells is a well-established area. One of the main approaches to targeting is to use antibodies or cell-specific ligands as the targeting element of a multifunctional molecule (e.g. Hudson P J. Expert Opin Investig Drugs 2000, 9: 1231-42; Borsi L, et al. Blood 2003, 102: 4384-92).

Antibodies have naturally evolved to act as the first line of defence in the mammalian immune system. They are complex glycoproteins which have exquisite specificity and tremendous diversity. This diversity comes about from programmed gene shuffling and targeted mutagenesis, resulting in a vast number of different antibody sequences. This diversity means that antibodies can bind to practically any target molecule which is usually protein in nature. It is now possible to mimic antibody selection and production in vitro, selecting for recombinant human antibodies against virtually any desired target (Hoogenboom H R. Nature Biotechnology 2005, 23: 1105-16).

Antibodies can bind with a high degree of specificity to target cells expressing the appropriate receptor. The affinity of an antibody is a measure of how well an antibody binds to the target (antigen). It is usually described by an equilibrium dissociation constant ($K_d$). For antibodies that need to be internalised, the association rate is more important since the dissociation rate is less critical if the antibody is taken into the cell. A variety of technology exists to select and manipulate antibodies which have desired structural and binding properties (Wu A M and Senter P D, Nature Biotechnology 2005, 23: 1137-46).

As with all biological molecules, the size of the antibody affects its pharmacokinetics in vivo (Deonarain, M P et al. 1997, Protein Eng. 10, 89-98; Batra S K et al. Curr Opin Biotechnol. 2002, 13: 603-8.). Larger molecules persist longer in the circulation due to slow clearance (large glycoproteins are cleared through specific uptake by the liver). For whole antibodies (molecular weight 150 KDa) which recognise a cancer cell antigen in an experimental mouse model system, 30-40% can be taken up by the tumour, but because they persist longer in the circulation, it takes 1-2 days for a tumour: blood ratio of more than one to be reached. Typical tumour: blood ratios are 5-10 by about day 3 (Boxer G M et al. Br. J. Cancer 1994, 69: 307-14.). From clinical trials of whole antibodies, the amount actually delivered to tumours is about 1% of that seen in mouse models, but with similar tumour to organ ratios (Epenetos A A et al. Cancer Res. 1986, 46: 3183-91). If another molecule is attached to the antibody, then the new size and chemicophysical properties determine the altered pharmacokinetics. Additionally, properties such as net charge and hydrophilicity can affect the targeting kinetics (Gangopadhyay, A et al. Nucl. Med. Biol 1996, 23: 257-61).

Some cell surface antigens are static or very slowly internalise when bound by a ligand such as an antibody. There are some which have a function that requires internalisation, such as cell signalling or uptake of metals and lipids. Antibodies can be used to deliver agents intracellularly through such antigens.

Monoclonal antibodies (MAbs) have, over recent years, changed the face of medicine by facilitating the development of drugs that can specifically target biological markers associated with disease [Carter P J. Nat Rev Immunol. 2006, 6:343-57]. This has many applications, from the inhibition of disease-related factors such as VEGF in cancer or TNF in inflammatory disease, to tumour destruction in cancer. In proliferative diseases, the affected cells often have cell-surface receptors that are associated with, or over-expressed on that cell type (e.g mutated normal cells in cancer [Scott A M et al. Nat Rev Cancer. 2012, 12:278-87] or over-stimulated immune cells in auto-immune disease [Chan A C & Carter P J. Nat Rev Immunol. 2010, 10:301-16]). Many of the tumour-associated receptors act as growth factors that cause uncontrolled signalling leading to tumour formation. Examples of such receptors include members of the epidermal growth factor receptor (EGFR) family (EGFR/erbB1, ErbB2/HER2, HER3 and HER4), Hepatocyte growth factor receptor, insulin-like growth factor-1 receptor and Notch receptor [Fauvel B & Yasri A. MAbs. 2014, 6:838-51; Ménard S et al. Oncogene. 2003, 22, 6570-8; Ranganathan P et al. Nat Rev Cancer. 2011, 11:338-51; Parikh R A et al. OncoTargets Ther. 2014, 7:969-83; Weroha S J & Haluska P. Endocrinol Metab Clin North Am. 2012, 41:335-50]

MAbs can bind to tumour-associated receptors and inhibit oncogenic signalling leading to tumour regression or ablation [Scott A M et al. Nat Rev Cancer. 2012, 12:278-87, 4; Fauvel B & Yasri A. MAbs. 2014, 6:838-51]. Whole MAbs of various immunoglobulin sub-classes can also elicit immune responses leading to tumour eradication [Vanneman M & Dranoff G. Nat. Rev. Cancer 2012, 12:237-251].

Tumours can evolve mechanisms to overcome MAb intervention, such as increasing receptor expression [Nahta R et al Nature Clinical Practice Oncology, 2006, 3, 269-280], up-regulating alternative oncogenic signalling pathways or mutations in signalling pathway proteins [Nahta R et al Nature Clinical Practice Oncology, 2006, 3, 269-280, Gallardo A, et al Br J Cancer. 2012, 106:1367-73] and dampening down the immune response [Pardoll D M. NatRev Cancer. 2012, 12:252-64]. Commercially-approved MAbs such as trastuzumab (HERCEPTIN®), cetuximab (ERBITUX®) and pannitumumab (VECTABIX®) can prolong survival for several months but are often seen as not being potent enough for significant cures [Scott A M et al. Nat Rev Cancer. 2012, 12:278-87, Sliwkowski M X & Mellman I. Science. 2013, 341:1192-8]. Additionally, patients can become resistant to MAb therapy leading to relapses, fewer treatment options and reduced survival [Nahta R et al Nature Clinical Practice Oncology, 2006, 3, 269-280; Brand™ et al. Cancer Biol Ther. 2011 11:777-92].

One desirable goal in the field of drug delivery is to specifically deliver a cytotoxic moiety to disease-affected areas in the human body such that the diseased cells are eradicated without affecting normal cells or eliciting unwanted or harmful side-effects. Attaching a cytotoxic payload to intact MAbs can increase their cell-killing potency and switch the cytotoxic mechanism of action away from immune-mediated and signalling mediated effects to a more direct tumour cell destruction [Flygare J A et al. Chem Biol Drug Des. 2013, 81:113-21; Sievers E L & Senter P D. Annu Rev Med. 2013; 64:15-29; Chari R V et al. Angew Chem Int Ed Engl. 2014, 53, 3796-827; Teicher B A & Chari R V. Clin Cancer Res. 2011, 17:6389-97]. This has the potential to overcome drug resistance to the 'free' antibody and any immune-related conditions that prevent a successful outcome [Barok M et al. Breast Cancer Res. 2011, 13:R46; Baron J M et al. J Oncol Pharm Pract. 2014. [Epub ahead of print]. These so-called antibody-drug conjugates (ADCs) are well-known in the art and have been subject to considerable research into generating potent, specific, safer and stable ADCs [Flygare J A et al. Chem Biol Drug Des. 2013, 81:113-21; Sievers E L & Senter P D. Annu Rev Med. 2013; 64:15-29; Chari R V et al. Angew Chem Int Ed Engl. 2014, 53, 3796-827; Teicher B A & Chari R V. Clin Cancer Res. 2011, 17:6389-97; Adair J R et al. Expert Opin Biol Ther. 2012, 12:1191-206; LoRusso P M et al. Clin Cancer Res. 2011, 17:6437-47].

The most recent research streams are beginning to show promise due to well-characterised/validated human or humanised antibodies being stably linked to extremely potent drugs that disrupt microtubule function (e.g. auristatins and maytansinoids [Alley S C et al. J Pharmacol Exp Ther. 2009, 330:932-8; Erickson H K et al. Cancer Res. 2006, 66:4426-33]) and DNA-damaging agents (e.g. calicheamycin and PBDs [Kung Sutherland M S et al. Blood 2013, 122:1455-63; de Vries J F et al. Leukemia. 2012, 26:255-64]). ADCs such as trastuzumab-emtansine (Kadcyla®) have demonstrated superior clinical efficacy (increased survival and lower side-effects) than the same un-conjugated antibody plus free chemotherapy drugs [Amiri-Kordestani L et al. Clin Cancer Res. 2014, 20:4436-41]. Less potent cytotoxic drugs such as doxorubicin are still being developed as ADCs but limitations arise due to not enough drug being delivered by the targeting MAb [Govindan S V et al. Mol Cancer Ther 2013, 12:968-78]. Work on improving ADCs and the conjugation of drugs to carrier molecules has focused on using polymers as linkers to join the carrier and the drug [Carlson B. Biotechnology Healthcare 2012, 9:28-31; U.S. Pat. No. 8,808,679 B2]. This approach is effective in linking the two molecules but increases the size and complexity of synthesis of the conjugates. Increasing the macromolecular size of an ADC leads to changes in pharmacokinetics such as increased blood half-life [Deonarain M P et al (2015) Exp. Opin. Drug Discov 10; 463-81; Constantinou A, et al (2010) Biotechnol Lett 32: 609-22] and pharmacodynamics such as decreased tumour penetration [Dennis M S et al (2007) Cancer Res 67: 254-61]). A direct approach to improving ADC efficacy is site-specific conjugation which results in more homogenous conjugates of low (typically 2-4) DAR (Drug Antibody Ratio), implying that high DAR is not an effective approach due to to increased toxicity from higher payload exposure and adverse reaction to aggregates of non-optimised high DAR species [Hamblett et al. Clin Cancer Res 2004, 10: 7063-7070].

A great deal of clinical experience has been obtained with ADCs [Amiri-Kordestani L et al. Clin Cancer Res. 2014, 20:4436-41] but significant limitations still exist [Lu D et al. Cancer Chemother Pharmacol. 2014, 74:399-410; Monjanel H et al. Br J Haematol. 2014, 166:306-8; Robak T & Robak E. Expert Opin Investig Drugs. 2014, 23:911-24.]. Using conjugation approaches described in the art, drug loading on the antibody is not high enough to deliver sufficient concentrations of drugs to the target tissue to lead to long-term cures [Teicher B A & Chari R V. Clin Cancer Res. 2011, 17:6389-97], or to produce a significant response where the target is expressed at low levels [Wang X Et al. Mol Cancer Ther. 2011, 10:1728-39]. Low drug loading is also detrimental when using drugs with relatively low toxicity, such as doxorubicin, taxanes and methotrexate as more of these drugs are needed to achieve the therapeutic effect needed. However, attempting to use higher loaded ADCs typically leads to ADCs with reduced binding function [Chari R V et al. Angew Chem Int Ed Engl. 2014, 53, 3796-827; Burke, P J et al. Bioconjugate Chem. 2009, 20, 1242-1250], reduced solubility [Chari R V et al. Angew Chem Int Ed Engl. 2014, 53, 3796-827; Hollander, I et al. Bioconjugate Chem. 2008, 19, 358-361; Burke, P J et al. Bioconjugate Chem. 2009, 20, 1242-1250; Zhao R Y et al. J Med Chem. 2011, 54:3606-23] and the tendency to aggregate [Chari R V et al. Angew Chem Int Ed Engl. 2014, 53, 3796-827; Hollander, I et al. Bioconjugate Chem. 2008, 19, 358-361; Burke, P J et al. Bioconjugate Chem. 2009, 20, 1242-1250; Zhao R Y et al. J Med Chem. 2011, 54:3606-23; King, H et al. Bioconjugate Chem. 1999, 10, 279-288], (all three of which lead to poor pharmacokinetic properties) [Hamblett, K J et al. Clin. Cancer Res. 2004, 10, 7063-7070; Shen B Q. Nat Biotechnol. 2012, 30:184-9.], reduced drug delivery, lower therapeutic efficacy, increased side effects and unwanted toxicity [Litvak-Greenfeld D & Benhar I. Adv Drug Deliv Rev. 2012, 64:1782-99] to tissues involved in drug metabolism and clearance such as the hepatic and renal system.

A further limitation with current antibodies and ADCs is the undesirable side-effects of long serum half-life (1-3 weeks) [Litvak-Greenfeld D & Benhar I. Adv Drug Deliv Rev. 2012, 64:1782-99; E. L. Sievers, et al. J. Clin. Oncol. 2001, 19, 3244-3254] which can lead to gastro-intestinal damage, peripheral neuropathy and immuno-suppression [J. J. Lee & S. M. Swain. J. Clin. Oncol. 2006, 24:1633-1642; M. A. Jordan & L. Wilson, Nat. Rev. Cancer 2004, 4, 253-265]. In addition, current whole antibody-based therapies and ADCs exhibit poor diffusion properties and lower tissue perfusion properties [Teicher B A & Chari R V. Clin Cancer Res. 2011, 17:6389-97; Jain R K. Adv Drug Deliv Rev. 2012, 64:353-365; Dennis M S et al. Cancer Res. 2007, 67:254-61] which result in a lower concentration reaching the core or poorest vascularised areas of the solid tumour [Teicher B A & Chari R V. Clin Cancer Res. 2011, 17:6389-97; Dennis M S et al. Cancer Res. 2007, 67:254-61.]. Hence, current ADCs are less effective against larger solid tumours [Teicher B A & Chari R V. Clin Cancer Res. 2011, 17:6389-97], poorly vascularised tumours, or tumours with a dense stroma.

Hamblett et al. Clin Cancer Res 2004, 10: 7063-7070 investigated in detail the drug loading of monomethyl auristatin E (MMAE) onto an anti-CD30 monoclonal antibody. They found that, whilst the IC50 potency measurement of the conjugate increased with the number of drug molecules coupled, the in vivo antitumour activity did not increase when increasing from 4 drugs per antibody to 8 drugs per antibody. Furthermore, the 8 drug loaded conjugates were poorly tolerated in vivo, with the number of conjugates that could be administered being halved from 4 drug loaded to 8 drug loaded. In addition, the 8 drug loaded conjugates were cleared from the body, twice as quickly as the 4 drug loaded conjugates. Hamblett identified that 4 drug loading of antibodies to be the maximum plausible in order to achieve best clinical effect (by balancing tumour activity, tolerance and clearance). This observation has been supported by many others [e.g. Chari R V et al. Angew Chem Int Ed Engl. 2014, 53, 3796-827].

Furthermore, it is known from Kim et al. Mol Cancer Ther 2008, 7: 2486-2497, that antibody fragments can couple to a maximum of four drug molecules before needing to resort to alternative strategies such as use of a polymer for coupling [US 2013/0101546].

WO 2014/068443 A1, WO 2014/134457 A2, WO 2013/082254 A1, WO 2012/104344 A1 and US 2010/0136033 A1 each describe drugs conjugated to antibody fragments. However, none of these documents suggest a way to overcome aggregation in antibody fragments, which would be necessary for high DAR ratios in a smaller protein than a whole IgG.

For example, WO 2014/068443 (Pfizer) describes conjugation onto lysine residues and a specific V-kappa Lysine-188 residue. They demonstrate average DARs on a whole IgG (150 kDa) of around 2-4, with a maximum DAR for some payloads of 7.8. This work would suggest that for a scFv fragment of 30 kDa (⅕ size) a skilled person would reasonably expect a DAR of no higher than 2.

WO 2014/134457 (Immunogen) describes direct and indirect lysine conjugations to make IgG-based ADCs of DAR around 4-5. Although DARs of up to 20 are proposed for full antibodies, this would equate to a DAR of around 4 for an scFv of ⅕ the size.

WO 2012/104344 (GenMab) describes an anti-CD74 whole antibody (HuMab-CD74) and conjugates using direct and indirect lysine approaches with a variety of payloads. The DARs disclosed range from 3.7 to 4.1, which may equate to, at best, a DAR of 1 for an antibody fragment that is ⅕ the size.

A recent review of the ADC therapy field (Chari et al. Angew. Chem. Int. Ed 2014, 53: 3796-3827) highlights that current ADCs are not sufficiently effective to be routinely used in the clinical setting. The recent marketing approval by the FDA of two ADC molecules shows that the principle of ADC can work, but with 30 years plus of research in this therapeutic area, for only two drugs to have been approved for the clinic demonstrates that these are the exception rather than rule due to difficulties in making the ADC work effectively.

Accordingly, there is a need to produce improved ADCs that reduce or remove the significant limitations of current ADC approaches.

The present invention now provides such improved ADCs which are optimised to reduce the limitations of current ADC therapies, as well as their use and processes for their manufacture.

In a first aspect of the invention there is provided a compound comprising a therapeutic agent coupled to a carrier molecule, with a minimum coupling ratio of 5:1; wherein the carrier molecule is (i) an antibody fragment or derivative thereof or (ii) an antibody mimetic or derivative thereof; and wherein the therapeutic agents are coupled onto a lysine amino acid residue; and further wherein the therapeutic agent is not a photosensitising agent.

The term "carrier molecule" includes the meaning of any agent to which the therapeutic agent is coupled. The carrier molecule comprises amino acids and includes peptides, polypeptides and proteins. In particular, the carrier molecule is intended to be an antibody fragment or antibody mimetic.

The term "coupling ratio" means the number of molecules of therapeutic agent coupled to one carrier molecule.

The term "photosensitising agent" (photosensitiser, photosensitising drug being used interchangeably) shall be taken to refer to a compound that belong to a class of drug that requires a secondary, physical intervention in order to activate its cytotoxic properties. The compound in its singlet state, absorbs a photon of light at a specific wavelength. This results in a short-lived excited singlet state. This can be converted by intersystem crossing to a longer-lived triplet state. This triplet state photosensitiser may have cytotoxic properties due to photooxidation by radicals, singlet oxygen and photoreaction not involving oxygen. The photo-dependent potency of a photosensitiser must be at least 1 µM when illuminated with a light source of at least 0.1 Joules using methods such as those described by Savellano M D & Hasan T [Clinical Cancer Res. 2005. 11:1658-58]. A photosensitiser can also be considered to be a class of drug that requires a secondary, physical intervention in order to activate its cytotoxic properties, whose said properties are the predominant mechanism of cell killing.

By a therapeutic agent which is not a photosensitising agent, we mean any therapeutic agent except a photosensitising agent. Such therapeutic agents possess none of the photophysical properties of a photosensitiser, i.e. they do not absorb a photon of light in order to enter an excited state. The photo-dependent potency of a non-photosensitiser must be no greater than 1 µM when illuminated with a light source of at least 0.1 Joules, and is preferably 0 µM [Kostron et al (2003) in Photodynamic Therapy: Methods and Protocols, (Comprehensive Series in Photochemical & Photobiological Sciences, Royal Society of Chemistry publishers)

Compounds comprising photosensitisers coupled to carrier molecules have been, similarly to other therapeutic agent conjugates, previously described (e.g. WO 2007/042775 and WO 2010/106341), however, such conjugates exhibit significant differences from non-photosensitiser drugs conjugates. For example, there is a clear rationale for spatial separation of photosensitisers in order to reduce and/or avoid quenching. The spatial separation of non-photosensitiser drugs has conventionally been believed to be irrelevant when considering therapeutic function as they are incapable of quenching (which is a purely light related phenomenon) or any spatially-interacting self-inhibition property and so it is now extremely surprising to find that by optimally spacing non-photosensitisers, improved ADC molecules can be produced.

Photosensitisers, due to their planar-hydrophobic structure causing blood protein binding, are well known for having a long serum half-life, which contributes to their skin photosensitivity [Hopper C. Lancet Oncol. 2000; 1 212-9; Korbelik M. Photochem Photobiol. 1993; 57:846-50]. Conjugating them onto hydrophilic antibodies speeds up the blood clearance reducing these side effects [Bhatti M, P et al. Int J Cancer. 2008, 122:1155-63; Palumbo A et al. Br J Cancer. 2011, 104:1106-15]. Conversely, conjugating small molecule non-photosensitiser drugs will slow down their clearance as they naturally clear quickly from the circulation [Pimm M V et al. Int J Cancer. 1988, 41:886-91]

The terms "nucleotide sequence" or "nucleic acid" or "polynucleotide" or "oligonucleotide" are used interchangeably and refer to a heteropolymer of nucleotides or the sequence of these nucleotides. These phrases also refer to DNA or RNA of genomic or synthetic origin which may be single-stranded or double-stranded and may represent the sense or the antisense strand, and to peptide nucleic acid (PNA) or to any DNA-like or RNA-like material. In the sequences herein A is adenine, C is cytosine, T is thymine, G is guanine and N is A, C, G or T (U). It is contemplated that where the polynucleotide is RNA, the T (thymine) in the sequences provided herein is substituted with U (uracil). Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "polypeptide" or "peptide" or "amino acid sequence" refer to an oligopeptide, peptide, polypeptide, or protein sequence or fragment thereof and to naturally occurring or synthetic molecules. A polypeptide "fragment," "portion," or "segment" is a stretch of amino acid residues of at least about 5 amino acids, preferably at least about 7 amino acids, more preferably at least about 9 amino acids and most preferably at least about 17 or more amino acids. To be active, any polypeptide must have sufficient length to display biological and/or immunological activity.

The terms "purified" or "substantially purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99% by weight, of the indicated biological macromolecules present (but water, buffers, and other small molecules, especially molecules having a molecular weight of less than 1 kDa, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "recombinant," when used herein to refer to a polypeptide or protein, means that a polypeptide or protein is derived from recombinant (e.g., microbial, insect, or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., E. coli, will be free of glycosylation modifications; polypeptides or proteins expressed in yeast will have a glycosylation pattern in general different from those expressed in mammalian cells.

The term "OptiLink' or "OptiLinked" used herein refers to the optimization of an antibody fragment according to the invention in order to maximize payload conjugation loading whilst minimizing conjugate aggregation in vitro or in vivo whilst retaining antibody binding function.

Alternative minimum coupling ratios to provide higher loading of therapeutic agent onto the carrier molecule include at least 6:1, at least 7:1, and at least 8:1 or more.

Coupling drug molecules to amino acid residues can occur at a number of different amino acids. Table 1 lists conjugation strategies directed at lysine residues showing coupling chemistries which can be used with this coupling method.

TABLE 1

Functional groups for coupling drugs onto lysine amino acids

| Residue(s) | Functional group | Coupling chemistry | Resulting bond |
|---|---|---|---|
| Lysine | Amine | Active-ester | Amide |
| | | Isothiocyanate | Isothiourea |
| | | Isocyanates | Isourea |
| | | Acyl azides | Amide |
| | | Sulphonyl chloride | Sulphonamide |
| | | Carbonyl, reduce. | Schiff Base, 2° amine |
| | | Epoxide | 2° Amine |
| | | Carbonates | Carbamate |
| | | Fluorobenzene deriv. | Arylamine |
| | | Imidoesters | Amidine |
| | | Carbodiimides | Amide |
| | | Anhydrides | Amide |

Antibody fragments and mimics vary in amino acid sequence and the number and spacing of functional groups to couple drugs to. The most common frequently used functional group for conjugation is the primary amine found at the N-terminus and on lysine residues. A major determinant of the effectiveness of a particular therapeutic-antibody fragment conjugate is the spatial separation of the residues to which therapeutic agent molecules are attached. These residues must be distinct and topologically separated on the surface of the antibody for effective coupling and optimal pharmacokinetics of the resulting conjugate.

Conjugatable residues are preferably in locations that can tolerate chemical modification without becoming unstable or prone to aggregation.

Generally, proteins fold to form a hydrophobic core at the centre of the molecule with a hydrophilic surface to enable solubility in physiological solvents. Basic residues such as lysines and arginines, acidic residues such as glutamates and aspartates, polar residues such as serines (and sometimes tyrosines), cysteines, glutamines and asparagines are all commonly found on the surface of proteins. In many examples these residues are involved in maintaining the structure and function of that protein. Lysine residues are the most commonly-occurring surface amino acid [Hermanson, G T, Bioconjugate Techniques, Chapter 1, pg 30, Academic Press (2008)] and react preferentially with NHS-esters at alkali pHs.

In the example of antibody fragments such as single-chain Fv, each domain is made up of a variable heavy (VH) and variable light (VL) domain. These can be one of any family of VH and VL domains. In the case of the antigen binding loops (complementarity determining regions, i.e. CDRs), these sequences are specific to the ability of that antibody to recognise its cognate antigen. These can be manipulated to alter the specificity or affinity of the antibody but for no other reasons. The major part of the domain sequence is the framework region. FIG. 1 (modified from Knappik et al. J. Mol. Biol. 2000, 296: 57-86) indicates which residues in a human variable domain tend to be present at the surface of the antibody and which areas tend to be interior as part of the core. Given the high degree of structural and sequence homology between antibodies, these regions can generally be applied to all antibody sequences. The surface framework regions tend to contain the charged or polar residues.

It is an advantage if the functional and physical properties of the therapeutic agent and the carrier molecule are qualitatively substantially unaltered in the coupled form in comparison to the properties when in an uncoupled form.

By qualitatively substantially unaltered we mean that the therapeutic agent retains its therapeutic function but that this may be quantitatively different when conjugated (e.g. the therapeutic function could be enhanced compared to the unconjugated drug); and that the carrier molecule binds to the same target(s) when conjugated as when unconjugated but that may be quantitatively different (e.g. binding affinity could be higher).

The term "binding affinity" includes the meaning of the strength of binding between a carrier molecule and its target (such as, but not limited to, an antibody fragment and an antigen).

The compound of the invention should possess an IC50 of <100 nM, preferably <1 nM, more preferably <10 pM, and even more preferably <0.1 pM.

It is preferable if the compound has an IC50 of up to 10-fold lower (i.e. 10-fold more potent) than the therapeutic agent when unconjugated. The IC50 may be at least 10-fold lower (which is the same as 10% of the original IC50) and preferably the potency will go up to 100% of the unconjugated 1050. Even more preferably, the potency is higher and so the percentage is preferably 200%, 500%, 1000% (i.e. 10-times more potent) or better. A drug maybe poorly potent on its own (e.g. cannot cross the cell membrane) but be very potent as an ADC (hence 1000% or better).

The half maximal inhibitory concentration (IC50) is a measure of the effectiveness of a substance in inhibiting a specific biological or biochemical function. This measure indicates how much of a particular drug or other substance (inhibitor) is needed to inhibit a given biological process (or component thereof) by half. Determination of the IC50 for a given compound is a routine matter, and typically is determined by constructing a dose-response curve and examining the effect of different concentrations of antagonist on reversing agonist activity. The IC50 value is calculated by determining the concentration needed to inhibit half of the maximum biological response of the agonist.

The compound should possess a murine serum half-life of at least 2 hours, preferably 4 hours, alternatively 8, 16, 32, 64 or 128 hours. Serum half life may also be measured in mice, or in humans. The compound preferably has a serum half-life of up to 5 times higher than the carrier molecule when unconjugated, preferably up to 10 times higher. The compound may possess a reduced half-life in comparison to the unconjugated form. A 50% drop in half-life, e.g from 4 hrs to 2 hrs is pharmacologically acceptable if associated with other advantageous features, such as low or reduced aggregation. Aggregation would lead to rapid clearance <1 hr for a scFv or similar sized fragments, reducing bioavailability and also potentially inducing harmful immune reactions. It is preferable if the half-life of the carrier molecule is maintained as close to that of the unconjugated carrier molecule, with a small drop tolerated. An increase of half-life up to 10-fold increase is desirable (e.g. 4 hrs to 20 hrs in mice).

Serum half-life is the calculated duration of time for a serum level of a compound to be reduced to half its initial value. Determination of the serum half-life for a given compound is a routine matter, and typically is determined by measuring the amounts of drug in the serum over time following compound administration to an organism. Serum half-life is important clinically, as it will determine the dosage regime required in order to consistently achieve a serum level of drug within a clinically effective range.

The compound of the invention should possess a solubility of at least 1 mg/ml in a physiologically-compatible buffer at room temperature (for example 20° C.) (e.g. phosphate-buffered saline, or saline). More preferably, 2 mg/ml, 4 mg/ml, 8 mg/ml, 10 mg/ml, 15 mg/ml or 20 mg/ml. In one embodiment the compound of the invention possesses said solubilities in the absence of additives or excipients. In an alternative embodiment the compound of the invention possesses said solubilities in the presence of one or more additives or excipients (e.g. when present as residual or non-removable amounts that are acceptable excipients to the regulatory bodies).

Conjugation reactions leading to the compound of the invention may also have additives or excipients to facilitate the reaction and compound solubility. Examples are polysorbate-20, tween-80, glycine, maltose, histidine, pluronic F-68, octanoic acid, N-acetyl tryptophan, benzyl alcohol, benzoic acid, propylene glycol, (chloro)butanol, isopropanol and glycerol [Hollander I. et al Bioconjugate Chem. 2008, 19:358-361; Patapoff T W & Esue O. Pharm Dev Technol. 2009, 14:659-64]. These are normally removed during processing but are sometimes present as residual or non-removable amounts that are acceptable excipients to the regulatory bodies.

The compounds of the invention preferably possess a solubility described above in the presence of up to 0.5% polysorbate, 1% glycerol, 0.5% glycine, 0.1% histidine, 0.5% chlorobutanol, 5% propylene glycol, 2% benzyl alcohol, 0.05% octanoic acid and/or 0.1% N-acetyl tryptophan.

The compound of the invention should exhibit an aggregation level of <5%, preferably <1% in a physiologically-compatible buffer (e.g. phosphate-buffered saline, or saline) at room temperature (for example 20° C.). Aggregation can be tested by analytical size-exclusion HPLC measuring the percentage of high molecular weight material compared to the conjugate eluting at a retention time characteristic of a monomeric conjugate.

The compound of the invention should have a higher drug to antibody ratio than has been achieved for a similarly massed protein with the added benefit that the drugs are favourably accessible to release via enzymic, physical or chemical mechanisms inside or outside of a cell.

Lysine residues are commonly found at the surface of antibody domains. In the case of members of the germline human VH1 family, there are 5-6 lysine residues, only one or two of which are close to each other. A definition of a residue being close to another can be one that is adjacent in the primary sequence hence adjacent in the 3-dimensional structure. Alternatively, a residue may be separated according to the primary sequence, but adjacent in space due to the structure of the fold of the antibody domain. A directly adjacent amino acid residue can be defined as 3-4 angstroms apart in space.

The coupling of therapeutics onto lysine residues which are directly adjacent will result in poorer pharmacokinetic and therapeutic effects (such as increased aggregation and poorer solubility). Coupling is more effective when lysine residues are further separated, preferably two amino acids apart (3.5 to 7.5 angstroms), more preferably three amino acids apart (7 to 12 angstroms), more preferably four amino acids apart (10-15 angstroms), even more preferably five amino acids apart (15-20 angstroms), yet even more preferably six amino acids apart (20-25 angstroms) or greater. Carrier molecules should be chosen, selected or engineered to possess these properties. The more lysine residues the carrier molecule possesses, with more optimal separation, the better that carrier molecule will be at forming effective and potent conjugates.

Methods of determining whether amino acid residues for therapeutic coupling are close or adjacent to one another are well known in the art. Clustal sequence alignment (using web resources from the European bioinformatics Institute) is a well-established tool for comparing primary amino-acid sequence. Furthermore, in the absence of full 3 dimensional structural data for a carrier molecule, it is possible to use well-established techniques such as homology modelling using known structures (for example, that of a murine scFv) to deduce probable structure of the carrier molecule, and thereby to identify whether residues for coupling are close or adjacent in space. The high degree of homology exhibited by, for example, antibodies and antibody fragments means these techniques can be applied with a high degree of confidence. Web resources for homology modelling are available, such as the Expert Bioinformatics Analysis System from the Swiss Institute of Bioinformatics which also provides the free desktop modelling programme SwissPDB Viewer. Also The Phyre server at Imperial College can generate a homology model [Kelley L A & Sternberg M J. Nat Protoc. 2009; 4: 363-71].

If the distribution of lysine residues is not favourable for conjugation and optimal pharmacokinetics, the carrier molecule may be altered using standard molecular biological techniques, such as site directed mutagenesis to remove poorly spaced residues (e.g. too closely positioned) or to introduce well-spaced residues.

The therapeutic agents may be directly coupled to the carrier molecule at the amino acid. Alternatively, the therapeutic agents may be indirectly coupled to the carrier molecule.

There are many ways to conjugate cytotoxic drugs to antibodies and antibody fragments [Ducry, L, (Ed) (2013), Antibody-Drug Conjugates book, Methods in Molecular Biology volume 1045, Chapters 9-12, Humana Press; Hermanson, G (2013) Bioconjugate Techniques book, Chapters 2-6, Academic Press]. This is summarised in Table 2. Lysine residues are favourable for conjugation because they can be present multiply on the surface of antibodies without causing detrimental effects such as unwanted cross-linking. For example, conjugation onto lysines can be direct (Table 2), using drugs or drug-linkers that possess and N-hydroxysuccinamide ester or isothiocyanate reactive group. Indirect methods for lysine conjugation include derivatising the amino group with a bifunctional linker (such as those available from Pierce Chemicals (Thermo) and Quanta Bioscience) to generate a secondary reactive group, such as 2-iminothiolane to generate a reactive thiol for conjugating to drugs or drug-linkers with thiol or maleimide reactive groups. Some lysine residues may be particularly prone to conjugation owing to enhanced nucleophilicity due to the microenvironment around that residue [Doppalapudi V R et al. Proc Natl Acad Sci USA. 2010, 107:22611-6.]. Further conjugation methods are known such as native chemical ligation [Hackenberger C P, & Schwarzer D. Angew Chem Int Ed Engl. 2008; 47:10030-74.], site specific conjugation including using enzymes [Behrens C R & Liu B. MAbs. 2014, 6:46-53], and disulphide bridging technologies [Castañeda, L et al. Chem Comm, 2013, 49, 8187-8189; Badescu G et al. Bioconjug Chem. 2014, 25:1124-36.]. Recent conjugation methods include the use of methylsulphonylphenyloxadiazole reactive linkers to form thioethers [Barbas C F B et al. Bioconjugate Chemistry, 2014, 25, 1402-1407], tyrosine selective labelling via the use of a tyrosine-click reaction [Barbas C F B et al. Bioconjugate Chemistry 2013, 24, 520-532 and the Inverse-electron Demand Diels-Alder (IeDDA) reaction between tetrazines and strained alkynes [Fox, J M. 2008, 130, 13518-13519], [Chin J W and Lang K Chemical reviews, 2014, 114, 4764-4806].

TABLE 2

Bonds for linking groups-Direct Conjugation

| Reactive group on protein | Complementary group on drug | Resulting linking group |
|---|---|---|
| Amines/Anilines | Activated esters | Amides |
| Amines/Anilines | Cyanates | Ureas |
| Amines/Anilines | Isothiocyanates | Thioureas |
| Amines/Anilines | Imidoester | Amidines |
| Amines/Anilines | Activated carboxylic acids | Amides |
| Amines/Anilines | Acyl azides | Amides |
| Amines/Anilines | Acyl halides | Amides |
| Amines/Anilines | Acyl nitriles | Amides |
| Amines/Anilines | Aryl halides | Aryl amines |
| Amines/Anilines | Alkyl halides | Alkyl amines |
| Amines/Anilines | Anhydrides | Amides/Imides |
| Amines/Anilines | Aldehydes | Imines |
| Amines/Anilines | Sulphonyl halides | Sulphonamides |
| Amines/Anilines | Sulphonate esters | Alkyl amines |
| Amines/Anilines | Halotriazines | Aminotriazines |
| Amines | Epoxides | Alkyl amines |
| Thiols | Maleimides | Thioethers |
| Thiols | Haloacetamides | Thioethers |
| Thiols | Alkyl halides | Thioethers |
| Thiols | Aryl halides | Aryl thioether |
| Thiols | Acrylamides | Thioethers |
| Thiols | Aziridines | Thioethers |
| Thiols | Epoxides | Thioethers |
| Thiols | Disulphides | Disulphides |
| Thiols | Vinylsulphones | Thioethers |
| Alcohols/Phenols | Acyl halides | Esters |
| Alcohols/Phenols | Acyl nitriles | Esters |
| Alcohols/Phenols | Alkyl halides | Ethers |
| Alcohols/Phenols | Anhydrides | Esters |
| Alcohols/Phenols | Halotriazines | Triazinyl ethers |
| Alcohols/Phenols | Isocyanates | Urethanes/Carbamates |
| Alcohols | Activated carboxylic acids | Esters |
| Alcohols | Phosphoramidites | Phosphite esters |
| Alcohols | Silyl halides | Silyl ethers |
| Alcohols | Epoxides | Ethers |
| Carboxylic acids | Alkyl halides | Esters |
| Carboxylic acids | Epoxides | Esters |
| Carboxylic acids | Diazoalkanes | Esters |
| Activated carboxylic acids | Amines/Anilines | Amides |
| Activated carboxylic acids | Alcohols | Esters |

TABLE 2-continued

Bonds for linking groups-Direct Conjugation

| Reactive group on protein | Complementary group on drug | Resulting linking group |
| --- | --- | --- |
| Activated carboxylic acids | Hydrazines | Hydrazides |
| Aldehydes/Ketones | Hydrazines | Hydrazones |
| Aldehydes/Ketones | Hydroxyamines | Oximes |
| Aldehydes/Ketones | Amines | Imines |
| Ketone (unnatural amino acids)) | Hydroxylamines | Oximes |
| Azides (unnatural amino acids) | Alkynes | 1,2,3-triazoles |
| Azides (unnatural amino acids) | Strained alkynes | 1,2,3-triazoles |
| Aldehyde (formyl glycine) | Hydrazines | Azacarboline |

One embodiment of the invention is the direct conjugation of drugs bearing an N-hydroxy-succinimide ester to multiple (n) lysine residues, where n>4. Another embodiment of this invention is the indirect conjugation to n lysine residues where cross-linker SMCC is used to modify surface lysine residues, generating a reducible thiol for conjugating to drugs or drug-linkers bearing a thiol or maleimide group.

Mixtures of drugs with the same reactive group can be used in the chemical conjugation reaction to generate conjugates with more than one cytotoxic therapeutic drug type or a combination of therapeutic drug and diagnostic agent such as a fluorescent dye [Fernandez-Fernandez A et al. Appl Biochem Biotechnol. 201, 165:1628-51.]. Such conjugates could potentially be useful for overcoming drug resistance or allowing combined imaging and treatment (theranostic).

By "small molecule" we mean molecules, whether naturally-occurring or artificially created (e.g., via chemical synthesis) that have a relatively low molecular weight. Preferred small molecules are biologically active in that they produce a local or systemic effect in animals, preferably mammals, more preferably humans. In certain preferred examples, the small molecule is a drug and the small molecule is referred to as "drug molecule" or "drug" or "therapeutic agent". In certain embodiments, the drug molecule has a molecular weight (MW) less than or equal to about 5 kDa. In other embodiments, the drug molecule has MW less than or equal to about 1.5 kDa. In other embodiments, the drug molecule is selected from vinca alkaloids, dolostatins, auristatins, tubulysins, duocarmycins, kinase inhibitors, ellipticines, MEK inhibitors, KSP inhibitors, DNA alkylating agents, DNA intercalators and Topoisomerase inhibitors and analogs thereof [Carmen Avendaño and J. Carlos Menendez (2008). The medicinal chemistry of anti-cancer drugs, Elsevier Press; Cragg G M et al (2012). Anti-cancer agents from natural products, $2^{nd}$ ed, CRC press]. Preferably, though not necessarily, the drug is one that has already been deemed safe and effective for use by an appropriate governmental agency or body, e.g., the FDA. For example, drugs for human use listed by the FDA are all considered suitable for use with this technology.

Types of drug molecules that can be used in practice include, but are not limited to, anti-cancer substances, radionuclides, vitamins, anti-AIDS substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents.

It is preferred that the carrier molecule binds selectively to a target. The target may be a target cell or an extracellular target molecule. The target cell is one to which the therapeutic agent is to be delivered, or is located in a tissue to which the therapeutic agent is to be delivered.

The terms "selective binding" and "binding selectivity" indicates that the variable regions of the antibodies of the invention recognise and bind polypeptides of the invention exclusively (i.e., able to distinguish the polypeptide of the invention from other similar polypeptides despite sequence identity, homology, or similarity found in the family of polypeptides), but may also interact with other proteins (for example, S. aureus protein A or other antibodies in ELISA techniques) through interactions with sequences outside the variable region of the antibodies, and in particular, in the constant region of the molecule. Screening assays to determine binding selectivity of an antibody of the invention are well known and routinely practiced in the art. For a comprehensive discussion of such assays, see Harlow et al. (Eds), Antibodies: A Laboratory Manual; Cold Spring Harbor Laboratory; Cold Spring Harbor, N.Y. (1988), Chapter 6.

The carrier molecule, on binding the target cell, may be internalised into the cell in order to bring the therapeutic agent to a site of action inside the cell. Alternatively, the carrier molecule, on binding the target or target cell, is not internalised into the cell, and instead the therapeutic agent acts outside of the cell. A further alternative is where the carrier molecule, following binding of the target, is decoupled from the therapeutic agent. In other words the therapeutic agent is released from the carrier to become free molecules. These free molecules may then act outside of the cell, or be taken up into the cell by a non-antibody dependent route.

The carrier molecule may, in one embodiment be an antibody fragment. The term "antibody fragment" shall be taken to refer to any antibody-based molecule which does not include all of the domains of a whole antibody. It is intended to embrace fragments of wildtype antibodies, synthetic antibodies, recombinant antibodies or antibody hybrids.

It is preferred if the antibody fragment excludes the Fc region of a whole antibody. In particular, it is preferred if the antibody fragment does not include the CH2 and CH3 regions of a whole antibody.

Antibody fragments that are suitable for use in this invention are selected from scFv, Fv, Fab, F(ab')2, Fab-SH, dsFv, bc-scFv, sdAb, di-scFvs (also known as bi-scFvs), Fcabs, domain antibodies, nanobodies, VHH domains, bispecific formats such as bispecific T-cell engagers, diabodies, and tandabs.

Antibody fragments are functional portions of whole immunoglobulins that possess advantageous properties over complete antibodies such as faster penetration into dense or solid tumours, reduced cross-reactivity with normal tissues and more rapid clearance from the circulation, thus reducing normal tissue exposure overall. It is well known in the art that antibody fragments demonstrate faster pharmacokinetics, dispersing into tissues and eliminating more rapidly (ADME-adsorption, distribution, metabolism and excretion properties). They are also easier to produce in more cost-effective systems such as microbial expression systems [de Marco A. Microb Cell Fact. 2009, 8:26; Spadiut O et al. Trends Biotechnol. 2014, 32:54-60].

Antibody fragments can be produced by chemical or enzymatic cleavage, but, more preferably, are produced using recombinant DNA technology. The latter allows for indefinite protein expression in prokaryotic or eukaryotic cell lines and genetic modification leading to fragments with enhanced or additional properties. Antibody fragments normally possess at least one variable (V-) domain because V-domains contain the complementarity-determining regions (CDRs) or loops for antigen binding [Carter P J. Nat Rev Immunol. 2006, 6: 343-57]. More recently, CDR-like loops have been inserted into non-variable domains (e.g. constant-heavy-3, CH3 domains) enabling these domains to bind to useful or predetermined targets [Wozniak-Knopp, G et al. Protein Eng. Des. Sel. 2010, 23, 289-297].

For antibody fragments to be used effectively as carrier vehicles for cytotoxic drugs, they must possess biophysical properties that allow high drug loading via chemical conjugation (or strong and specific non-covalent interactions) without detrimentally affecting protein stability, antibody-antigen binding, and drug-favourable properties such as solubility, aggregation and immunogenicity. Very rarely are these features inherent to antibody fragments [Worn A & Pluckthun A. J Mol Biol. 2001, 305:989-1010] so these additional benefits must be engineered into antibody fragments to make them practically useful [Schaefer J V & Plückthun A. Protein Eng Des Sel. 2012, 25:485-506]. One example of such a feature is the incorporation of additional or more optimally distributed surface lysine residues onto antibody fragments, thus increasing its capacity for drug conjugation using amine-directed chemistry. Other amino acids could be used, such as optimally distributed cysteines, tyrosines, glutamates, aspartates, arginines, asparagines, histidines and serines, but lysines are more preferable due to the well-established and successful chemical approaches for conjugation and relative inertness to conjugation without specific activating groups [Ducry, L, (Ed) (2013), Antibody-Drug Conjugates book, Methods in Molecular Biology volume 1045, Chapter 10, Humana Press]. Non-natural amino acids such as p-Acetylphenylalanine and formyl-glycine can also be used [Behrens C R & Liu B. MAbs. 2014, 6:46-53]. The identification of positions for antibody fragment modification can be by direct analysis of the 3-dimensional structure of the antibody fragment (or parental whole antibody), if available, or by homology modelling using a number of software resources such as Phyre [Kelley L A & Sternberg M J. Nat Protoc. 2009; 4: 363-71]. The criteria for selecting positions include: (1) the use of amino acids already favoured or conserved at that position (identified from databases such as IMGT or Kabat [Patrick Chames (ed.), *Antibody Engineering: Methods and Protocols, Second Edition*, Methods in Molecular Biology, vol. 907, Chapter 1]) or through practical demonstration by making and testing antibody fragment mutants; (2) Distribution of residues away from positions that would interfere with antigen binding; and, (3) Separation of conjugating residues so that they do not sterically hinder (or predicted to hinder) each other during chemical reactions or drug release reactions or form highly hydrophobic patches leading to aggregation The optimisation of protein surface lysine residues can be achieved by increasing, decreasing or re-spacing (for example, through site-directed mutagenesis) so that they are more accessible to bio-conjugation, allowing more complete and therefore more homogeneous conjugation reactions, and at the same time as not adversely affecting antigen binding, protein stability, solubility or aggregation properties. Residues can be manipulated singly, step by step or multiply.

The nucleotide sequence encoding the antibody fragment or optimized antibody fragment to be expressed can be made by mutagenesis of an existing gene sequence or by gene synthesis, inserted into a cloning vector for sequence/structure confirmation and re-cloned into a vector bearing the appropriate regulatory elements for protein expression, using established molecular biology methods such as those described by Sambrook et al [Molecular Cloning book (2000), $3^{rd}$ Ed, Cold Spring Harbour] or [Patrick Chames (ed.), Antibody Engineering: Methods and Protocols, Second Edition, Methods in Molecular Biology, vol. 907, Chapter 18-23]. These elements include promoters, enhancers, terminators, translation regulatory sequences and marker genes for clone selection (e.g. carbenicillin for *E. coli*, neomycin for mammalian cells).

Prokaryotic expression systems can be used that are repressible, constitutive or inducible. Appropriate *E. coli* promoters include Lac, Tac, T7, T4, SP6, T3, Lambda PR/PL, Trp, RecA and Heat-shock promoters. Alternative prokaryotic hosts include *Bacillus* and other bacteria with corresponding promoters.

*E. coli* may be used as the host [de Marco A. Microb Cell Fact. 2009, 8:26; Spadiut O et al. Trends Biotechnol. 2014, 32:54-60] and appropriate strains include K12 or B-derivatives such as JM109, TG1, HB2151, XL1, BL21, BL21 (DE3), *E. Coli* SHUFFLE®, *E. Coli* ORIGAMI®, ROSETTA® and others from suppliers such as New England Biolabs or Merck.

Vector-expression systems include ones that allow for periplasmic secretion (using a pelB or ompA leader sequence appended to the antibody fragment gene(s) to allow disulphide bond formation [de Marco A. Microb Cell Fact. 2009, 8:26] or cytosolic expression in a redox-modified host to allow disulphide bond formation [Sonoda H et al. Protein Expr Purif. 2010, 70:248-53]. Additional fusion proteins can be appended to aid folding and purification, such as thioredoxin reductase (trx) [Sonoda H et al. Protein Expr Purif. 2010, 70:248-53], which are subsequently removed by proteolysis through a specifically introduced peptide cleavage tag (such as TEV or factor-Xa) available commercially from suppliers such as Promega. Specific embodiments of this invention include periplasmic expression using a vector such as pET20b in *E. coli* BL21(DE3) and cytosolic expression using vector pET32Xa/LIC in *E. coli* SHUFFLE® [Lobstein J et al Microb Cell Fact. 2012, 11:56]. Engineered antibodies that do not need intrachain disulphides do need to be secreted into the periplasmic space.

Nucleic acids can also be expressed in eukaryotic hosts such as yeast, insect and mammalian cells [Patrick Chames (ed.), Antibody Engineering: Methods and Protocols, Second Edition, Methods in Molecular Biology, vol. 907, Chapter 18-23]]. Yeast cells include *Pichia pastoris* and *Saccharomyces cerevisiae*, insect cells include *Drosophila* and mammalian cells include rodent (CHO, ATCC-CCL61, SP2/0), non-human primate (COS-7, ATCC CRL1651) and human cells (HEK ATCC 85257). Appropriate promoters and regulatory elements should be used such as those found in the pPIC series of vectors used for *Pichia* expression, pBLUEBAC used for insect cell expression and pCDNA1/2/3/4 used for mammalian cell expression. Examples of mammalian cell expression promoters include SV40, CMV, IgH with appropriate enhancers such as SV40 enhancer, IgH or Kappa enhancer, etc. For eukaryotic expression, the appropriate secretion signal must be appended to the gene for passage through the secretory system to allow protein folding, glycosylation (if needed), disulphide bond formation and extracellular translocation. One example of a mammalian secretion signal sequence is the immunoglobulin signal sequence.

Proteins expressed in heterologous hosts can be isolated and purified using a number of different approaches [Scopes (1993) Protein Purification: Principles and Practice (Springer Advanced Texts in Chemistry)]. Culture supernatant can be collected by centrifugation, cells can be lysed (e.g. chemical detergents) or physical disrupted (e.g. French Press, sonication) and the soluble or insoluble fractions retained. If the protein is soluble, ion-exchange, affinity (using pre-engineered tags such as poly-HIS, FLAG, cMyc) and size-exclusion chromatography can be used under native conditions. If the protein is insoluble, chemical denaturation (e.g. by Urea) followed by refolding [Deonarain M P & Epenetos A A. Br J Cancer. 1998, 77:537-46] or purification under denaturing conditions (e.g. poly-HIS immobilised metal affinity chromatography, IMAC) can be used. Final protein purity is assessed using analytical tools such as SDS-PAGE, SEC, Amino acid analysis or Mass spectrometry and final protein function is assessed using ELISA, flow cytometry, immunohistochemistry or cell biological assay [Harlow & Lane (1998) Using antibodies, Cold Spring Harbour] or Biacore-SPR [Van Regenmortel M H et al. J. Mol Recognit. 1998, 11:163-7].

The carrier molecule may, in one embodiment, be an antibody mimetic. The term "antibody mimetic" shall be taken to refer to organic compounds that, like antibodies, can specifically bind antigens, but that are not structurally related to antibodies. They are usually artificial peptides or proteins with a molar mass of about 3 to 20 kDa. Nucleic acids and small molecules can be considered antibody mimetics, but antibody mimetics do not include artificial antibodies, antibody fragments and fusion proteins composed from these. Some types of antibody mimetics have antibody-like peptide conformations, such as beta-sheets.

Antibody mimetics [Wurch T et al. Trends Biotechnol. 2012, 30:575-82] suitable for use in the invention are DARPins, affibodies, affitins, anticalins, avimers, kunitz domain peptides, adnectins, centyrins, Fynomers, IgNARs and monobodies.

The carrier molecule may be humanised or human.

Humanised antibodies are suitable for administration to humans without invoking an immune response by the human against the administered immunoglobulin. Humanised forms of antibodies are intact immunoglobulins, immunoglobulin chains or fragments thereof (such as Fv, Fab, Fab', F(ab')2 or other antigen-binding subsequences of antibodies) that are principally comprised of the sequence of a human immunoglobulin, and contain minimal sequence derived from a non-human immunoglobulin. Humanisation can be performed following the method of Winter and co-workers (Jones et al., Nature, 321:522-525 (1986); Riechmann et al., Nature, 332:323-327 (1988); Verhoeyen et al., Science, 239:1534-1536 (1988)). In some instances, Fv framework residues of the human immunoglobulin are replaced by corresponding non-human residues. Humanised antibodies can also comprise residues that are found neither in the recipient antibody nor in the imported CDR or framework sequences. In general, the humanised antibody will comprise substantially all of at least one, and typically two, variable regions, in which all or substantially all of the CDR regions correspond to those of a non-human immunoglobulin and all or substantially all of the framework regions are those of a human immunoglobulin consensus sequence. The humanised antibody optimally also will comprise at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Preferred targets for the carrier molecule of the compounds of the invention are the cell surface or tumour markers, including, but not limited to, 5T4, AOC3, C242, CA-125, CCL11, CCR 5, CD2, CD3, CD4, CD5, CD15, CD18, CD19, CD20, CD22, CD23, CD25, CD28, CD30, CD31, CD33, CD37, CD38, CD40, CD41, CD44, CD51, CD52, CD54, CD56, CD62E, CD62P, CD62 L, CD70, CD74, CD80, CD125, CD138, CD141, CD147, CD152, CD 154, CD326, CEA, CTLA-4, EGFR, ErbB2, ErbB3, EpCAM, folate receptor, FAP, fibronectin splice variants (EDA, EDB, CSIII), GD2, GD3, GPNMB, HGF, HER2, ICAM, IGF-1 receptor, VEGFR1, EphA2, TRPV1, CFTR, gpNMB, CA9, Cripto, ACE, APP, adrenergic receptor-beta2, Claudine 3, Mesothelin, lactadherin, IL-2 receptor, IL-4 receptor, IL-13 receptor, integrins (including α4, αvβ3, αvβ5, αvβ6, α1β4, α4β1, α4β7, α5β1, α6β4, αIIbβ3 intergins), IFN-α, IFN-γ, IgE, IgE, IGF-1 receptor, IL-1, IL-12, IL-23, IL-13, IL-22, IL-4, IL-5, IL-6, interferon receptor, ITGB2 (CD18), LFA-1 (CD11a), L-selectin (CD62 L), mucin, MUC1, myostatin, NCA-90, NGF, PDGFRα, phosphatidylserine, prostatic carcinoma cell, *Pseudomonas aeruginosa*, rabies, RANKL, respiratory syncytial virus, Rhesus factor, SLAMF7, sphingosine-1-phosphate, TAG-72, T-cell receptor, tenascin C, TGF-1, TGE-β2, TGF-β, TNF-α, TRAIL-R1, TRAIL-R2, tumour antigen CTAA16.88, VEGF-A, VEGFR2, vimentin, matrix receptors and similar targets, apoptotic markers such as phosphocholine In particular, it is preferred if the carrier molecule binds specifically to HER2, EGFR, HER3, MUC1, EpCAM, CEA, Fibronectin-EDB, CD19, CD20, CD22, LeY, CD30, CD33, CD79b, GPNMB, PSMA, CD56, CD37, Folate receptor, CA6, CD27 L, MUC16, CD66e, CD74, Trop-2 or guanylate cyclase.

The carrier molecules of the invention may be antibody fragments derived from or with equivalent binding specificity to any of the following whole antibodies: 3F8, abagovomab, abciximab (REOPRO™), adalimumab (HUMIRA™), adecatumumab, afelimomab, afutuzumab, alacizumab, ALD518, alemtuzumab (CAMPATH™), altumomab, amatuximab, anatumomab, anrukinzumab, apolizumab, arcitumomab (CEA-SCANT™), aselizumab, atlizumab (tocilizumab, Actemra, RoActemra), atorolimumab, bapineuzumab, basiliximab (SIMULECT™), bavituximab, bectumomab (LYMPHOSCAN™), belimumab (BENLYSTA™), benralizumab, bertilimumab, besilesomab (SCINITIMUN™), bevacizumab (AVASTIN™), biciromab (FIBRISCINT™), bivatuzumab, blinatumomab, brentuximab, briakinumab, canakinumab (ILARIS), cantuzumab, capromab, catumaxomab (REMOVAB™), CC49, cedelizumab, certolizumab, cetuximab (ERBITUX™), citatuzumab, cixutumumab, clenoliximab, clivatuzumab, conatumumab, CR6261, dacetuzumab, daclizumab (ZENAPAX™) daratumumab, denosumab (PROLIA™), detumomab, dorlimomab, dorlixizumab, ecromeximab, eculizumab (SOLIRIS™), edobacomab, edrecolomab (PANOREX™), efalizumab (RAPTIVA™), efungumab (MYCOGRAB™), elotuzumab, elsilimomab, enlimomab, epitumomab, epratuzumab, erlizumab, ertumaxomab (REXOMUN™), etaracizumab (ABEGRIN), exbivirumab, fanolesomab (NEUTROSPEC™), faralimomab, farletuzumab, felvizumab, fezakinumab, figitumumab, fontolizumab (HuZAF™), foravirumab, fresolimumab, galiximab, gantenerumab, gavilimomab, gemtuzumab girentuximab, glembatumumab, golimumab (SIMPONI™), gomiliximab, ibalizumab, ibritumomab, igovomab (INDIMACIS-125™), imciromab (MYOSCINT™), infliximab (REMICADE™), intetumumab, inolimomab, inotuzumab, ipilimumab, iratumumab, keliximab, labetuzumab (CEA-CIDE™), lebrikizumab, lemalesomab, lerdelimumab, lexatumumab, libivirumab, lintuzumab, lucatumumab, lumiliximab, mapatumumab, maslimomab, matuzumab, mepolizumab (BOSATRIA™), metelimumab, milatuzumab, minretumomab, mitumomab, morolimumab, motavizumab (NUMAX), muromonab-CD3 (ORTHOCLONE OKT3™), nacolomab, naptumomab, natalizumab (TYSABRI™), nebacumab, necitumumab, nerelimomab, nimotuzumab (THERACIM™), nofetumomab, ocrelizumab, odulimomab, ofatumumab (ARZERRA™), olaratumab, omalizumab (XOLAIR), ontecizumab, oportuzumab, oregovomab (OVAREX™), otelixizumab, pagibaximab, palivizumab (SYNAGIS™), panitumumab (VECTIBIX™), panobacumab, pascolizumab, pemtumomab (THERAGYN™), pertuzumab (OMNITARG™), pexelizumab, pintumomab, priliximab, pritumumab, PRO140, rafivirumab, ramucirumab, ranibizumab (LUCENTIS™), raxibacumab, regavirumab, reslizumab, rilotumumab, rituximab (RITUXAN™), robatumumab, rontalizumab, rovelizumab (LEUKARREST™), ruplizumab (ANTOVA™), satumomab pendetide, sevirumab, sibrotuzumab, sifalimumab, siltuximab, siplizumab, solanezumab, sonepcizumab, sontuzumab, stamulumab, sulesomab (LEUKOSCAN™), tacatuzumab (AFPCIDE™), tetraxetan, tadocizumab, talizumab, tanezumab, taplitumomab paptox, tefibazumab (AUREXIS™) telimomab, tenatumomab, teneliximab, teplizumab, TGN1412, ticilimumab (tremelimumab), tigatuzumab, TNX-650, tocilizumab (atlizumab, ACTEMRA™), toralizumab, tositumomab (BEXXAR™), trastuzumab (HERCEPTIN™), tremelimumab, tucotuzumab, tuvirumab, urtoxazumab, ustekinumab (STELERA™), vapaliximab, vedolizumab, veltuzumab, vepalimomab, visilizumab (NUVION™), volociximab (HUMASPECT™), votumumab, zalutumumab (HuMEX-EGFr™), zanolimumab (HuMAX-CD4™), ziralimumab and zolimomab.

The therapeutic agent is preferably a cytotoxic agent or a cytostatic agent.

By cytotoxic agent we mean an agent which is toxic to cells, typically by killing the cells. The toxicity can lead to cell death by necrosis or apoptosis.

By cytostatic agent we mean an agent which inhibits or stops cell growth and/or multiplication.

Preferably, the therapeutic agent is selected from the following classes of therapeutic agent: cell cycle progression inhibitors, angiogenesis inhibitors, MAPK signaling pathway inhibitors, PI3K/m-TOR/AKT pathway inhibitors, kinase inhibitors, RTK inihbitors, HDAC inhibitors, protein chaperone inhibitors, PARP inhibitors, Wnt/Hedgehog/Notch signalling pathway inhibitors, RNA polymerase inhibitors. DNA-binding drugs, DNA damaging drugs, DNA alkylating drugs, microtubule stabilizing agents, microtubule destabilizing agents, platinum compounds, kinase inhibitors, pyridocarbazole and its derivatives, and topoisomerase I and II inhibitors.

Examples of DNA-binding or alkylating drugs include, CC-1065 and its analogues, anthracyclines (e.g. doxorubicin, epirubicin, idarubicin, daunorubicin) and its analogues, ellipticine and its derivatives, alkylating agents, such as calicheamicins, dactinomycines, mitromycines, pyrrolobenzodiazepines, and derivatives.

Examples of CC-1065 analogues include duocarmycin SA, duocarmycin C1, duocarmycin C2, duocarmycin B2, DU-86, KW-2189, bizelesin, seco-adozelesin, and its derivatives.

Examples of microtubule stabilizing and destabilizing agents include taxane compounds, such as paclitaxel, docetaxel; maytansinoids, dolostatins, cemadotins, auristatins and its analogues, tubulysin A and B derivatives, vinca alkaloid derivatives, epothilones and cryptophycins.

Examples of maytansinoids or maytansinoid analogs include maytansinol and maytansinol analogues, maytansine or DM-1 and DM-4. Examples of auristatins include auristatin E (a derivative of dolastatin-10), auristatin EB, auristatin EFP, monomethyl auristatin E (MMAE), monomethyl auristatin F (MMAF), auristatin F and dolastatin. Examples of vinca alkaloids include vincristine, vinblastine, vindesine, and navelbine (vinorelbine). Examples of epothilone compounds include epothilone A, B, C, D, E and F, and derivatives thereof. Examples of platinum compounds include cisplatin (PLATINOL®), carboplatin (PARAPLATIN®), oxaliplatin (ELOXATINE®), iproplatin, onnaplatin, and tetraplatin. Examples of topoisomerase I inhibitors include camptothecin, camptothecin, derivatives, camptothecin analoguess and non-natural camptothecins, such as, for example, CPT-11 (irinotecan), SN-38, topotecan, 9-aminocamptothecin, 9-bromocamptothecin, diflomotecan, rubitecan, silatecan, lurtotecan, exatecan, belotecan, gimatecan, karenitecin, lurtotecan and S39625.

Examples of angiogenesis inhibitors include VEGF inhibitors, MetAP2 inhibitors, P1GF inhibitors, VGFR inhibitors, PDGFR inhibitors. Examples of VGFR and PDGFR inhibitors include sorafenib (NEXAVAR®), sunitinib (SUTENT®) and vatalanib. Examples of cell cycle progression inhibitors include CDK inhibitors such as, for example, BMS-387032 and PD0332991; Rho-kinase inhibitors for example GSK429286; checkpoint kinase inhibitors such as, for example, AZD7762; aurora kinase inhibitors such as, for example, AZD1152, MLN8054 and MLN8237; PLK inhibitors for example, BI 2536, B16727 (Volasertib), GSK461364, ON-01910 (Estybon); and KSP inhibitors such as, for example, SB 743921, SB 715992 (ispinesib), MK-0731, AZD8477, AZ3146 and ARRY-520.

Examples of PI3K/m-TOR/AKT signalling pathway inhibitors include phosphoinositide 3-kinase (PI3K) inhibitors, GSK-3 inhibitors, ATM inhibitors, DNA-PK inhibitors and PDK-1 inhibitors.

Examples of PI3 kinases include BEZ235, BGT226, BKM120, CAL101, CAL263, demethoxyviridin, GDC-0941, GSK615, IC87114, LY294002, Palomid 529, perifosine, PF-04691502, PX-866, SAR245408, SAR245409, SF1126, Wortmannin, XL147 and XL765. Examples of AKT inhibitors include AT7867. Examples of MAPK signalling pathway inhibitors include MEK, Ras, JNK, B-Raf and p38 MAPK inhibitors. Examples of MEK inhibitors include GDC-0973, GSK1120212, MSC1936369B, AS703026, R05126766 and R04987655, PD0325901, AZD6244, AZD 8330 and GDC-0973. Examples of B-raf inhibitors include CDC-0879, PLX-4032, and SB590885.

Examples of p38 MAPK inhibitors include BIRB 796, LY2228820 and SB 202190.

Examples of Receptor tyrosine kinases (RTK) modulators/inhibitors include anti-ErbB2 receptor drugs such as AEE788 (NVP-AEE 788), BIBW2992, (Afatinib), Lapatinib, Erlotinib (TARCEVA®), and Gefitinib (IRESSA®).

Examples of multi-specific RTK inhibitors include AP24534 (Ponatinib) that targets FGFR, FLT-3, VEGFR-PDGFR and Bcr-Abl receptors; ABT-869 (Linifanib) that targets FLT-3 and VEGFR-PDGFR receptors; AZD2171 that targets VEGFR-PDGFR, Flt-1 and VEGF receptors; CHR-258 (Dovitinib) that targets VEGFR-PDGFR, FGFR, Flt-3, and c-Kit receptors; Sunitinib (SUTENT™) that targets VEGFR, PDGFR, KIT, FLT-3 and CSF-IR; Sorafenib (NEXAVAR®) and Vatalanib that target VEGFR, PDGFR, serine/threonine kinases of the Raf/Mek/Erk pathway and ellipticines.

Examples of protein chaperone inhibitors include HSP90 inhibitors such as 17AAG derivatives, BIIB021, BIIB028, SNX-5422, NVP-AUY-922 and KW-2478. Examples of HDAC inhibitors include Belinostat (PXD101), CUDC-101, Droxinostat, ITF2357 (Givinostat, Gavinostat), JNJ-26481585, LAQ824 (NVP-LAQ824, Dacinostat), LBH-589 (Panobinostat), MC1568, MGCD0103 (Mocetinostat), MS-275 (Entinostat), PCI-24781, Pyroxamide (NSC 696085), SB939, Trichostatin A and Vorinostat (SAHA). Examples of PARP inhibitors include iniparib (BSI 201), olaparib (AZD-2281), ABT-888 (Veliparib), AG014699, CEP 9722, MK 4827, KU-0059436 (AZD2281), LT-673, 3-aminobenzamide, A-966492, and AZD2461. Examples of Wnt/Hedgehog signaling pathway inhibitors include vismodegib (RG3616/GDC-0449), cyclopamine (11-deoxojervine) (Hedgehog pathway inhibitors) and XAV-939 (Wnt pathway inhibitor). Examples of Notch pathway inhibitors include gamma-secretase inhibitors MK0752, R04929097, PF-03084,014, LY450139, BMS-708163, gamma-secretase modifiers MPC-7869 and dominant-negative mastermind/CSL/notch compounds.

Examples of RNA polymerase inhibitors include amatoxins such as α-amanitins, β-amanitins, γ-amanitins, ε-amanitins, amanullin, amanullic acid, amaninamide, amanin, and proamanullin.

Drug payloads can be synthetically modified to make them conjugatable to biomolecules such as antibodies using a variety of approaches (Table 2). Such chemical modifications are described in [Chari R V et al. Angew Chem Int Ed Engl. 2014, 53, 3796-827]. Examples include the derivation of maytansine, MMAE and MMAF, doxorubicin, cemadotin, SN38, and P5 a pentapeptide present in dolastatin-15 and pyrrolobezodiazepine dimers (PBDs). Maytansinoids are well known in the art and suitable derivatives for conjugation on to cell-binding agents can be prepared synthetically according to known methods fully disclosed in U.S. Pat. Nos. 5,208,020, 5,416,064, 7,276497 and [Chari R V et al. J. Med. Chem. 2006, 49, 4392] and [Chari R V et al. J. Med. Chem. 2011, 22, 717]. Reacting at thiol terminated maytansinoids with heterobifunctional linkers gives rise to non-reducible stable links terminated with reactive NHS esters for direct conjugation on to cell-binding agents as disclosed in WO 2010/141566 and [Chari R V et al.] J. Med. Chem. 2011, 54, 3606. The heterobifunctional linkers contain either a negatively charged sulfonate group or a hydrophilic, non-charged PEG group in addition to an amine-reactive N-hydroxysuccinimide NHS-ester and sulfhydryl reactive termini.

Auristatins including monomethyl auristatin E (MMAE) are described in US Patent No. 20060074008 and [Senter P D et al.] Nature Biotechnology 2003, 21, 778 which disclose a linker with a protease sensitive valine-citrulline dipeptide as a cleavage site for cathepsin B and a self-immolative p-aminobenzyl carbamate. Monomethyl auristatin F (MMAF) conjugates with a non-cleavable linker is described in US Patent No. 20110070428.

The CC-1065 and analogues of the duocarmycin family of cyclopropylindole DNA alkylating agents are disclosed in [Goldmacher V S et al. Cancer Research, 1995, 55, 4079] and U.S. Pat. No. 8,680,293.

The pyrrobenzodiazepines dimers (PBD's) and conjugates have been described in [Senter P D et al. Bioconjugate Chemistry 2013, 24: 1256; McEarchern J A et al. Blood, 2013, 122: 1455] and US Patent No. 2014234346 and WO 2014 031566

Daunorubicin/Doxorubicin analogues are also suitable payloads and have been disclosed in [Firestone R A et al. J. Controlled Release, 1996, 39: 251] and WO2012024223 as maleimido terminated drugs. A cathepsin B releasable doxorubicin is disclosed in [Dubowchik G M et al. Bioconjugate Chemistry, 2002, 13, 855]. More potent derivatives, doxorubicin-2-pyrrolino and morpholino-doxorubicin are disclosed in [Senter P D et al. Bioorg. Med. Chem. Lett 2006, 16: 358] and WO2014124227. Nemorubicin (a metabolite of doxorubicin) derivatives and conjugates with reactive ester groups are disclosed in US Patent No. 2014227299

Taxanes that can be used are disclosed in [Ojima I et al. J. Med. Chem. 2002, 45, 5620] and [Ojima I Acc. Chem. Res 2008, 41, 108] and U.S. Pat. No. 72,766,499

SN-38 the active metabolite of the topoisomerase inhibitor irinotecan (a campthothecin derivative) are suitable payloads and conjugates with cleavable and PEG incorporated linkers are disclosed in [Goldenberg D M et al. J. Med. Chem. 2008, 51: 6916] and WO2010/093395

The cryptophycins are among the most potent antimitotic agents and conjugates fdormed via maleimides and reactive esters are disclosed in WO 2011/001052.

Tubulysins have structural similiarity to dolastatin-10 and display high potency as tubulin modifiers. These and simpler pretubulysin variants are disclosed in WO2014/0227295 and [Kazmaier U et al. Eur. J. Org. Chem. 2011, 3050].

A class of potent drugs recently investigated for use as payloads, are the RNA polymerase II inhibitors such as alpha-amanitin, a bicycle octapeptide component of amatoxins. Conjugates on to lysine residues are formed by activating the amine terminated amanitin overnight with dissuccinimidyl carbonate followed by reaction with the cell-binding agent as disclosed in WO2012/041504

Preferred therapeutic agents are selected from cemadotin, P5 (an early precursor of cematodin), P5-$C_5$ (P5 with a 5-carbon spacer), doxorubicin, ellipticine, MMAE, MMAF, paclitaxel, auristatins, maytansines, dolostatins, camptothecin, SN-38 and pyrrolobenzodiazepine dimers (PBDs), PNU-159862 and indolino-benzodiazepine dimers (IGNs).

Specific examples of compounds according to the invention include, but are not limited to where:
   (i) the carrier molecule is an scFv and the therapeutic agent is cemadotin;
   (ii) the carrier molecule is an scFv and the therapeutic agent is doxorubicin
   (iii) the carrier molecule is an scFv and the therapeutic agent is ellipticine.
   (iv) the carrier molecule is an scFv and the therapeutic agent is MMAE.
   (v) the carrier molecule is an scFv and the therapeutic agent (P5)-$C_5$.
   (vi) the carrier molecule is an scFv and the therapeutic agent is a maytansine
   (vii) the carrier molecule is an scFv and the therapeutic agent is a pyrrolobenzodiazepine dimer (PBD).
   (viii) the carrier molecule is an scFv and the therapeutic agent is MMAF.

These specific examples can use any scFv as the carrier molecule, but a preferred example of an scFv is one that binds to HER2, for example scFv (C6.5) or its modified form, scFv (TCT) (SEQ ID NO: 2 see Example 27). Alternative preferred examples of scFv are those having the amino acid sequence of SEQ ID NO.4 or SEQ ID NO. 5.

In a second aspect of the invention there is provided a pharmaceutical composition comprising the compound of the first aspect of the invention and a pharmaceutically-acceptable carrier, excipient or diluent.

In a third aspect of the invention, there is provided a compound or composition of the first or second aspects for use in the diagnosis, treatment and/or prevention of disease.

In a fourth aspect of the invention, there is provided a compound or composition of the first or second aspects for use in the diagnosis, treatment and/or prevention of a disease selected from cancer, benign tumours, infectious diseases including bacterial, viral, fungal, trypanosome, nematode and prion infections, cardiovascular disease, and autoimmune disease.

In a fifth aspect of the invention, there is provided a compound or composition as defined in any of the first and second aspects for use in the manufacture of a medicament for the treatment and/or prevention of a disease selected from cancer, benign tumours, infectious diseases including bacterial, viral, fungal, trypanosome, nematode and prion infections, cardiovascular disease, and autoimmune disease.

In a sixth aspect of the invention, there is provided a method of treating or preventing a disease selected from cancer, benign tumours, infectious diseases including bacterial, viral, fungal, trypanosome, nematode and prion infections, cardiovascular disease, and autoimmune disease.

In the third, fourth, fifth and sixth aspects of the invention, the disease may be cancers such as:

Solid tumors, including but not limited to: sarcoma, fibrosarcoma, myxosarcoma, liposarcoma, chondrosarcoma, osteogenic sarcoma, choriocarcinoma, chordoma, angiosarcoma, thyroid, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer (e.g., gastrointestinal cancer), oral cancer, nasal cancer, throat cancer, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, seminoma, embryonal carcinoma, Wilms' tumor, cervical cancer, Peritoneal cancer, hepatocellular cancer, hepatoma, salivary cancer, vulval cancer, penile cancer, anal cancer, head and neck cancer, renal cell carcinoma, Acute anaplastic large cell carcinoma, Cutaneous anaplastic large cell carcinoma, uterine cancer, testicular cancer, small cell lung carcinoma, bladder carcinoma, lung cancer, non-small cell lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, Haematological cancers, including but not limited to: acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute non-lymphocytic leukemia, acute undifferentiated leukemia, chronic myelocytic leukemia (CML), chronic lymphocytic leukemia (CLL), hairy cell leukemia, multiple myeloma, acute and chronic leukemias, Lymphomas such as Hodgkin's disease, non-Hodgkin's Lymphoma, Multiple myeloma, Waldenström's macroglobulinemia, Heavy chain disease, Polycythemia vera.

The disease may alternatively be autoimmune disease such as: active chronic hepatitis, addison's disease, allergic alveolitis, allergic reaction, allergic rhinitis, alport's syndrome, anaphylaxis, ankylosing spondylitis, anti-phospholipid syndrome, arthritis, ascariasis, aspergillosis, atrophic allergy, atrophic dermatitis, atrophic rhinitis, behcet's disease, bronchial asthma, caplan's syndrome, cardiomyopathy, celiac disease, chagas' disease, chronic glomerulonephritis, cogan's syndrome, cold agglutinin disease, congenital rubella infection, CREST syndrome, crohn's disease, cryoglobulinemia, cushing's syndrome, dermatomyositis, discoid lupus, dressler's syndrome, Eaton-Lambert syndrome, echovirus infection, encephalomyelitis, endocrine ophthalmopathy, Epstein-Barr virus infection, equine heaves, erythematosis, Evan's Syndrome, Felty's Syndrome, Fibromyalgia, Fuch's Cyclitis, gastric atrophy, gastrointestinal allergy, giant cell arteritis, glomerulonephritis, goodpasture's syndrome, graft vs host Disease, Graves' disease, Guillain-Barre disease, Hashimoto's thyroiditis, hemolytic anemia, Henoch-Schonlein purpura, idiopathic adrenal atrophy, idiopathic pulmonary fibrosis, IgA nephropathy, inflammatory bowel diseases, insulin-dependent diabetes mellitus, juvenile arthritis, juvenile diabetes mellitus (Type I), Lambert-Eaton syndrome, laminitis, lichen planus, lupoid hepatitis, lymphopenia, Meniere's disease, mixed connective tissue disease, multiple sclerosis, myasthenia gravis, pernicious anemia, polyglandular syndromes, presenile dementia, primary agammaglobulinemia, primary biliary cirrhosis, psoriasis, psoriatic arthritis, raynauds phenomenon, recurrent abortion, Reiter's syndrome, rheumatic fever, rheumatoid arthritis, Sampter's syndrome, schistosomiasis, Schmidt's syndrome, scleroderna, Shulman's syndrome, Sjorgen's syndrome, sympathetic ophthalmia, systemic lupus erythematosus, temporal arteritis, thyroiditis, thrombocytopenia, thyrotoxicosis, toxic epidermal necrolysis, type B Insulin Resistance, type I diabetes mellitus, ulcerative colitis, uveitis, vitiligo, Wegener's granulomatosis.

Preferably, the disease is selected from cancer of the colon, lung, breast, head/neck, prostate, skin, stomach/gastrointestinal, bladder, glioma, renal, ovarian, thyroid and bone.

In a seventh aspect of the invention, there is provided a process of making a compound as defined in the first or second aspects, the process comprising the steps of:
 (i) providing a therapeutic agent;
 (ii) providing a carrier molecule;
 (iii) conjugating the therapeutic agent and the carrier molecule in the presence of at least one polar aprotic solvent and an aqueous buffer.

The term "aprotic solvent" means a solvent that has no OH groups and therefore cannot donate a hydrogen bond.

Appropriate polar aprotic solvents are (but are not limited to) the group consisting of: dimethyl sulfoxide (DMSO); acetonitrile; N,N-dimethylformamide (DMF); Dimethylacetamide (DMA); HMPA; dioxane; tetrahydrofuran (THF); carbon disulfide; glyme and diglyme; 2-butanone (MEK); sulpholane; nitromethane; N-methylpyrrolidone; pyridine; and acetone. Other polar aprotic solvents which may be used are well known to those skilled in the art.

The step of conjugating the therapeutic agent and the carrier molecule as part of this process is preferably conducted using any one or combination thereof of the following parameters:

a temperature between about 0° C. and about 37° C., preferably about 10 to about 30° C.
  a pH between about 6.0 and about 10.0, preferably about 7.5 to about 9.
  for between 0.1 hours and 48 hours.

The process of the invention may also include one or more further steps selected from:

(iv) using excipients to facilitate the reaction
  (v) pre-incubation of solvent and buffer components to minimize adverse mixing effects
  (vi) temporally-controlled addition of reaction components
  (vii) combining the compound with a pharmaceutically-acceptable carrier to form a pharmaceutical composition.

EXAMPLES

Examples embodying an aspect of the invention will now be described with reference to the following figures in which:

FIG. 1. Surface/solvent accessibility of amino acids residues in human variable domains Modified from Knappik et al (2000) J. Mol. Biol 296, 57-86. The grey-scale indicate the percentage Surface/solvent accessible, from dark (=high) to light (=low). Numbering scheme according to Honegger A & Pluckthun A [J. Mol. Biol. 2001, 309:657-70]. Around 70% is considered to be predominantly solvent exposed.

Figure 2:
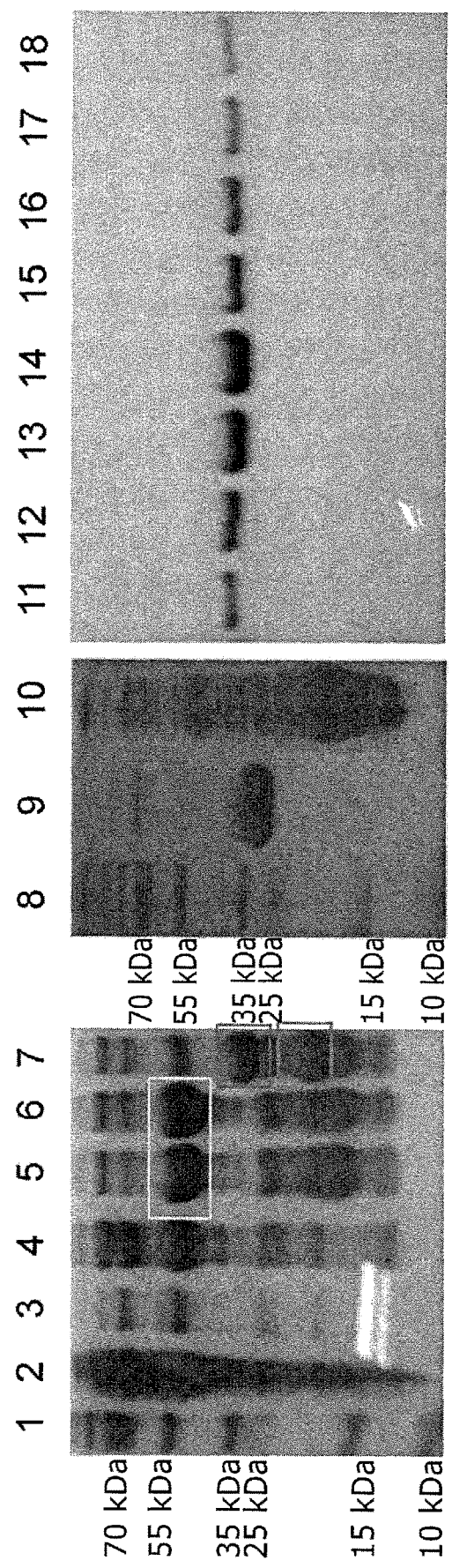

FIG. 2. Purification of scFv-TCT
  Lane 1: Molecular Markers
  Lane 2: Clarified lysate after $2^{nd}$ pass through Ni-NTA resin
  Lane 3: Final wash with Wash Buffer 1
  Lane 4: $1^{st}$ wash with Wash Buffer 2
  Lane 5: Elution fraction
  Lane 6: Pooled elution fraction after dialysis in TEV cleavage buffer. The rectangle denotes the fusion-TCT.
  Lane 7: 16 hours after TEV cleavage initiation. The upper square denotes the cleaved scFv (TCT). The lower square denotes the cleaved thioredoxin fusion partner.
  Lane 8: Molecular Markers
  Lane 9: Cleaved TCT
  Lane 10: Proteins remaining bound to Ni-NTA
  Lanes 11-18: Fractions from size exclusion column (35 kDa), of FIG. 20

Figure 3:
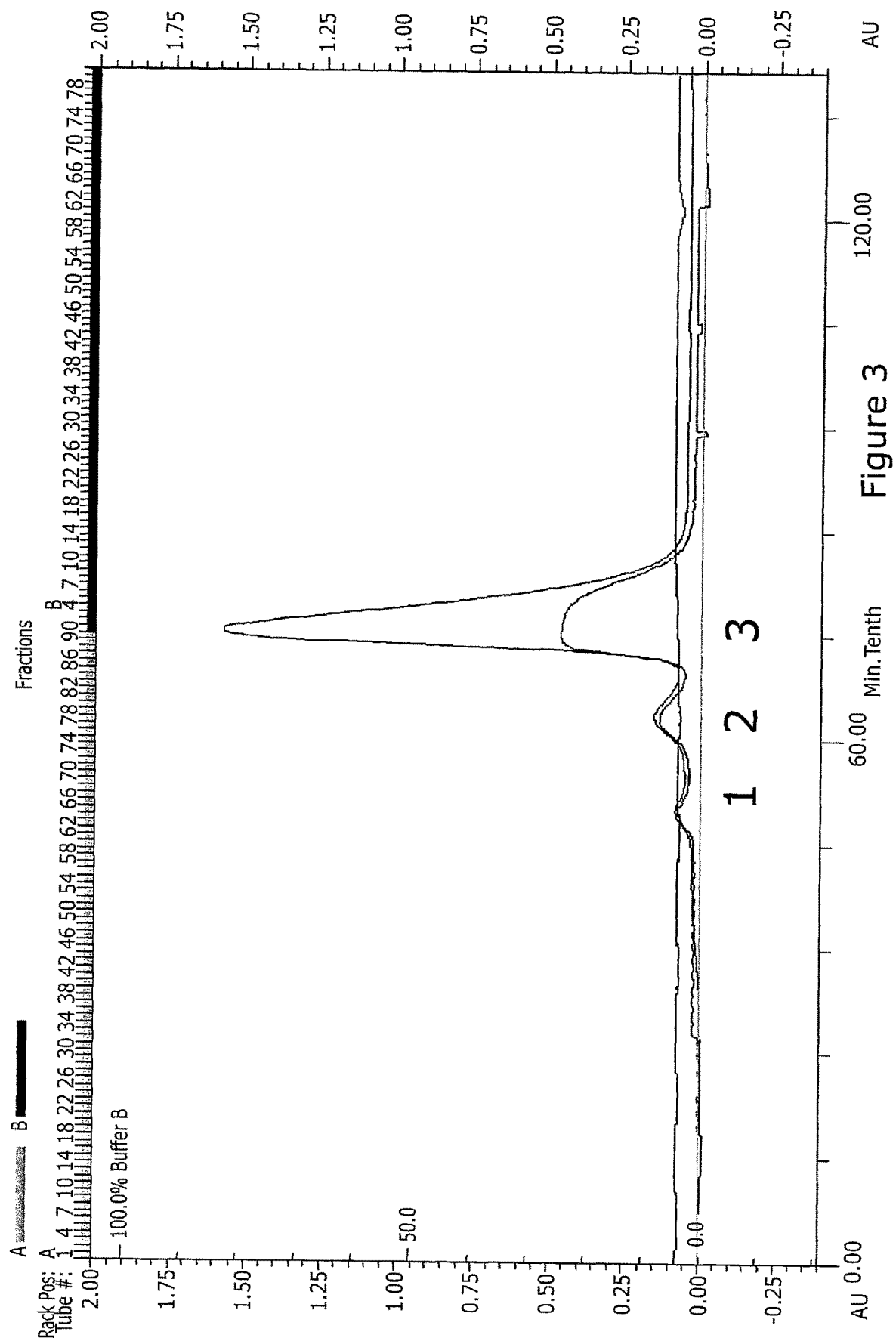
Figure 19:
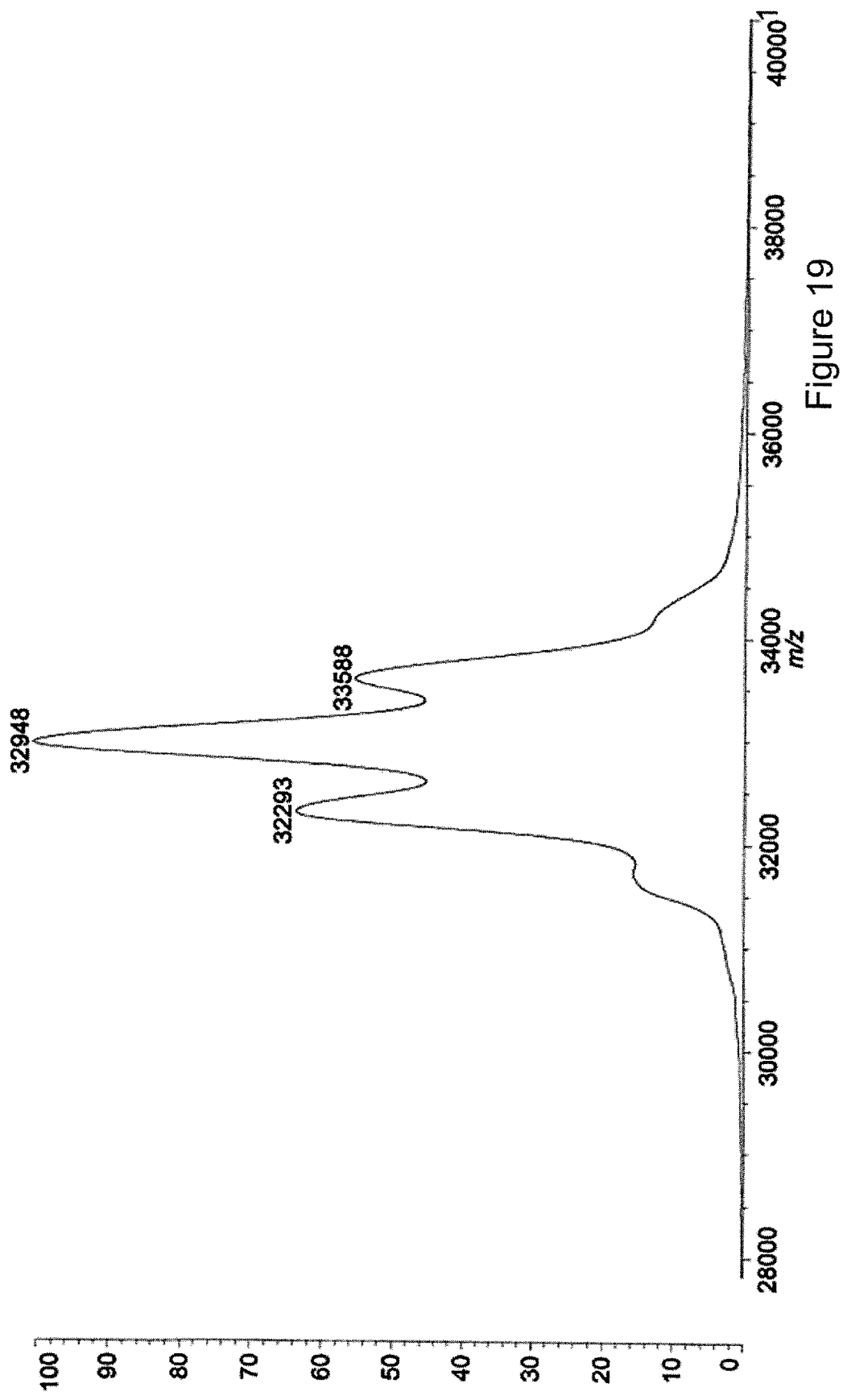

FIG. 3. Purification of scFv-TCT by size exclusion chromatography on a superdex-75 column in PBS buffer
  Peak 1—too dilute to appear on coomassie-stained PAGE gel, high molecular weight contaminants
  Peak 2—High molecular weight aggregates of scFv TCT.
  Peak 3—Pure monomeric scFv TCT, corresponding to Lanes 11-18 on the gel (FIG. 19)

Figure 4:
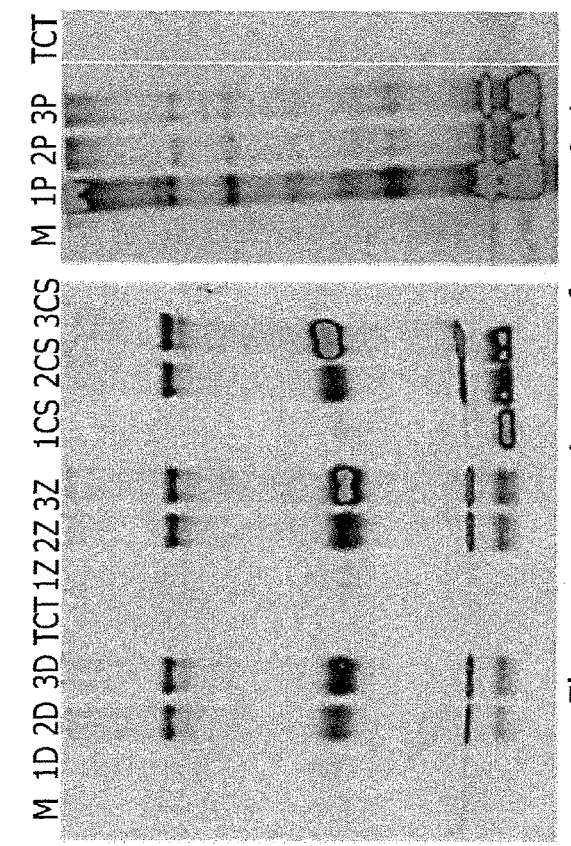
Figure 4:
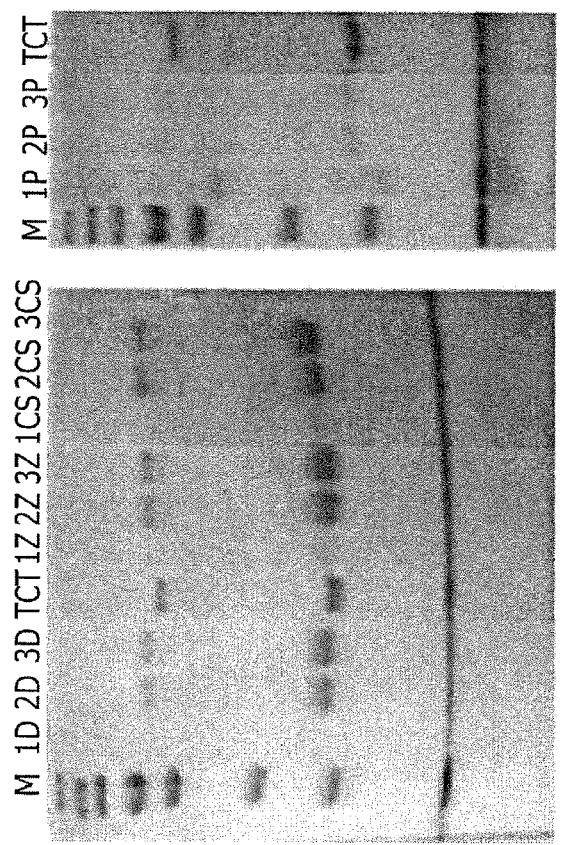

FIG. 4. SDS-PAGE of ScFv (TCT)-Ellipticine conjugates Ellipticine (compound 21) conjugates. 1=32 equivalents, 14% DMSO; 2=16 equivalents, 14% DMSO; 3=16 equivalent, 6% DMSO; D=dialysed, Z=Zeba column desalted; CS=soluble crude reaction; P=insoluble/precipitated crude reaction. Sample loading=2.4 μg (ADCs), 1.9 μg (scFv).
  MW markers (M), kDa top to bottom: 250, 130, 100, 70, 55, 35, 25, 15, 10

Figure 5:
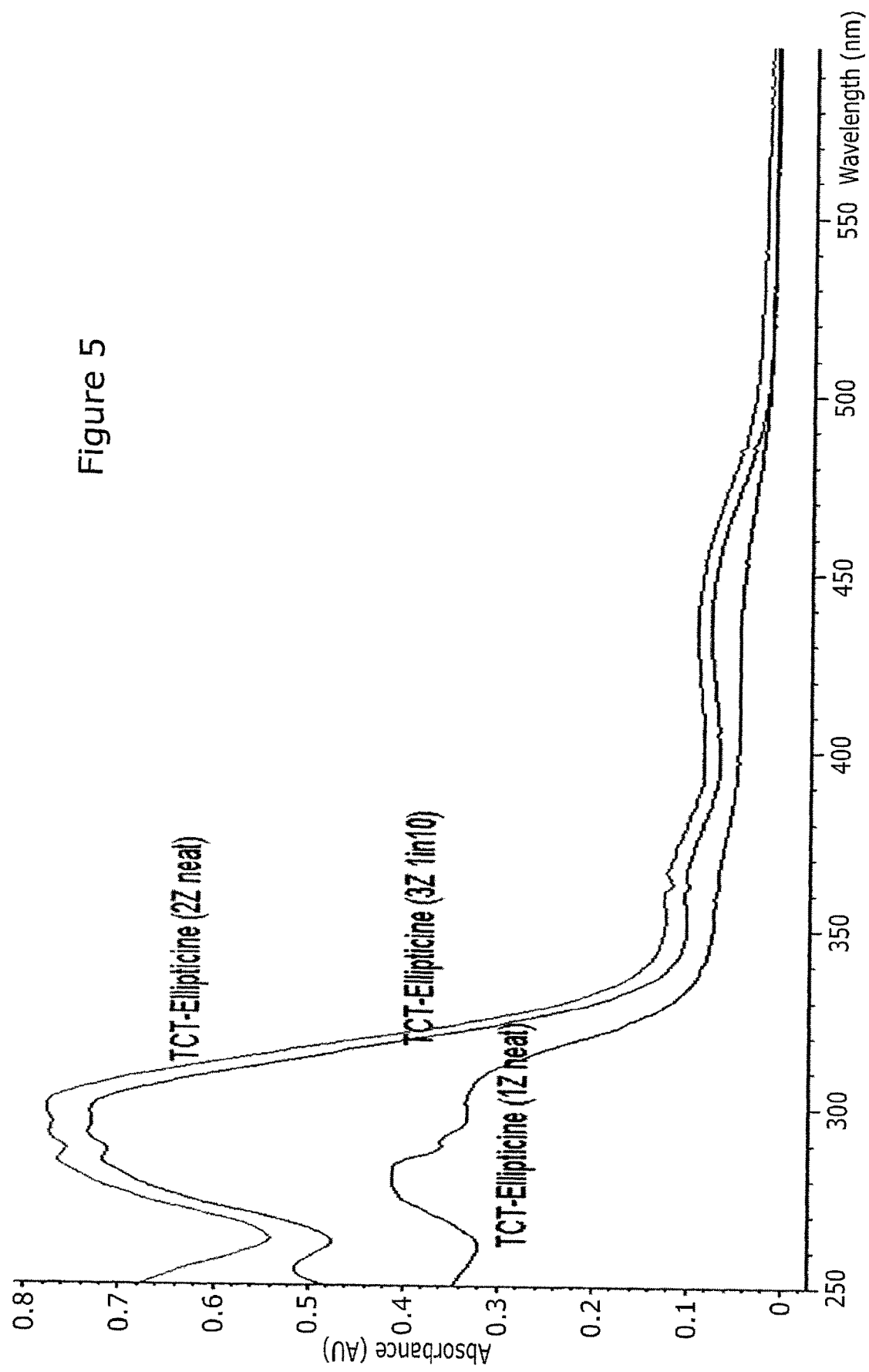

FIG. 5. UV-Vis of scFv (TCT)-Ellipticine conjugates

Figure 6:
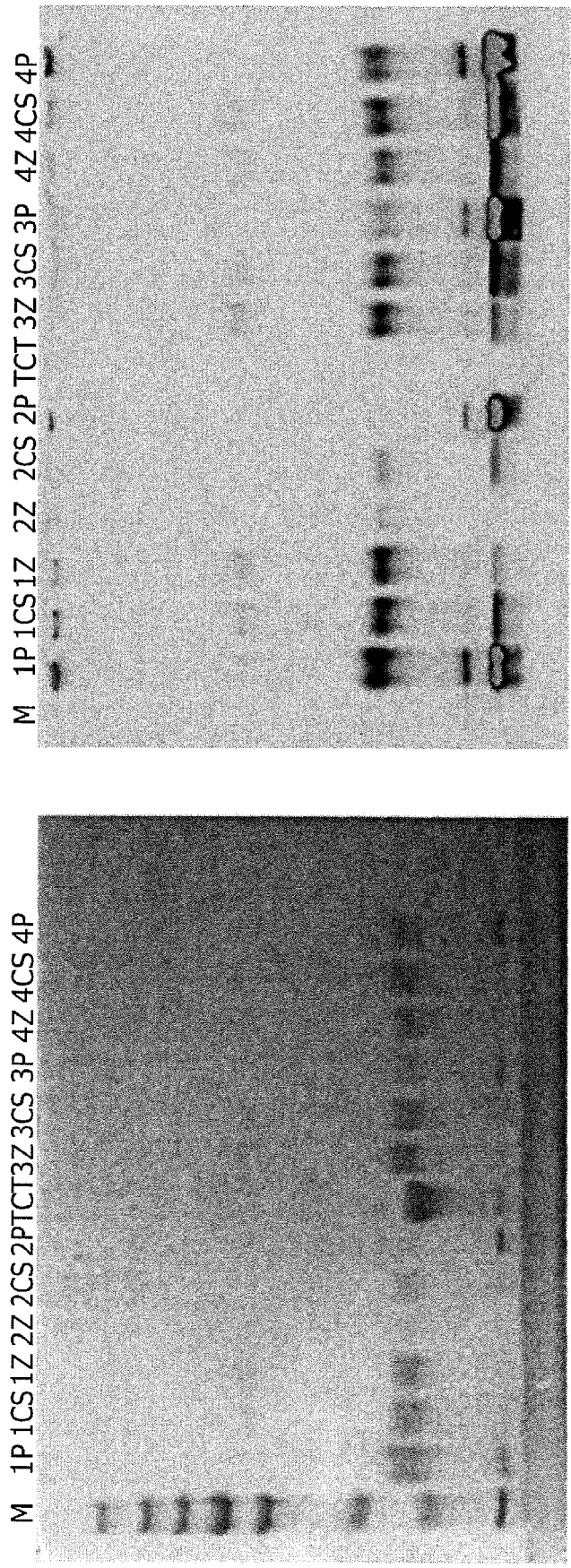

FIG. 6. SDS-PAGE comparing Ellipticine and PEG-Ellipticine scFv conjugates
Ellipticine (compound 21) and PEG-Ellipticine (compound 23) conjugates. 1=scFv (TCT)-PEG-Ellipticine, 20 equivalents; 2=scFv (TCT)-Ellipticine, 20 equivalents; 3=scFv (TCT)-PEG-Ellipticine, 32 equivalents; 4=scFv (TCT)-PEG-Ellipticine, 64 equivalents; Z=Zeba column desalted; CS=soluble crude reaction; P=insoluble/precipitated crude reaction. Sample loading=1.8 μg. MW markers (M), kDa top to bottom: 250, 130, 100, 70, 55, 35, 25, 15, 10

Figure 7:

FIG. 7. SDS-PAGE of sample 2: ScFv (TCT)-Ellipticine conjugates D=dialysed; Z=Zeba column desalted; C=soluble crude reaction; P=insoluble/precipitated crude reaction. Ell=Ellipticine Sample loading=2.5 μg. MW markers (M), kDa top to bottom: 250, 130, 100, 70, 55, 35, 25, 15, 10

Figure 8:
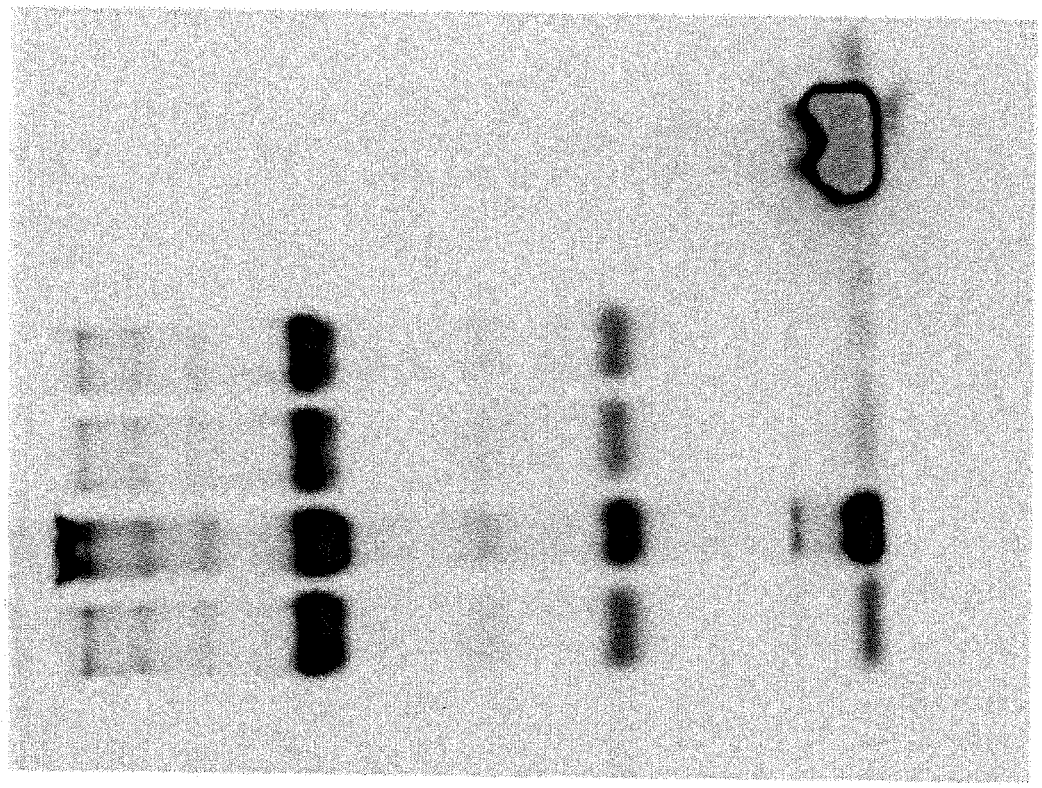
Figure 8:
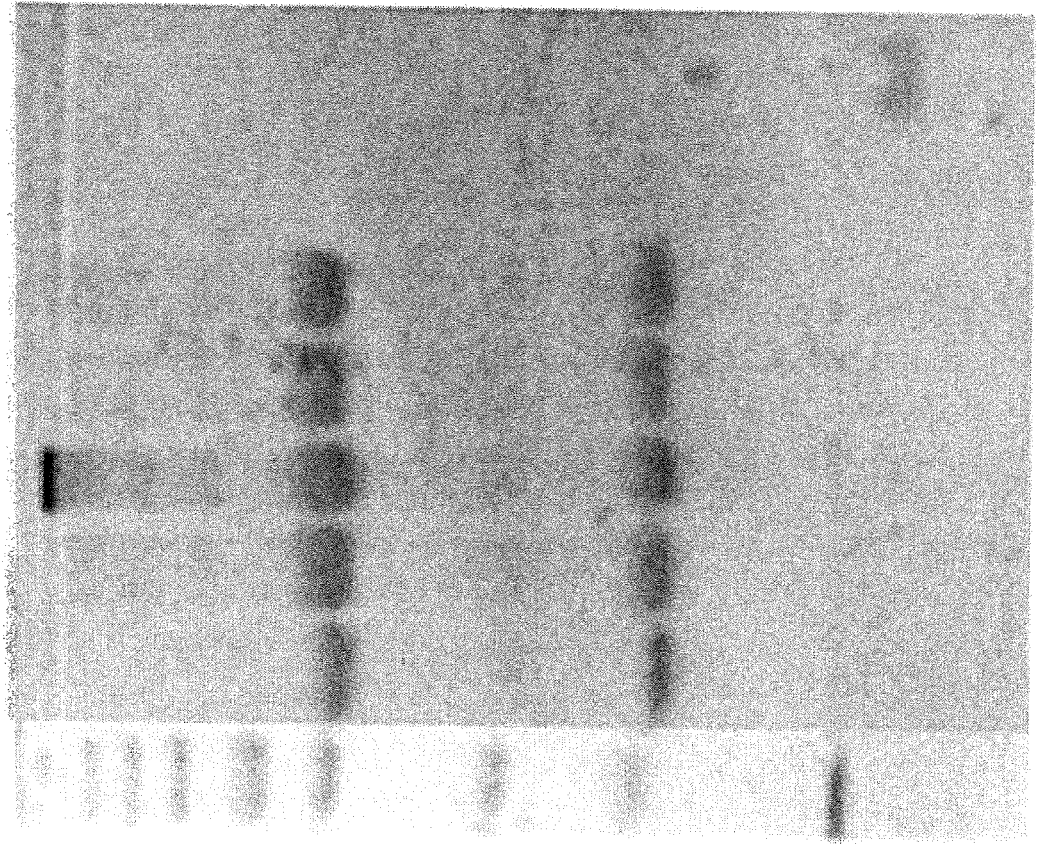

FIG. 8. SDS-PAGE of sample 4: Whole IgG-Ellipticine conjugates D=dialysed; Z=Zeba column desalted; C=soluble crude reaction; P=insoluble/precipitated crude reaction, Ell=Ellipticine. Sample loading=2.5 μg. MW markers (M), kDa top to bottom: 250, 130, 100, 70, 55, 35, 25, 15, 10

Figure 9:
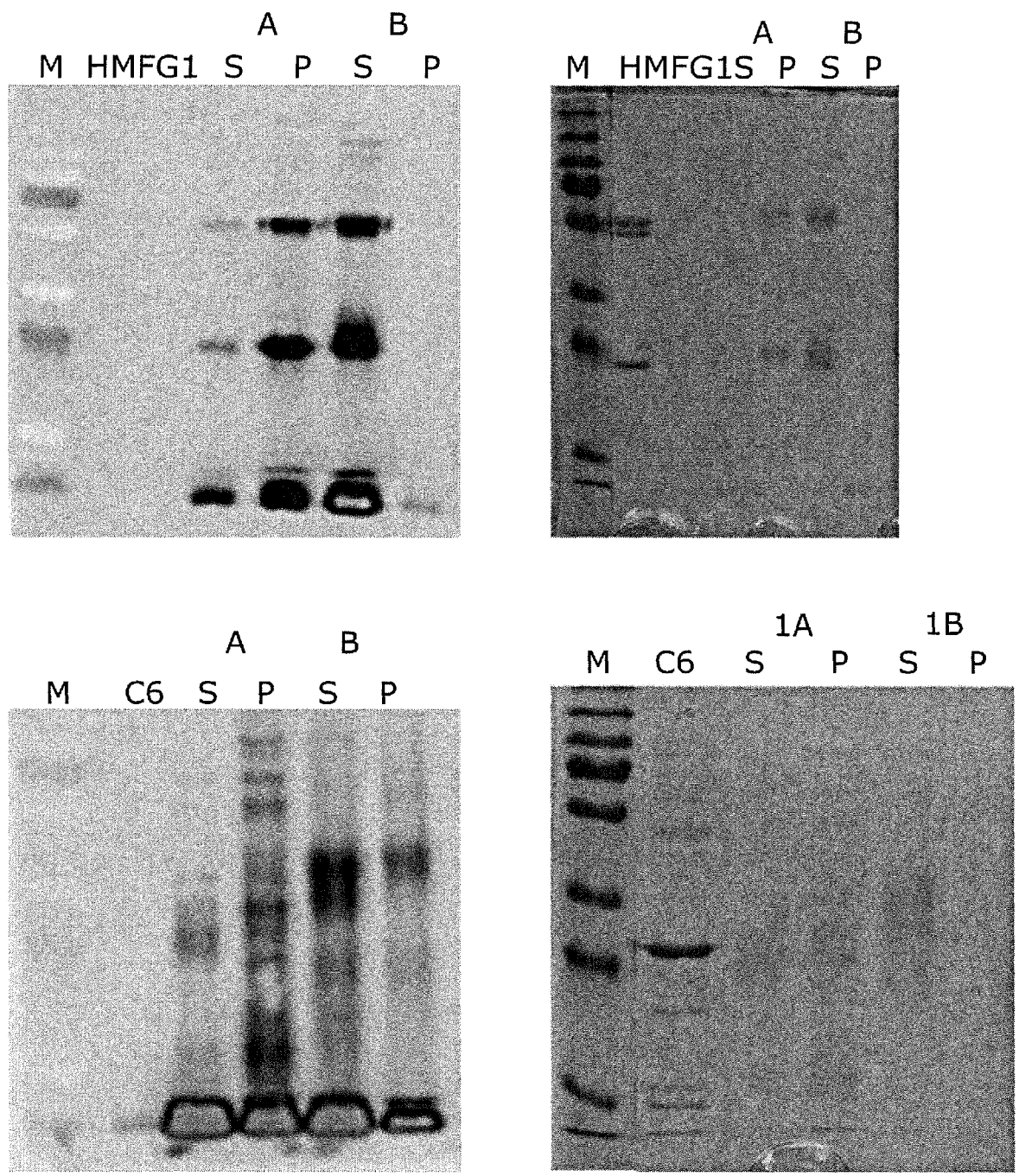

FIG. 9. SDS-PAGE of two-step conjugation of doxorubicin derivatives to C6.5 scFv
Upper panel, HMFG1 IgG conjugates, Lower panel C6.5 scFv conjugates.
HMFG1/C6=free antibody, S=soluble fraction, P=precipitate, A=Doxorubicin-maleimide (compound 12) conjugates, B=Doxorubicin-PEG-maleimide (compound 48) conjugates.
MW markers (M), kDa top to bottom: 250, 130, 100, 70, 55, 35, 25, 15, 10

Figure 10:
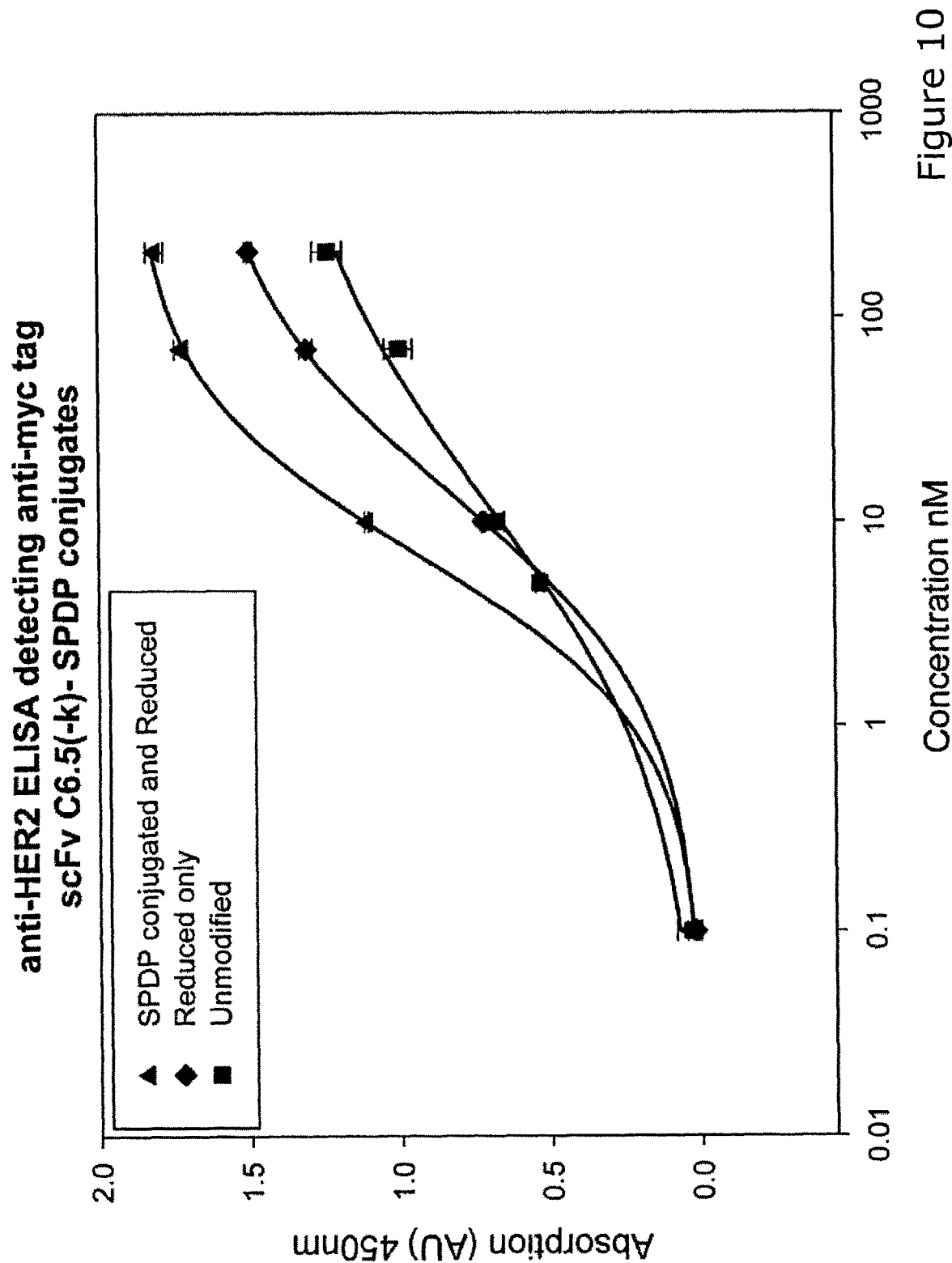

FIG. 10. ELISA on HER2 antigen of C6.5 scFv conjugated to SPDP linker

Figure 11:
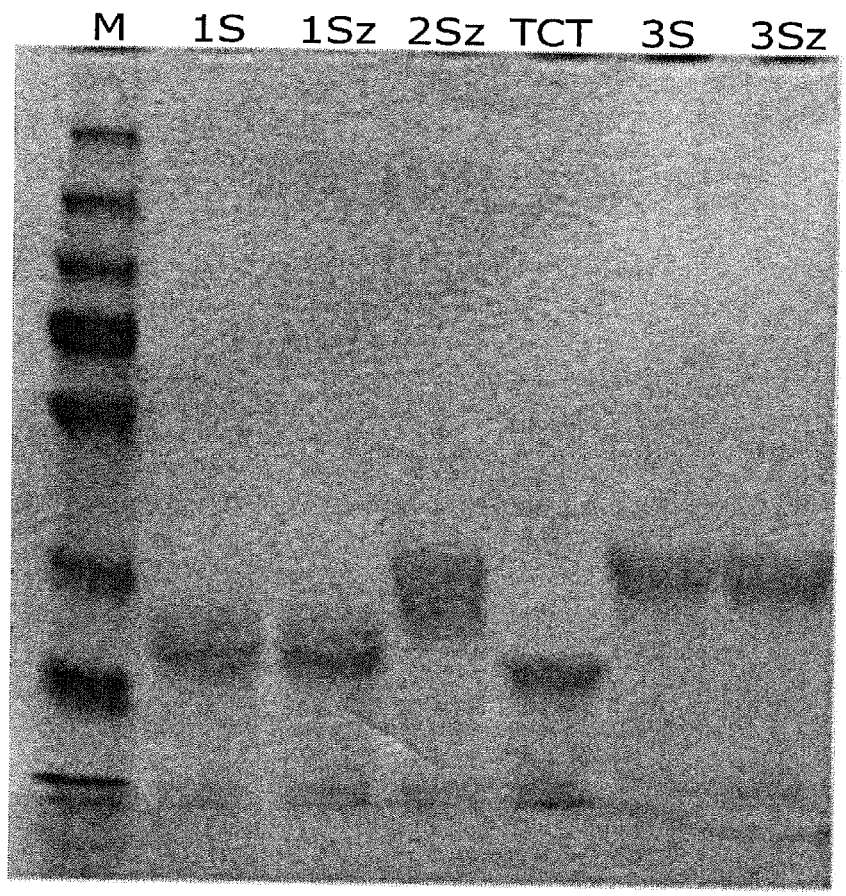

FIG. 11. SDS-PAGE Gel of ScFv (TCT)-Cemadotin ADCs after HPLC-SEC purification
MW markers (M), kDa top to bottom: 250, 130, 100, 70, 55, 35, 25, 15, 10. Cemadotin (compound 2) conjugates (compound 69). 1=16 drug equivalents; 2=48 drug equivalents; 3=112 drug equivalents; S=HPLC-SEC purification; Z=further Zeba buffer exchange.

FIG. 12. scFv and scFv-cemadotin ADCs analysed by HPLC-SEC
  a) Calibration markers for G2000SWxI SEC column to confirm sizes of eluted proteins and conjugates. The column was run at 1 ml/min in PBS/20% isopropanol. The values were:

| RT (min) | Molecular Weight (kDa) | Sample |
| --- | --- | --- |
| 6.43 | 80 | Alcohol dehydrogenase |
| 8.48 | 30 | Carbonic anhydrase |
| 11.25 | 13 | Lysozyme |
| 10.9 | <1 | Cemadotin | b) Upper trace, scFv (TCT), lower trace, scFv (TCT)-Cemadotin ADC sample-1 analyses by SEC-HPLC, The column was run at 0.5 ml/min in PBS/20% isopropanol.
  c) Upper trace, scFv (TCT)-Cemadotin ADC sample-2, middle trace, scFv (TCT)-Cemadotin ADC sample-3 analyses by SEC-HPLC, lower trace-UV-Vis spectrum confirming protein/peptide content. The column was run at 0.5 ml/min in PBS/20% isopropanol.

FIG. 13. (a) TIC, (b) ESI-MS, (c) deconvoluted-MS, and calculated DAR of the ScFv (TCT)-Cemadotin ADC sample 2

Figure 14A:
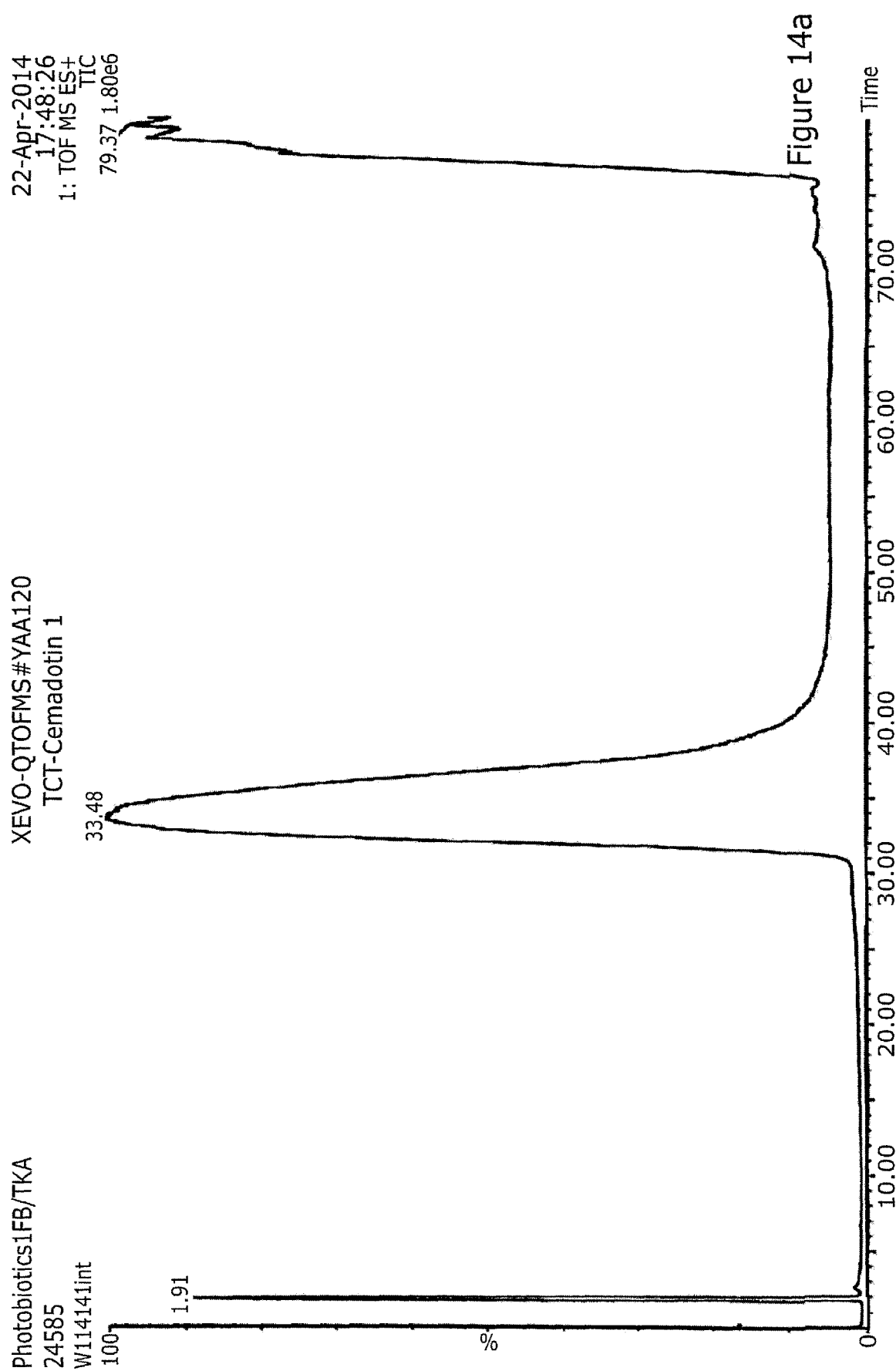
Figure 14B:
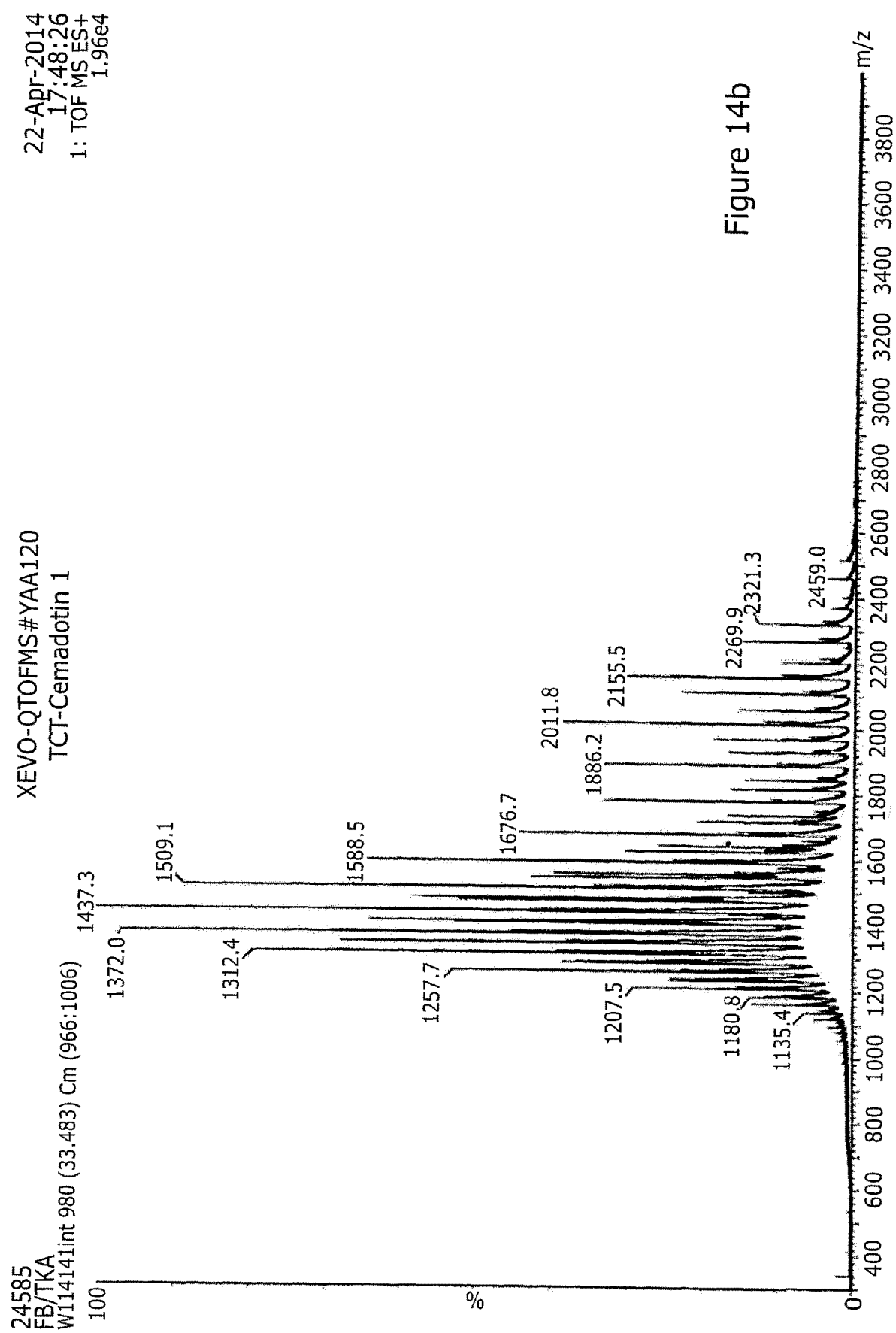
Figure 14C:
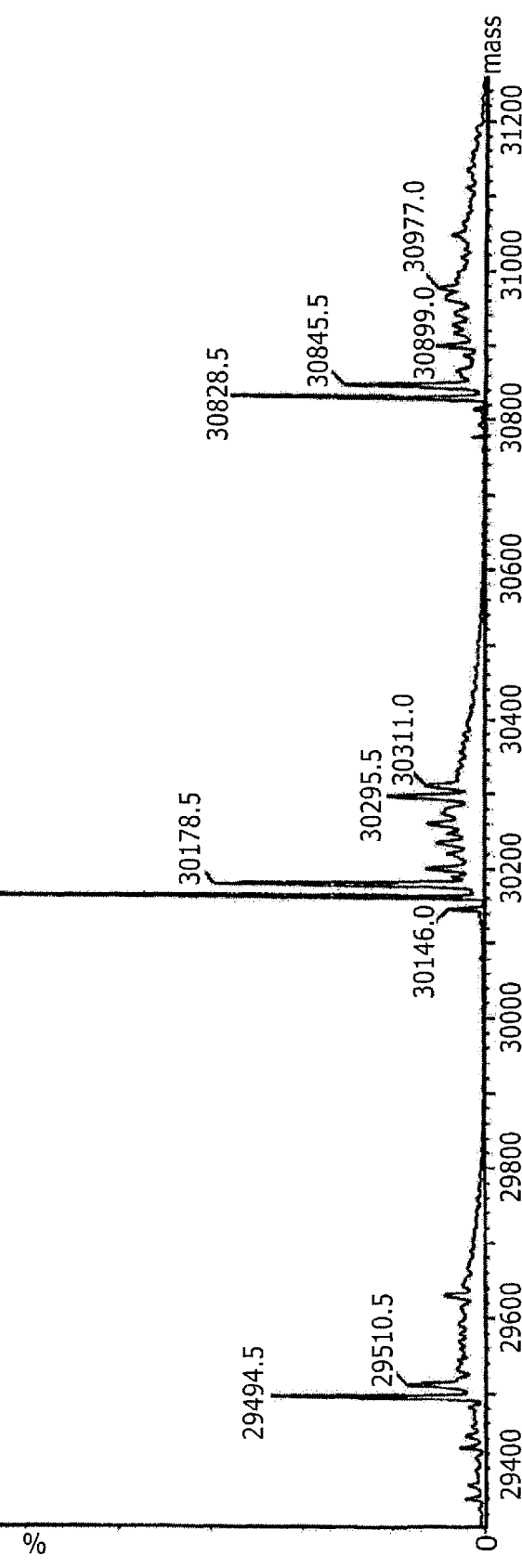

FIG. 14. (a) TIC, (b) ESI-MS, (c) deconvoluted-MS, and calculated DAR of the ScFv (TCT)-Cemadotin ADC sample 1

Figure 15A:
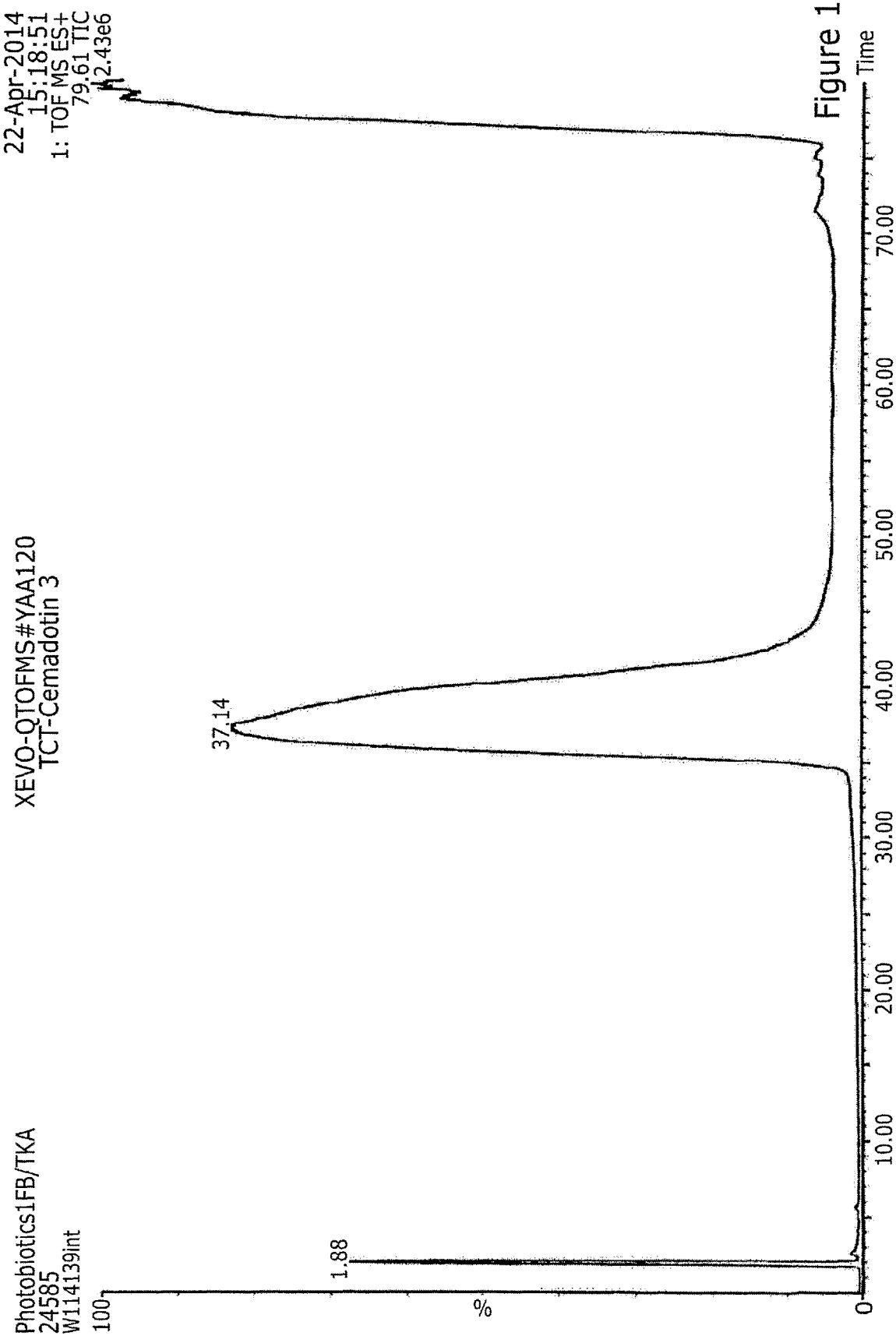
Figure 15B:
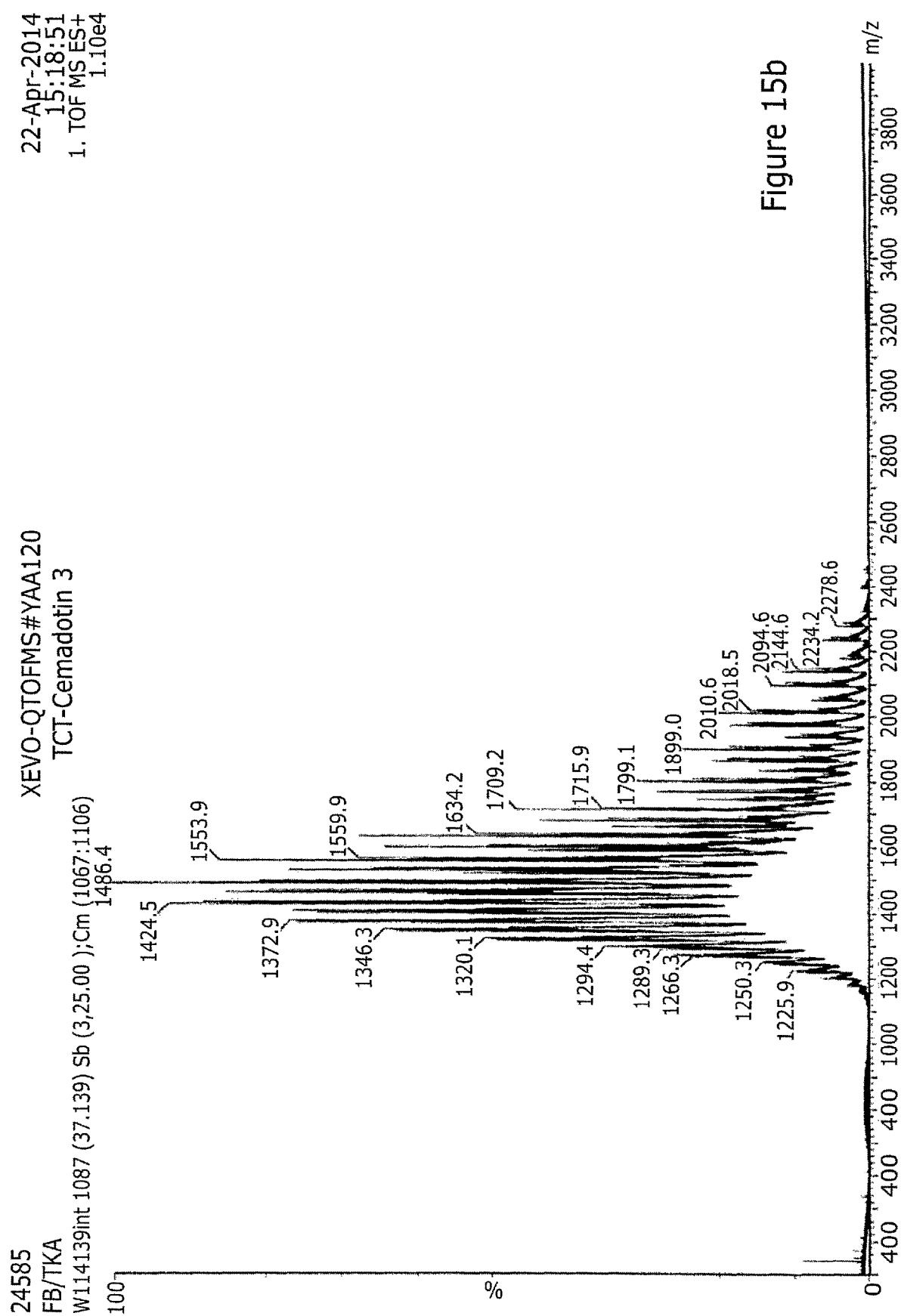
Figure 15C:
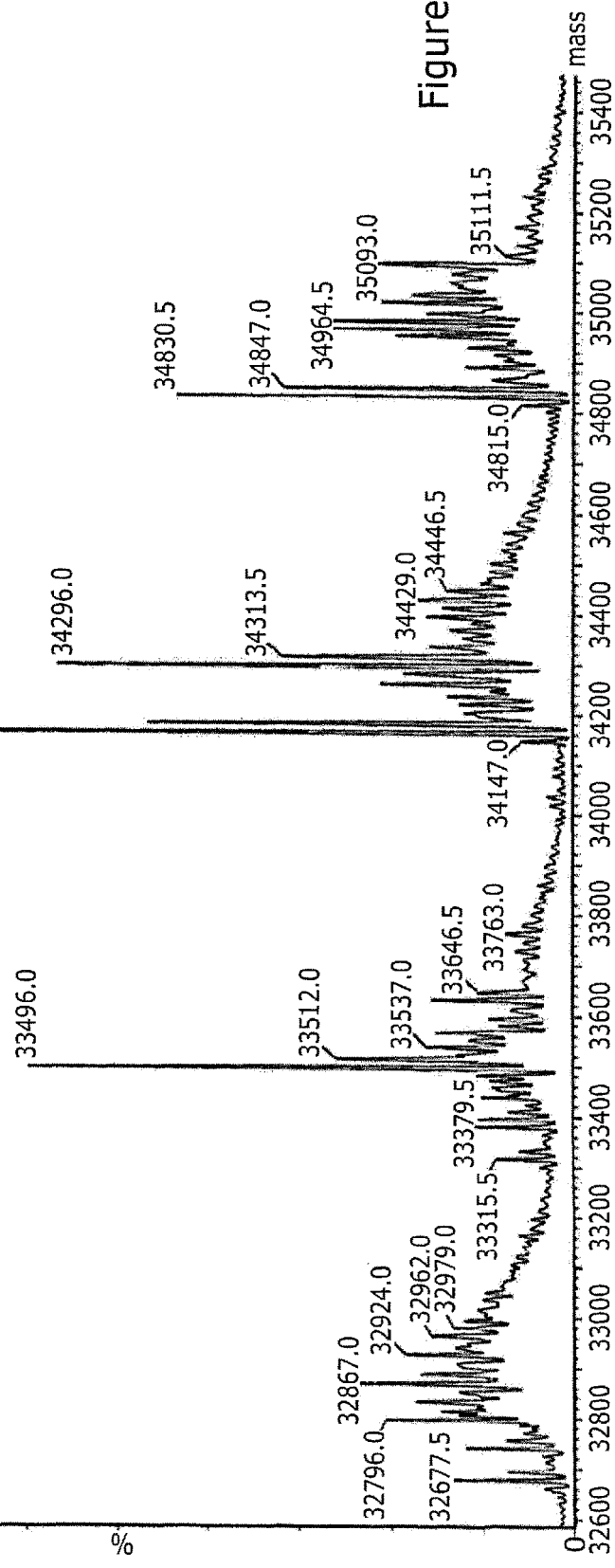

FIG. 15. (a) TIC, (b) ESI-MS, (c) deconvoluted-MS, and calculated DAR of the ScFv (TCT)-Cemadotin ADC sample 3

FIG. 16. (a) TIC, (b) ESI-MS, (c) deconvoluted-MS, and calculated DAR of the ScFv (TCT)

Figure 17:
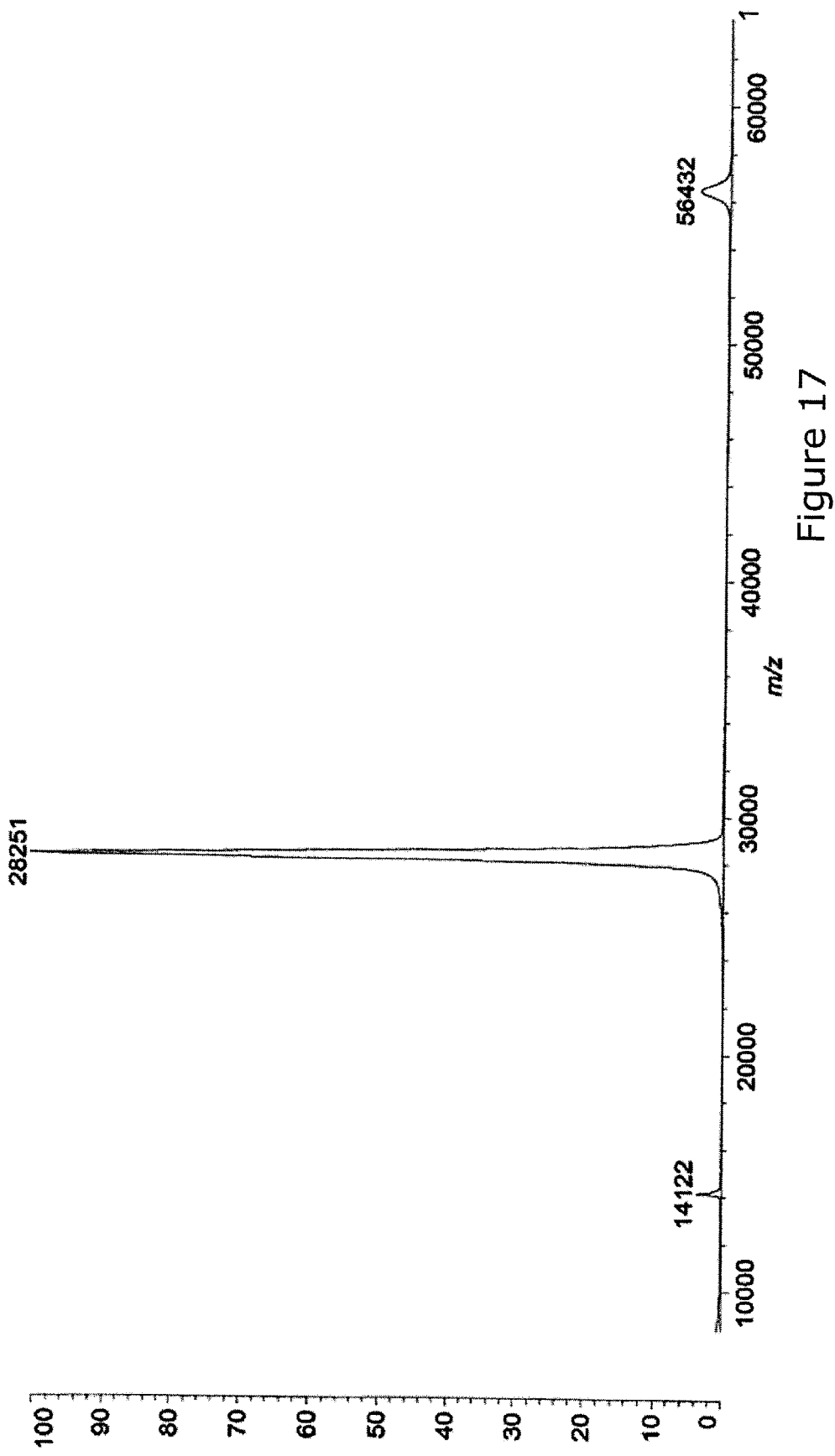

FIG. 17. MALDI-MS of scFv (TCT)

Figure 18:
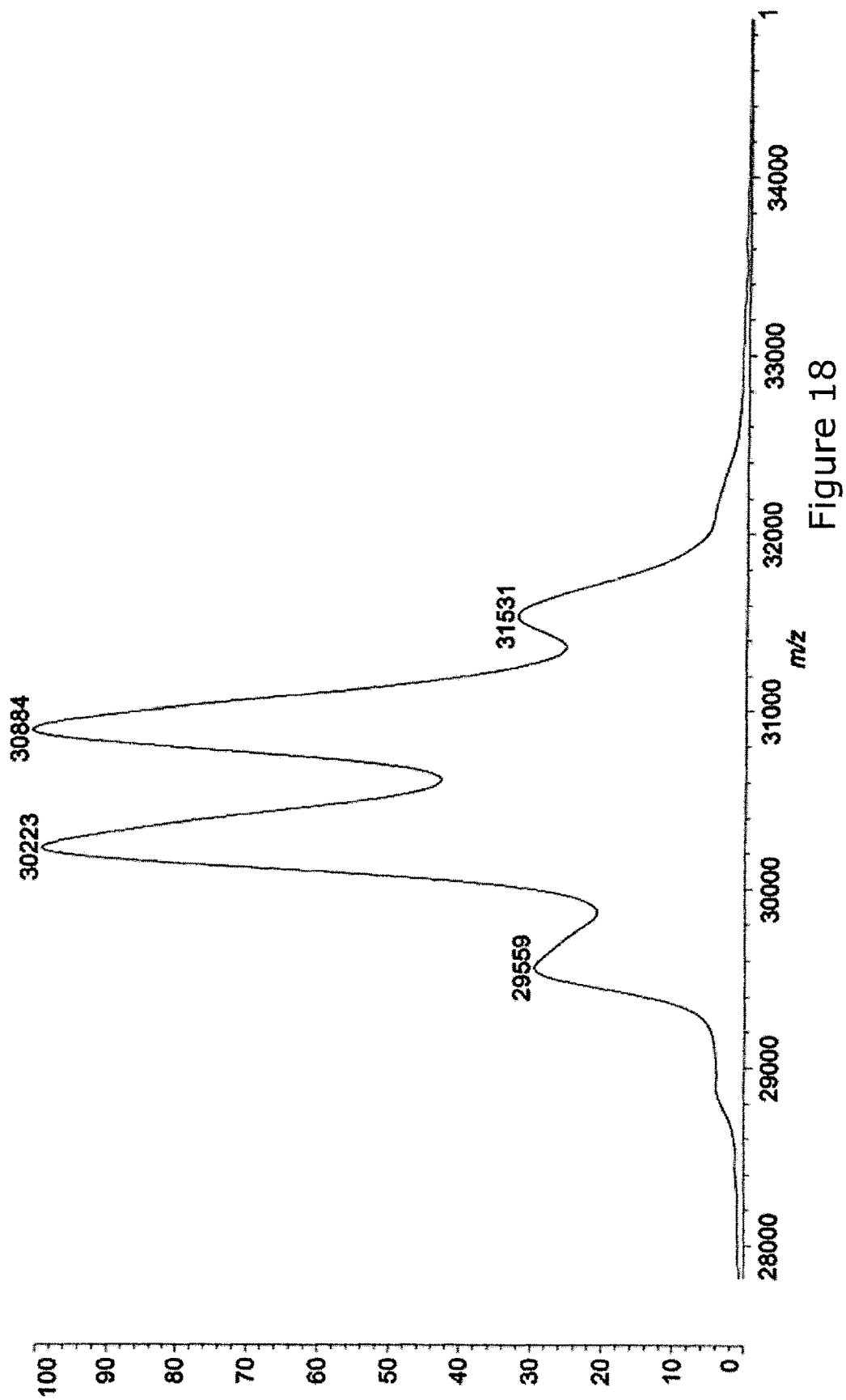

FIG. 18. MALDI-MS of scFv (TCT)-Cemadotin ADC sample 1

FIG. 19. MALDI-MS of scFv (TCT)-Cemadotin ADC sample 2

Figure 20:
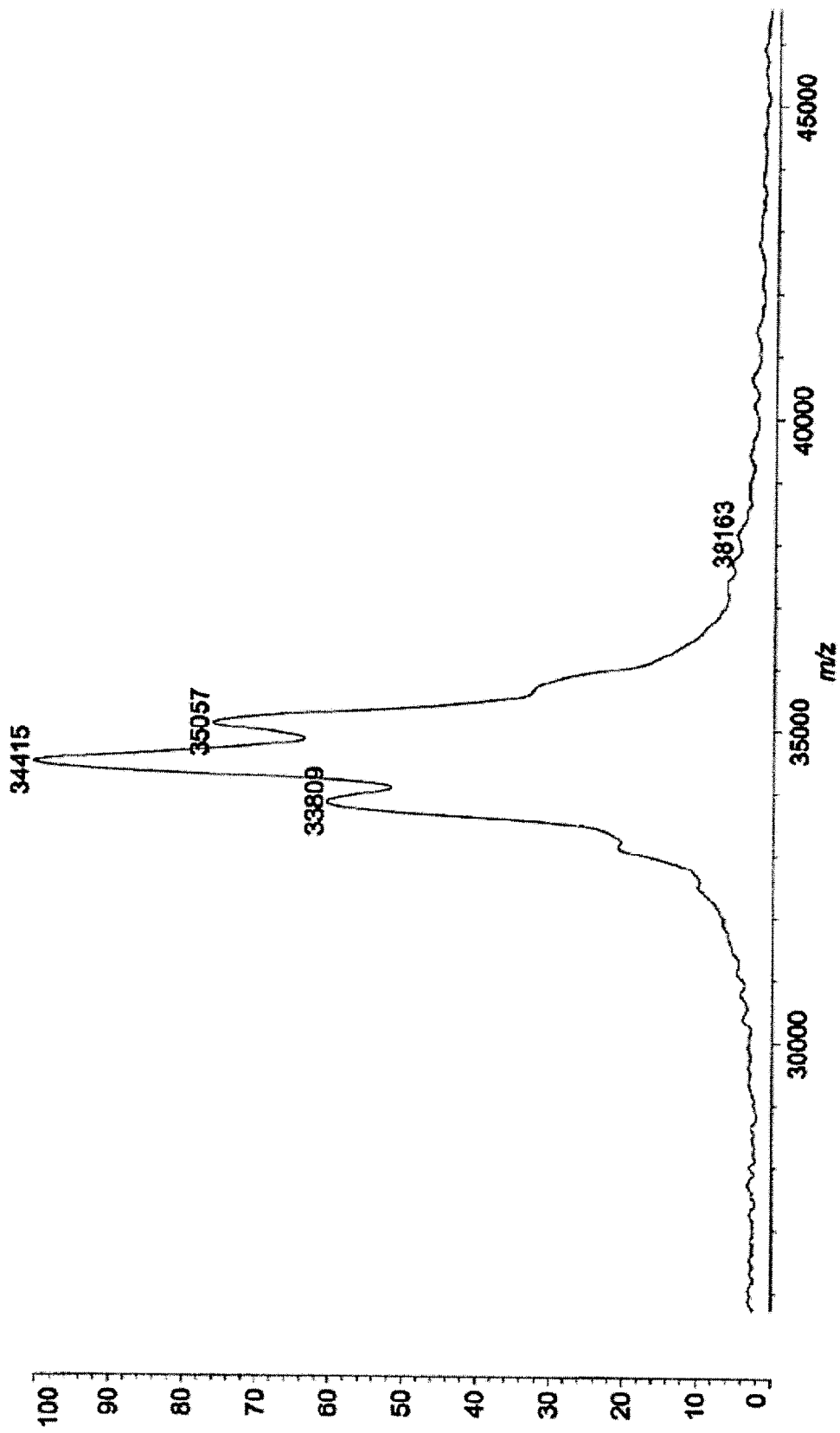

FIG. 20. MALDI-MS of scFv (TCT)-Cemadotin ADC sample 3

Figure 21:
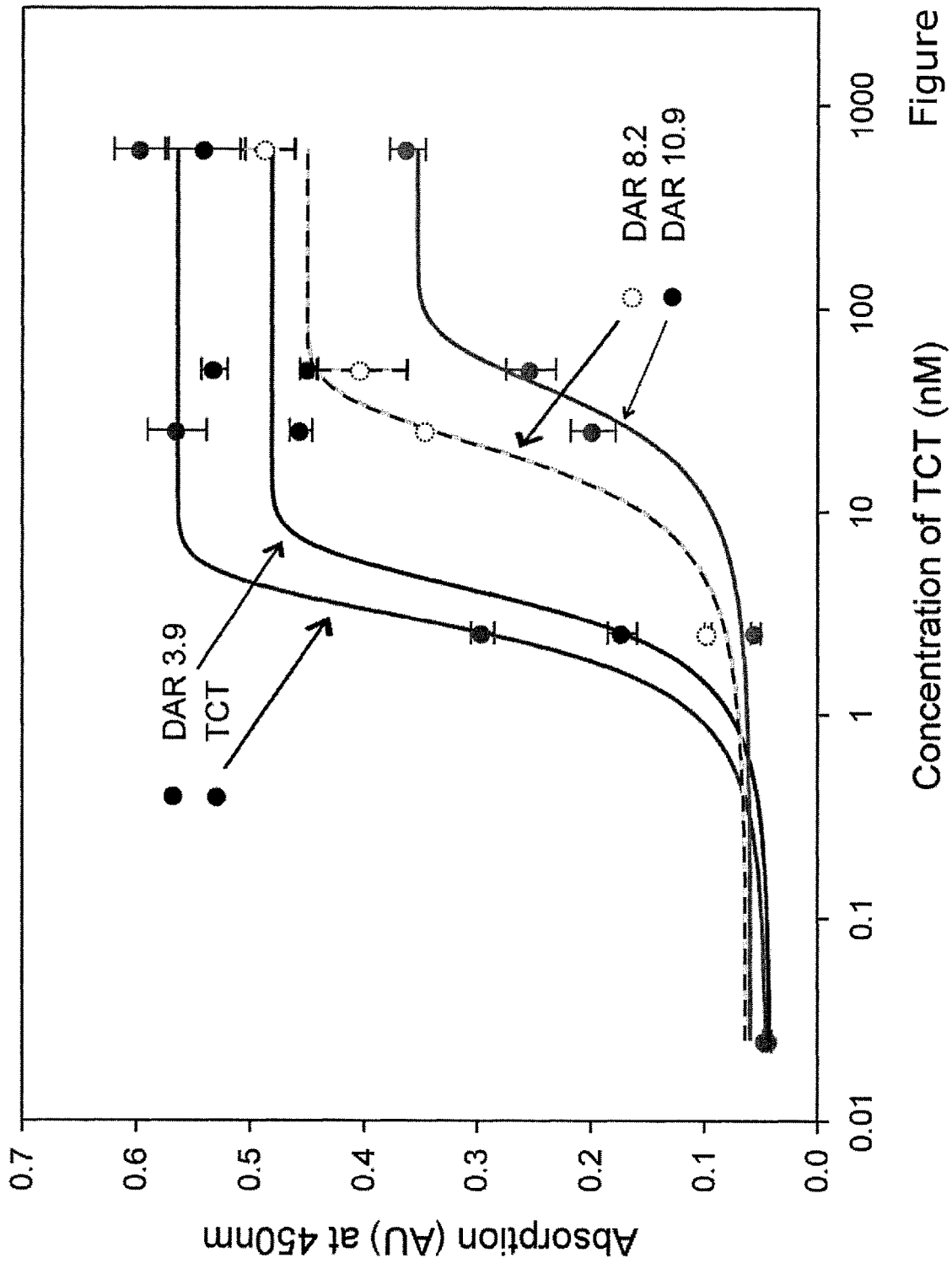

FIG. 21 ELISA of scFv (TCT) Cemadotin ADCs on HER2

Figure 22:
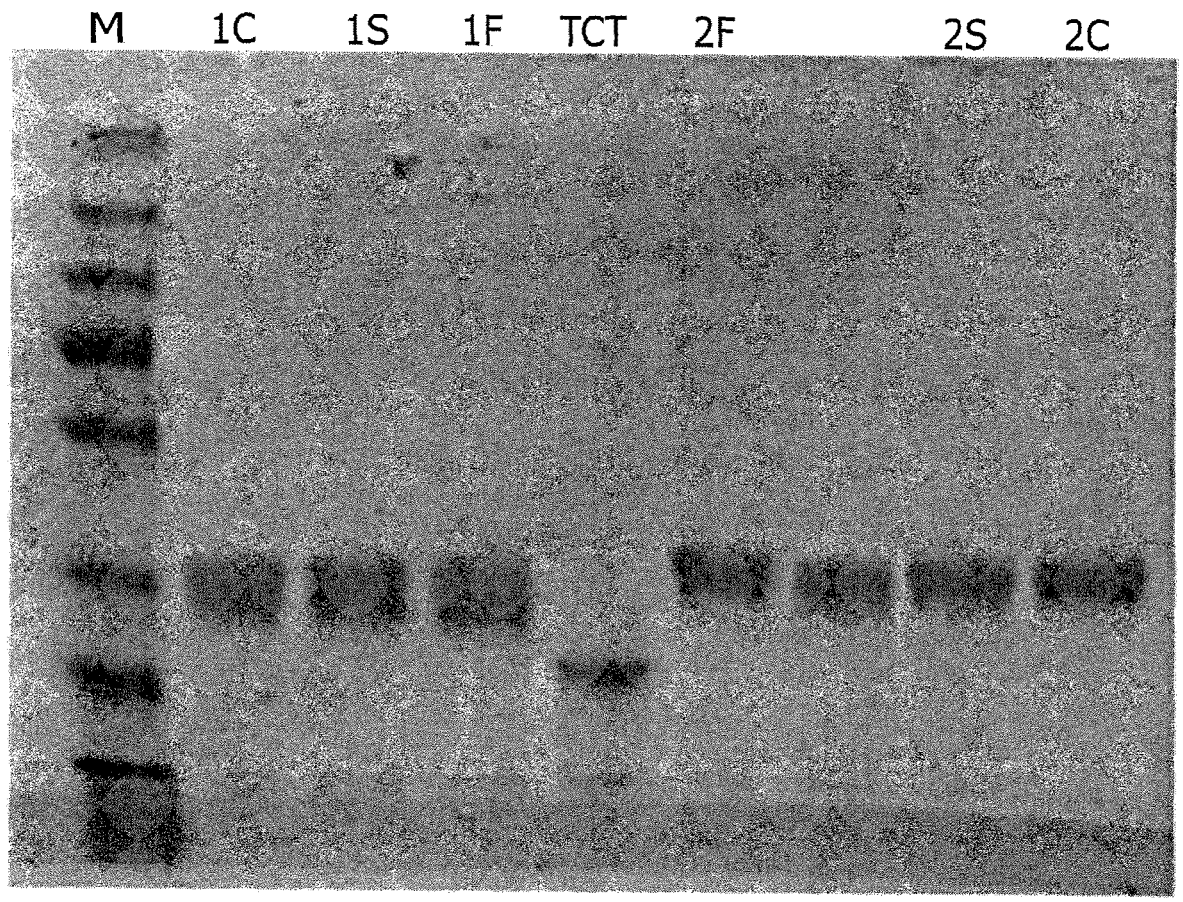

FIG. 22. SDS-PAGE of scFv (TCT)-P5C5 ADCs

P5C5 drug (compound 6) and conjugates (compound 71). 1=scFv (TCT)-P5C5, 30 equivalents; 2=scFv (TCT)-P5C5, 112 equivalents; C=crude rereaction mix; S=sample after SEC purification and concentrating; F=final sample after SEC purification, concentrating, and buffer exchange. Sample loading=2 µg.

MW markers (M), kDa top to bottom: 250, 130, 100, 70, 55, 35, 25, 15, 10

Figure 23A:
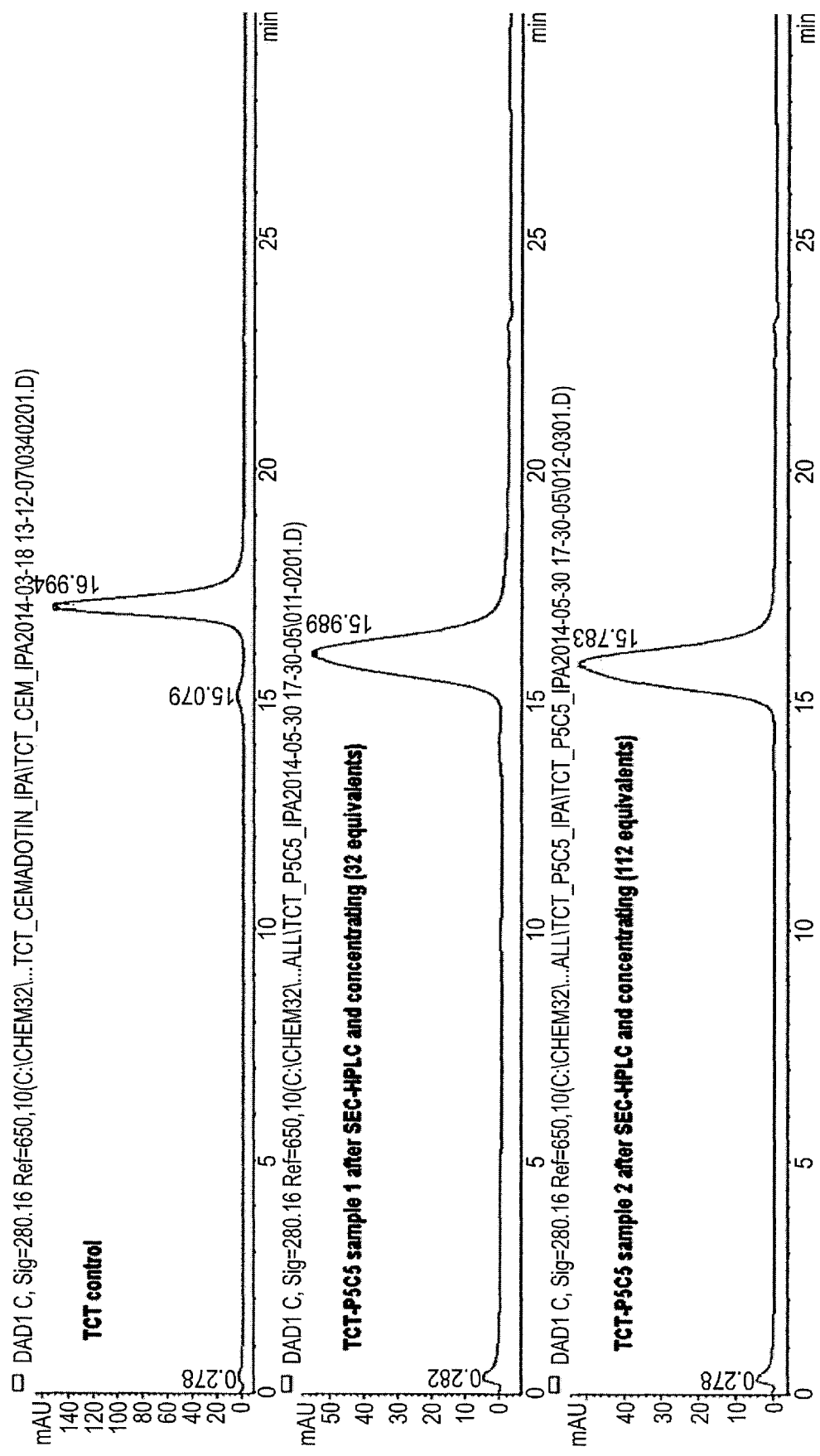
Figure 23B:
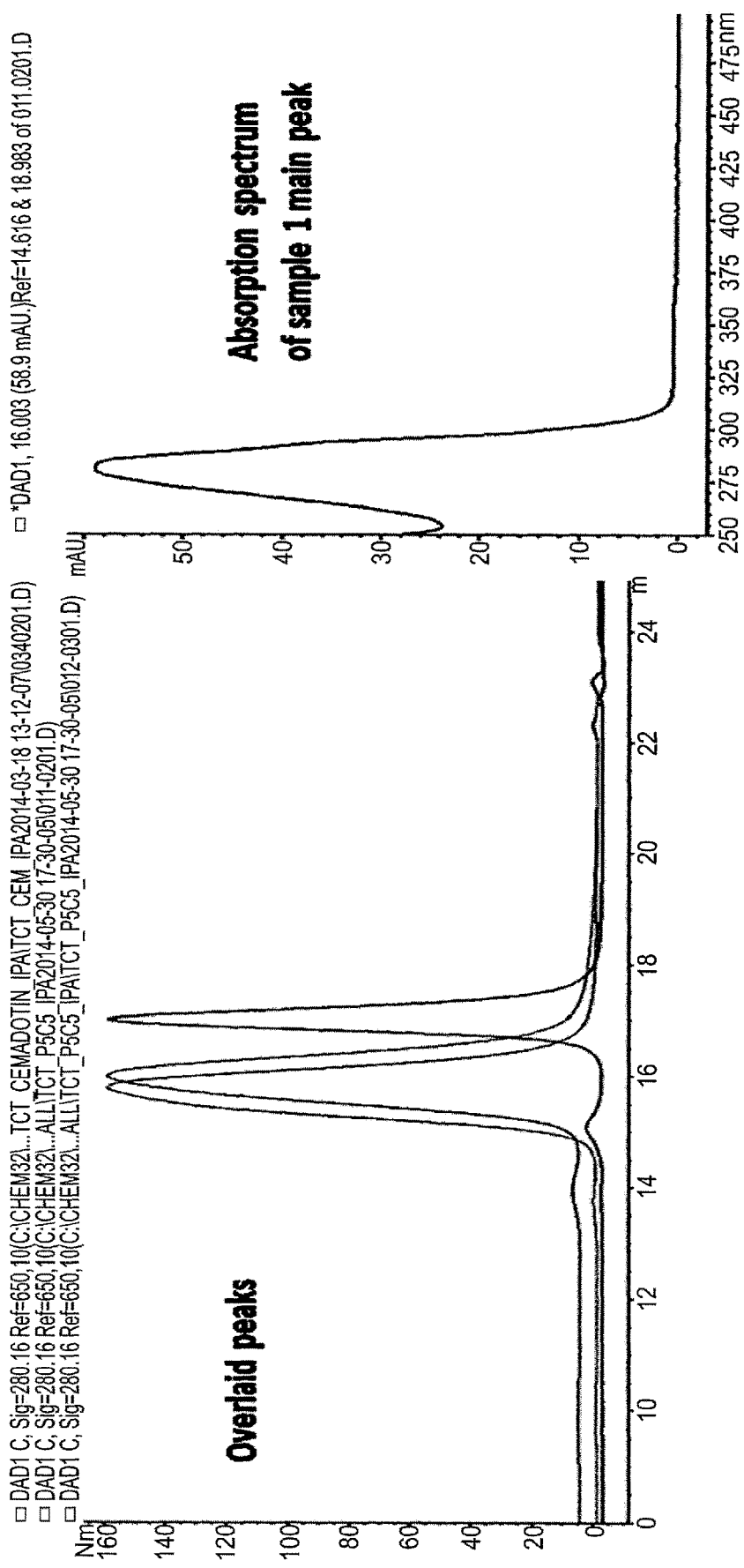

FIG. 23. Analytical HPLC traces of samples post SEC purification-monitored at 280 nm
  a) Upper trace, scFv (TCT), middle trace, scFv (TCT)-P5C5 ADC (30 equiv), lower trace scFv (TCT)-P5C5 ADC (112 equiv). The column was run at 0.5 ml/min in PBS/20% isopropanol.
  b) Left trace, Comparison of scFv and scFv-ADCs from (a) showing earlier retention due to drug loading (15.7 and 15.9 min compared to the scFv elution of 16.9 min), but non-aggregated monomeric peaks, right trace-UV-Vis trace of one of the ADCs showing protein/peptide spectrum. The column was run at 0.5 ml/min in PBS/20% isopropanol.

Figure 24:
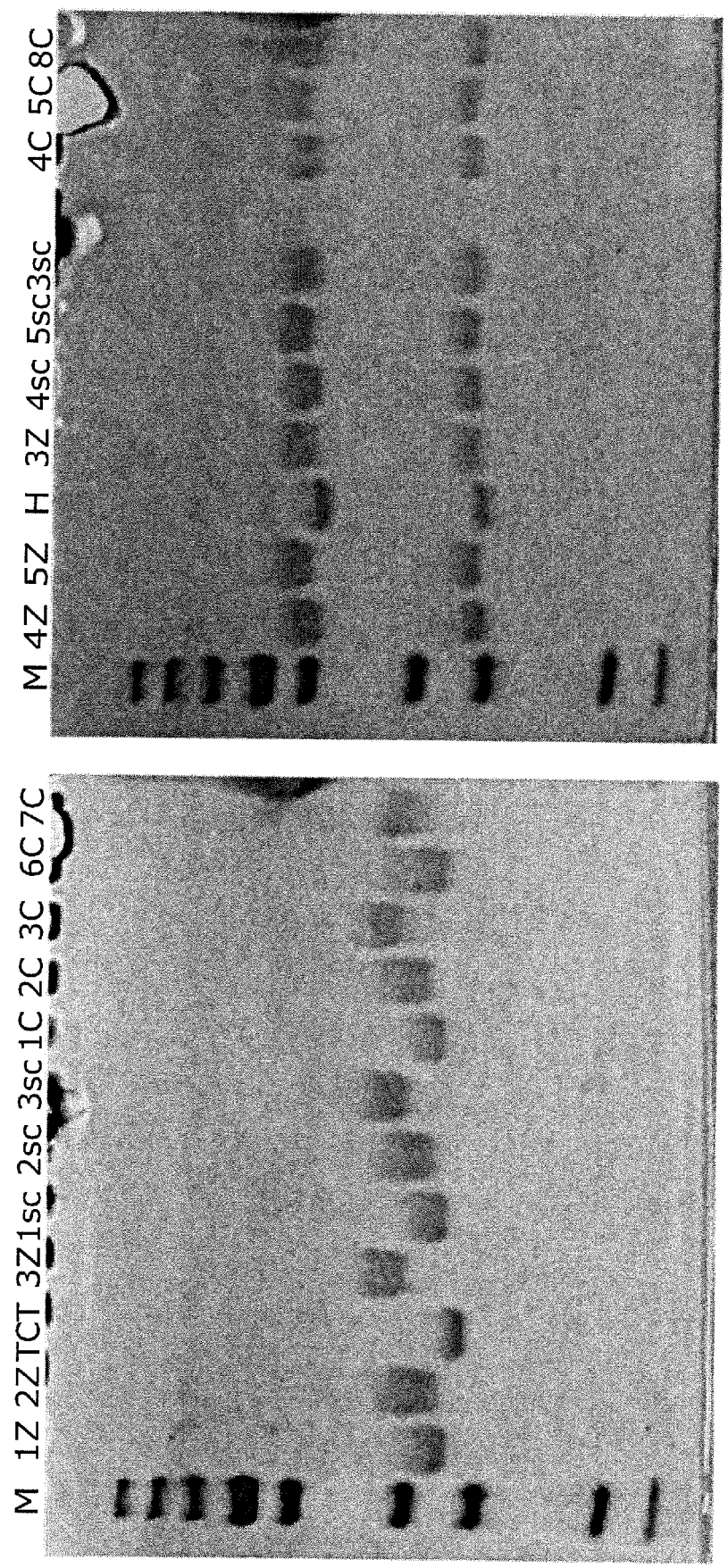

FIG. 24. SDS-PAGE of various ADCs

P5C5 drug (compound 6), CemadotinC5 drug (compound 4) and conjugates (compound 71). 1=scFv (TCT)-P5C5, 16 equivalents; 2=scFv (TCT)-P5C5, 30 equivalents; 3=scFv (TCT)-P5C5, 112 equivalents; 4=Trastuzumab-P5C5, 16 equivalents; 5=Trastuzumab-P5C5, 32 equivalents; 6-7=scFv (TCT)-Cemadotin-C5; 8=Trastuzumab-Cemadotin-C5; Z=final Zeba desalted sample; Sc=sample after HPLC-SEC and concentration; C=crude reaction mix. Sample loading=1.9 µg.

MW markers (M), kDa top to bottom: 250, 130, 100, 70, 55, 35, 25, 15, 10.

Figure 25:
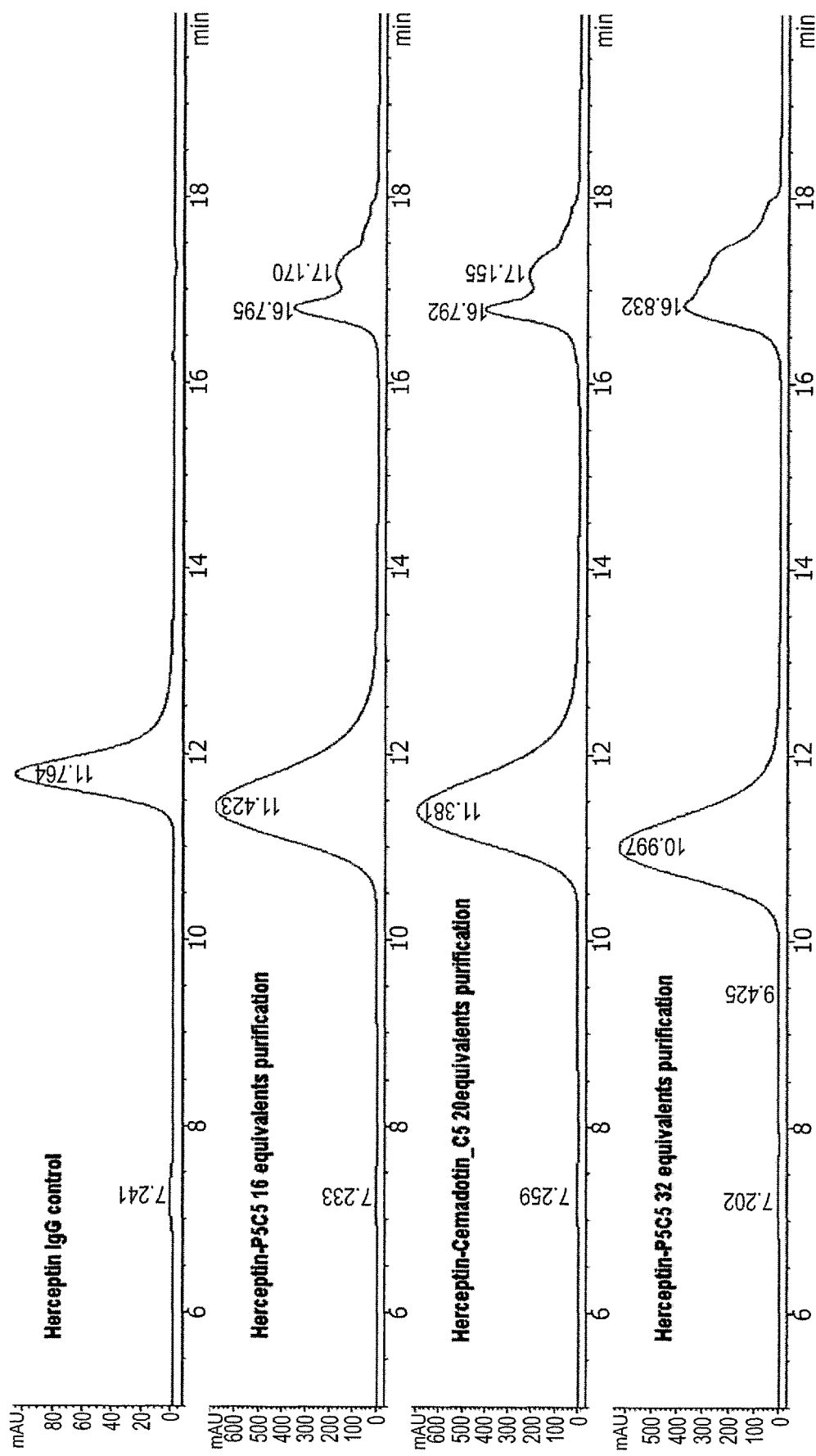

FIG. 25. HPLC purification traces of Trastuzumab conjugates (A280 nm)

Upper trace shows the free trastuzumab IgG, the lower 3 traces show various ADCs at different conjugation reaction equivalents. Samples were run on a G3000SWxl column calibrated with markers. The column was run at 0.5 ml/min in PBS/20% isopropanol. The markers eluted as follows:

| Molecular weight (kDa) | Retention time (mins) | Sample |
|---|---|---|
| 223.8 | 18.1 | beta amylase |
| 146.8 | 18.9 | alcohol dehydrogenase |
| 66.5 | 21.2 | BSA |
| 29 | 23.7 | carbonic anhydrase |
| 14.5 | 29.7 | lysozyme |

The IgG (retention time=11.7 min) and the IgG-ADCs (retention time=10.9-11.4 min) all elute at around 150 kDa indicating little/no aggregation.

Figure 26:
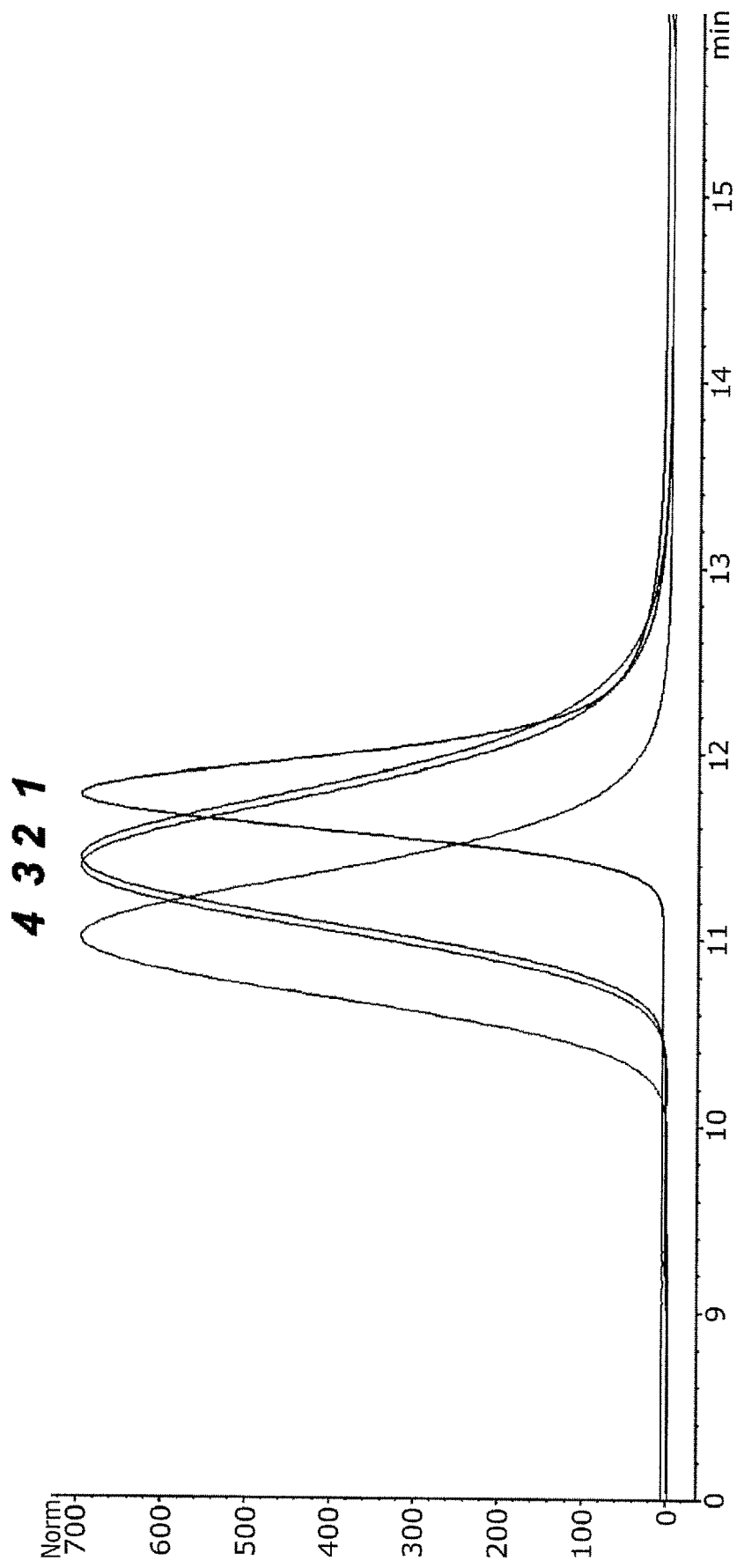

FIG. 26. HPLC purification traces of Trastuzumab conjugates (A280 nm) from FIG. 25 overlaid for comparison Peak 1=Trastuzumab, 2=Trastuzumab-P5C5 (16 equivalents conjugation reaction), 3=2=Trastuzumab-cemadotin (16 equivalents conjugation reaction), 2=Trastuzumab-P5C5 (32 equivalents conjugation reaction)

Figure 27:
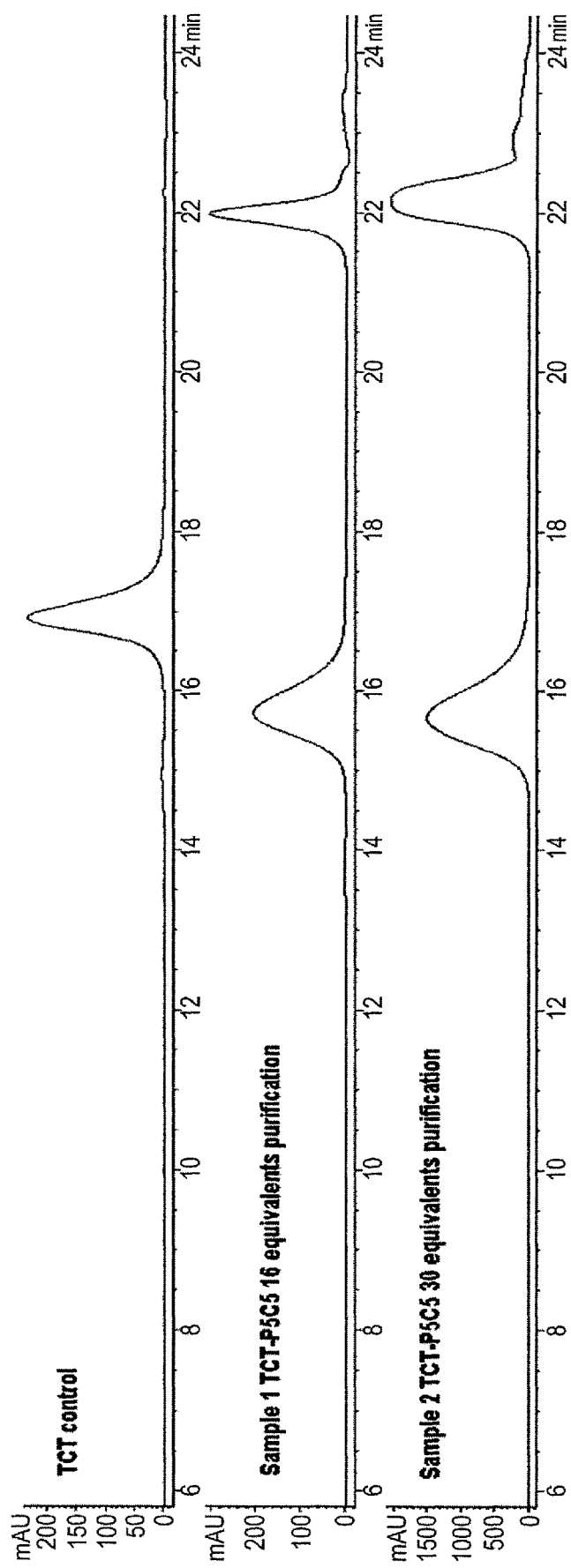
Figure 27:
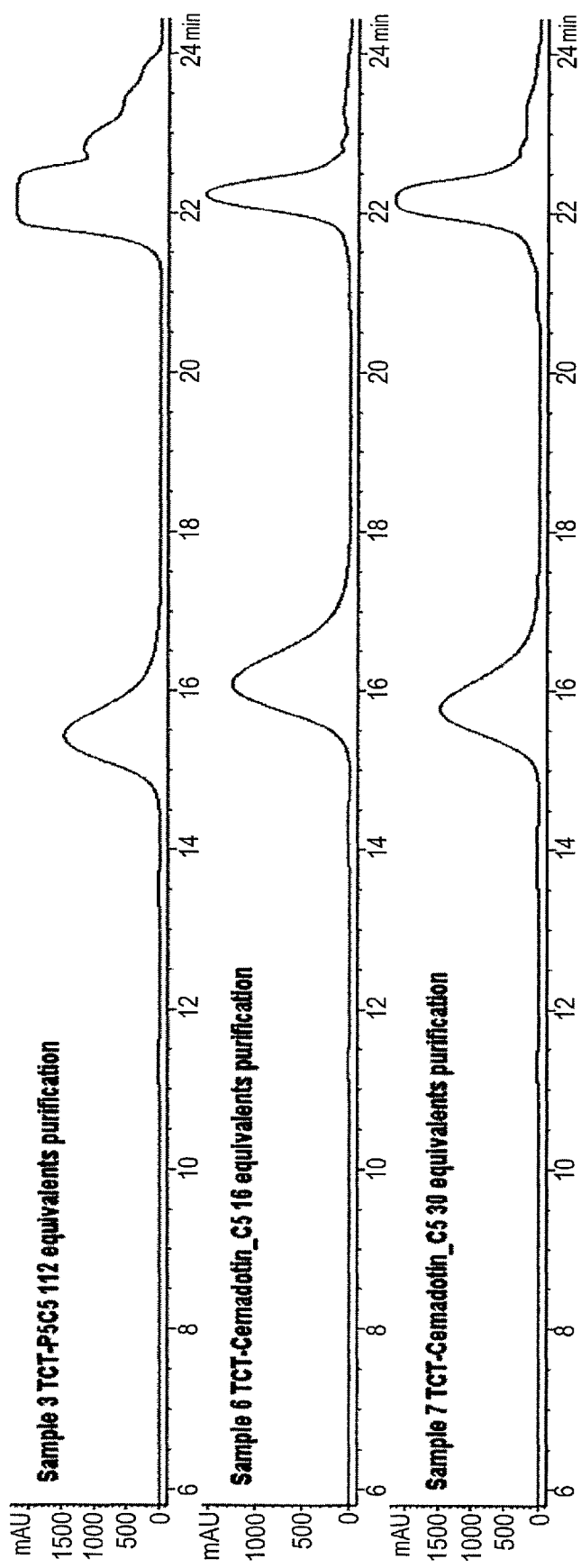

FIG. 27. HPLC purification traces of scFv (TCT)-P5C5 conjugates (A280 nm)

The scFv (TCT)-P5-C5 ADCs had faster retention times (15.7 min, 15.6 min and 15.4 with increasing conjugation equivalents and hence DAR) than the free scFv (retention time=16.9 min). The scFv (TCT)-Cemadotin retention times were 16.1 min and 15.7 with increasing DAR). All still remained in the range of monomeric scFv with little or no aggregation. The column was run at 0.5 ml/min in PBS/20% isopropanol.

Figure 28:
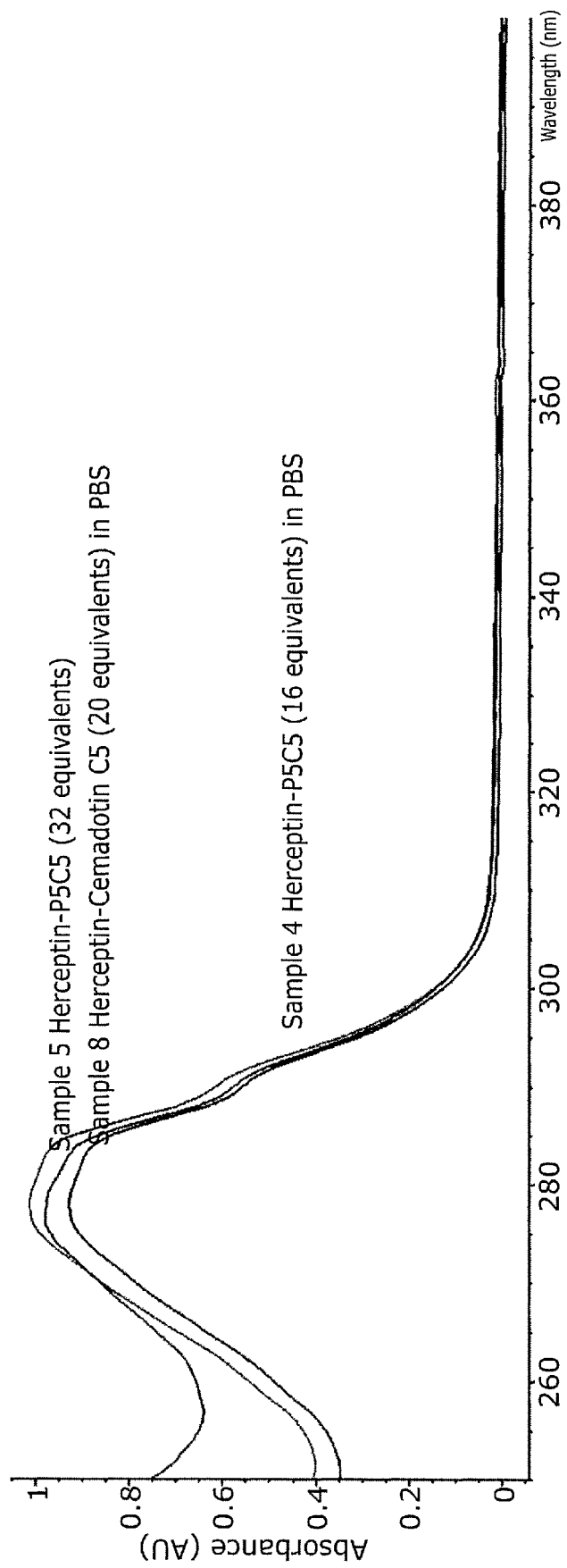

FIG. 28. UV/Vis absorption spectrum of Trastuzumab-P5C5 in PBS

Figure 29:
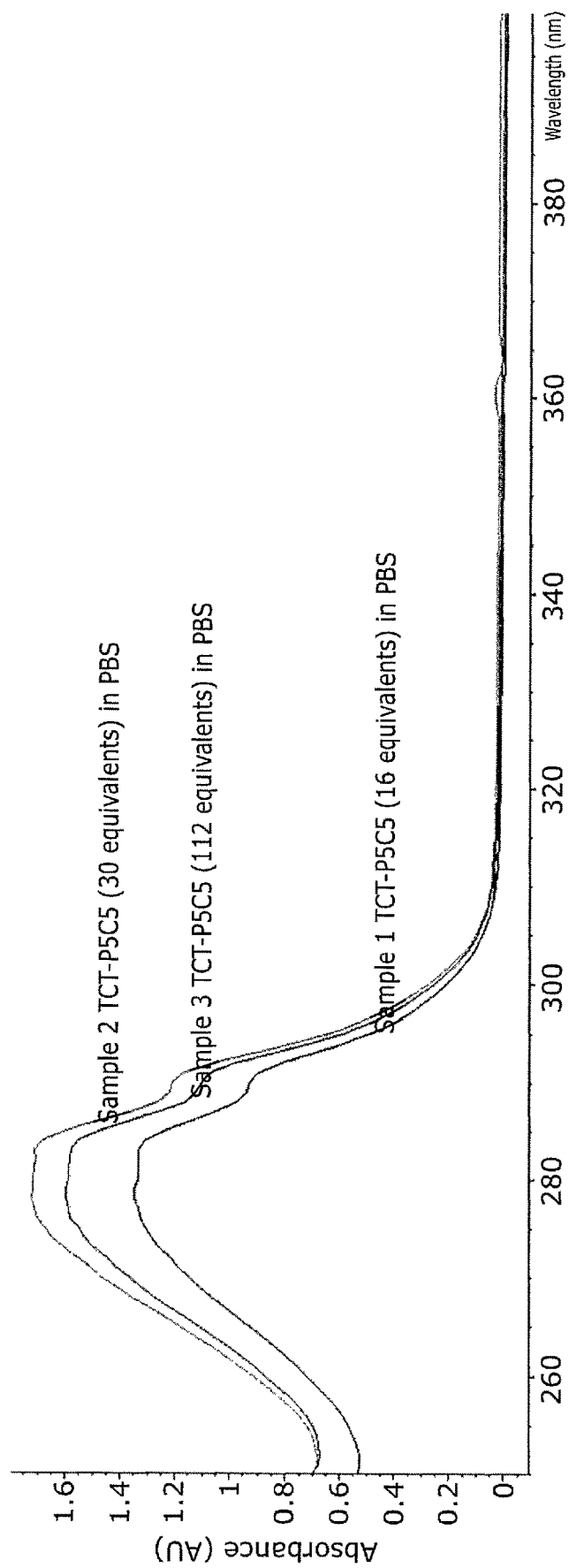

FIG. 29. UV/Vis absorption spectrum of scFv (TCT)-P5C5 conjugates in PBS

Figure 30:
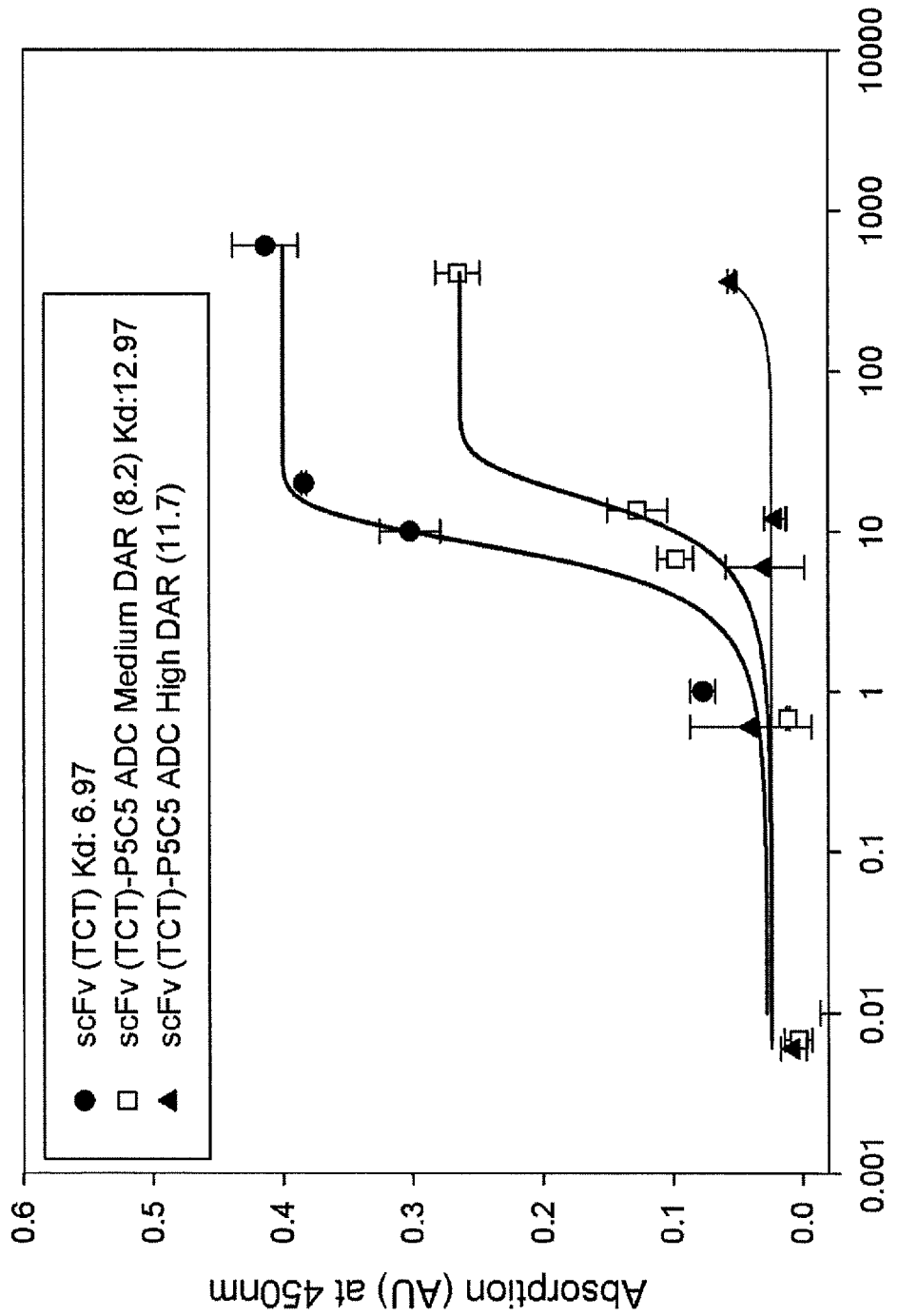

FIG. 30. ELISA of scFv (TCT) P5-C5 ADCs on HER2

Figure 31:
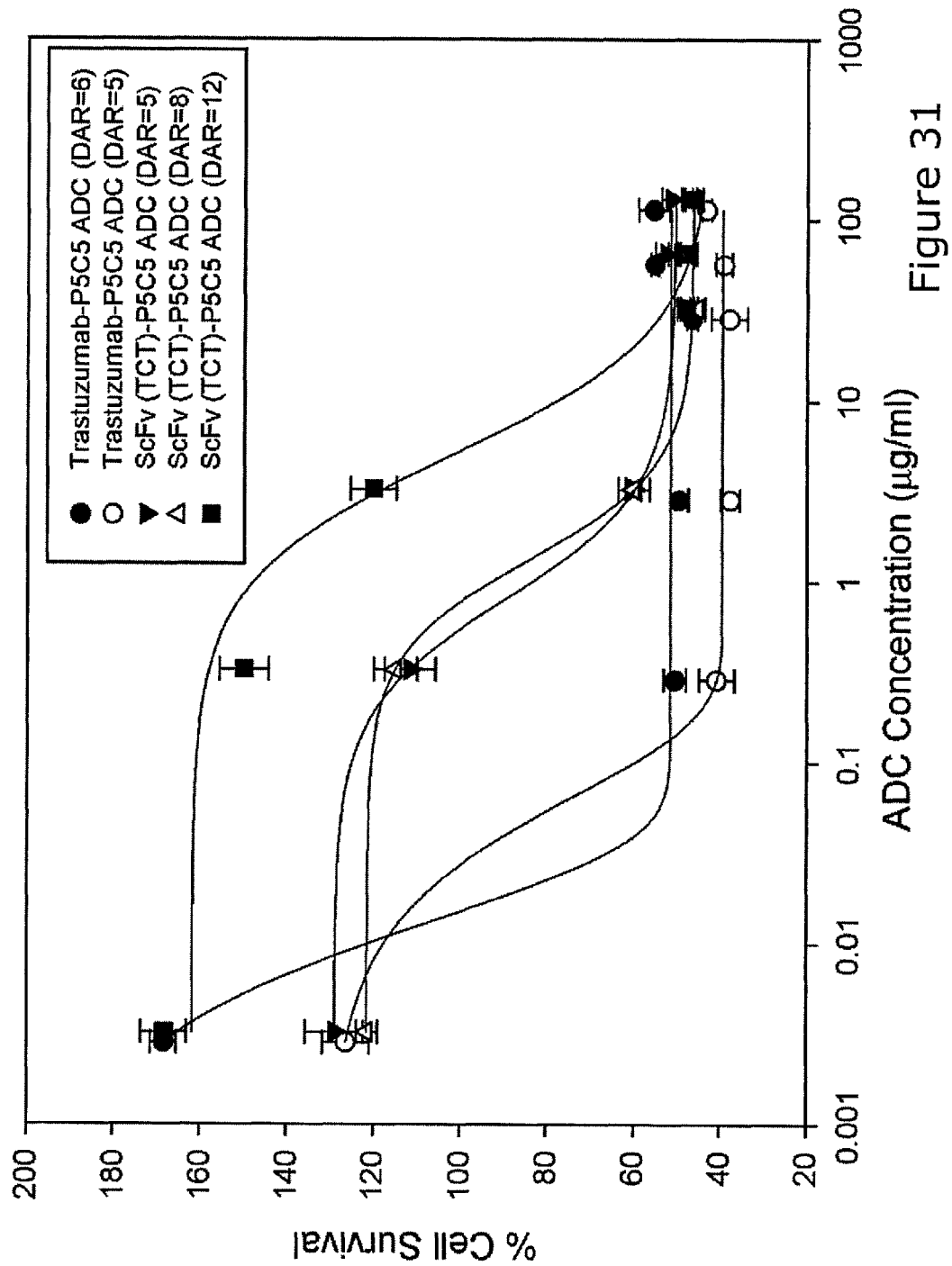
Figure 32:
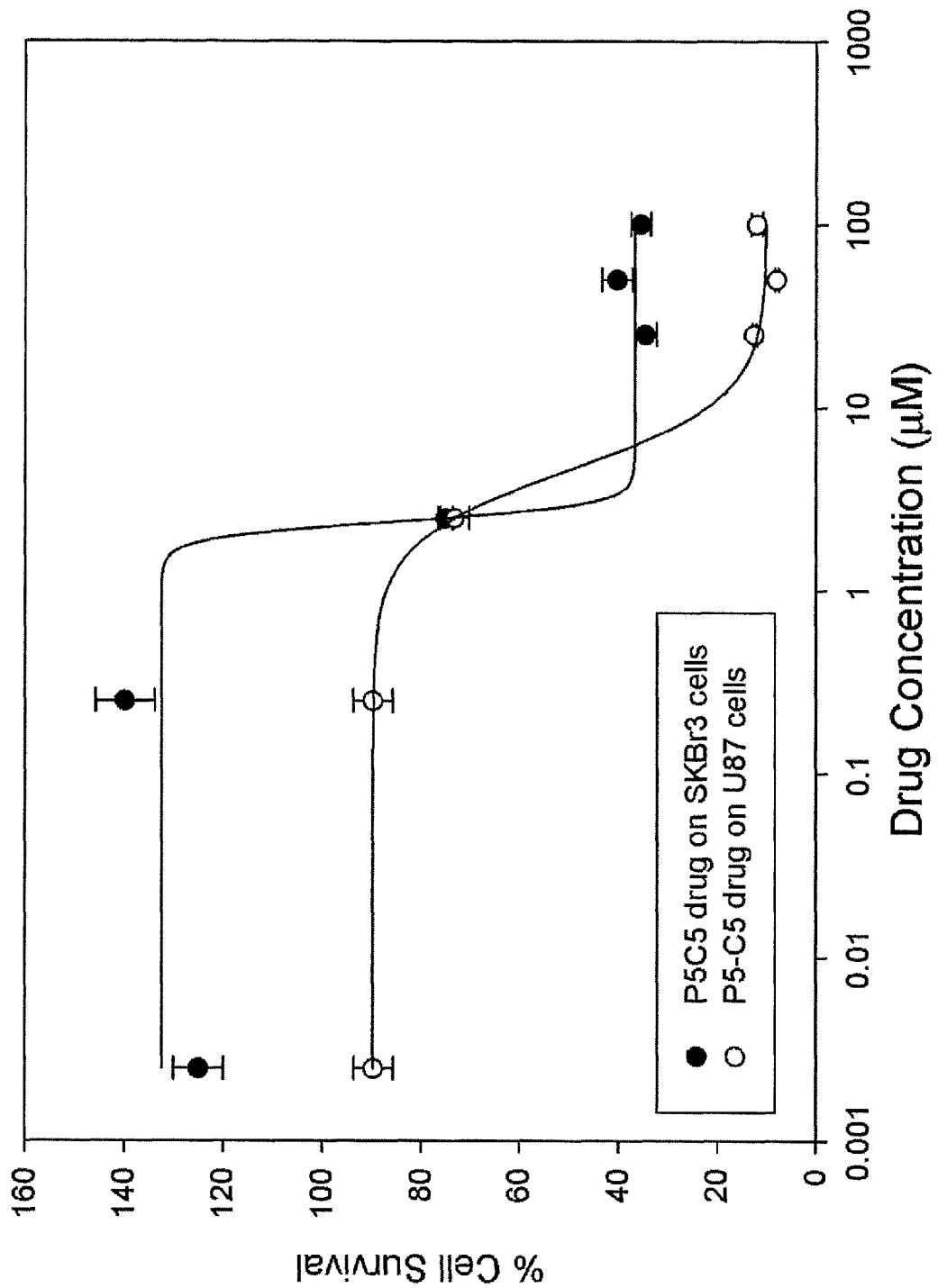
Figure 33:
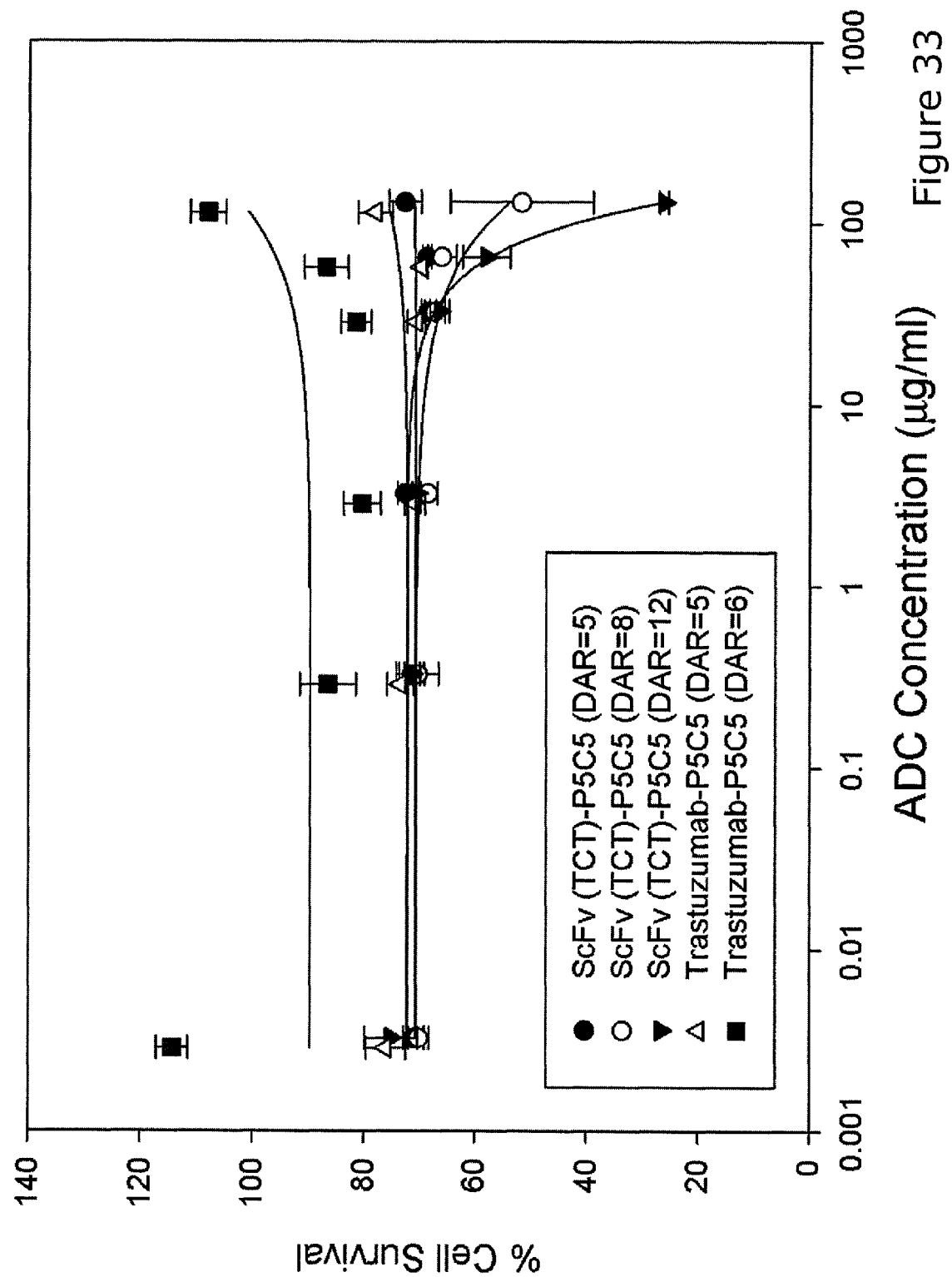
Figure 36:
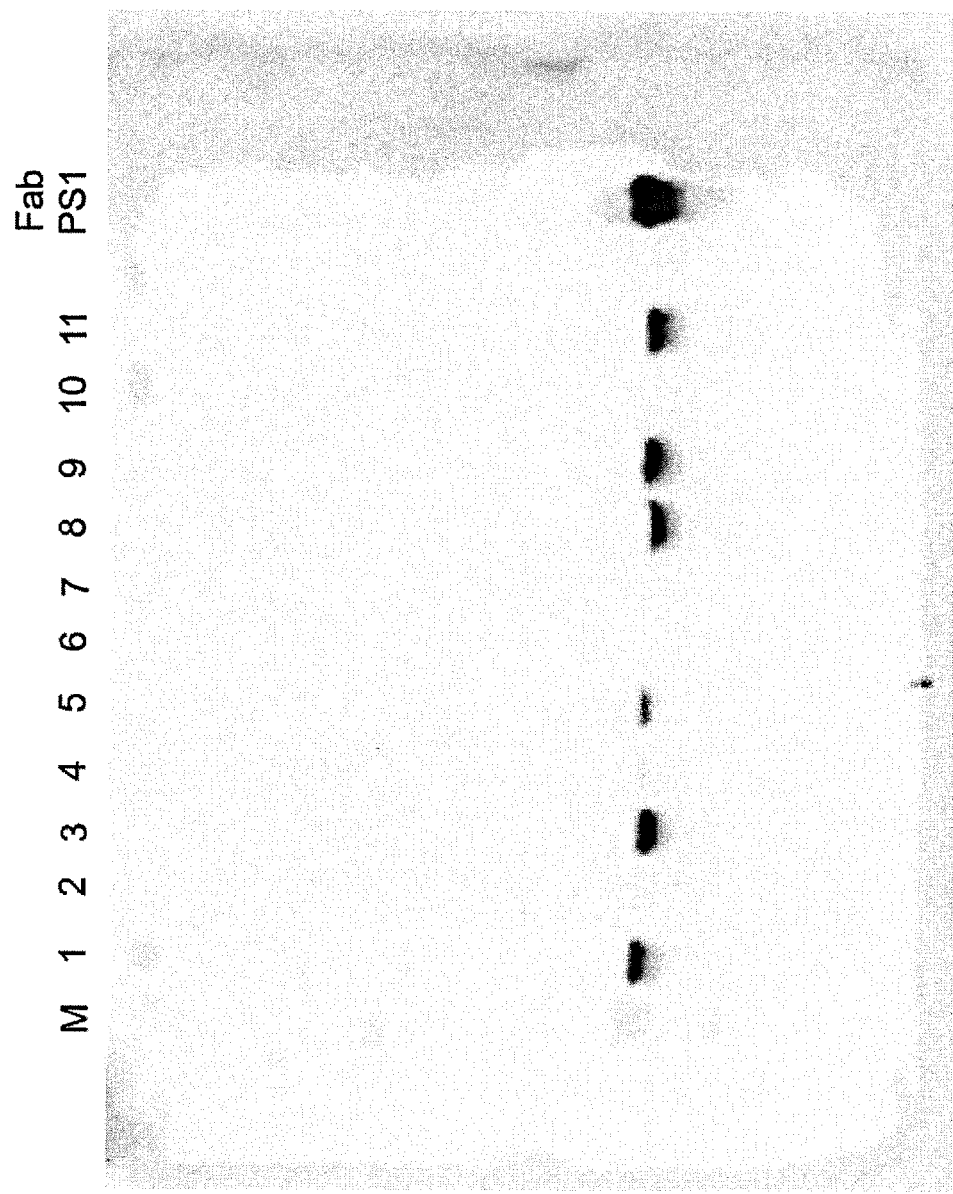
Figure 37:
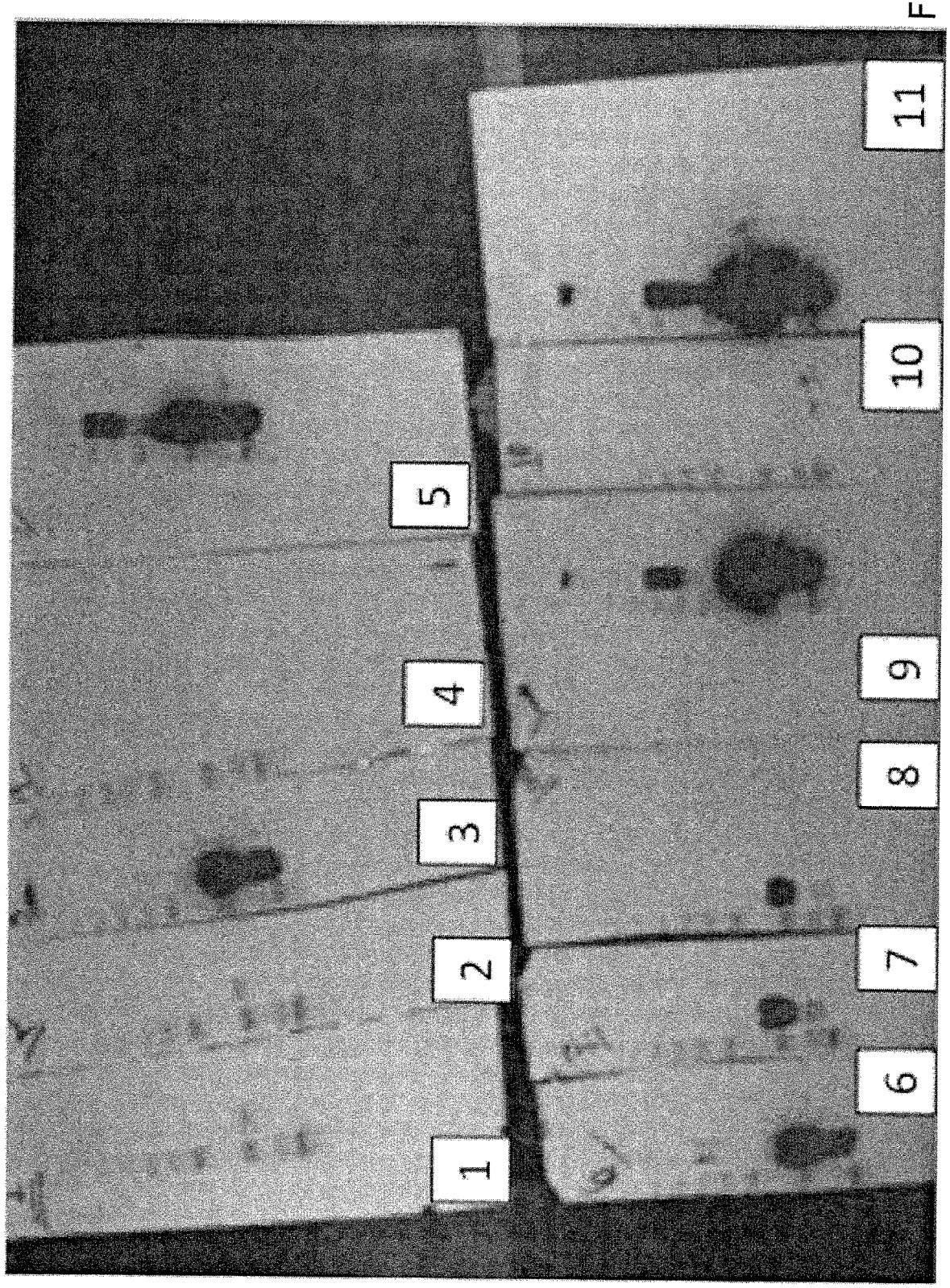

FIG. 31. Dose-response cell killing activity of P5C5-based ADCs on HER2-expressing SKBr3 cells FIG. 32. Dose-response cell killing activity of free P5C5 drug on HER2-expressing SKBr3 cells and HER2-negative U87 cells FIG. 33. Dose-response cell killing activity of P5C5-based ADCs on HER2-negative U87 cells FIG. 34. ELISA testing of candidate mouse sera immunised with scFv-Cemadotin ADCs FIG. 35. ELISA of candidate hybridoma clones for anti-scFv-Cemadotin MAbs FIG. 36. Candidate Hybridoma media supernatant detection of murine Mab by Western Blot, using anti-mouse peroxidase secondary antibody FIG. 37. Candidate Hybridoma conditioned media used to detect scFv-Cemadotin ADCs by Western Blot Blots 1-3 and 5-7, 10, and 11 are loaded as follows: Marker; ADC; TCT; and free Cemadotin.

Blots 4 and 8 are loaded as follows: Marker; ADC; and free Cemadotin.

Figure 38:
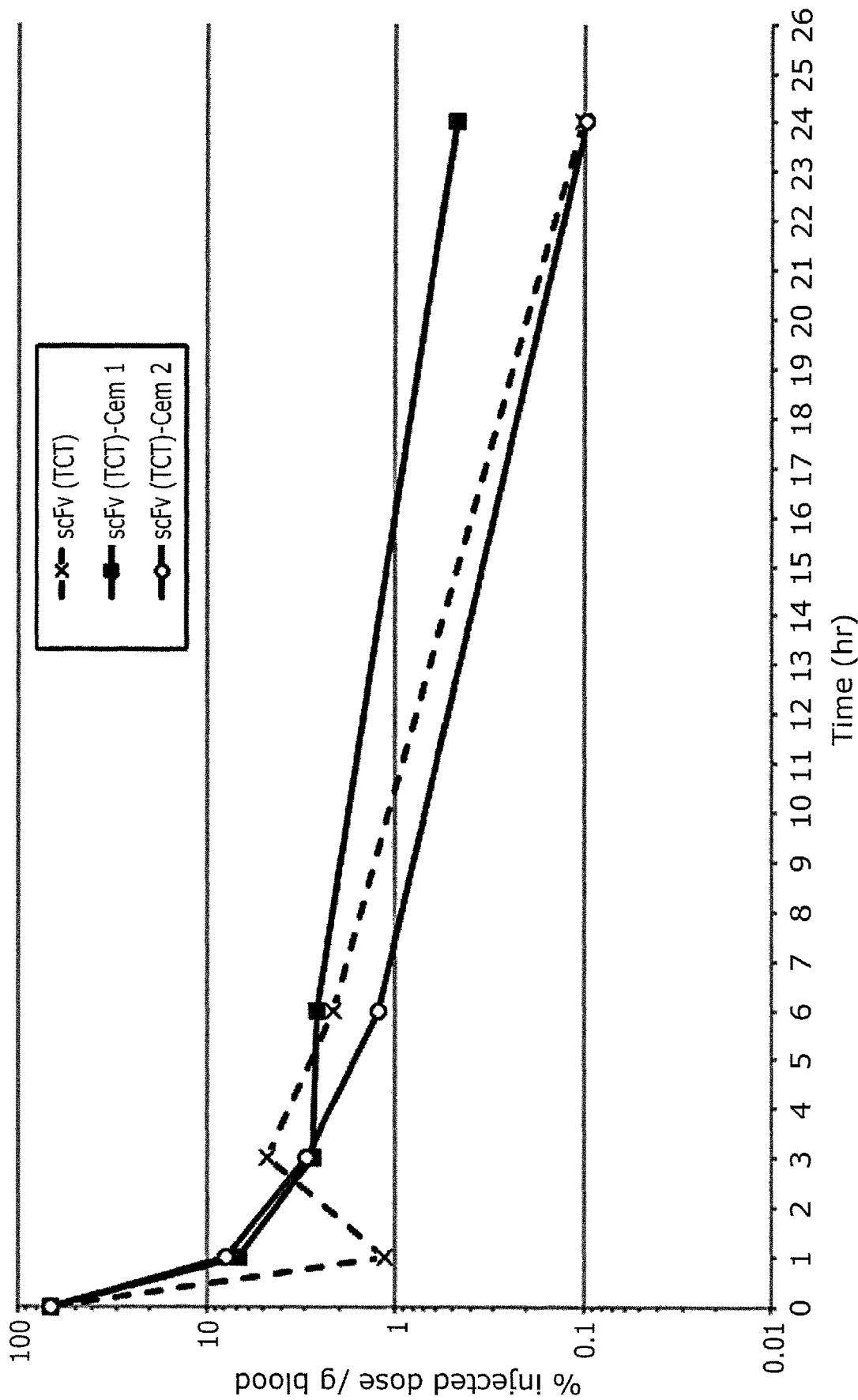

FIG. 38. Blood clearance of radiolabelled scFv (TCT)-Cemadotin conjugates.

Cemadotin conjugate (compound 69).

Figure 39:
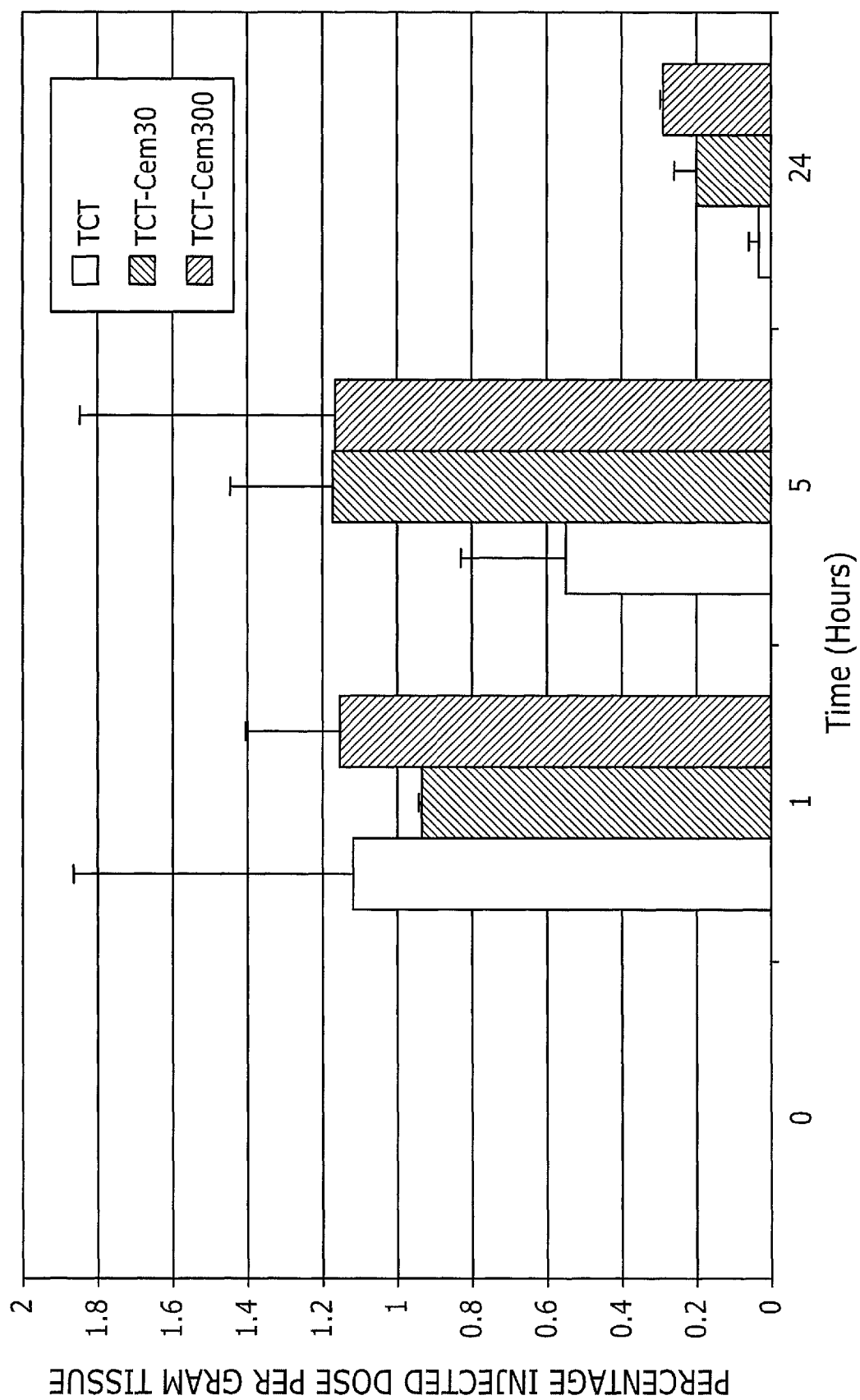

FIG. 39. Spleen uptake of radiolabelled scFv (TCT)-Cemadotin conjugates.

Cemadotin conjugate (compound 69).

Figure 40:
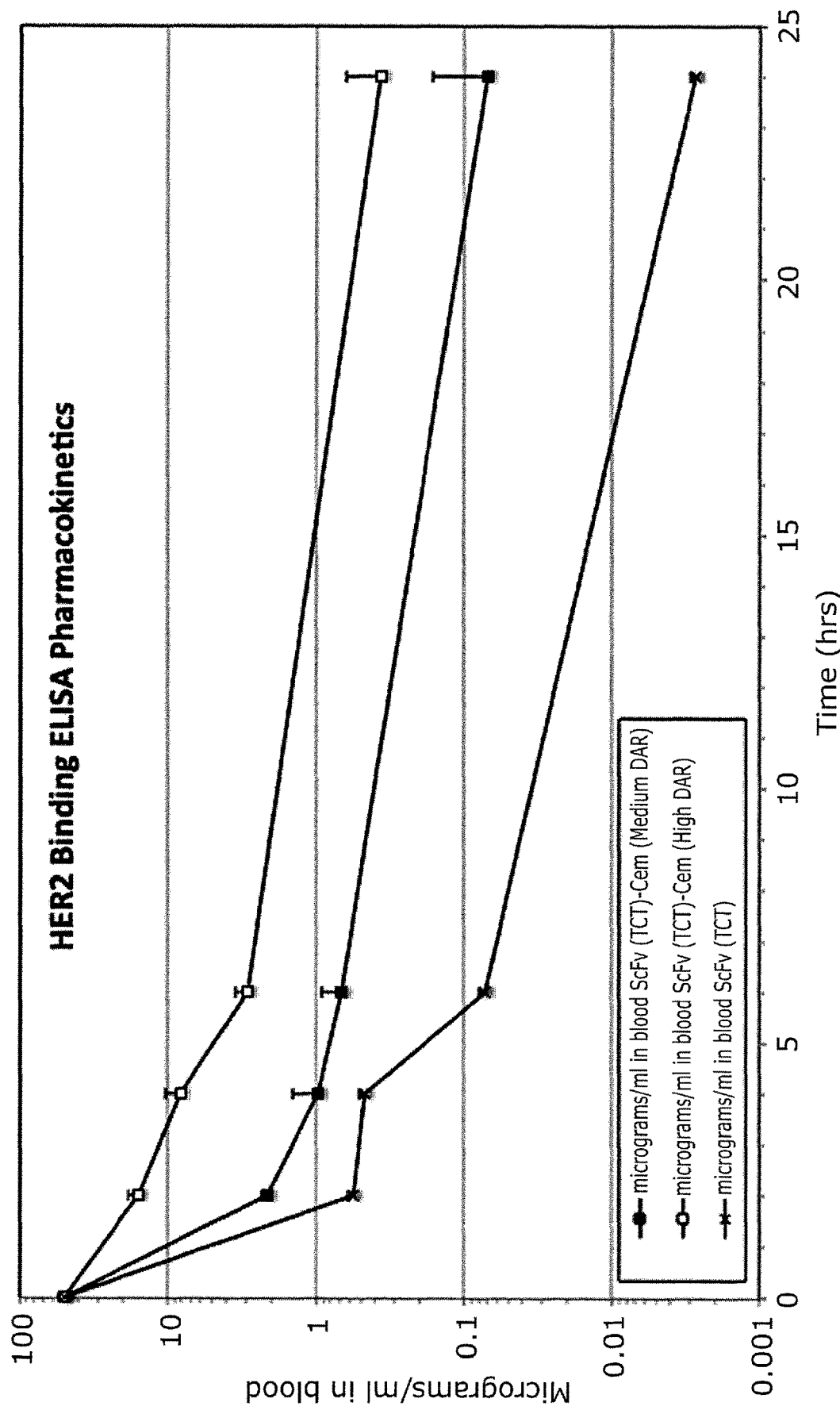

FIG. 40. Pharmacokinetic profile showing blood clearance of scFv-TCT and scFv-TCT-ADCs measured by total antibody ELISA.

Cemadotin conjugate (compound 69).

Figure 41:
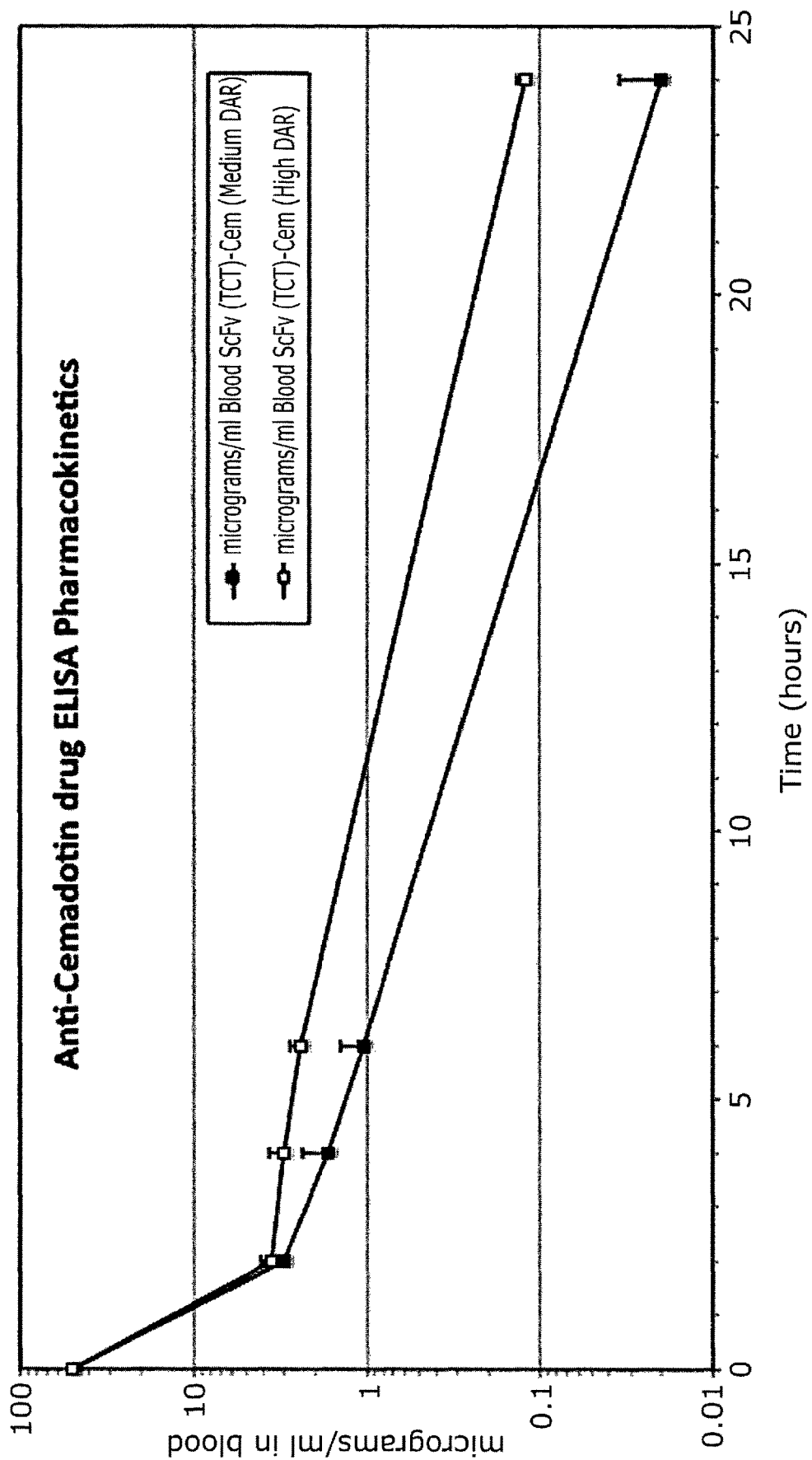

FIG. 41. Pharmacokinetic profile showing blood clearance of scFv-TCT-ADCs measured by total ADC ELISA.

Cemadotin conjugate (compound 69).

Figure 42:
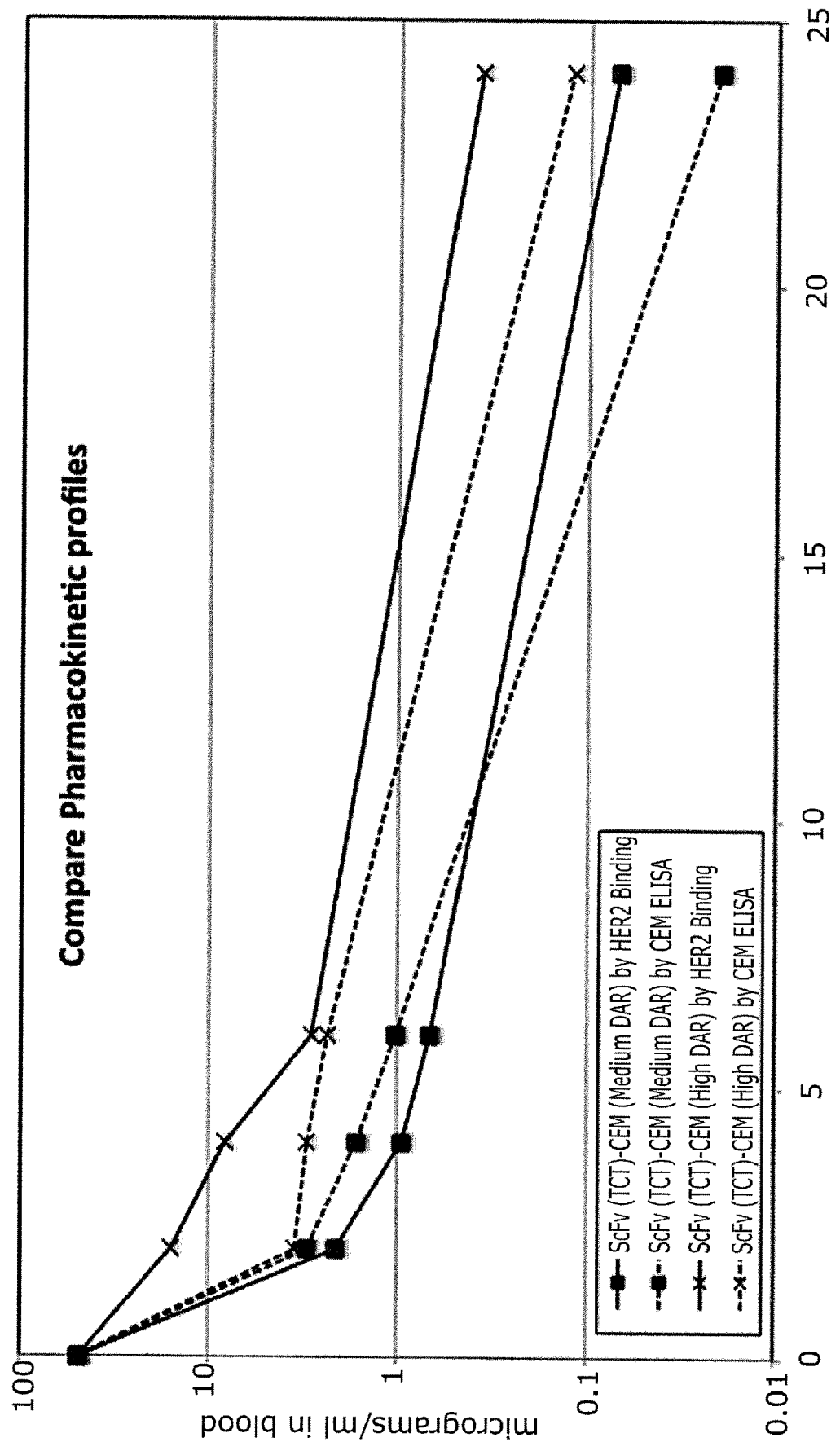

FIG. 42. Comparative pharmacokinetic profile showing similarities in the blood clearance of scFv-TCT and scFv-TCT-ADCs measured both assays used in FIGS. 40 & 41.

Figure 43:
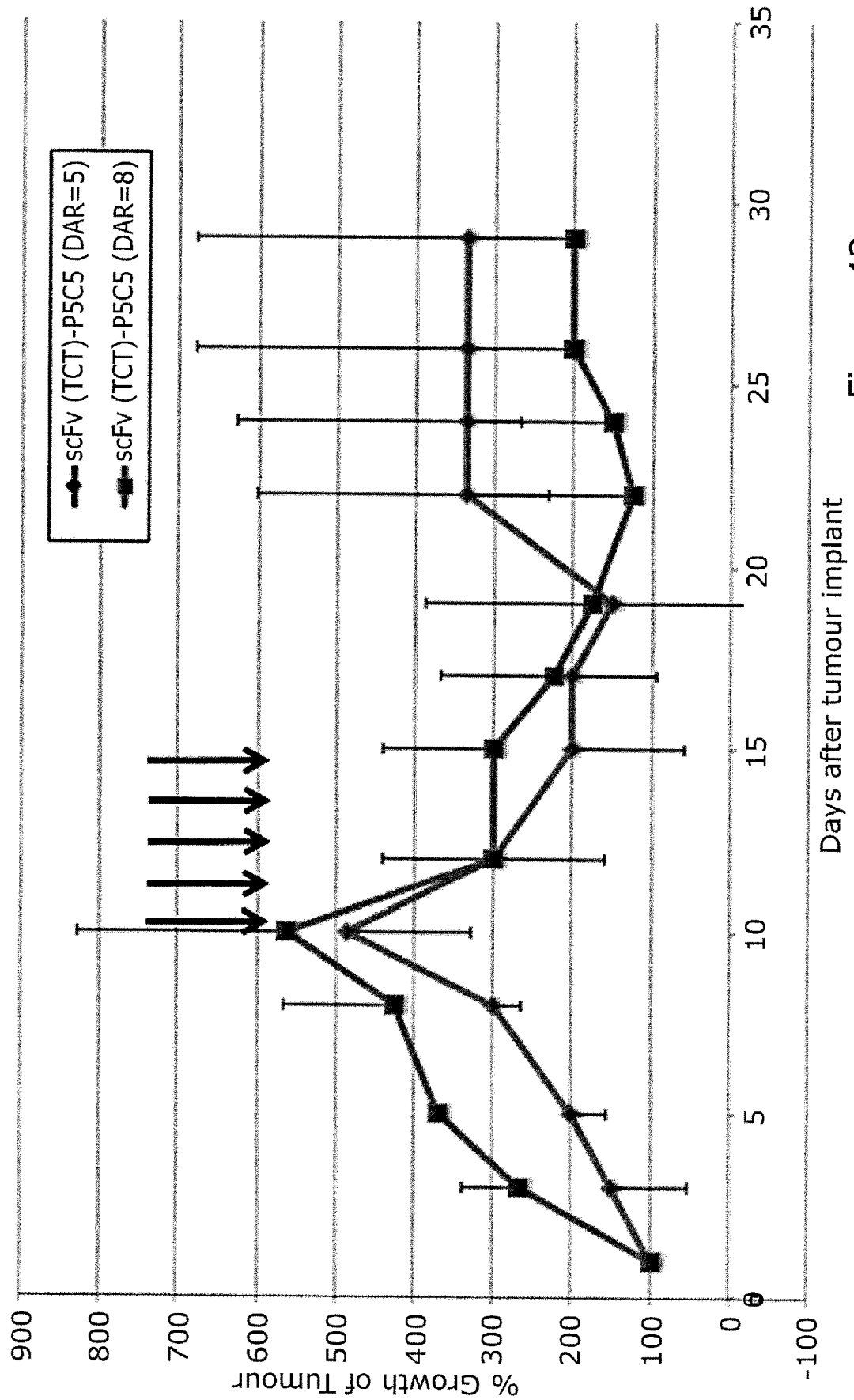

FIG. 43. Tumour regression studies in nude mice bearing SKBr3 tumour xenografts treated with two scFv (TCT)-P5C5 ADC DARs.

P5C5 conjugate (compound 71).

Figure 44:
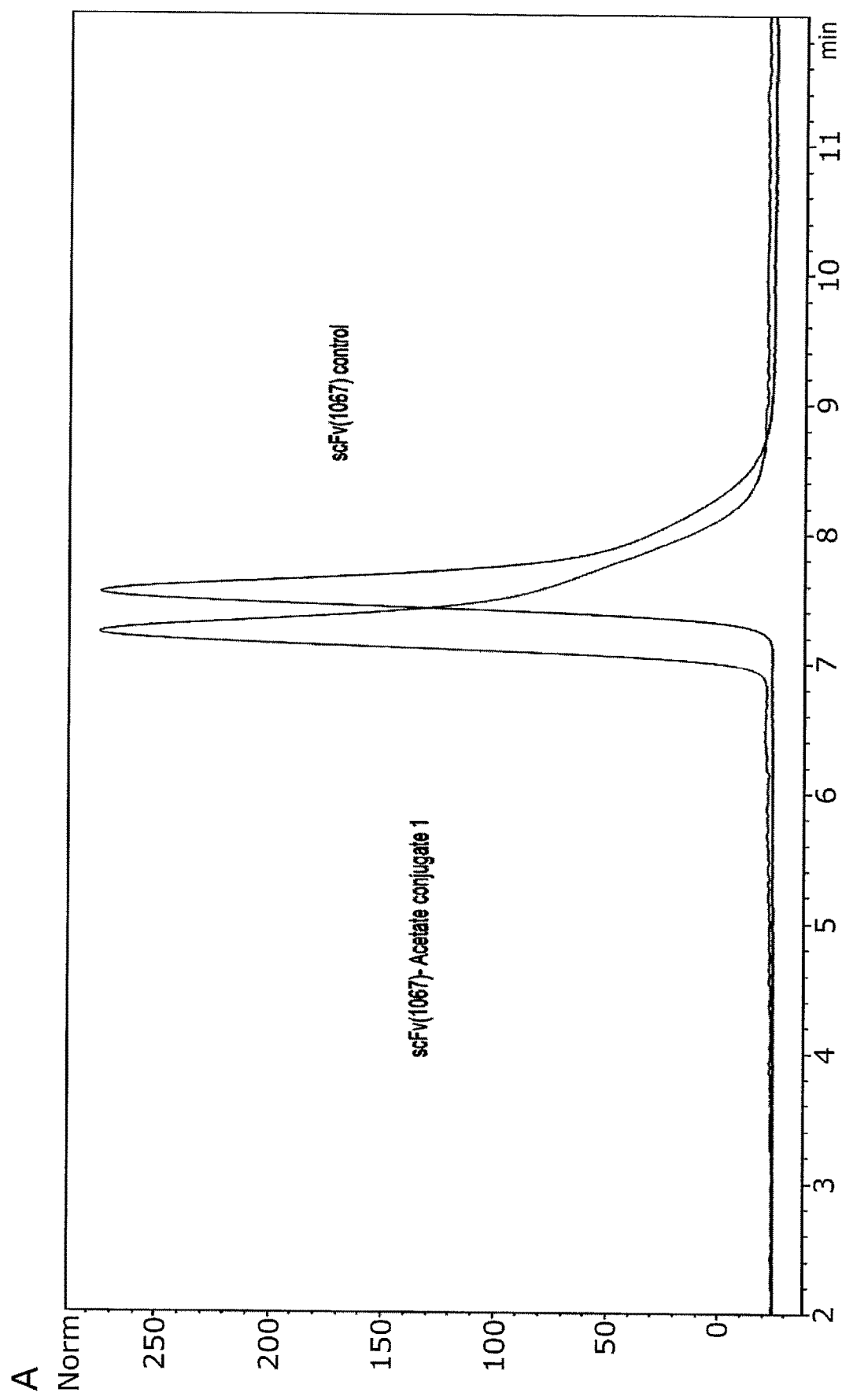
Figure 44:
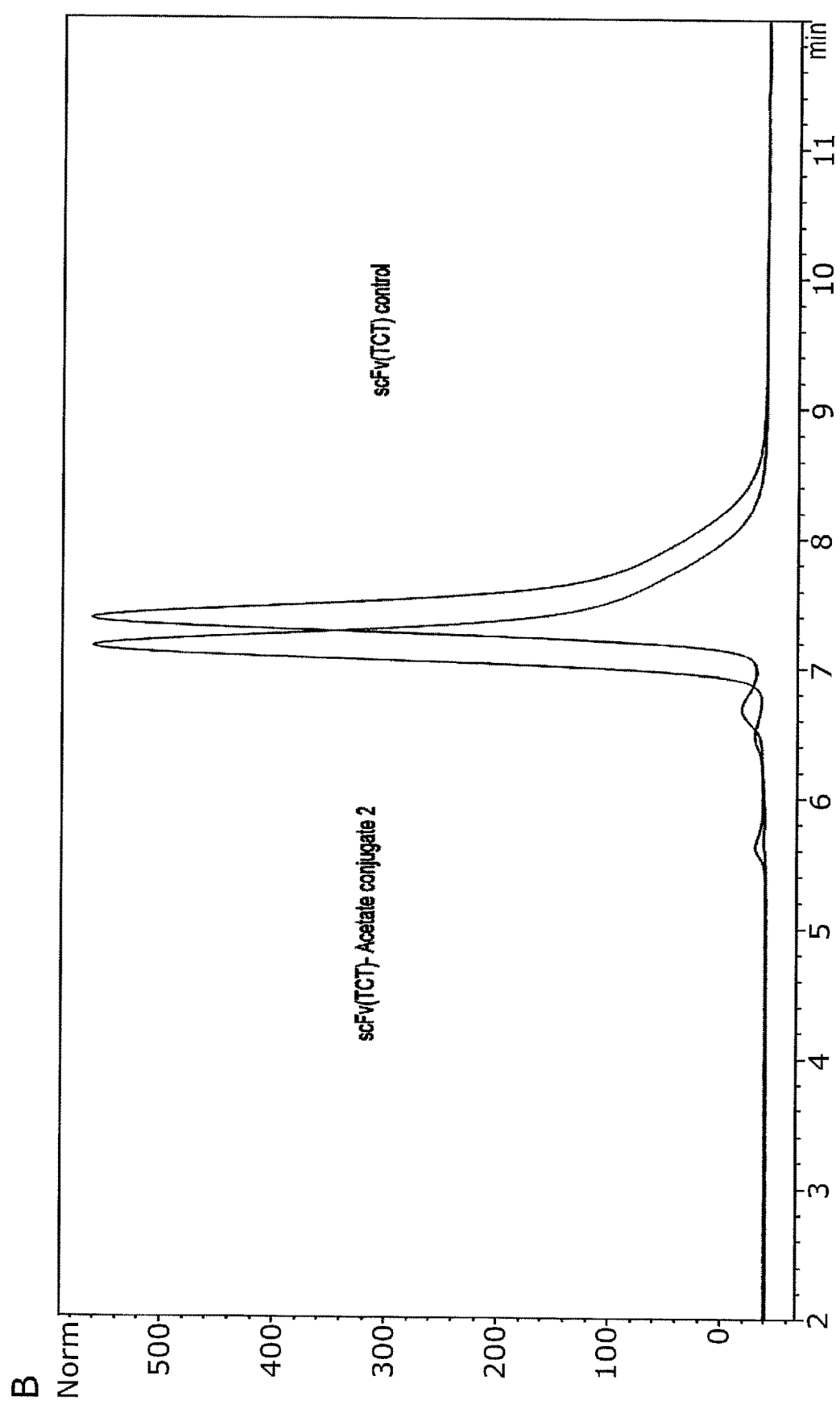

FIG. 44. HPLC SEC traces (A280 nm) for (A) scFv (TCT1067)-Acetate and (B) scFv (TCT)-Acetate purified conjugates run at 0.5 ml/min and compared to the respective unconjugated antibodies.

Figure 45:
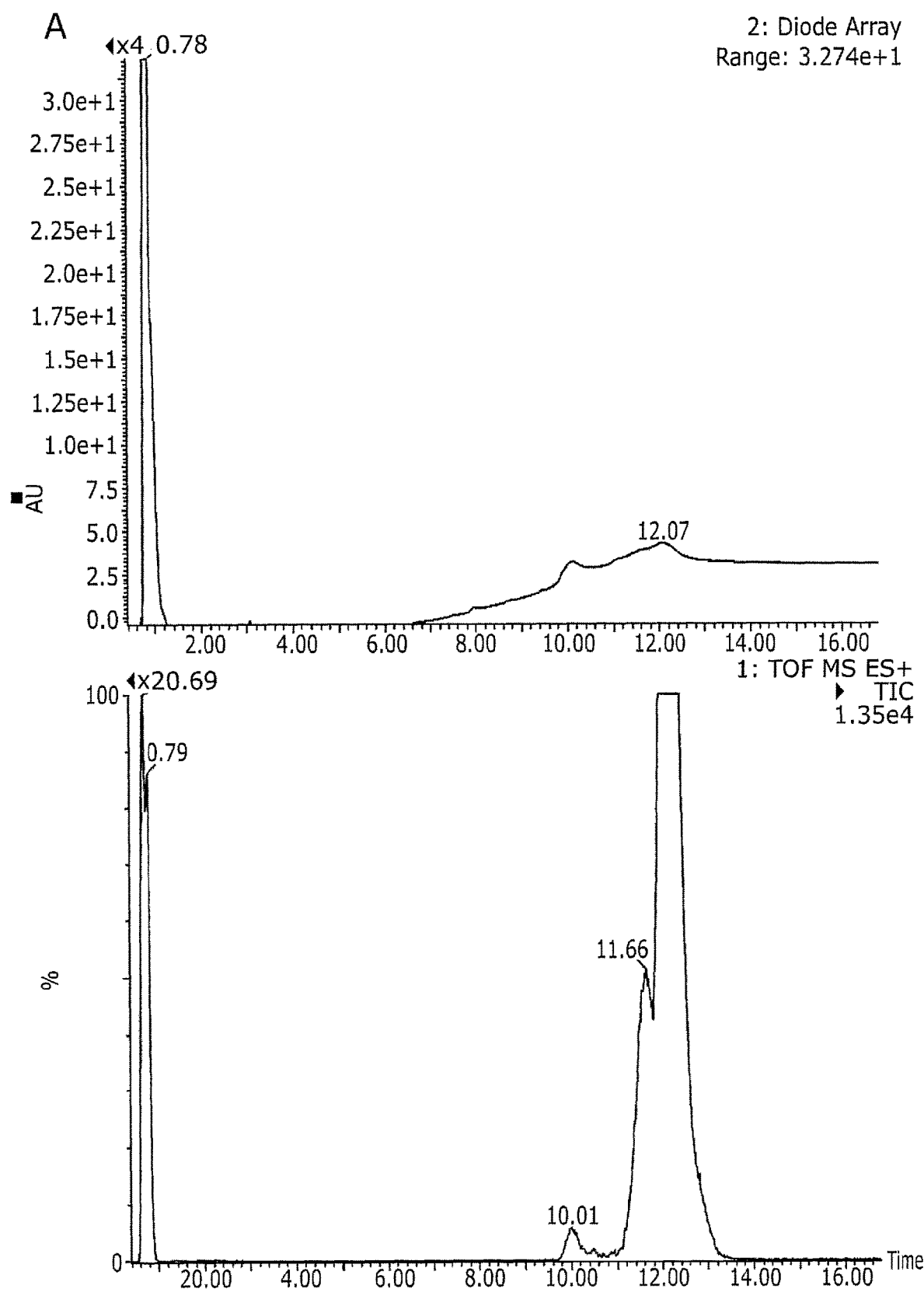
Figure 45:
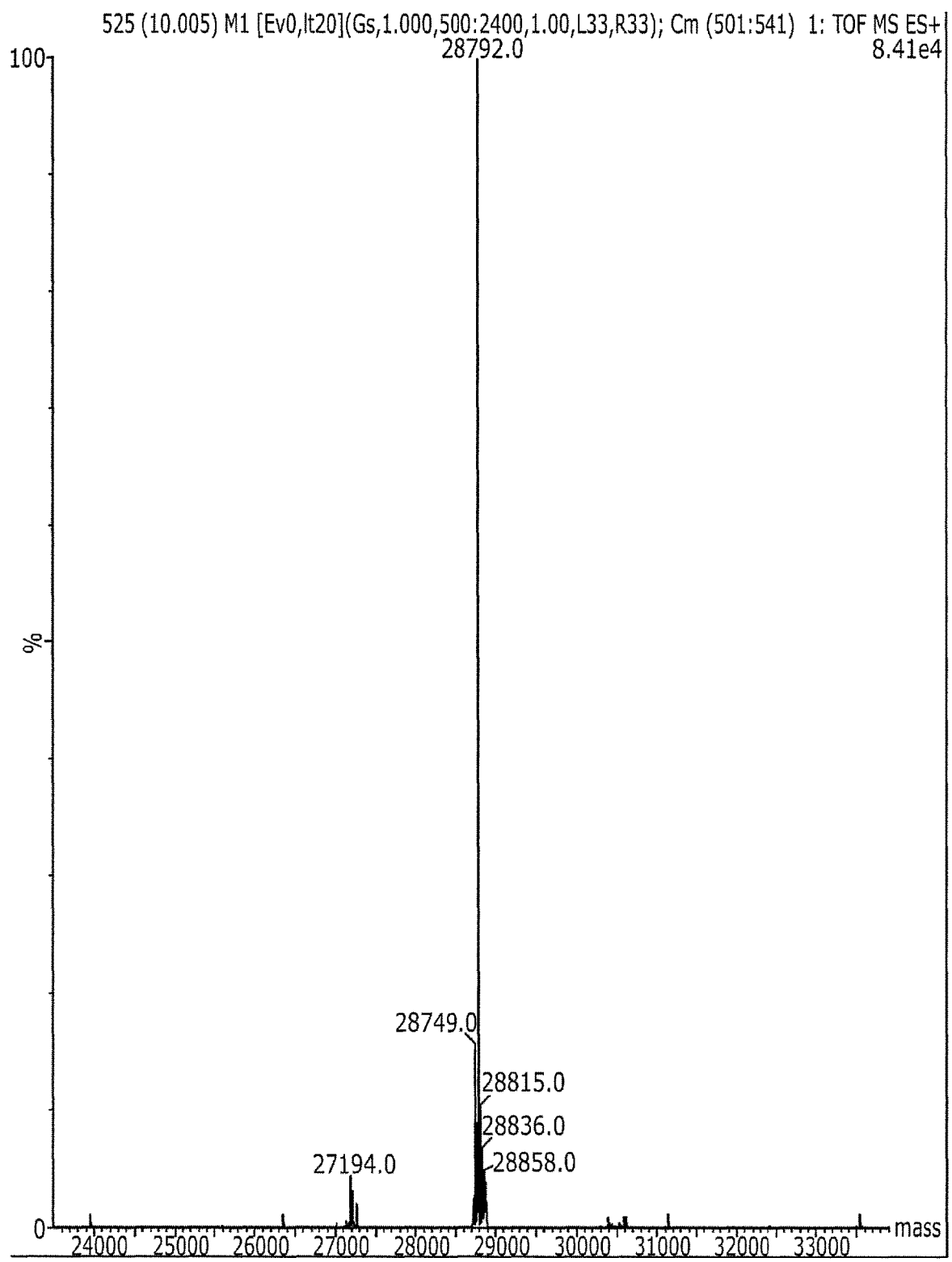

FIG. 45. LCMS data for the scFv (TCT)-Acetate conjugate.

(A) is the LCMS trace (UV and TIC) and (B) is the deconvoluted mass for the main peak at 10 mins.

Figure 46:
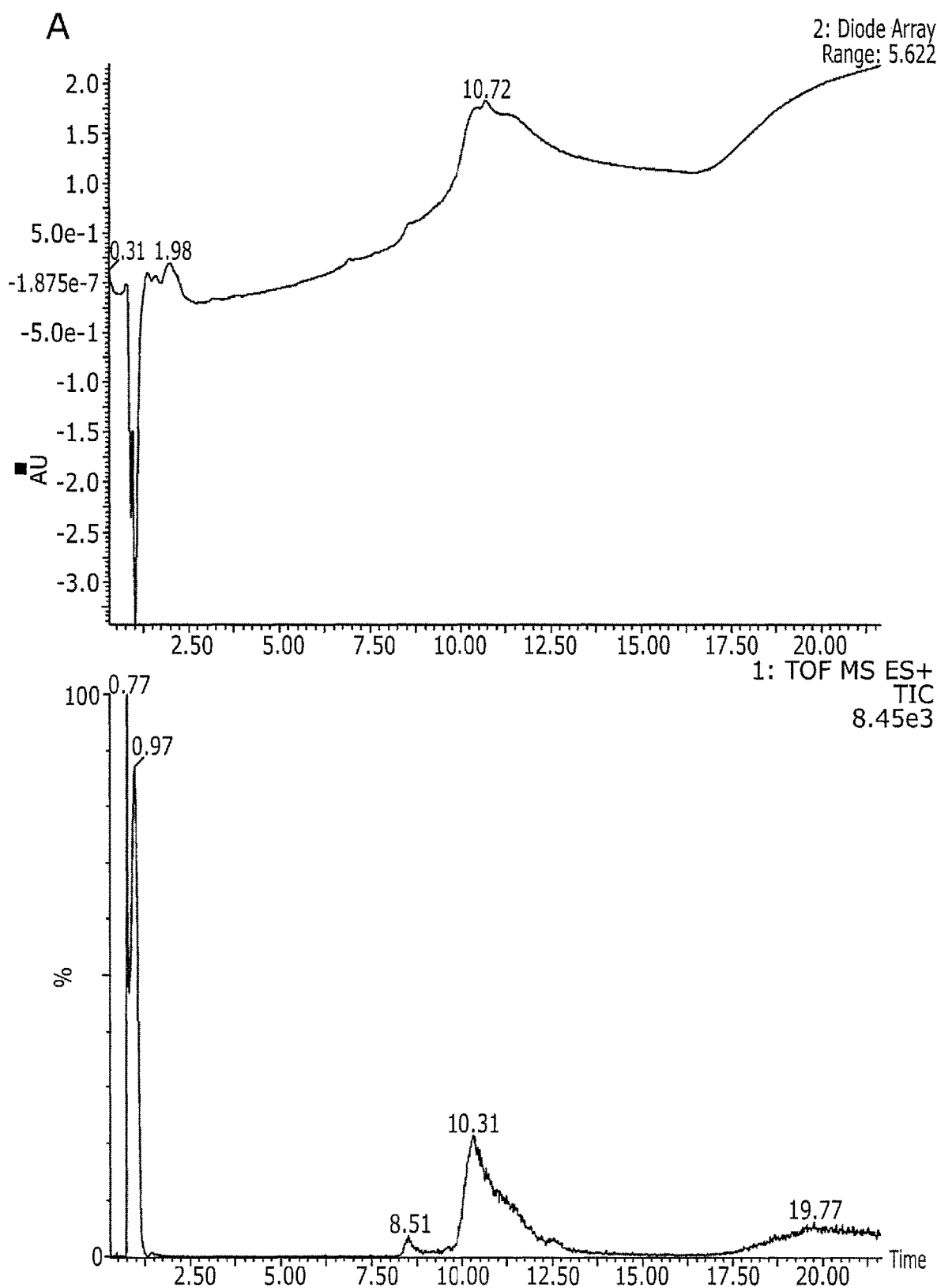
Figure 46:
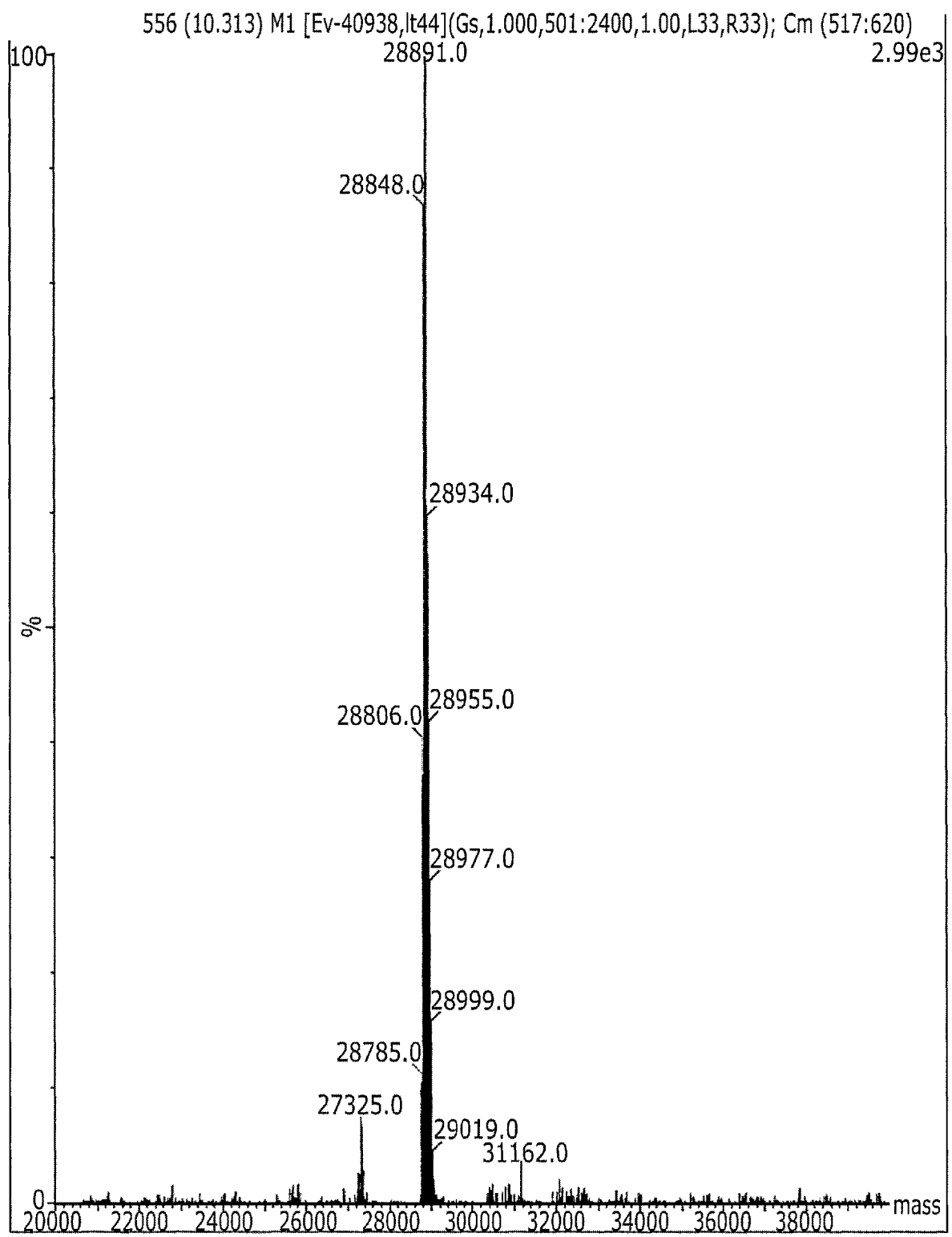

FIG. 46. LCMS data for the scFv (TCT1067)-Acetate conjugate.

(A) is the LCMS trace (UV and TIC) and (B) is the deconvoluted mass for the main peak at 10.3 mins.

Figure 47:
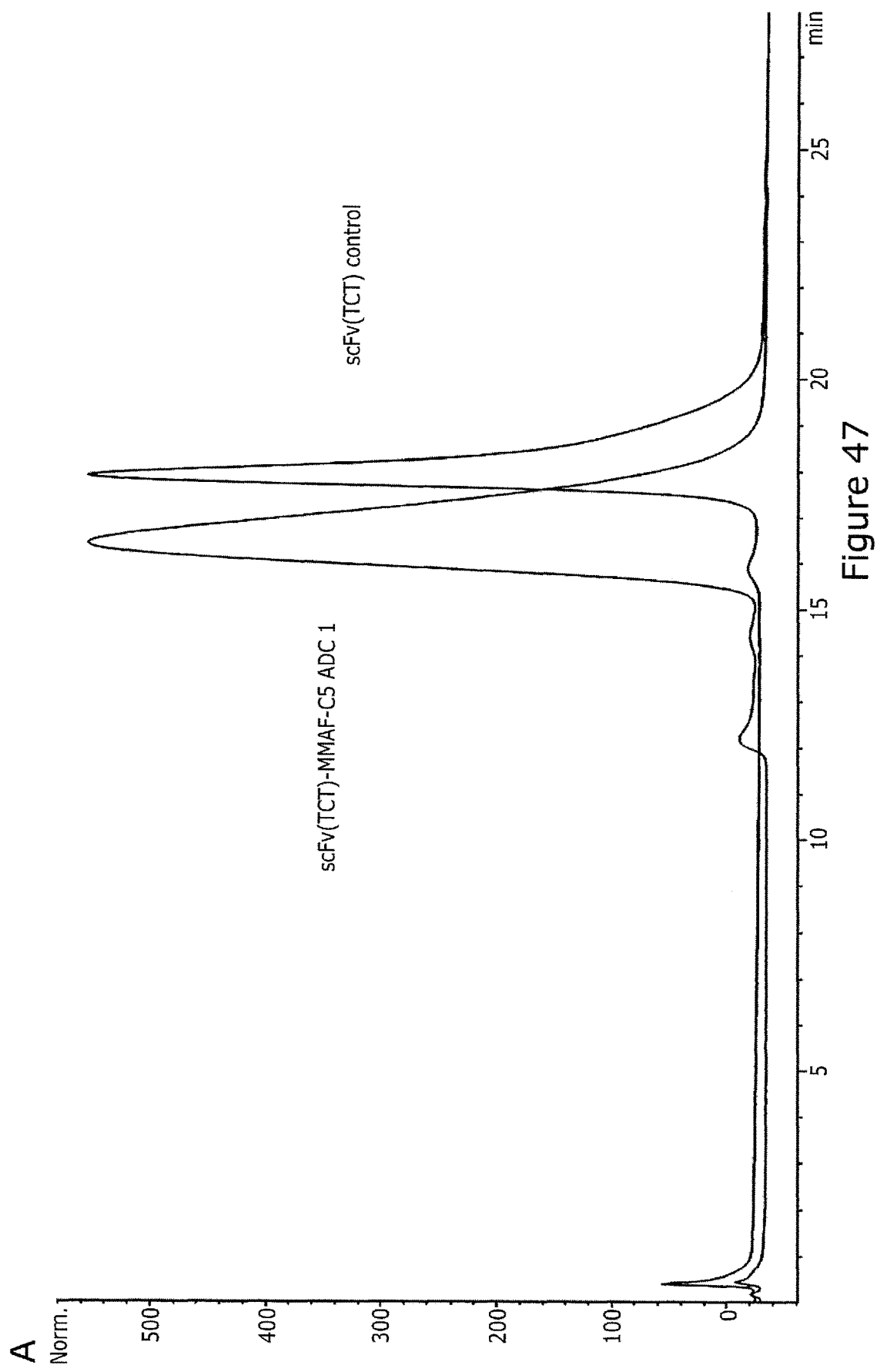
Figure 47:
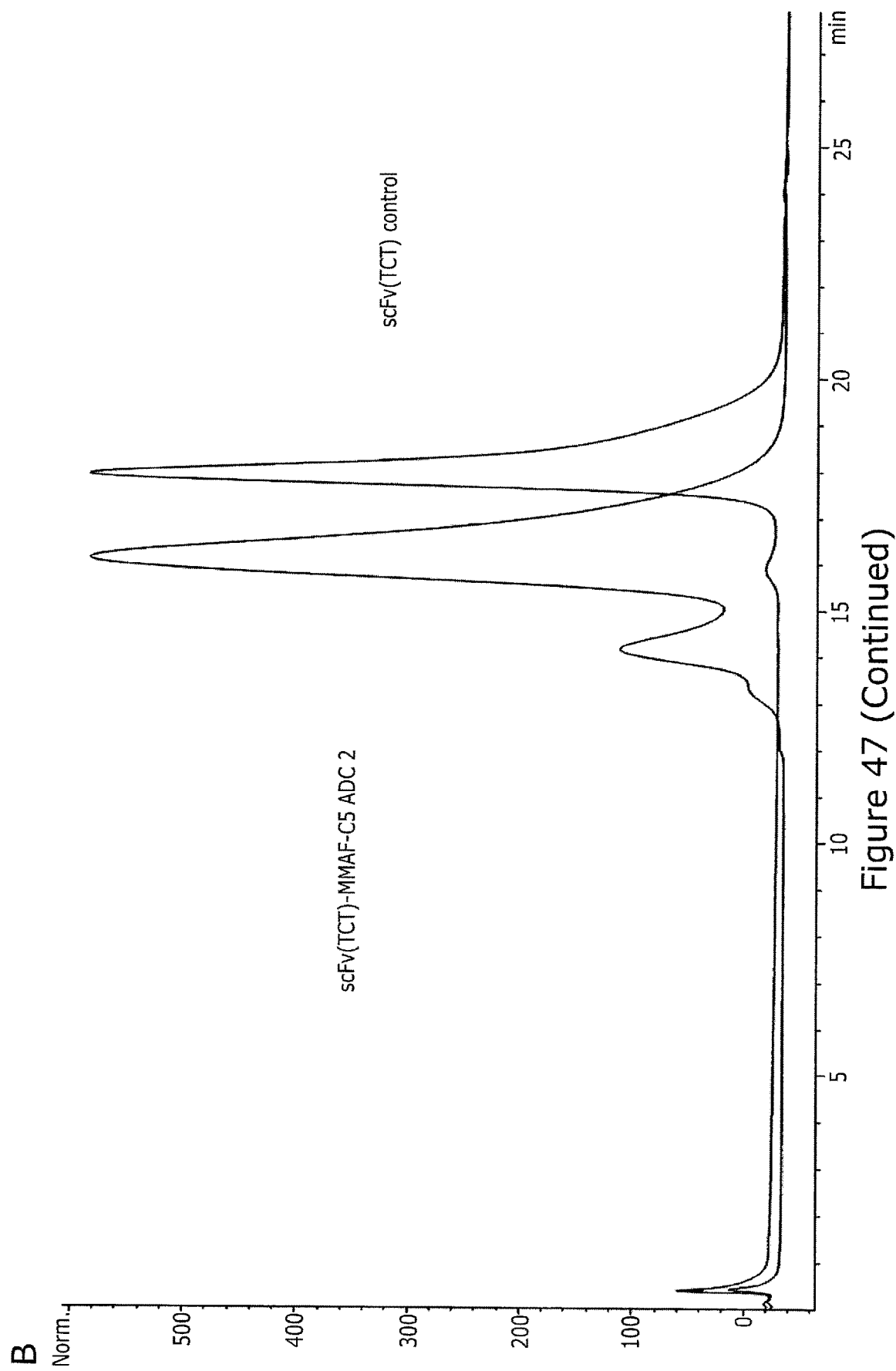

FIG. 47. HPLC SEC traces (A280 nm) for (A) scFv (TCT)-MMAF-C5 ADC 1 and (B) scFv (TCT)-MMAF-C5 ADC 2 purified conjugates run at 1 ml/min and compared to the unconjugated antibody.

Figure 48:
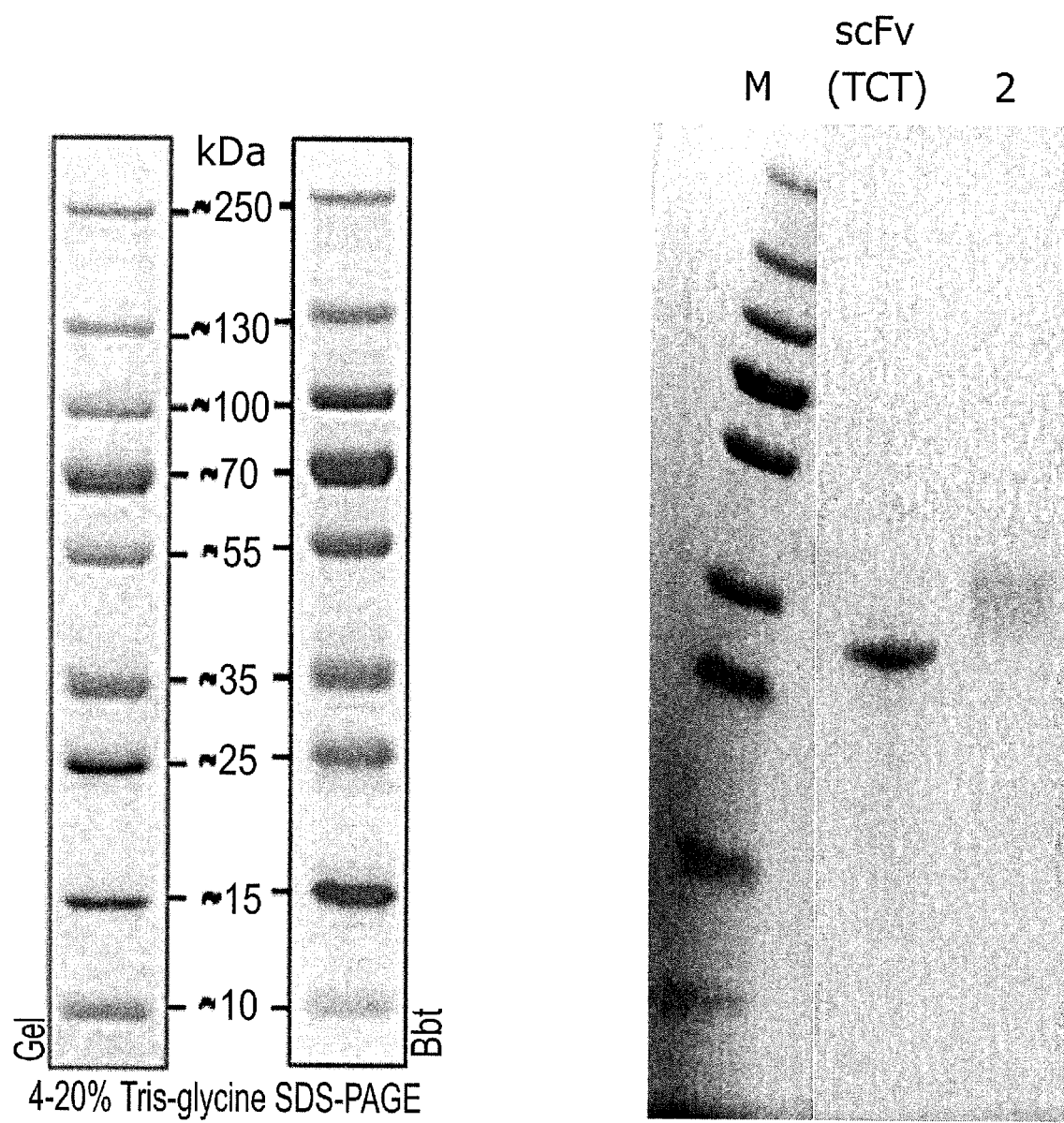

FIG. 48. SDS-PAGE reducing gel (12%) showing scFv (TCT)-MMAF-C5 ADC 2 in comparison with scFv (TCT) unconjugated antibody.

Size markers used are shown.

Figure 49:
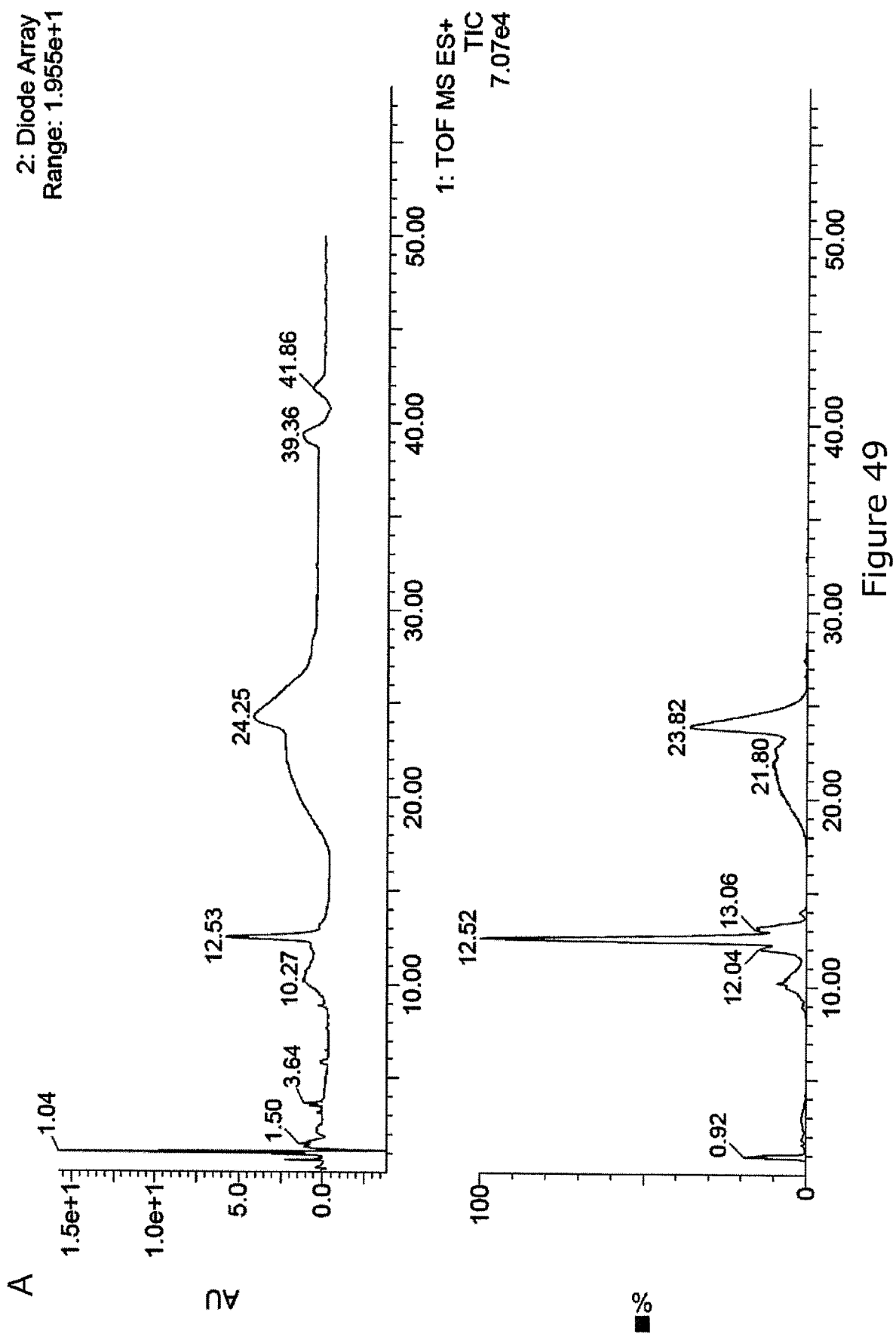
Figure 49:
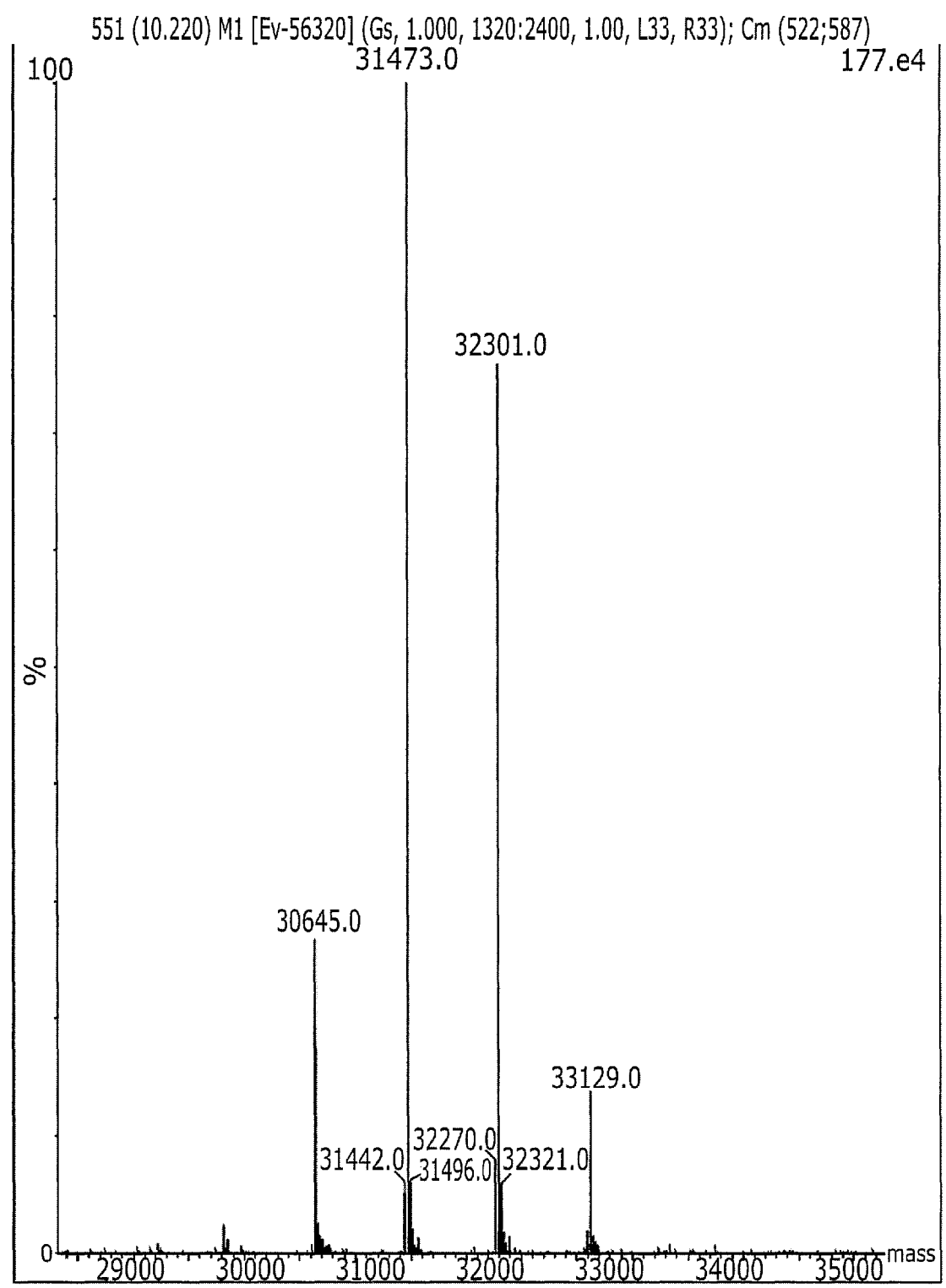

FIG. 49. LCMS data for scFv (TCT)-MMAF-C5 ADC 1.

(A) is the LCMS trace (UV and TIC) and (B) is the deconvoluted mass for the main peak at 10.2 mins.

Figure 50:
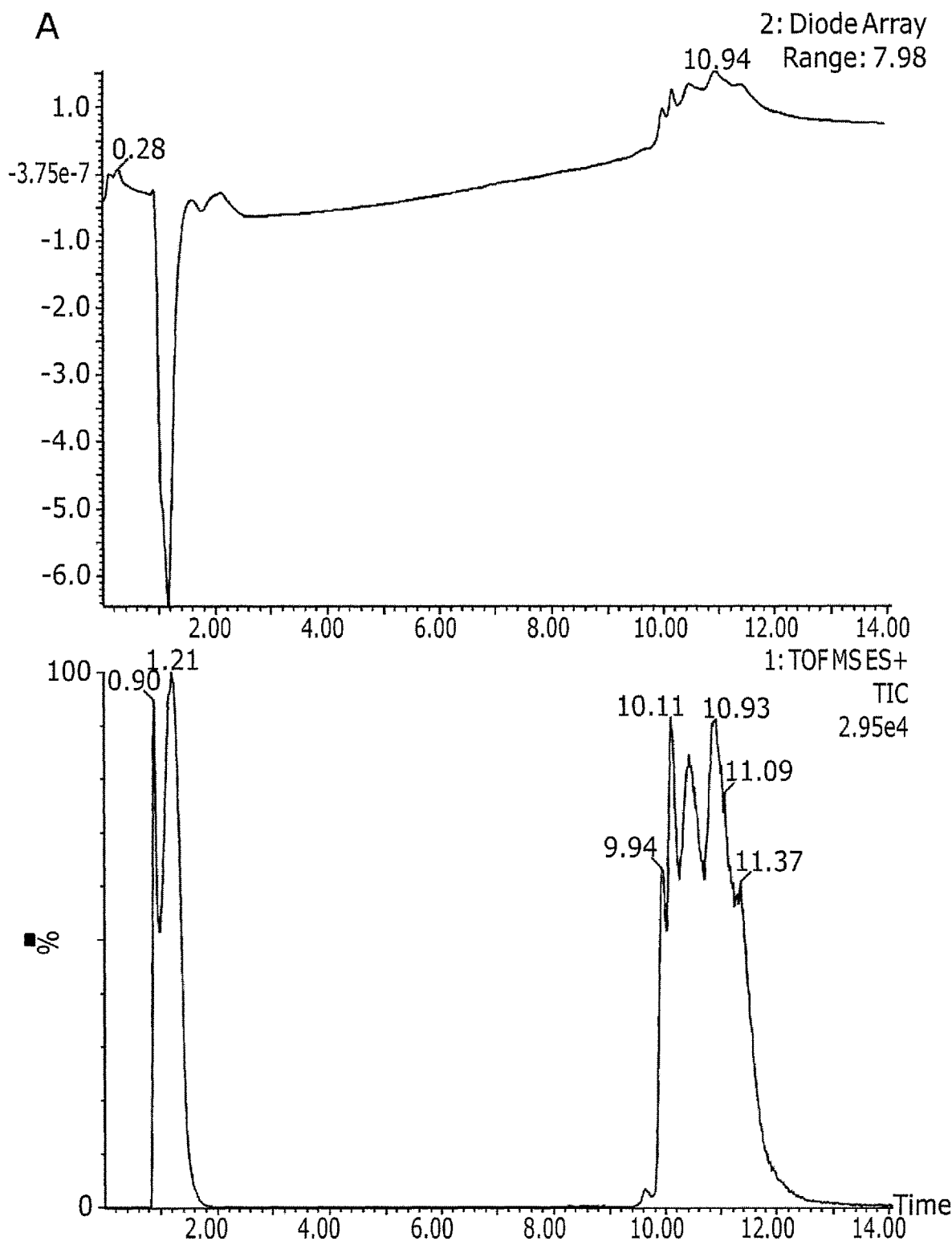
Figure 50:
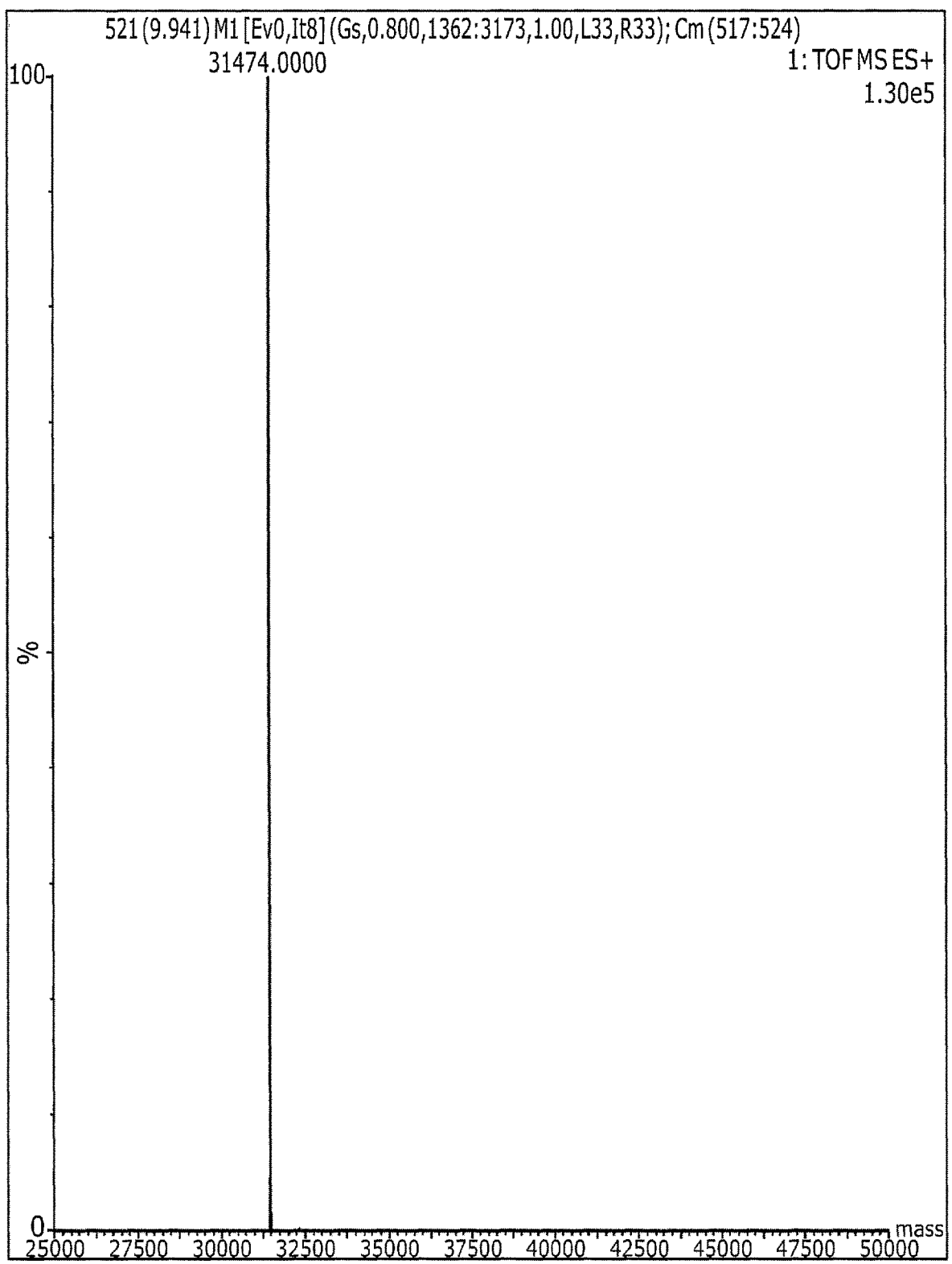
Figure 50:
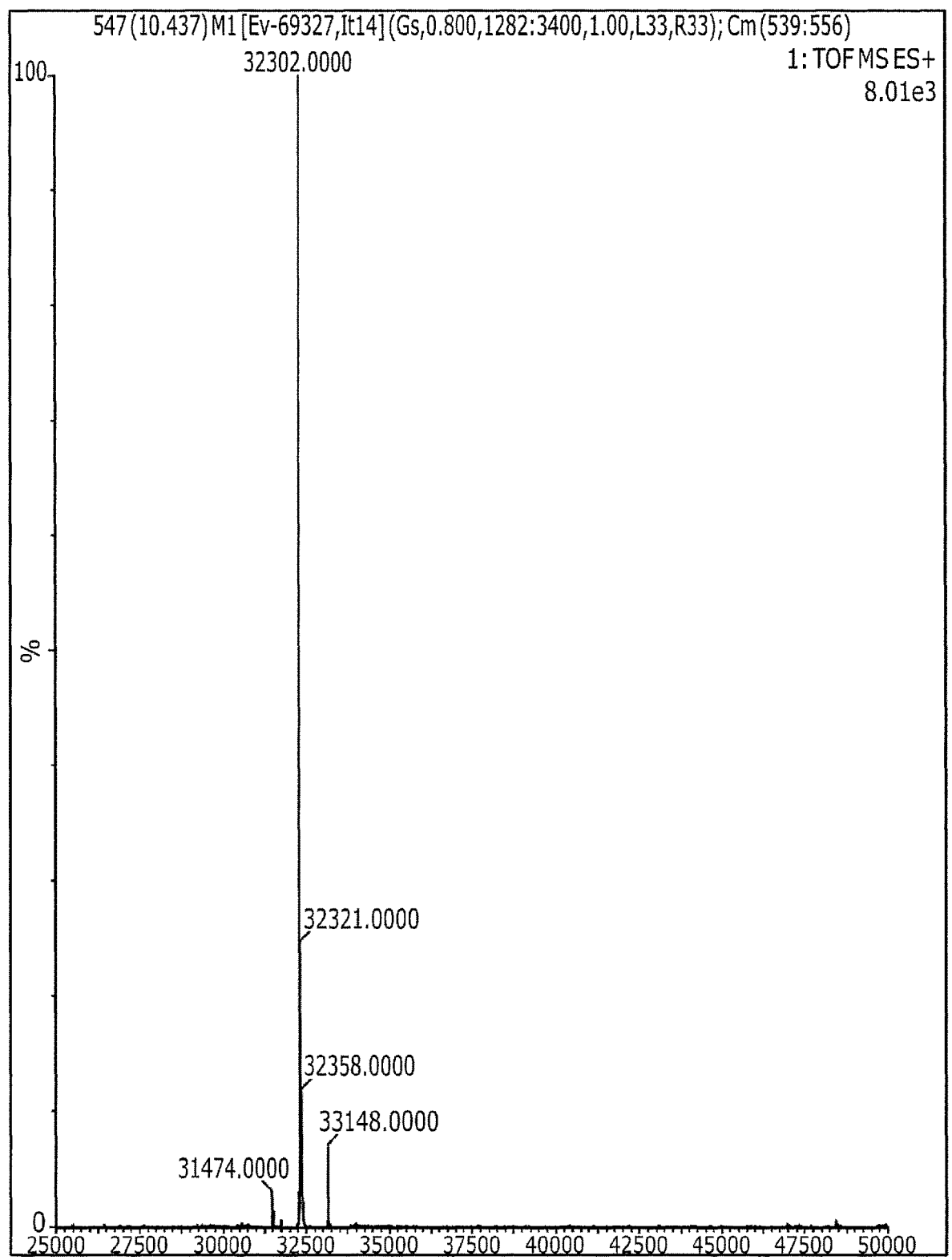
Figure 50:
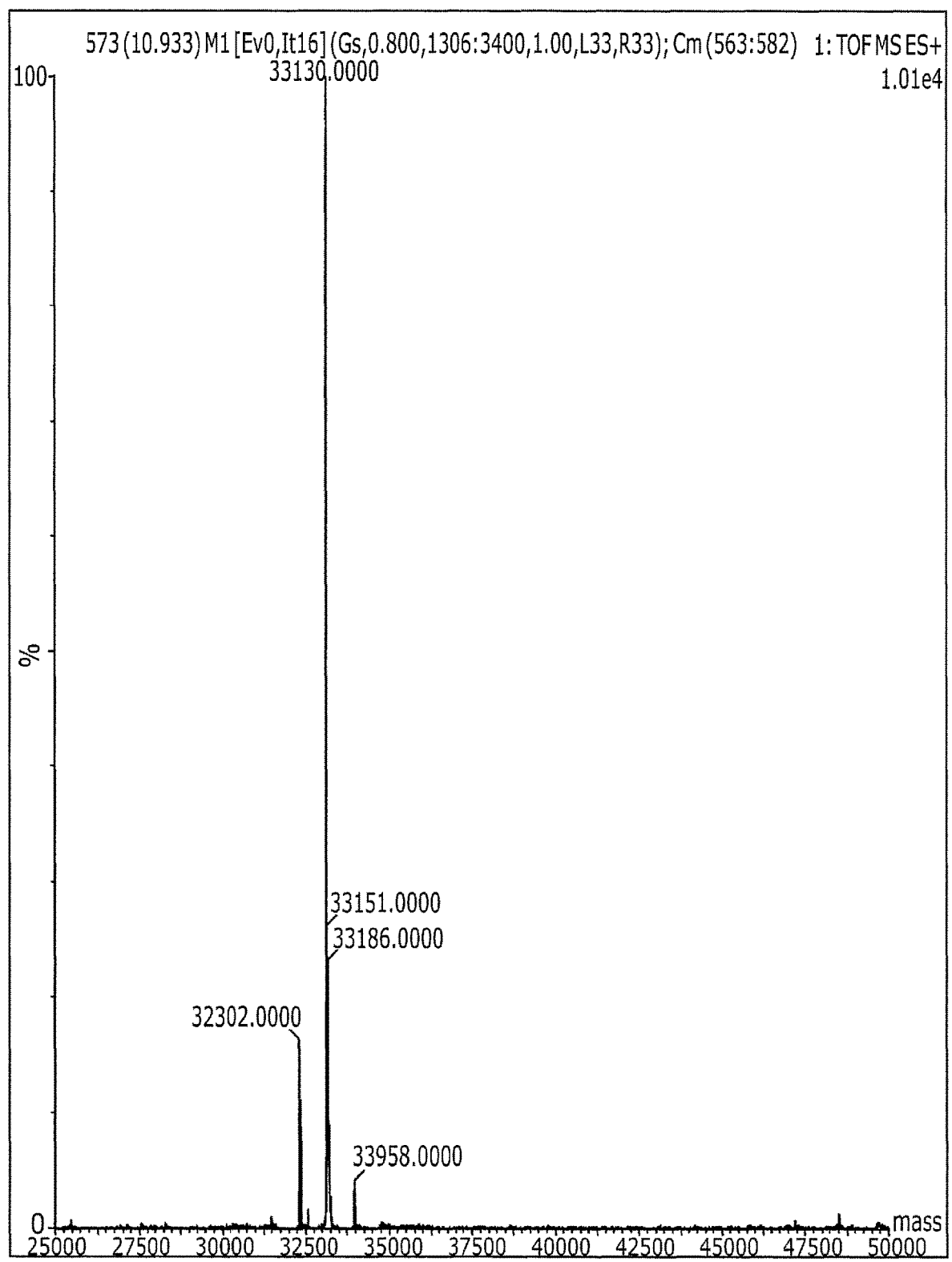
Figure 50:
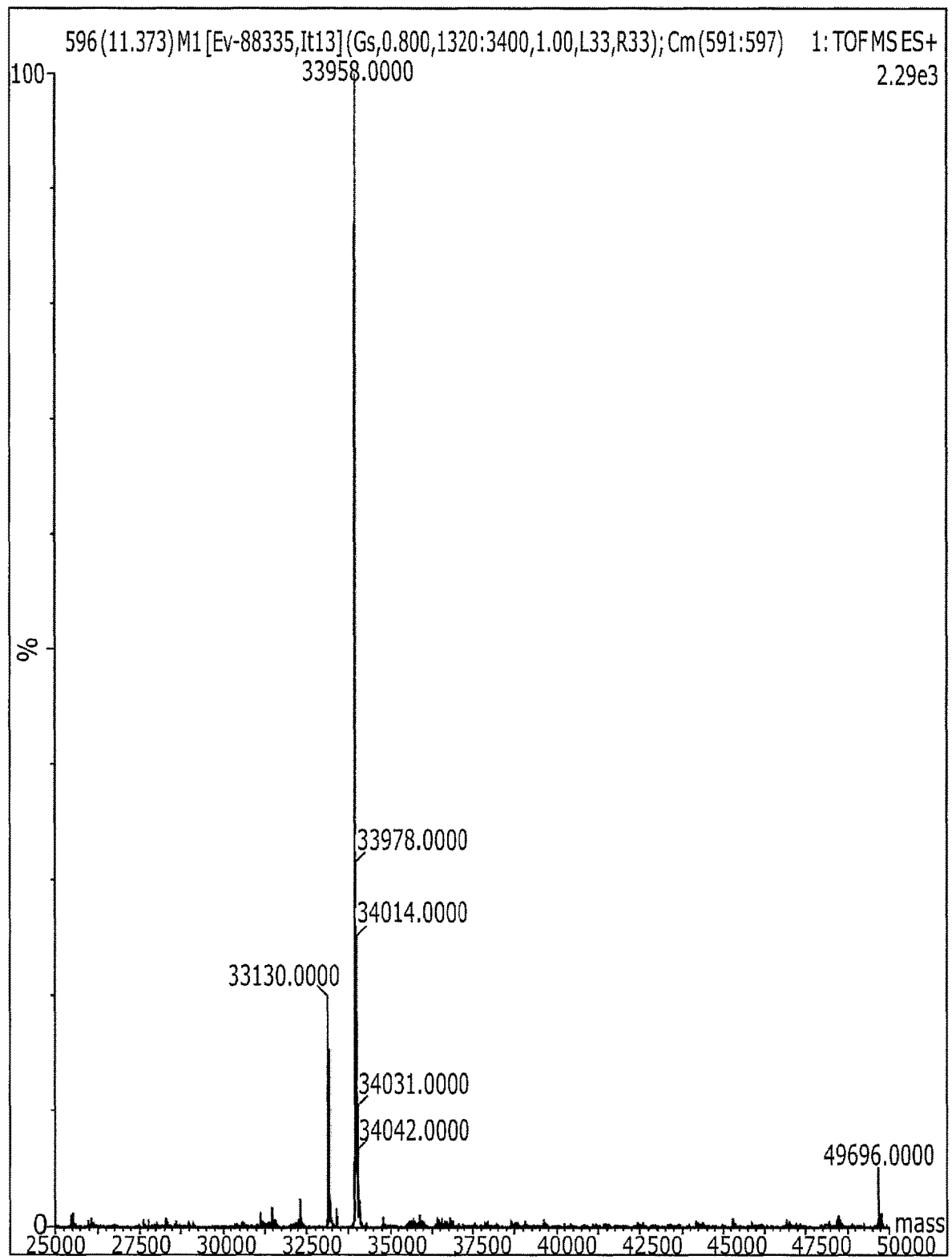

FIG. 50. LCMS data for scFv (TCT)-MMAF-C5 ADC 2.

(A) is the LCMS trace (UV and TIC) and (B-E) show the deconvoluted masses for the main peaks 10-12 mins.

Figure 51:
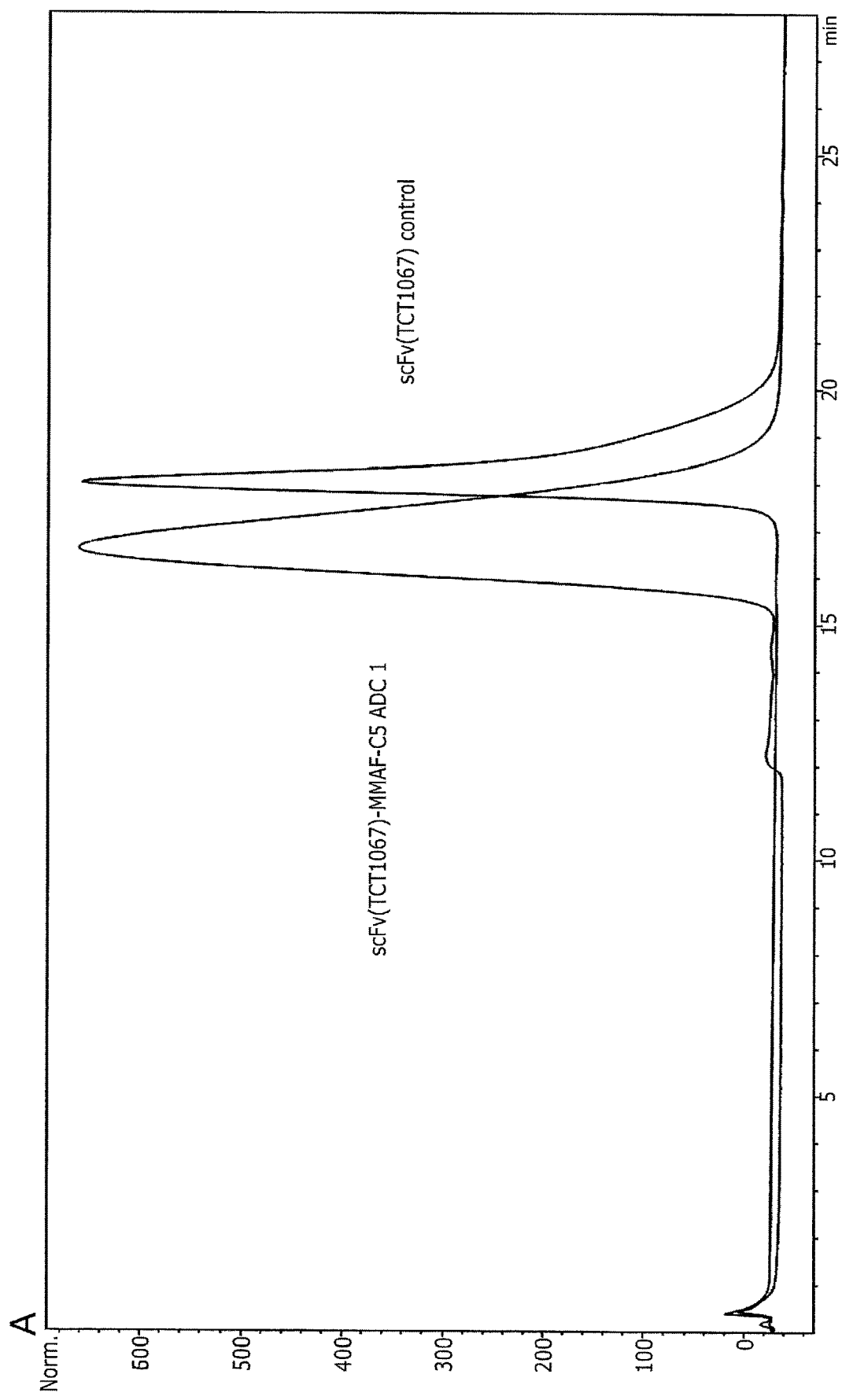
Figure 51:
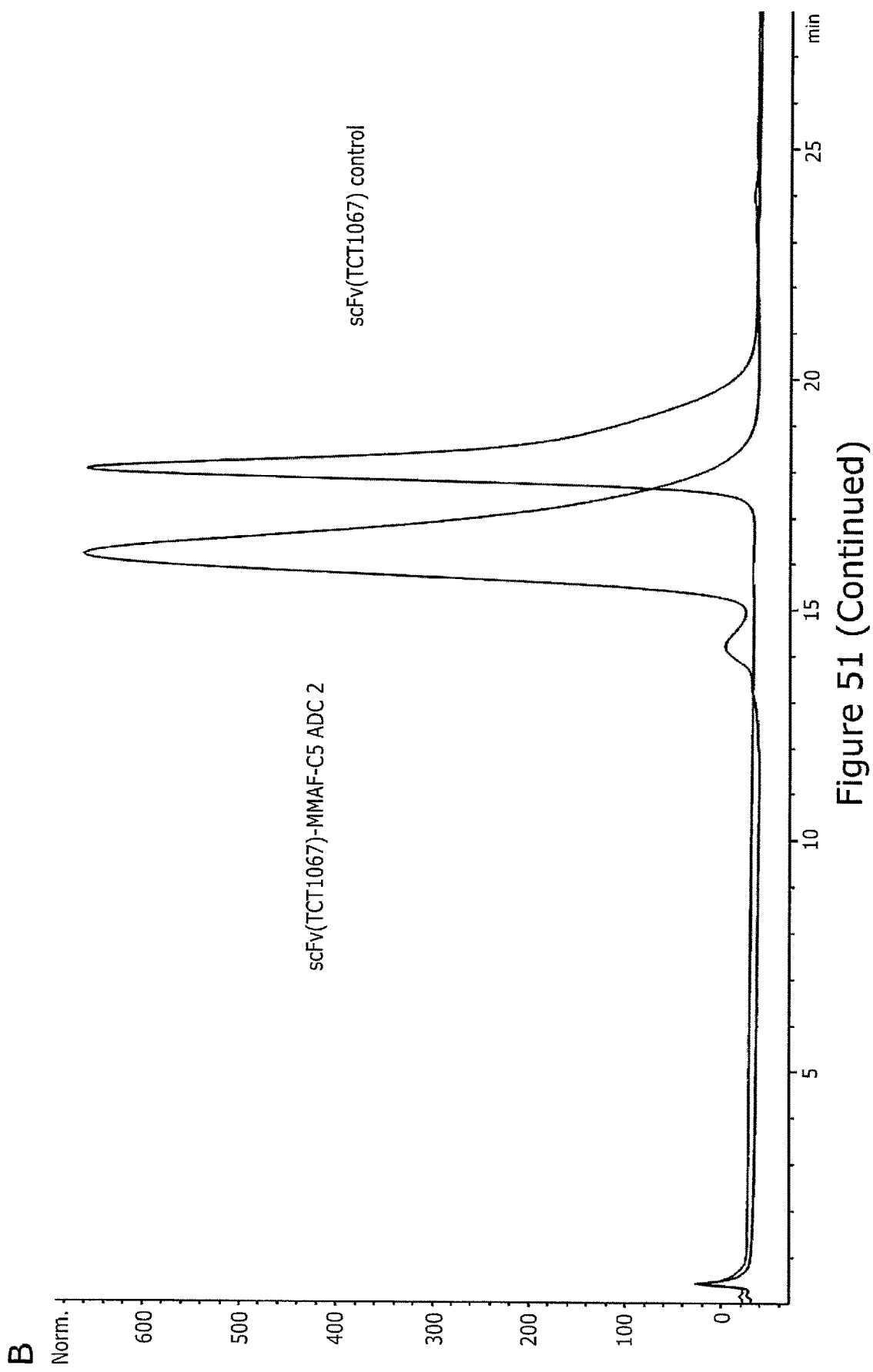

FIG. 51. HPLC SEC traces (A280 nm) for (A) scFv (TCT1067)-MMAF-C5 ADC 1 and (B) scFv (TCT1067)-MMAF-C5 ADC 2 purified conjugates run at 1 ml/min and compared to unconjugated antibody.

Figure 52:
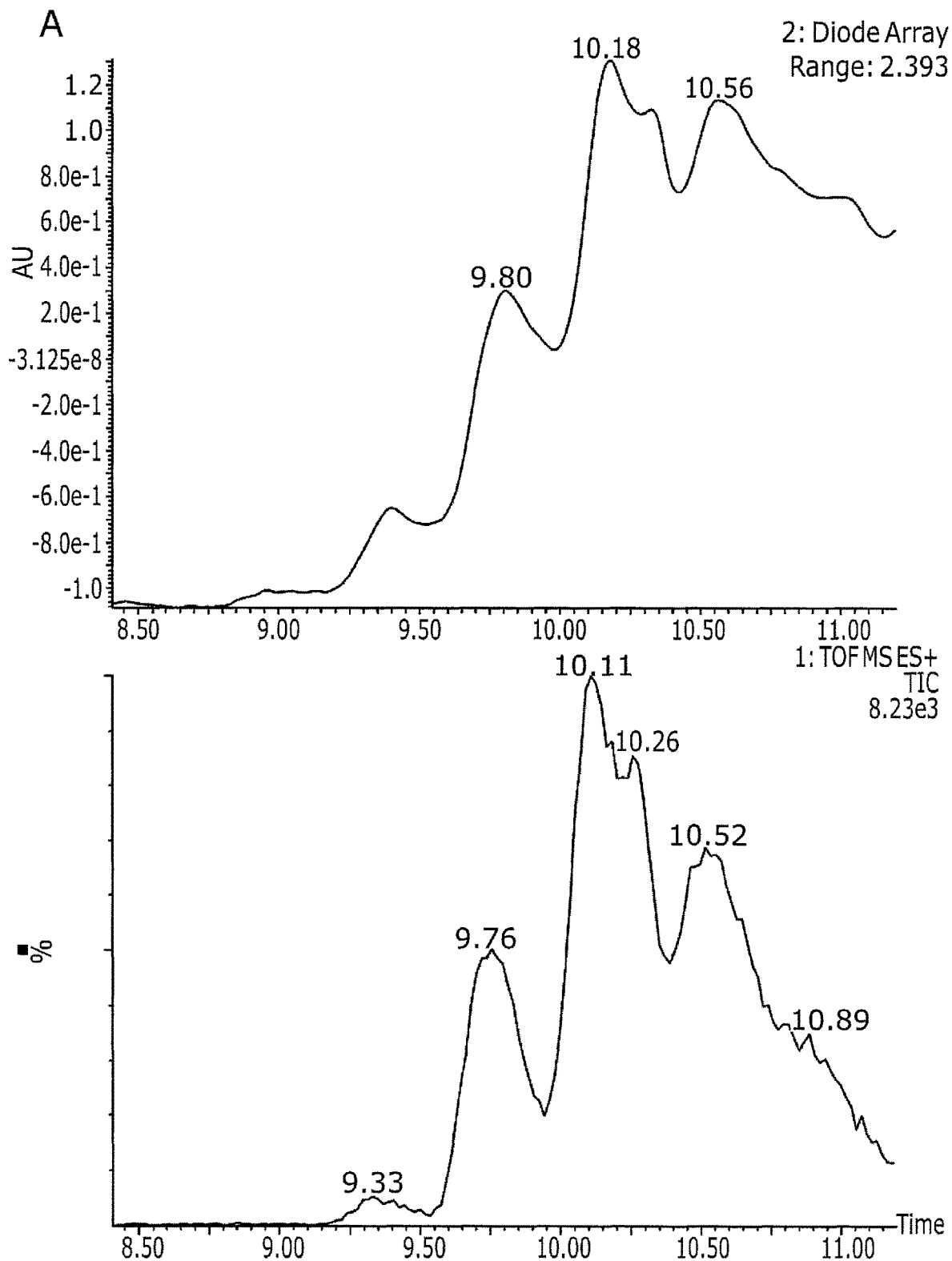
Figure 52:
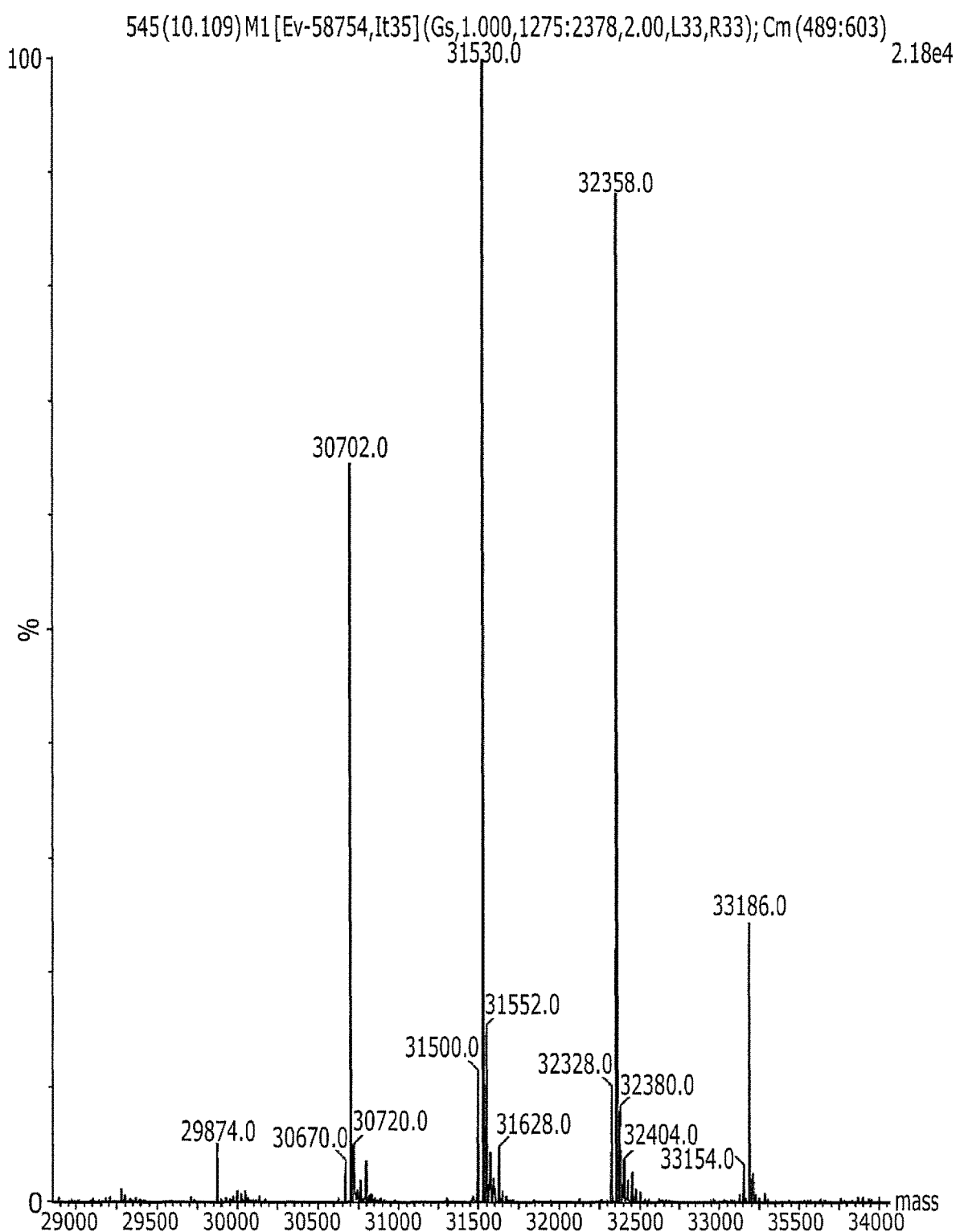
Figure 52:
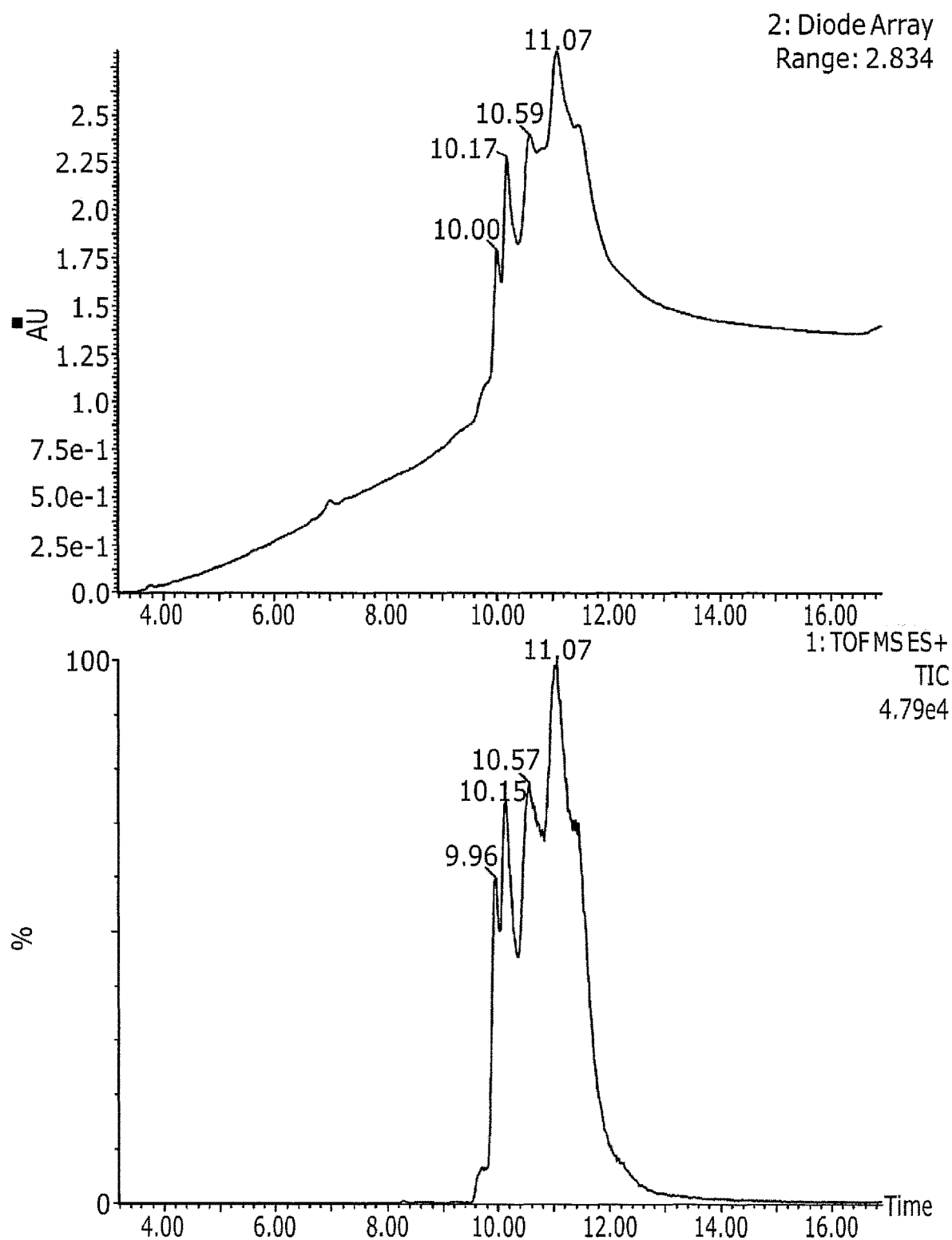
Figure 52:
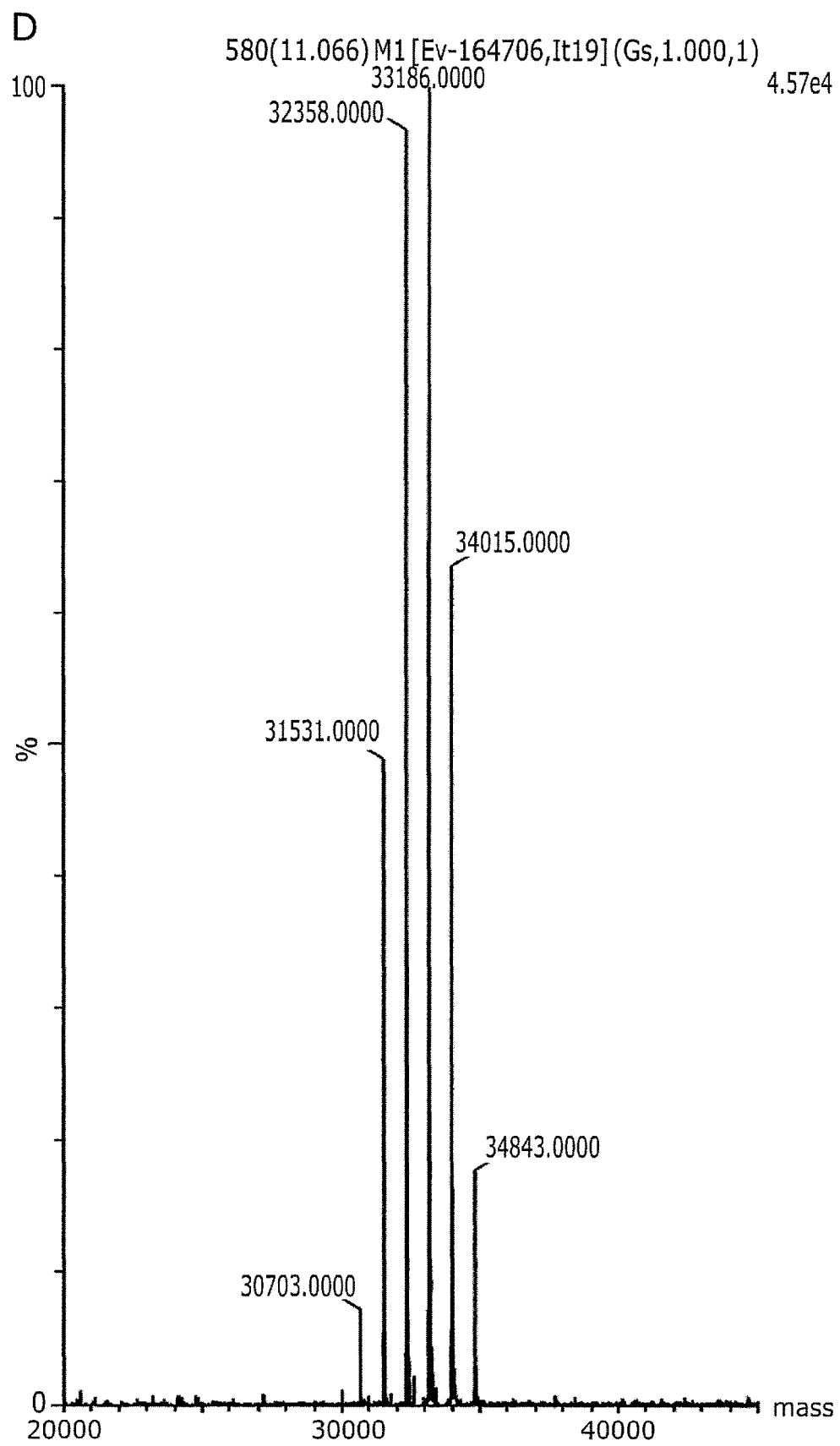

FIG. 52. LCMS data for scFv (TCT1067)-MMAF-C5 ADC 1 and ADC 2.

(A) and (B) are the LCMS data for scFv (TCT1067)-MMAF-C5 ADC1 where (A) is the LCMS trace (UV and TIC) and (B) is the deconvoluted mass for the main peaks between 9.3-10.6 mins. (C) and (D) are the LCMS data for scFv (TCT1067)-MMAF-C5 ADC2 where (C) is the LCMS trace (UV and TIC) and (D) is the deconvoluted mass for the main peaks between 9.9-12 mins.

Figure 53:
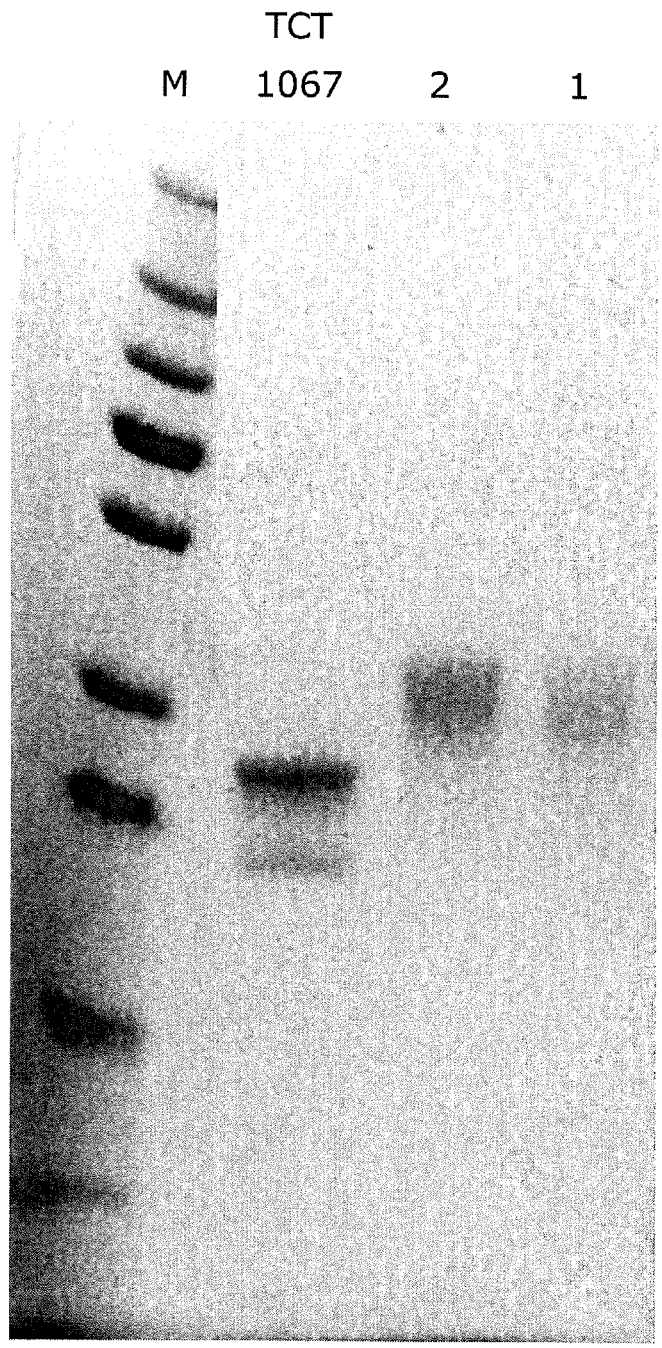

FIG. 53. SDS-PAGE reducing gel (12%) showing scFv (TCT1067)-MMAF-C5 ADC 1 and 2 in comparison with scFv (TCT1067) unconjugated antibody. Size markers as shown in FIG. 48.

Figure 54:
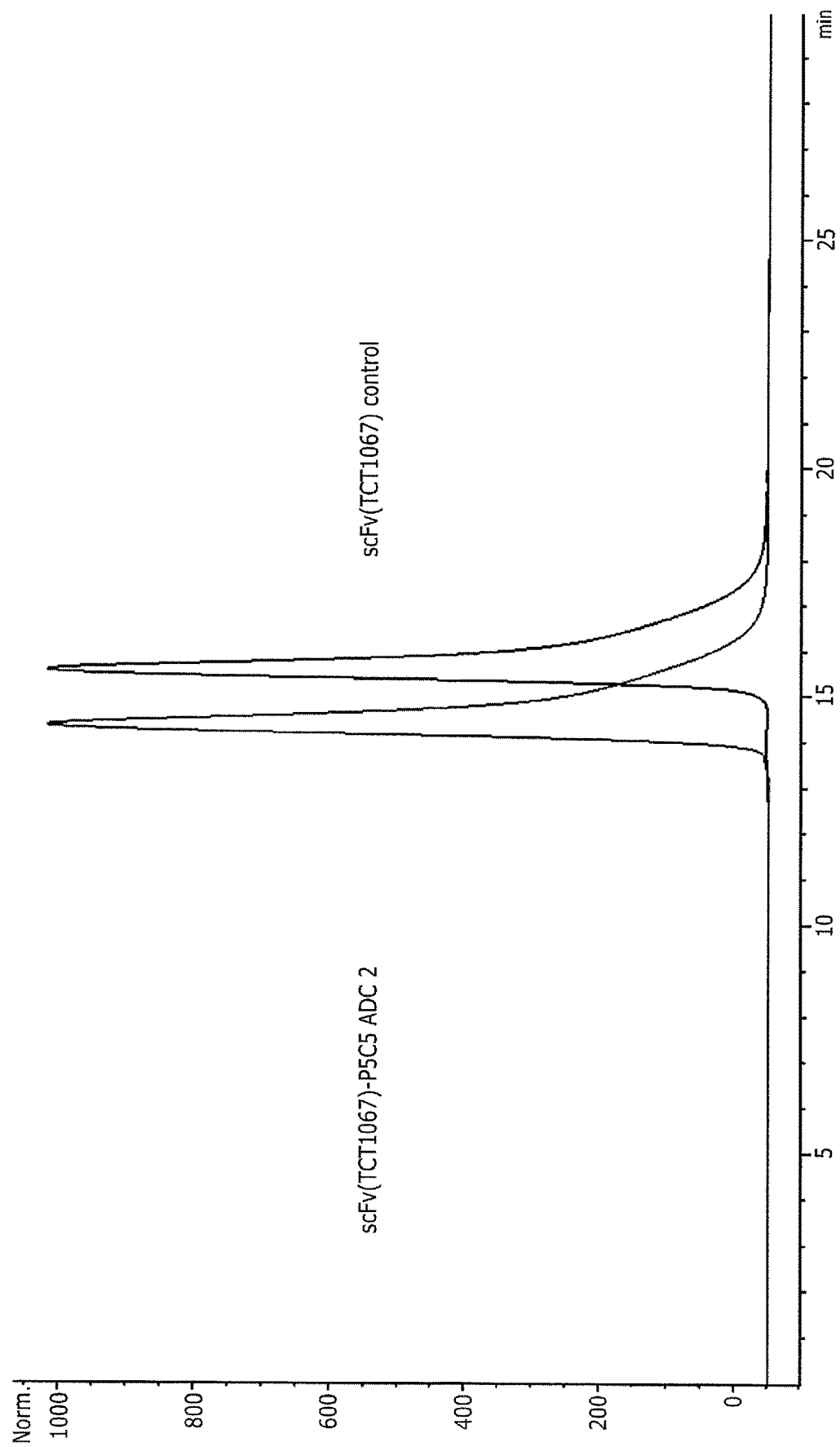

FIG. 54. HPLC SEC traces (A280 nm) for scFv (TCT1067)-P5-C5 ADC 1 run at 1 ml/min and compared to the unconjugated antibody.

Figure 55:
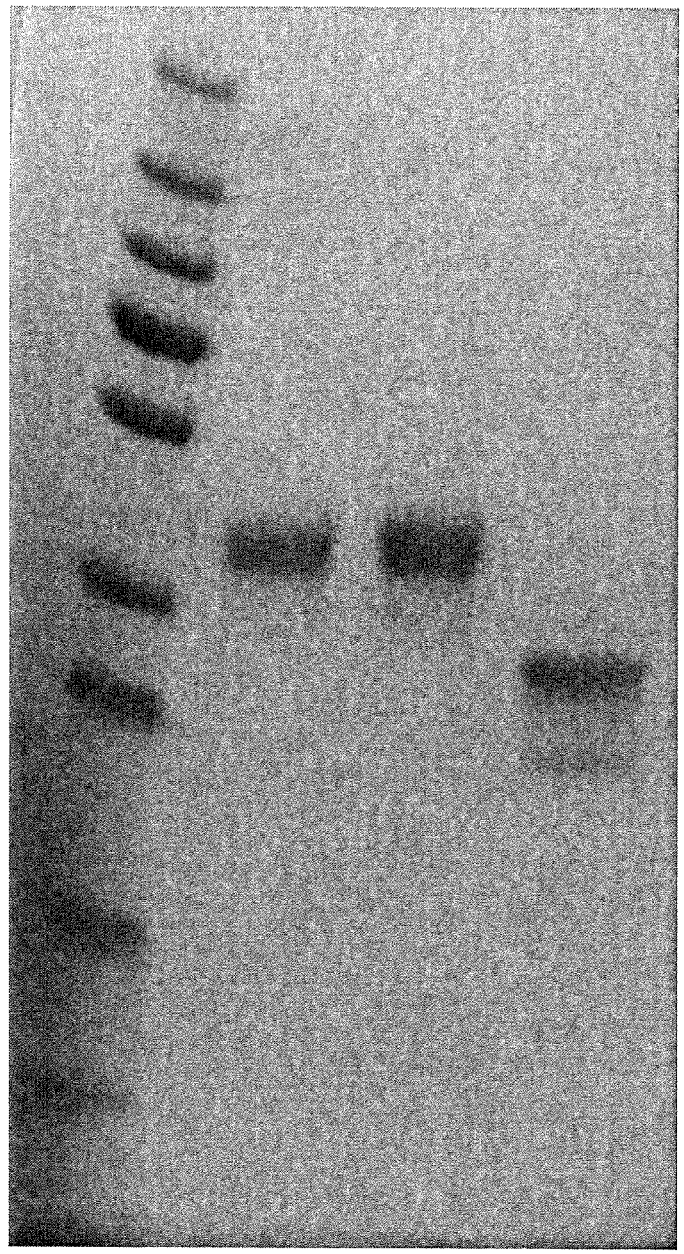

FIG. 55. SDS-PAGE reducing gel (12%) showing scFv (TCT1067)-P5-C5 ADC 1 in comparison with the scFv (TCT1067) unconjugated antibody. Size markers as shown in FIG. 48.

Figure 56:
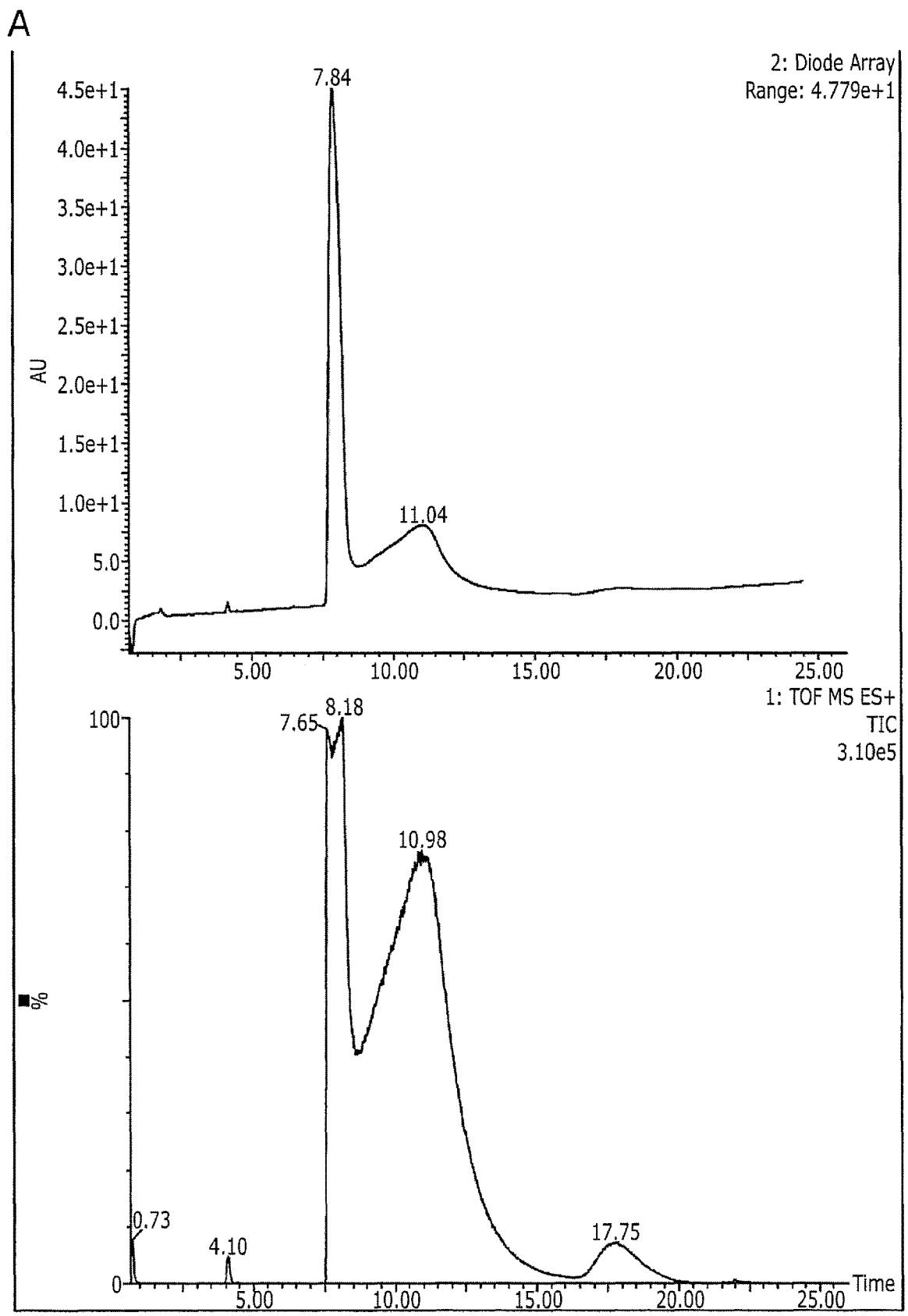
Figure 56:
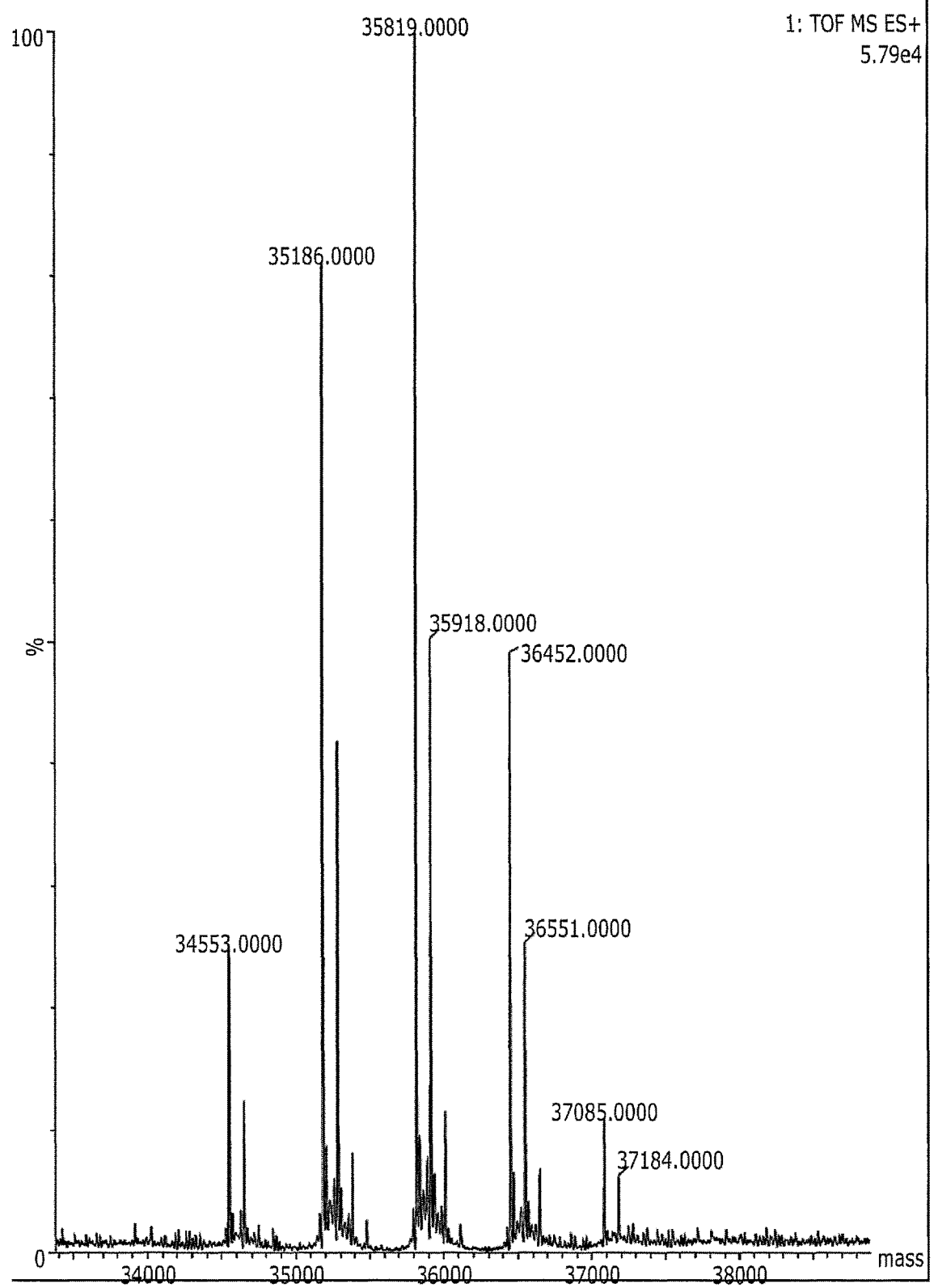

FIG. 56. LCMS data for scFv (TCT1067)-P5-C5 ADC 1.

(A) is the LCMS trace (UV and TIC) and (B) is the deconvoluted mass for the main peak at 8.2 mins.

Figure 57:
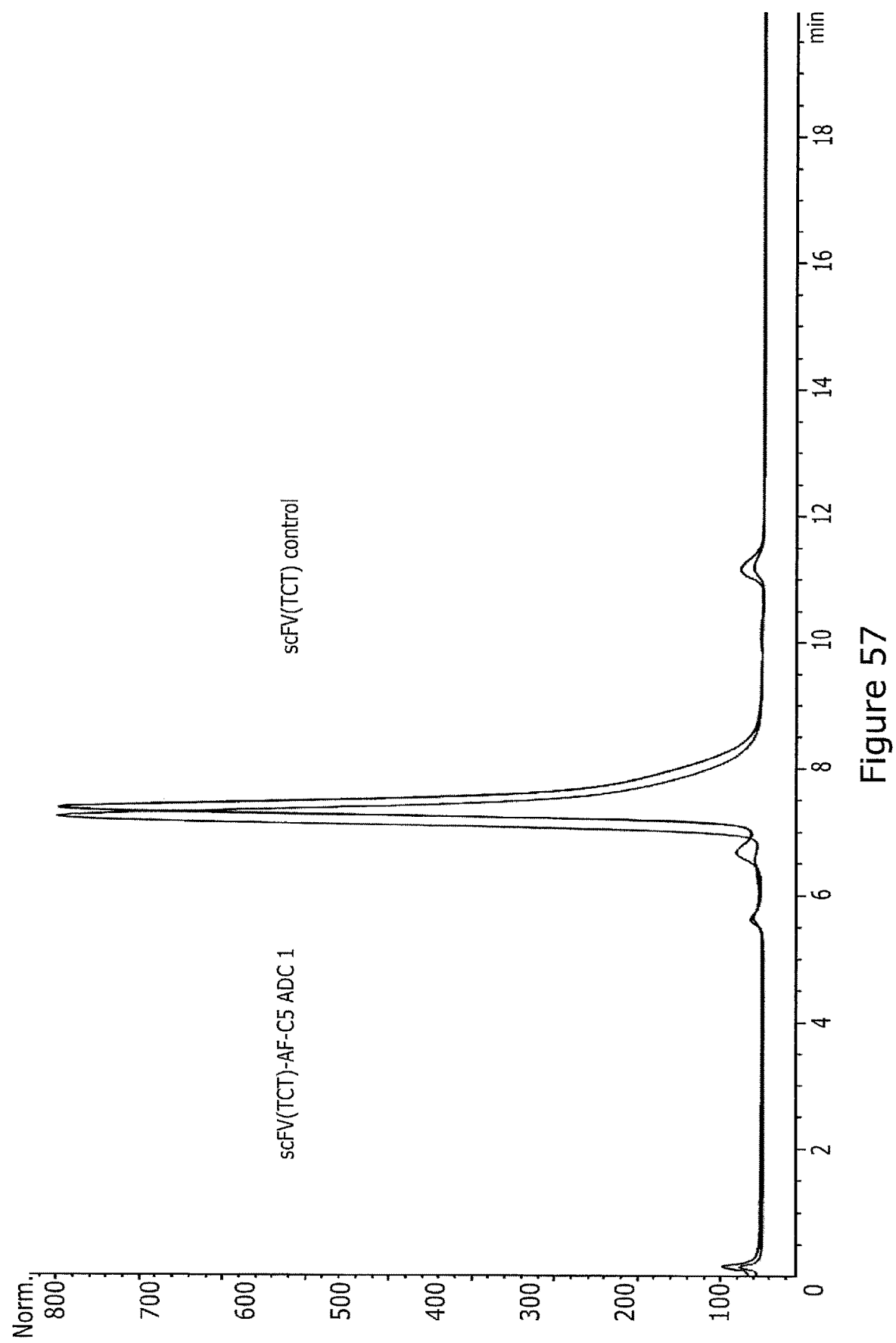

FIG. 57. HPLC SEC traces (A280 nm) for scFv (TCT)-AF-C5 ADC 1 run at 0.5 ml/min and compared to the unconjugated antibody.

Figure 58:
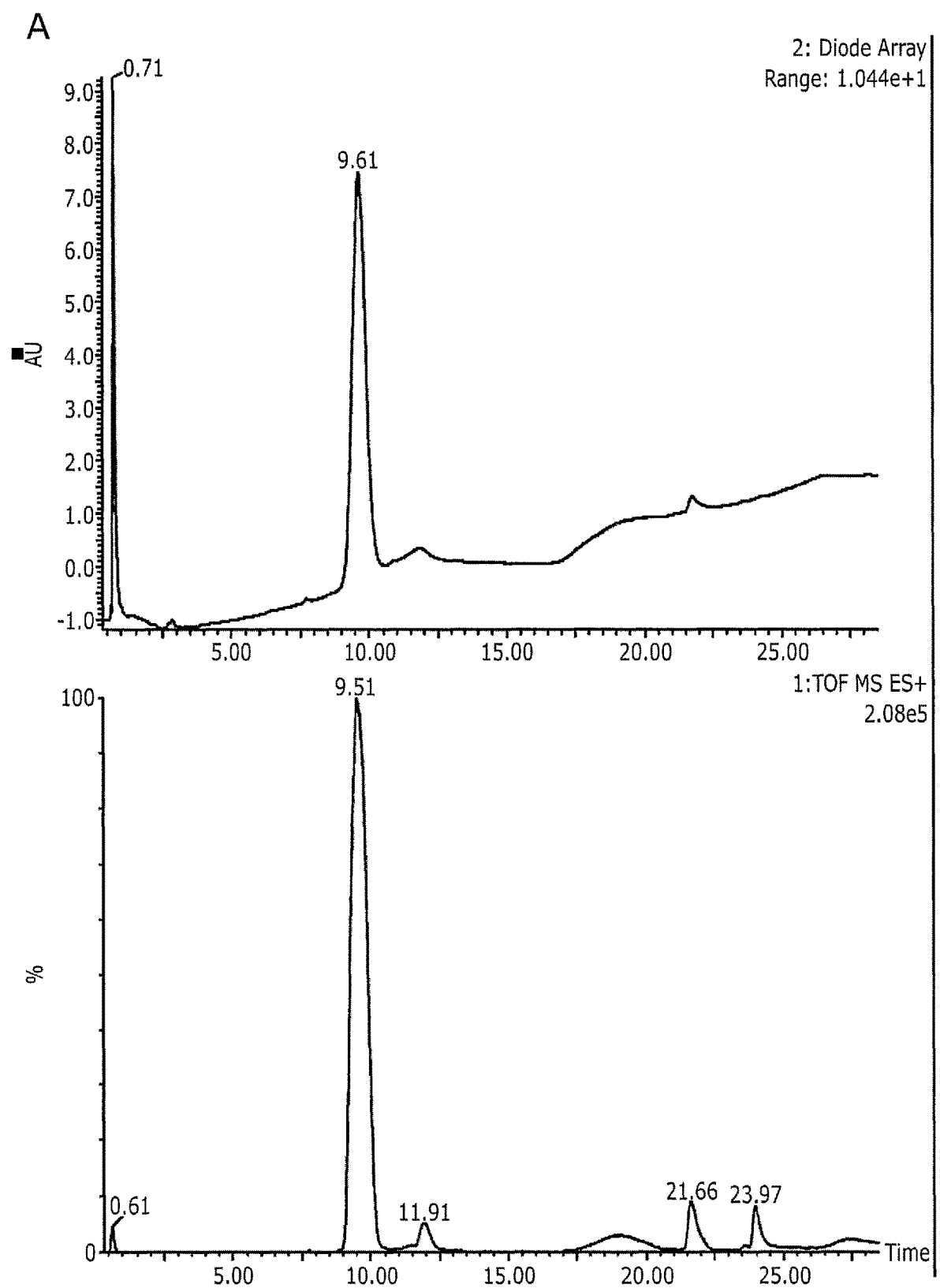
Figure 58:
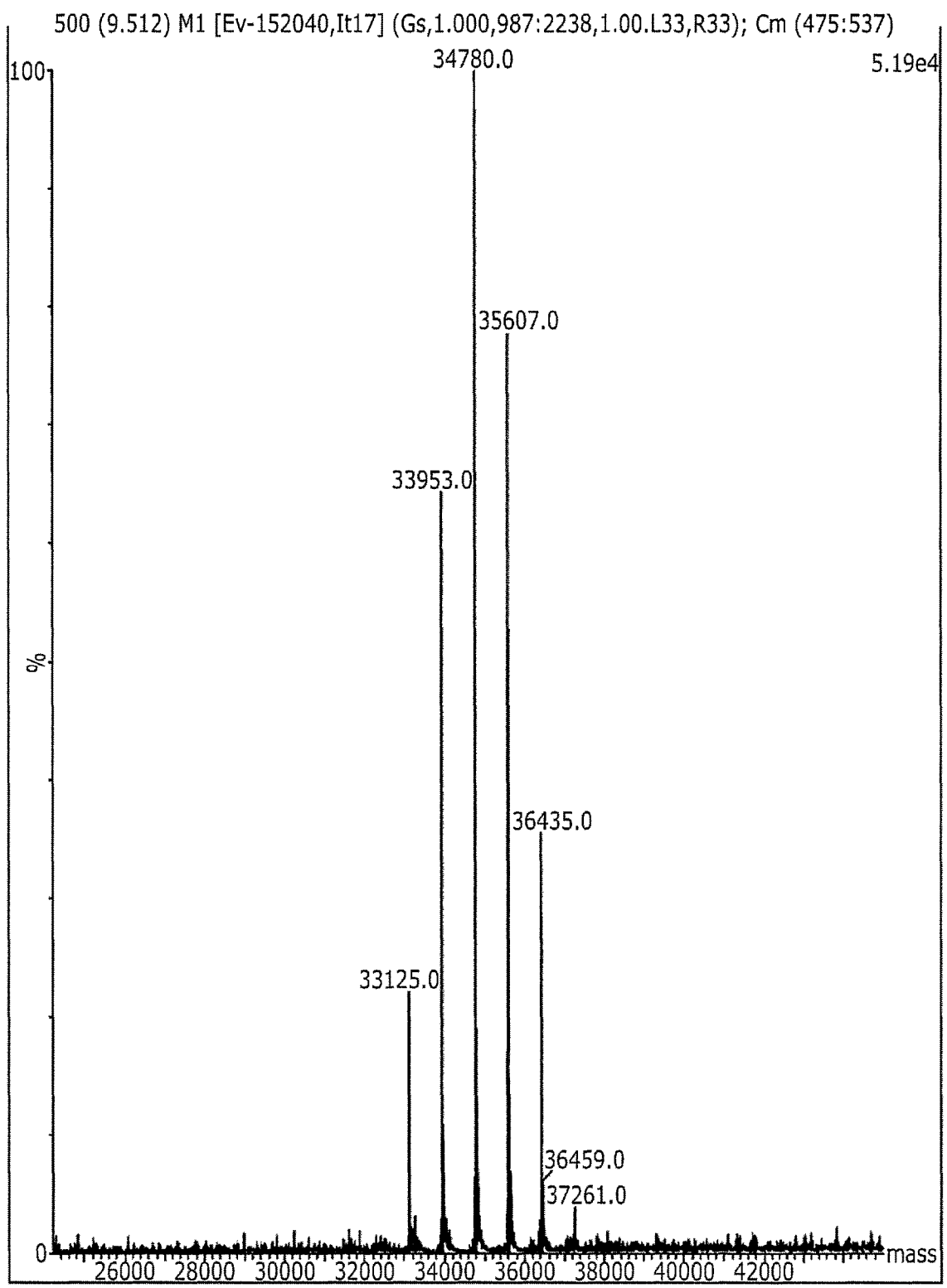

FIG. 58. LCMS data for scFv (TCT)-AF-C5 ADC 1.

(A) is the LCMS trace (UV and TIC) and (B) is the deconvoluted mass for the main peak at 9.5 mins.

Figure 59:
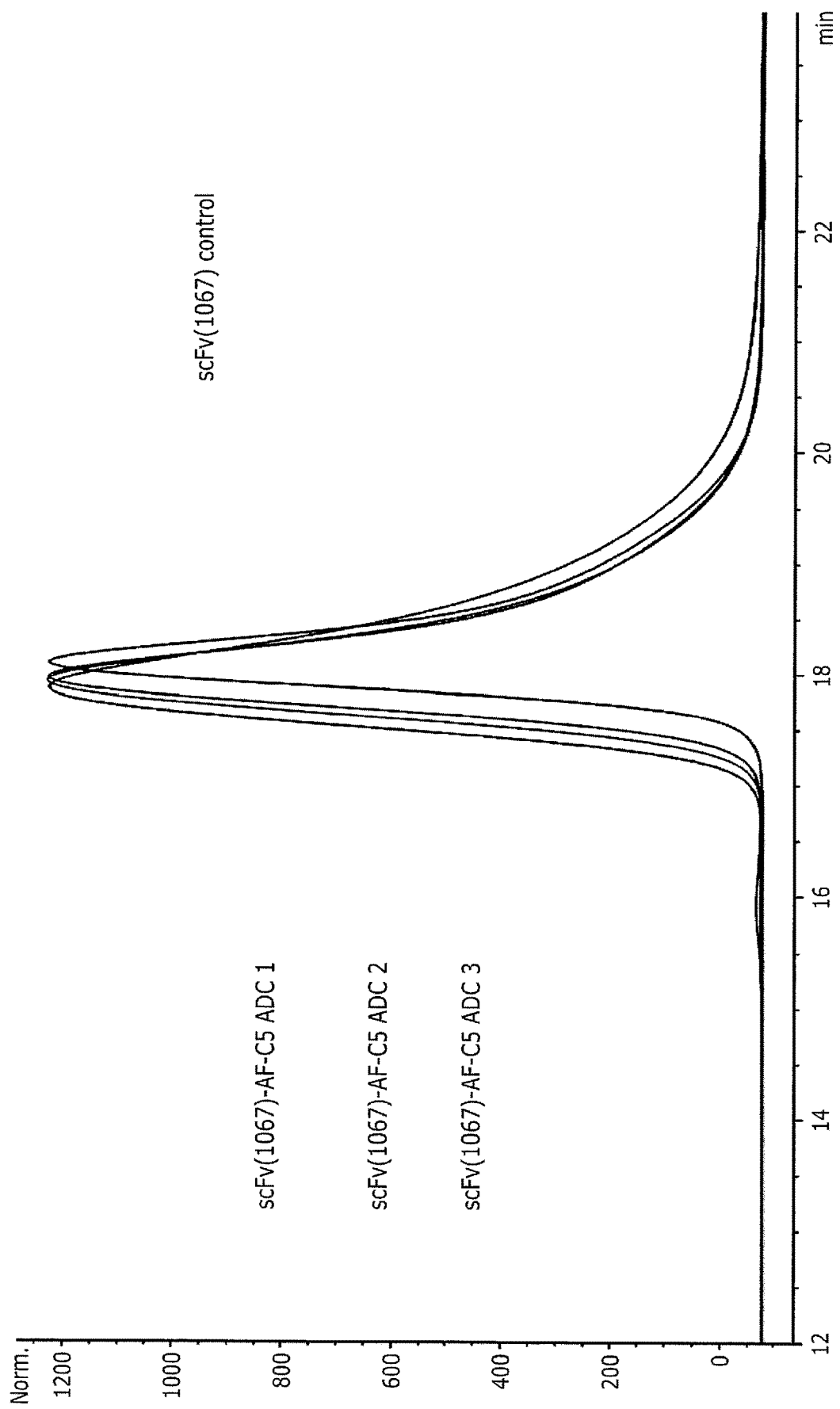

FIG. 59. HPLC SEC traces (A280 nm) for scFv (TCT1067)-AF-C5 ADC 1, 2 and 3 run at 1 ml/min and compared to the unconjugated antibody.

Figure 60:
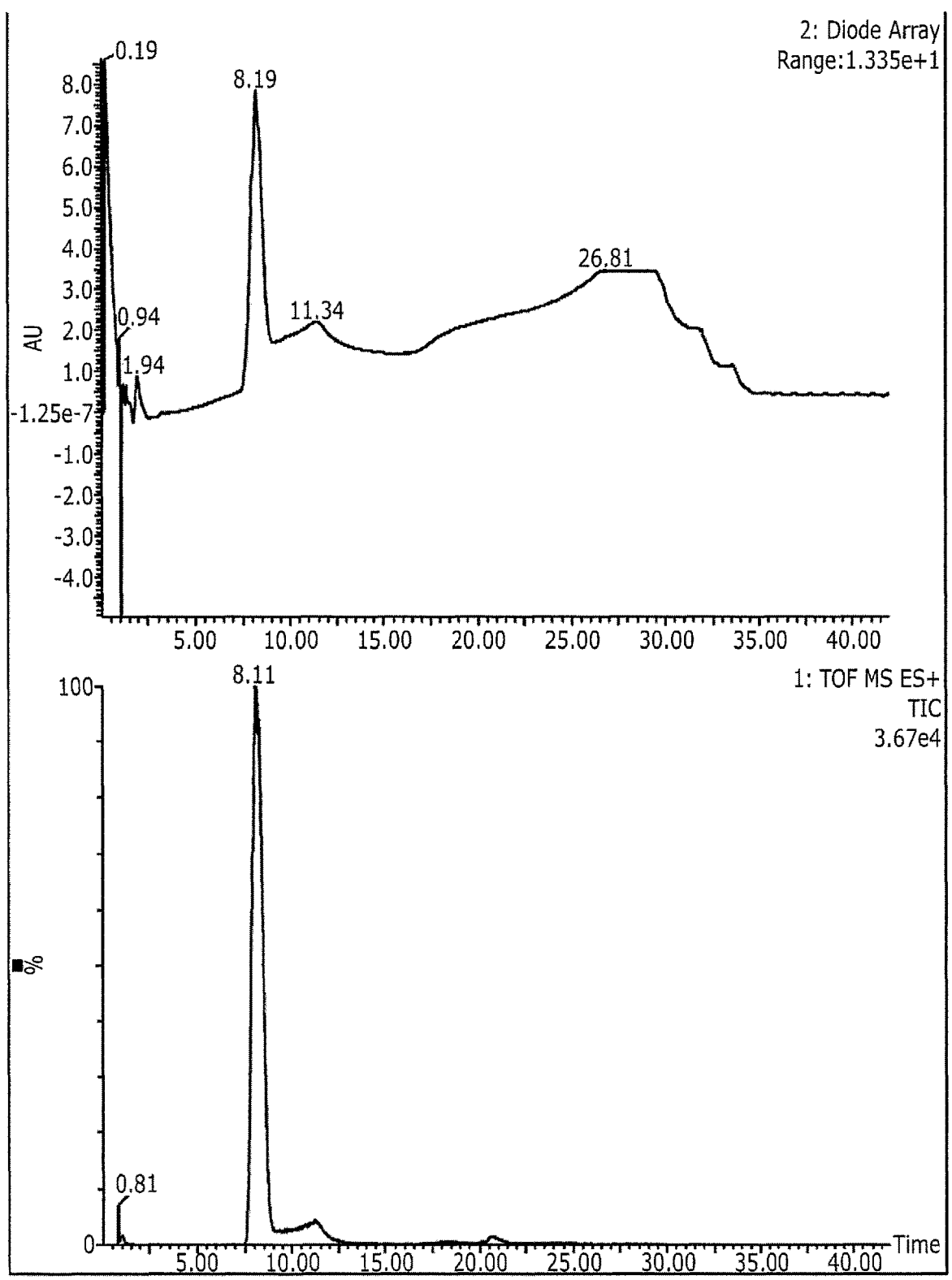
Figure 60:
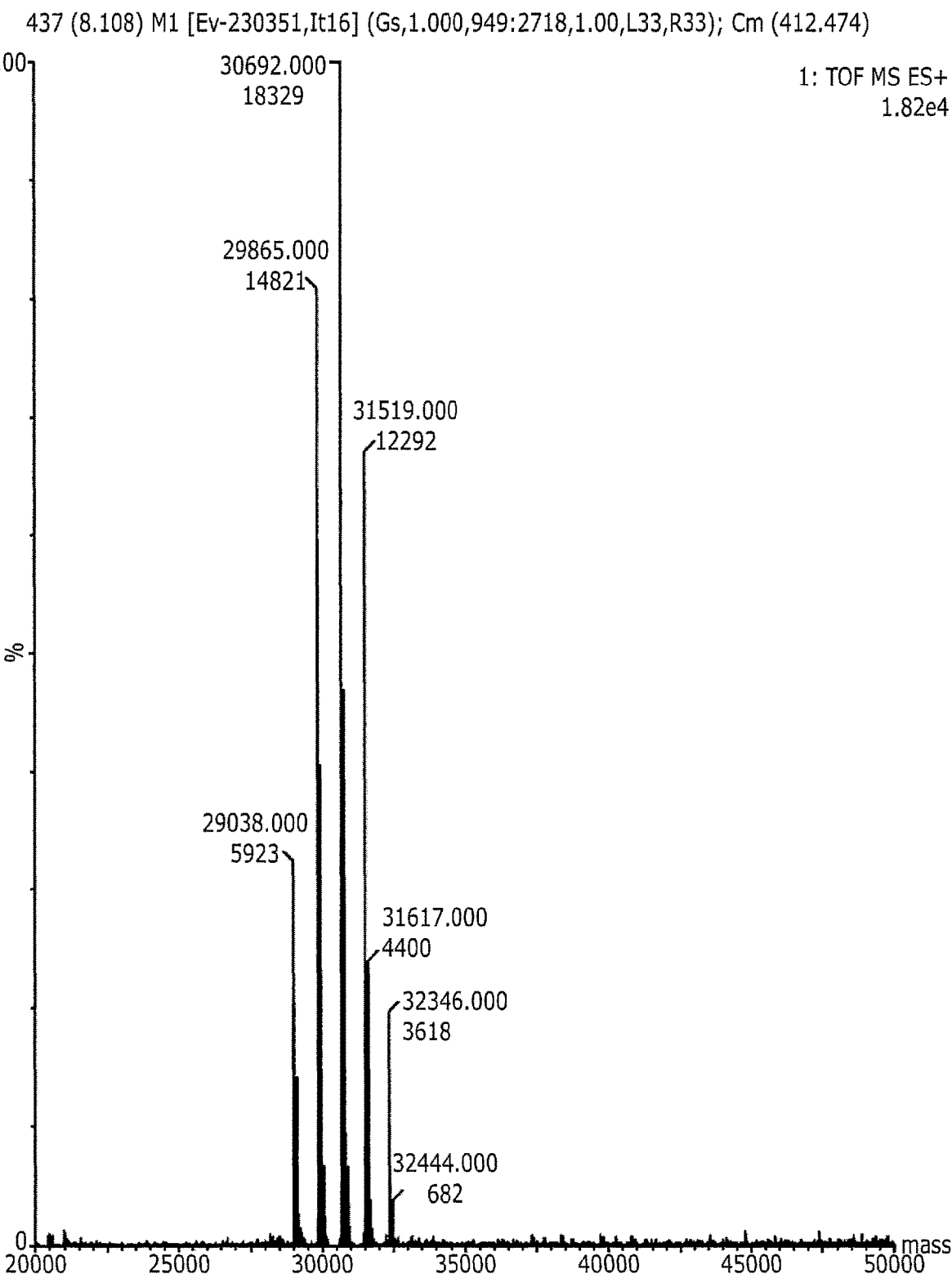
Figure 60:
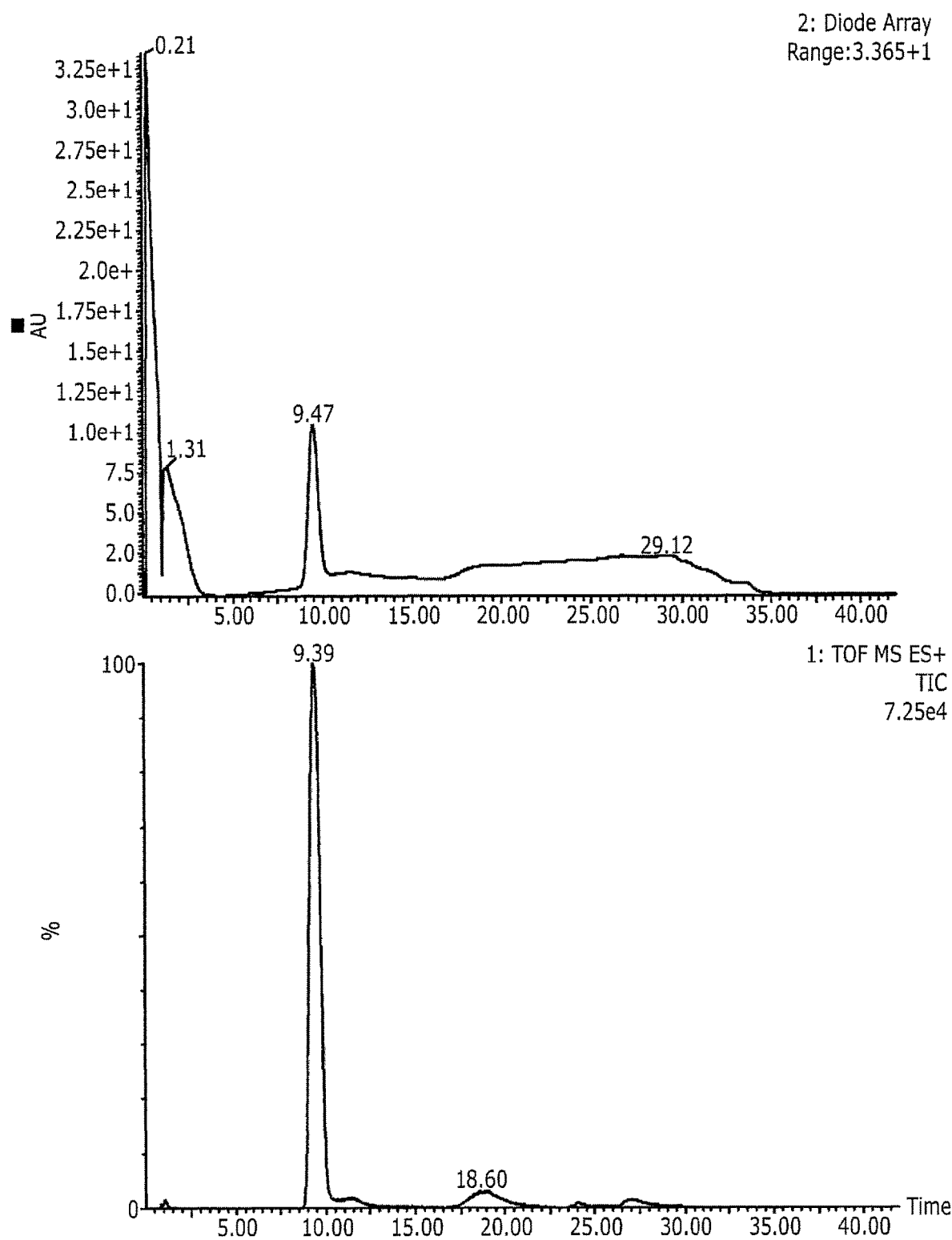
Figure 60:
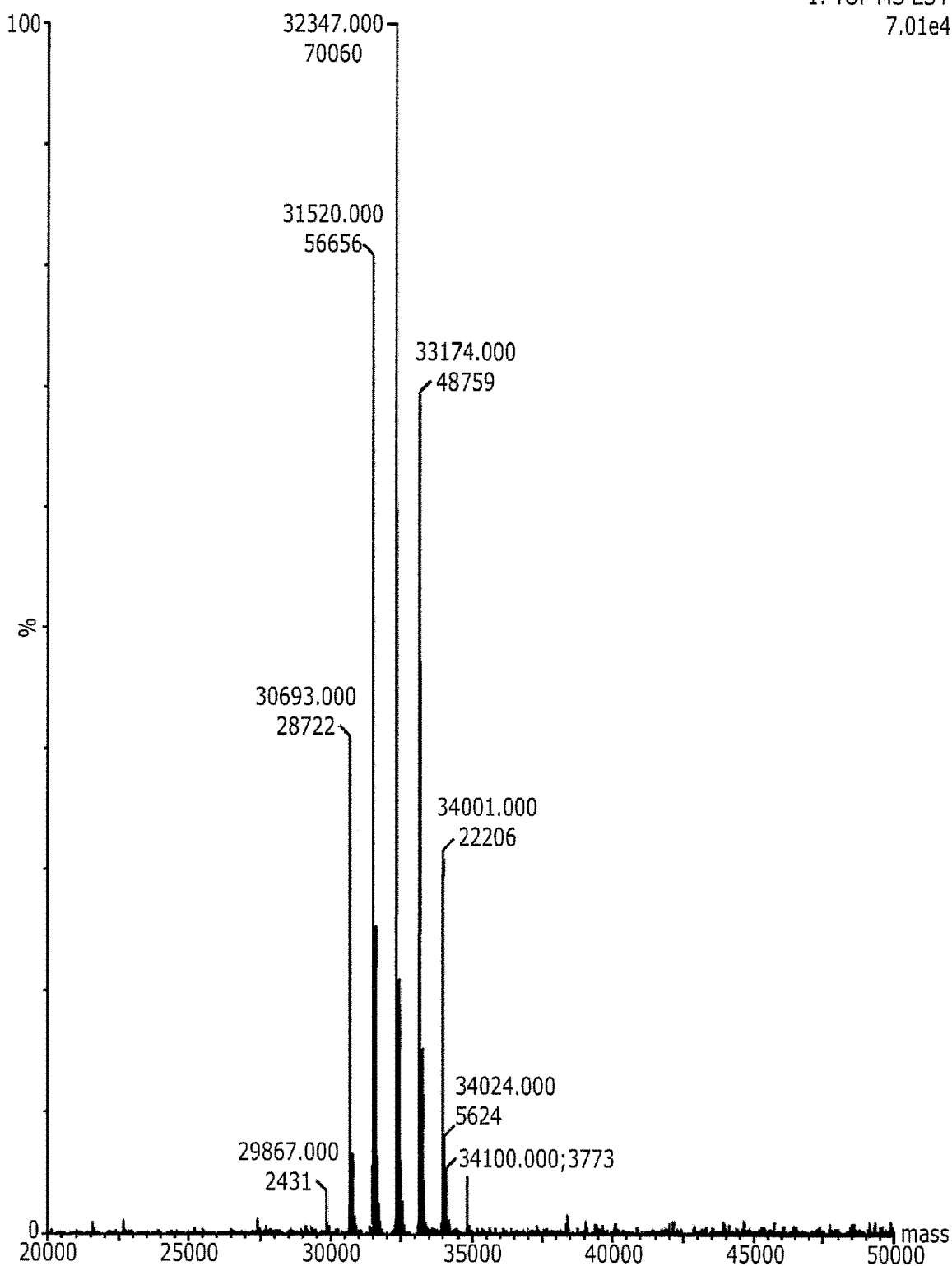
Figure 60:
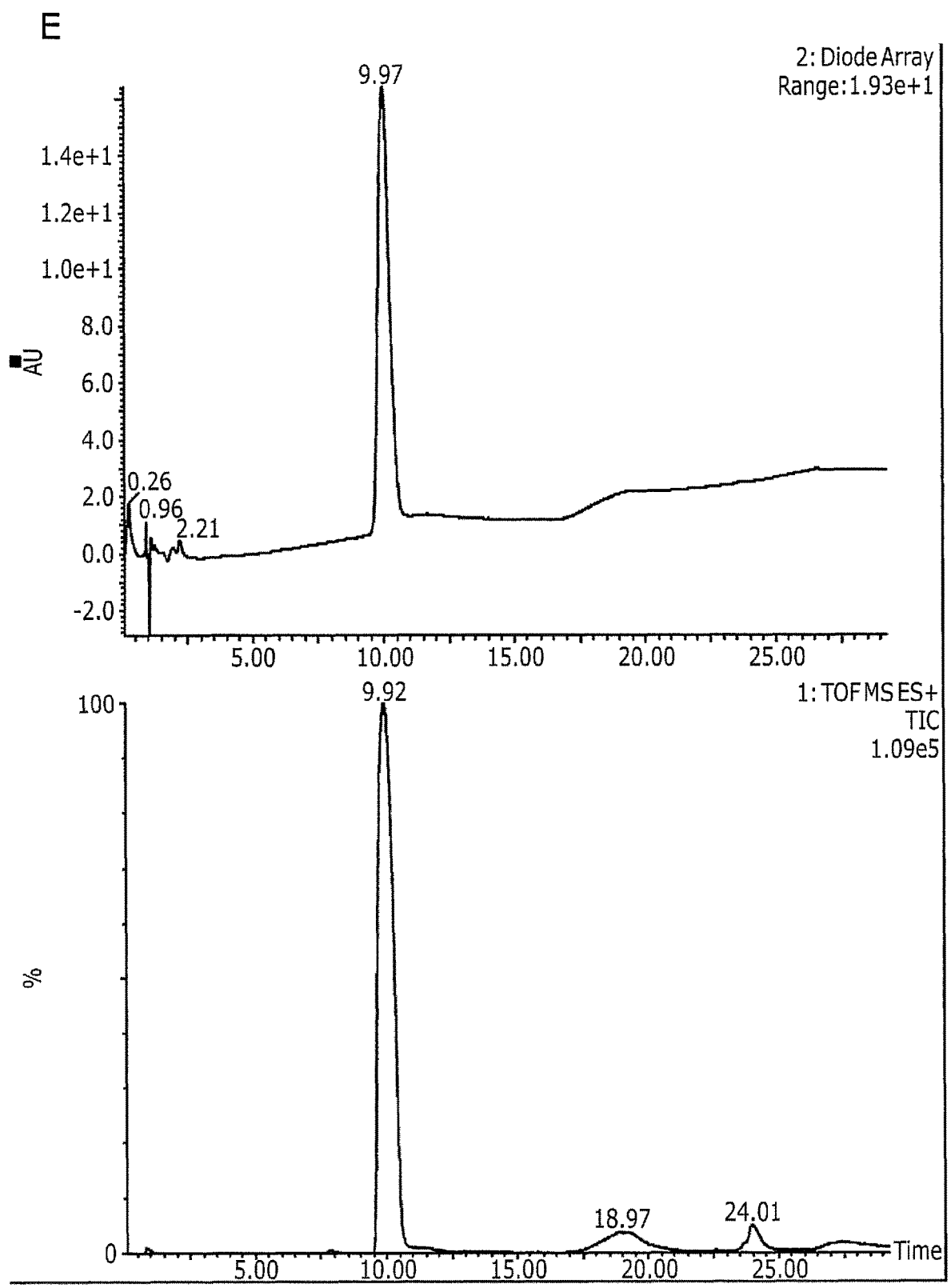
Figure 60:
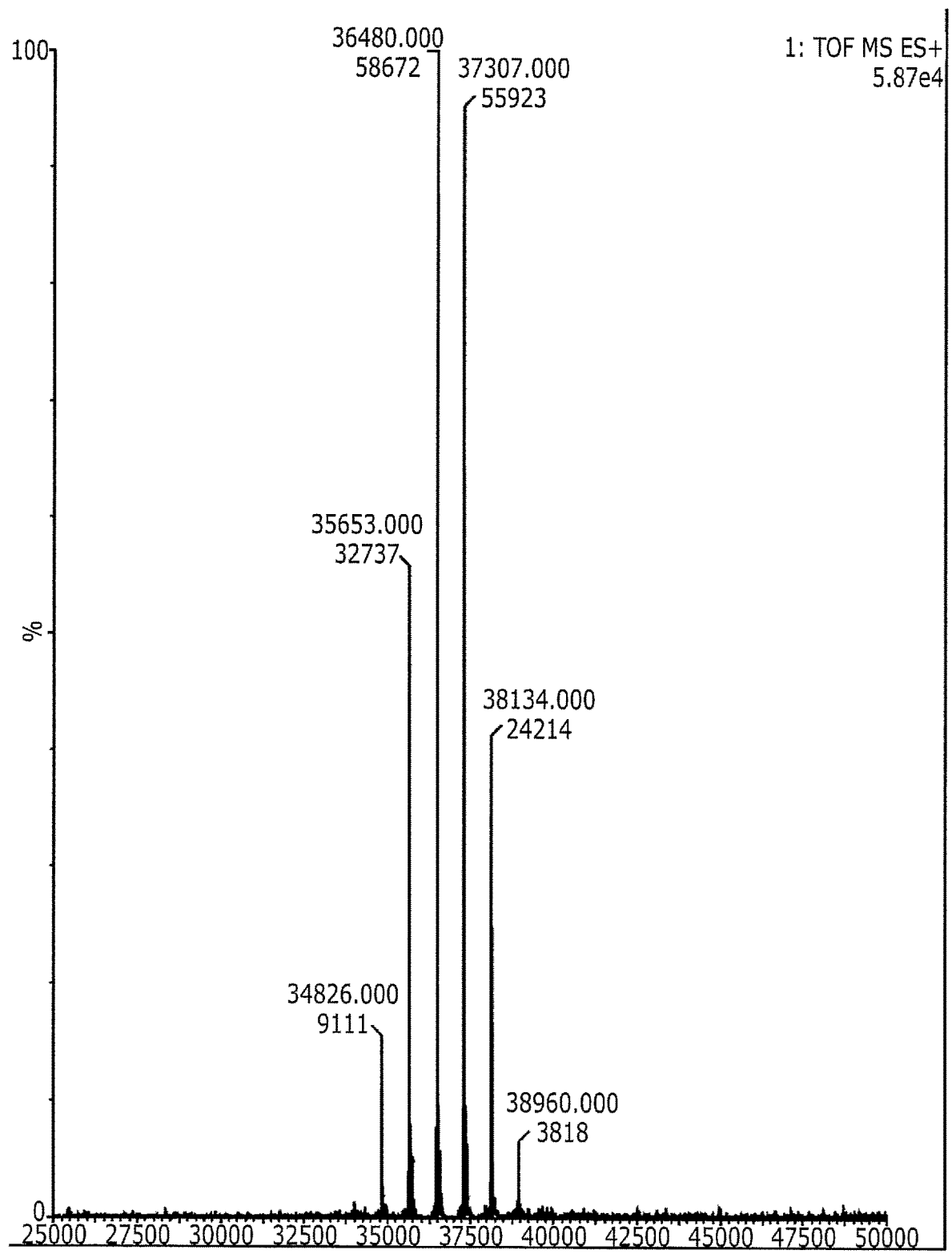

FIG. 60. LCMS data for scFv (TCT)-AF-C5 ADC 1, 2, and 3.

(A) and (B) are the LCMS data for scFv (TCT) ADC 1 where (A) is the LCMS trace (UV and TIC) and (B) is the deconvoluted mass for the main peak at 8.1 mins. (C) and (D) are the LCMS data for scFv (TCT)-AF-C5 ADC 2 where (C) is the LCMS trace (UV and TIC) and (D) is the deconvoluted mass for the main peak at 9.4 mins. (E) and (F) are the LCMS data for scFv (TCT)-AF-C5 ADC 3 where (E) is the LCMS trace (UV and TIC) and (F) is the deconvoluted mass for the main peak at 9.9 mins.

Figure 61:
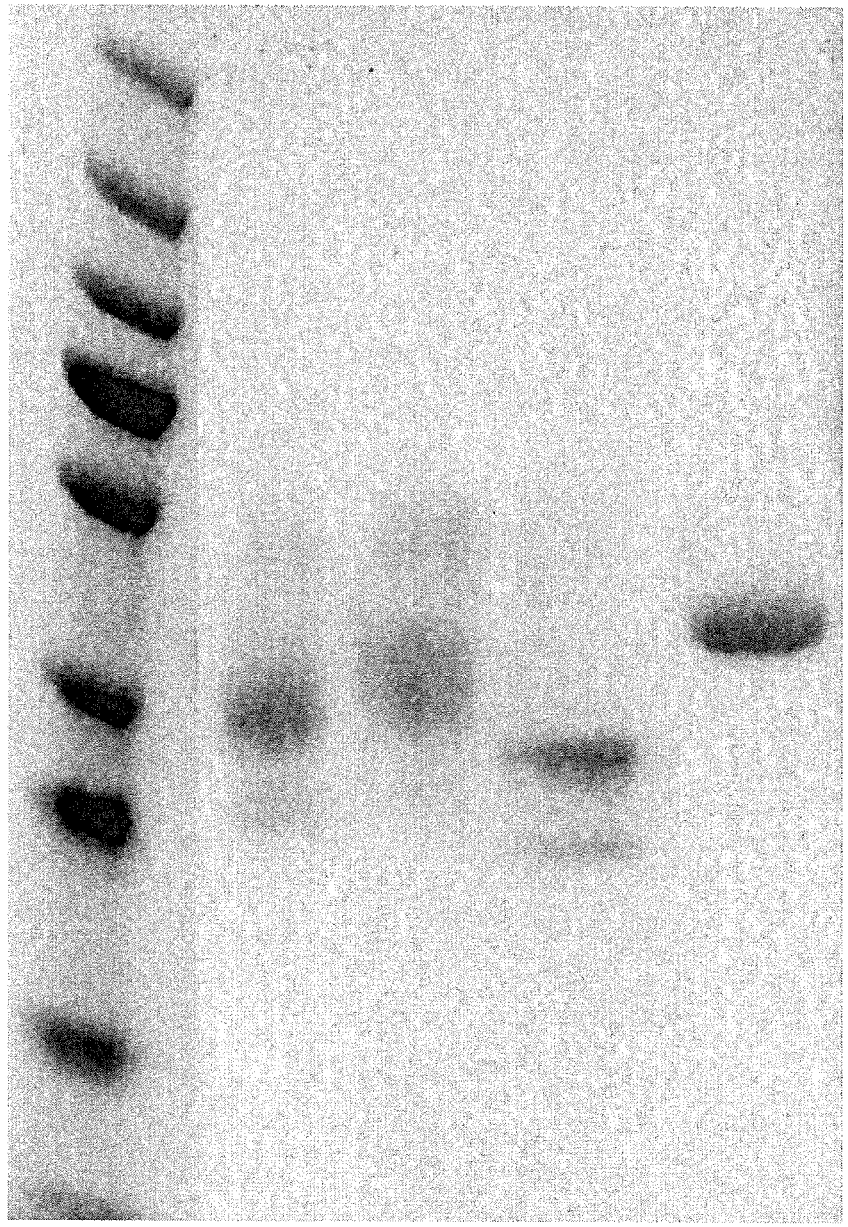

FIG. 61. SDS-PAGE reducing gel (12%) showing scFv TCT-AF-C5 ADC 1, 2 and 3 in comparison with the scFv (TCT1067) unconjugated antibody.

Size markers as shown in FIG. 48.

Figure 62:
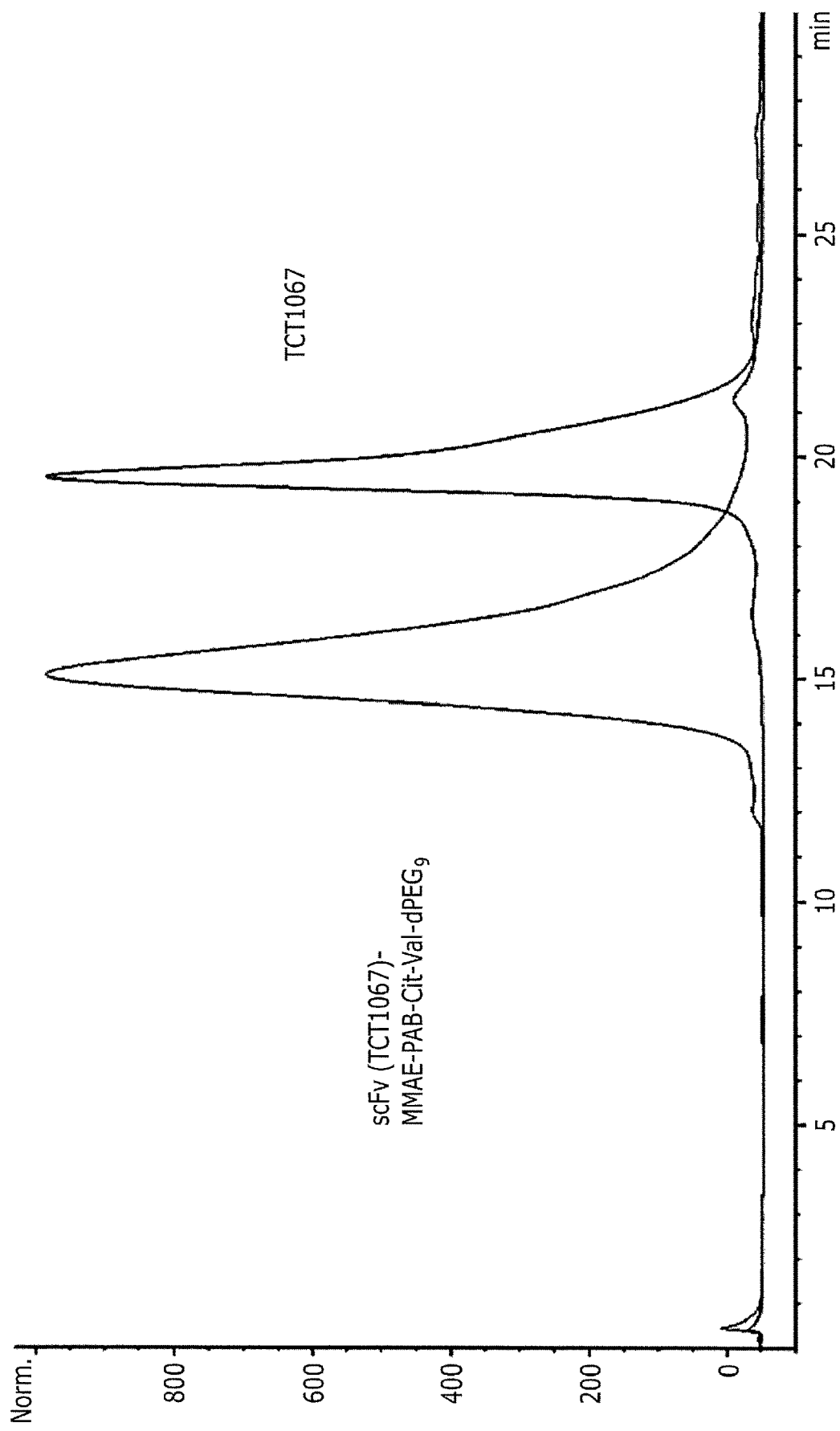

FIG. 62. HPLC SEC traces (A280 nm) for scFv (TCT1067)-MMAE-PAB-Cit-Val-dPEG9 ADC 1 run at 1 ml/min and compared to the unconjugated antibody.

Figure 63:
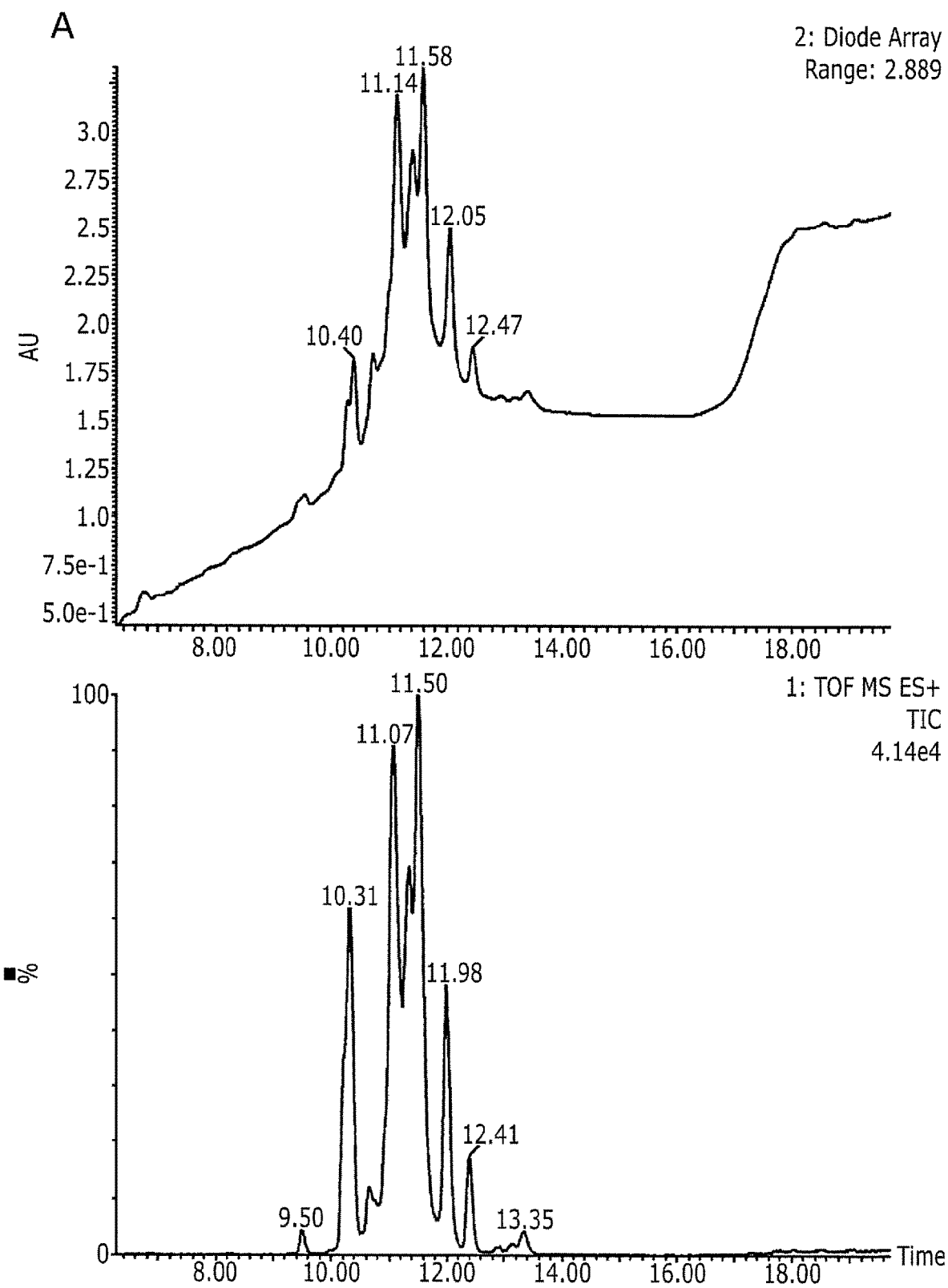
Figure 63:
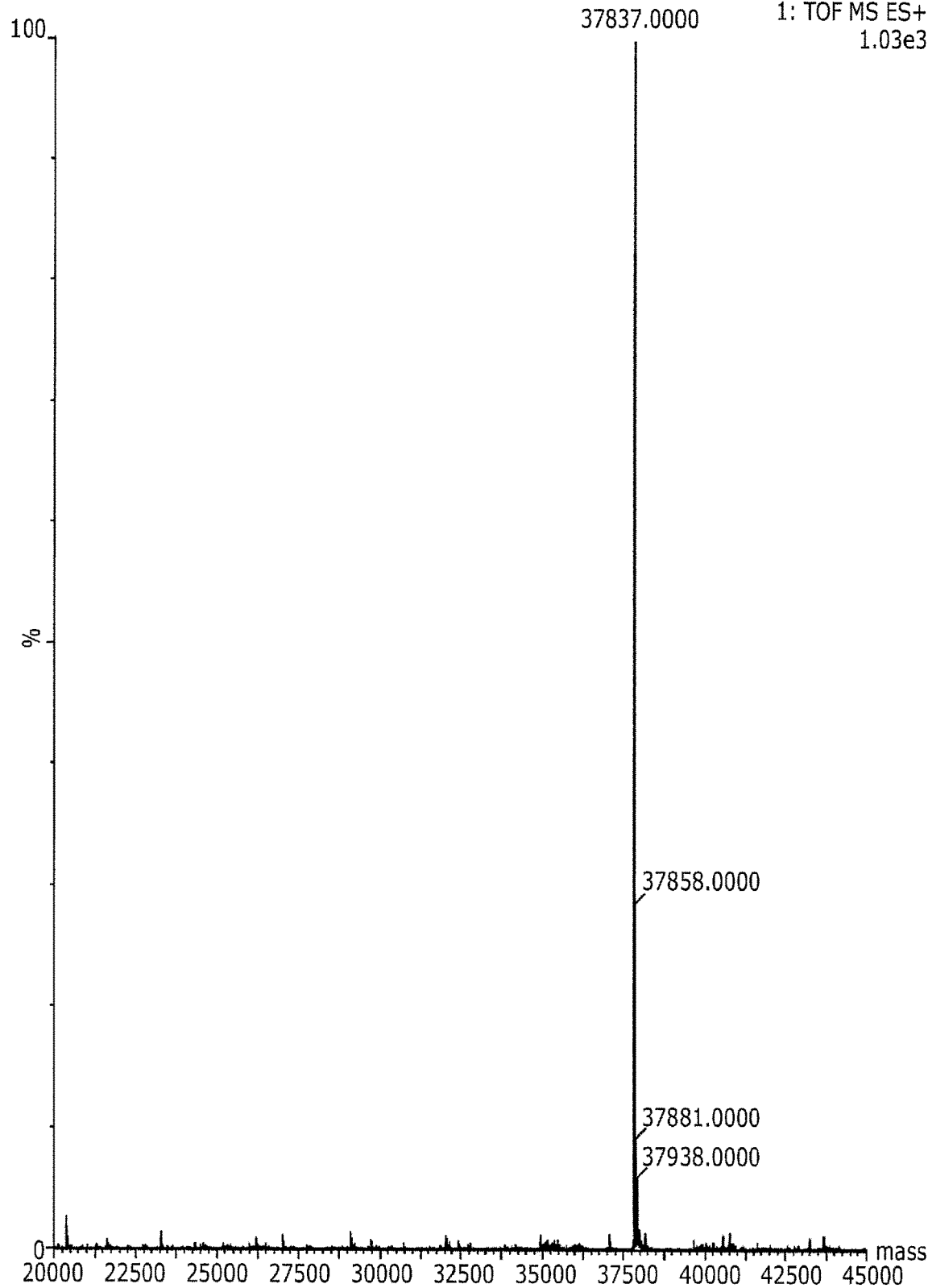
Figure 63:
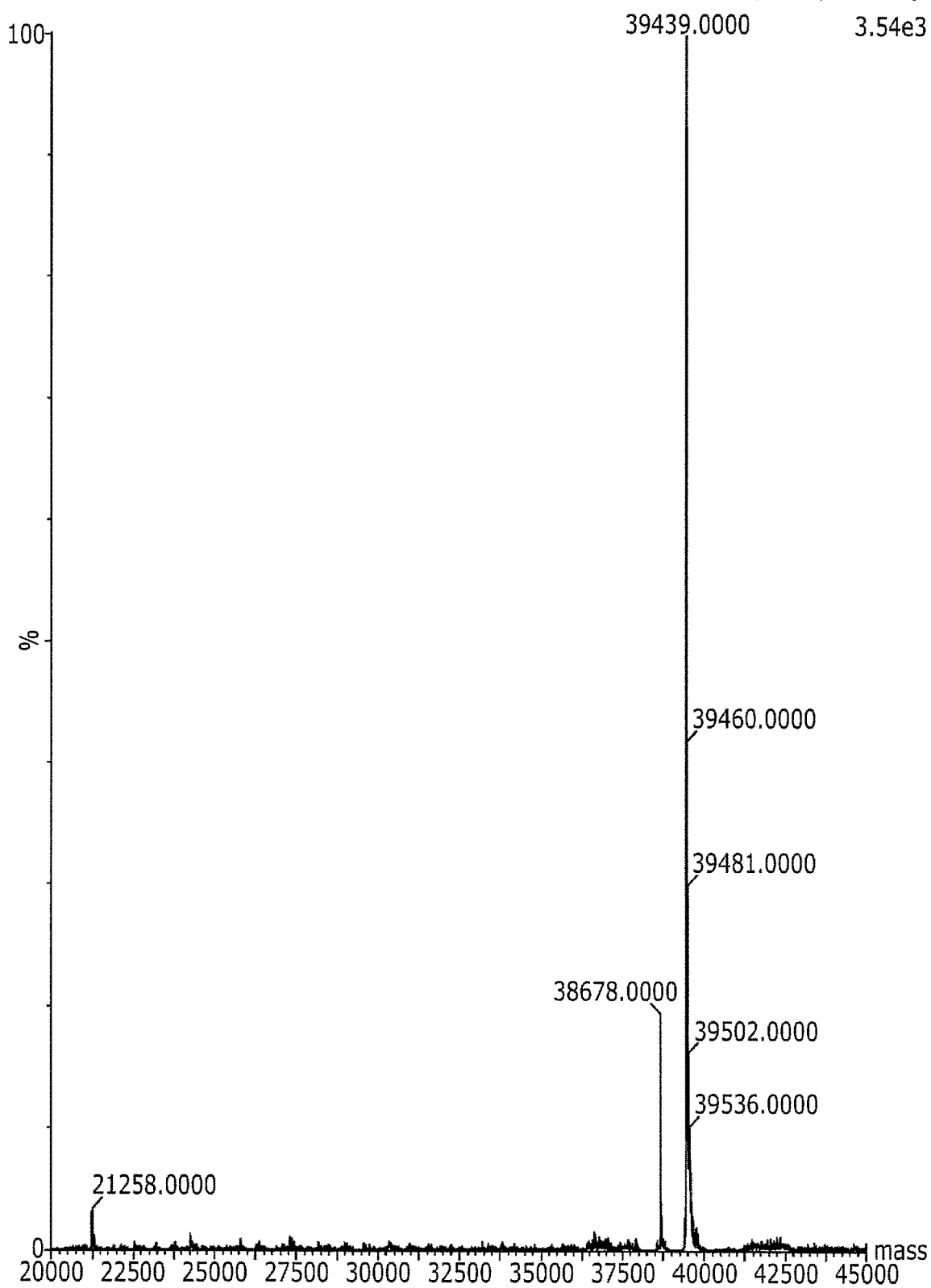
Figure 63:
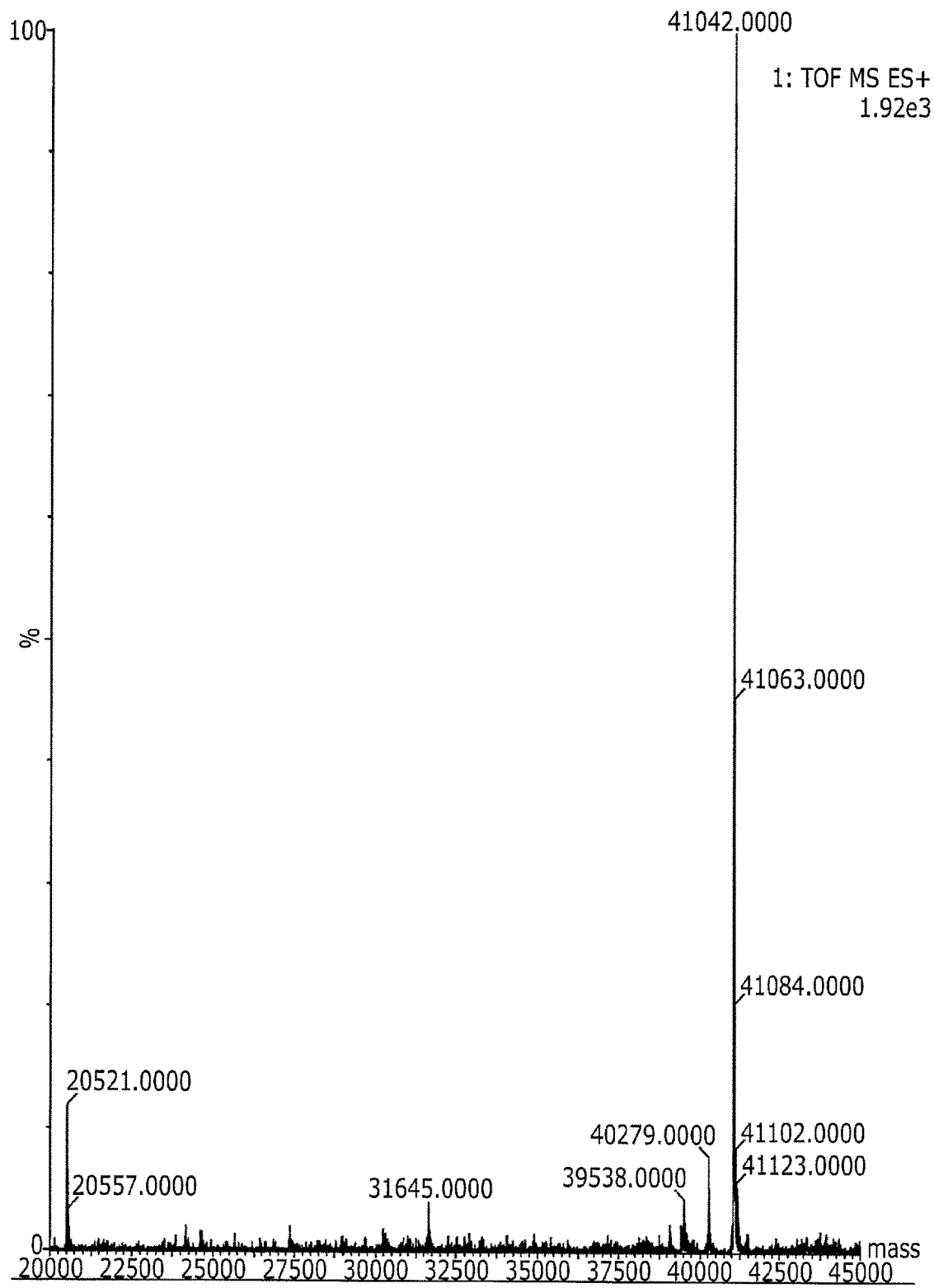
Figure 63:
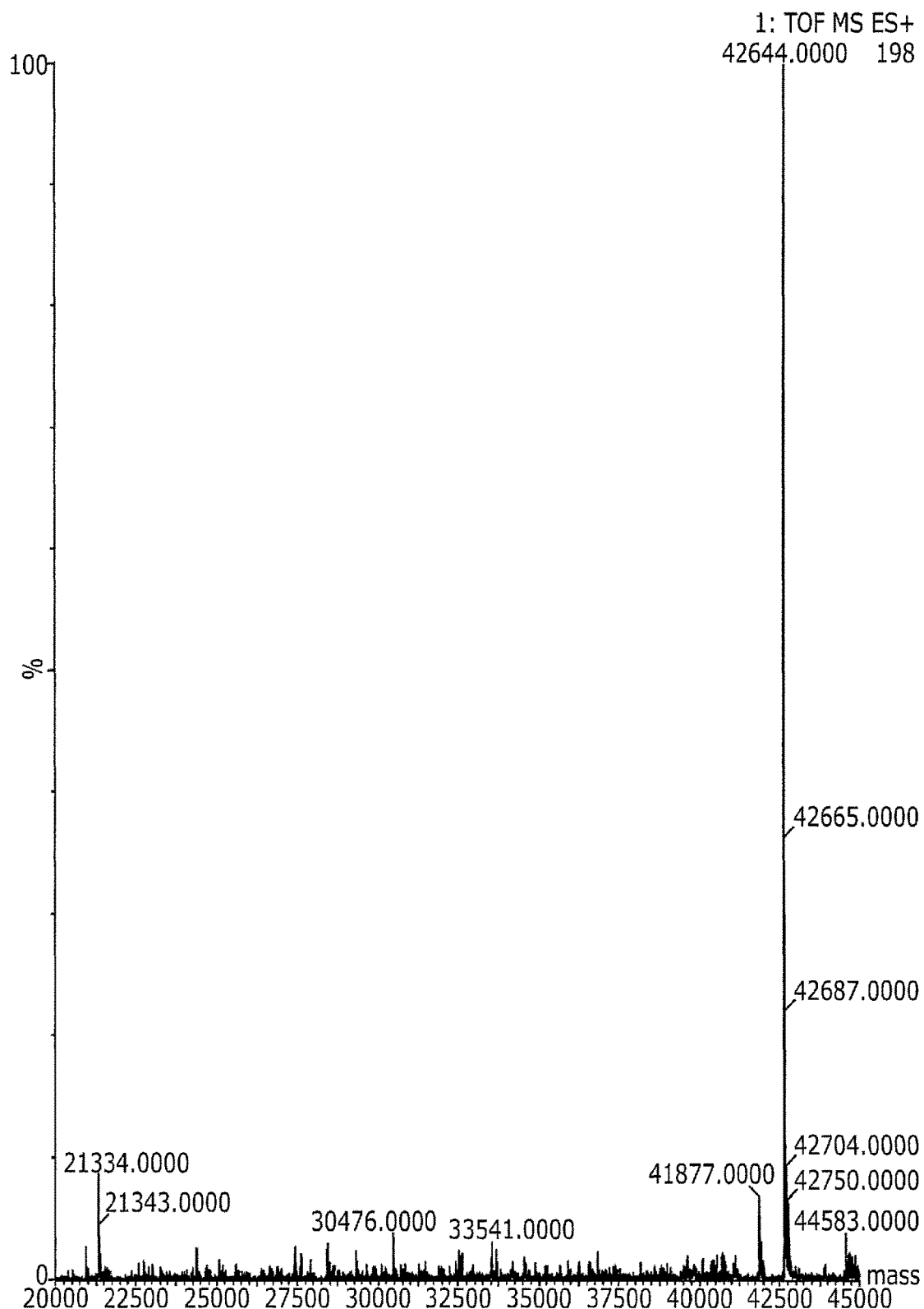

FIG. 63. LCMS data for scFv (TCT1067)-MMAE-PAB-Cit-Val-dPEG9 ADC 1.

(A) is the LCMS trace (UV and TIC) and (B-E) show the deconvoluted masses for the main peaks.

Figure 64:
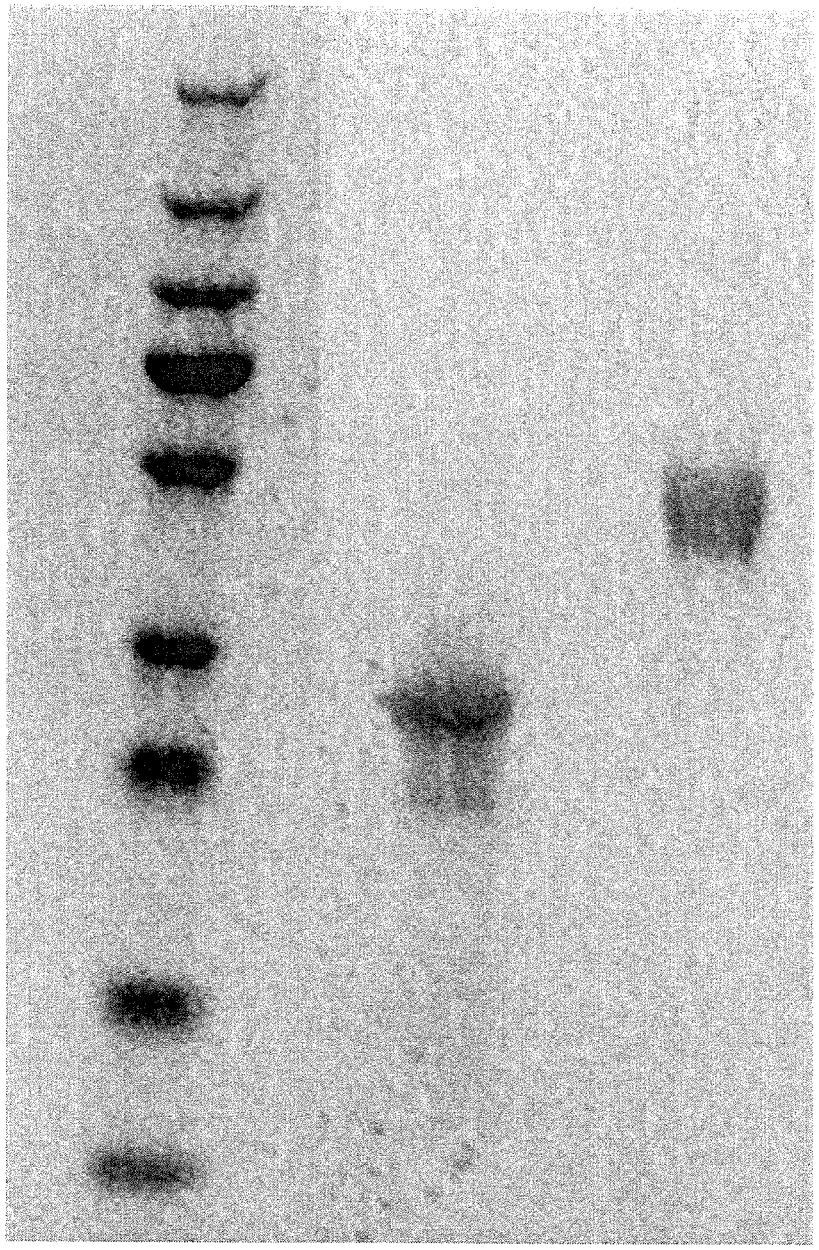

FIG. 64. SDS-PAGE reducing gel (12%) showing scFv (TCT1067)-MMAE-PAB-Cit-Val-dPEG9 ADC 1 in comparison with the scFv (TCT1067) unconjugated antibody.

Size markers as shown in FIG. 48.

Figure 65:
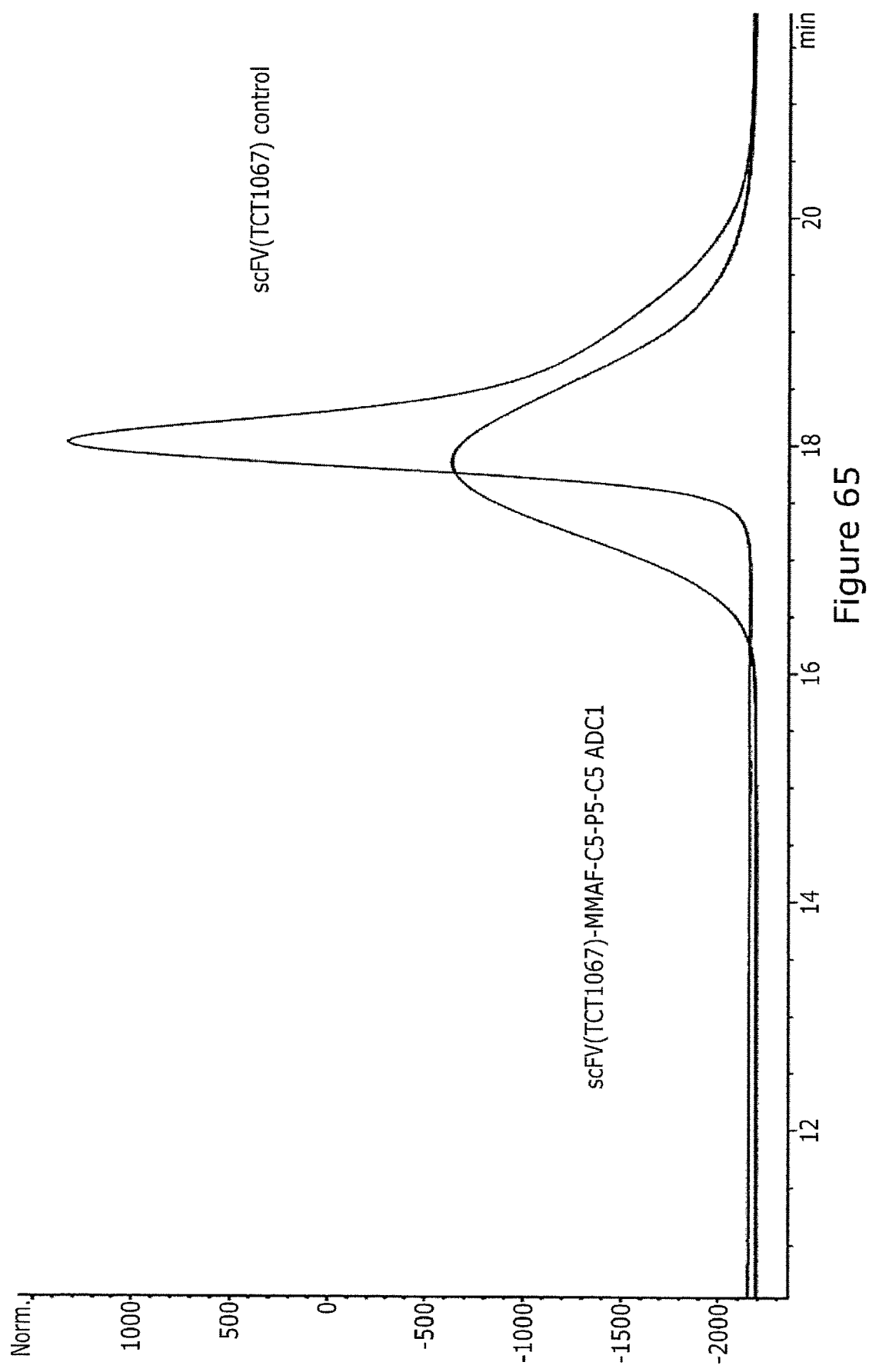

FIG. 65. HPLC SEC traces (A280 nm) for scFv (TCT1067)-MMAF-C5-P5-C5 ADC 1 run at 1 ml/min and compared to the unconjugated antibody.

Figure 66:
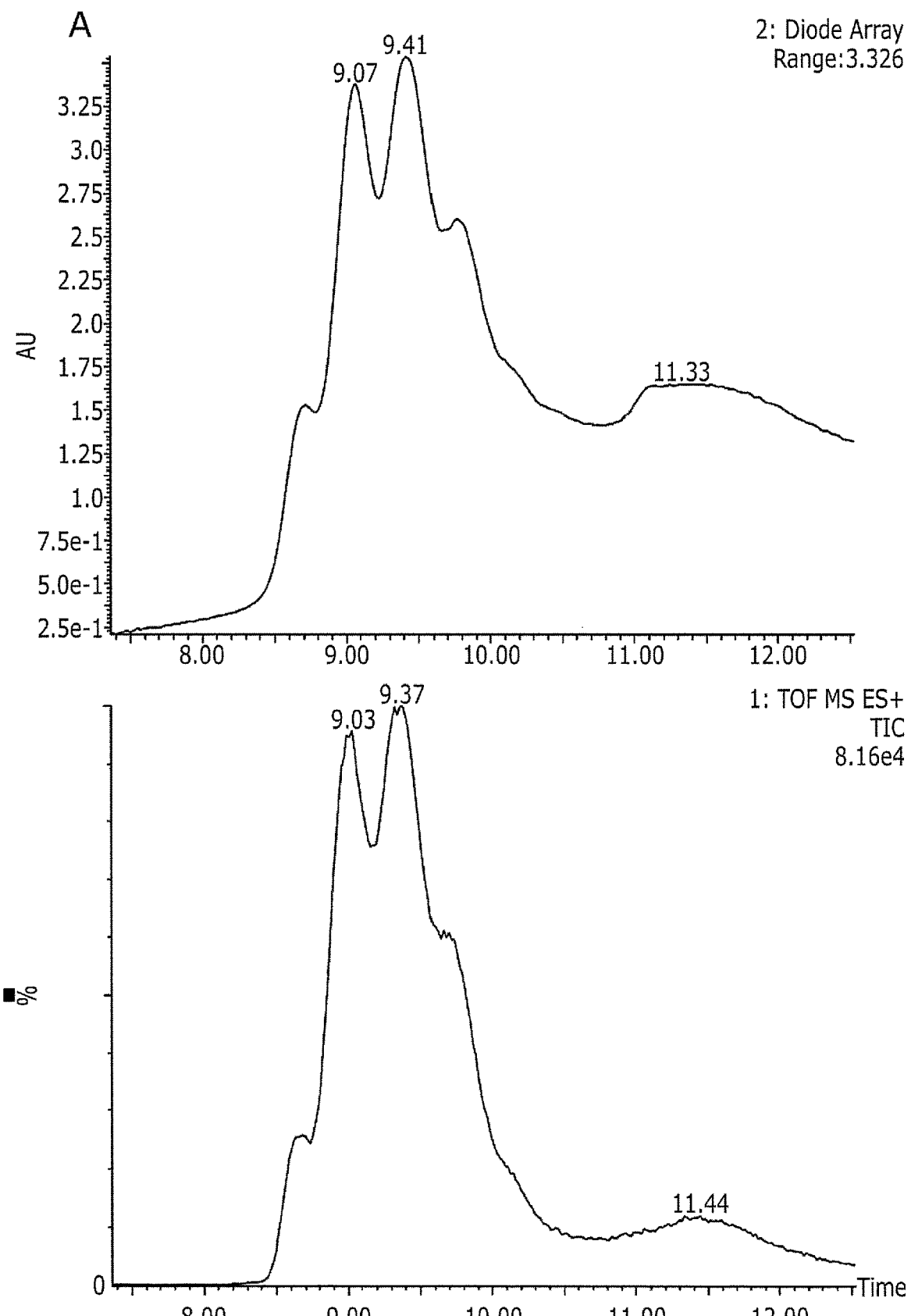
Figure 66:
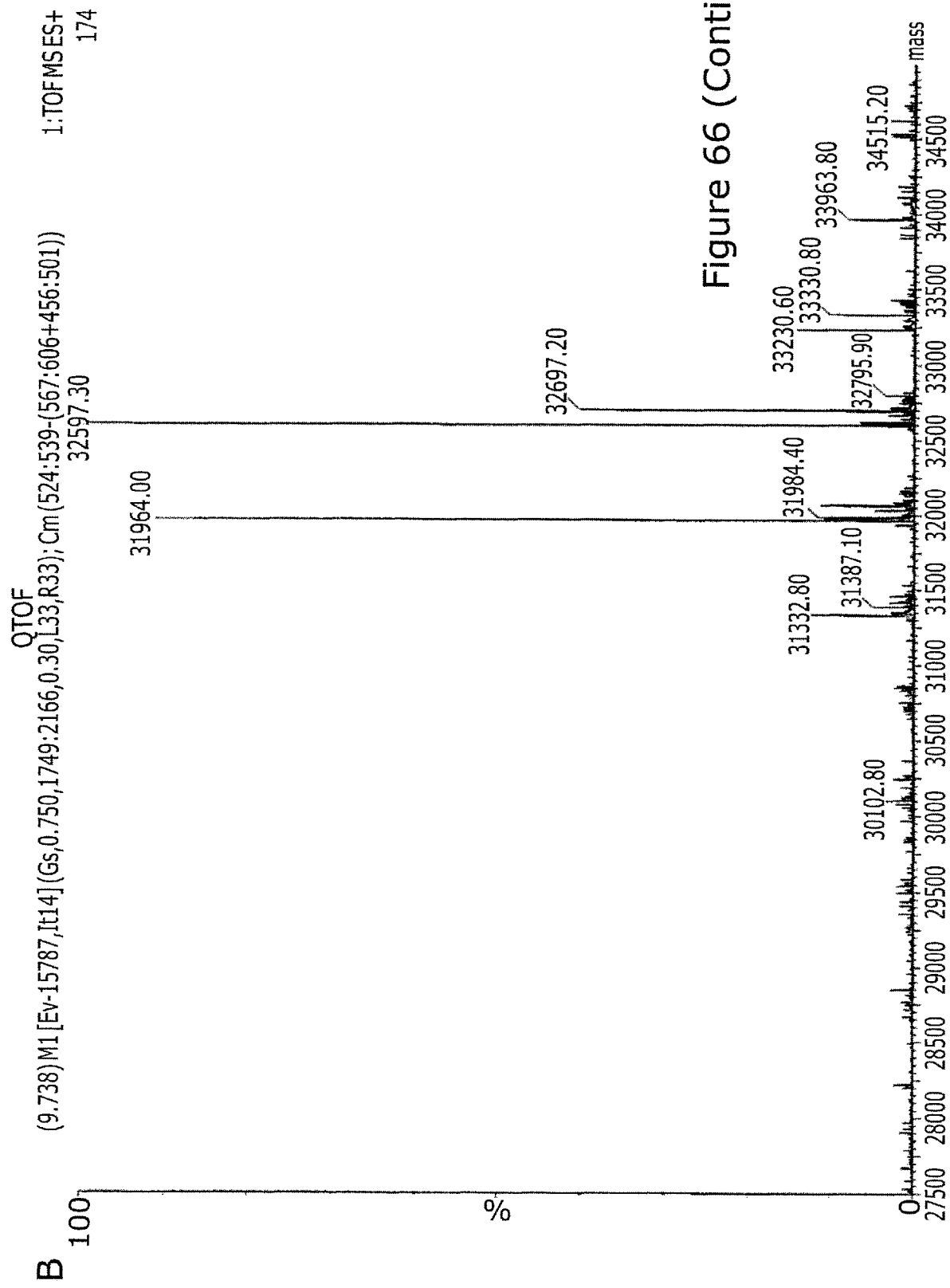
Figure 66:
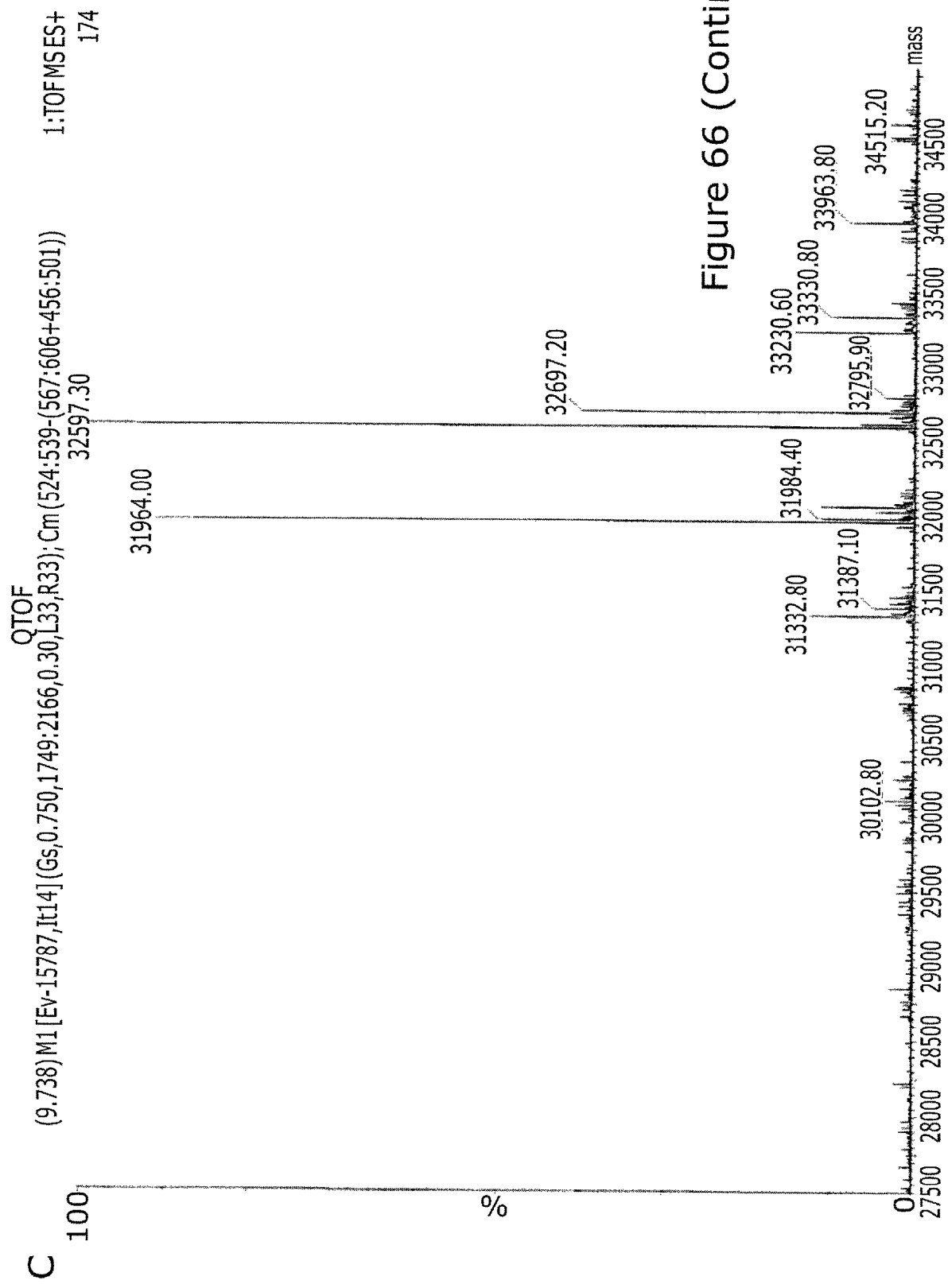
Figure 66:
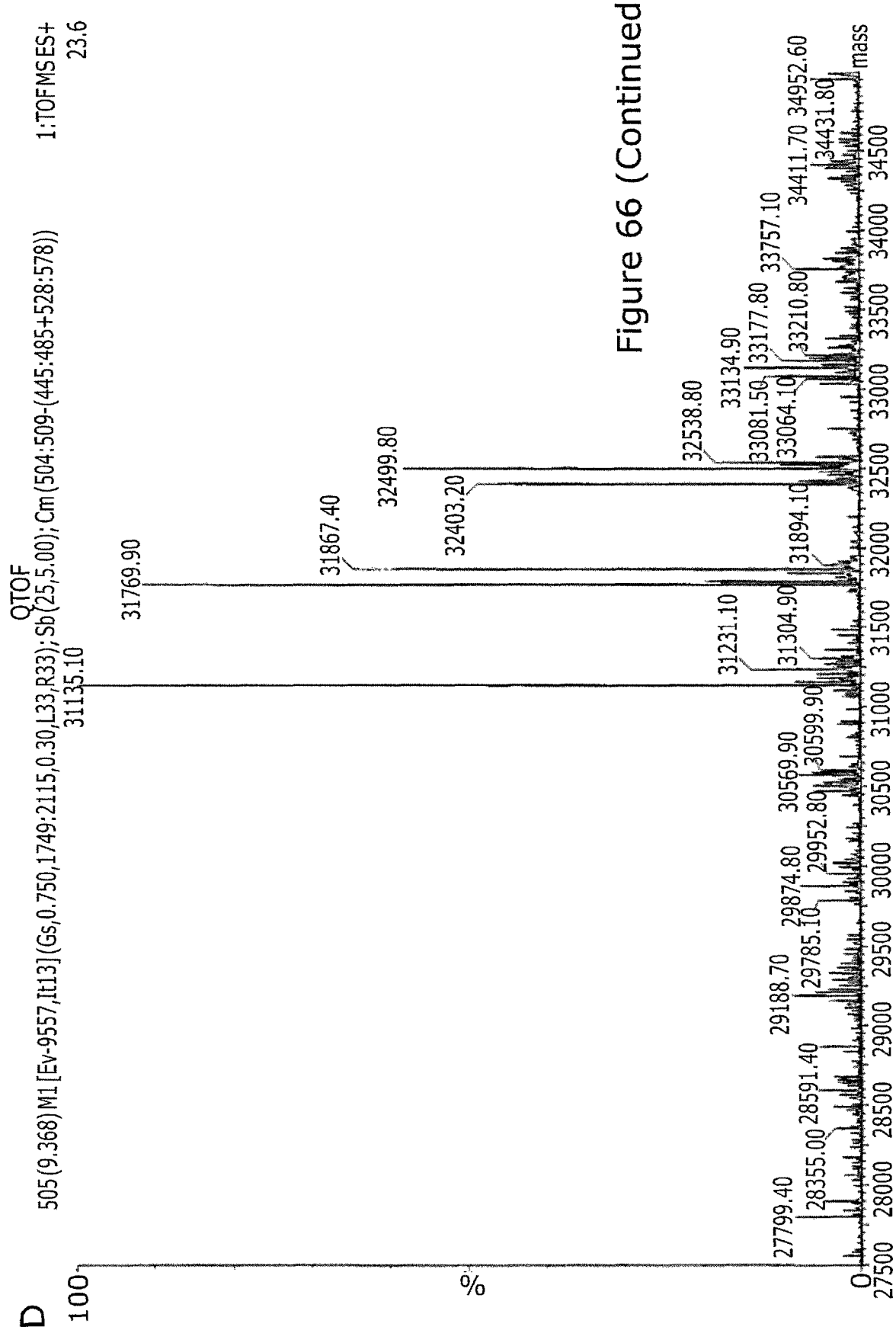
Figure 66:
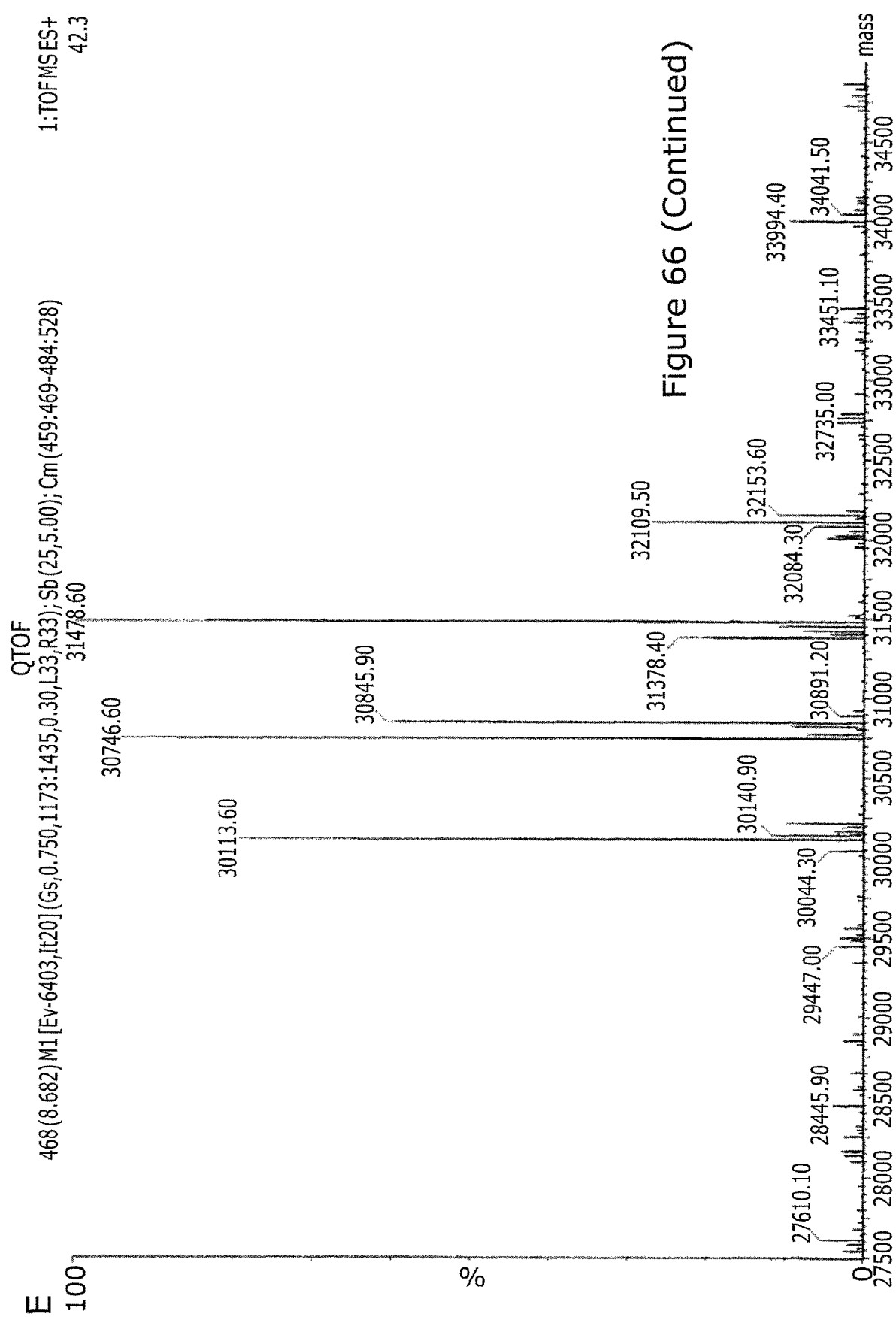
Figure 66:

FIG. 66. LCMS data for scFv (TCT1067)-MMAF-C5-P5-C5 ADC 1.

(A) is the LCMS trace (UV and TIC) and (B-F) show the deconvoluted masses for the main peaks.

Figure 67:
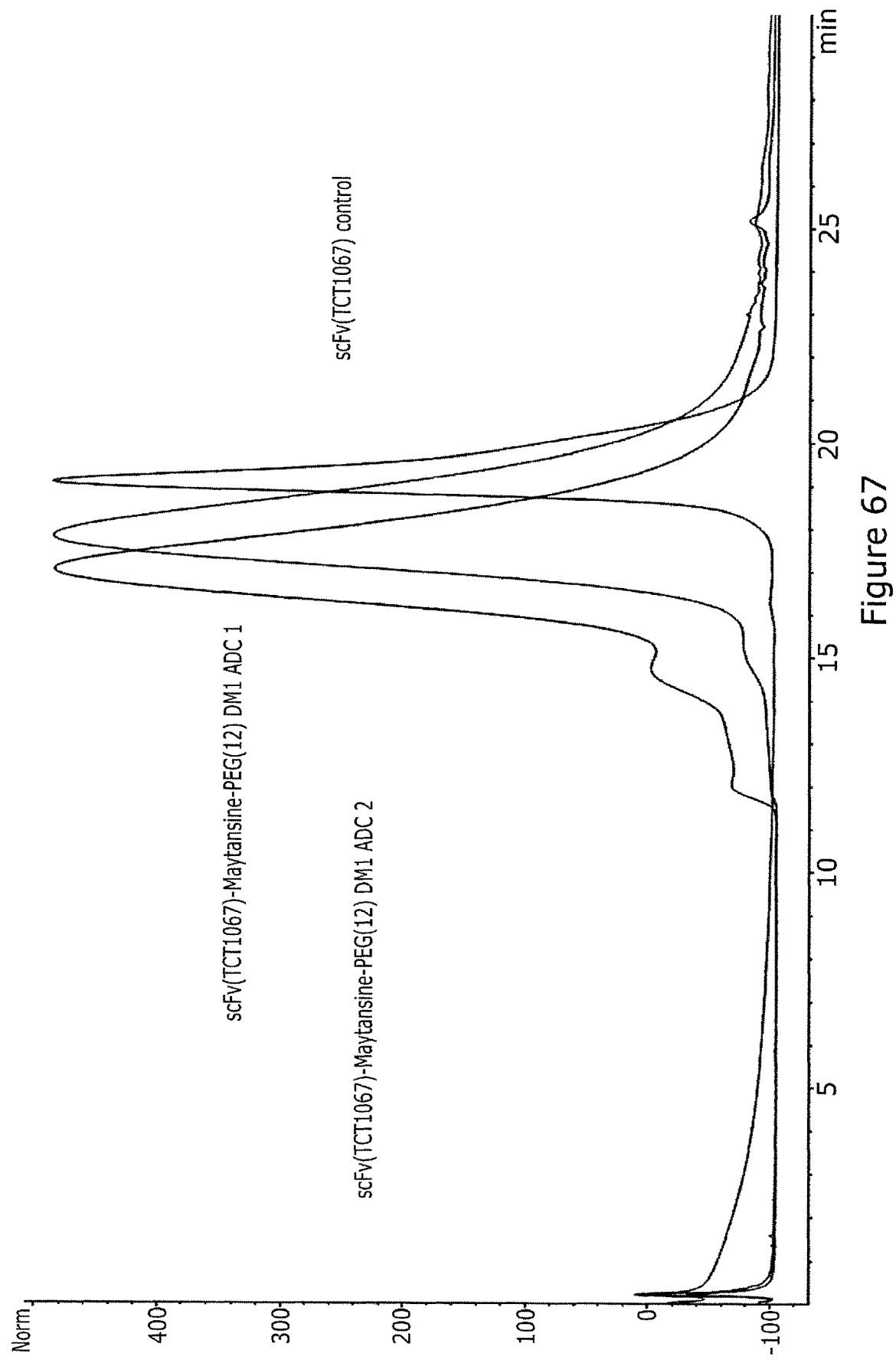

FIG. 67. HPLC SEC traces (A280 nm) for scFv (TCT1067)-Maytansine-PEG(12) DM1 ADC 1 and 2 run at 1 ml/min and compared to the unconjugated antibody.

Figure 68:
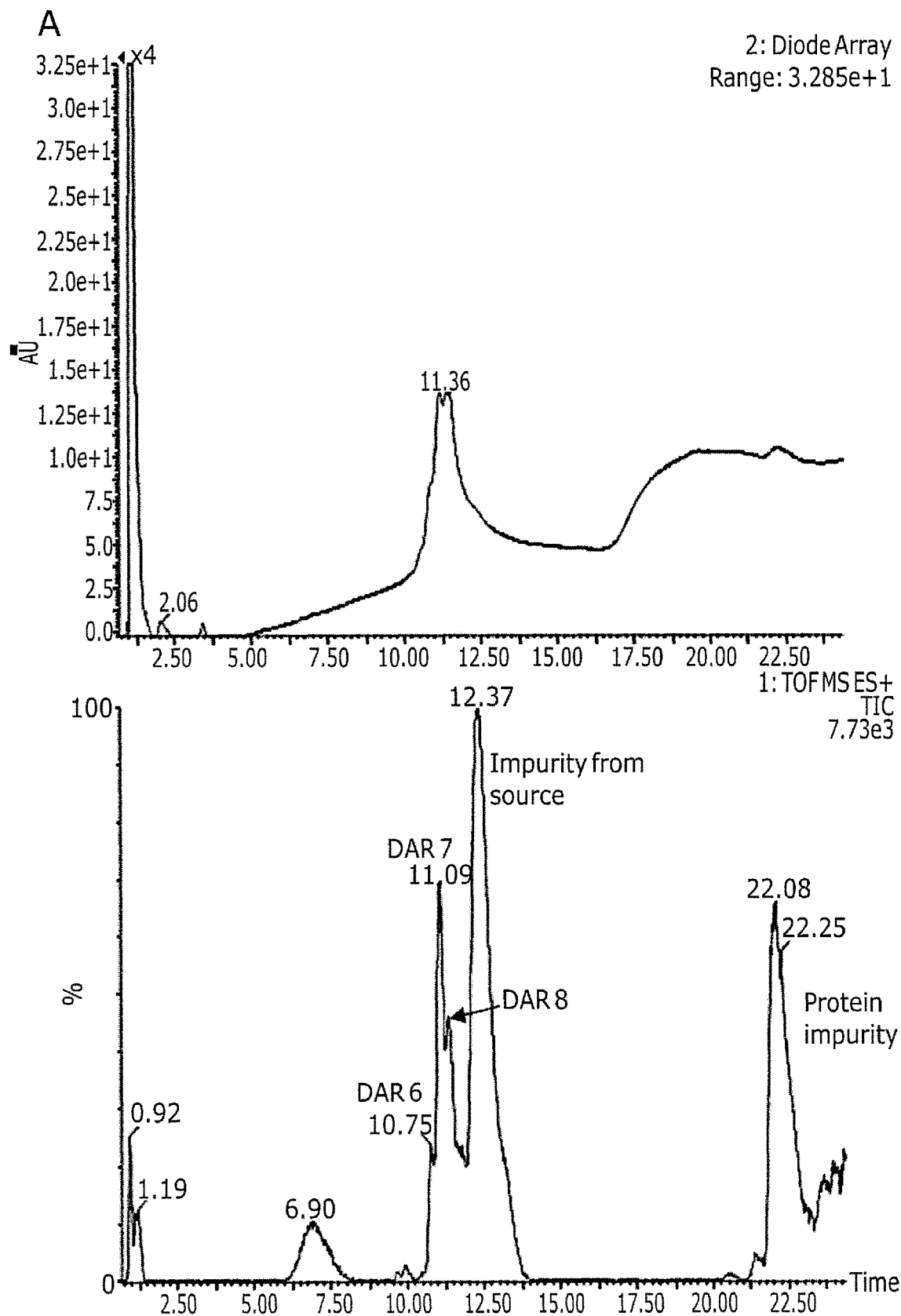
Figure 68:
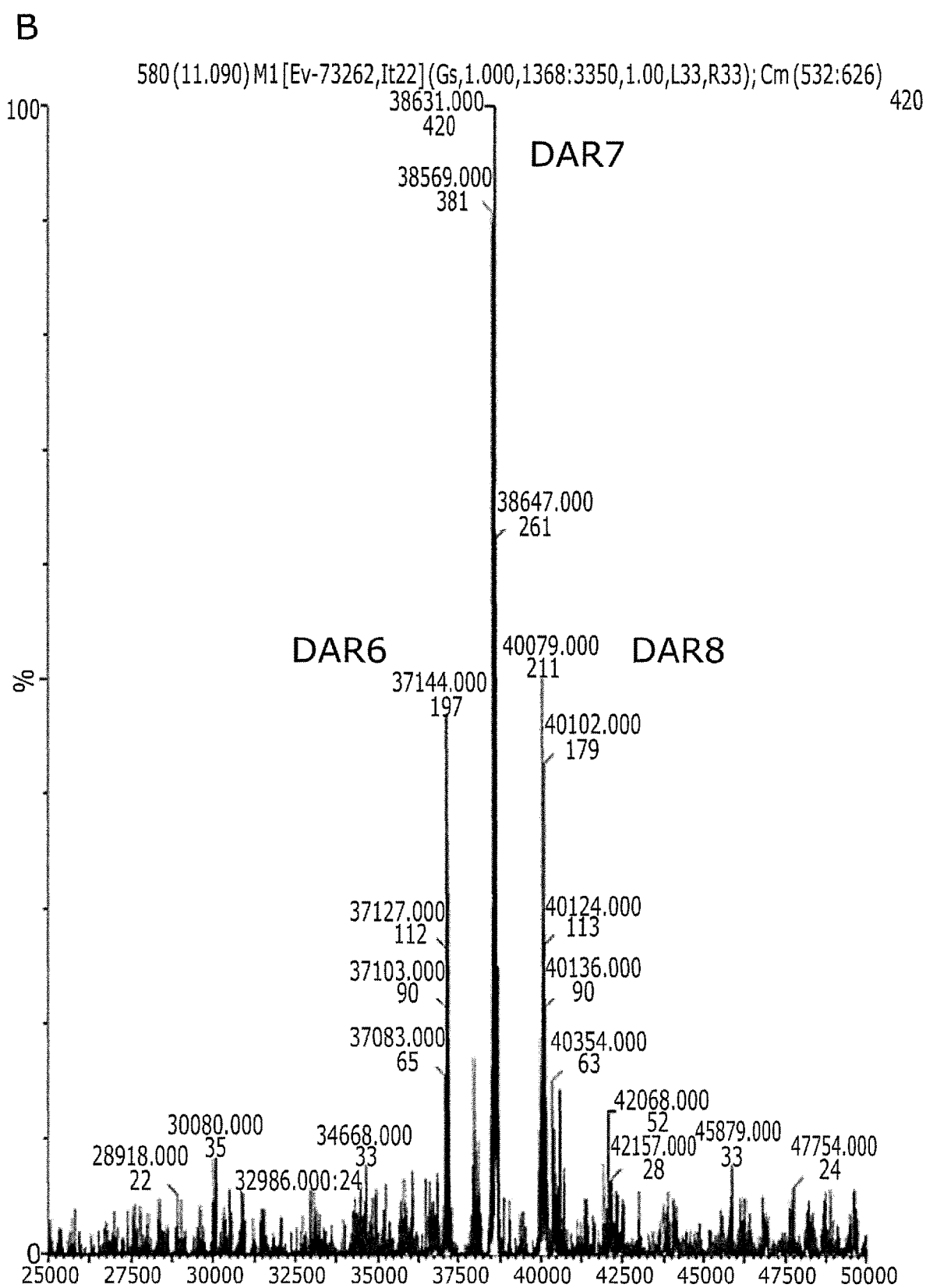
Figure 68:
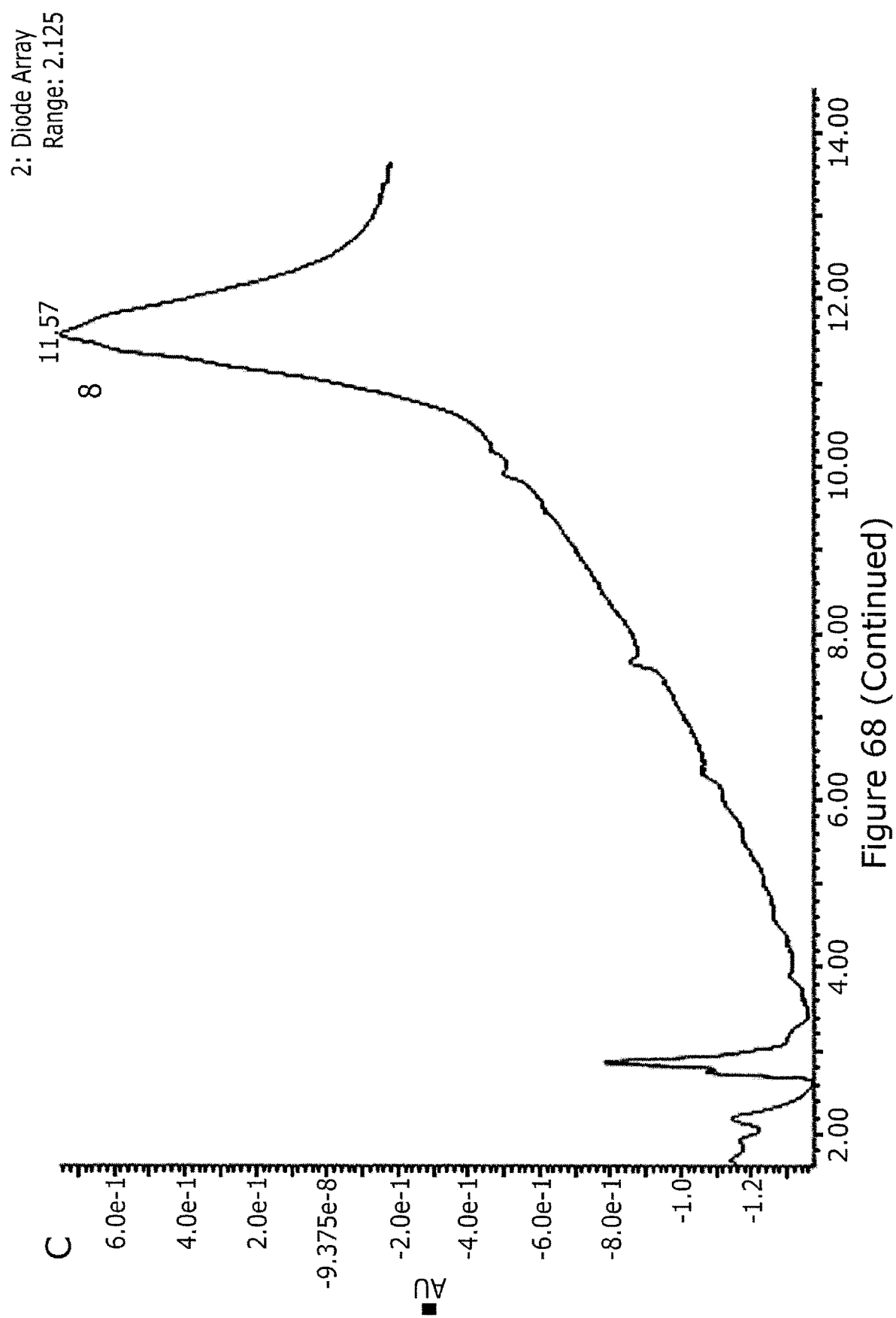
Figure 68:
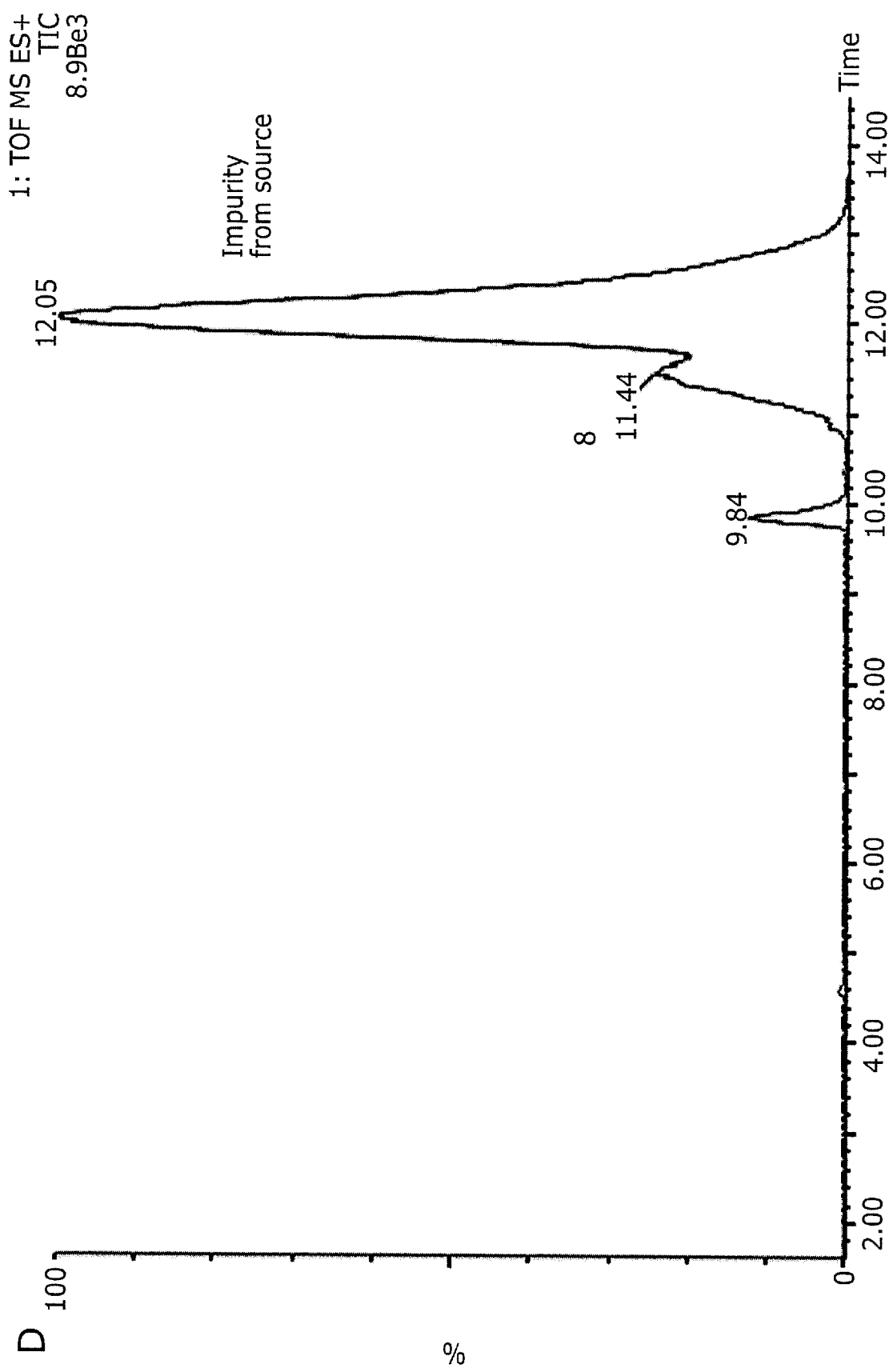

FIG. 68. LCMS data for scFv (TCT1067-Maytansine-PEG(12) DM1 ADC 1 and 2.

(A) and (B) are the LCMS data for scFv (TCT1067)-Maytansine-(PEG12) DM1 ADC 1 where (A) is the LCMS trace (UV and TIC), and (B) shows the deconvoluted masses for the main peak. (C) and (D) are the LCMS data for scFv (TCT1067-Maytansine-PEG(12) DM1 ADC 2 where (C) is the UV LCMS trace and (D) is the TIC LCMS trace indicating the DAR of the species present in the sample.

FIG. 69. SDS-PAGE reducing gel (12%) showing scFv (TCT1067)-Maytansine-PEG(12) DM1 ADC 1 and 2 in comparison with the scFv (TCT1067) unconjugated antibody.

Size markers are as shown in (A)

Figure 70:
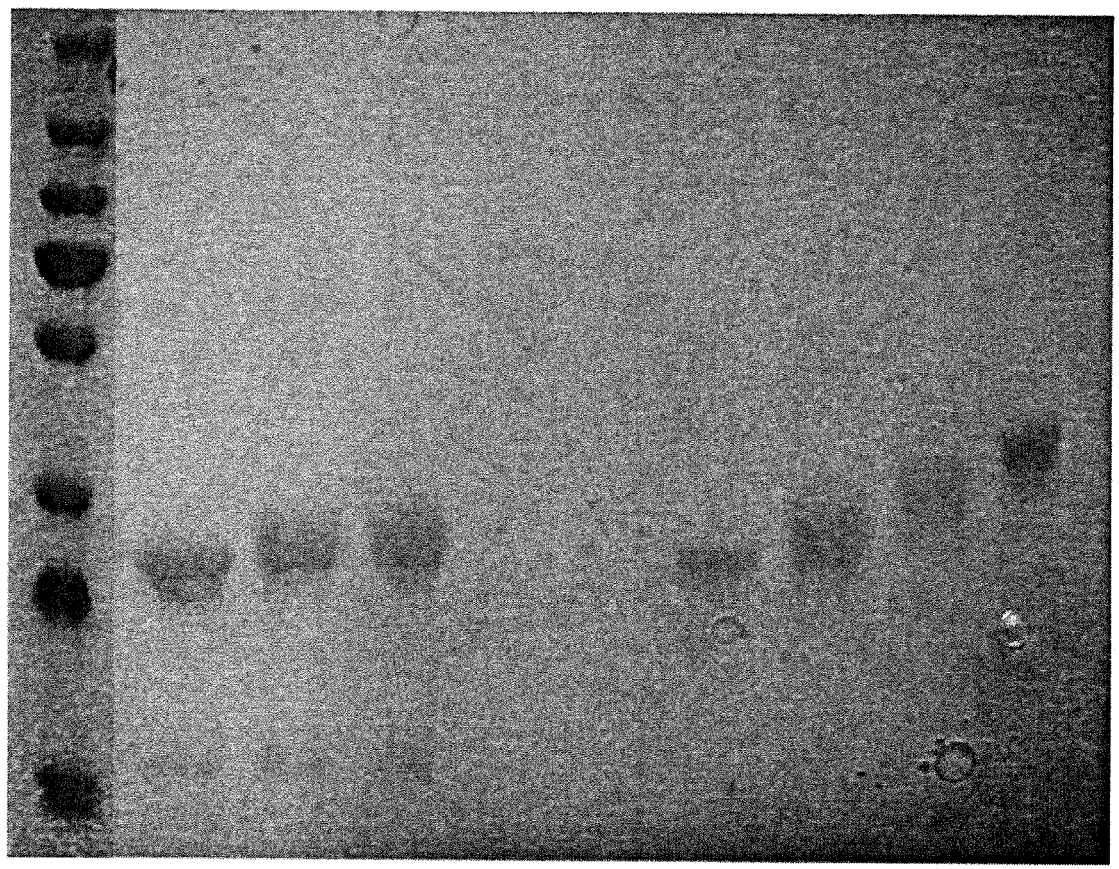

FIG. 70. Coomassie-stained SDS-PAGE gel of the reactions 1, 2, 4, 5, and 6 described in Table 45. Reaction 3 yielded no soluble protein.

M=molecular weight markers.
P=unconjugated scFv (panitumumab),
T=unconjugated scFv (TCT1067).

The higher DAR species migrate more slowly due to increased molecular weight, with the scFv (TCT1067) conjugates demonstrating an increasing DAR. Size markers as shown in FIG. 68.

Figure 71:
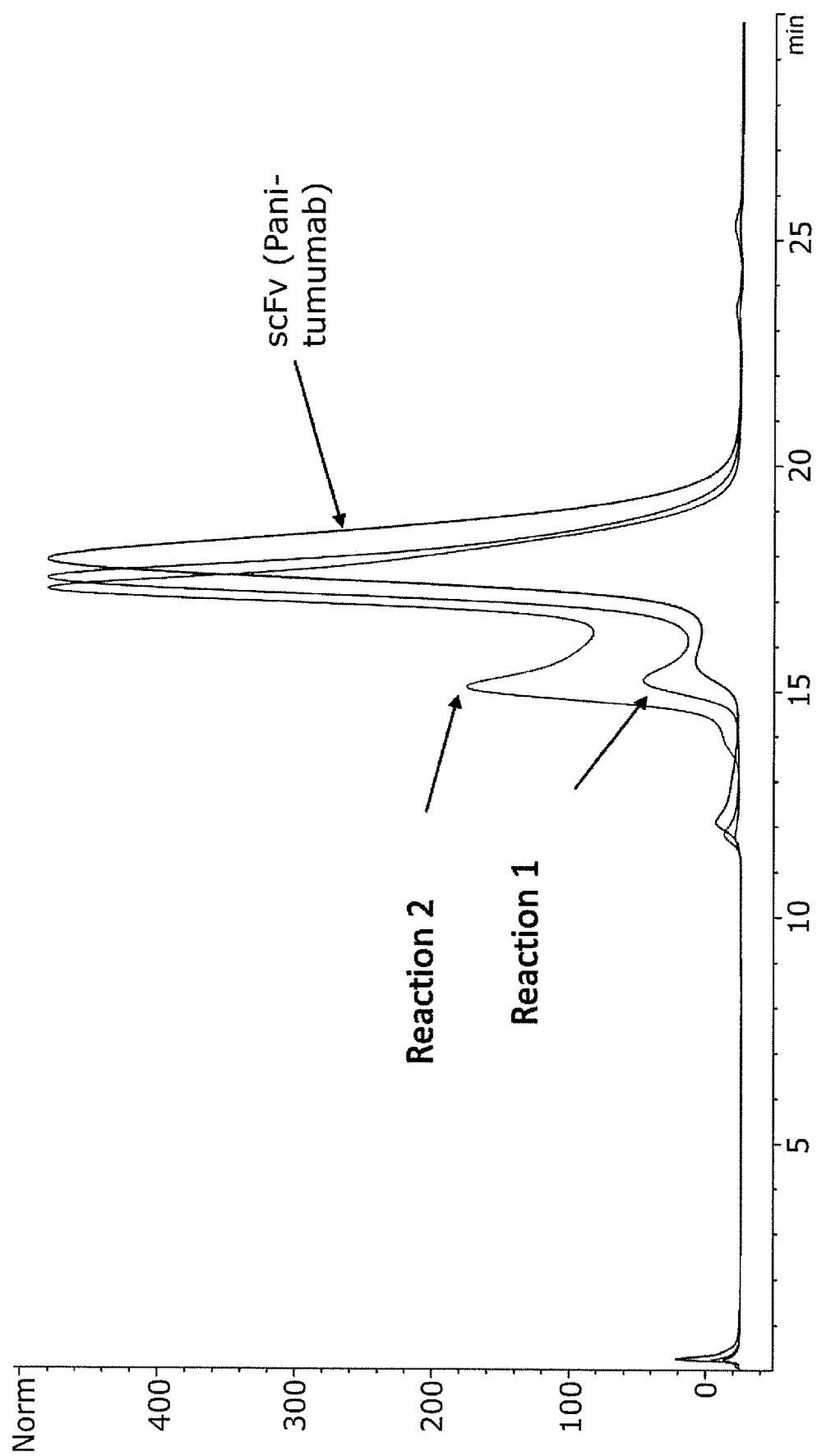
Figure 71:
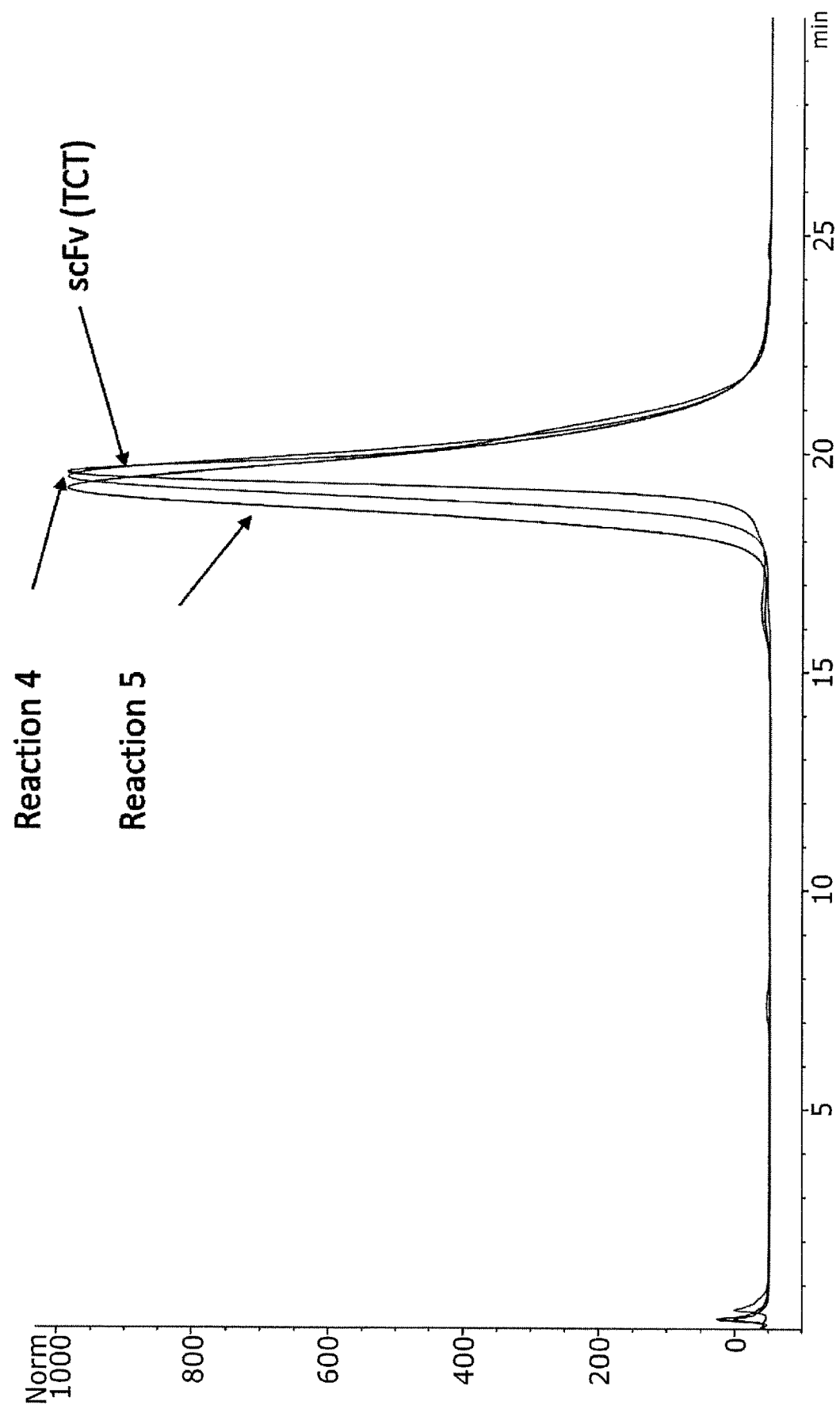

FIG. 71. HPLC SEC traces (A280 nm) for (A) scFv (Panitumumab)-AF-C5 ADC and (B) scFv (TCT1067)-AF-C5 run at 1 ml/min and compared to the unconjugated antibodies.

Figure 72:
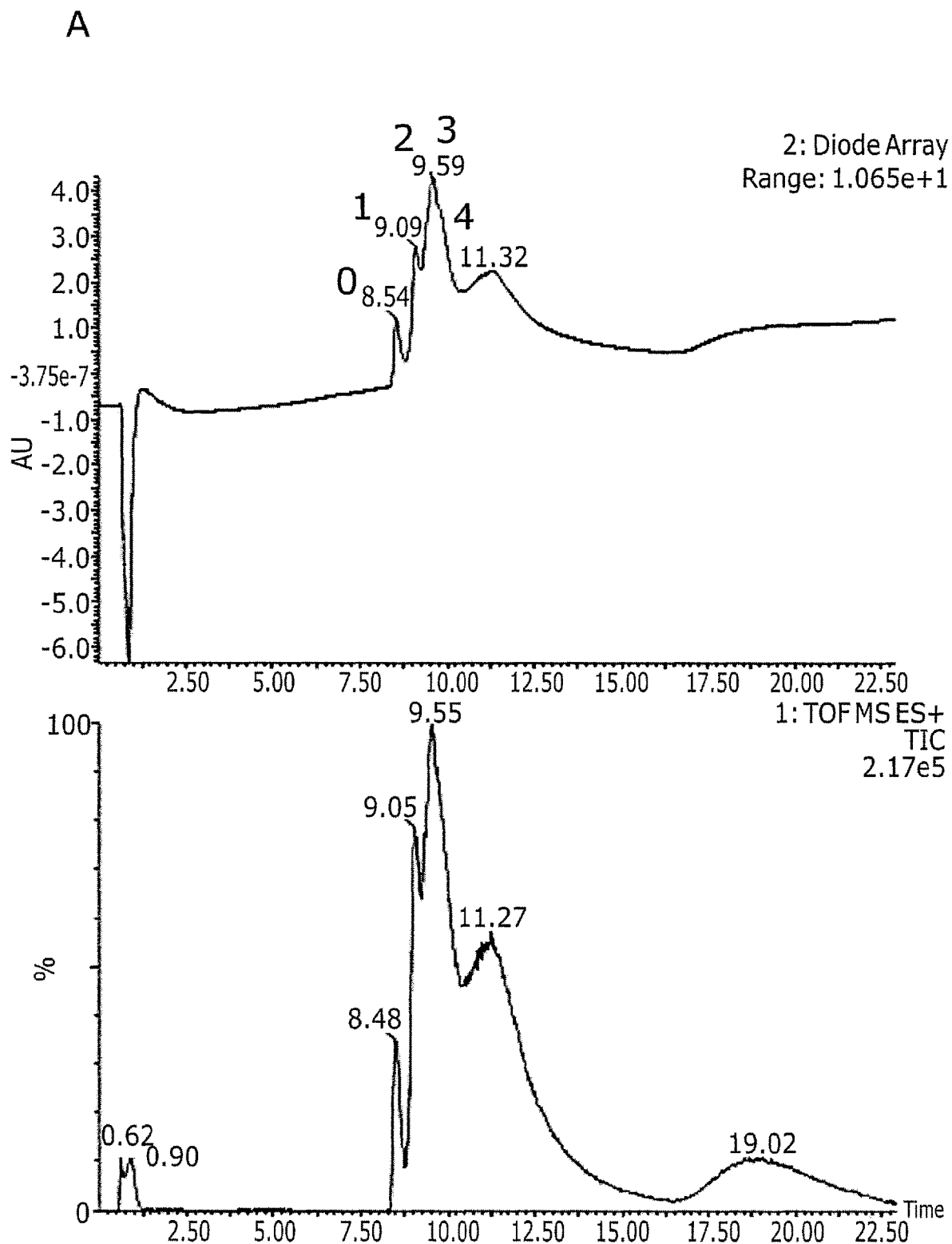
Figure 72:
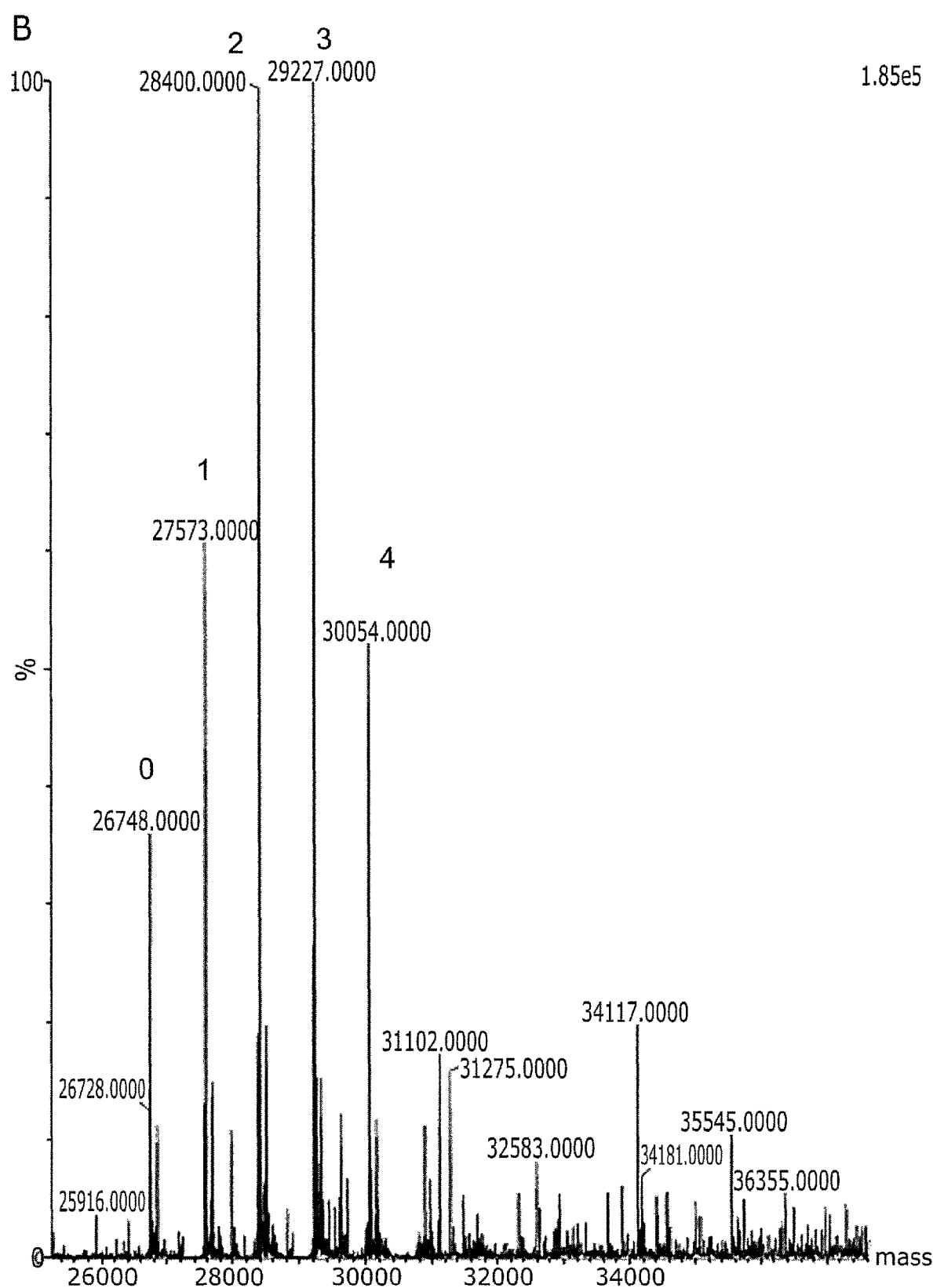
Figure 72:
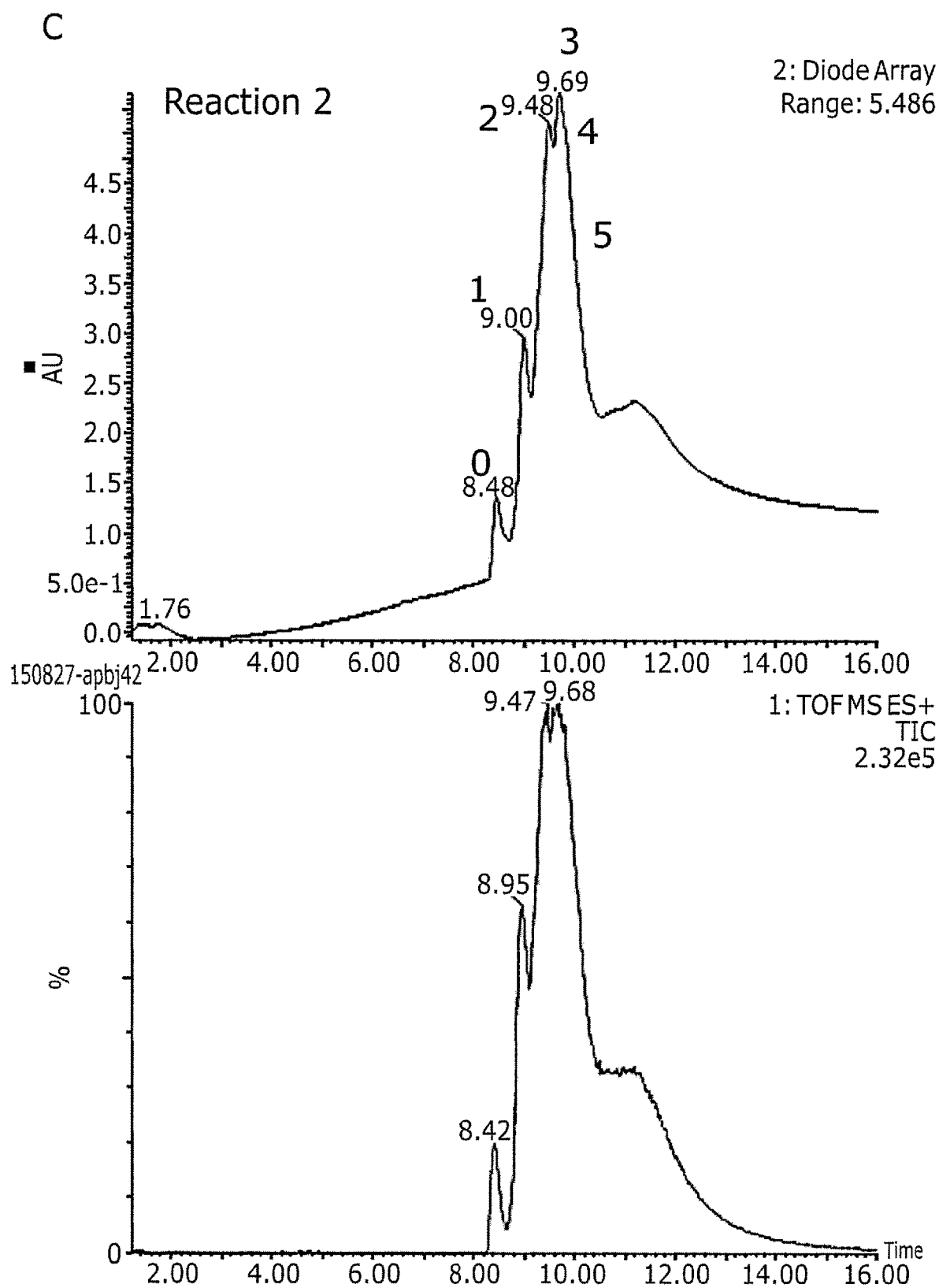
Figure 72:
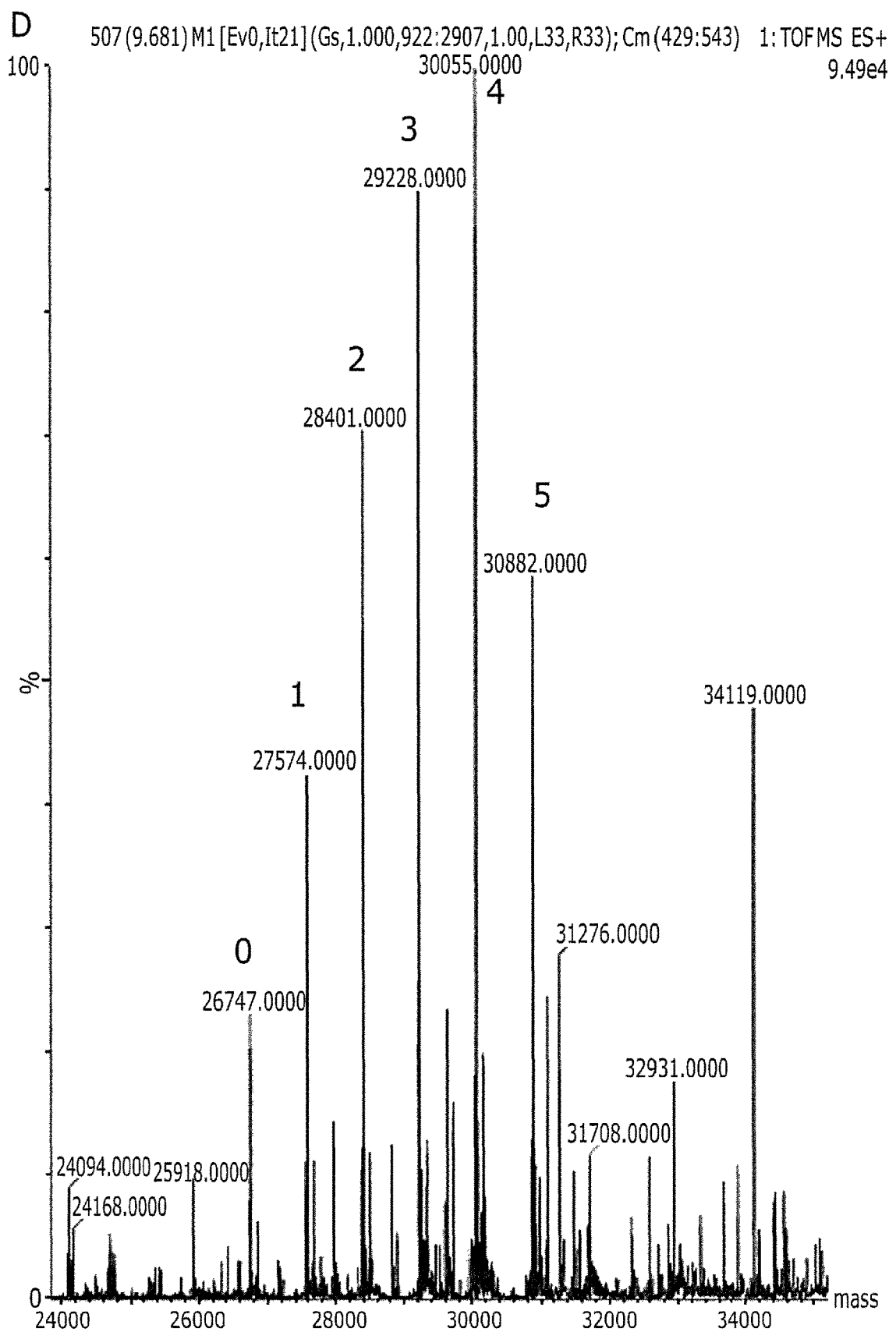
Figure 72:
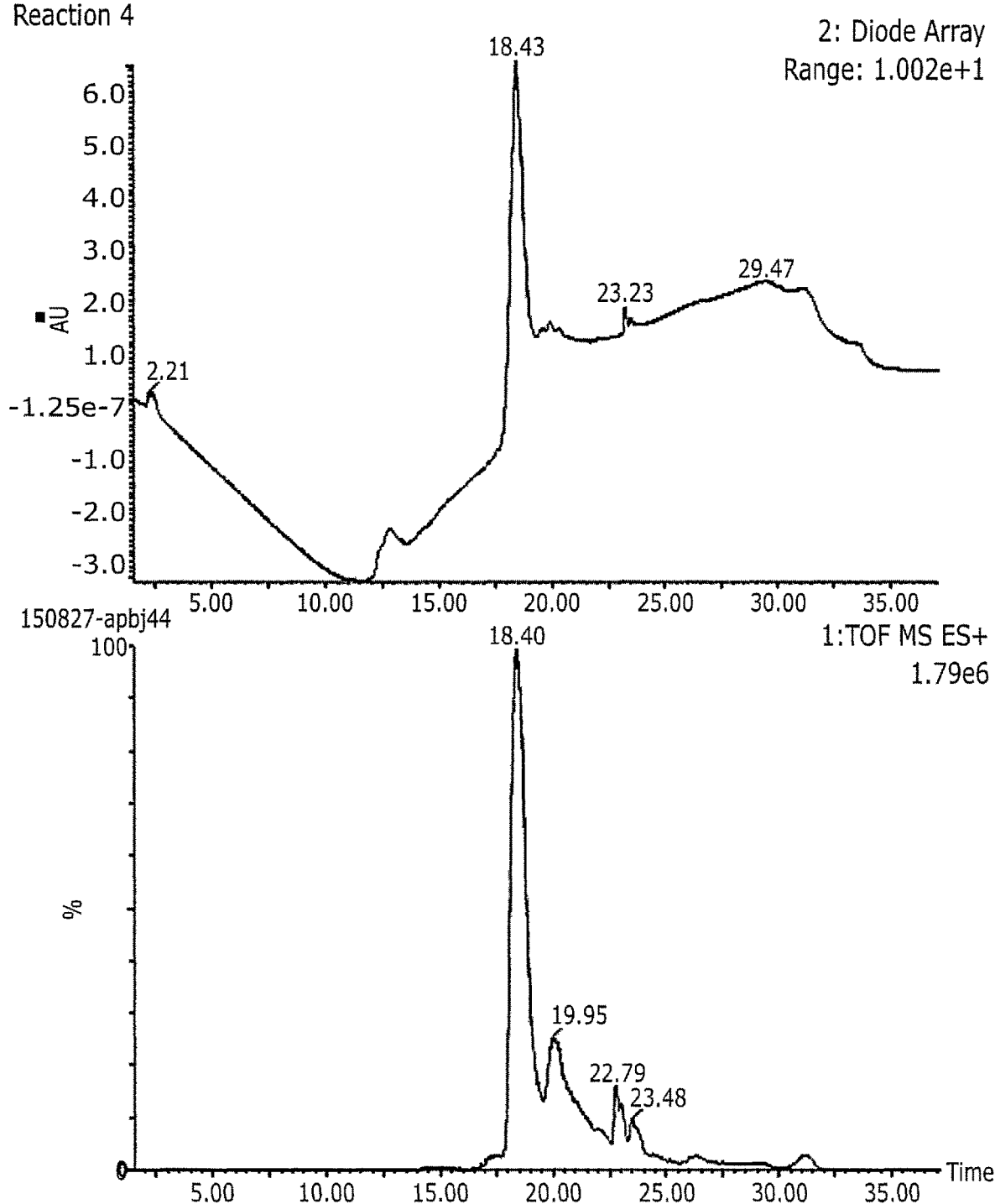
Figure 72:
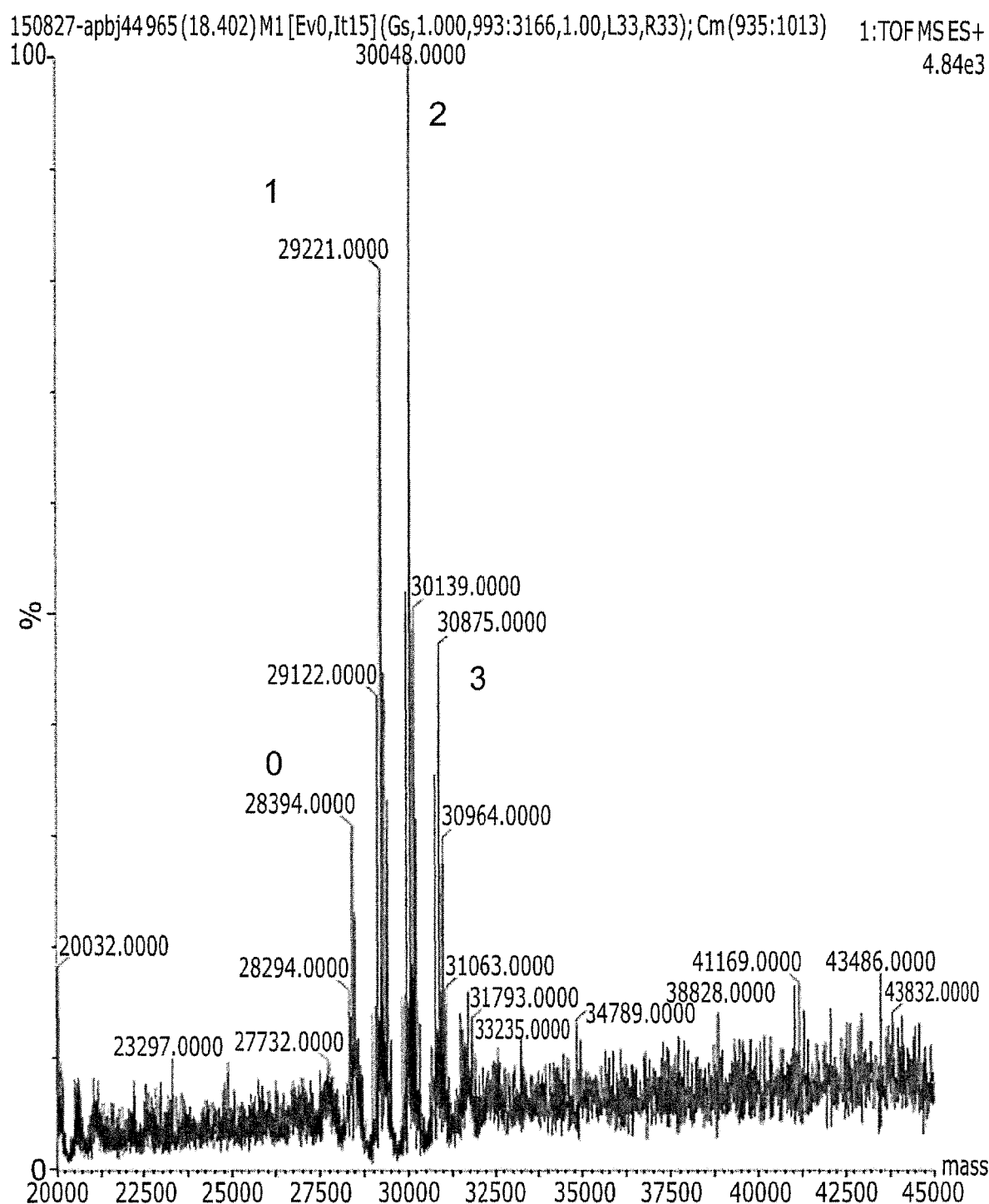
Figure 72:
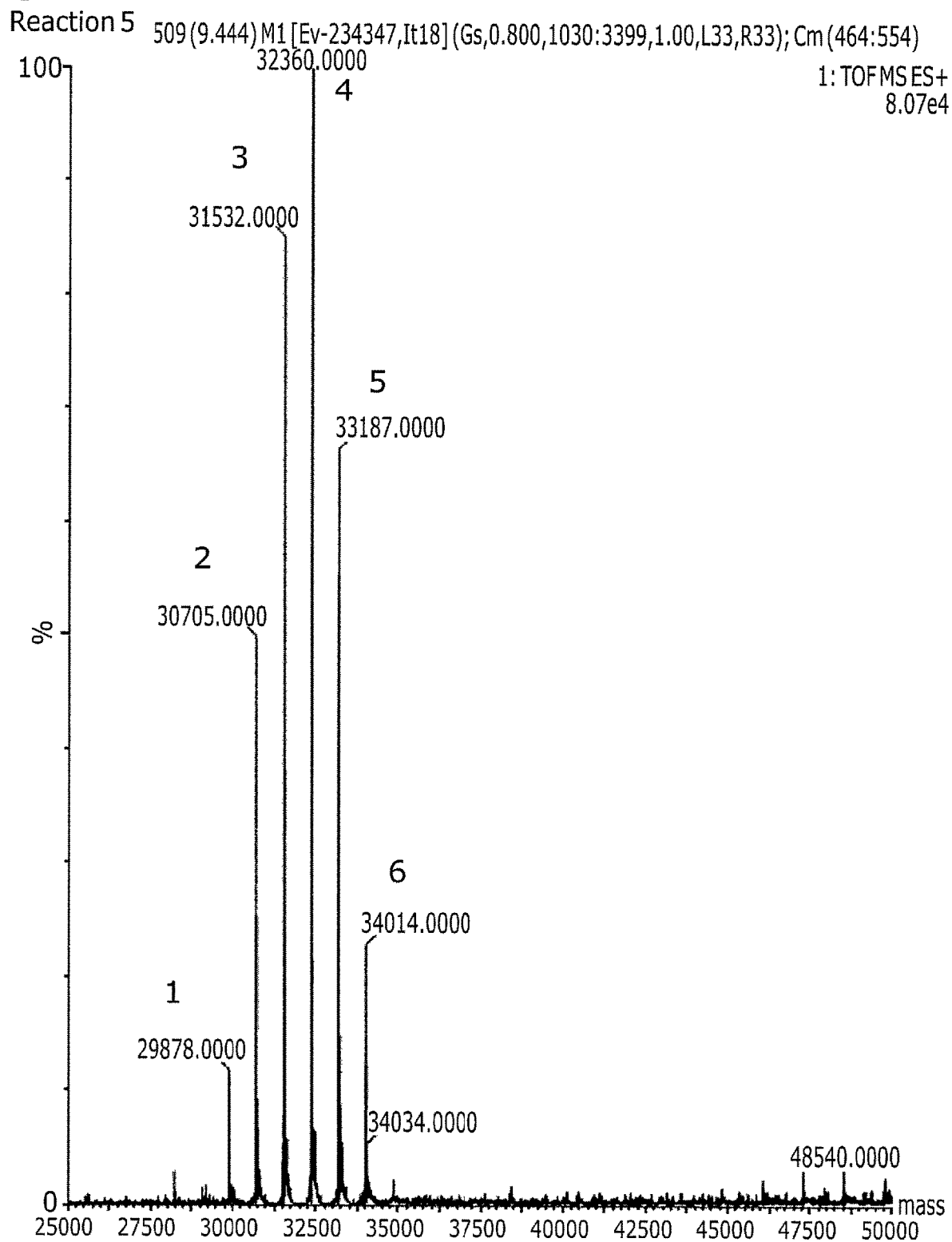
Figure 72:
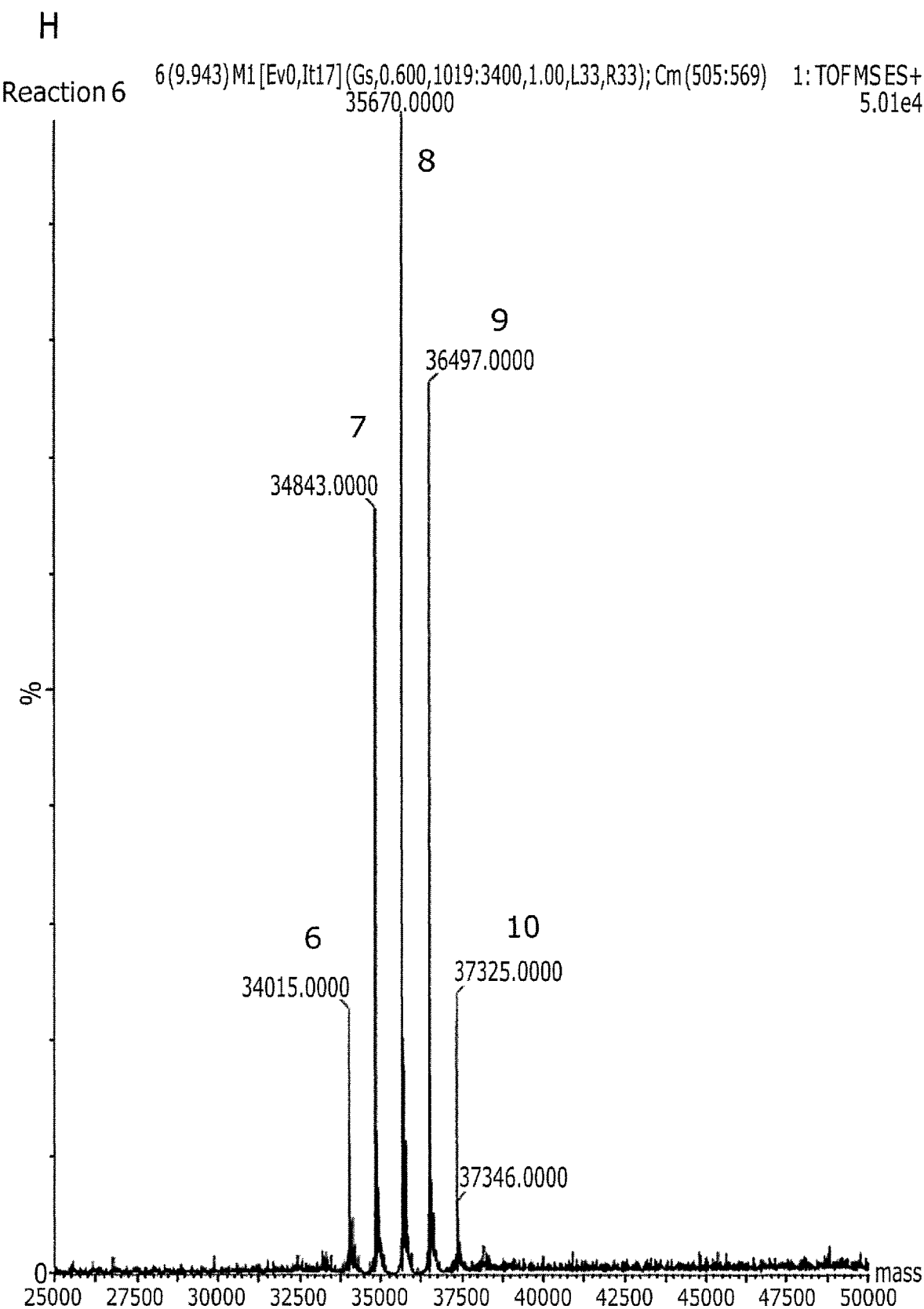

FIG. 72. LCMS data for scFv (Pani-AF-C5) ADCs 1, 2, and 4-6.

(A) and (B) is the LCMS data for scFv (Pani-AF-C5) ADC 1, where (A) is the LCMS trace (UV and TIC) and (B) shows the deconvoluted masses for the main peaks of sample 1. (C) is the LCMS trace (UV and TIC) and (D) shows the deconvoluted masses for the main peaks of sample 2. (E)-(H) is the LCMS data for scFv (TCT1067-AF-C5) ADCs 4-6 where (E) is the LCMS trace (UV and TIC) for sample 4, (F) shows the deconvoluted masses for the main peak of sample 4, (G) shows the deconvoluted masses for sample 5 and (H) shows the deconvoluted masses for sample 6.

Figure 73A:
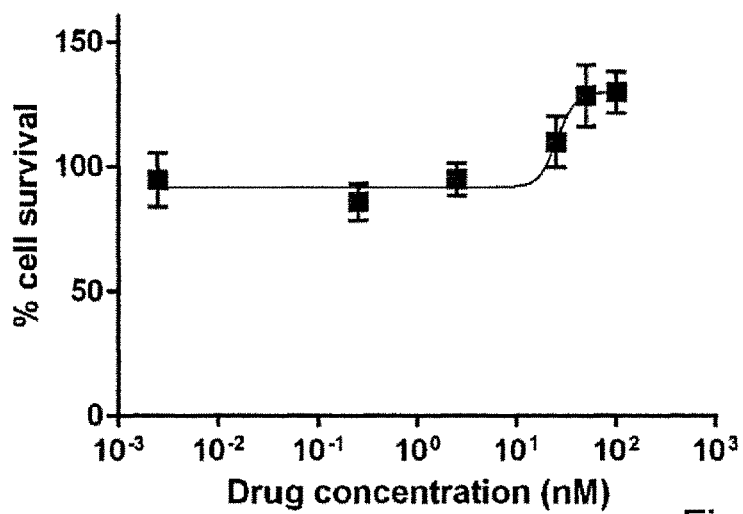
Figure 73B:
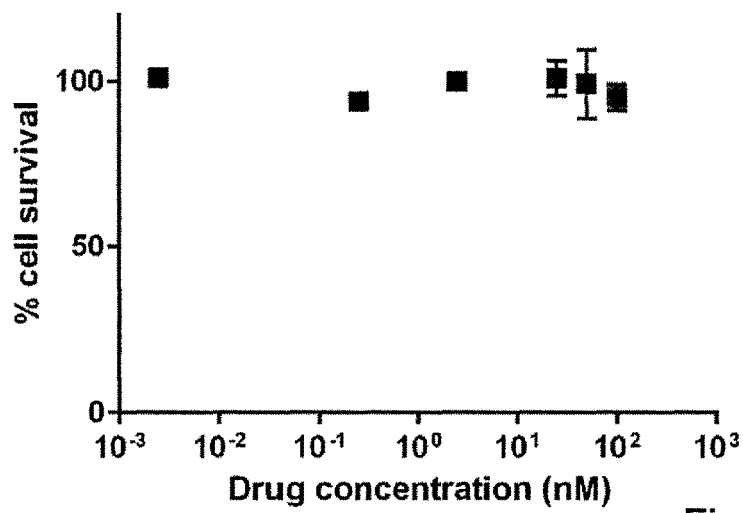
Figure 73C:
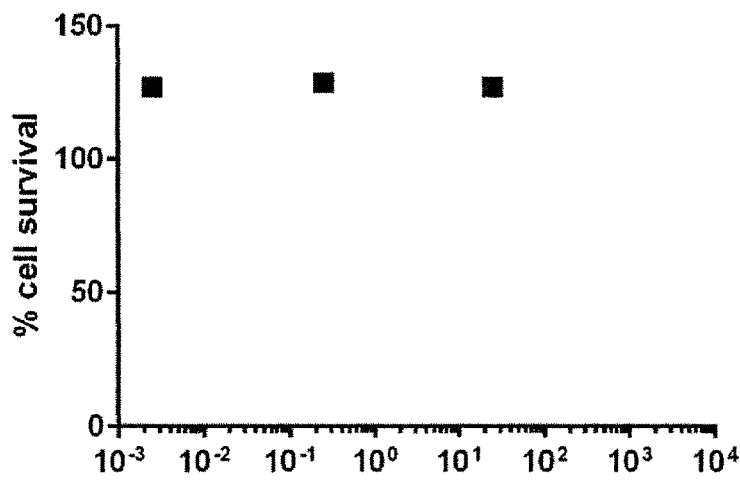

FIG. 73. In vitro cytotoxicity plots of free MMAF.

Cell killing dose-response profiles of free MMAF cytotoxin on (A) U87 cells (B) SKBr3 cells (C) BT474 cells.

Figure 74A:
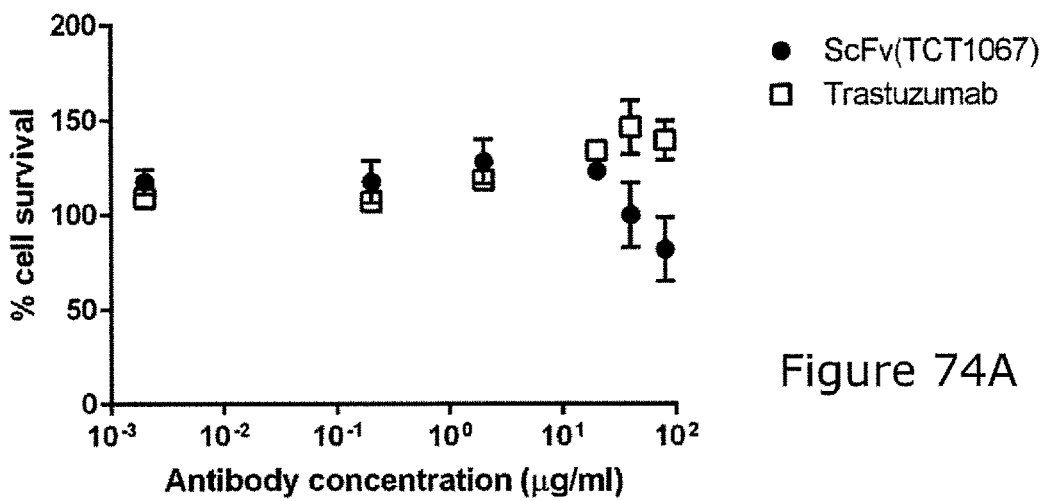
Figure 74B:
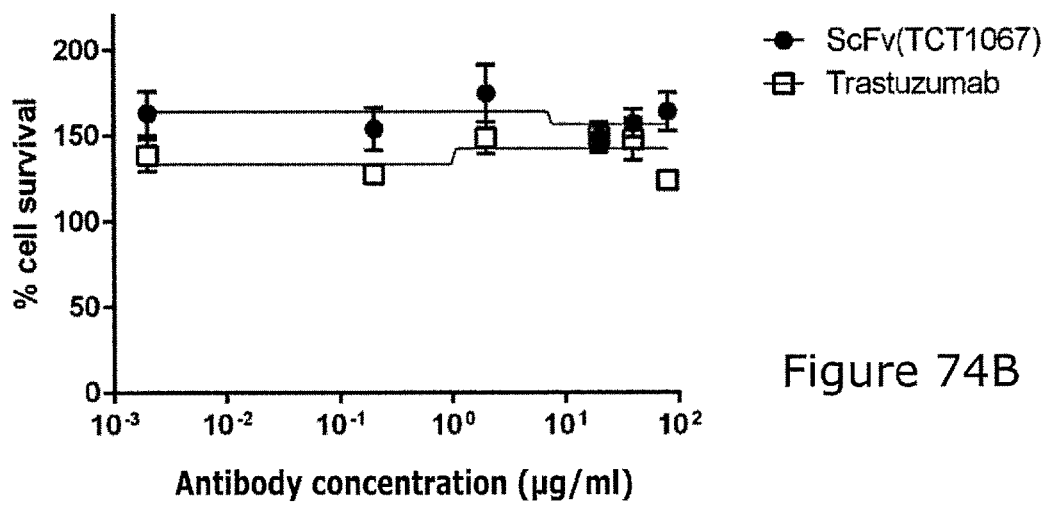
Figure 74C:
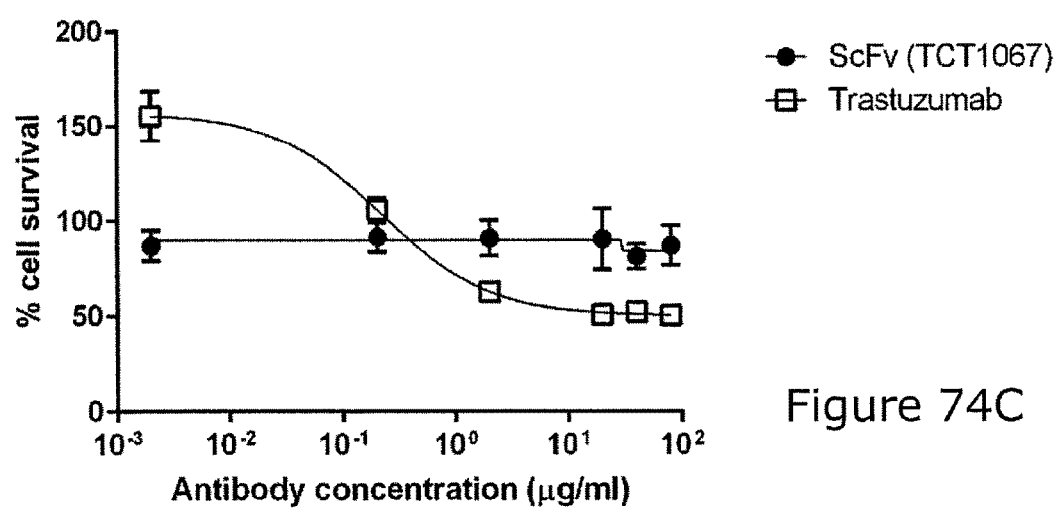

FIG. 74. In vitro cytotoxicity plots of unconjugated antibodies.

Figure 75:
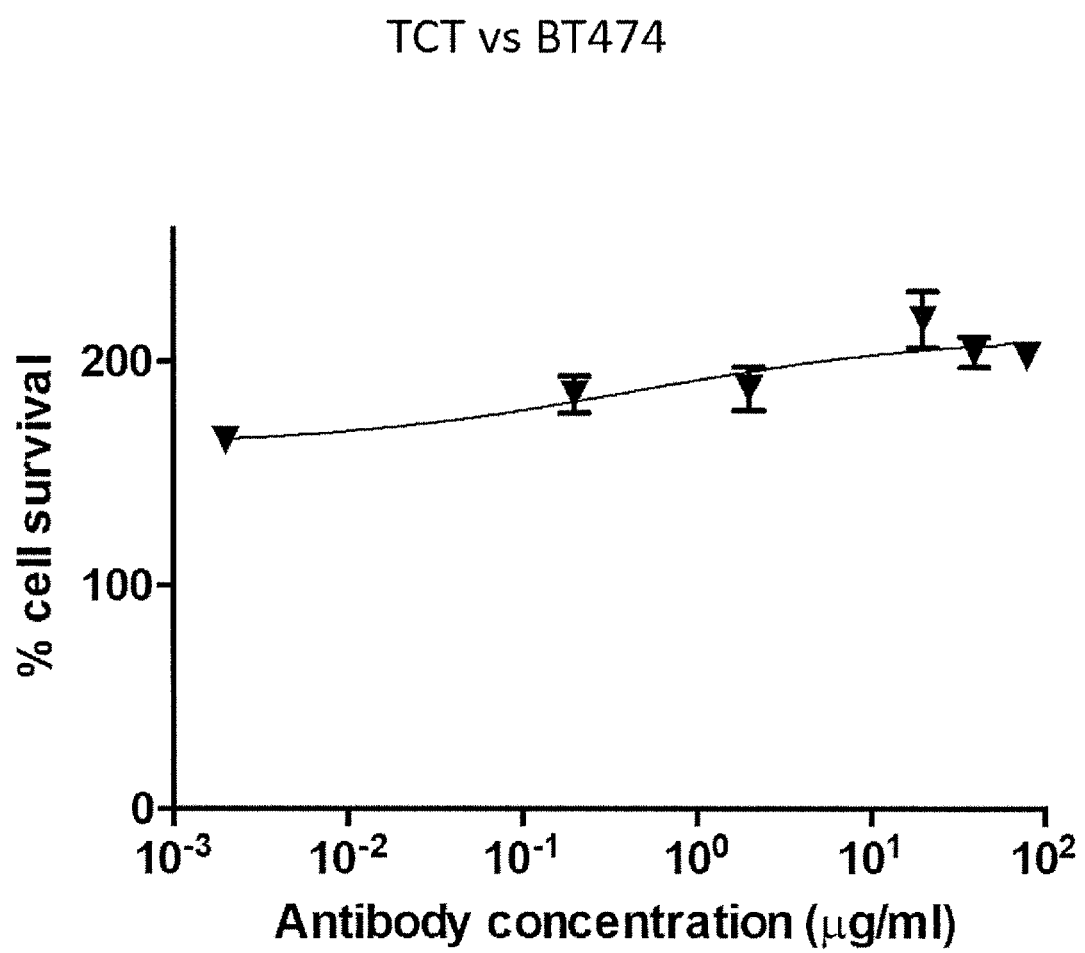

Cell killing dose-response profiles of unconjugated scFv (TCT1067) and trastuzumab on (A) U87 cells (B) BT474 cells (C) SKBr3 cells FIG. 75. In vitro cytotoxicity plots of unconjugated antibody.

Cell killing dose-response profiles of unconjugated scFv (TCT) on BT474 cells.

Figure 76A:
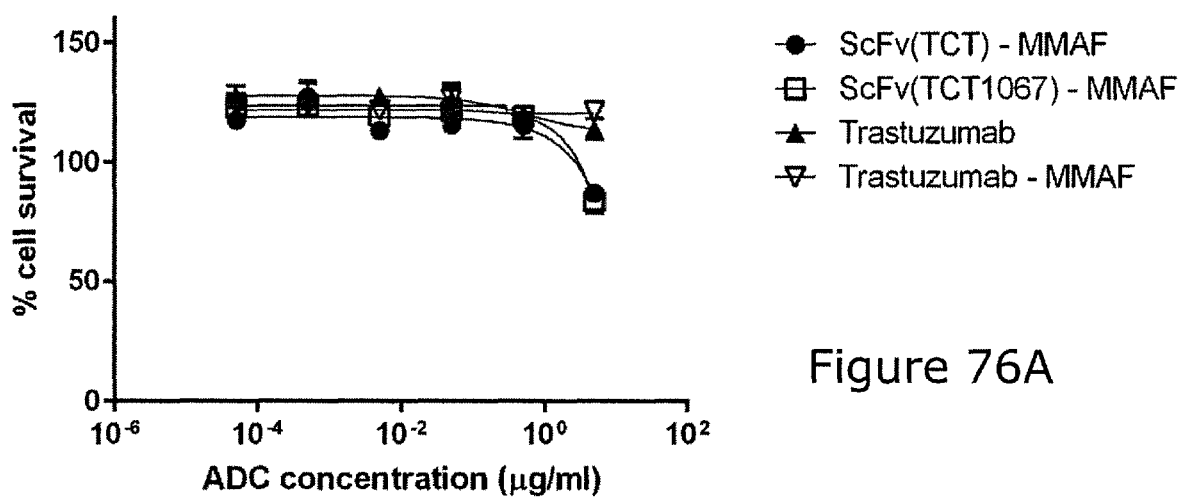
Figure 76B:
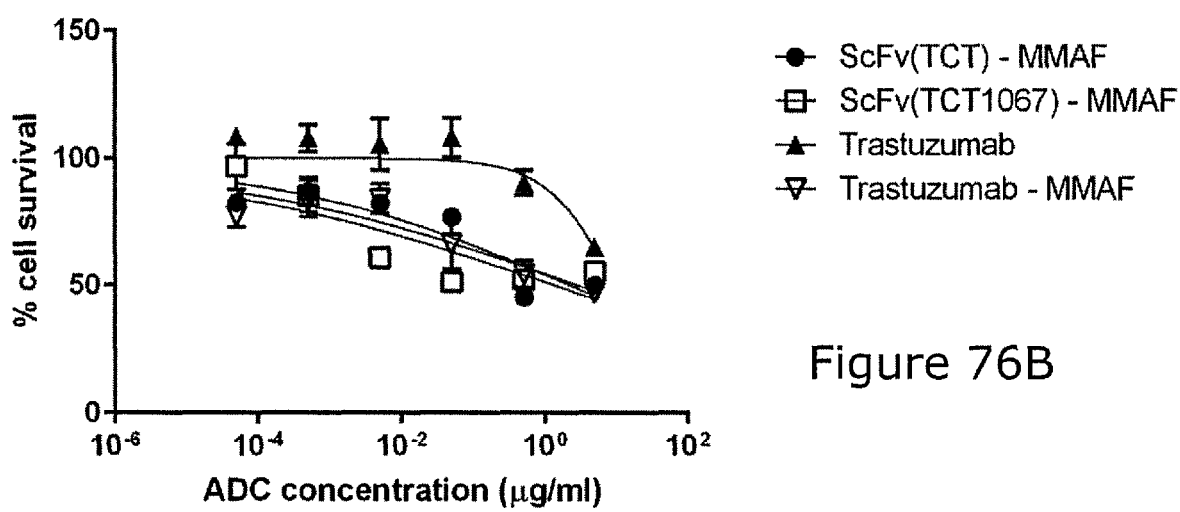
Figure 76C:
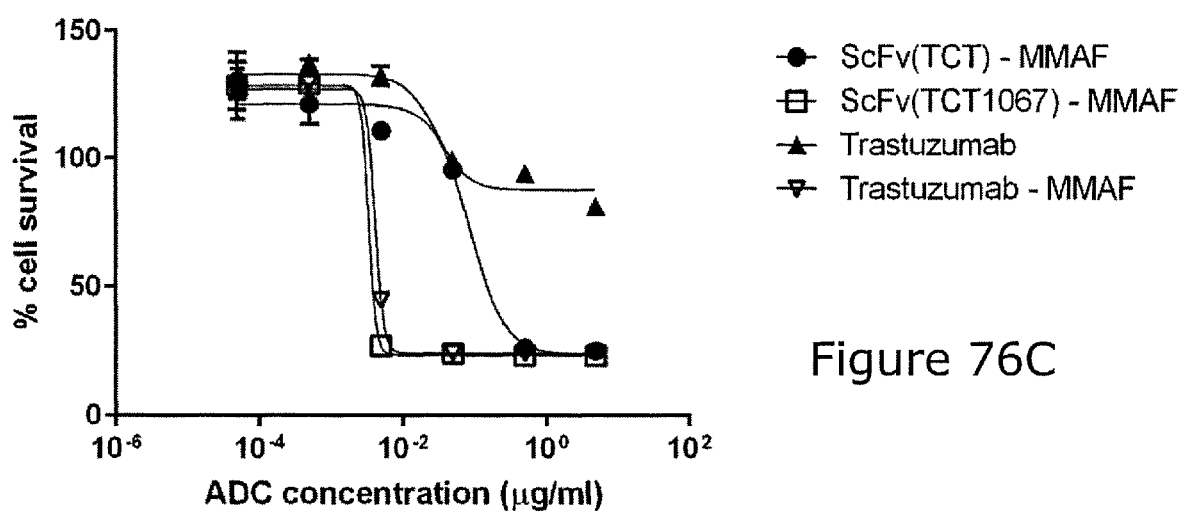

FIG. 76. In vitro cytotoxicity plots of MMAF-based ADCs.

Cell killing dose-response profiles of antibody fragment ADCs scFv (TCT)-MMAF-C5 DAR 6.6, scFv (TCT0167)-MMAF-C5 DAR 6.4, Unconjugated trastuzumab and trastuzumab-MMAF-C5 on (A) U87 cells (B) BT474 cells (C) SKBr3 cells.

Figure 77A:
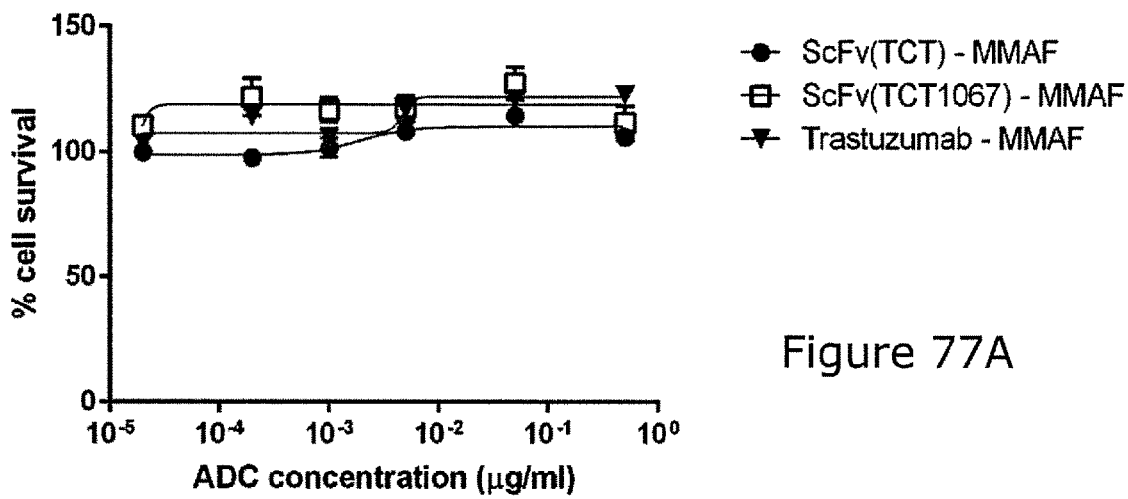
Figure 77B:
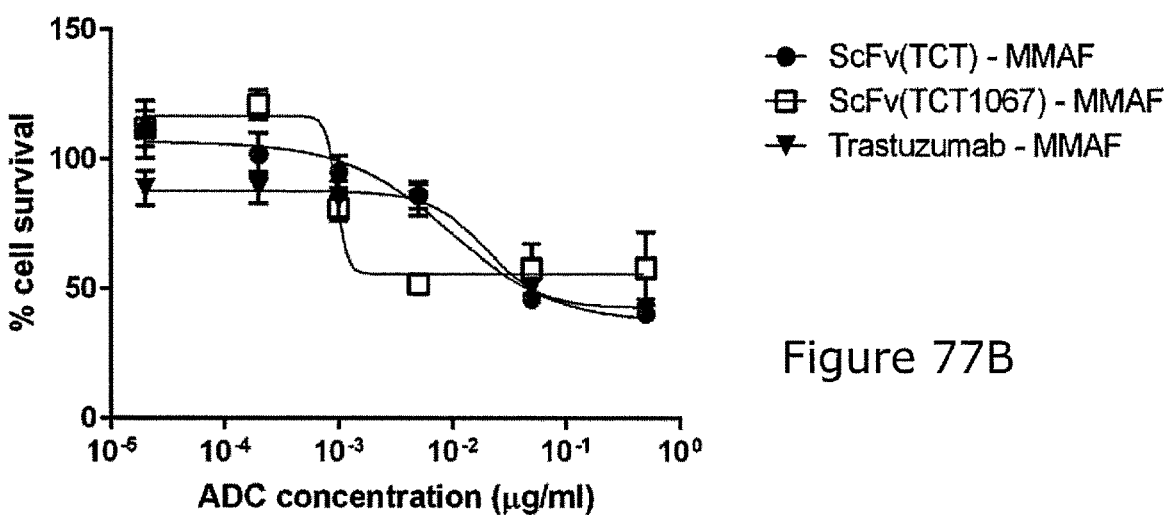
Figure 77C:
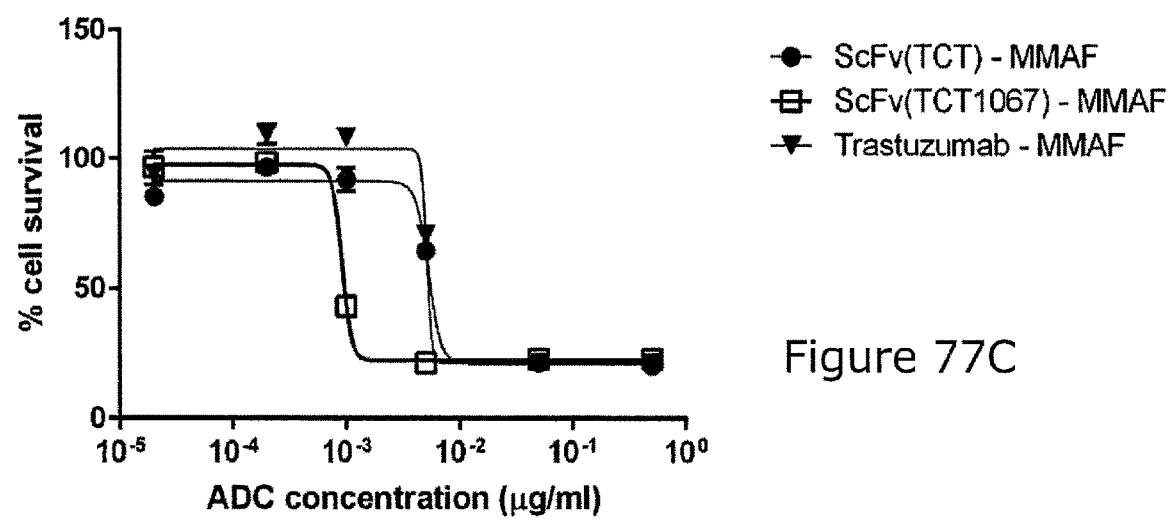

FIG. 77. In vitro cytotoxicity plots of MMAF-based ADCs.

Cell killing dose-response profiles of antibody fragment conjugates scFv (TCT)-MMAF-C5 DAR 8, scFv (TCT0167)-MMAF-C5 DAR 8.7 and trastuzumab-MMAF-C5 on (A) U87 cells (B) BT474 cells (C) SKBr3 cells.

Figure 78A:
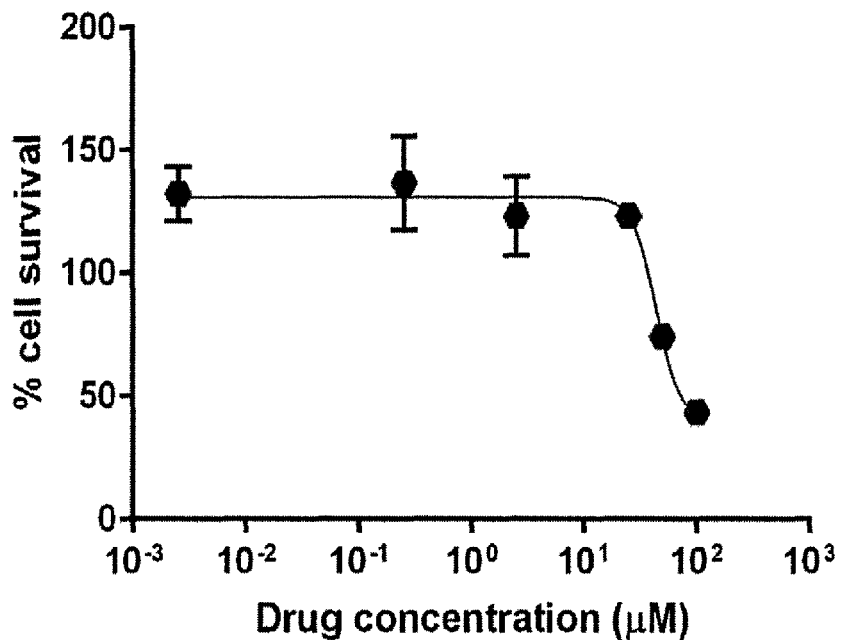
Figure 78B:
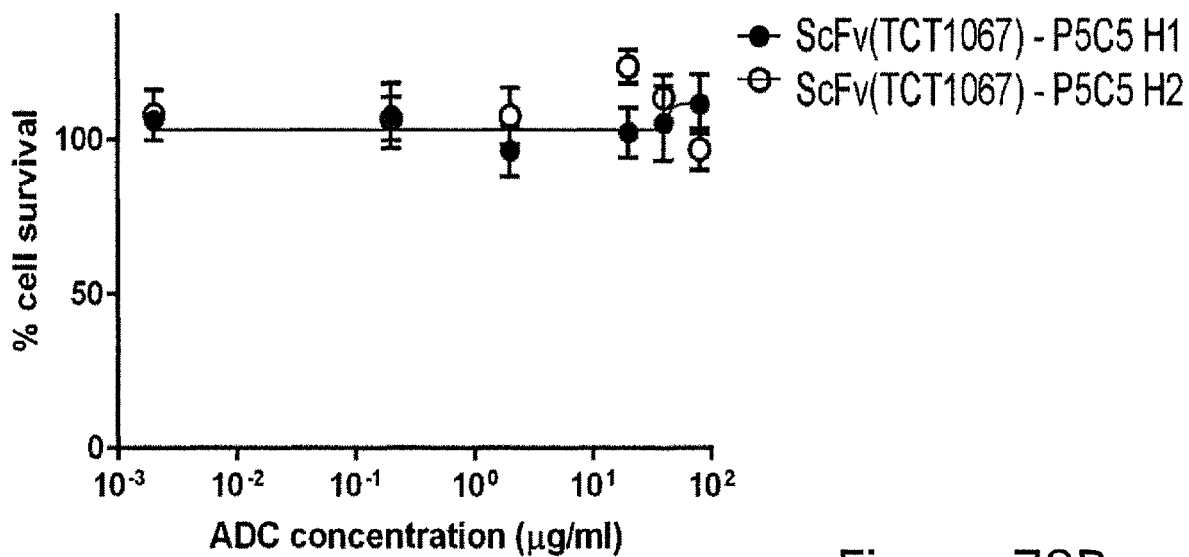

FIG. 78. In vitro cytotoxicity plots of P5-C5-based ADCs.

Cell killing dose-response profiles of (A) Free P5-C5 drug and (B) antibody fragment conjugates scFv (TCT1067)-P5-C5 DAR 10.6 (H1) and DAR 12.5 (H2) on U87 cells.

Figure 79A:
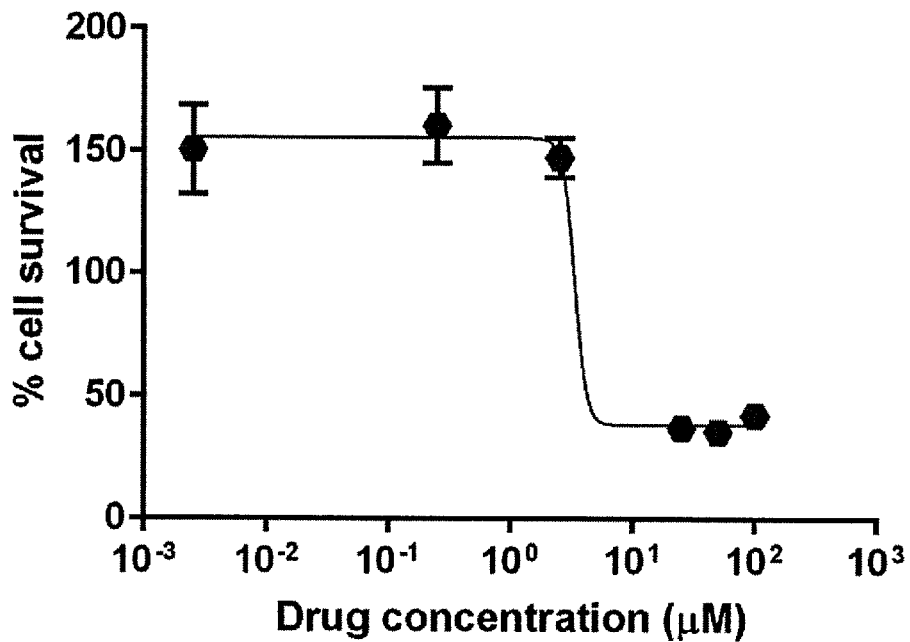
Figure 79B:
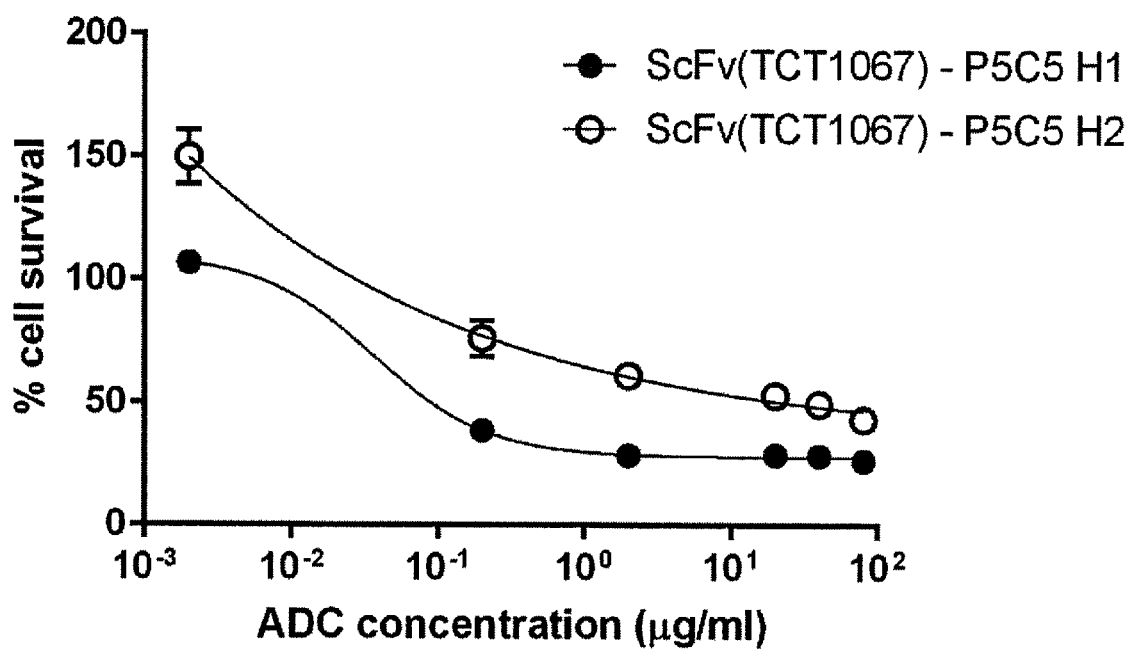

FIG. 79. In vitro cytotoxicity plots of P5-C5-based ADCs.

Cell killing dose-response profiles of (A) Free P5-C5 drug and (B) antibody fragment conjugates scFv (TCT1067)-P5-C5 DAR 10.6 (H1) and DAR 12.5 (H2) on SKBr3 cells.

Figure 80A:
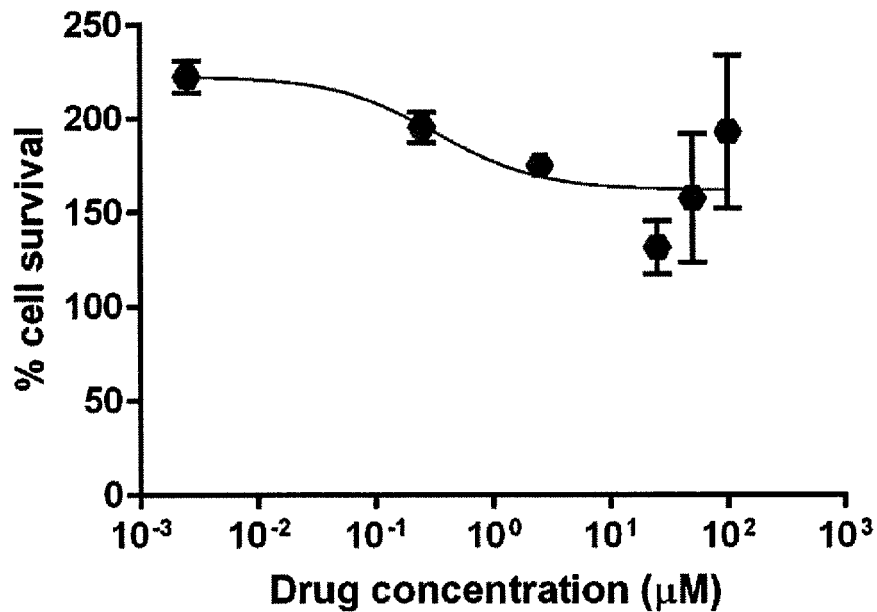
Figure 80B:
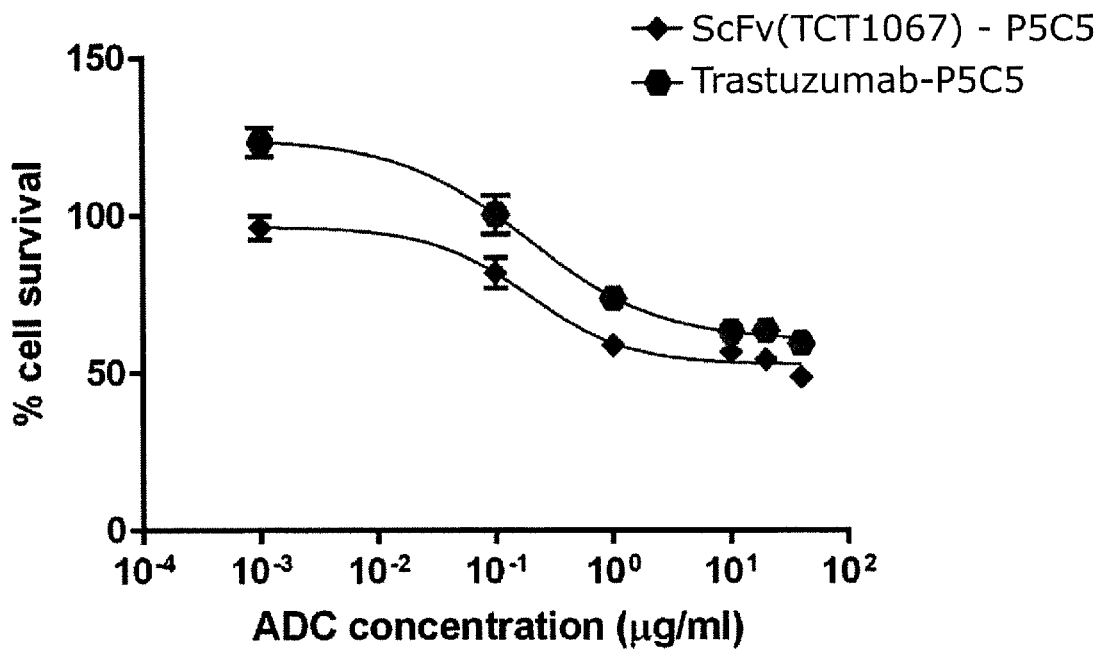

FIG. 80. In vitro cytotoxicity plots of P5-C5-based ADCs.

Cell killing dose-response profiles of (A) Free P5-C5 drug and (B) antibody conjugates scFv (TCT1067)-P5-C5 DAR 10.6 (H1) and trastuzumab DAR6 on BT474 cells.

Figure 81A:
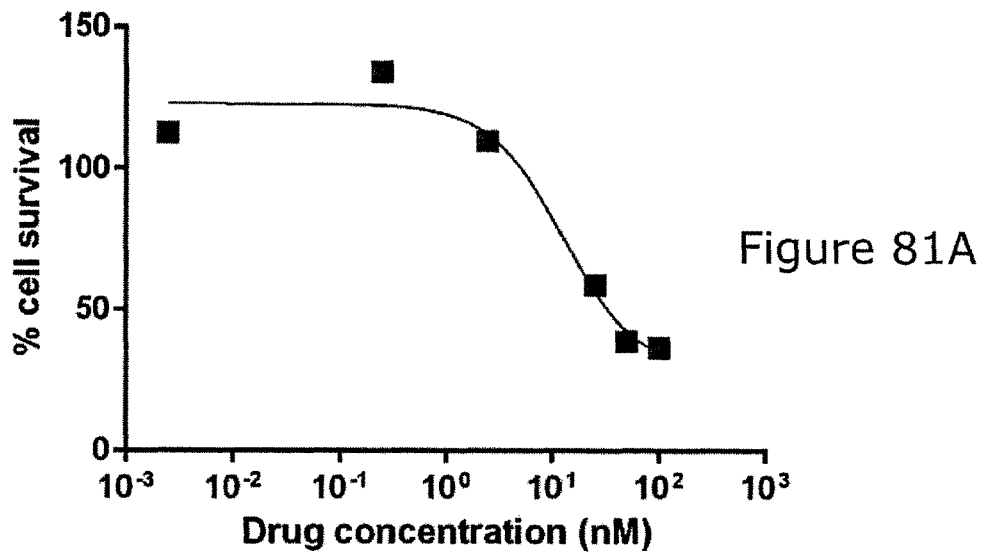
Figure 81B:
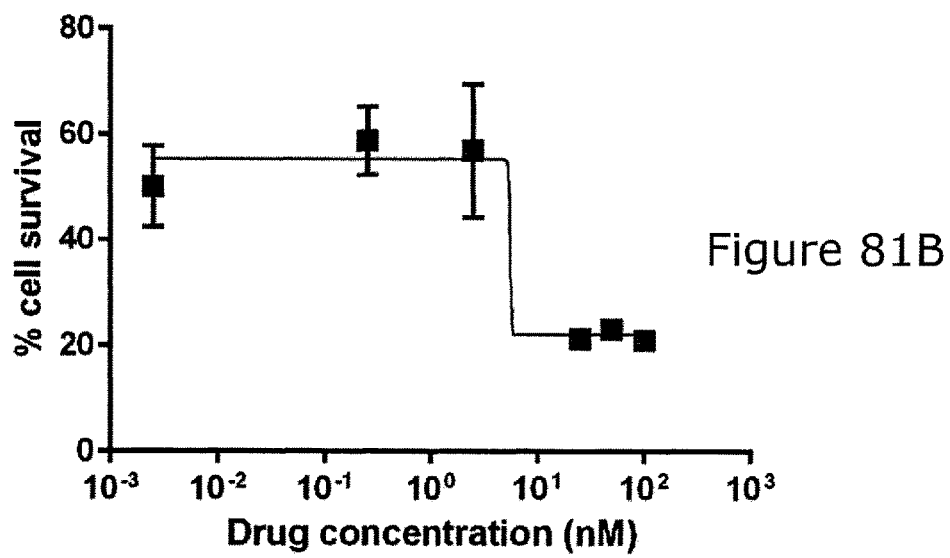
Figure 81C:
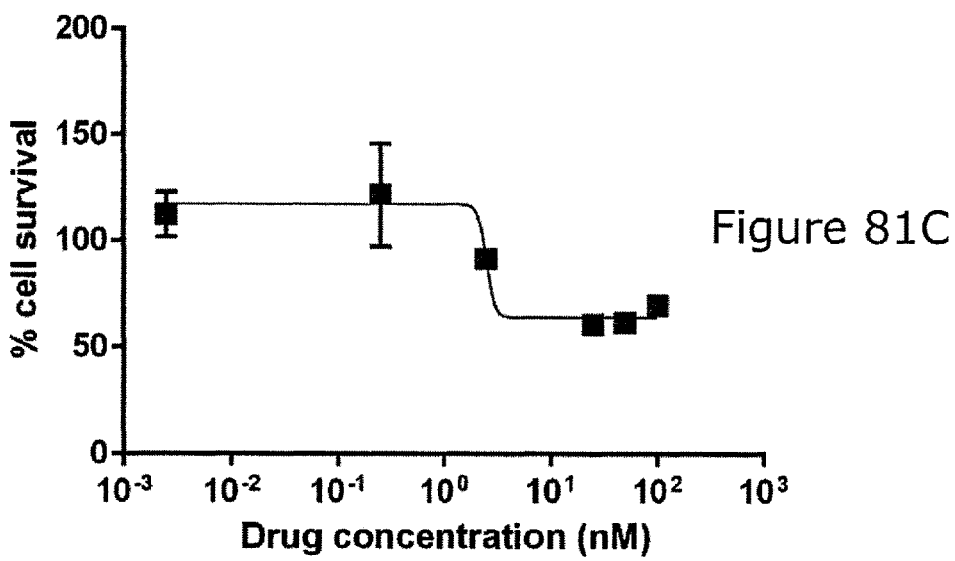

FIG. 81. In vitro cytotoxicity plots of free Auristatin F.

Cell killing dose-response profiles of free Auristatin cytotoxin on (A) U87 cells (B) SKBr3 cells (C) BT474 cells.

Figure 82A:
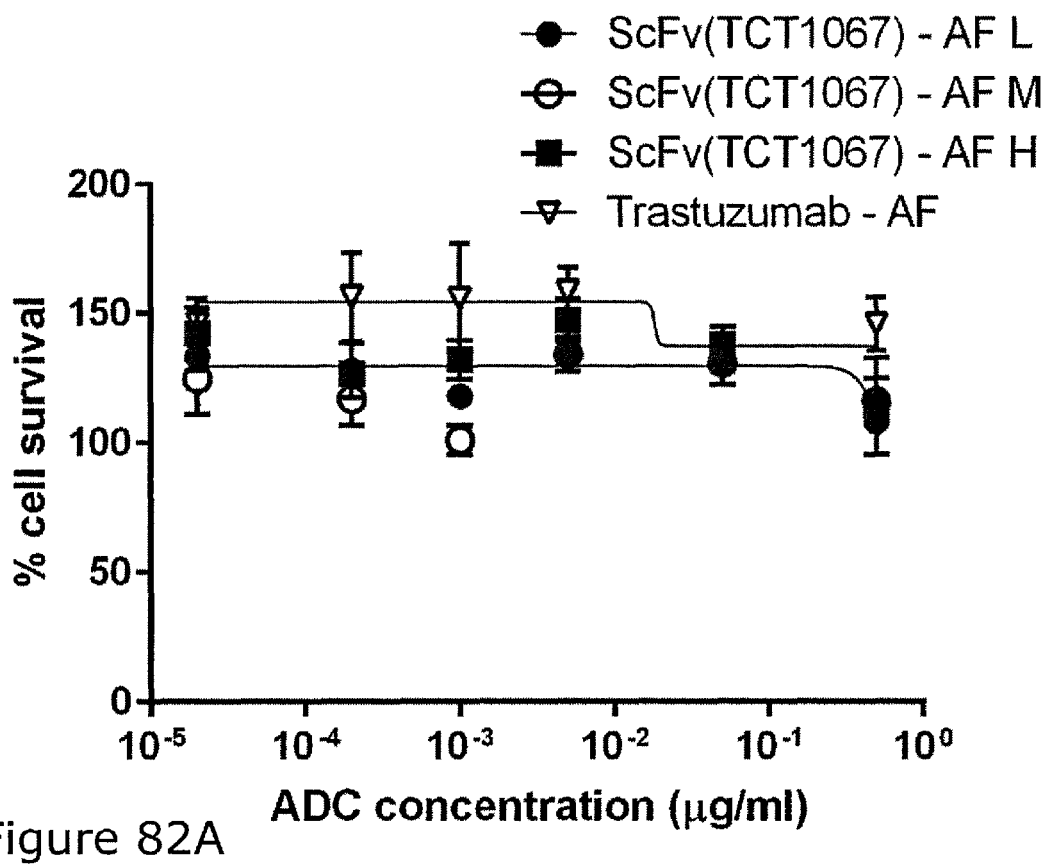
Figure 82B:
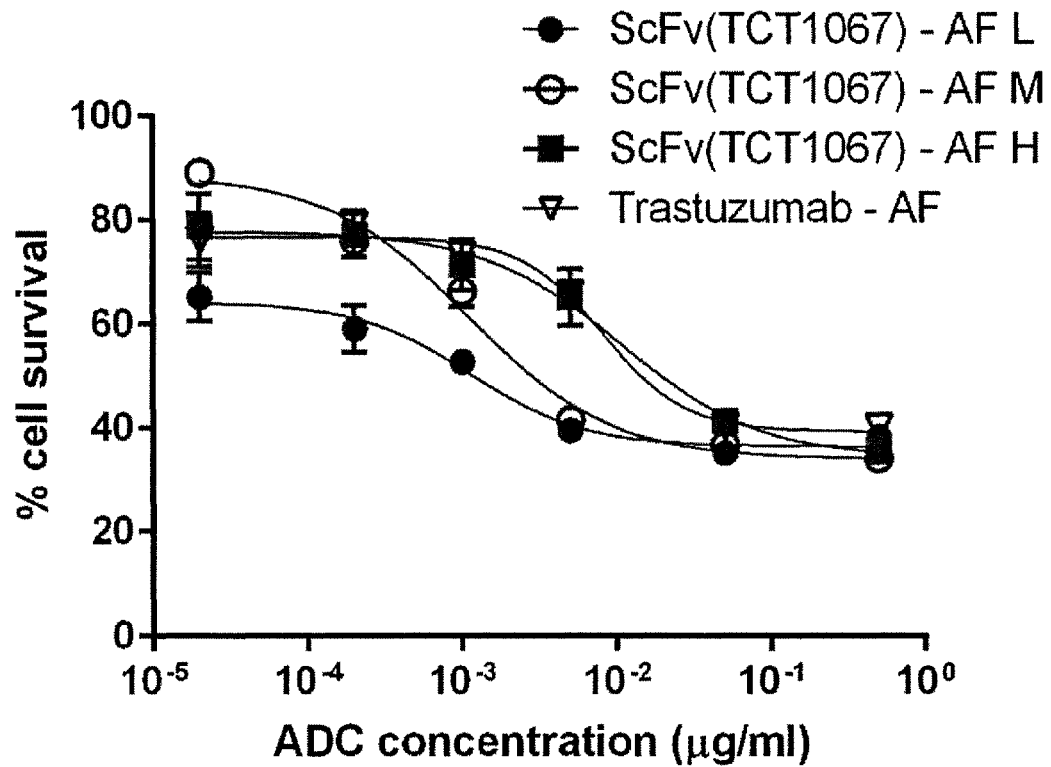
Figure 82:
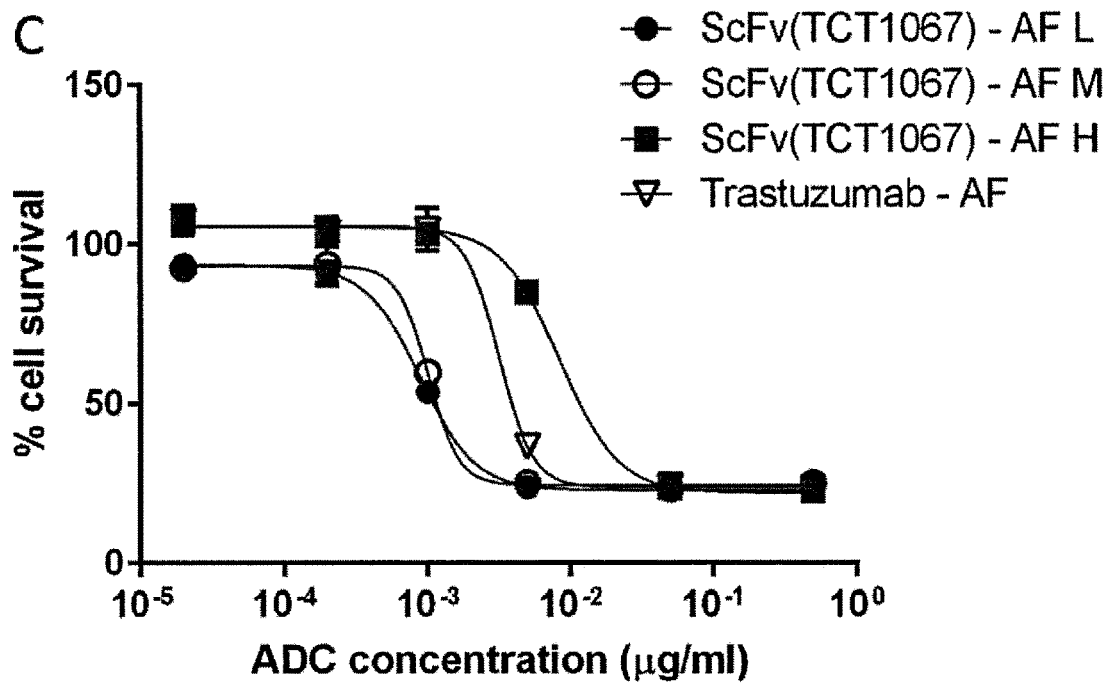
Figure 82:
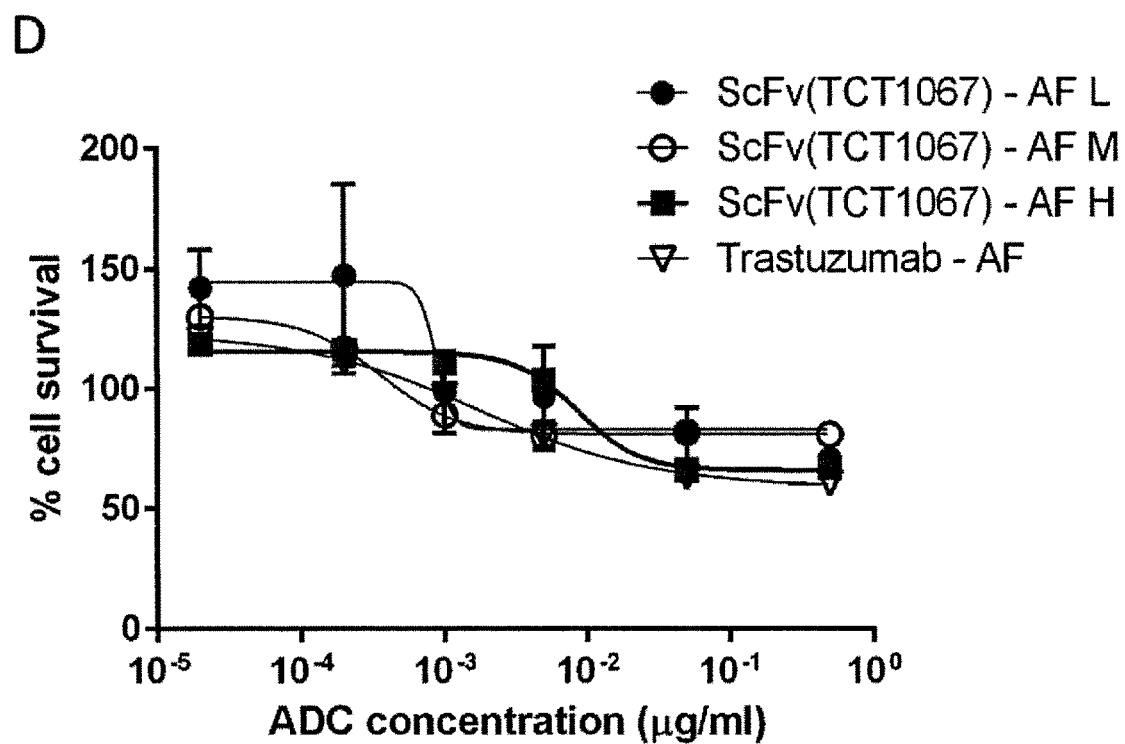

FIG. 82. In vitro cytotoxicity plots of Auristatin F-based ADCs.

Cell killing dose-response profile of antibody fragment ADCs scFv (TCT1067)-AF-C5, DAR 2.7 (L), scFv (TCT1067)-AF-C5, DAR 6.2 (M), scFv (TCT1067)-AF-C5, DAR 11.8 (H) and trastuzumab-AF-C5, DAR 4.8 on (A) U87 cells (B) BT474 cells (C) SKBr3 cells (D) NCI-N87 cells.

Figure 83A:
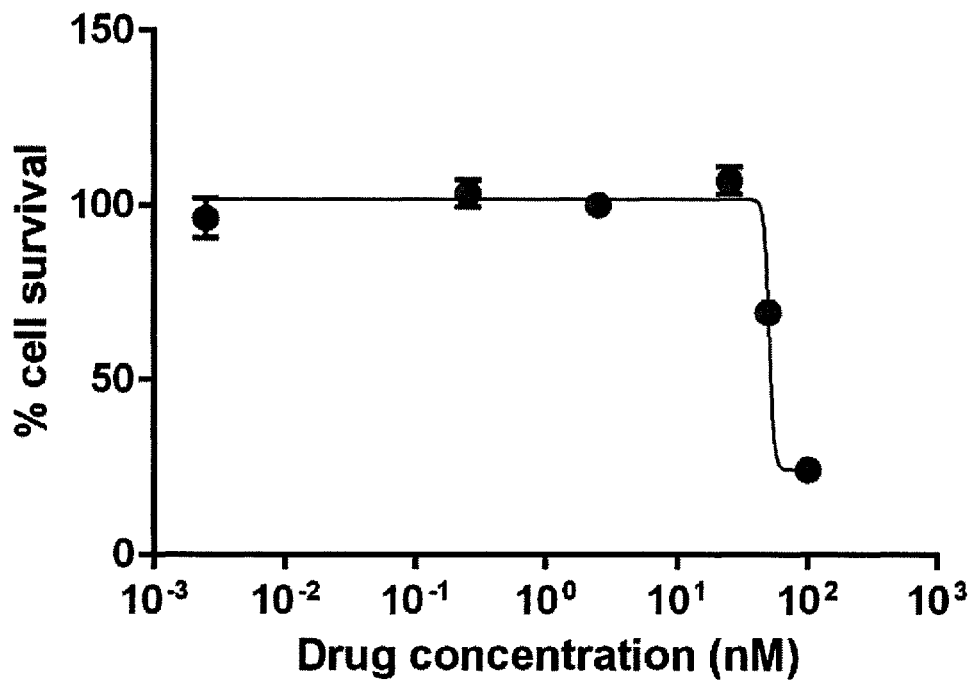
Figure 83B:
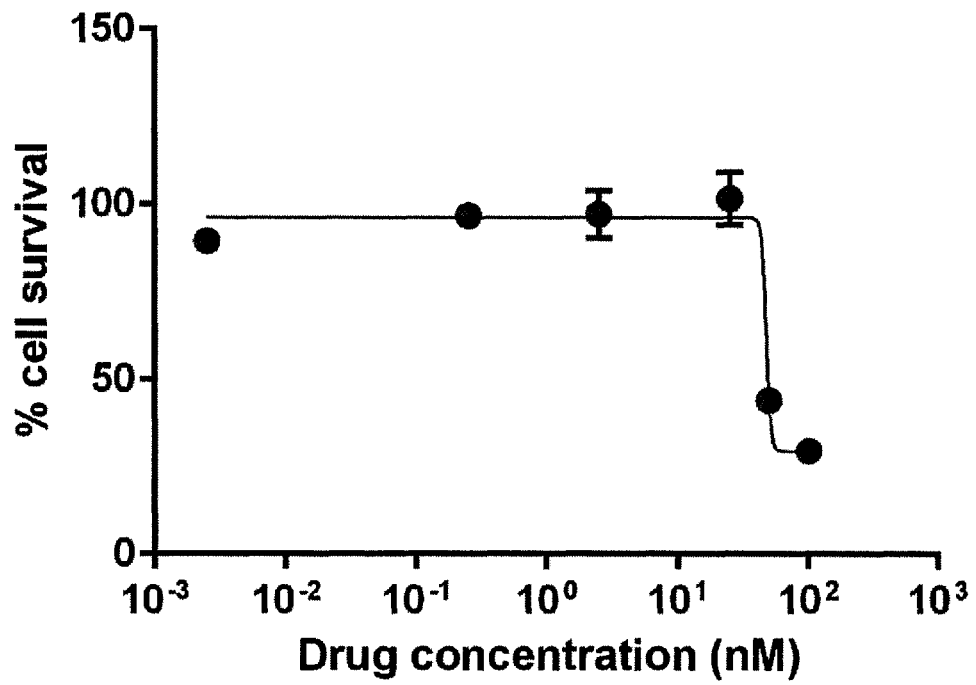

FIG. 83. In vitro cytotoxicity plots of free DM1 drug.

Figure 84A:
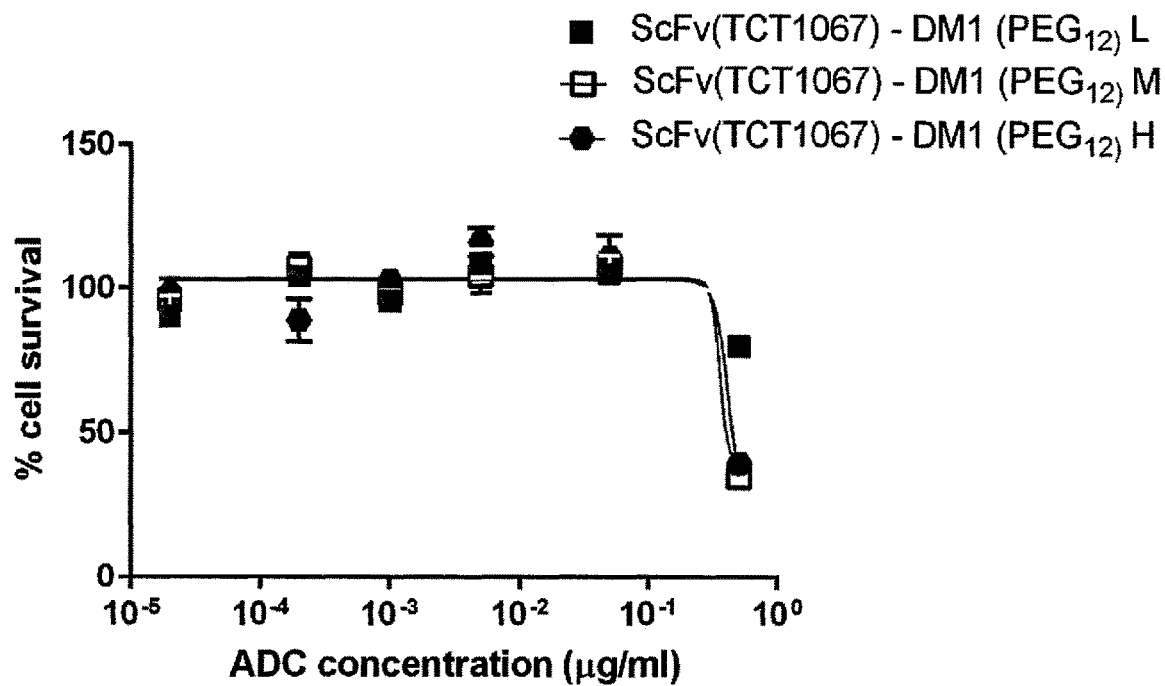
Figure 84B:
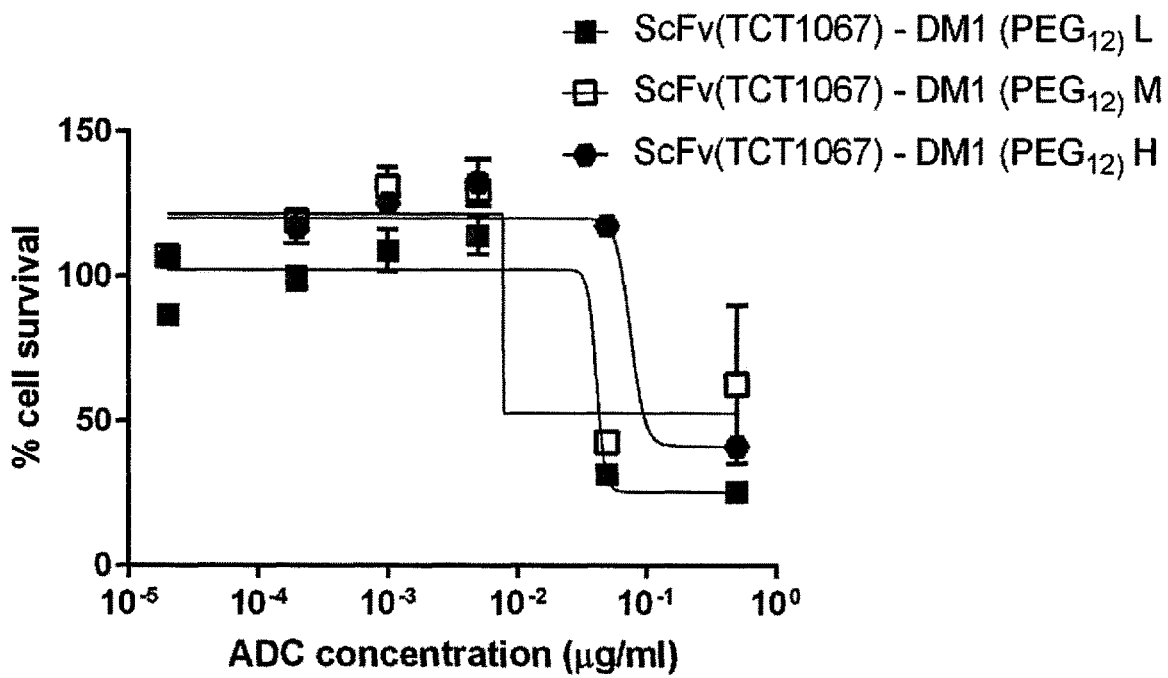

Cell killing dose-response profiles of free DM1-PEG9 cytotoxin on (A) U87 cells (B) SKBr3 cells FIG. 84. In vitro cytotoxicity plots of DM1-(dPEG12)-based ADCs.

Cell-killing dose-response profiles of antibody fragment ADCs scFv (TCT1067)-DM1-(dPEG12), DAR 3.5 (L), scFv (TCT1067)-DM1-(dPEG12) DAR 5.5 (M), scFv (TCT1067)-DM1-(dPEG12), DAR 8 (H) on (A) U87 cells (B) SKBr3 cells.

Figure 85A:
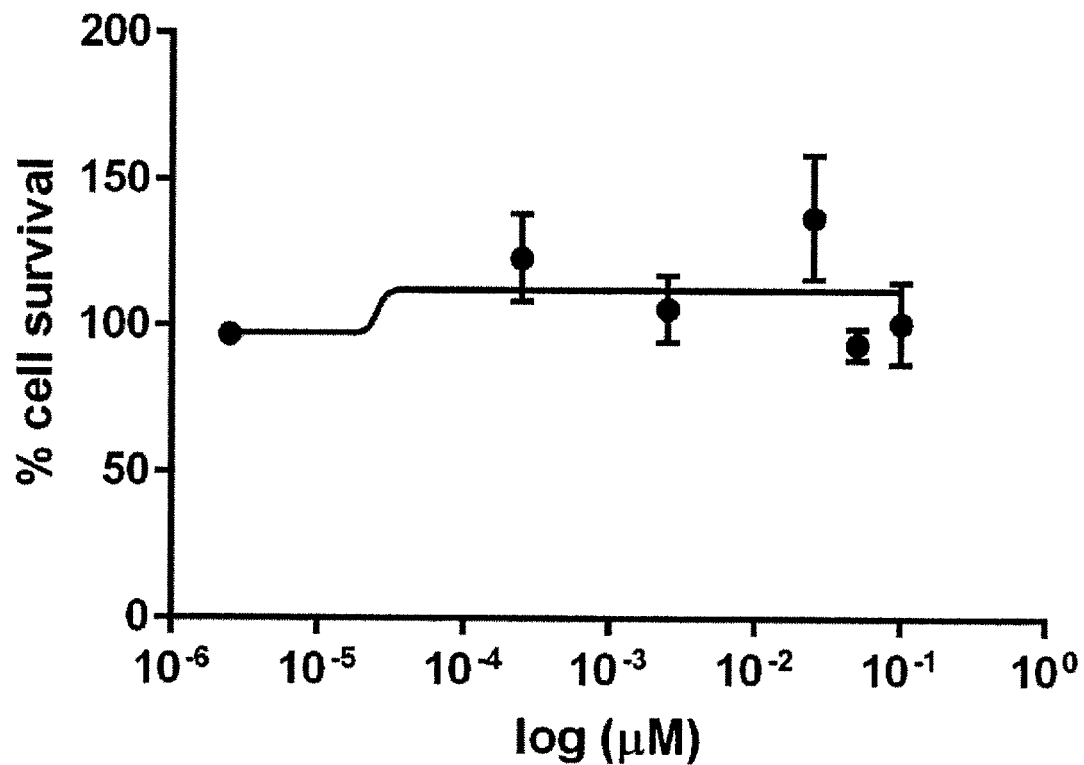
Figure 85B:
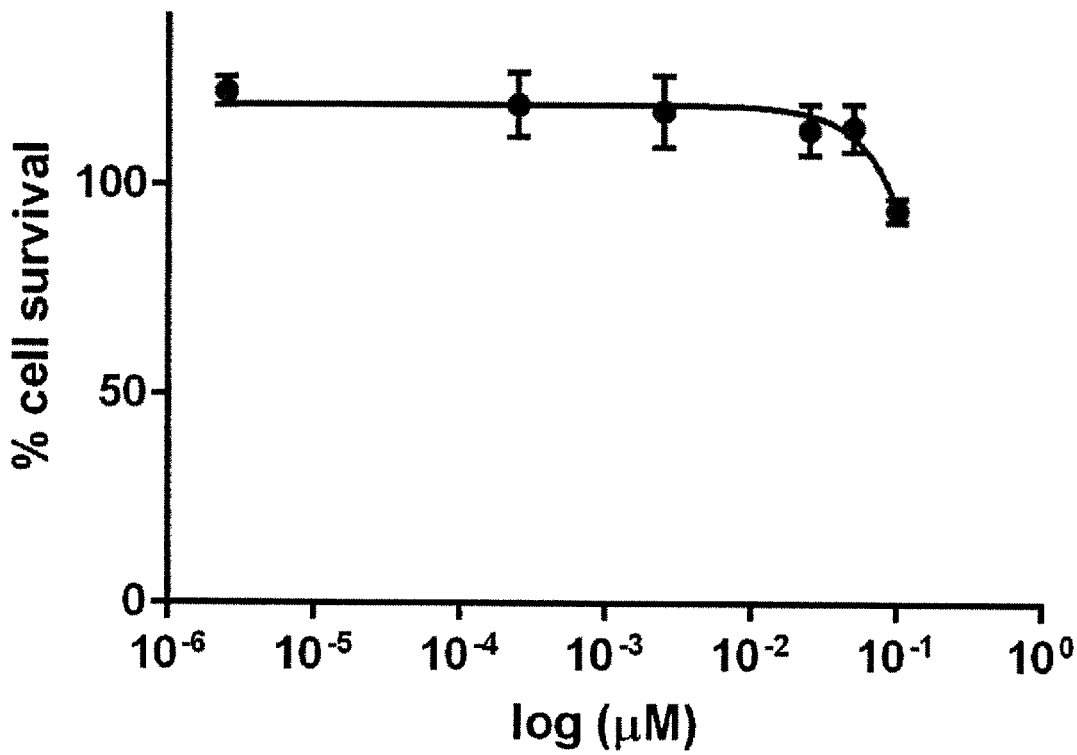

FIG. 85. In vitro cytotoxicity plots of free MMAE drug.

Figure 86A:
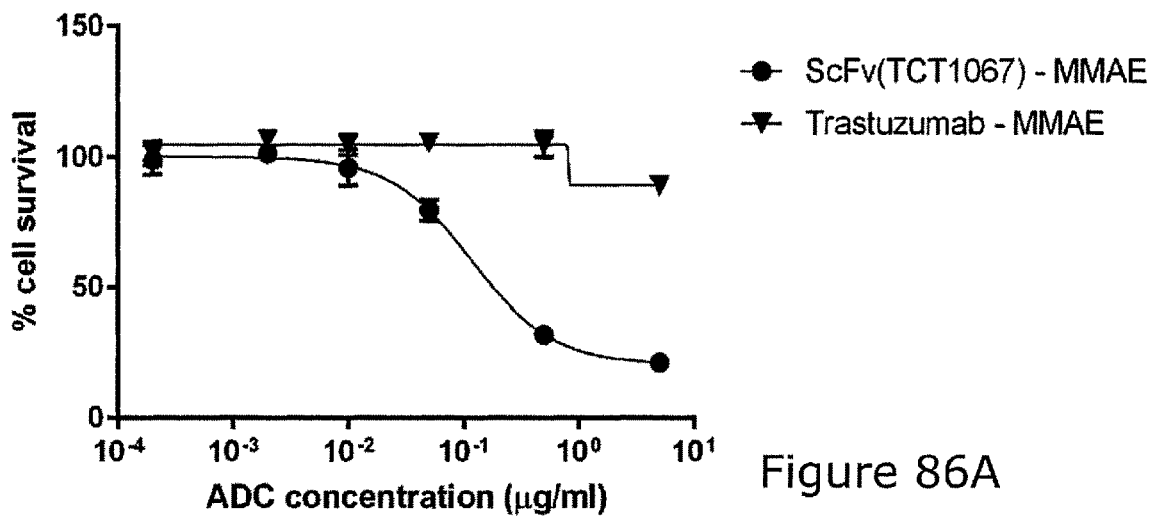
Figure 86B:
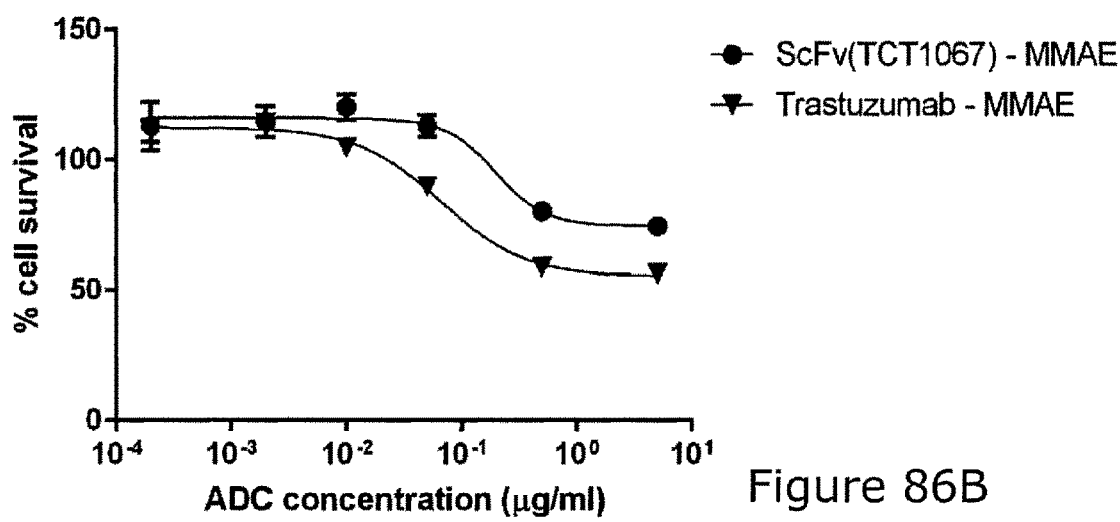
Figure 86C:
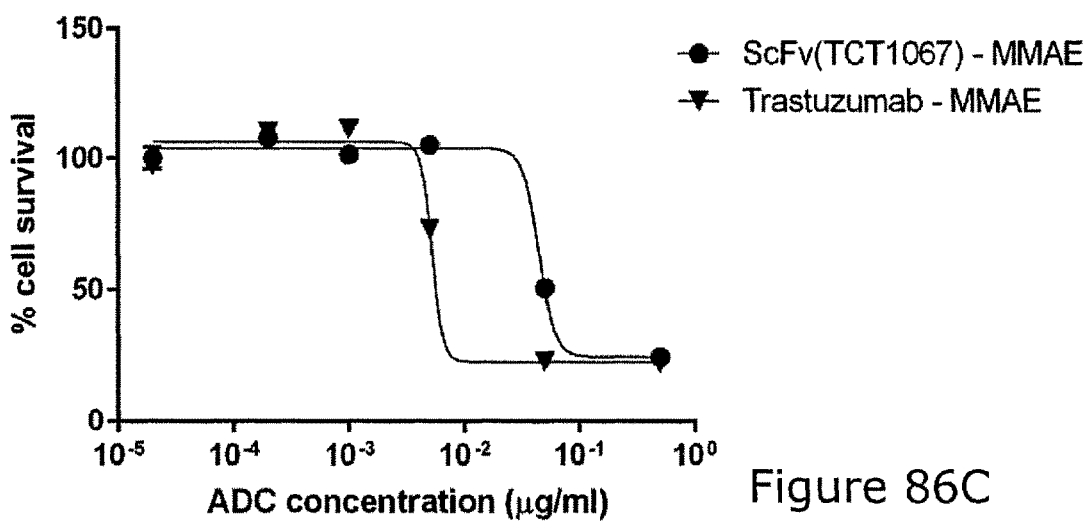

Cell killing dose-response profiles of free MMAE cytotoxin on (A) U87 cells (B) SKBr3 cells FIG. 86. In vitro cytotoxicity plots of MMAE-based ADCs.

Figure 87A:
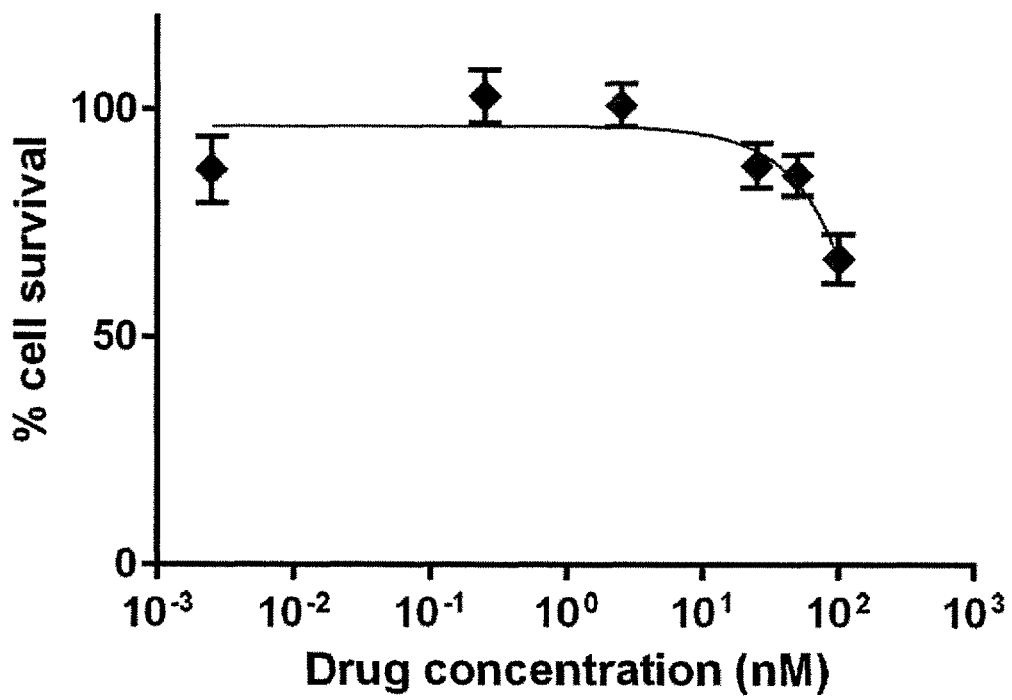
Figure 87B:
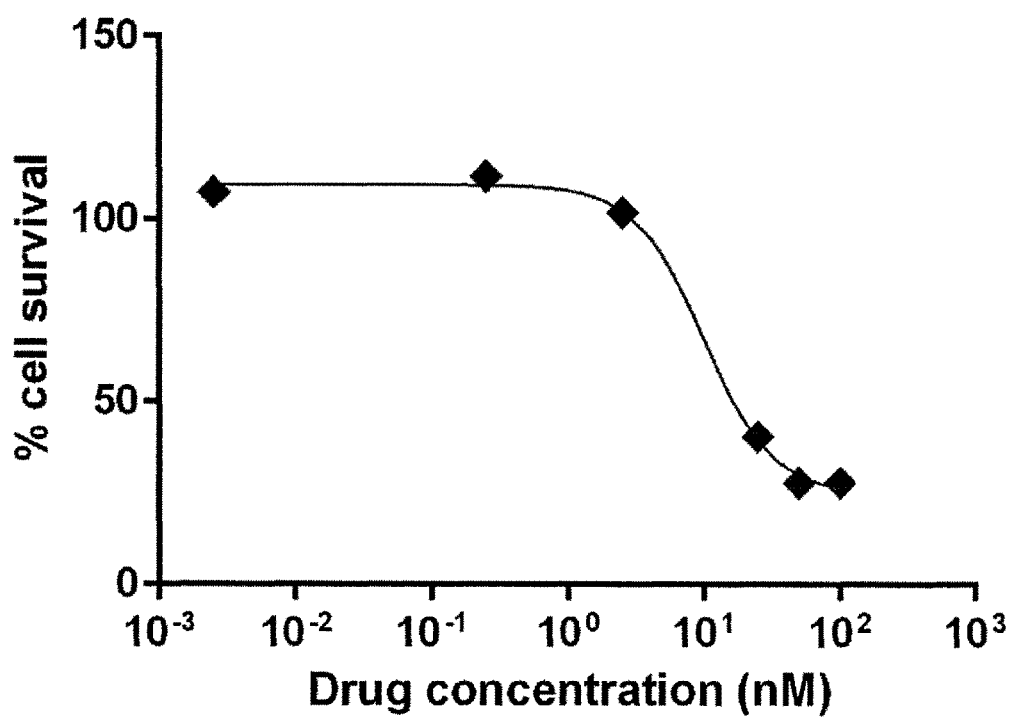

Cell killing dose-response profiles of antibody fragment ADCs scFv (TCT1067)-MMAE-PAB-Cit-Val-dPEG9, DAR9 and Trastuzumab-MMAE-PAB-Cit-Val-dPEG9, DAR 4 on (A) U87 cells (B) BT474 cells (C) SKBr3 cells FIG. 87. In vitro cytotoxicity plots of free Auristatin drug for 4 and 96 hrs.

Figure 88A:
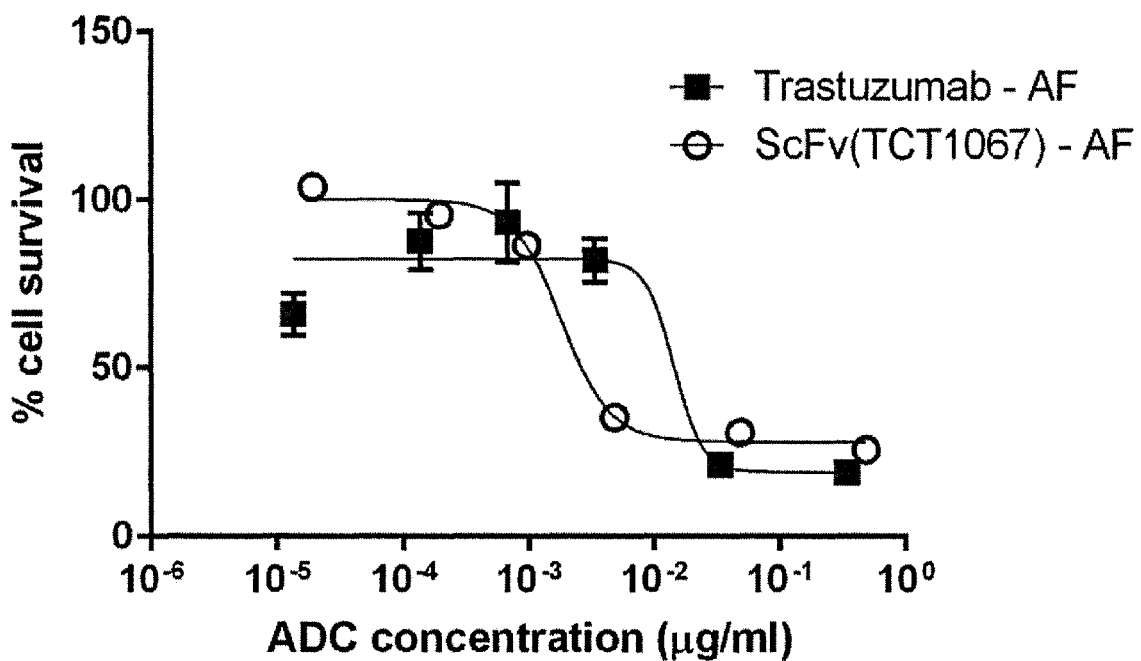
Figure 88B:
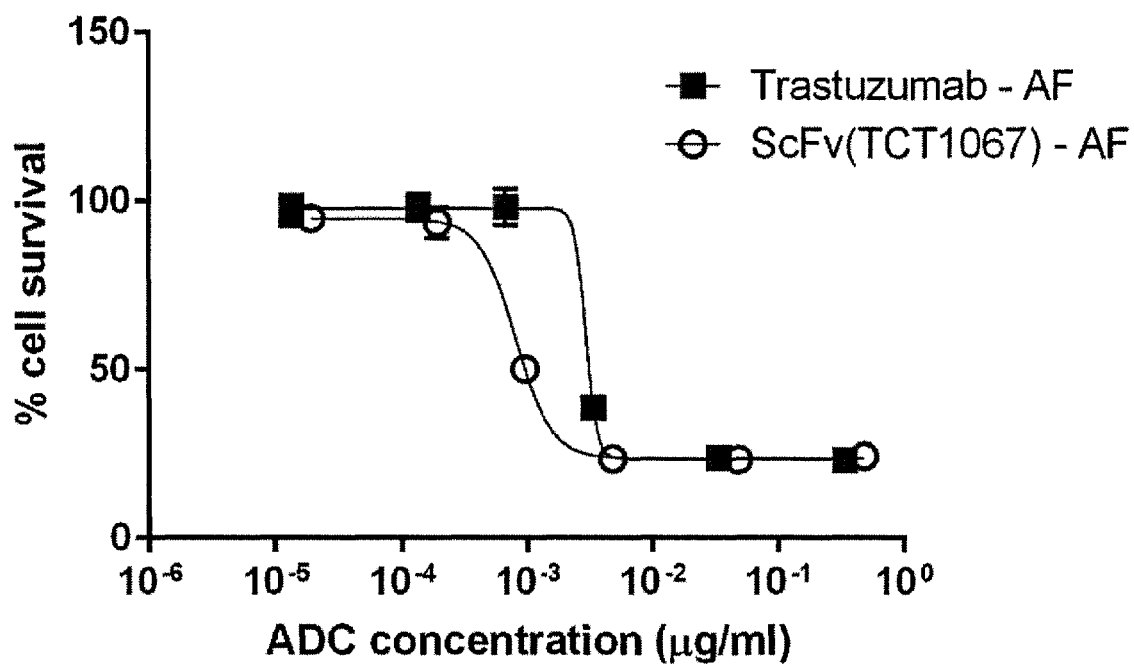

Cell killing dose-response profiles of free Auristatin cytotoxin on SKBr3 cells for (A) 4 and (B) 96 hours incubation FIG. 88. In vitro cytotoxicity plots of trastuzumab and scFv (1067)-Auristatin-C5 conjugates for 4 and 96 hrs.

Cell killing dose-response profiles of trastuzumab-Auristatin-C5 and scFv (1067)-Auristatin-C5 on SKBr3 cells for (A) 4 and (B) 96 hours incubation.

Figure 89:
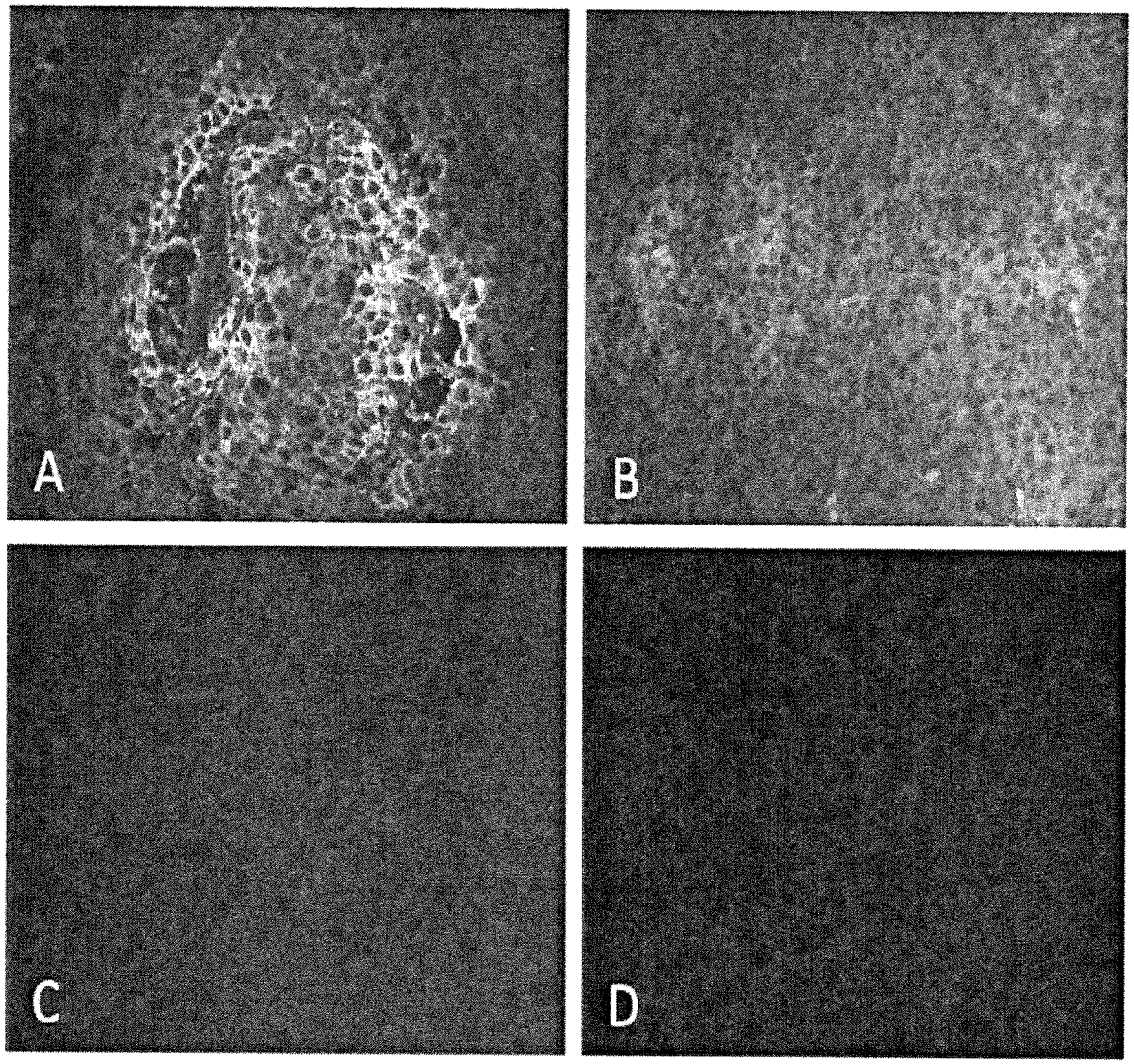

FIG. 89. Fluorescent images from BT474 tumour sections after 2 hrs administration of scFv and IgG-ADCs.

(A) High affinity scFv (TCT1067)-P5C5 conjugate, (B) Medium affinity scFv (TCT)-P5C5 conjugate, (C) Trastuzumab-P5C5 conjugate (D) Saline administered control.

Figure 90:
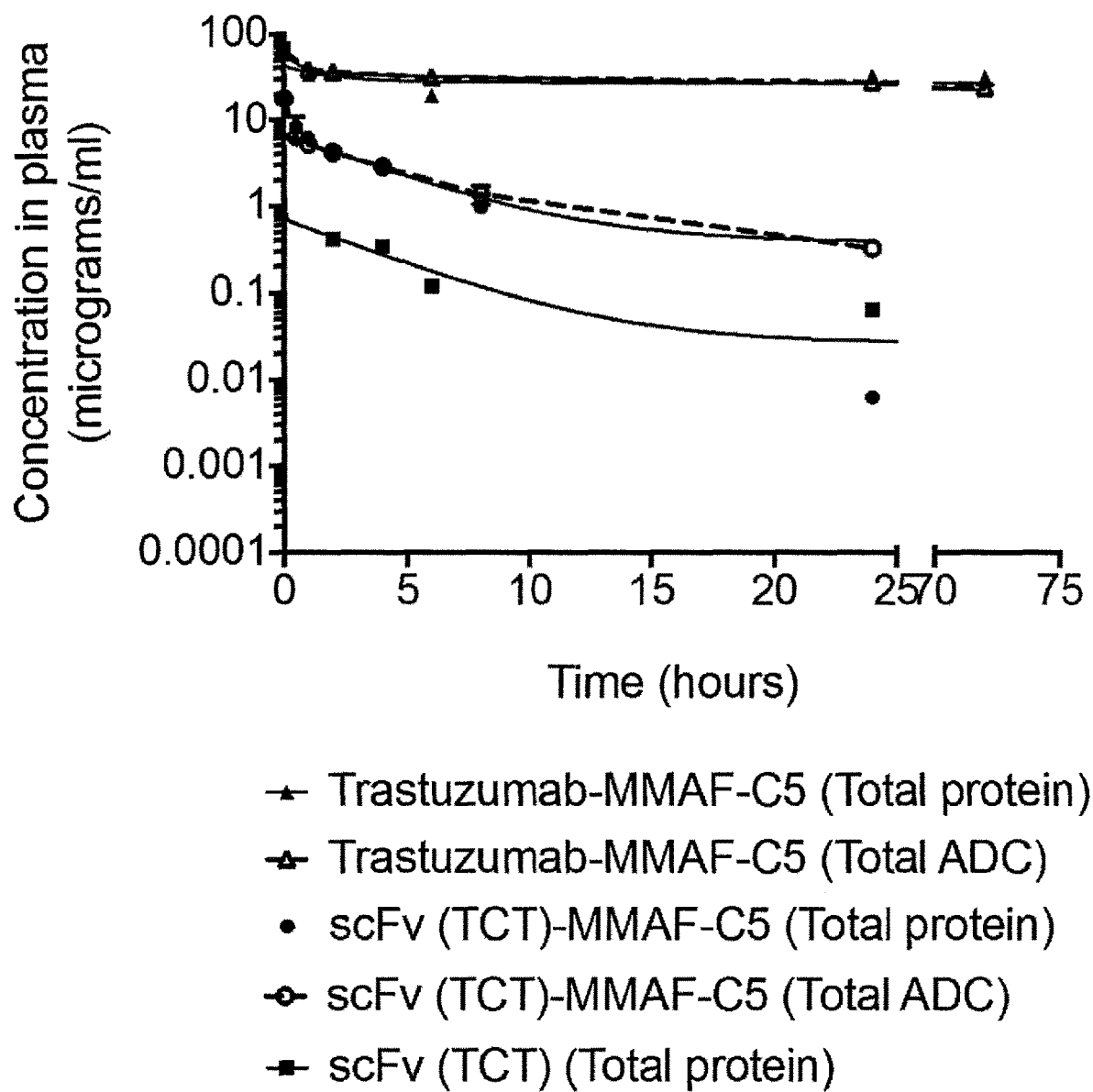

FIG. 90. Pharmacokinetic clearance analysis of scFv (TCT)-MMAF-C5 and controls (compounds 118) in a murine model.

A single i.v. dose was injected into female BALB/c mice at 5 mg/kg. Plasma samples were taken at time points indicated and analysed by ELISA using anti-protein detection (total protein, indicated by solid lines, closed symbols) and where relevant anti-drug detection (total ADC, indicated by dashed lines, open symbols). The SE of the mean of each group and experimental triplicates are shown. ADC scFv (TCT)-MMAF-C5 (circles) (n=3), trastuzumab-MMAF-C5 (triangles) (n=3) and scFv (TCT) (squares) (n=4). Control scFv (TCT) values supplied from a separate PK study.

Figure 91:
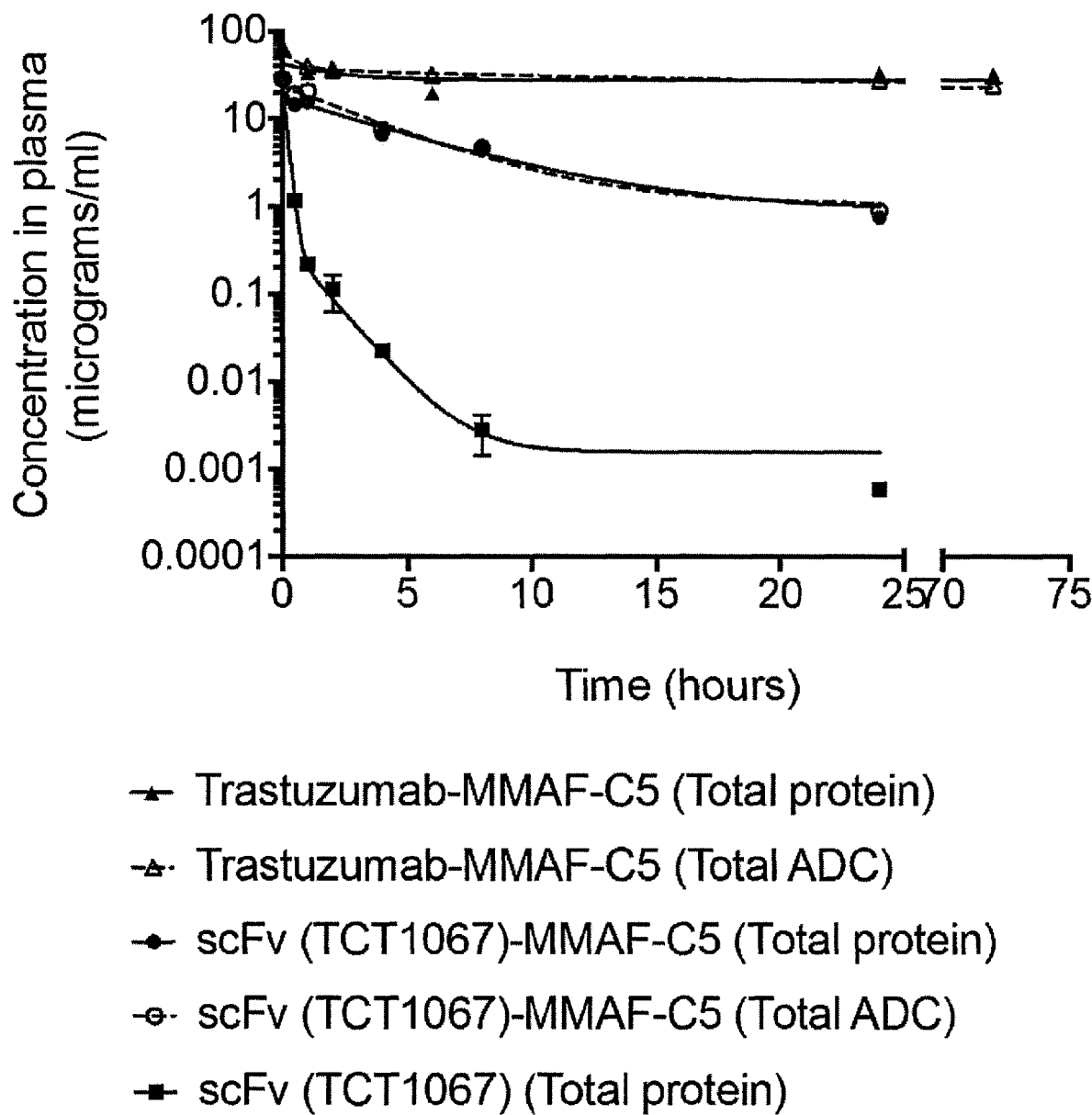

FIG. 91. Pharmacokinetic clearance analysis of scFv (TCT1067)-MMAF-C5 and controls (compounds 118) in a murine model.

A single i.v. dose was injected into female BALB/c mice at 5 mg/kg. Plasma samples were taken at time points indicated and analysed by ELISA using anti-protein detection (total protein, indicated by solid lines, closed symbols) and where relevant anti-drug detection (total ADC, indicated by dashed lines, open symbols). The SE of the mean of each group and experimental triplicates are shown. ADC scFv (TCT1067)-MMAF-C5 (circles) (n=3), trastuzumab-MMAF-C5 (triangles) (n=3) and scFv (TCT1067) (squares) (n=3).

Figure 92:
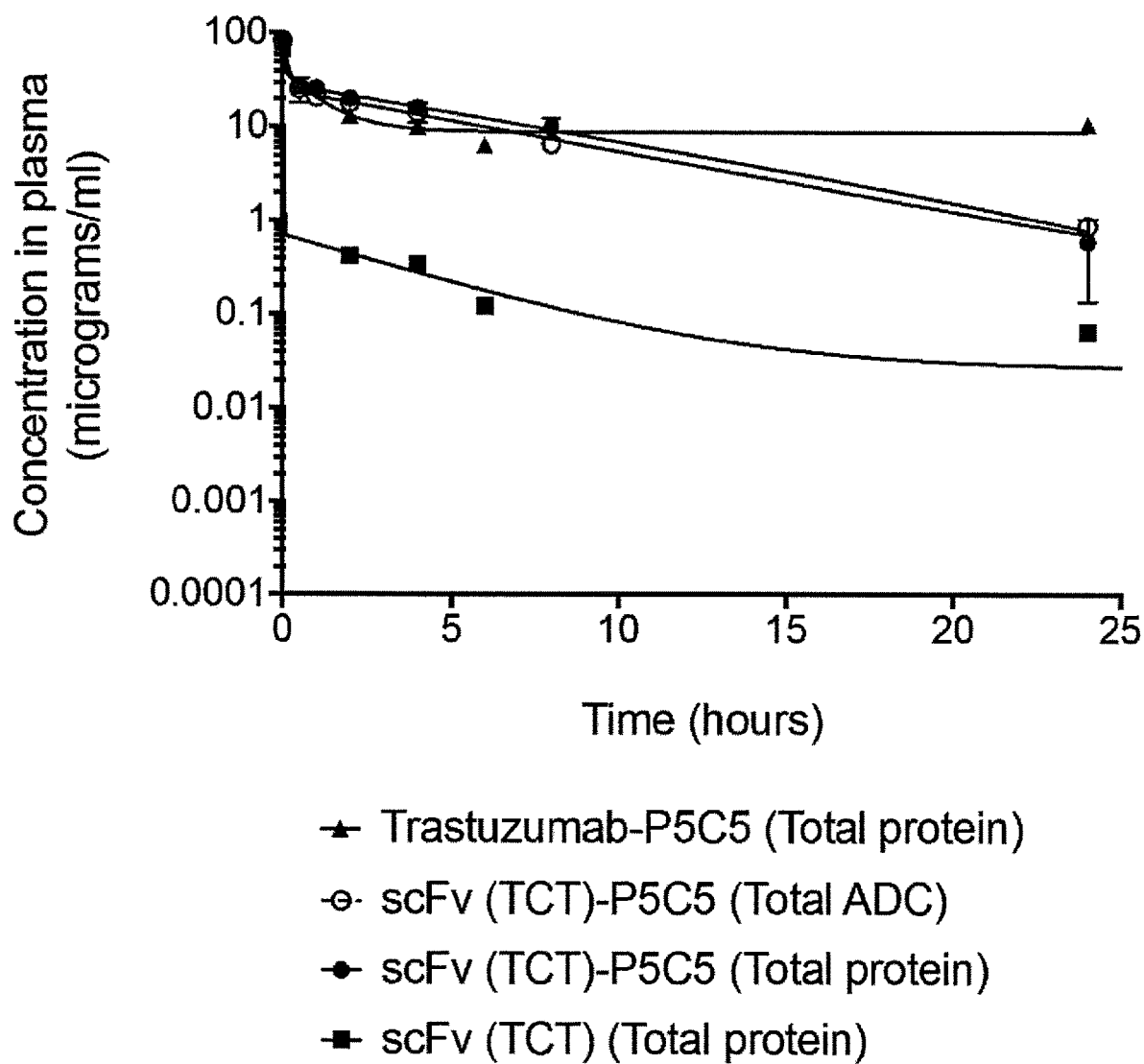

FIG. 92. Pharmacokinetic clearance analysis of scFv (TCT)-P5C5 and controls (compounds 71) in a murine model.

A single i.v. dose was injected into female BALB/c mice at 5 mg/kg. Plasma samples were taken at time points indicated and analysed by ELISA using anti-protein detection (total protein, indicated by solid lines, closed symbols) and where relevant anti-drug detection (total ADC, indicated by dashed lines, open symbols). The SE of the mean of each group and experimental triplicates are shown. ADC scFv (TCT)-P5C5 (circles) (n=3), trastuzumab-P5C5 (triangles)

(n=3) and scFv (TCT) (squares) (n=4). Control scFv (TCT) and trastuzumab-P5C5 values supplied from a separate PK study.

Figure 93:
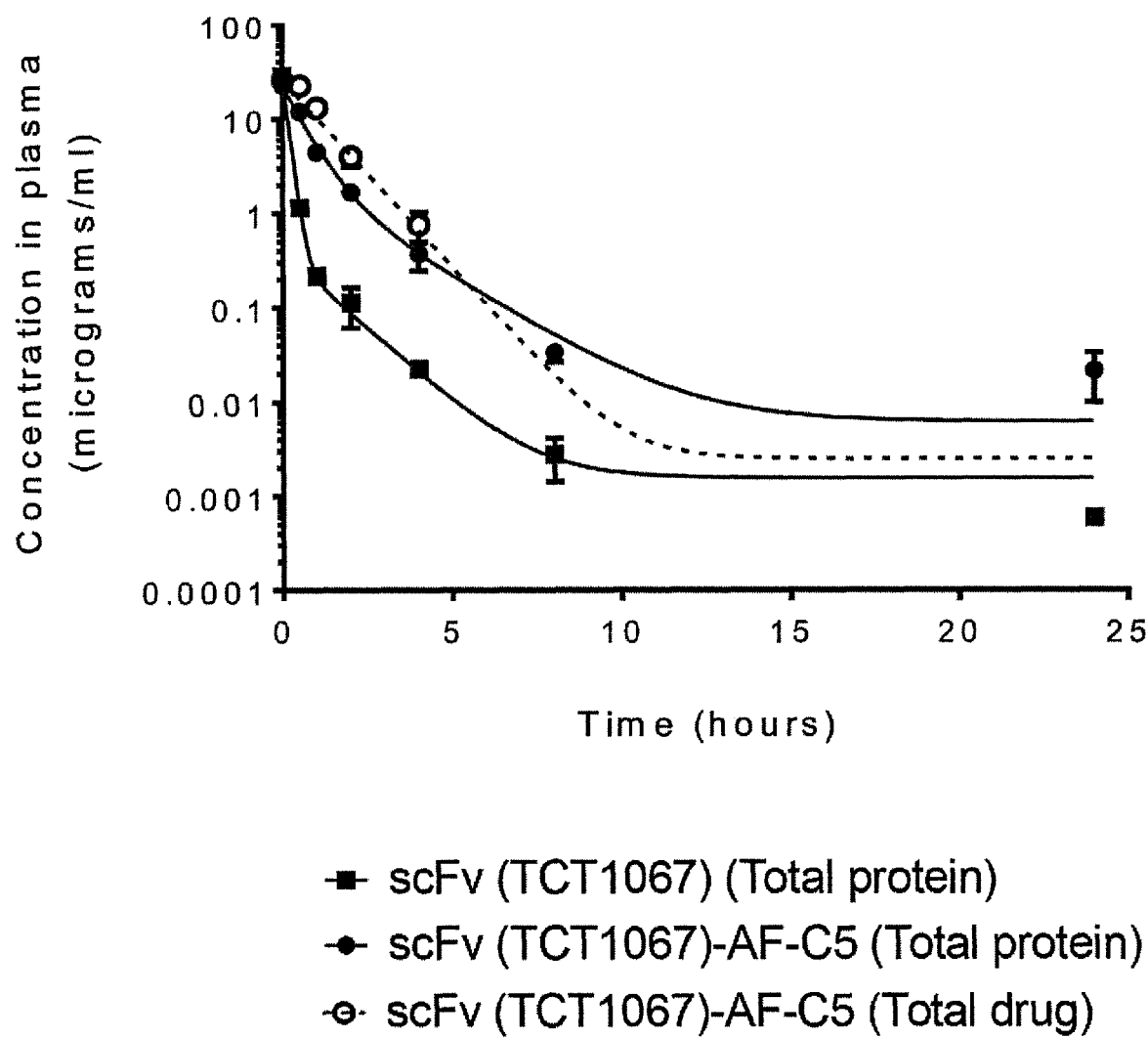

FIG. 93. Pharmacokinetic clearance analysis of scFv (TCT1067)-AF-C5 and control (compounds 122) in a murine model.

A single i.v. dose was injected into female BALB/c mice at 2 mg/kg. Plasma samples were taken at time points indicated and analysed by ELISA using anti-protein detection (total protein, indicated by solid lines, closed symbols) and where relevant anti-drug detection (total ADC, indicated by dashed lines, open symbols). The SE of the mean of each group and experimental triplicates are shown. ADC scFv (TCT1067)-AF-C5 (circles) (n=3) and scFv (TCT1067) (squares) (n=3).

Figure 94:
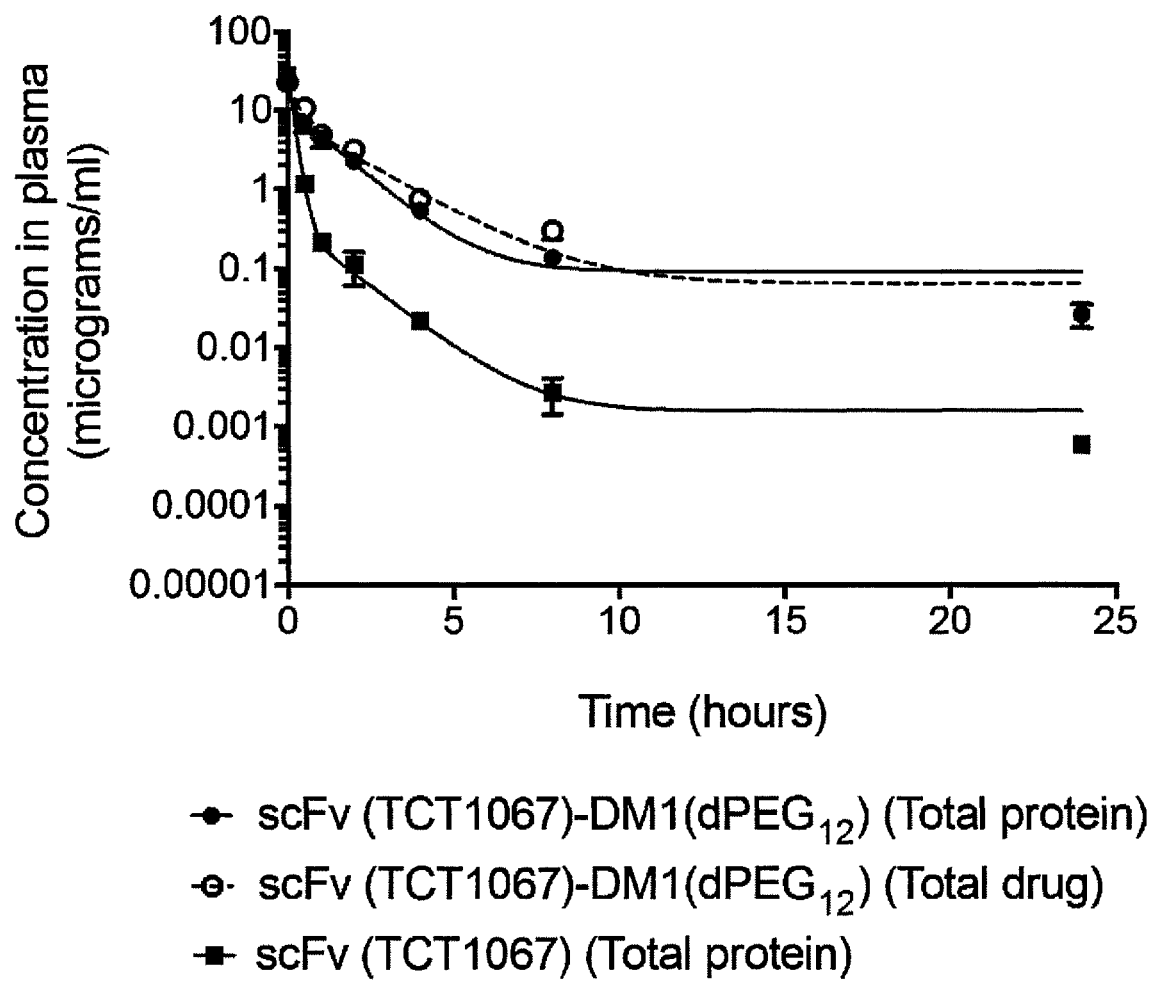

FIG. 94. Pharmacokinetic clearance analysis of scFv (TCT1067)-DM1 (dPEG$_{12}$) and control (compounds 124) in a murine model.

A single i.v. dose was injected into female BALB/c mice at 2 mg/kg. Plasma samples were taken at time points indicated and analysed by ELISA using anti-protein detection (total protein, indicated by solid lines, closed symbols) and where relevant anti-drug detection (total ADC, indicated by dashed lines, open symbols). The SE of the mean of each group and experimental triplicates are shown. ADC scFv (TCT1067)-DM1 (dPEG$_{12}$) (circles) (n=3) and scFv (TCT1067) (squares) (n=3).

Figure 95:
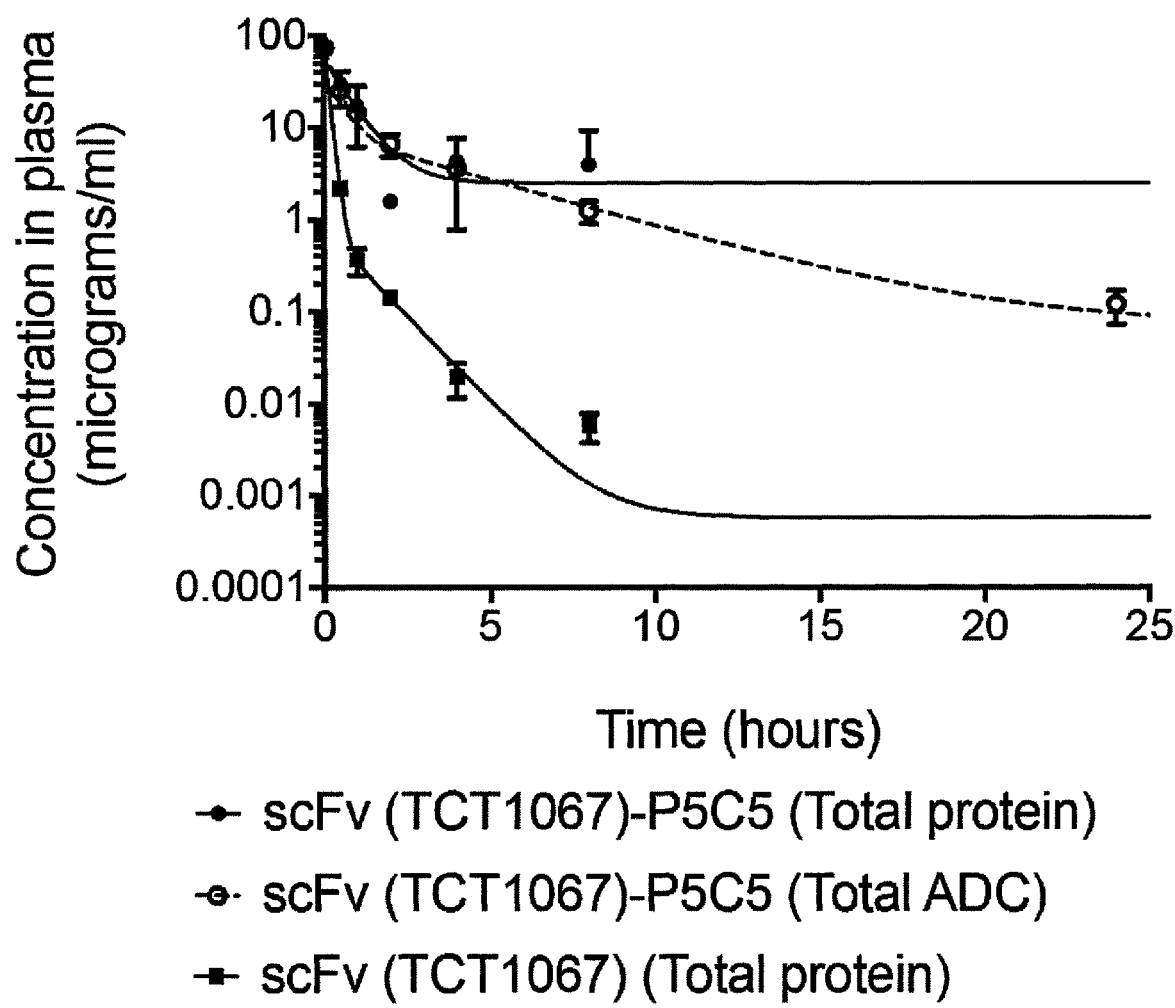
Figure 95:
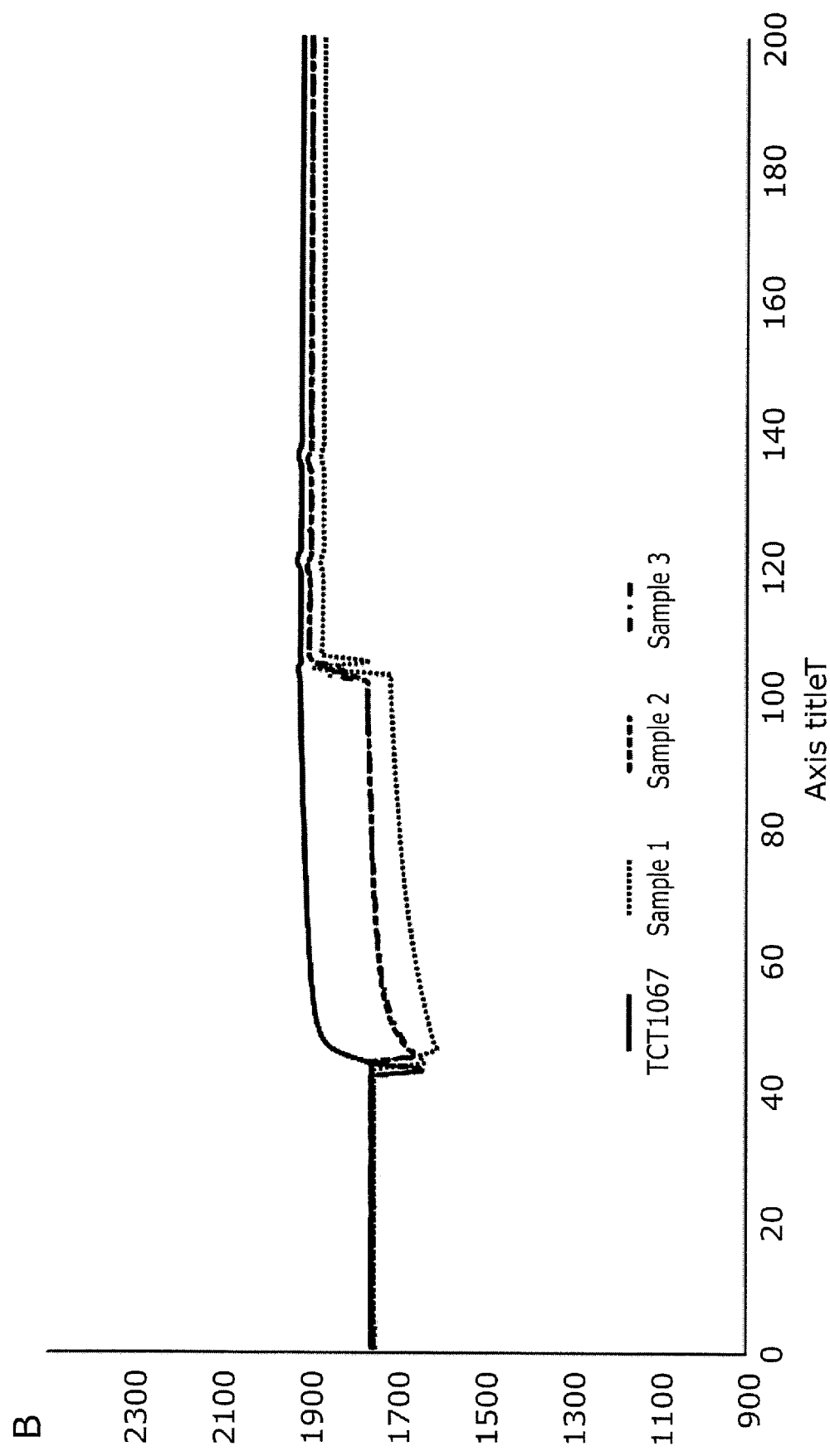
Figure 95:
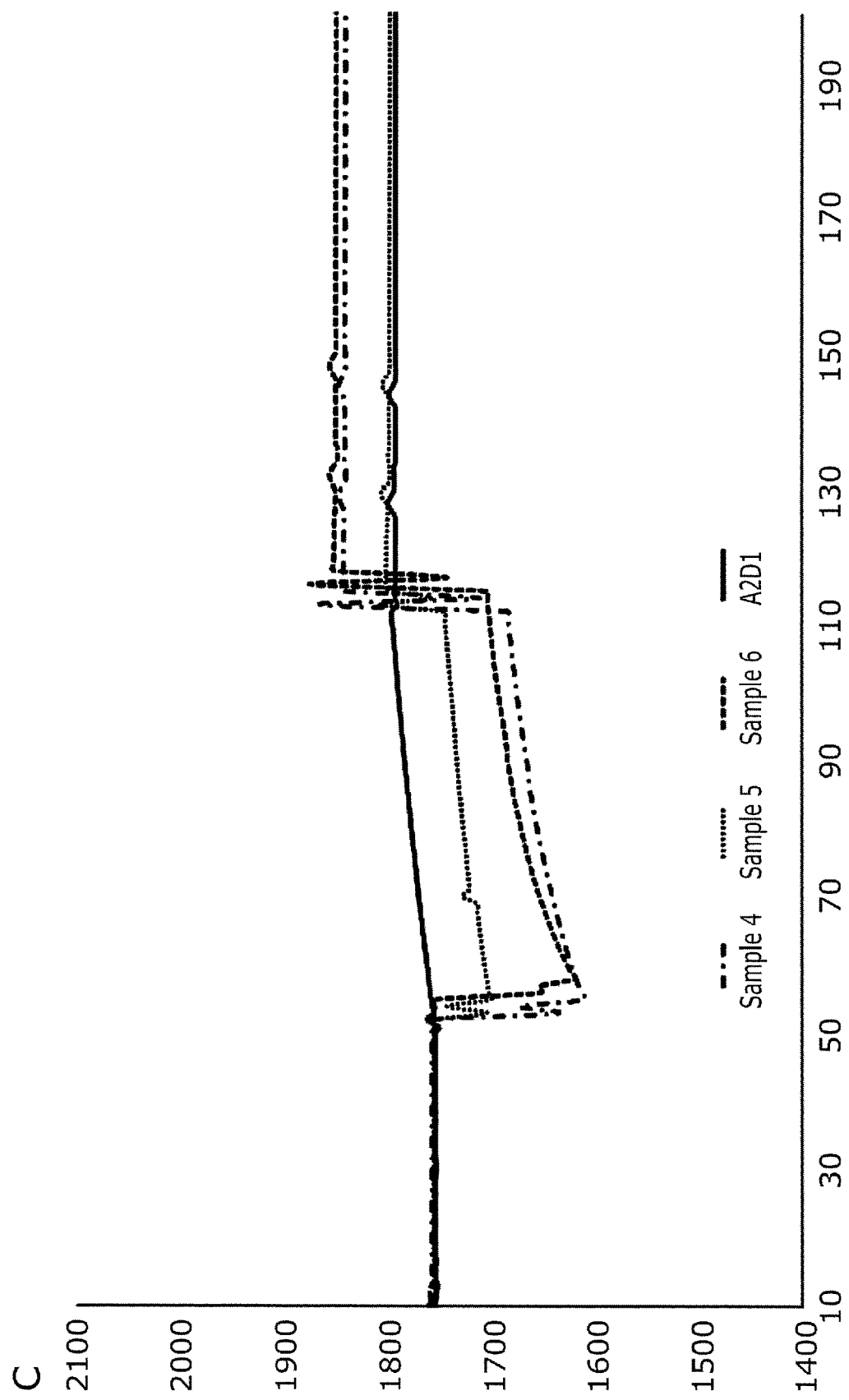

FIG. 95. Pharmacokinetic clearance analysis of scFv (TCT1067)-P5-C5 and control (compounds 124) in a rat model.

(A) A single i.v. dose was injected into male Sprague-Dawley rats at 4 mg/kg. Plasma samples were taken at time points indicated and analysed by ELISA using anti-protein detection (total protein, indicated by solid lines, closed symbols) and where relevant anti-drug detection (total ADC, indicated by dashed lines, open symbols). The SE of the mean of each group and experimental triplicates are shown. ADC scFv (TCT1067)-P5C5 (circles) (n=3) and scFv (TCT1067) (squares) (n=3). (B) 10-fold concentrated urine collected over 24 hours analysed on a HER2-Biacore SPR chip for the scFv (TCT1067)-injected rats, 3 animal samples. The scFv reference is shown. The bulk shifts in the urine samples are due to the concentration of urine components. (C) 10-fold concentrated urine collected over 24 hours analysed on a HER2-Biacore SPR chip for the scFv (TCT1067)-P5C5 conjugate-injected rats, 3 animal samples. The scFv (TCT1067)-P5C5 reference is shown. The bulk shifts in the urine samples are due to the concentration of urine components.

Figure 96:
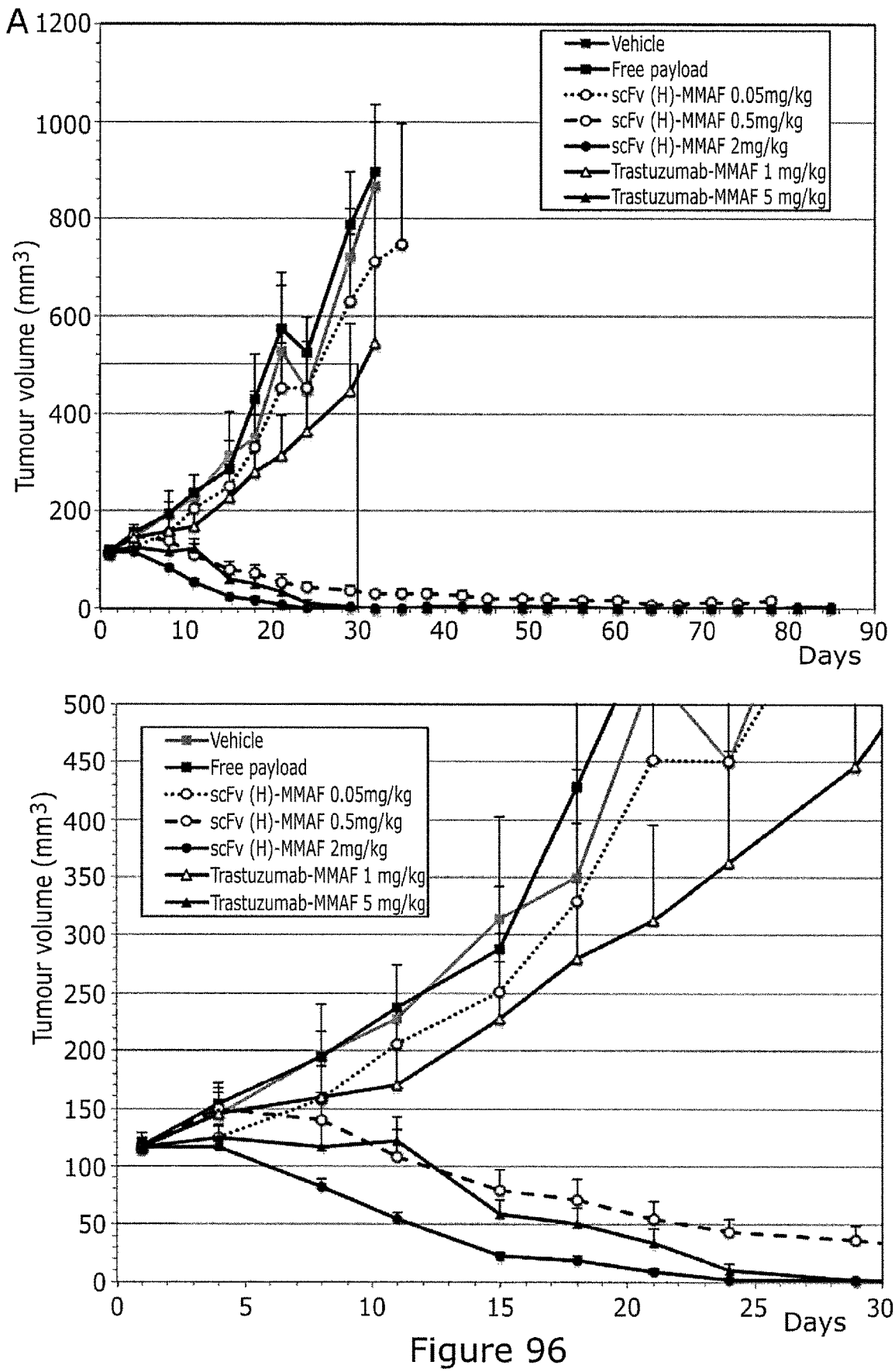
Figure 96:
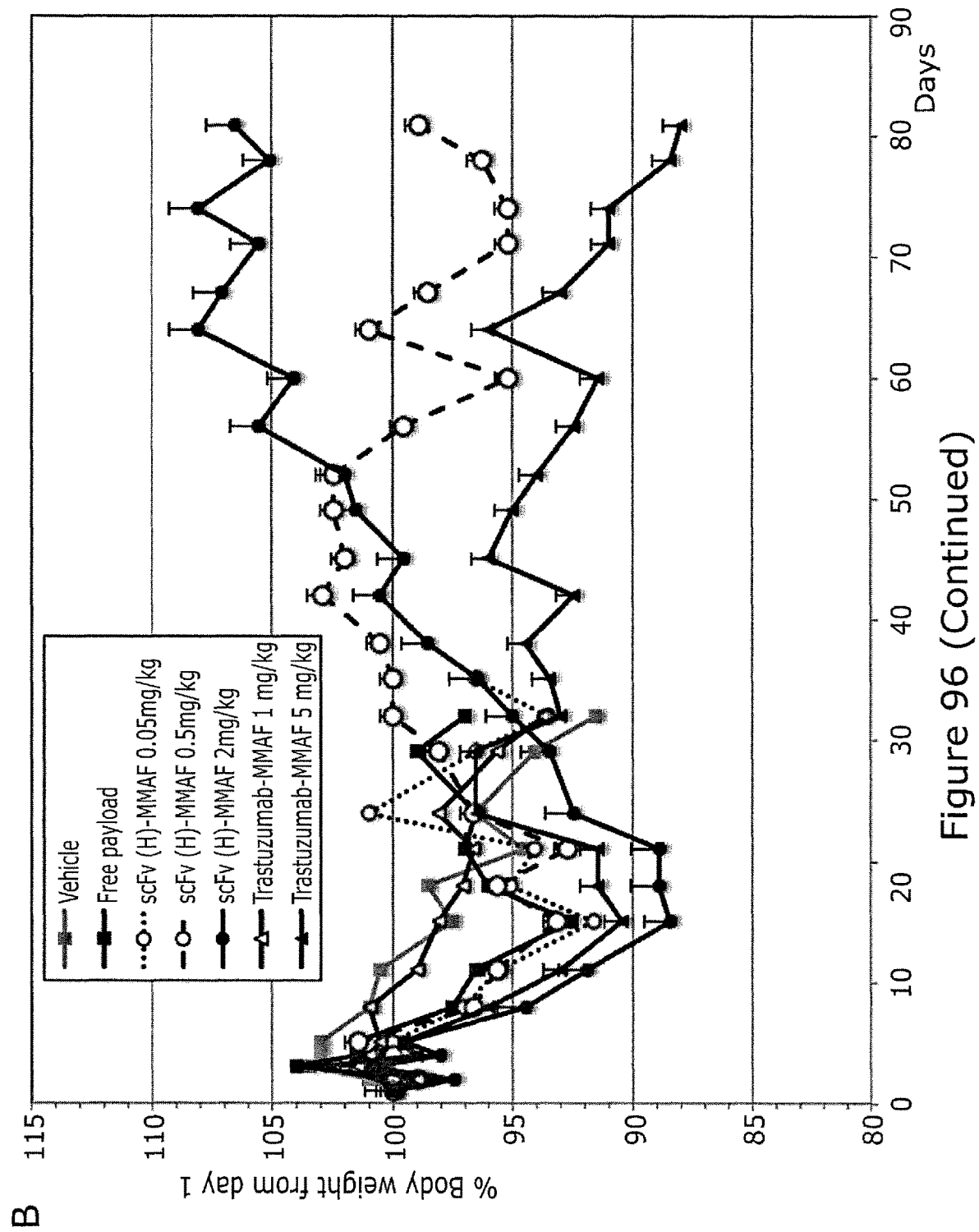

FIG. 96. Tumour growth inhibition or eradication in a BT474 xenograft model with scFv (TCT1067)-MMAF-C5, Trastuzumab-MMAF-C5 conjugates (compounds 118) and Free MMAF therapeutic agents.

(A) Tumour volume against time (days) is plotted with 3 doses of scFv (TCT1067)-MMAF-C5 ADC (circles), 2 doses of trastuzumab-MMAF-C5 conjugate (triangles) and controls (squares). Each group consists of 6 animals and the SE of the mean is shown. Inset is a zoomed-in view of the first 30 days). The second plot is an enlargement of a portion of the first plot (shown by the boxed region). (B) The percentage change in body weight from the start of the treatment of the same groups in (A).

Figure 97:
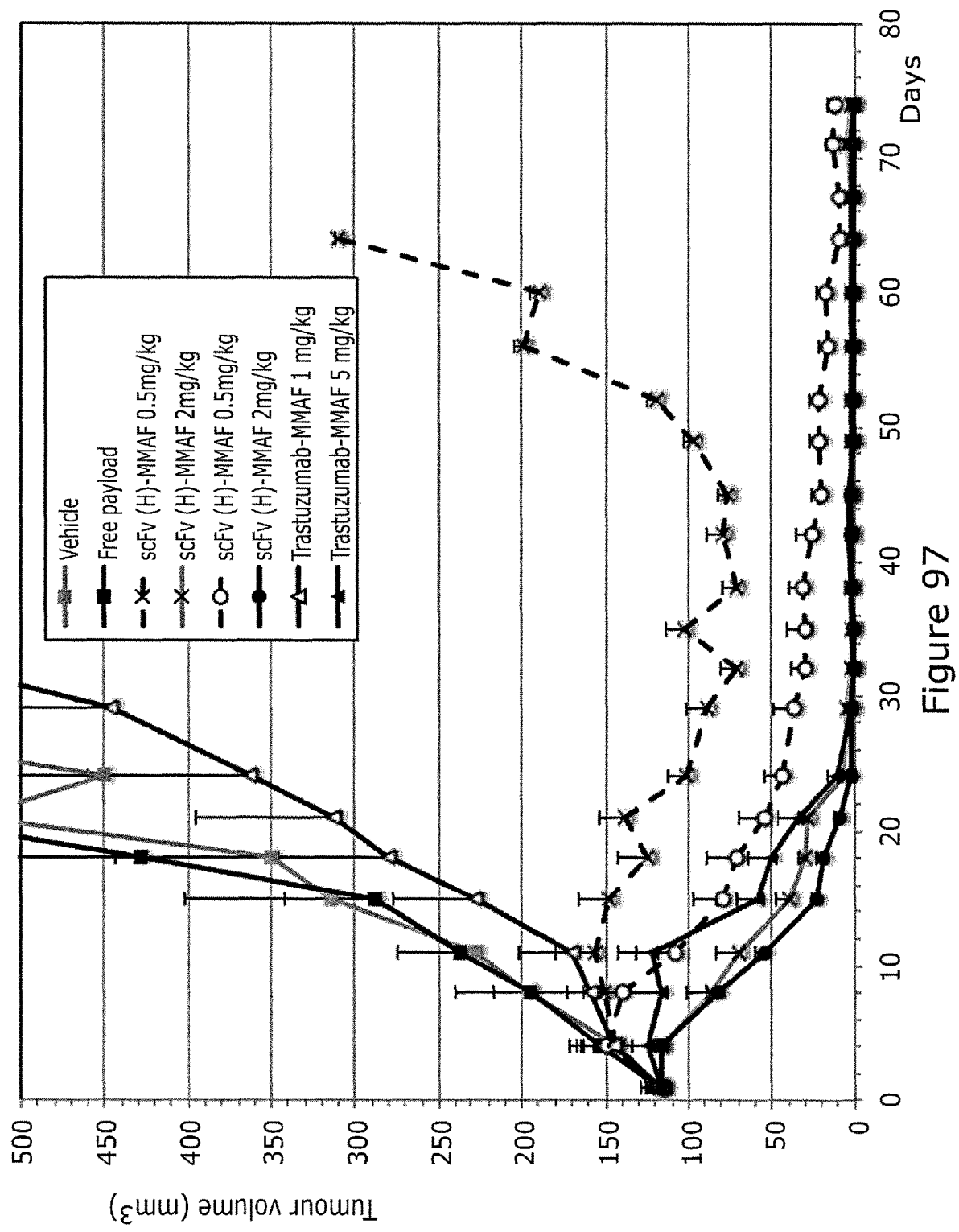
Figure 97:
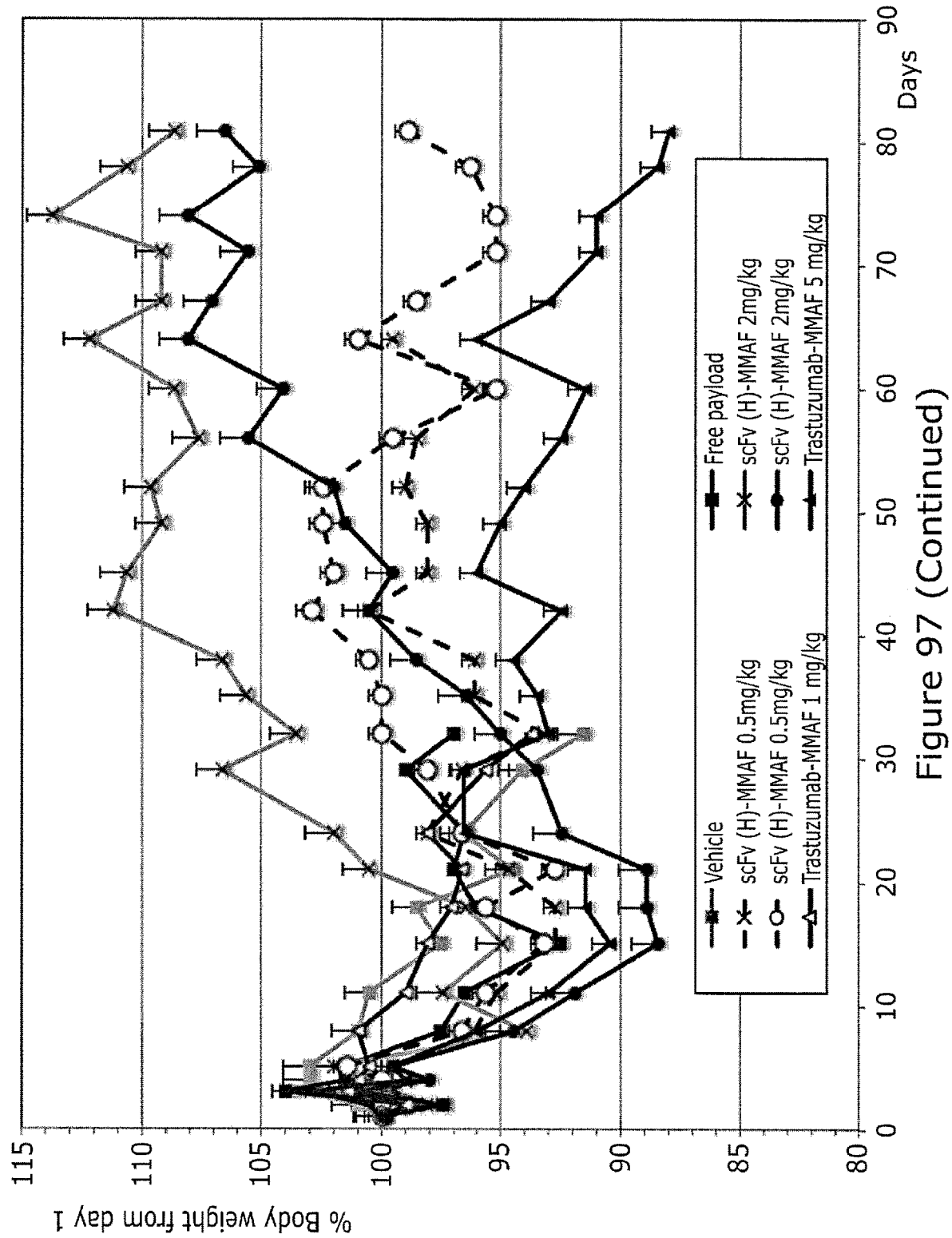

FIG. 97. Tumour growth inhibition or eradication in a BT474 xenograft model with scFv (TCT)-MMAF-C5, Trastuzumab-MMAF-C5 conjugates (compounds 118) and Free MMAF therapeutic agents.

(A) Tumour volume against time (days) is plotted with 2 doses of scFv (TCT1067)-MMAF-C5 ADC (circles), 2 doses of scFv (TCT)-MMAF-C5 ADC (crosses), 2 doses of trastuzumab-MMAF-C5 conjugate (triangles) and controls (squares). Each group consists of 6 animals and the SE of the mean is shown.

(B) The percentage change in body weight from the start of the treatment of the same groups in (A).

Figure 98:
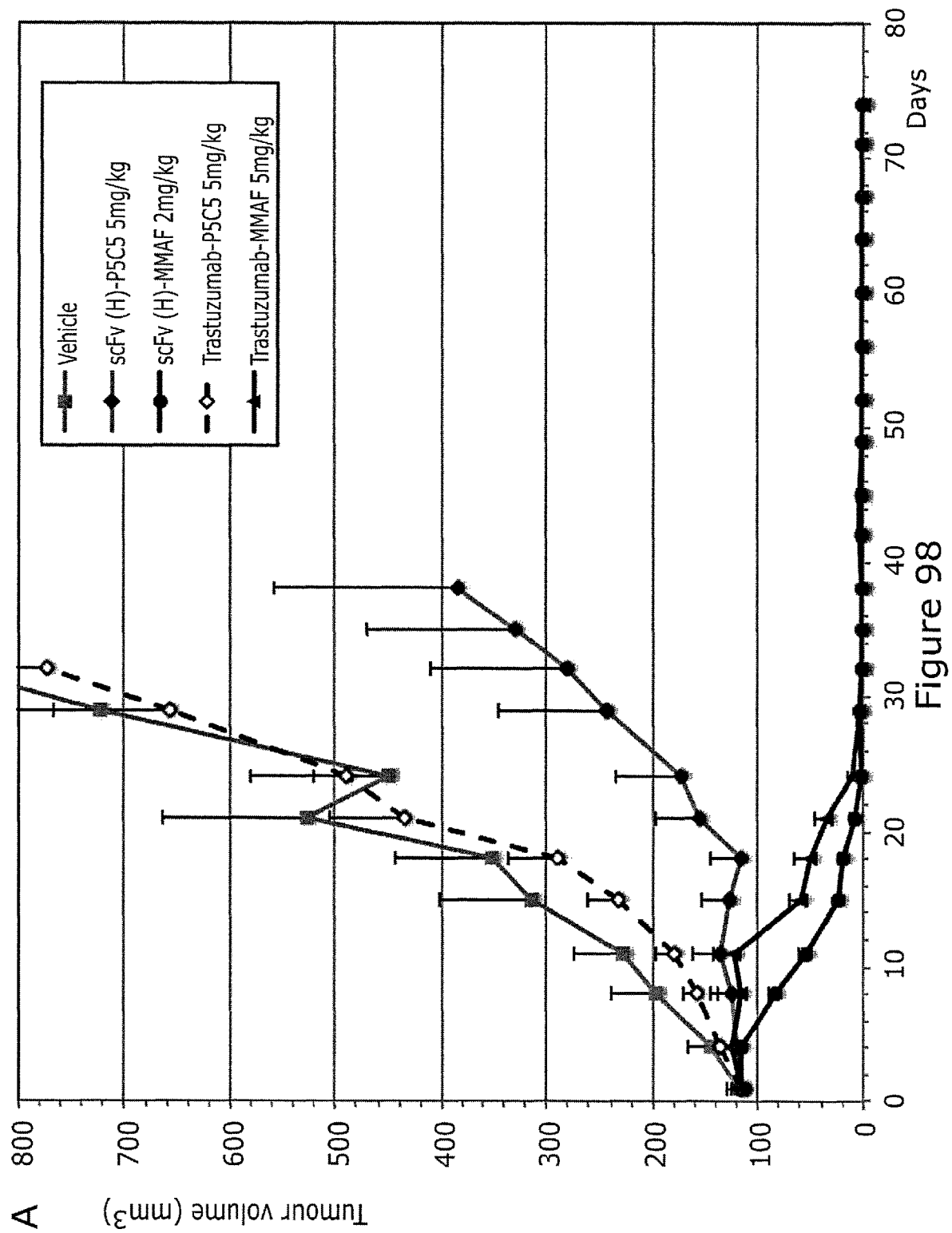
Figure 98:
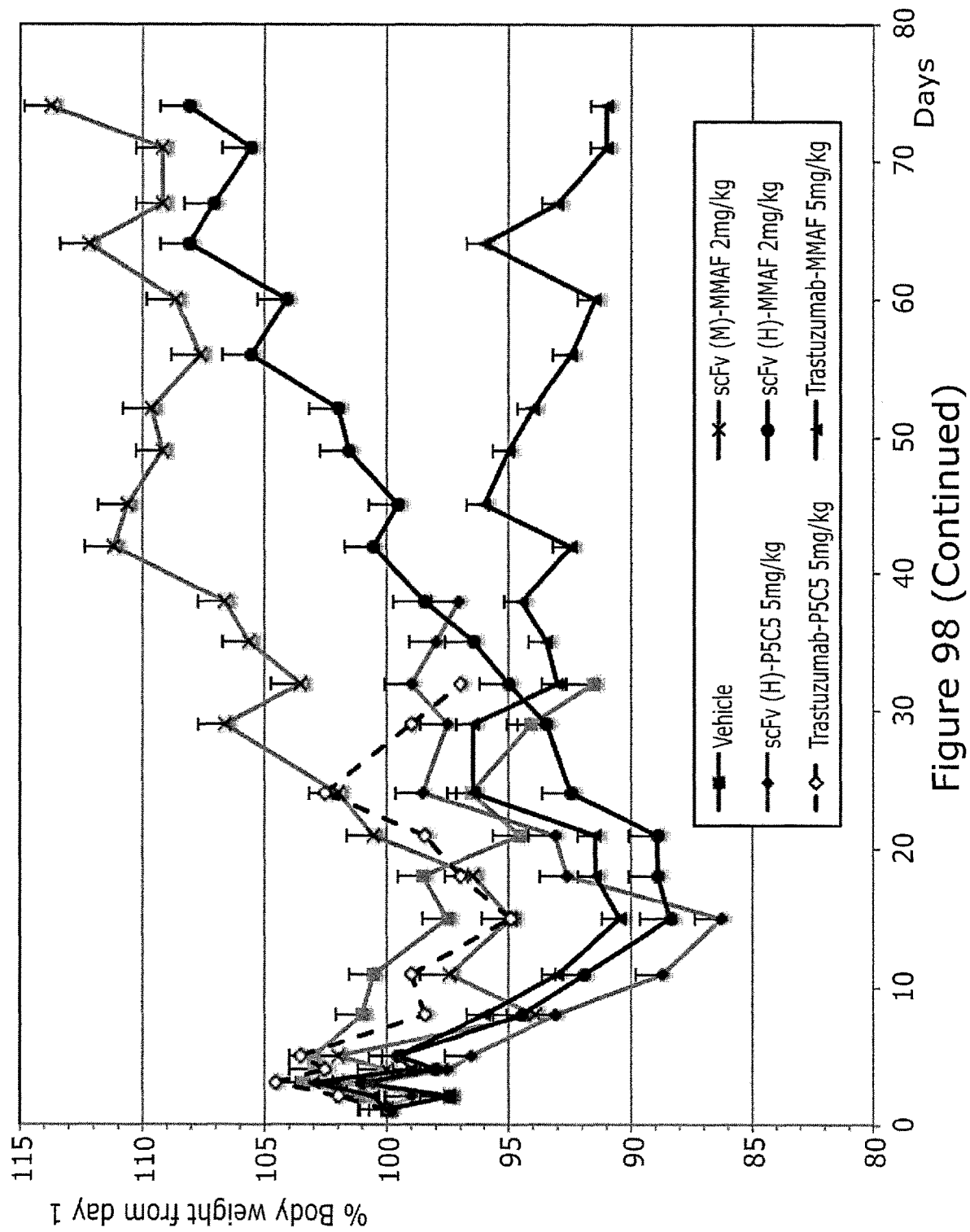

FIG. 98. Tumour growth inhibition or eradication in BT474 xenograft model with scFv (TCT1067)-P5C5 and Trastuzumab-P5C5 conjugates (compounds 71).

(A) Tumour volume against time (days) is plotted with one dosing regimen of scFv (TCT1067)-P5-C5 ADC (diamonds), one dosing regimen of scFv (TCT1067)-MMAF-C5 ADC (circle), one dosing regimen of trastuzumab-MMAF conjugate (triangles), one dosing regimen of trastuzumab-P5-C5 conjugate (diamonds) and controls (squares). Each group consists of 6 animals and the SE of the mean is shown. (B) The percentage change in body weight from the start of the treatment of the same groups in (A).

Figure 99:
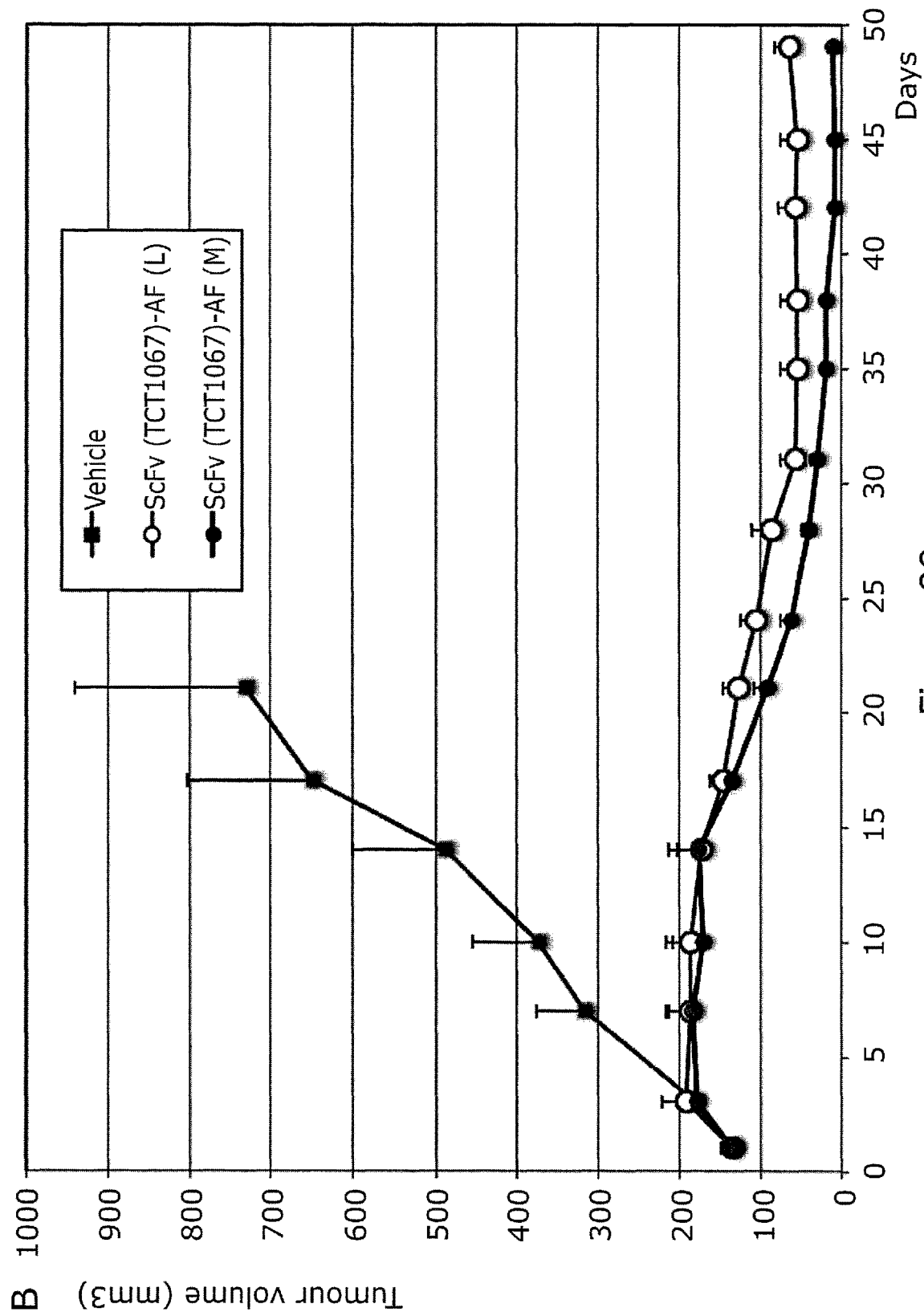
Figure 99:
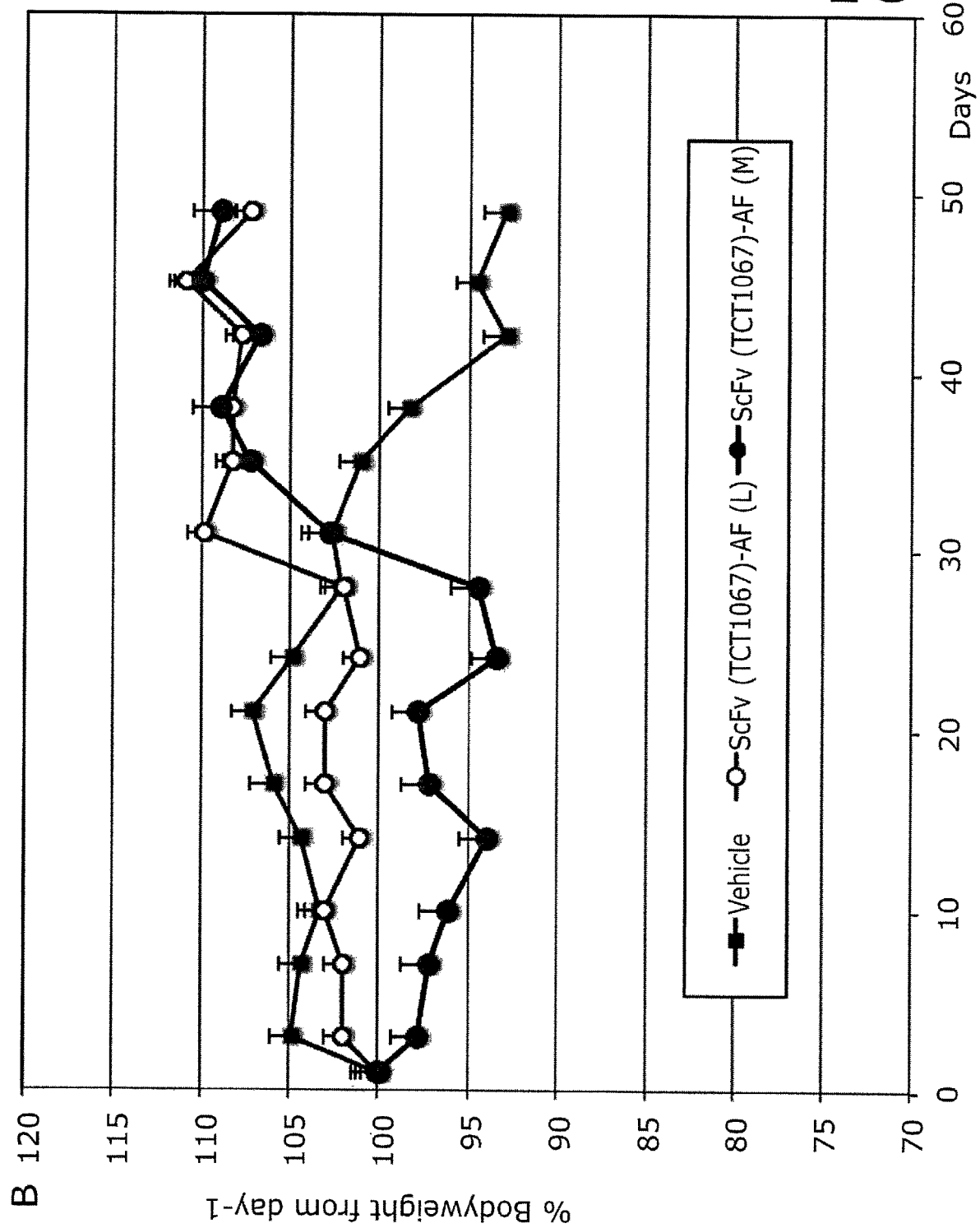

FIG. 99. Tumour growth inhibition or eradication in a BT474 human breast cancer xenograft model with scFv (TCT1067)-AF-C5 conjugates (121) at two different DARs.

(A) Tumour volume against time (days) is plotted for two therapeutic agents, scFv (TCT1067)-AuristatinF (L) Low DAR, 2.7 and. scFv (TCT1067)-AuristatinF (M) medium DAR, 5.7 and vehicle control. Each group consists of 6 animals and the SE of the mean is shown. (B) The percentage change in body weight from the start of the treatment of the same groups in (A).

Figure 100:
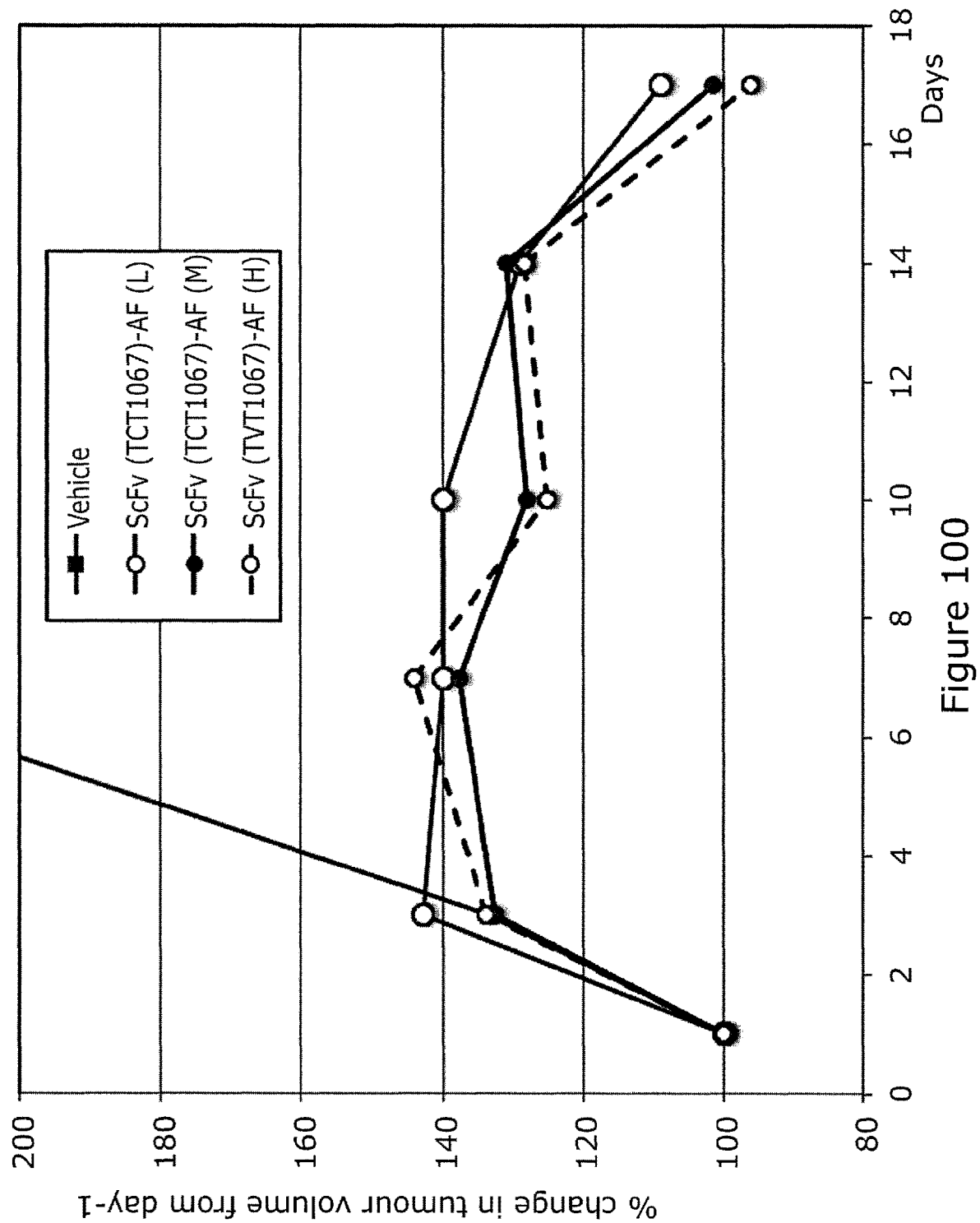

FIG. 100. Tumour growth inhibition or eradication in a BT474 human breast cancer xenograft model with scFv (TCT1067)-AF-C5 conjugates (121) at three different DARs.

Tumour volume against time (days) is plotted for two therapeutic agents, scFv (TCT1067)-AuristatinF (L) Low DAR, 2.7 and. scFv (TCT1067)-AuristatinF (M) medium DAR, 5.7, scFv (TCT1067)-AuristatinF (H) High DAR, 11 and vehicle control. Each group consists of 6 animals and the SE of the mean is shown.

Figure 101:
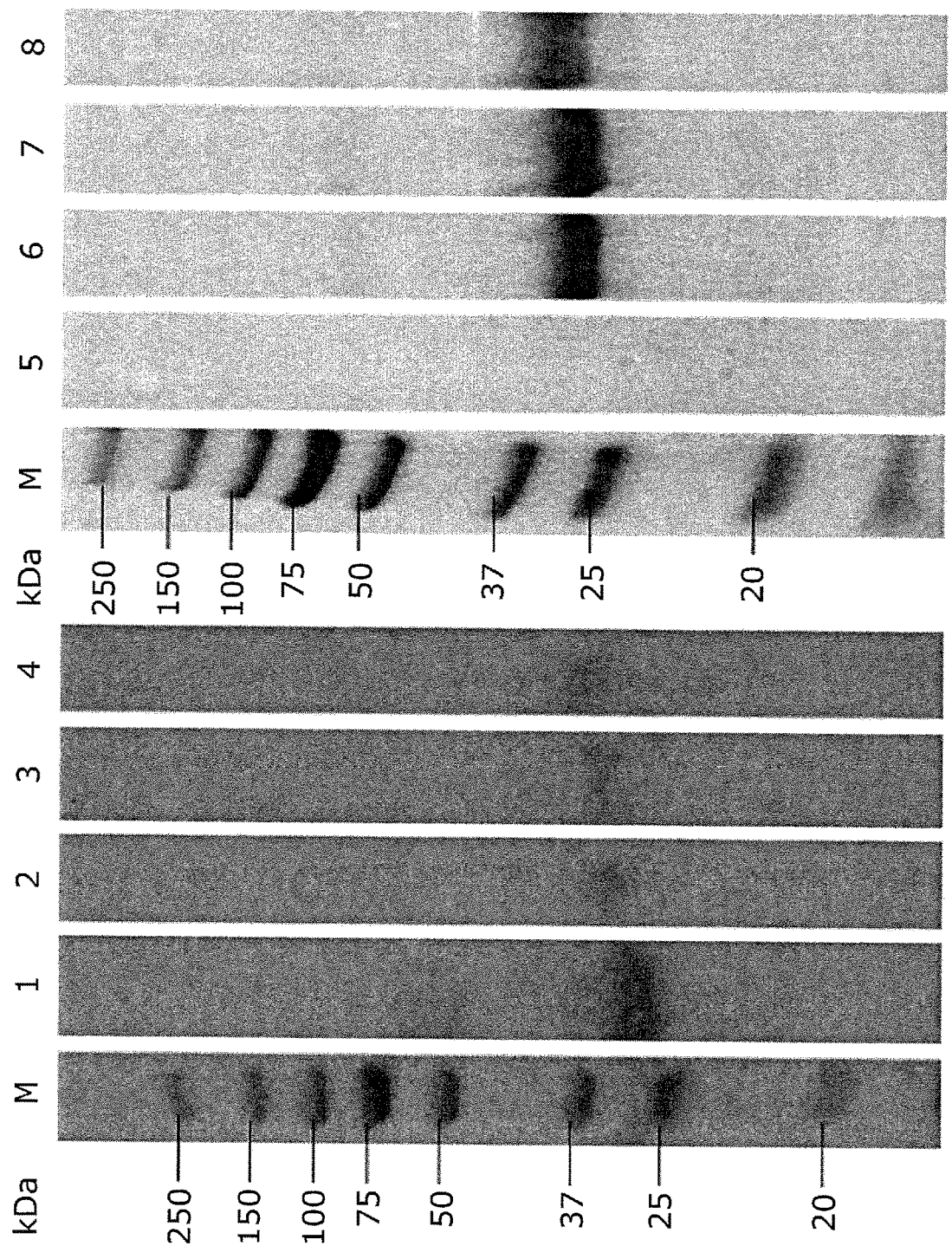

FIG. 101. SDS PAGE of scFv (TCT) conjugates with TCO-PEG4-NHS.

Lanes 2-4 are purified antibody fragment (scFv) conjugate.
1=unmodified scFv (TCT) stock;
2=scFv (TCT) conjugate with 4 drug equivalent;
3=TCT conjugate with 6 drug equivalent;
4=scFv (TCT) conjugate with 16 drug equivalent.
Lanes 6-8 are antibody fragment conjugates before purification.
6=scFv (TCT) conjugate with 4 drug;
7=scFv (TCT) conjugate with 6 drug equivalent;
8=scFv (TCT) conjugate with 16 drug equivalent.
Size markers used are shown.

Figure 102:
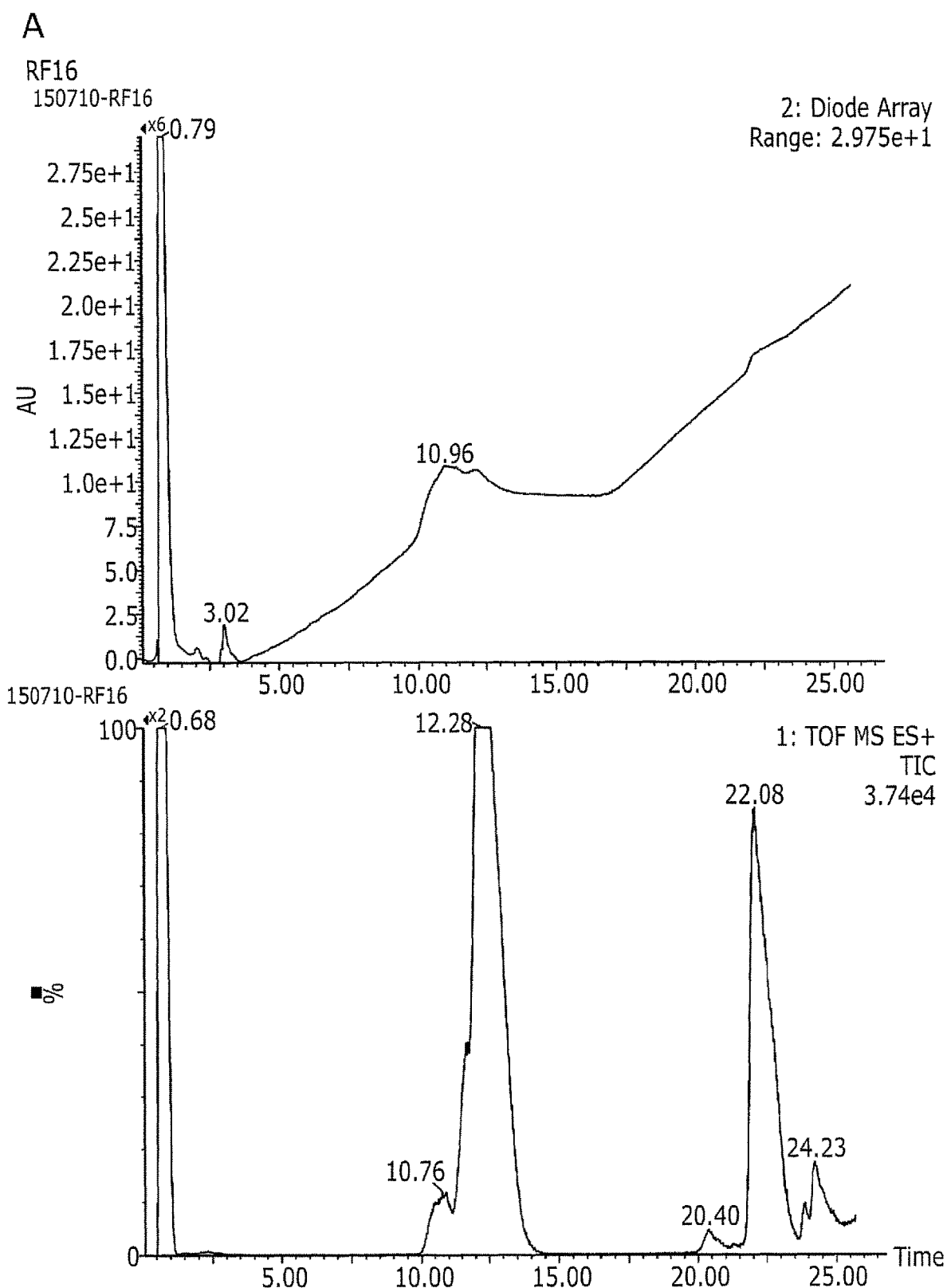
Figure 102:
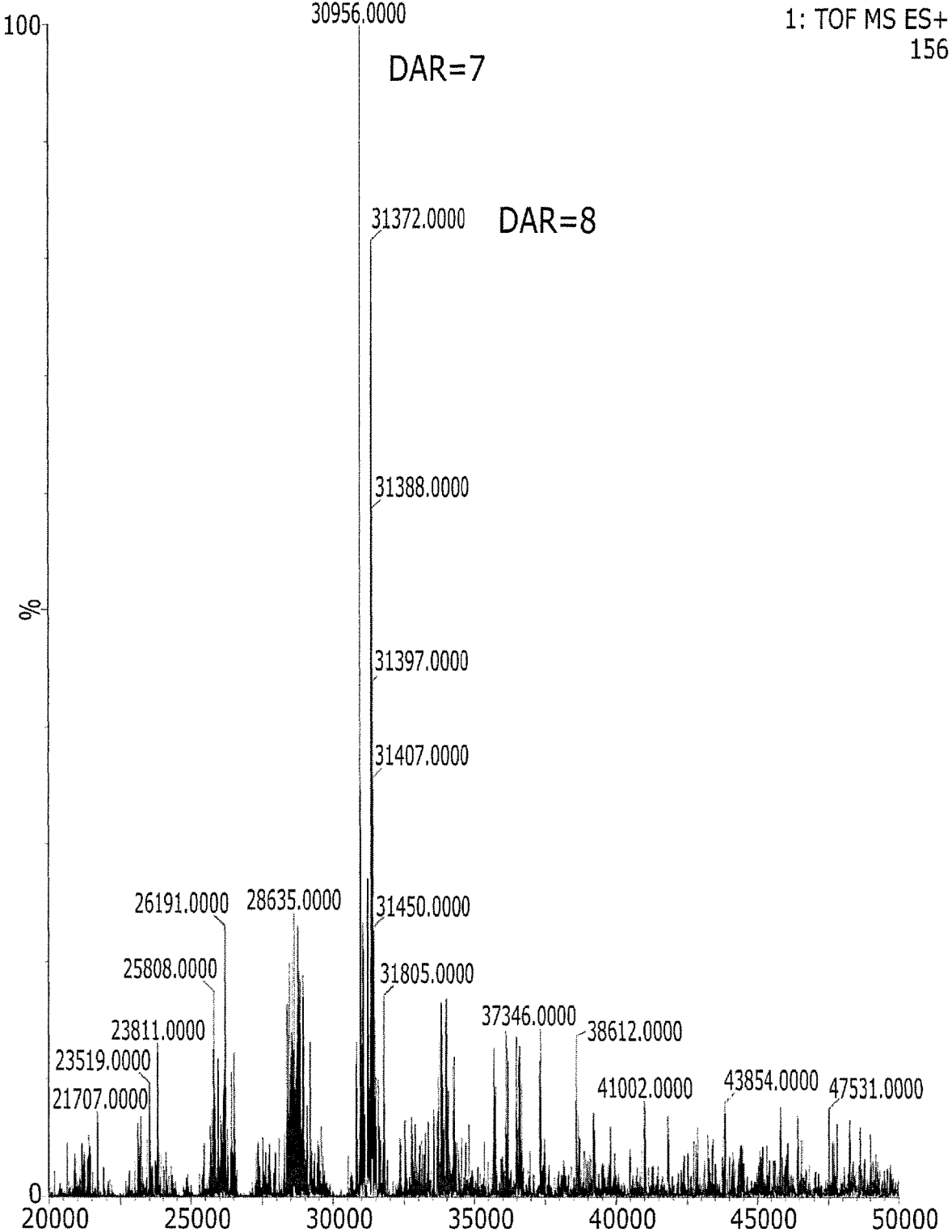

FIG. 102. LCMS data for scFv (TCT)-TCO-PEG4.
(A) is the LCMS trace (UV and TIC) and (B) is the deconvoluted mass for the main peak at 10.76 mins.

Figure 103:
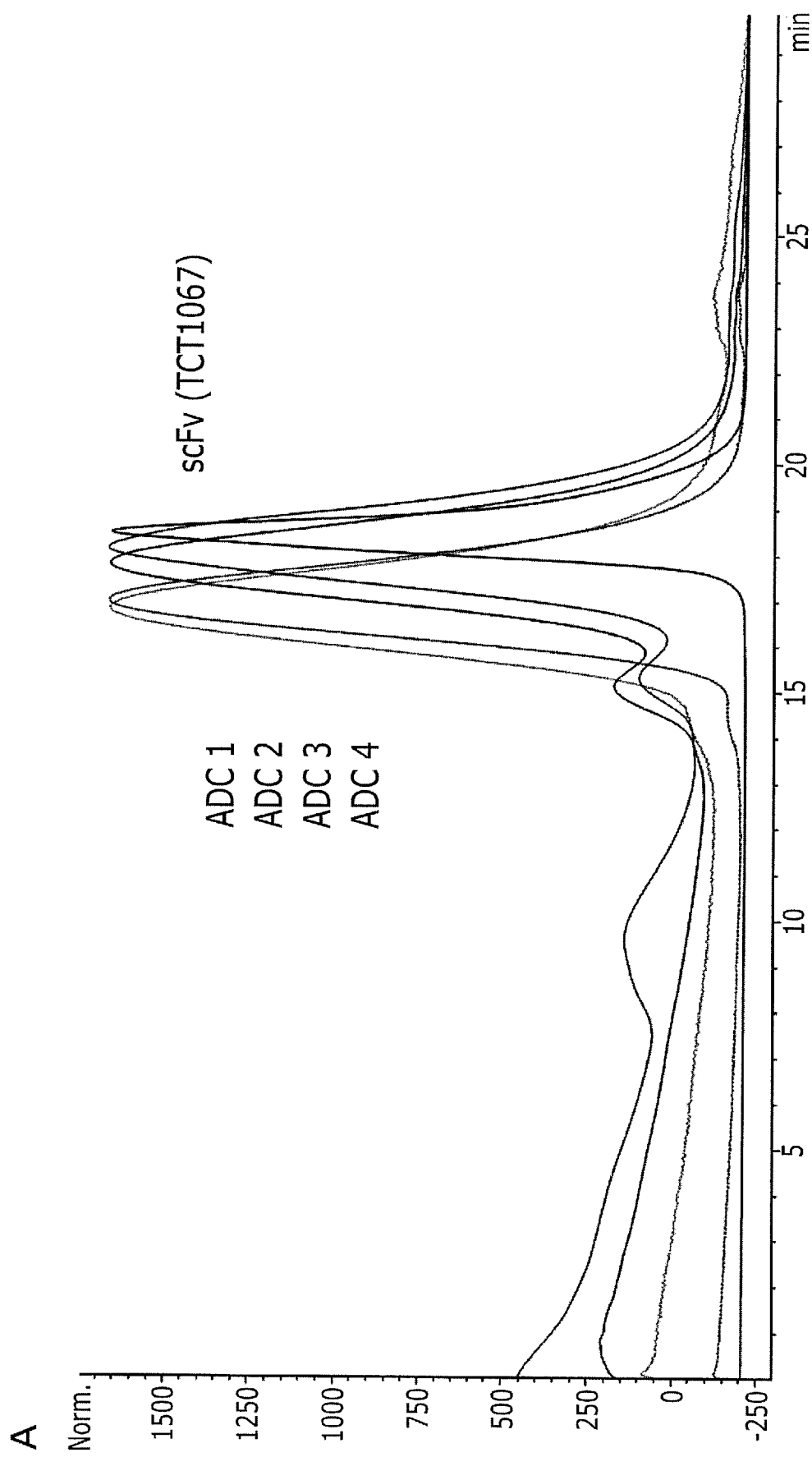
Figure 103:
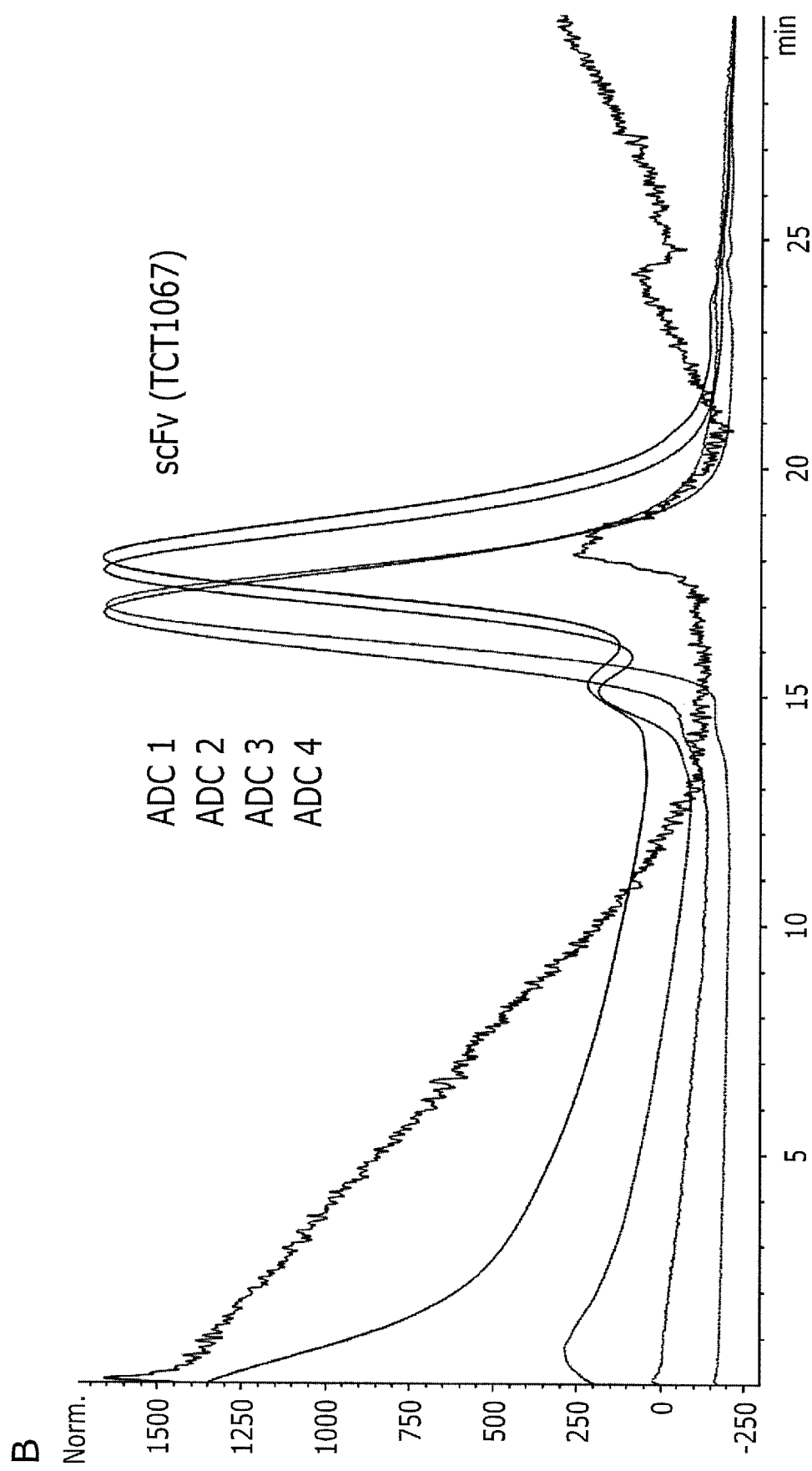

FIG. 103: HPLC SEC traces for scFv(TCT-1067)-5N38-(DNMEA)-PAB-Cit-Val-dPEG$_5$ ADCs 1, 2, 3, 4 run at 1 ml/min and compared to the unconjugated scFv (TCT1067). (A) Profile for absorbance at 280 nm (B) Profile for absorbance at 360 nm FIG. 104: SDS-PAGE reducing gel (4-20%) showing scFv (TCT1067)-SN38-(DNMEA)-PAB-Cit-Val-dPEG$_5$ conjugates 1 and 2 in comparison with unconjugated scFv (TCT1067).

Figure 105:
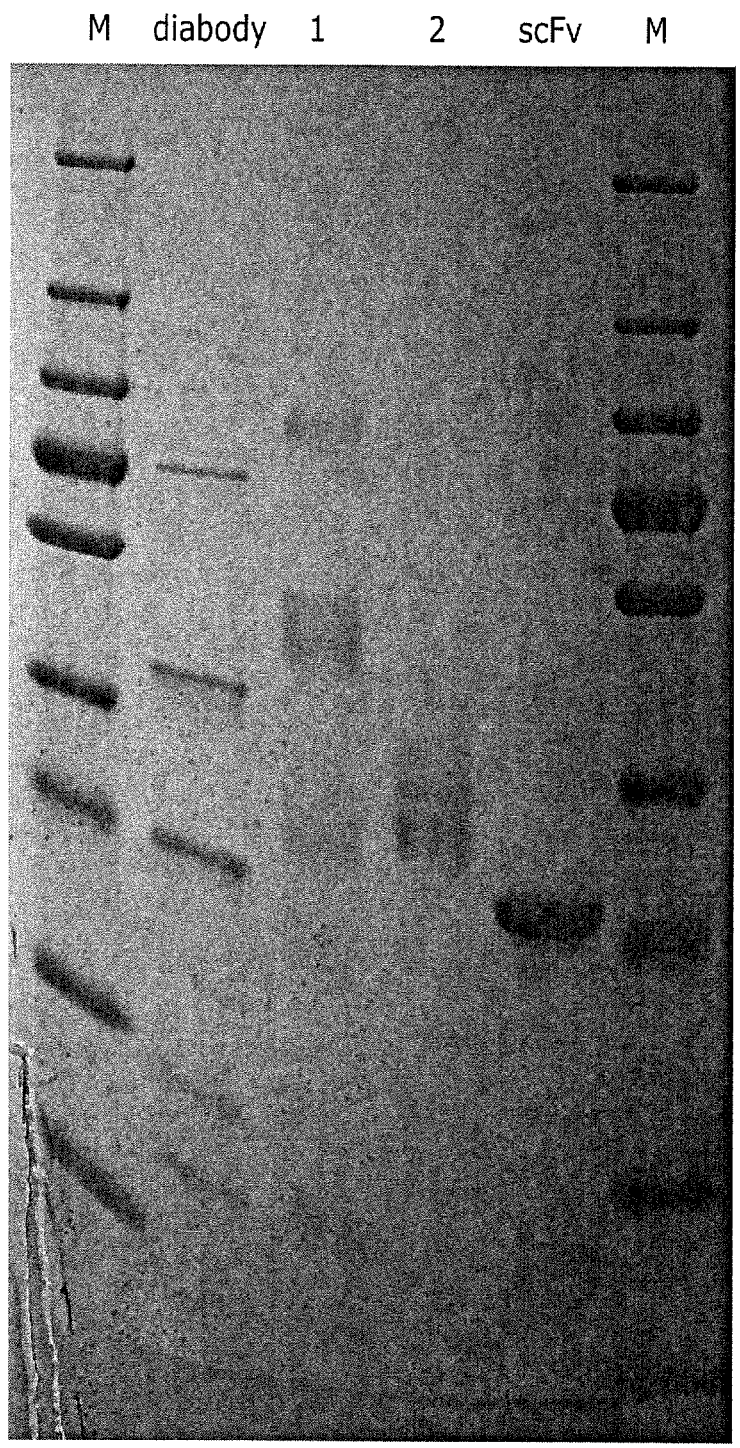

FIG. 105: SDS PAGE reducing gel (4-20%) showing diabody (TCT)-AF-C5 and scFv (TCT)-AF-C5 conjugates against their respective unconjugated antibodies, diabody (TCT) and scFv (TCT).

COMMON FACTORS TO ALL EXAMPLES

All SDS-PAGE gels are reducing.

TABLE 3

Molar extinction coefficients used in examples

| Item | Molar extinction coefficient |
|---|---|
| $\varepsilon$280 nm for C6.5 andscFv (TCT) | 65422 |
| $\varepsilon$280 nm for HMFG1 IgG | 210000 |
| $\varepsilon$343 nm thione | 8080 |
| $\varepsilon$280 nm thione | 5100 |
| $\varepsilon$Doxorubicin 488 nm | 11294 |
| $\varepsilon$Doxorubicin 280 nm | 8487 |
| $\varepsilon$Doxorubicin-PEG 488 nm | 10218 |
| $\varepsilon$Doxorubicin-PEG 280 nm | 14021 |
| $\varepsilon$Ellipticine 429 nm | 3603 |
| $\varepsilon$Ellipticine 280 nm | 22990 |

TABLE 3-continued

Molar extinction coefficients used in examples

| Item | Molar extinction coefficient |
|---|---|
| $\varepsilon$Ellipticine-PEG 429 nm | 1810 |
| $\varepsilon$Ellipticine-PEG 280 nm | 8838 |

Synthetic Experimental Procedures

Experiments were generally carried out under inert atmosphere (nitrogen) especially in cases where oxygen- or moisture sensitive reagents or intermediates were employed unless otherwise stated. Commercial solvents and reagents were the best grade available and used without further purification. Anhydrous solvents were obtained from either Acros or Sigma-Aldrich. Reactions were followed by thin-layer chromatography (tic), LCMS or HPLC and purifications carried out by either Biotage automated chromatography using normal or reverse phase supports or by reverse phase HPLC. Reverse phase fractions from either the Biotage or HPLC were concentrated via lyophilisation/freeze-drying. Mass spectrometry data is reported from LCMS or by direct injection using electro-spray (ES) as ionisation mode unless otherwise stated. Chemical shifts for both proton and carbon nuclear magnetic resonance (NMR) are expressed as part per million (ppm) with the deuterated solvent as internal reference.

Example 1—Preparation of Cemadotin-NHS (2)

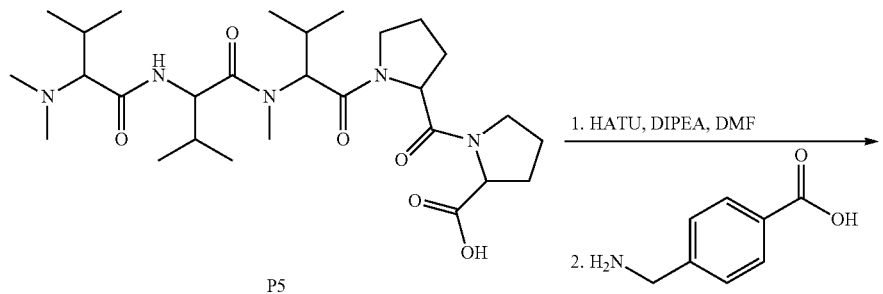

P5

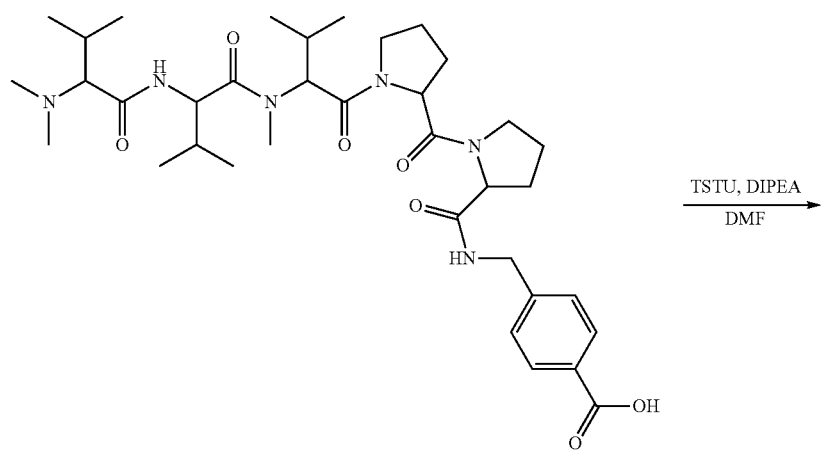

Cemadotin—$CO_2H$ (1)

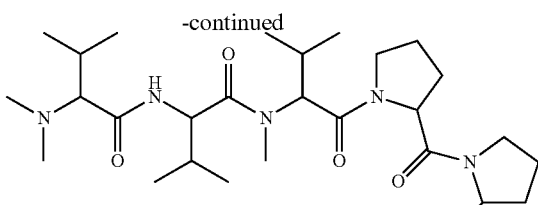
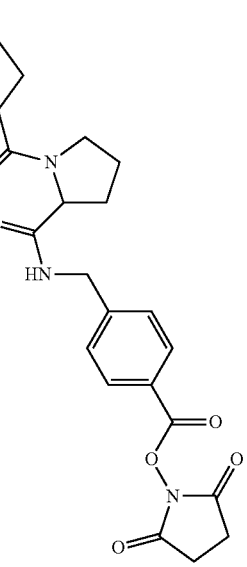

Cemadotin—NHS (2)

To a stirred solution of P5 (100 mg, 0.18 mmol) in DMF (5 mL), HATU (62 mg, 0.16 mmol) was added, followed by N,N-diisopropylethylamine (DIPEA) (63 μL, 0.36 mmol), and the resultant mixture was stirred at room temperature for 30 min. The reaction mixture was then added dropwise over 10 min to a slurry of 4-(aminomethyl)benzoic acid (30 mg, 0.20 mmol) in DMF (5 mL) and stirred at room temperature under nitrogen for 30 min, concentrated under reduced pressure, and purified by preparative HPLC (MeCN in $H_2O$ [0.1% TFA]; 4 mL/min; 4 min 20% MeCN, 20-23% over 2 min, 23-25% over 14 min, 25-30% over 2 min, 30-80% over 3 min, 5 min 80% MeCN) collecting $t_R$=9.96 min to give the title product 1 85 mg, (69%) as a white solid. HRMS (m/z) calculated for $C_{36}H_{57}N_6O$ 685.4289 [M+H] found 685.4307; $^1$H NMR (400 MHz, DMSO-$d_6$) δ 12.86 (br. s, 1H), 9.62 (br. s, 1H), 8.92 (br. s, 1H), 8.40 (t, J=6.0 Hz, 1H), 7.87 (d, J=8.0 Hz, 2H), 7.36 (d, J=8.2 Hz, 2H), 6.55 (br. s, 1H), 4.99 (d, J=11.0 Hz, 1H), 4.61-4.51 (m, 2H), 4.42-4.24 (m, 3H), 3.77-3.63 (m, 3H), 3.60-3.51 (m, 2H), 3.09 (s, 3H), 2.78 (s, 3H), 2.75 (s, 3H), 2.32-2.22 (m, 1H), 2.20-1.87 (m, 8H), 1.86-1.69 (m, 3H), 1.00-0.93 (m, 6H), 0.88 (dd, J=11.8, 6.6 Hz, 6H), 0.71 (d, J=6.7 Hz, 3H) ppm.

To a stirred solution of cemadotin acid 1 (15 mg, 0.02 mmol) and DIPEA (16 μL 0.09 mmol) in DMF (2 mL) TSTU (12 mg, 0.04 mmol) was added and stirred at room temperature under nitrogen for 1 h, concentrated under reduced pressure, and purified by preparative HPLC (MeCN in $H_2O$ [0.1% TFA]; 4 mL/min; 25-35% MeCN over 20 min, 35-80% over 5 min, 2 min at 80% MeCN) collecting $t_R$=12.29 min to give the title product 2 13 mg, (76%) as a white solid; HRMS (ES) (m/z) calculated for $C_{40}H_{60}N_7O_9$ [M+H] 782.4453 found: 784.4449 $^1$H NMR (400 MHz, DMSO-$d_6$) δ 9.64 (br. s, 1H), 9.18-9.13 (m, 1H), 8.93 (br. s, 1H), 8.39 (t, J=6.3 Hz, 1H), 8.07 (d, J=8.2 Hz, 2H), 7.85 (d, J=8.1 Hz, 2H), 7.58 (d, J=8.1 Hz, 2H), 7.35 (d, J=8.0 Hz, 2H), 6.55 (br. s, 4H), 4.99 (d, J=10.9 Hz, 1H), 4.61 (d, J=5.9 Hz, 2H), 4.58-4.52 (m, 2H), 4.42-4.22 (m, 3H), 3.77-3.63 (m, 3H), 3.60-3.51 (m, 2H), 3.08 (s, 3H), 2.89 (s, 3H), 2.81-2.72 (br. d, 5H), 2.69-2.66 (m, 1H), 2.32-2.22 (m, 1H), 2.20-2.05 (m, 3H), 2.00-1.87 (m, 3H), 1.85-1.69 (m, 3H), 1.00-0.93 (m, 6H), 0.91-0.81 (m, 6H), 0.71 (d, J=6.7 Hz, 3H) ppm.

Example 2—Preparation of Cemadotin $C_5$—NHS (4)

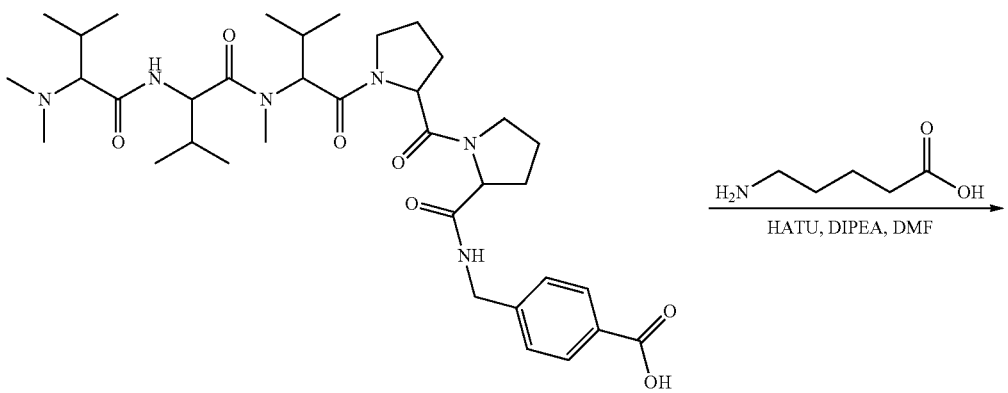

Cemadotin—$CO_2H$ (1)

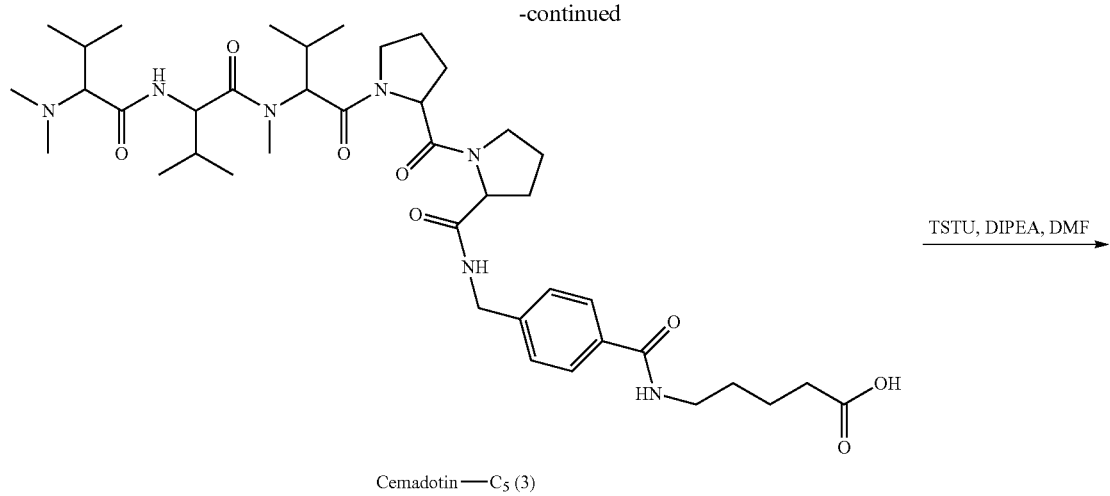

Cemadotin—C₅ (3)

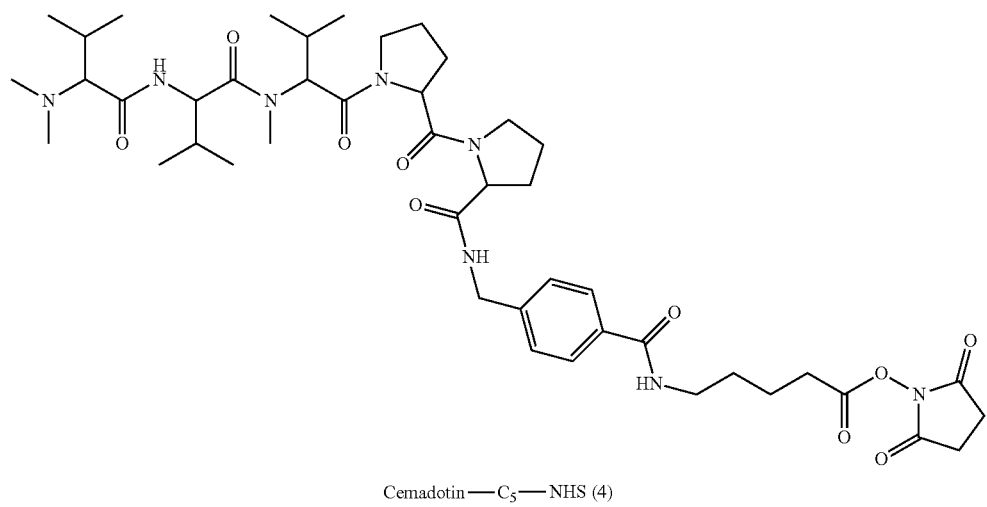

Cemadotin—C₅—NHS (4)

To a stirred solution of cemadotin acid 1 (20 mg, 0.03 mmol) in dry DMF (1.5 mL), HATU (10 mg, 0.03 mmol) was added, followed by DIPEA (10 µL, 0.06 mmol), and the resultant mixture was stirred at room temperature under nitrogen for 30 min. The reaction mixture was then added dropwise over 10 min to a slurry of 5-aminovaleric acid (3.8 mg, 0.03 mmol) in dry DMF (1.5 mL) and stirred at room temperature for 30 min, concentrated under reduced pressure, and purified by preparative HPLC (MeCN in H₂O [0.1% TFA]; 4 mL/min; 4 min 20% MeCN, 20-23% over 2 min, 23-25% over 14 min, 25-30% over 2 min, 30-80% over 3 min, 5 min 80% MeCN) collecting $t_R$=12.18 min to give the title product 3 20 mg, (88%) as a white solid; HRMS (m/z) calculated for $C_{41}H_{66}N_7O_8$ [M+H] 784.4973 found: 784.4921; NMR (400 MHz, DMSO-d6) b 9.64 (br. s, 1H), 8.93 (br. s, 1H), 8.45 (t, J=5.8 Hz, 1H), 8.36 (t, J=6.1 Hz, 1H), 7.77 (d, J=7.8 Hz, 2H), 7.30 (d, J=8.0 Hz, 2H), 6.56 (br. s, 2H), 4.99 (d, J=10.9 Hz, 1H), 4.60-4.51 (m, 2H), 4.42-4.30 (m, 2H), 4.28-4.20 (m, 1H), 3.77-3.62 (m, 3H), 3.60-3.52 (m, 2H), 3.28 (q, J=6.4 Hz, 3H), 3.09 (s, 3H), 2.81 (s, 3H), 2.80-2.70 (m, 3H), 2.35-2.22 (m, 2H), 2.18-1.88 (m, 7H), 1.85-1.58 (m, 7H), 1.29-1.22 (m, 2H), 0.99-0.93 (m, 5H), 0.90-0.81 (m, 8H), 0.71 (d, J=6.9 Hz, 2H) ppm.

To a stirred solution of cemadotin C5 3 (20 mg, 0.03 mmol) and DIPEA (10 µL 0.06 mmol) in dry DMF (2 mL), TSTU (14 mg, 0.05 mmol) was added, and the resultant mixture was stirred at room temperature under nitrogen for 1 h, concentrated under reduced pressure, and purified by preparative HPLC (MeCN in H₂O [0.1% TFA]; 3 mL/min; 25-35% MeCN over 20 min, 35-80% over 5 min, 8 min at 80% MeCN) collecting $t_R$=12.13 min to give the title product 4 15 mg, (65%) as a white solid; MS (m/z) 881.5 [M+H]; ¹H NMR (400 MHz, DMSO-d6) δ 9.64 (br. s, 1H), 8.93 (br. s, 1H), 8.45 (t, J=5.8 Hz, 1H), 8.36 (t, J=6.1 Hz, 1H), 7.77 (d, J=7.8 Hz, 2H), 7.30 (d, J=8.0 Hz, 2H), 6.56 (br. s, 2H), 4.99 (d, J=10.9 Hz, 1H), 4.60-4.51 (m, 2H), 4.42-4.30 (m, 2H), 4.28-4.20 (m, 1H), 3.77-3.62 (m, 3H), 3.60-3.52 (m, 2H), 3.28 (q, J=6.4 Hz, 3H), 3.09 (s, 3H), 2.81 (s, 3H), 2.80-2.70 (m, 7H), 2.35-2.22 (m, 2H), 2.18-1.88 (m, 7H), 1.85-1.58 (m, 7H), 1.29-1.22 (m, 2H), 0.99-0.93 (m, 5H), 0.90-0.81 (m, 8H), 0.71 (d, J=6.9 Hz, 2H) ppm.

Example 3—Preparation of P5-O₅—NHS (6)

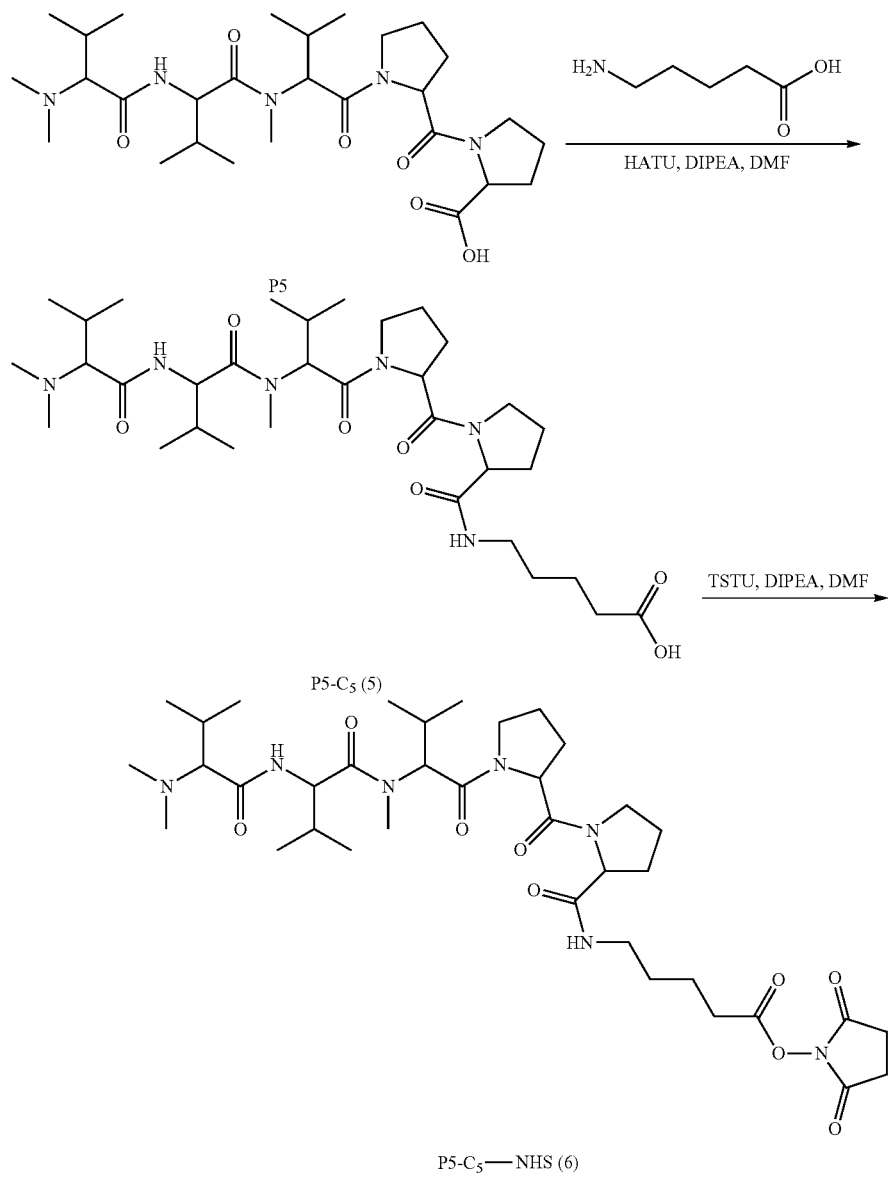

To a stirred solution of P5 (100 mg, 0.18 mmol) in dry DMF (5 mL), HATU (62 mg, 0.16 mmol) was added, followed by DIPEA (63 μL, 0.36 mmol), and the resultant mixture was stirred at room temperature under nitrogen for 30 min. The reaction mixture was then added dropwise over 10 min to a slurry of 5-aminovaleric acid (23 mg, 0.20 mmol) in dry DMF (5 mL) and stirred at room temperature for 30 min, concentrated under reduced pressure, and purified by preparative HPLC (MeCN in H₂O [0.1% TFA]; 4 mL/min; 4 min 10% MeCN, 10-20% over 4 min, 20-30% over 8 min, 2 min 30% MeCN) collecting $t_R$=13.58 min to give the title product 5 93 mg, (79%) as a white solid; MS (m/z) 651.4 [M+H]; ¹H NMR (400 MHz, DMSO-d₆) δ 9.59 (br. s, 1H), 8.92 (d, J=7.7 Hz, 1H), 7.78 (t, J=5.8 HZ, 0.6H), 7.73 (t, J=5.8 Hz, 0.4H), 4.97 (d, J=11.0 Hz, 1H), 4.57 (t, J=8.2 Hz, 1H), 4.51 (dd, J=8.4, 5.2 Hz, 1H), 4.23 (dd, J=8.4, 3.7 Hz, 1H), 3.75-3.68 (m, 3H), 3.66-3.59 (m, 1H), 3.57-3.50 (m, 2H), 3.25-3.11 (m, 1H), 3.08 (s, 3H), 3.01-2.89 (m, 1H), 2.77 (dd, J=14.2, 4.2 Hz, 6H), 2.67 (t, J=7.3 Hz, 1H), 2.60 (s, 1H), 2.32-2.24 (m, 1H), 2.22-2.09 (m, 3H), 2.06-1.99 (m, 2H), 1.96-1.86 (m, 3H), 1.84-1.68 (m, 3H), 1.64-1.56 (m, 2H), 1.50-1.43 (m, 2H), 0.96 (dd, J=9.4, 6.6 Hz, 6H), 0.88-0.82 (m, 9H), 0.71 (d, J=6.6 Hz, 3H) ppm.

To a stirred solution of P5C5 5 (93 mg, 0.14 mmol) and DIPEA (58 μL 0.33 mmol) in dry DMF (10 mL), TSTU (76 mg, 0.25 mmol) was added, and the resultant mixture was stirred at room temperature under nitrogen for 1 h, concentrated under reduced pressure, and purified by preparative HPLC (MeCN in H₂O [0.1% TFA]; 4 mL/min; 4 min 15% MeCN, 15-30% over 8 min, 5 min at 30%, 30-40% over 2 min, 3 min at 40% MeCN) collecting $t_R$=13.29 min to give the title product 6 78 mg, (73%) as a white solid; MS (m/z) 748.4 [M+H]; ¹H NMR (400 MHz, DMSO-d₆) δ 9.59 (br. s, 1H), 8.92 (d, J=7.7 Hz, 1H), 7.78 (t, J=5.8 HZ, 0.6H), 7.73 (t, J=5.8 Hz, 0.4H), 4.97 (d, J=11.0 Hz, 1H), 4.57 (t, J=8.2 Hz, 1H), 4.51 (dd, J=8.4, 5.2 Hz, 1H), 4.23 (dd, J=8.4, 3.7

Hz, 1H), 3.75-3.68 (m, 3H), 3.66-3.59 (m, 1H), 3.57-3.50 (m, 2H), 3.25-3.11 (m, 1H), 3.08 (s, 3H), 3.01-2.89 (m, 1H), 2.82 (s, 3H), 2.77 (dd, J=14.2, 4.2 Hz, 6H), 2.67 (t, J=7.3 Hz, 1H), 2.60 (s, 1H), 2.32-2.24 (m, 1H), 2.22-2.09 (m, 3H), 2.06-1.99 (m, 2H), 1.96-1.86 (m, 3H), 1.84-1.68 (m, 3H), 1.64-1.56 (m, 2H), 1.50-1.43 (m, 2H), 0.96 (dd, J=9.4, 6.6 Hz, 6H), 0.88-0.82 (m, 9H), 0.71 (d, J=6.6 Hz, 3H) ppm.

Example 4—Preparation of Doxorubicin-dPEG$_{(7)}$-NHS: (7)

clear dark-red solution. This was taken up in a 5 ml syringe and added dropwise over 20 min. to a stirred solution of the bis-dPEG$_7$-NHS (24.1 mg, 0.039 mmol) and DIPEA (22.5 μl, 0.13 mmol) in dry DMF (2 ml). The resulting solution was then stirred at room temperature under nitrogen for 3 h and evaporated under high vacuum to give a dark red-orange oil. This was purified by flash chromatography [silica gel: 10% MeOH/DCM] and the appropriate fractions (R$_f$ 0.38) collected, combined and evaporated to give the title product

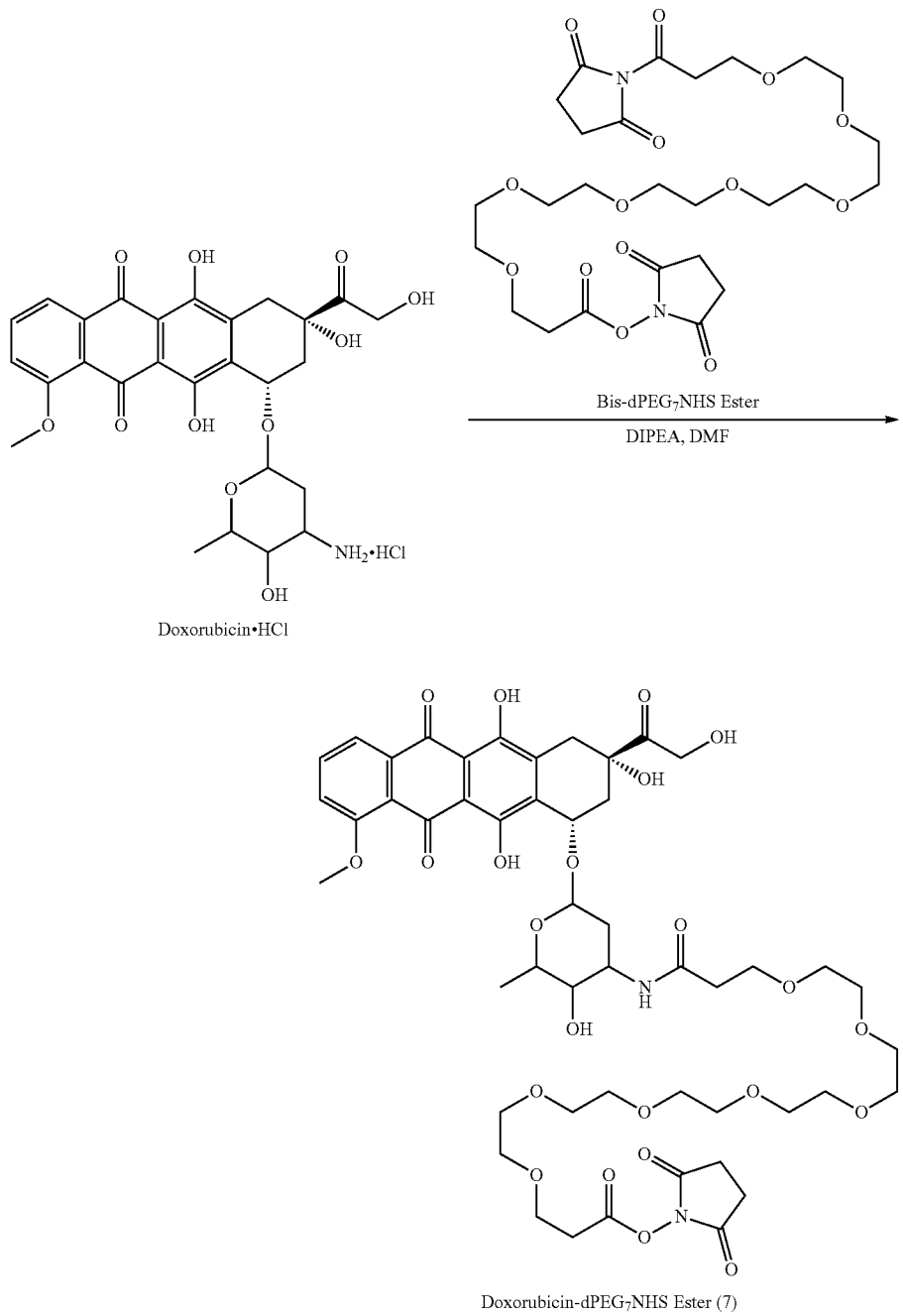

To a stirred suspension of doxorubicin.HCl (15 mg, 0.026 mmol) in dry DMF (2 ml) DIPEA (22.5 μl, 0.013 mmol) was added and stirred under nitrogen for 30 min. resulting in a 7 10.4 mg (39%) as a red-orange viscous oil; MS (m/z) calculated for $C_{49}H_{64}N_2O_{23}Na$ 1071.3798 (M+Na) found 1071.3805

Example 5—Preparation of
Doxorubicin-dPEG$_8$-NHS Ester (10)
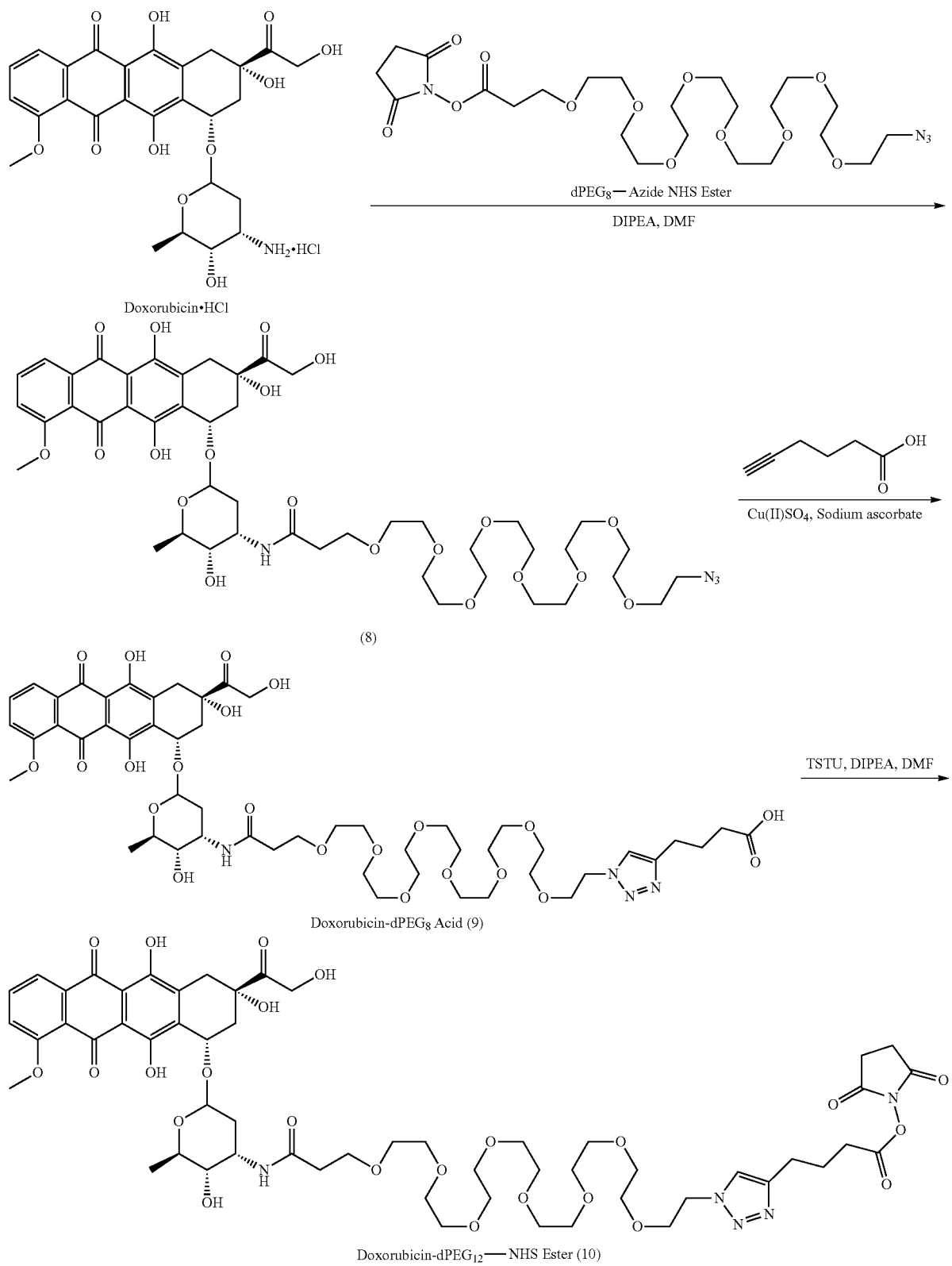
Doxorubicin hydrochloride (94 mg, 0.161 mmol) was dissolved in anhydrous DMF (10 mL) and DIPEA (89 µl, 0.483 mmol) was added. The mixture was stirred for 10 min, after which NHS-PEG$_8$-N$_3$ (100 mg, 0.177 mmol) was added followed by stirring for 18 h at room temperature under nitrogen in the dark. The reaction mixture was evaporated under vacuum and purified by flash chromatography [silca gel: 5% MeOH/DCM] To give the desired Dox-dPEG$_8$-azide 8 as a red oil 121 mg, (76%). (R$_f$ 0.395, 5% MeOH/DCM); MS (m/z): 1010.44 [M$^+$+NH$_4$], 1015.39 [M$^+$+Na], 1031.37 [M+$_+$K], $^1$H NMR (CDCl$_3$): δ 14.00 (1H, s, 6-OH), 13.31 (1H, s, 11-OH), 8.08 (1H, d, J=8 Hz, 3-H), 7.84 (1H, t, J=8 Hz, 2-H), 7.43 (1H, d, J=8 Hz, 1-H), 5.53 (1H, d, J=4 Hz, c-OH), 5.33 (1H, s, 1'-OH), 4.79 (2H, s, 14-H), 4.19-4.11 (5H, m, CH3-O—, 5'-H, 7-H), 3.71-3.64 (33H, m, 3'-H, —CH$_2$—O—(CH$_2$—CH$_2$—O)$_7$—CH$_2$—), 3.42 (2H, t, J=8 Hz, —CH$_2$—N$_3$), 3.34-3.05 (2H, q, J=20 Hz, 10-H), 2.46-2.16 (3H, m, 4'-H, b-H, d-H), 1.94-1.77 (4H, m, 2'-H, 8'-H), 1.31 (3H, d, J=8 Hz, 6'-H).

To a solution of Dox-dPEG$_8$-azide 8 (120 mg, 0.121 mmol) in 2.5 mL of tert-butanol/water (1:1 v:v) a solution of 5-hexynoic acid (14 mg, 0.121 mmol) in 2.5 mL of tert-butanol/water (1:1) was added. The reaction was stirred at room temperature for 30 min, followed by addition of copper (II) sulfate (2 mg, 0.012 mmol) and (+)-sodium L-ascorbate (5 mg, 0.024 mmol). The reaction was warmed to 40° C. and stirred for 24 h. The reaction mixture was then diluted with DCM (15 mL) and a solution of citric acid added until pH 4 was reached. The organic layer was then washed with brine (2×10 mL) and the aqueous layers combined and back-extracted with DCM (4×10 mL). The organic fractions were combined, dried over sodium sulfate, filtered, and concentrated to give a dark red residue. This was purified flash chromatography [silica gel: DCM increasing upto 20% MeOH/DCM) to give the product 9 as a red solid 53.4 mg, (40%). (R$_f$ 0.20, 10% MeOH/DCM); MS (m/z): 1106.05 [M++H], 1128.00 [M$^+$+Na $^1$H NMR (CDCl$_3$): δ 14.01 (1H, s, 6-OH), 13.33 (1H, s, 11-OH), 8.08 (1H, d, J=8 Hz, 3-H), 7.82 (1H, t, J=8 Hz, 2-H), 7.64 (1H, s, —N—CH=CN—), 7.44 (1H, d, J=8 Hz, 1-H), 5.55 (1H, d, J=4 Hz, c-OH), 5.33 (1H, s, 1'-OH), 4.81 (2H, s, 14-H), 4.55 (2H, t, J=4 Hz, —CH=CN—CH$_2$—), 4.16-4.11 (5H, m, CH$_3$—O—, 5'-H, 7-H), 3.86 (2H, t, J=8 Hz, —O—CH$_2$—CH$_2$—CN—), 3.70-3.62 (33H, m, 3'-H, —(CH$_2$—CH$_2$—O)$_5$—CH$_2$—), 3.35-3.06 (2H, q, J=20 Hz, 10-H), 2.83 (2H, t, J=4 Hz, —CH$_2$—COOH), 2.47-2.16 (2H, m, b-H, d-H), 2.07-2.02 (3H, m, 2'-H, 4'-H), 1.83-1.79 (2H, m, 8-H), 1.36-1.28 (5H, m, 6'-H, —CH$_2$—CH$_2$—CH$_2$—COOH).]. A solution of the Dox-dPEG$_8$ acid is stirred in dry DMF with TSTU and DIPEA for 1 h. The solvent is taken off using high vacuum and the residue purified by reverse phase HPLC to give the NHS ester derivative 10.

Example 6—Preparation of Doxorubicin-dPEG$_{12}$-SPDP (11)

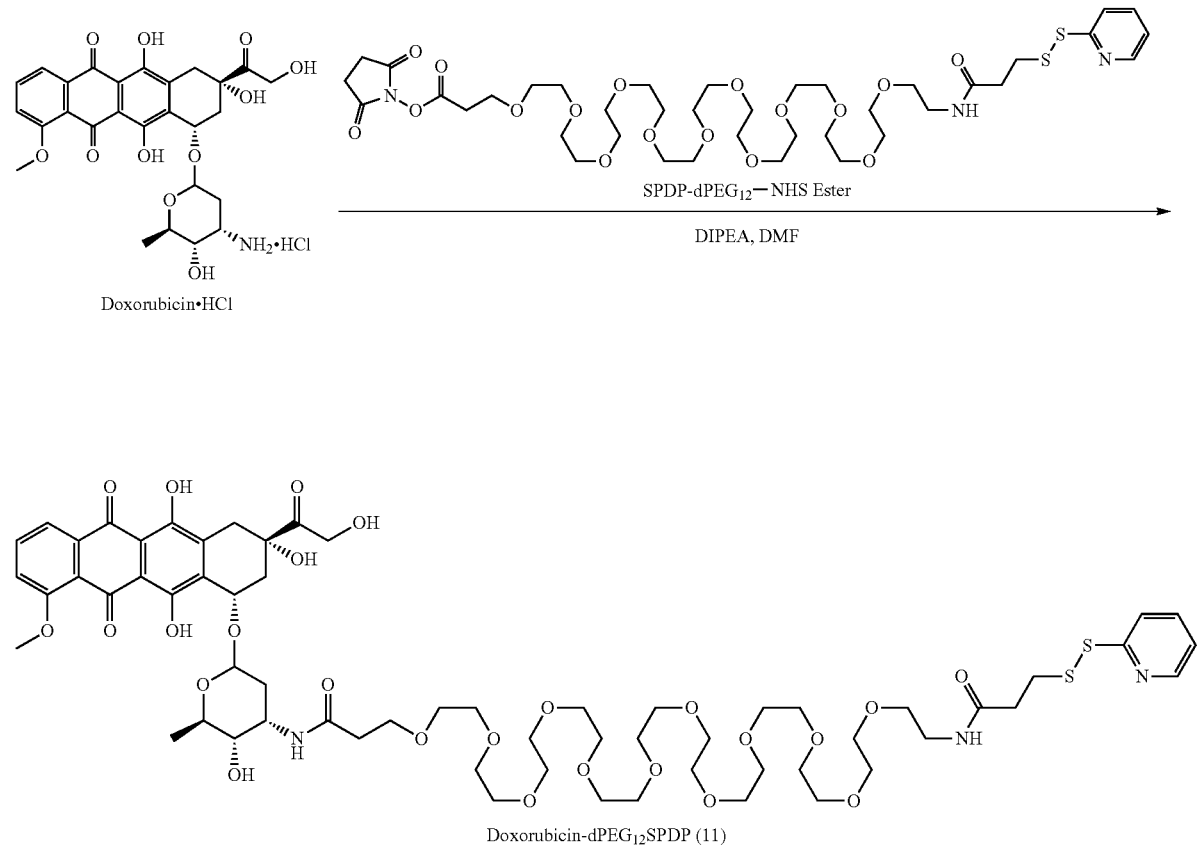

Doxorubicin-dPEG$_{12}$SPDP (11)

To a stirred suspension of Dox.HCl (10 mg, 0.0172 mmol) in dry DMF (2 ml) DIPEA (7.7 μl) was added and the reaction mixture stirred for 10 min. under nitrogen to give a clear red solution. To this, SPDP-dPEG$_{12}$-NHS ester (17.3 mg, 0.044 mmol) dissolved in dry DMF (1 ml) was added and the reaction stirred at room temperature, under nitrogen and protected from light overnight. The DMF was removed by high vacuum and the dark red oil purified by flash chromatography [silica gel: 10% MeOH/DCM R$_f$ 0.36] to give the desired product 11 16.2 mg (70%) as a red viscous oil; HRMS (m/z) calculated for C$_{62}$H$_{85}$N$_8$O$_{21}$S$_2$ [M+H] 1341.5271 found: 1341.5380

Example 7—Preparation of Doxorubicin-SMCC (12)

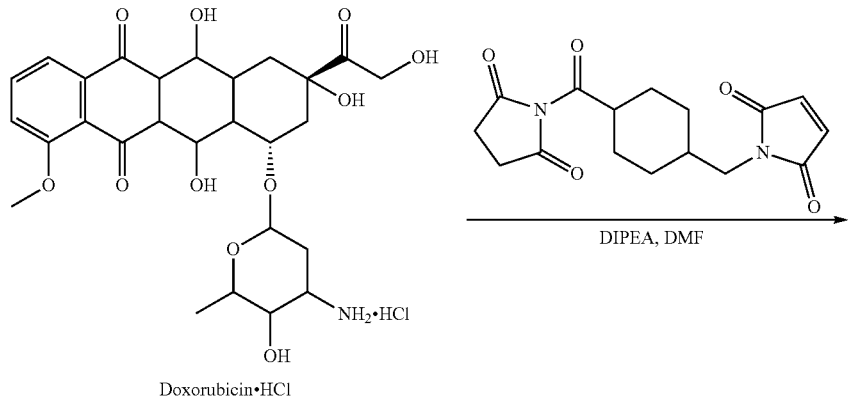

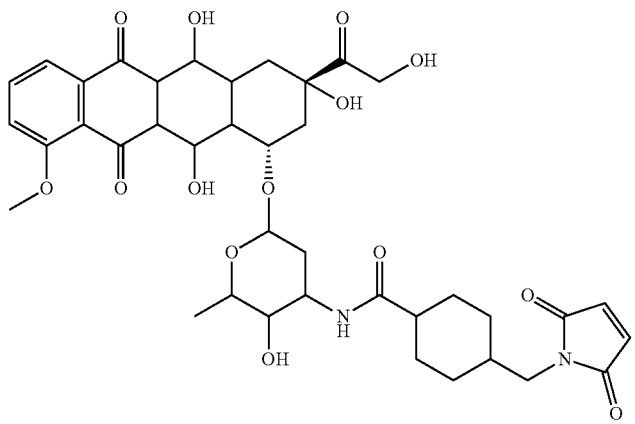

To a suspension of Dox.HCl (0.05 g, 0.086 mmol) in dry DMF (10 ml) SMCC cross-linker (0.0346 g, 0.104 mmol) and DIPEA (22.5 µl, 0.129 mmol) were added and the reaction stirred at room temperature for 12 h under nitrogen shielded from light. The suspension goes into solution within 1 h. The solvent was taken off under high vacuum at 35° C. to give a dark-red residue. This was taken up in DCM (50 ml), washed with brine, dried over $MgSO_4$, filtered and evaporated to give a dark-red solid. This was purified by flash column chromatography [silica gel: 1-5% MeOH/DCM, $R_f$ 0.25] to give 12 as a orange-red solid 0.053 g (78%). MS (m/z) found 785.25 (M+Na) calculated for $C_{39}H_{42}N_2O_{14}Na$

Example 8—Preparation of Doxorubicin-PAB-Cit-Val-dPEG$_7$-NHS Ester (16)

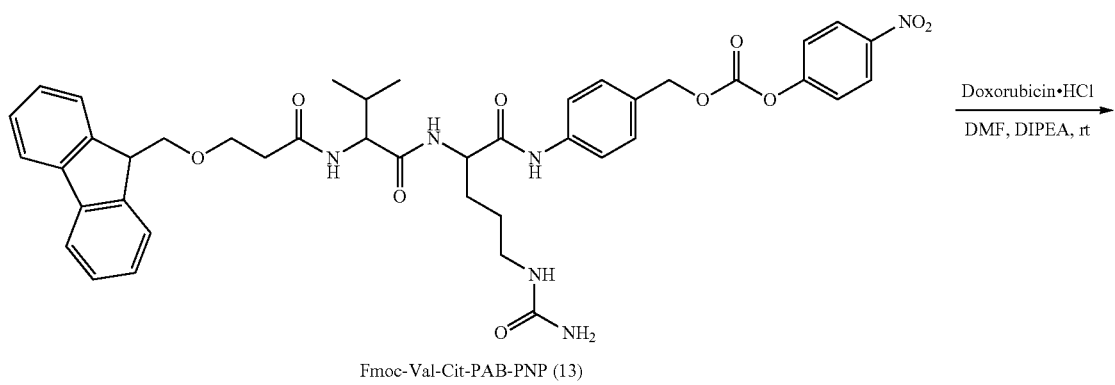

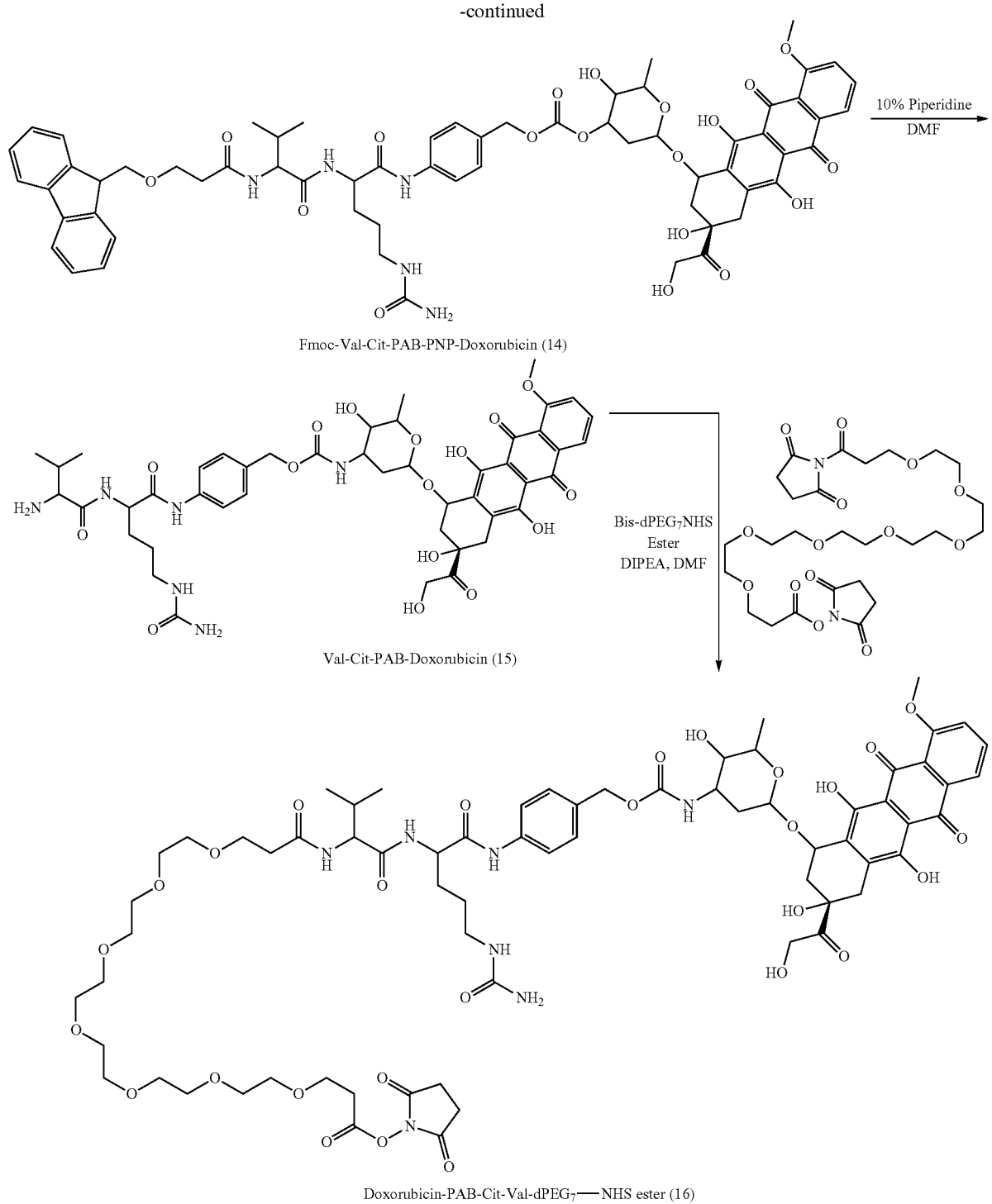

To a suspension of Dox.HCl (25 mg, 0.043 mmol) and Fmoc-Val-Cit-PNP 13 (30 mg, 0.039 mmol) in dry DMF (1 ml) DIPEA (7.5 µl, 0.043 mmol) was added, resulting in a dark-red solution. This was stirred at room temperature under nitrogen for 24 h after which the solvent was evaporated under high vacuum and the residue triturated with dry diethyl ether to give a red solid $R_f$ 0.22 [silica gel: 10% MeOH/DCM]. Purification by flash chromatography [silica gel: 5% MeOH/DCM] gave the desired product 14 as a red solid 25.2 mg (55%); HRMS (m/z) calculated for $C_{61}H_{67}N_6O_{18}$ [M+H] 1171.4512 found: 1171.4534

To a stirred solution of 14 (20 mg, 0.017 mmol) in dry DCM (5 ml) piperidine (10 mol %) was added. The bright red predominantly in solution mixture immediately became a dark brown clear solution and was stirred for 10 min. after which all the solvent was taken off to give the desired compound 15 a red sticky solid. HRMS (m/z) calculated for $C_{46}H_{57}N_6O_{16}$ [M+H] 949.3831 found: 949.3874. This was used without further purification in the the preparation of 16.

A solution of compound 15 in dry DMF is added dropwise over 20 min. to a stirred solution of bis-dPEG$_7$-NHS and DIPEA (22.5 µl, 0.13 mmol) in dry DMF. The resulting solution is then stirred at room temperature under nitrogen for 3 h and evaporated under high vacuum to give a dark red-orange oil. This is purified by flash chromatography [silica gel: 10% MeOH/DCM] and the appropriate fractions collected, combined and evaporated to give the title product 16 as a red-orange viscous oil.

Example 9—Preparation of Camptothecin-dPEG$_3$-NHS Ester (19)

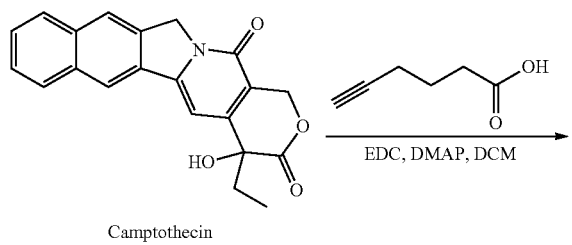

Camptothecin

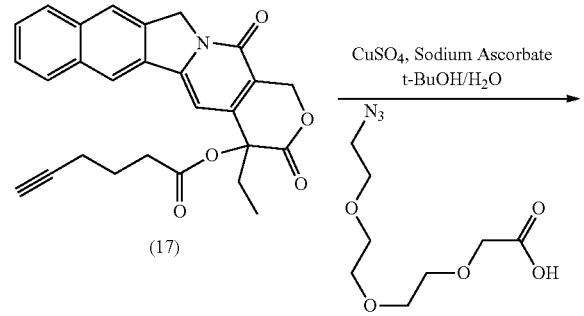

(17)

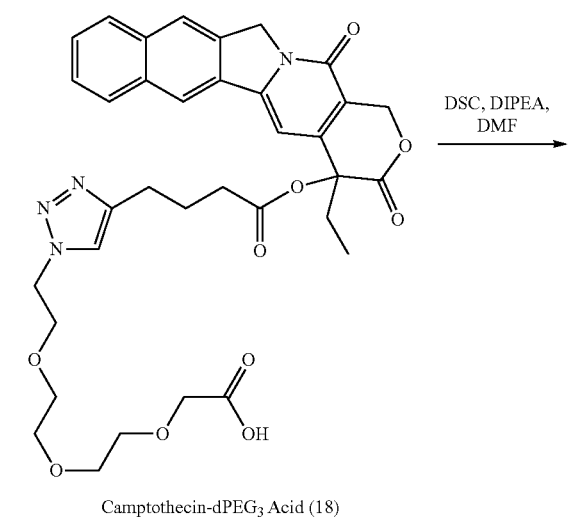

Camptothecin-dPEG$_3$ Acid (18)

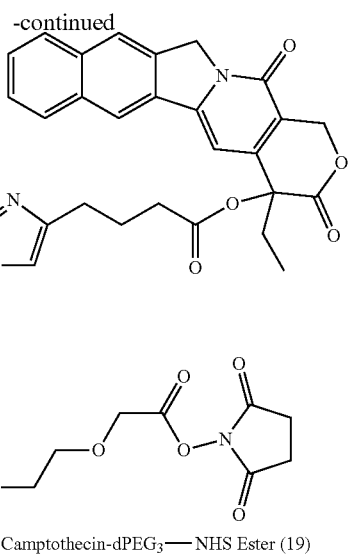

Camptothecin-dPEG$_3$—NHS Ester (19)

To a stirred solution of camptothecin (400.0 mg, 1.1 mmol) in dry DCM (100 ml) were subsequently added 5-hexynoic acid (319.8 mg, 2.9 mmol), EDC (437.1 mg, 2.28 mmol) and DMAP (139.4 mg, 1.14 mmol). The yellow suspension was left stirring at RT under N$_2$ and in the dark for 16 hours. The resulting light brown solution was washed with H$_2$O (120 ml) and extracted with DCM (100 mL).

Organic phases were combined, washed with brine (100 mL), dried over MgSO$_4$ and concentrated in vacuo. The crude was purified by flash chromatography [silica gel: with a 1-3% MeOH/DCM gradient] to give the camptothecin alkyne 17 as an off-white/yellow powder 471.1 mg, (91.6%); HRMS (m/z): calculated for $C_{26}H_{22}N_2O_5$ 443.1623 [M+H], found 443.1607. $^1$H NMR (400 MHz, CDCl3): δ=8.43 (s, 1H), 8.25 (d, J=8.5 Hz, 1H), 7.97 (d, J=8.3 Hz, 1H), 7.86 (ddd, J=8.5, 6.8, 1.5 Hz, 1H), 7.70 (t, J=7.8 Hz, 1H), 7.28 (s, 1H), 5.71 (d, J=17.3 Hz, 1H), 5.43 (d, J=17.2 Hz, 1H), 5.32 (s, 2H), 2.78-2.59 (m, 2H), 2.35-2.28 (m, 3H), 2.18 (dq, J=13.6, 7.5 Hz, 1H), 2.05 (t, J=2.6 Hz, 1H), 1.90 (p, 7.2 Hz, 2H), 1.01 (t, J=7.5 Hz, 3H); $^{13}$C NMR (100 MHz, CDCl3): δ=172.1, 167.5, 157.4, 152.4, 148.9, 146.2, 146.0, 131.2, 130.70, 129.6, 128.5, 128.2, 128.1, 120.3, 96.0, 83.0, 75.9, 69.5, 67.1, 49.9, 32.4, 31.9, 23.2, 17.7, 7.6; IR Amax: 3302.5, 2984.3, 2943.6, 1753.6, 1737.5, 1669.3, 1624.3, 1564.1, 1446.8, 1405.6, 1365.6, 1351.3, 1296.6, 1234.1, 1205.3, 1166.5, 1131.8, 1088.4, 1045.3, 1011.2, 976.5, 946.6, 909.3, 825.4, 786.2, 762.2, 722.4, 652.0;

To a stirred solution of the camptothecin alkyne 17 (60 mg, 0.136 mmol) in 15 ml 1:2 H$_2$O: tert-butanol were subsequently added 63.2 mg azido-PEG$_3$-acid (0.271 mmol, 2 eq), 2.7 mg Na ascorbate (0.0136 mmol, 0.1 eq) and 2.2 mg CuSO$_4$ (0.0136 mmol, 0.1 eq). The white suspension was stirred at 80° C. under N$_2$ and in the dark for 5 h. After the clear solution was cooled down to RT, 15 ml DCM and 15 ml distilled H$_2$O were added and the organic layer was separated. The obtained organics were washed with 25 ml 0.5M HCl and 25 ml 1:1 1M HCl:brine (organic layer becomes a fluorescent yellow), dried over Na$_2$SO$_4$ and concentrated in vacuo. The crude was purified by flash chromatography [silica gel: 10-15% MeOH/DCM gradient, followed by 0.1% formic acid 10% MeOH/DCM. The appropriate fractions were combined, concentrated in vacuo and washed with hot ether under reflux for 1 hour. A yellow, sticky solid was obtained as the desired product 18 71 mg (78.4%); HRMS (m/z): 676.2644 [M+H], calculated mass 676.2669. $^1$H NMR (400 MHz, CDCl$_3$): δ=8.44 (s, 1H, 5-CH-aromatic), 8.28 (d, J=8.6 Hz, 1H, 4-CH-aromatic), 7.97 (d, J=8.2 Hz, 1H, 1-CH-aromatic), 7.87 (t, J=7.7 Hz, 1H, 3-CH-aromatic), 7.70 (t, J=7.6 Hz, 1H, 2-CH-aromatic), 7.30 (s, 1H, 7-CH-aromatic), 5.71 (d, J=17.2 Hz, 1H, 8-CH2-O), 5.44 (d, J=17.2 Hz, 1H, 8-CH2-O), 5.33 (s, 2H, 6-CH2-N), 4.52 (td, J=4.8, 1.9 Hz, 2H), 4.18 (s, 2H), 3.86 (t, J=5.2 Hz, 2H), 3.75 (dd, J=5.8, 3.1 Hz, 2H), 3.68-3.57 (m, 6H), 2.82 (t, J=7.4 Hz, 3H), 2.68-2.49 (m, 3H), 2.31 (dq, J=14.8, 7.4 Hz, 1H), 2.18 (dq, J=14.7, 7.4 Hz, 1H), 2.06 (p, J=7.4 Hz, 2H), 1.01 (t, J=7.5 Hz, 3H, 10-CH3); $^{13}$C NMR (100 MHz, CDCl$_3$): δ=172.39, 167.73, 157.40, 152.23, 146.08, 131.52, 130.86, 129.36, 128.56, 128.23, 122.57, 120.29, 96.37, 75.82, 70.39, 69.50, 67.13, 50.12, 49.99, 32.84, 31.81, 24.43, 24.24, 7.59; IR cm$^{-1}$: 3422.20, 2913.21, 1745.90, 1664.85, 1616.45, 1562.85, 1501.82, 1457.03, 1404.63, 1352.03, 1299.22, 1231.80, 1132.95, 1088.07, 1048.25, 994.41, 947.36, 815.25, 787.33, 763.06, 724.93.

To a stirred solution of the camptothecin acid 18 acid (10 mg) were added 160.3 mg disuccinimidyl carbonate (DSC) (0.64 mmols) and 24 mg triethylamine (0.24 mmols) in dry DMF (3 ml). The yellow solution was left stirring at RT, under N$_2$ and in the dark. Further addition of 160.4 mg DSC (43 eq) and 24.1 mg triethylamine was carried out after 16 hours. After 6 more hours, the reaction was stopped and concentrated in vacuo to give an orange oil. This was redissolved in 15 ml DCM, washed with 15 ml 0.5M HCl and 15 ml brine and dried over Na$_2$SO$_4$. This work-up procedure was repeated twice, and one last wash was performed with 2×5 ml H$_2$O and 5 ml brine. The dried organics were filtered and concentrated in vacuo and lyophilized to give the desired compound 19 as a white hygroscopic powder 9 mg. MS (m/z): 773.2832 (M+1), 796.2639 (M+Na)

Example 10—Preparation of Ellipticine-C$_6$—NHS Ester (21)

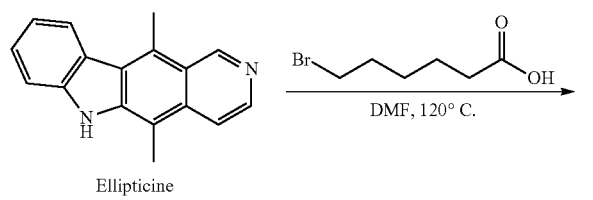

Ellipticine

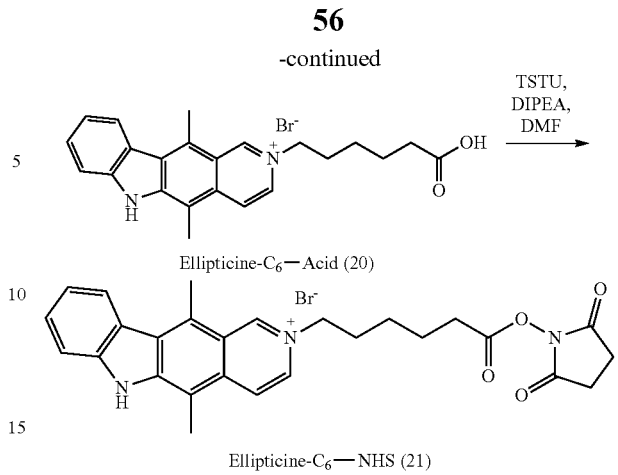

Ellipticine-C$_6$—Acid (20)

Ellipticine-C$_6$—NHS (21)

To a solution of ellipticine (35 mg, 0.14 mmol) in dry DMF (5 ml), 6-bromohexanoic (55.4 mg, 0.284 mmol) acid was added and the reaction mixture stirred at 120° C. for 4 hr and then at room temperature for a further 12 hr to give a mustards-yellow precipitate. This was filtered and washed with cold anhydrous ether. Some precipitation was also observed in the filtrate which was also collected. The total combined yield obtained of compound 20 was 49.1 mg (78%). Analysis by TLC [silica gel:MeCN:Water:KNO3 (satd.)] showed the product to be a single yellow spot (R$_f$ 0.55, Ellipticine R$_f$ 0.67). HRMS (m/z) calculated for C$_{23}$H$_{25}$N$_2$O$_2$ 361.1916 (M+1) found 361.1924

To a partial suspension of the acid 20 (10 mg, 0.023 mmol) in dry DMF (1.5 ml), TSTU (12 mg, 0.04 mmol) followed by DIPEA (16.2 μl, 0.093 mmol) were added and the reaction mixture stirred for 1 h at room temperature under nitrogen. Over the course of the reaction the suspension slowly gave way to a clear mustard-yellow coloured solution. The reaction was followed by TLC [silica gel:MeCN:Water:KNO3 (satd.)] and once complete, the DMF was taken off using high vacuum keeping the temperature below 30° C. The residue was triturated with anhydrous ether and air dried to give the ester 21 as a mustard-yellow coloured solid; HRMS (m/z) calculated for C$_{27}$H$_{28}$BrN$_3$O$_4$

Example 11—Preparation of Ellipticine-PEG$_4$-NHS Ester (23)

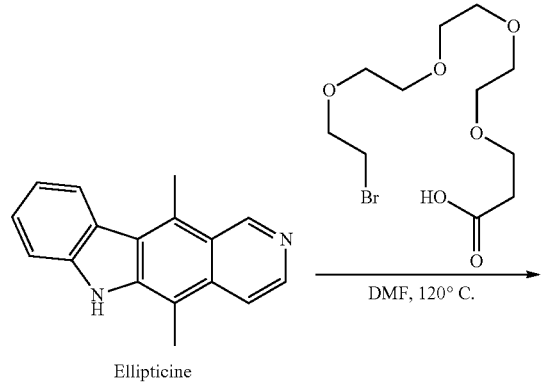

Ellipticine

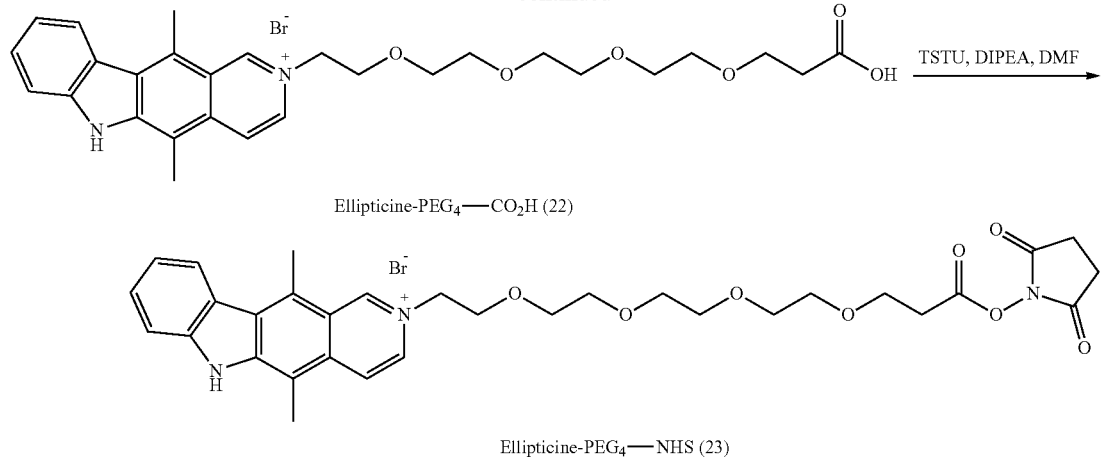

Ellipticine-PEG₄—CO₂H (22)

Ellipticine-PEG₄—NHS (23)

To a stirred solution of ellipticine (0.035 g, 0.142 mmol) in dry DMF (4 ml) under nitrogen, Br-PEG₄-acid (0.0936 g, 0.0284 mmol) dissolved in dry DMF (1 ml) was added. The reaction was stirred at 120° C. for 4 h, allowed to cool and stirred at room temperature for a further 12 h. The DMF was taken off using high vacuum and the residue purified by preparative HPLC [Chromolith HighResolution RP-18e 100×4.6 mm] 100% 10 mM Na₃PO₄/pH7 to 100% MeCN over 27 mins step gradient at 20° C., detecting at 280 and 435 nm collecting $t_R$ 7.9 min to give the acid 22 as a yellow hygroscopic solid 40.6 mg (50%); HRMS (m/z) calculated for $C_{25}H_{35}N_2O_6$ M-Br) 495.2495 found 495.2498

The ellipticine-PEG₄-acid 22 (0.0143 g, 0.00256 mmol) was dissolved in dry DMSO (1 ml) and stirred under nitrogen. To this, TSTU (0.0136 g, 0.00451 mmol) was added followed by DIPEA (18.5 µl, 0.105 mmol) and the bright yellow solution was stirred at room temperature under nitrogen for 1 h. The solvent was taken under high vacuum and the sticky residue triturated with dry ether and after decanting the ether, dried under high vacuum to give 23 as a yellow sticky solid 11.4 mg (66%); HRMS (m/z) calculated for $C_{32}H_{38}N_3O$ (M-Br) 592.2659 found 592.2643

Example 12—Preparation of Ellipticine-PAB-Cit-Val-dPEG₃-NHS Ester (29)

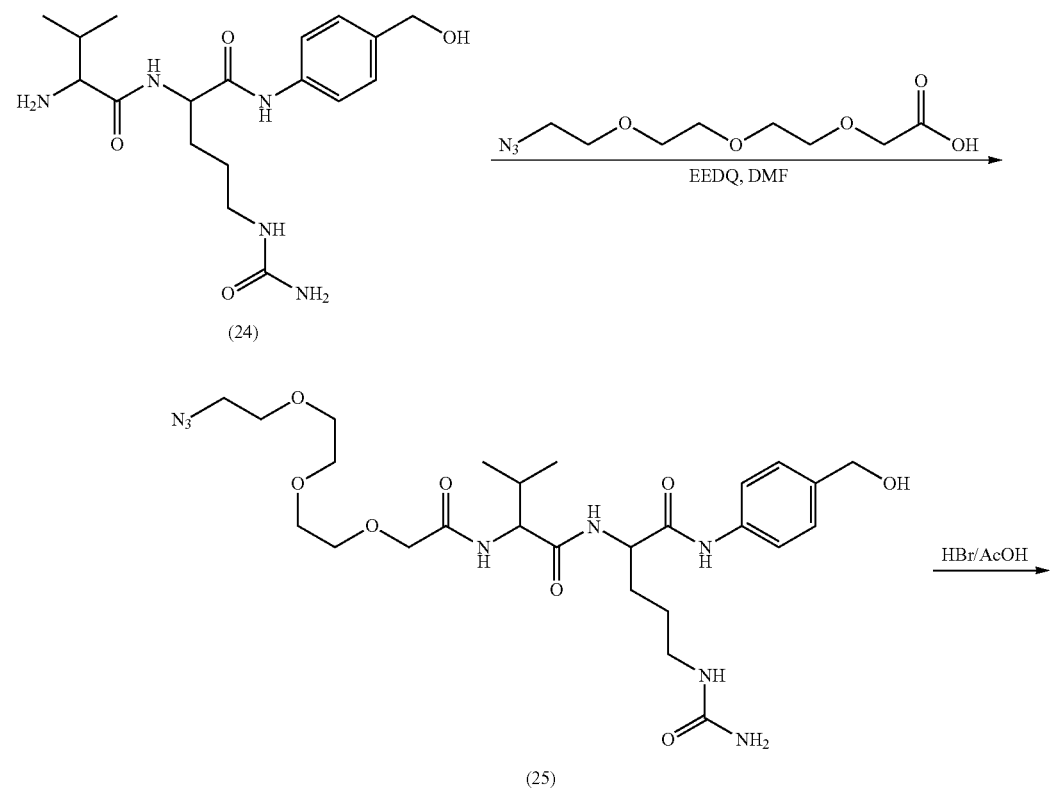

-continued

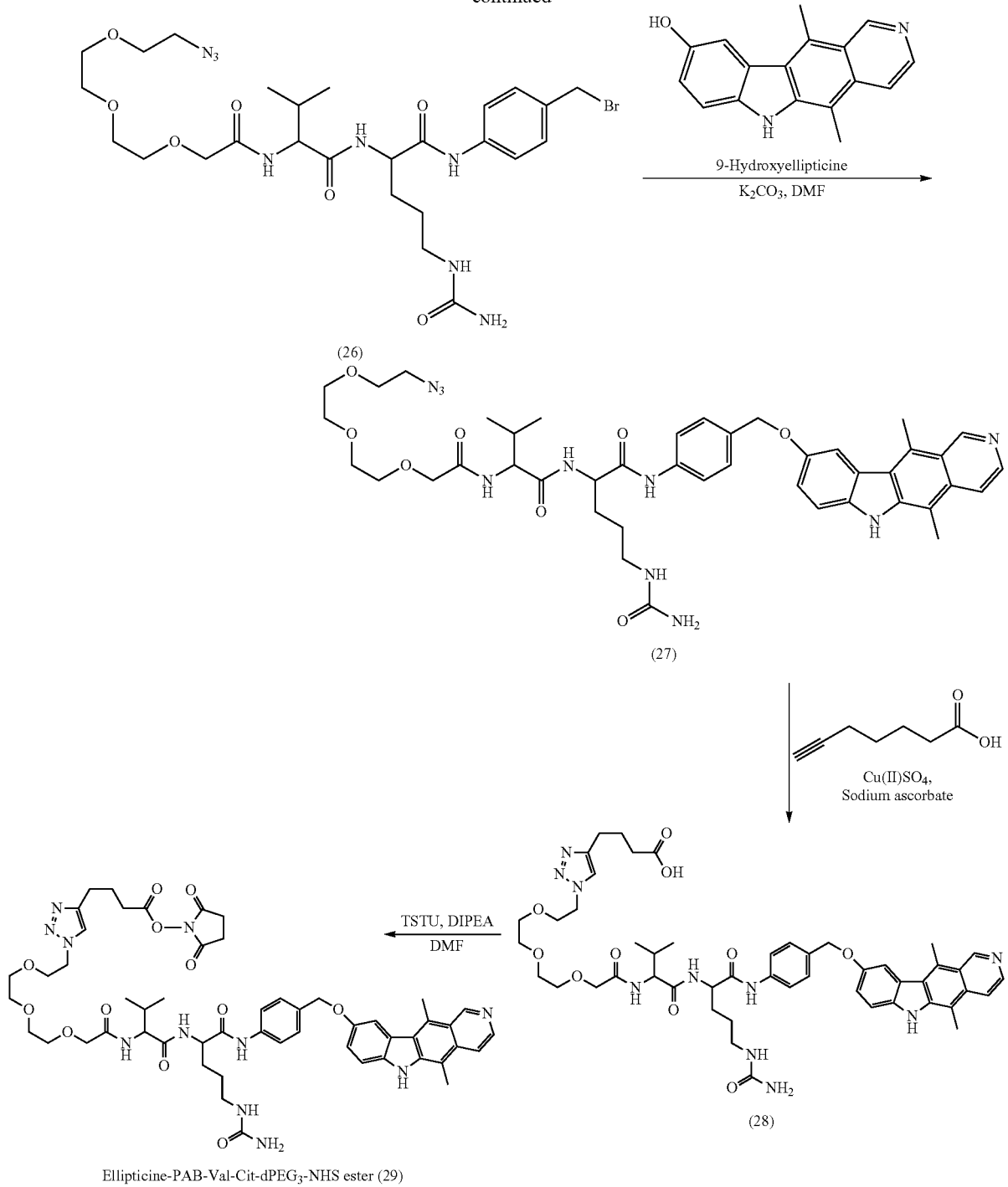

Ellipticine-PAB-Val-Cit-dPEG₃-NHS ester (29)

To a stirred solution of Cit-Val-PAB-OH (24) (0.10 g, 0.43 mmol) in dry DMF (8 mL), 11-Azido-3,6,9-trioxaundecanoic acid (0.16 g, 0.43 mmol) in dry DMF (1 mL) was added. EEDQ (2-Ethoxy-1-Ethoxycarbonyl-1,2-dihydro quinoline (100 mg, 0.5 mmol) was then added and the solution was stirred at room temperature under nitrogen overnight. The solvent was removed in vacuo and purified by flash chromatography [silica gel: 10% MeOH/DCM] to yield the product 25 (0.21 g (82%) as a white solid. mp 139° C.; HRMS (m/z) calculated for $C_{26}H_{42}N_8O_8$ 617.3023 [M+Na]. Found 617.2999, IR 3270, 2925, 2103, 1629, 1538, 1272, 1094, 799 cm$^{-1}$; $^1$H NMR (400 MHz, MeOD) δ 7.54 (m, 2H), 7.29 (d, J=8.7 Hz, 2H), 4.43-4.52 (m, 2H), 4.30 (d, J=7.2 Hz, 2H), 4.05 (s, 2H), 3.59-3.77 (m, 10H), 3.30 (m, 2H), 3.04-3.25 (m, 2H), 2.04-2.17 (m, 1H), 1.67-1.95 (m, 2H), 1.57 (m, 2H), 0.97 (m, 6H); NMR (100 MHz, DMSO-d6) δ 17.9, 19.2, 26.8, 29.3, 31.1, 39.6, 49.9, 53.2, 56.5, 62.6, 69.2, 69.6, 69.6, 69.7, 69.8, 70.3, 118.8, 126.9, 17.5, 158.9, 170.3, 170.7;

To a stirred solution of the PEG$_5$ azide linker 25 in dry CH$_2$Cl$_2$ (60 mg in 2 mL), HBr (33% in AcOH, 1M, 0.04 mL) was added in a dropwise. After 10 min, the flask was put on ice, NaHCO$_3$ was than added slowly, and the solution was stirred for 30 min. After stirring, the solution was filtered, washed with water and diethyl ether and dried in vacuo to yield the bezyl bromide derivative 26 (20 mg (33%) as a cream solid; HRMS (m/z) calculated for C$_{26}$H$_{42}$N$_8$O$_7$Br 657.2360 (M+1). Found 657.2357. $^1$H NMR (400 MHz, MeOD) δ 7.63-7.50 (m, 2H), 7.43-7.21 (m, 2H), 4.60-4.47 (m, 2H), 4.33-4.24 (m, 1H), 4.06 (s, 2H), 3.88-3.60 (m, 10H), 3.52 (s, 2H), 3.30-3.1 (m, 2H), 2.20-2.07 (m, 1H), 2.00-1.72 (m, 2H), 1.72-1.54 (m, 2H), 1.09-0.90 (m, 6H);

9-Hydroxyellipticine (10 mg, 0.04 mmol) and K$_2$CO$_3$ (0.12 g, 0.08 mmol) were dissolved in dry DMF (4 mL) and stirred for 5 min. The brominated linker 26 (30 mg, 0.04 mmol) was added as a solution in dry DMF and the mixture was stirred at room temperature for 17 hours. A black solid was obtained after concentration in vacuo, which was then dissolved in CHCl$_3$:MeOH 9:1, washed with water, dried, and concentrated to give the alkylated ellipticine derivative 27 24 mg (76%) as a dark brown solid; MS (m/z) 840 [M]+; HRMS (m/z) calculated for C$_{43}$H$_{55}$N$_{10}$O$_8$ 839.4204. Found 839.4202. IR 3272, 2937, 2107, 1646, 1526, 1462, 1415, 1254, 1103, 807 cm-1; $^1$H NMR (400 MHz, MeOD) δ 8.38-8.10 (m, 1H), 8.01 (s, 1H), 7.99-7.81 (m, 1H), 7.75 (d, J=8.0 Hz, 1H), 7.68-7.48 (m, 2H), 7.48-7.32 (m, 1H), 7.30-6.98 (m, 1H), 5.84 (s, OH), 4.54 (dd, J=1.5, 8.9 Hz, 1H), 4.31 (q, J=7.8 Hz, 1H), 4.08 (d, J=9.3 Hz, 2H), 3.92-3.46 (m, 9H), 3.35 (d, J=17.3 Hz, 12H), 3.17 (d, J=18.8 Hz, 3H), 3.02 (s, 3H), 2.89 (s, 3H), 2.70 (d, J=7.6 Hz, 2H), 1.90 (s, 1H), 1.78 (s, 1H), 1.60 (s, 2H), 1.06-0.86 (m, 6H);

The azide ellipticine derivative 28 undergoes 1,3 cycloaddition with hexynoic-acid under 'click' conditions using Cu(II)SO$_4$ and ascorbic acid to give the derivative with a carboxylic acid 28. Activating this terminal carboxylic acid of derivative 28 with TSTU and DIPEA in dry DMF will give the activated succinimidyl ester derivative 29.

Example 13—Preparation of Ellipticine-N-PAB-Cit-Val-dPEG$_3$-NHS Ester (33)

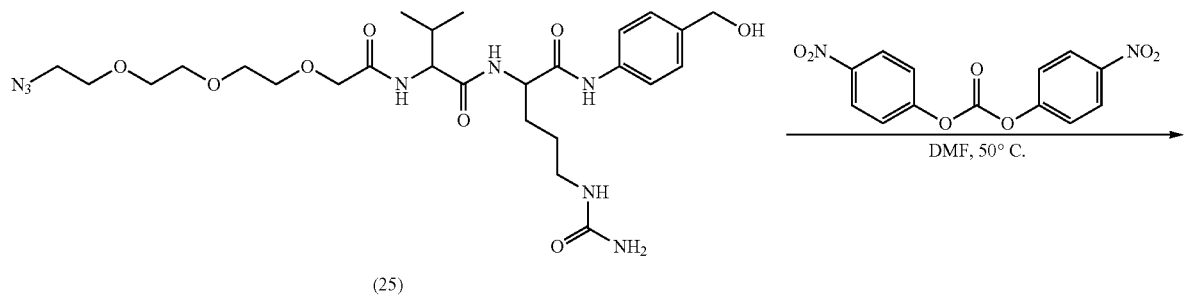

(25)

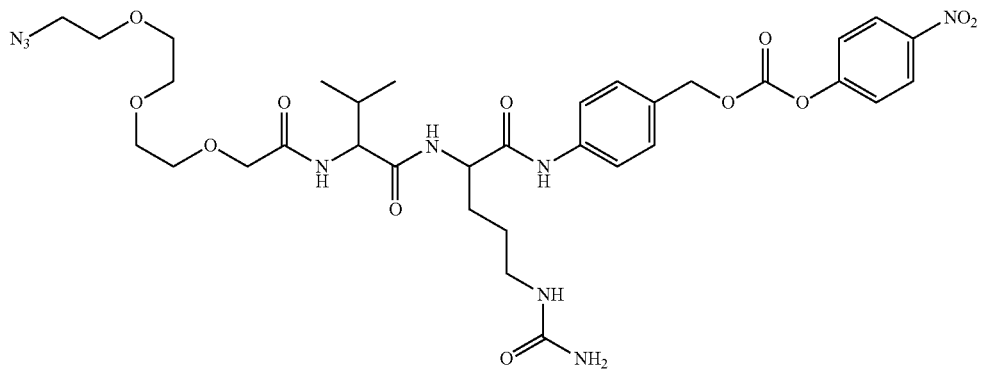

(30)

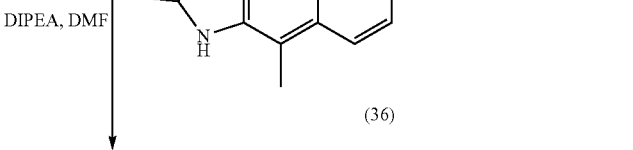

(36)

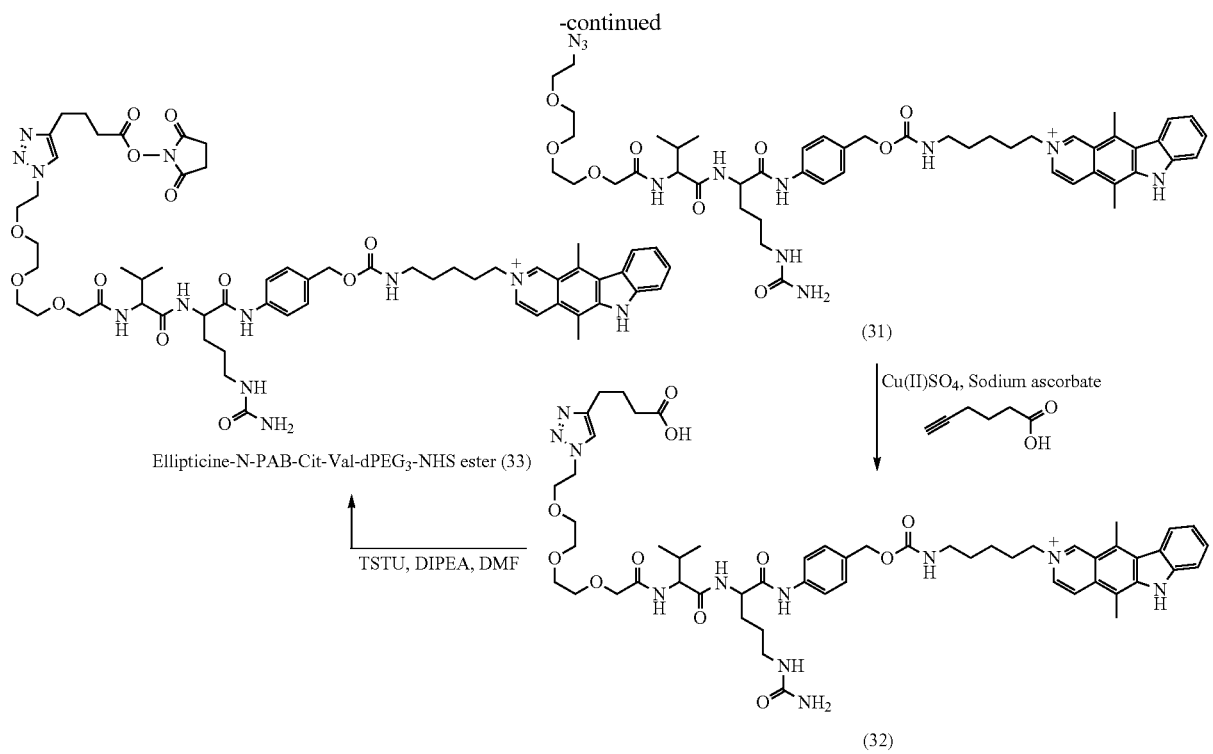

Ellipticine-N-PAB-Cit-Val-dPEG$_3$-NHS ester (33)

(31)

(32)

Example 14—Preparation of N-Ellipticinepentyl amine (36)

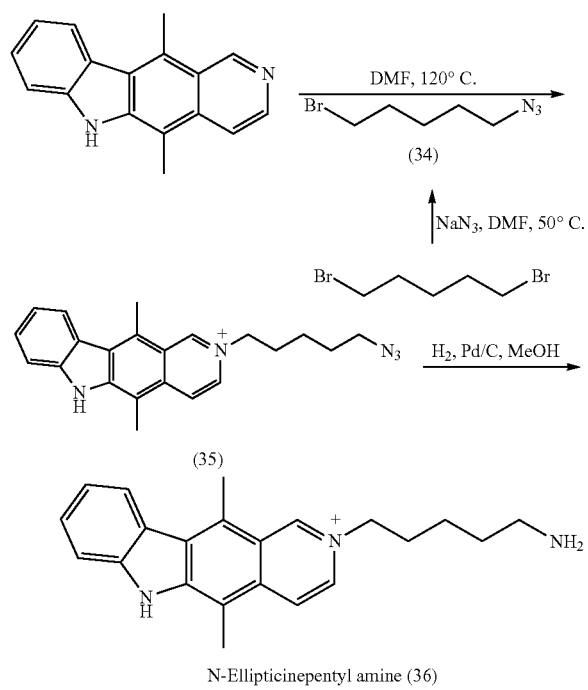

N-Ellipticinepentyl amine (36)

Sodium azide (0.6 g, 9.6 mmol) was dissolved in DMF (20 mL) and 1,5-dibromopentane (1.2 mL, 8.7 mmol) was added. The mixture was heated to 50° C. overnight with a blast shield in place. The solution was cooled to 0° C. and water (20 mL) was added. The mixture was then extracted with EtOAc (3×20 mL), washed with water (20 mL) and brine (20 mL), dried over Na$_2$SO$_4$, and concentrated to form an oil that was purified by column chromatography with n-hexane to yield 34 (1.5 g, 90%) as a clear oil. Azide staining reagent was used to follow the azide, and iodine visualization was used to stain for the starting dibromopentane, the first compound off the column. $^1$H NMR (400 MHz, CDCl3) δ 3.44 (t, J=6.7 Hz, 2H), 3.32 (t, J=6.7 Hz, 2H), 1.92 (p, J=7.0 Hz, 2H), 1.69-1.61 (m, 2H), 1.61-1.51 (m, 2H).

Ellipticine (50 mg g, 0.2 mmol) was added to 1-azido-5-bromopentane 34 (80 mg, 0.4 mmol) in DMF (10 mL) and heated to 120° C. for 4 hours, followed by stirring at room temperature for three days. The orange suspension was treated with ether (10 mL) and filtered to give the quaternised ellipticine derivative 35 64 mg (90%) as a yellow solid. m.p. decomposed without melting >150° C. IR 3065, 2088, 1598, 1578, 1463, 1420, 1401, 1154, 744, 716, 606 cm$^{-1}$; $^1$H NMR (400 MHz, DMSO-d6) δ 12.16 (s, 1H), 10.09 (s, 1H), 8.62-8.52 (m, 1H), 8.44 (dd, J=11.7, 7.6 Hz, 2H), 7.71-7.57 (m, 2H), 7.37 (s, 1H), 4.72 (t, J=7.5 Hz, 2H), 3.37 (m, 4H), 3.30 (s, 3H), 2.84 (s, 3H), 1.62 (p, J=7.0 Hz, 2H), 1.51-1.28 (m, 2H); $^1$C NMR (100 MHz, DMSO-d6) δ 206.5, 146.5, 144.3, 142.6, 13.3, 12.5, 10.8, 128.7, 125.6, 124.4, 122.1, 120.8, 120.2, 111.6, 110.45, 59.2, 50.4, 30.4, 27.7, 22.9, 15.1, 12.1; MS (ES+) m/z 358 [M]$^+$; HRMS (m/z) mass calculated for C$_{22}$H$_{24}$N$_5$ 358.2032. Found 358.2036.

The Ellipticine azide 35 (10 mg, 0.036 mmol) was dissolved in methanol (2 mL). Pd/C was added and a hydrogen balloon was attached to the stirring solution. After 6.5 hours the reaction mixture was filtered through celite and concentrated in vacuo to give the ellipticine amine 36 (7.0 mg, 58%) as bright orange crystals.

Importantly, reduction of the pyridine ring can occur when left under hydrogen overnight so careful monitoring by TLC (MeCN:H$_2$O:KNO$_3$ 8:1:1) is required. m.p. decomposed without melting >150° C. IR 2934, 1598, 1578, 1419, 1244, 1176, 747, 628 cm$^{-1}$; $^1$H NMR (400 MHz, MeOD) δ 9.86 (d, J=1.1 Hz, 1H), 8.38-8.27 (m, 3H), 7.64-7.54 (m, 2H), 7.36 (ddd, J=8.0, 6.5, 1.7 Hz, 1H), 4.81-4.71 (m, 2H), 3.25 (s, 3H), 3.00-2.92 (m, 2H), 2.78 (s, 3H), 2.18 (ddd, J=12.2, 10.2, 6.8 Hz, 2H), 1.83-1.72 (m, 2H), 1.59 (m, 2H); $^{13}$C NMR (100 MHz, MeOD) δ 146.5, 144.3, 142.6, 133.3, 132.5, 130.8, 128.7, 125.9, 124.4, 122.1, 120.8, 120.5, 120.1, 111.6, 110.4, 59.2, 48.5, 40.1, 39.9, 39.7, 39.4, 39.2, 39.0, 38.8, 30.3, 26.9, 22.6, 15.2, 15.1, 12.0; MS (m/z) 332 [M]$^+$; HRMS (m/z) calculated for C$_{22}$H$_{26}$N$_3$ 322.2127. Found 332.2123.

The PEG$_5$ azide linker 25 (20 mg, 0.03 mmol) and bisnitrophenyl carbonate (30 mg, 0.10 mmol) were dissolved in DMF (2 mL). DIPEA (0.1 mL, 0.07 mmol) was added and the solution was heated to 50° C. for 3 hours. The DMF was removed in vacuo, water was added, and the product was extracted with CH$_2$Cl$_2$:MeOH 9:1, before being dried and concentrated to yield activated p-nitrophenyl derivative 30 20 mg (74%) as a dark yellow oil. IR 1652, 1590, 1516, 1498, 134, 1288, 1216, 1109, 850, 753, 629 cm$^{-1}$; $^1$H NMR (400 MHz, MeOD) 8.30-8.39 (m, 2H), 7.61-7.71 (m, 2H), 7.40-7.53 (m, 4H), 5.28 (s, 2H), 4.50-4.61 (m, 1H), 4.33 (d, J=7.1 Hz, 1H), 4.09 (s, 2H), 3.64-3.79 (m, 10H), 3.22-3.14 (m, 1H), 2.16 (h, J=6.9 Hz, 1H), 1.79-1.92 (m, 2H), 8.6 Hz, 2H), 1.60 (m, 6H); MS (ES+) 782 [M+Na]; $^{13}$C NMR (100 MHz, MeOD) δ 172.0, 171.3, 171.0, 163.8, 163.8, 161.1, 155.8, 152.6, 145.3, 140.4, 130.6, 129.2, 125.7, 121.9, 119.8, 115.1, 70.8, 70.3, 70.2, 70.1, 69.7, 50.4, 48.3, 48.1, 47.8, 47.6, 47.4, 47.2, 47.1, 30.9, 18.4, 17.4; HRMS (m/z) calculated for C$_{33}$H$_{45}$N$_9$O$_{12}$ 782.3170 [M+Na]$^+$. Found 782.3173.

The ellipticine amine 36 (11 mg, 0.03 mmol) and the activated linker 30 (24 mg, 0.03 mmol) were dissolved in dry DMF. DIPEA (6 μL, added via Gilson pipette, 0.035 mmol) was added and the reaction mixture stirred in the dark at room temperature for 24 hours. The product was precipitated by addition of diethyl ether and centrifuged. The supernatant was removed and the resulting solid was washed with diethyl ether and dried to give the ellipticine linker derivative 31 10 mg, (36%) as a yellow solid. MS (ES+) m/z 952 [M]$^+$; HRMS calculated for C$_{49}$H$_{66}$N$_{11}$ 952.5045. Found 952.4993.

The azide ellipticine derivative 31 undergoes 1,3 cycloaddition with hexynoic-acid under 'click' conditions using Cu(II)SO$_4$ and ascorbic acid to give the derivative 32. Activating the terminal carboxylic acid of derivative 32 with TSTU and DIPEA in dry DMF will give the succinimidyl ester derivative 33.

Example 15—Preparation of 6-Maleimidocaproyl-MMAE (37)

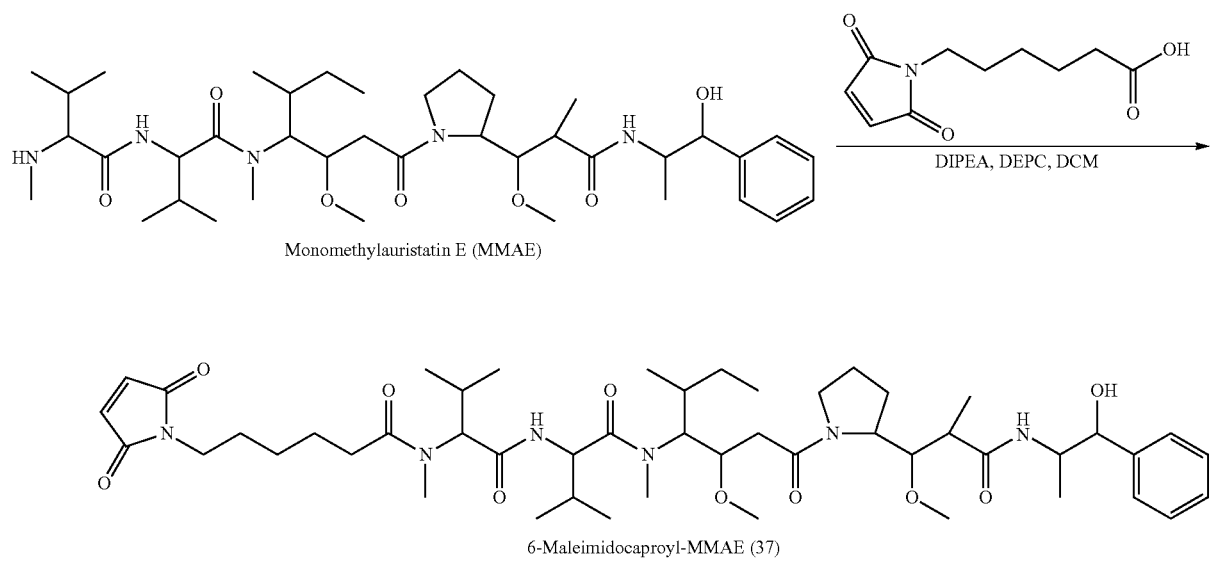

To a suspension of MMAE (0.05 g, 0.0694 mmol) in freshly distilled dry DCM (2 ml), 6-maleimidocaproic acid (0.0221 g, 0.104 mmol) was added followed by diethylcyanophosphonate (21 μl, 0.139 mmol) and DIPEA (37 μl, 0.208 mmol). On addition of DIPEA, the reaction mixture became clear and was stirred at room temperature under nitrogen for 12 h, TLC [silica gel: 5% MeOH/DCM, R$_f$ 0.31]. The reaction mixture was diluted with DCM (30 ml) and washed with 10% citric acid (2×20 ml), water (20 ml), brine (20 ml) and concentrated to dryness. The crude was purified by flash column chromatography [silica gel: 5% MeOH/DCM] to give 6-Maleimidocaproyl-MMAE 37 as a white solid 0.023 g (36%). MS (m/z) found 911.58 (M+1) calculated for C$_{49}$H$_{79}$N$_6$O$_{10}$

Example 16—Preparation of 6-Maleimidocaproyl-Val-Cit-PAB-MMAE (40)

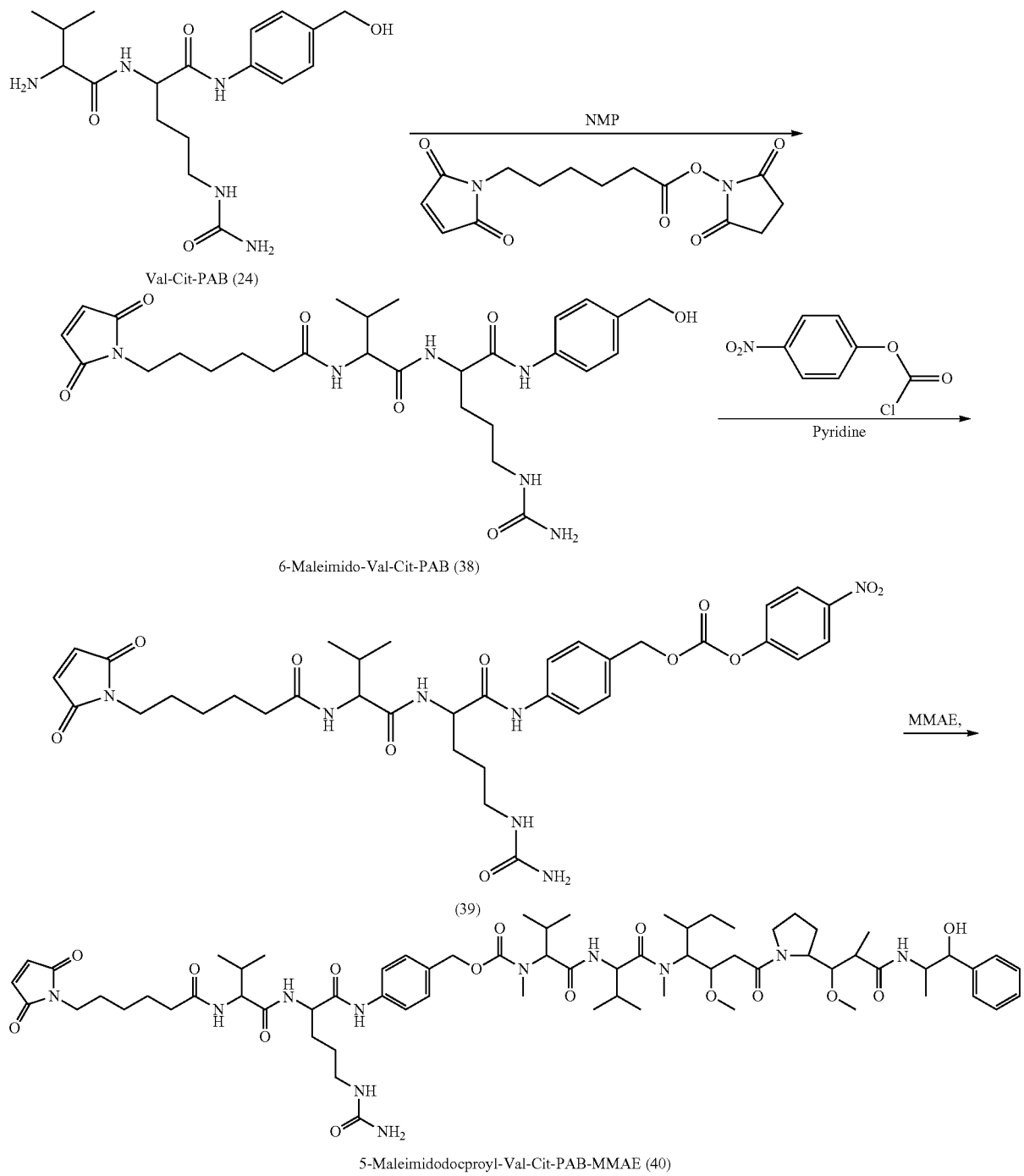

MeOH/DCM $R_f$ 0.21. MS (m/z) 572.653 (M+1) calculated for $C_{28}H_{41}N_6O_7$

To a stirred solution of val-cit-PAB 24 (0.11 g, 0.29 mmol) in dry N-methylpyrrolidinone, NMP (5 ml) under nitrogen, N-succinimidyl-6-maleimidohexanoate (0.0983 g, 0.318 mmol) was added and the resulting light-brown solution stirred at room temperature for 16 h. The NMP was removed by high vacuum at <40° C. The resulting thick oily residue was triturated with dry ether (20 ml) the solid collected by filtration and washed several times with dry ether and air dried to give the desired product 38 an off-white powder 0.16 g (98%). TLC [silica gel: 10%

To stirred solution of 6-maleimidocaproyl-val-cit-PAB 38 in dry DMF under nitrogen, bis-(p-nitrophenyl)carbonate was added followed by DIPEA, resulting in a colour change from colourless to bright yellow. The solution was stirred at room temperature under nitrogen for 1 h after which the DMF was removed by high vacuum to give an oily residue. This was triturated with ethyl acetate for 15 min resulting in precipitation which was completed by the addition of ether. The solid was collected and washed well with ether and air dried to give an off-white solid. TLC [silica gel: 10%

MeOH/DCM R$_f$ 0.46]. This was purified by chromatography [silica gel: 5-10% MeOH/DCM gradient elution] to give the activated linker 39 as a white solid 0.006 g, (46%). MS (m/z) 738 . . . 3091 (M+H), HRMS (m/z) calculated for C$_{35}$H$_{43}$N$_7$O$_{11}$Na M+Na 760.2918 found 760.2922

The activated linker 39 (50 mg, 0.068 mmol), MMAE (32.6 mg, 0.045 mmol) and N-hydroxybenzotriazole (1.4 mg, 0.0091 mmol) are stirred in dry DMF (1 ml) for 2 min. after which a drop of pyridine is added and the reaction stirred for 24 h. The solvent is then removed by high vacuum and the residue purified by reverse-phase preparative HPLC to give the desired product 40 after lyopholisation as a white powder; MS (m/z) 1316.7 (M+H).

Example 17—Preparation of Paclitaxel-dPEG$_6$-NHS Ester (44)

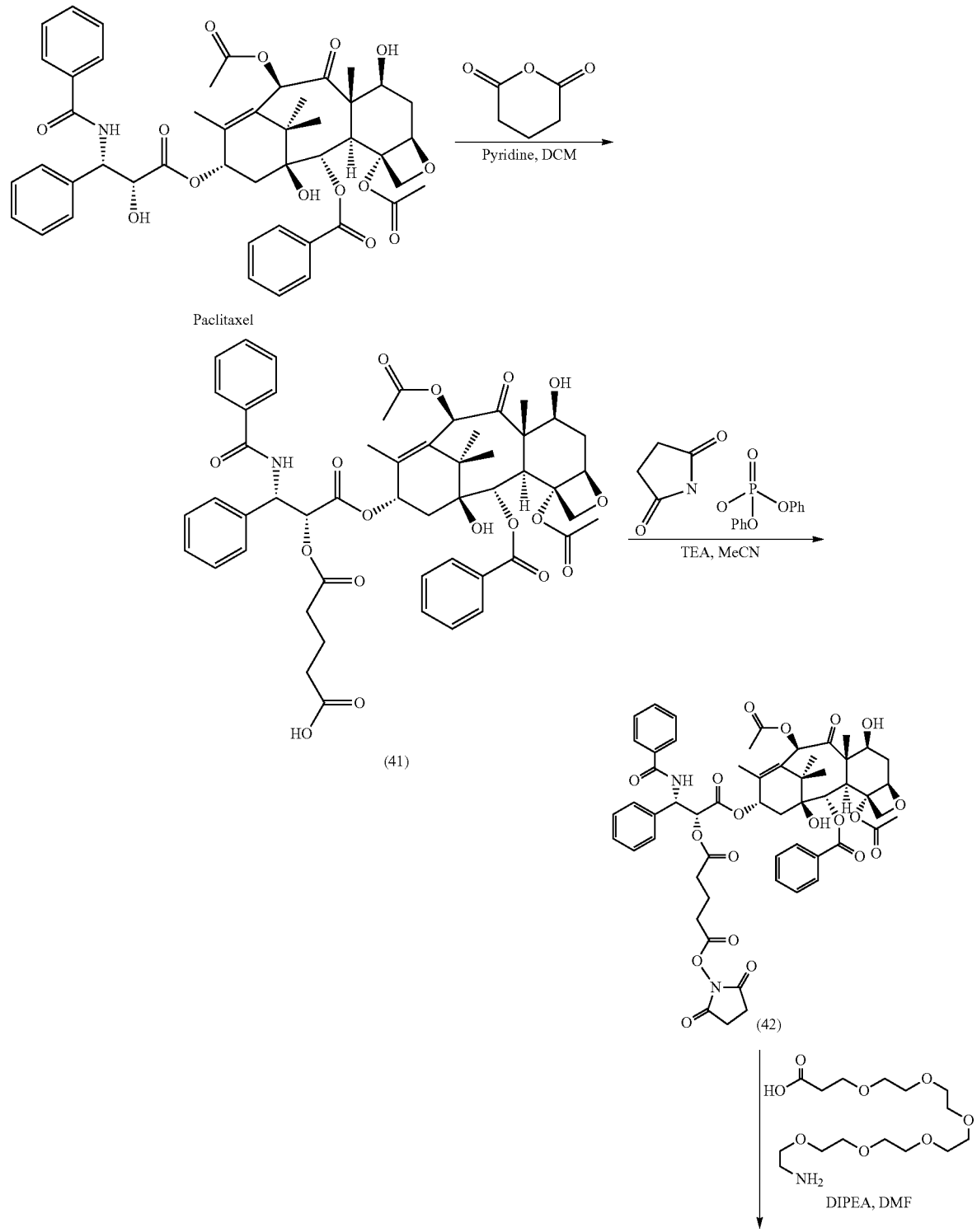

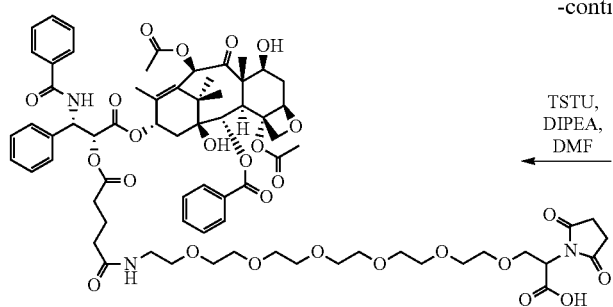

Paclitaxeld-PEG<sub>6</sub> NHS Ester (44)    (43)

Paclitaxel (100 mg, 0.12 mmol) and glutaric anhydride (17 mg, 0.14 mmol) were dissolved in dry DCM (10 ml) and stirred for 10 min, followed by addition of dry pyridine (100 µl, 0.0013 mmol). The reaction mixture was stirred for 3 days at room temperature and evaporated under vacuum. The residue obtained was recrystallized from DCM to afford the paclitaxel acid 41 as a white solid 60.7 mg (52.3%). ($R_f$ 0.26, 3% MeOH/DCM). $^1$H NMR (CDCl$_3$): δ 8.16 (2H, d, J=4 Hz, 23-H, 27-H), 7.78 (2H, d, J=4 Hz, 39-H, 43-H), 7.66-7.36 (11H, CH, Ar), 6.28 (2H, m, 10-H, 13-H), 6.01 (1H, q, J=4 Hz, 3'-H), 5.71 (1H, d, J=7.2 Hz, 2-H), 5.52 (1H, d, J=3.2 Hz, 2'-H), 5.00 (1H, d, J=8 Hz, 5-H), 4.47 (1H, q, J=6.4 Hz, 7-H), 4.29 (2H, d, J=8.4 Hz, 20-H), 3.83 (1H, d, J=6.8 Hz, 3-H), 2.53-2.16 (15H, m, 7-OH, 6-H, 14-H, g2-H, g4-H, 29-H, 31-H), 2.06-1.70 (7H, m, 1-OH, g3-H, 6-H, 18-H, 19-H), 1.28-1.16 (6H, m, 16-H, 17-H). MS (m/z): 968.36 [M$^+$], 985.39 [M$^+$+NH$_4$], 990.35 [M$^+$+Na]. (Theoretical: $C_{52}H_{57}NO_{17}$ 968.01).

To a stirred solution of paclitaxel acid 41 (26 mg, 0.027 mmol) and SDPP (20 mg, 0.058 mmol) in dry acetonitrile (5 ml), TEA (20 µl, 0.143 mmol) was added. The reaction mixture was stirred overnight at room temperature under nitrogen, followed by evaporation and purification by silica gel chromatography (MeOH/DCM=3:97) to give paclitaxel NHS ester 42 as a white solid 38 mg (76%). ($R_f$ 0.48). $^1$H NMR (CDCl$_3$): δ 8.15 (2H, d, J=7.6 Hz, 23-H, 27-H), 7.72 (2H, d, J=7.6 Hz, 39-H, 43-H), 7.64-7.37 (11H, CH, Ar), 6.28 (2H, m, 10-H, 13-H), 6.01 (1H, q, J=4 Hz, 3'-H), 5.71 (1H, d, J=7.2 Hz, 2-H), 5.52 (1H, d, J=3.2 Hz, 2'-H), 5.00 (1H, d, J=8 Hz, 5-H), 4.47 (1H, q, J=6.4 Hz, 7-H), 4.29 (2H, d, J=8.4 Hz, 20-H), 3.83 (1H, d, J=6.8 Hz, 3-H), 2.99-2.36 (15H, m, 7-OH, 6-H, 14-H, g2-H, g4-H, 29-H, 31-H), 2.29-1.82 (15H, m, 1-OH, g3-H, 6-H, 18-H, 19-H, n3-H, n4-H), 1.28-1.16 (6H, m, 16-H, 17-H). MS (m/z): 1065.38 [M$^+$], 1087.36 [M$^+$+Na]. (Theoretical: $C_{56}H_{60}N_2O_{19}$ 1065.08).

To a solution of the paclitaxel NHS ester 42 (32 mg, 0.03 mmol) in dry DCM (5 mL), H$_2$N-PEG$_6$-COOH (10.6 mg, 0.03 mmol) and TEA (5 µl, 0.03 mmol) were added. The reaction mixture was stirred overnight under nitrogen, followed by washing with HCl (2×10 mL, 0.1 M) and brine (2×10 mL). The organic layer was dried over sodium sulfate, filtered, and concentrated to give 43 as a clear oil 25 mg, (64%). [Silica gel: 5% MeOH/DCM $R_f$ 0.16]. $^1$H NMR (CDCl$_3$): δ 8.16 (2H, d, J=7.6 Hz, 23-H, 27-H), 7.86 (2H, d, J=7.6 Hz, 39-H, 43-H), 7.65-7.30 (11H, CH, Ar), 6.28 (2H, m, 10-H, 13-H), 6.01 (1H, q, J=4 Hz, 3'-H), 5.71 (1H, d, J=7.2 Hz, 2-H), 5.50 (1H, d, J=3.2 Hz, 2'-H), 5.00 (1H, d, J=8 Hz, 5-H), 4.47 (1H, q, J=6.4 Hz, 7-H), 4.29 (2H, d, J=8.4 Hz, 20-H), 3.83 (1H, d, J=6.8 Hz, 3-H), 3.73-3.47 (24H, m, —CO—NH—(CH$_2$—CH$_2$—O)$_6$—CH$_2$—), 2.62-1.87 (24H, m, 7-OH, 6-H, 14-H, 18-H, g2-H, g4-H, 29-H, 31-H, 1-OH, g3-H, 6-H, 19-H), 1.28-1.16 (6H, m, 16-H, 17-H). MS (m/z): 1303.56 [M$^+$], 1325.56 [M$^+$+Na], 1341.55 [M++K]. (Theoretical: $C_{67}H_{86}N_2O_{23}$ 1303.40).

To a stirred solution of paclitaxel-PEG$_5$-acid 43 (22 mg, 0.017 mmol) in anhydrous DMF (2 mL), TSTU (11 mg, 0.034 mmol) and DIPEA (15 µl, 0.085 mmol) were added. The reaction mixture was stirred for 2 h at room temperature under nitrogen, followed by concentration to afford the crude product as a yellow oil. This was purified by flash chromatography [silica gel, 3-5% MeOH/DCM] to afford the NHS ester 44 15.2 mg (64%). [silica gel 3% MeOH/DCM $R_f$ 0.18]. $^1$H NMR (CDCl$_3$): δ 8.16 (2H, d, J=7.6 Hz, 23-H, 27-H), 7.86 (2H, d, J=7.6 Hz, 39-H, 43-H), 7.65-7.30 (11H, CH, Ar), 6.28 (2H, m, 10-H, 13-H), 6.01 (1H, q, J=4 Hz, 3'-H), 5.71 (1H, d, J=7.2 Hz, 2-H), 5.50 (1H, d, J=3.2 Hz, 2'-H), 5.00 (1H, d, J=8 Hz, 5-H), 4.47 (1H, q, J=6.4 Hz, 7-H), 4.29 (2H, d, J=8.4 Hz, 20-H), 3.83 (1H, d, J=6.8 Hz, 3-H), 3.73-3.47 (24H, m, —CO—NH—(CH$_2$—CH$_2$—O)$_6$—CH$_2$—), 2.62-1.87 (28H, m, 7-OH, 6-H, 14-H, 18-H, g2-H, g4-H, 29-H, 31-H, 1-OH, g3-H, 6-H, 19-H, n3-H, n4-H), 1.28-1.16 (6H, m, 16-H, 17-H). MS (m/z): 1400.60 [M$^+$], 1417.62 [M$^+$+NH$_4$], 1422.58 [M$^+$+Na], 1338.60 [M++K]. (Theoretical: $C_{71}H_{89}N_3O_{26}$ 1400.47).

Example 18—Preparation of
Paclitaxel-PAB-Val-Cit-dPEG₇ NHS Ester (47)
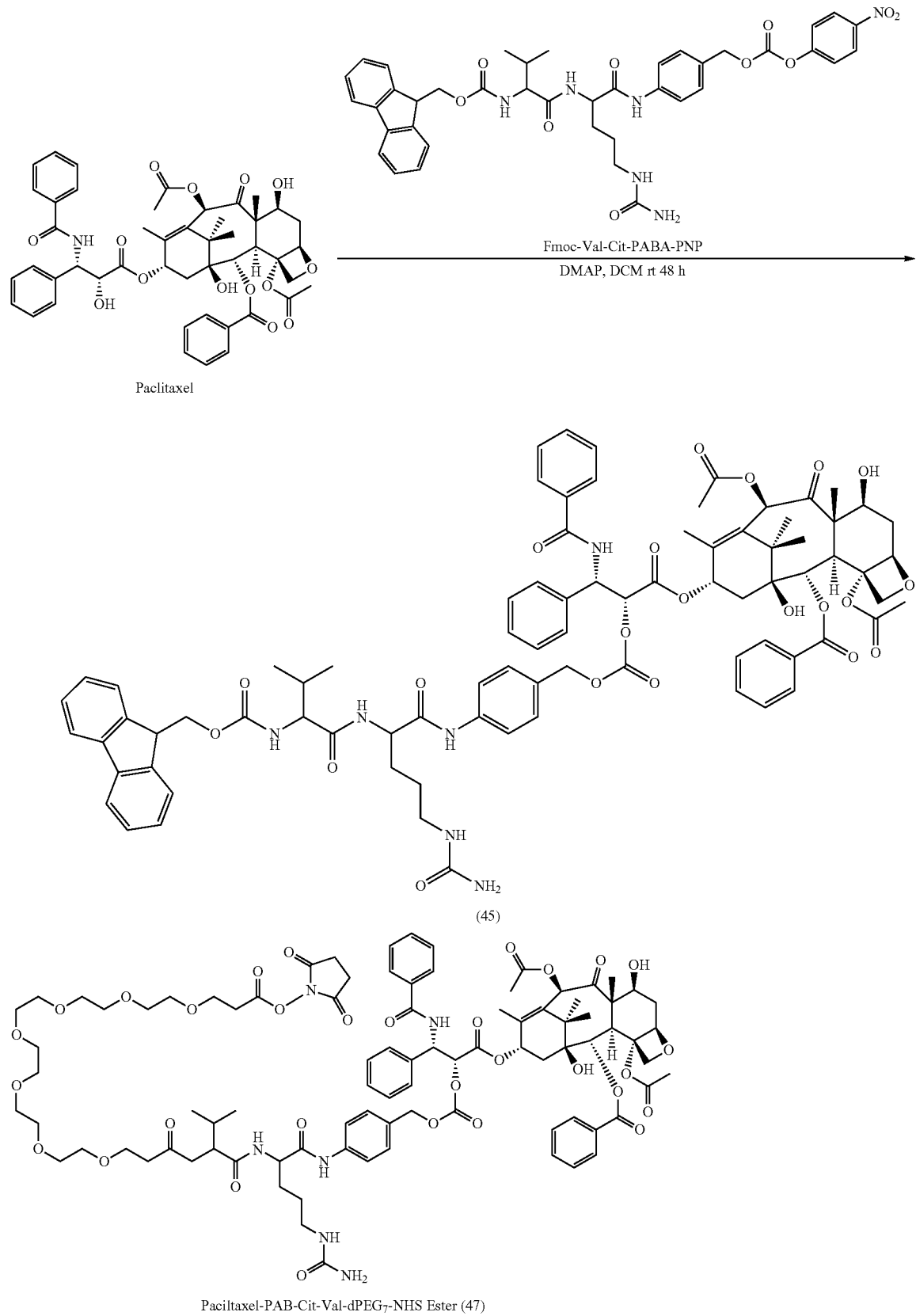

-continued

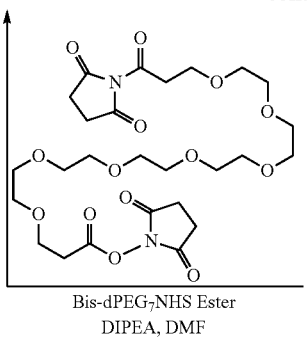

Bis-dPEG₇NHS Ester
DIPEA, DMF

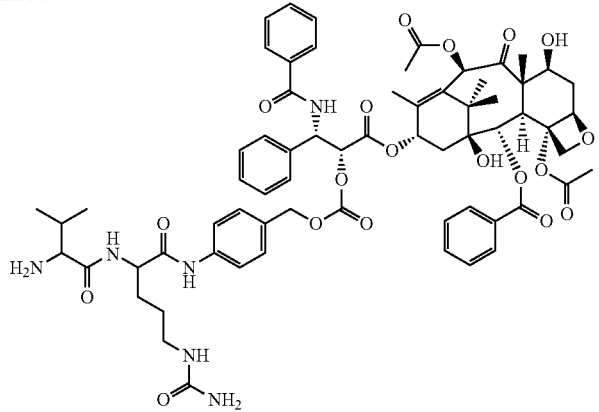

(46)

To a stirred mixture of paclitaxel (100 mg, 0.117 mmol) and Fmoc-Val-Cit-PAB (74.8 mg, 0.00976 mmol) in dry DCM (10 ml) DMAP (14.3 mg, 0.117 mmol) is added and stirred at room temperature under nitrogen for 48 h. The solvent is evaporated to give a light-yellow crystalline solid which is purified by flash column chromatography [silica gel: 3-5% MeOH/Chloroform] giving the desired compound 45.

To a stirred solution of 45 in dry THF, DBU is added and stirred for 10 min. after which the solvent is removed to give the deprotected derivative 46 which is used without further purification.

A solution of 46 in dry DCM is added dropwise over 20-30 min. to a stirred solution of the bis-dPEG₇ NHS ester in dry DCM under nitrogen after which it is stirred for 2 h, quenched by the addition of water, back-extracted with DCM and the combined organic extracts dried and evaporated to give crude 47.

Example 19—Preparation of
Doxorubicin-dPEG$_{12}$-Maleimide (48)

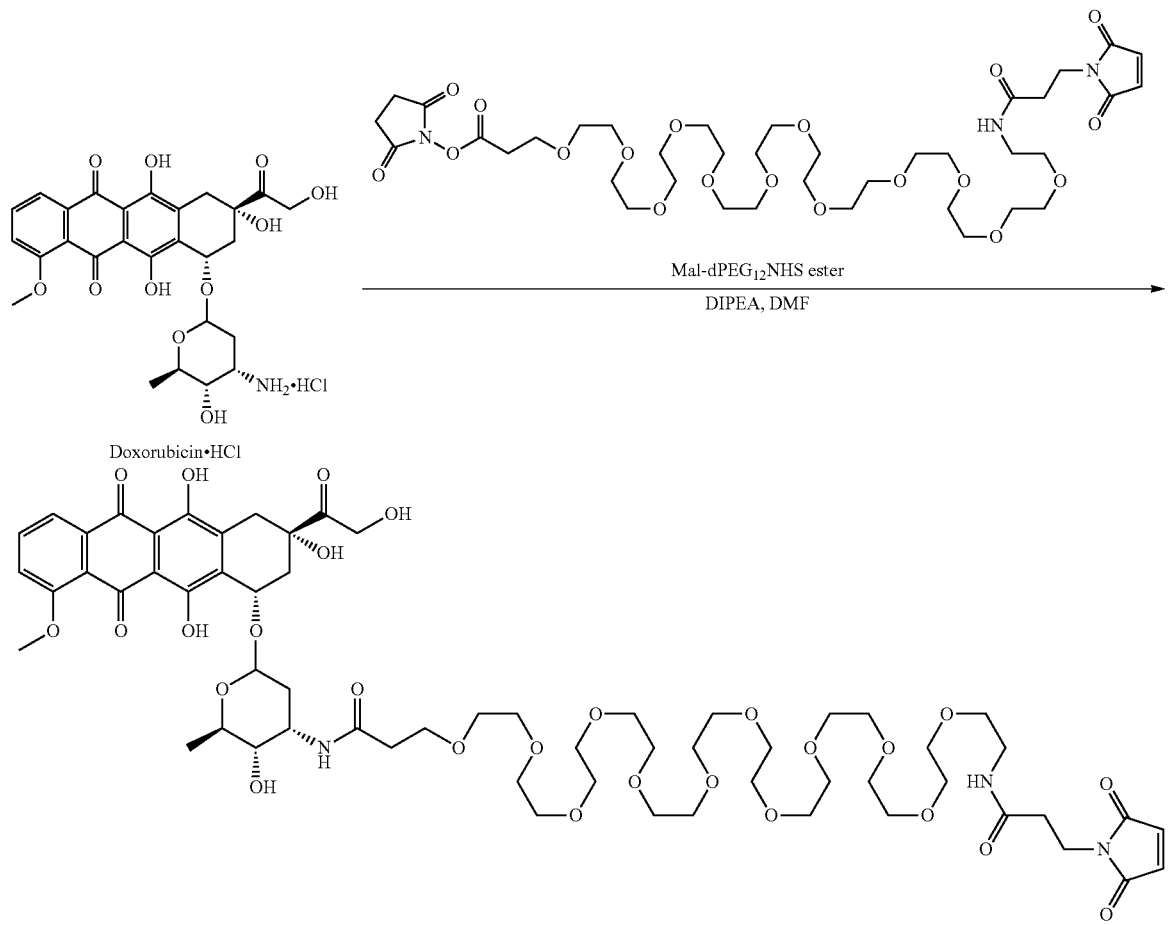

Doxorubicin-dPEG$_{12}$-Maleimide (48)

To a stirred suspension of Dox.HCl (10 mg, 0.017 mmol) in dry DMF (2 ml) DIPEA (7.7 μl) was added and the reaction mixture stirred for 10 min. under nitrogen to give a clear red solution. To this, Maleimide-dPEG$_{12}$ NHS ester (16.4 mg, 0.019 mmol) dissolved in dry DMF (1 ml) was added and the reaction stirred at room temperature, under nitrogen and protected from light overnight. The DMF was removed by high vacuum and the dark red oil purified by flash chromatography [silica gel: 10% MeOH/DCM R$_f$ 0.5] to give the desired product 48 17.8 mg (80%) as a red viscous oil; HRMS (m/z) calculated for $C_{61}H_{87}N_3O_{27}Na$ [M+Na] 1316.5424 found: 1316.5601

Example 20—Preparation of Cemadotin-SH (53)

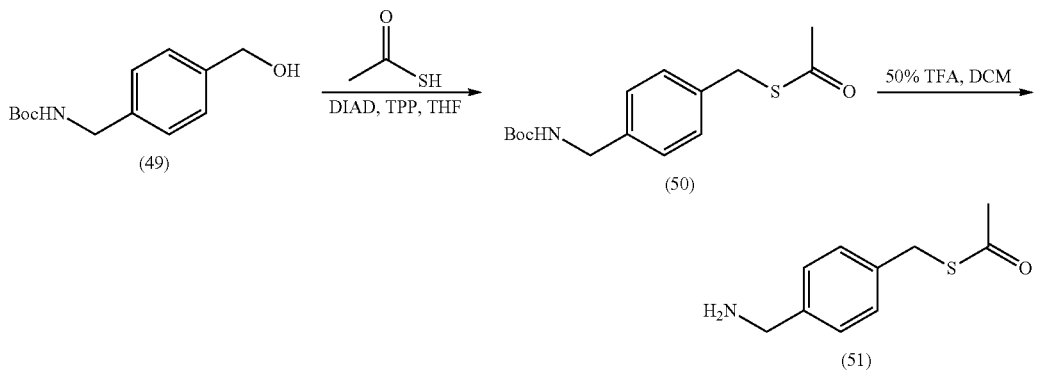

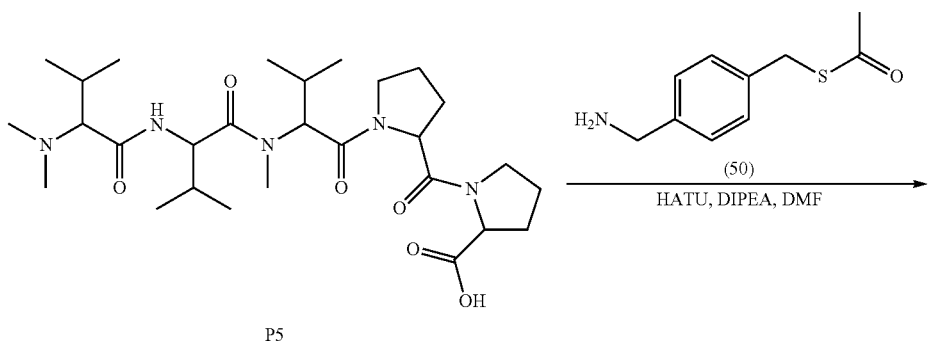

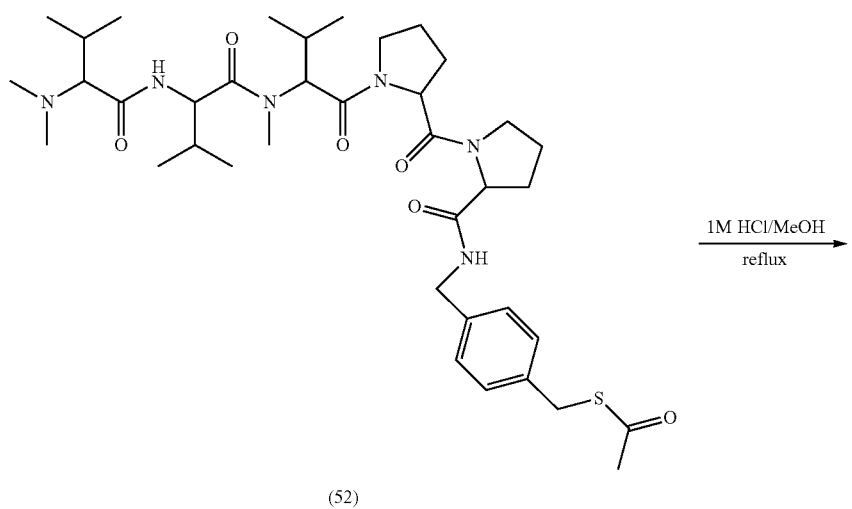

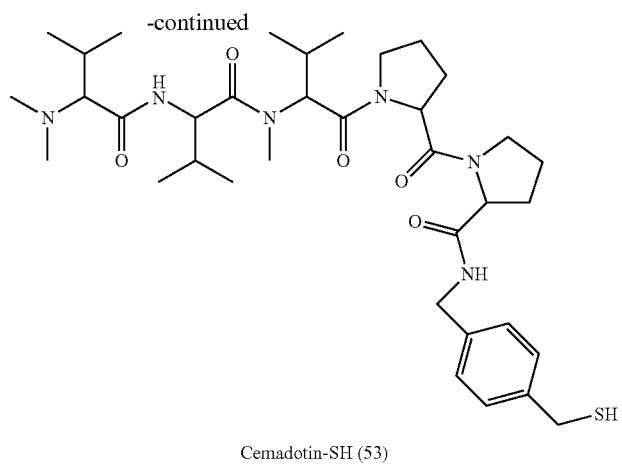
Cemadotin-SH (53)
Example 21—Preparation of Cemadotin-OH (54)
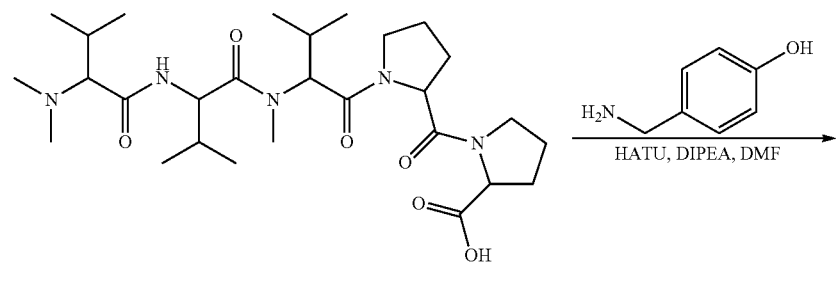
P5
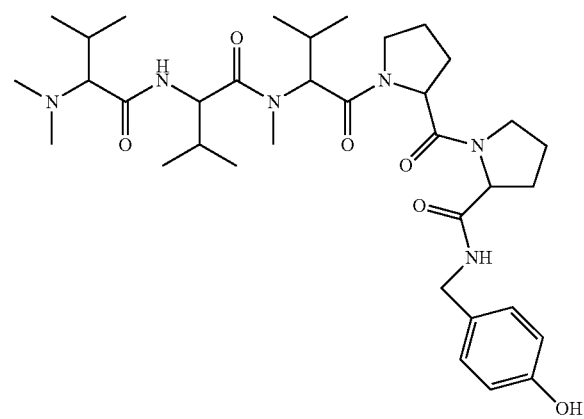
Cemadotin-OH (54)

Example 22—Preparation of
Cemadotin-O-PAB-Cit-Val-PEG₅-NHS Ester (57)
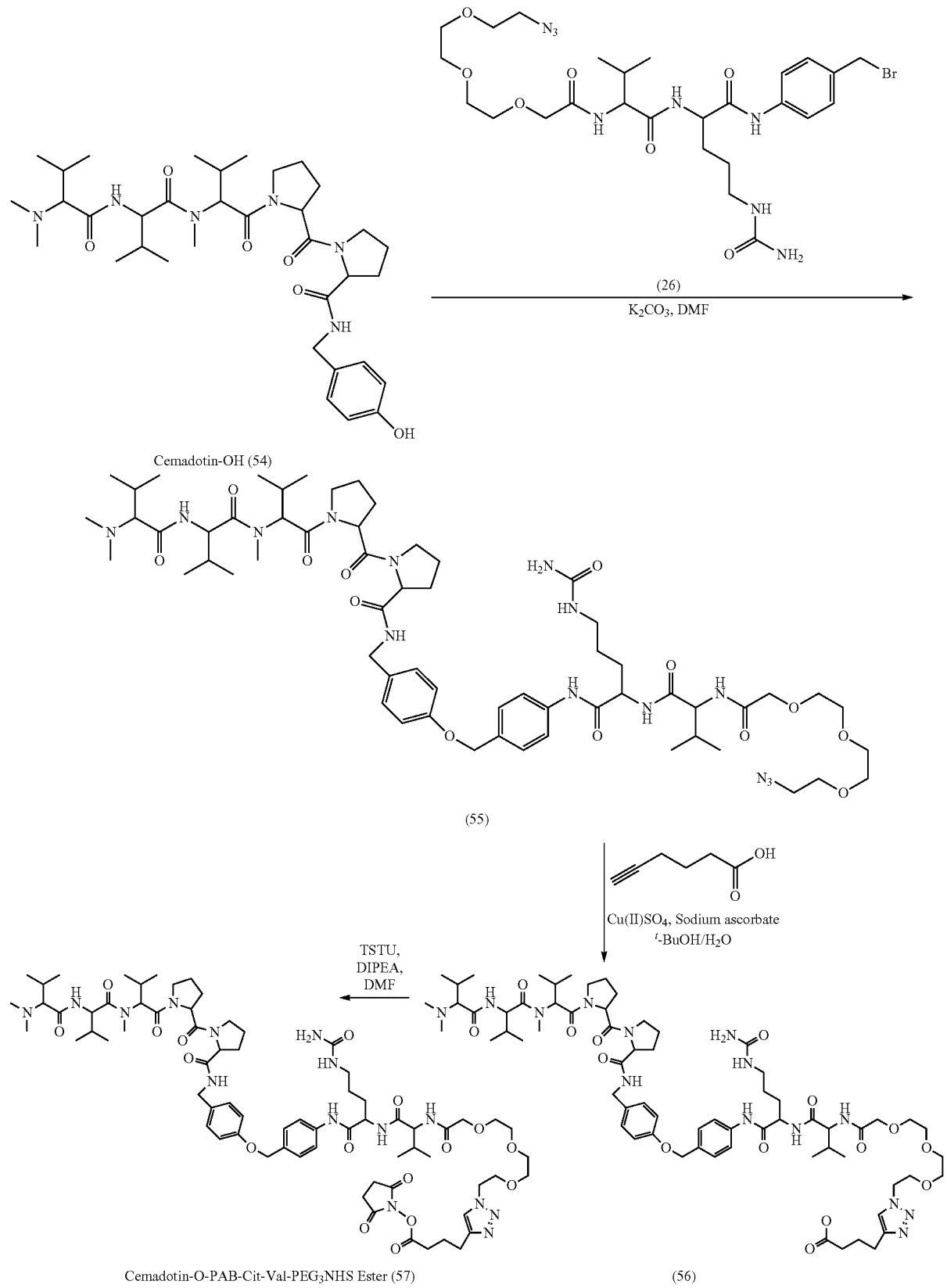

Example 23—Preparation of Seco CBI-β-Glucuronide-NHS Ester (65)
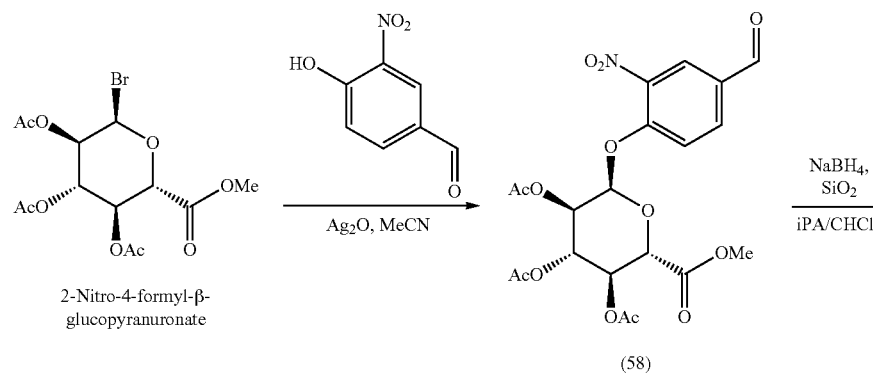
(58)
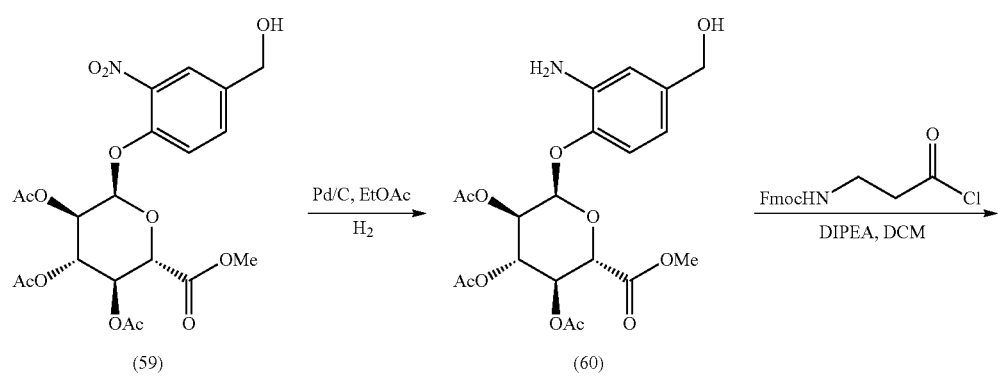
(59)　(60)
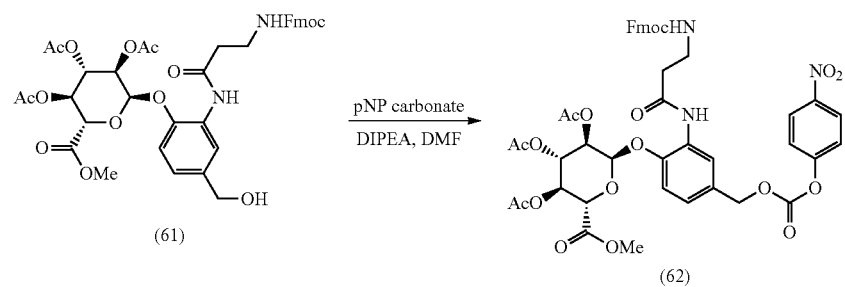
(61)　(62)
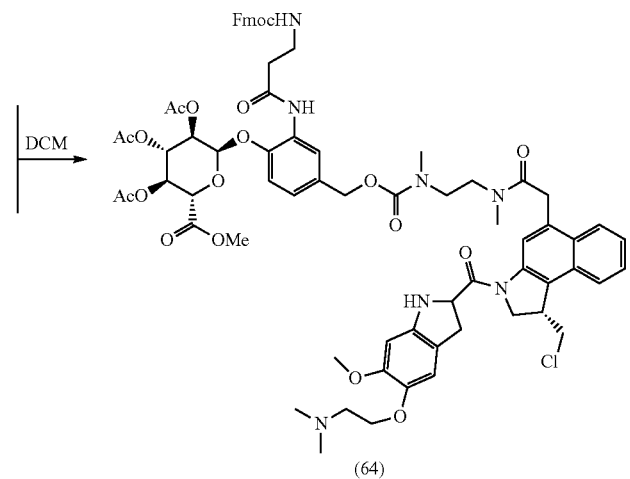
(64)

-continued
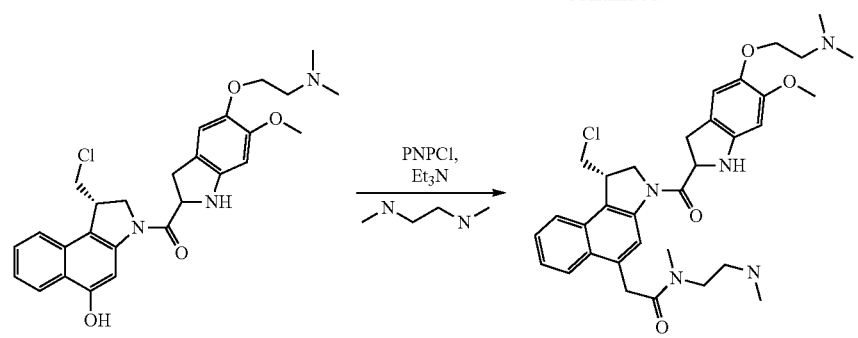
Duocarmycin seco-CBI
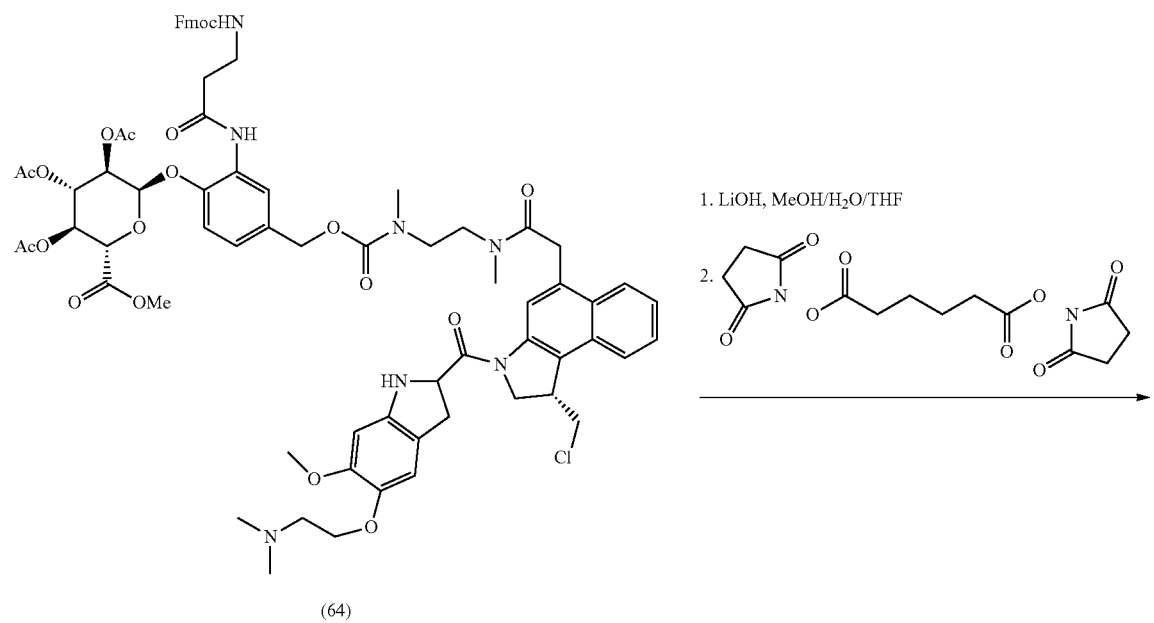
(64)
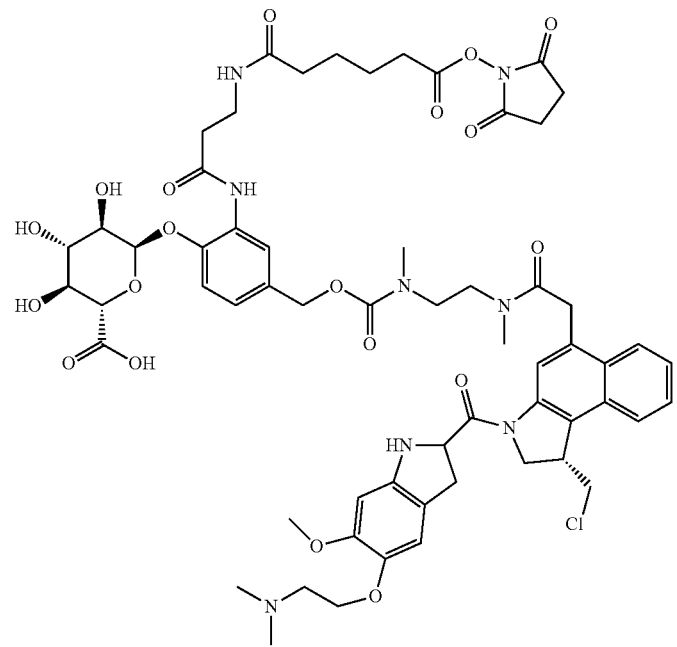
seco CBI-β-glucuronide-NHS ester (65)

Example 24—Preparation of 6-Maleimidocaproyl-SGD-1910 (67)
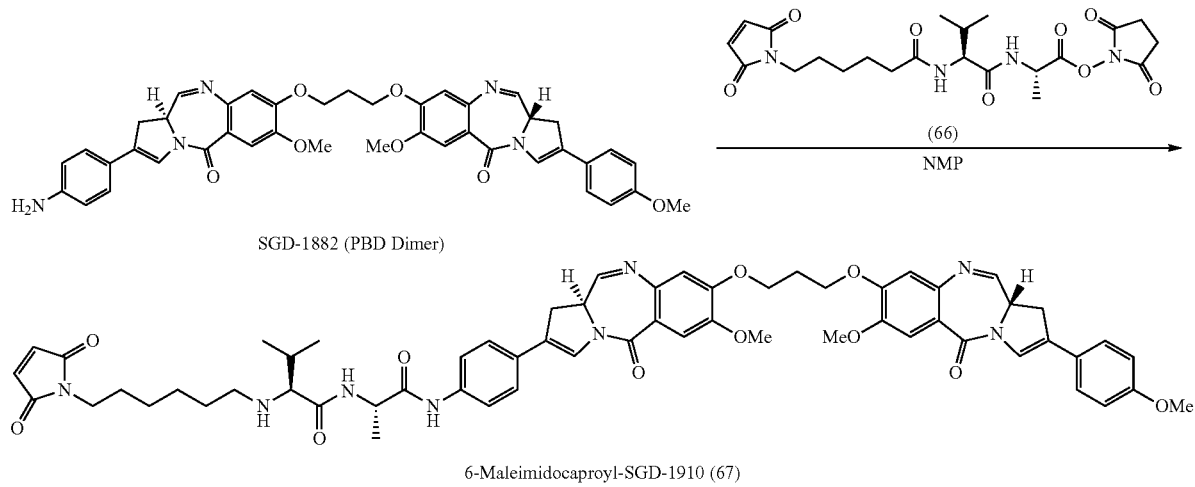
Example 25—Preparation of Maytansinol DM4 Mal-PEG$_4$-NHS Ester (68)
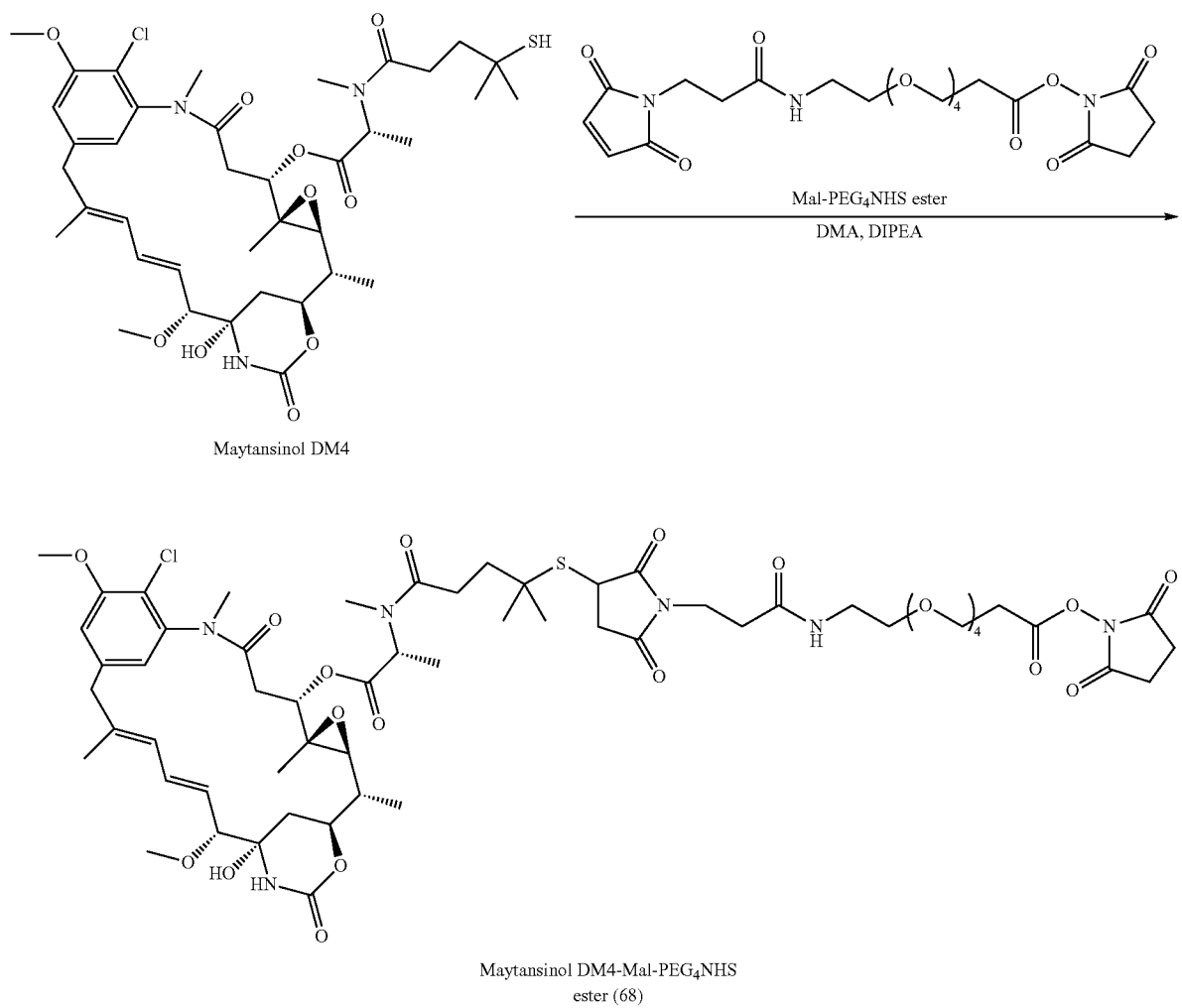

Example 26—Scheme for the Synthesis of Conjugates
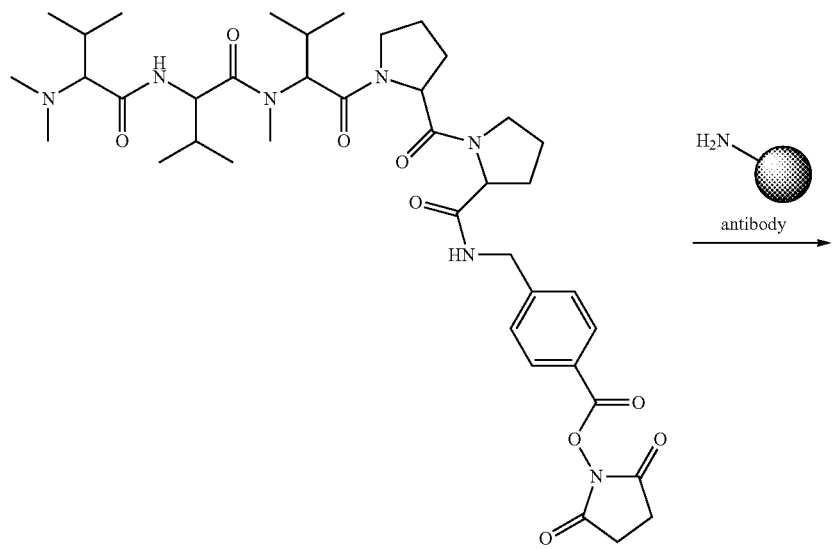
Cemadotin-NHS (2)
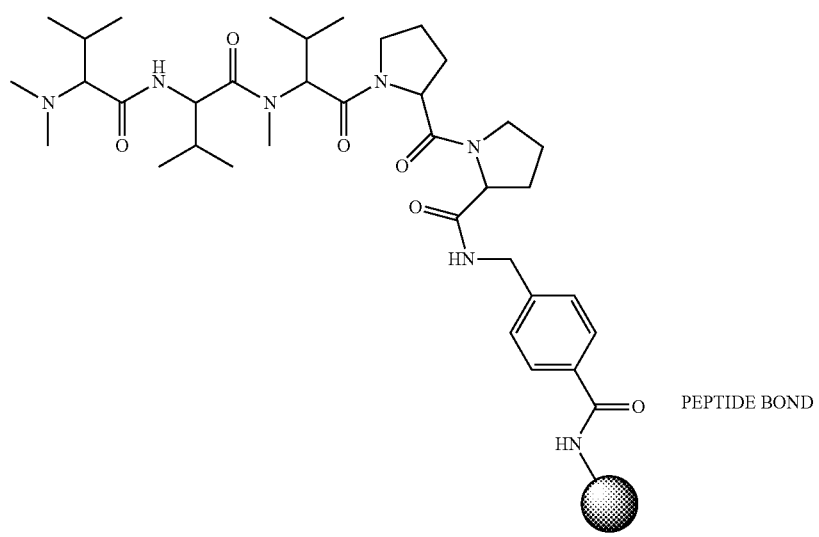
Cemadotin Conjugate (69)
via a peptide bond -continued
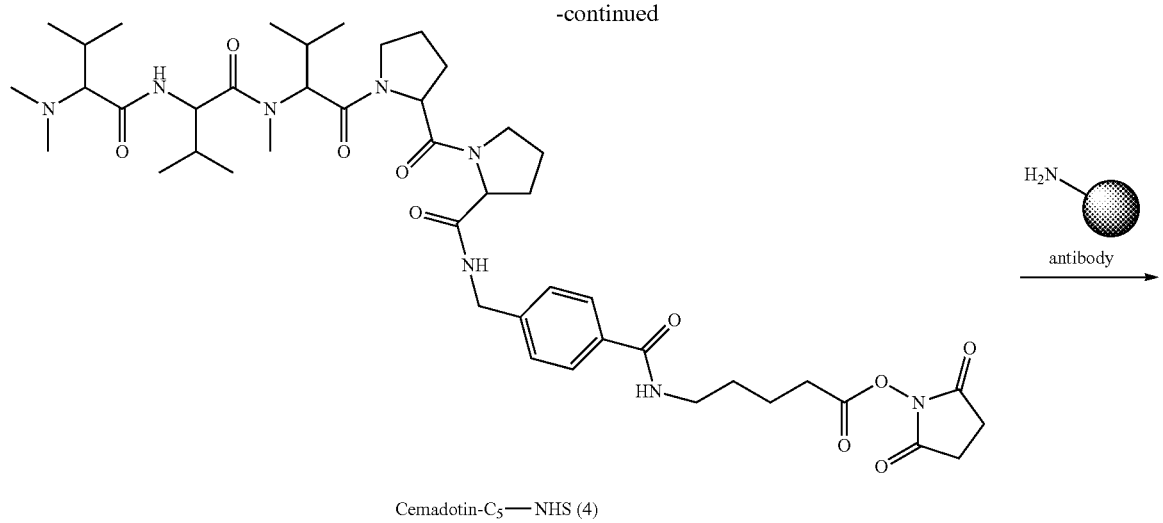
Cemadotin-C₅—NHS (4)
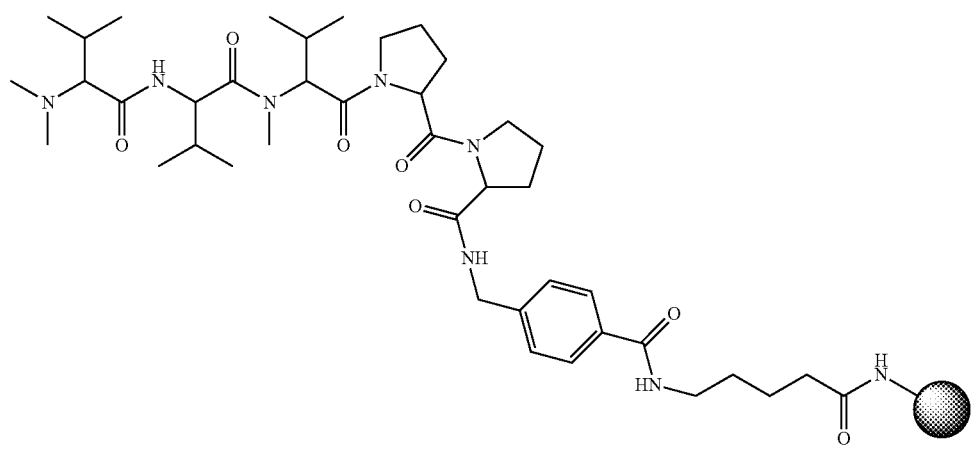
Cemadotin-C₅-conjugate (70)
via a peptide bond
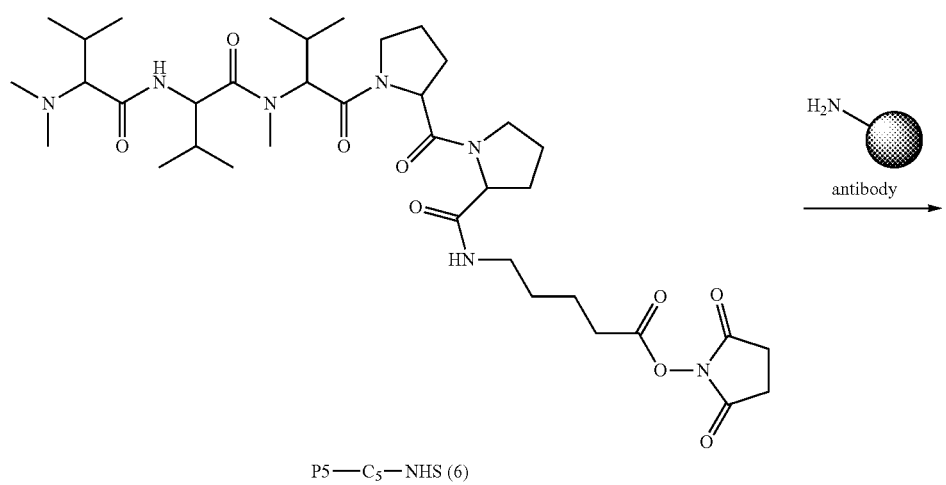
P5—C₅—NHS (6)

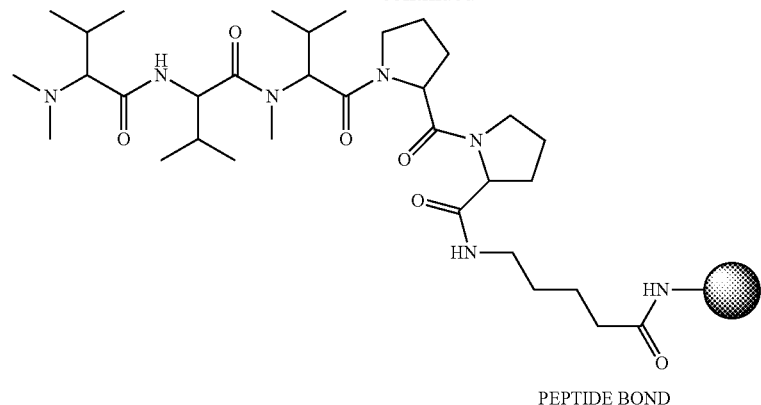
P5—C5 Conjugate (71)
via a peptide bond
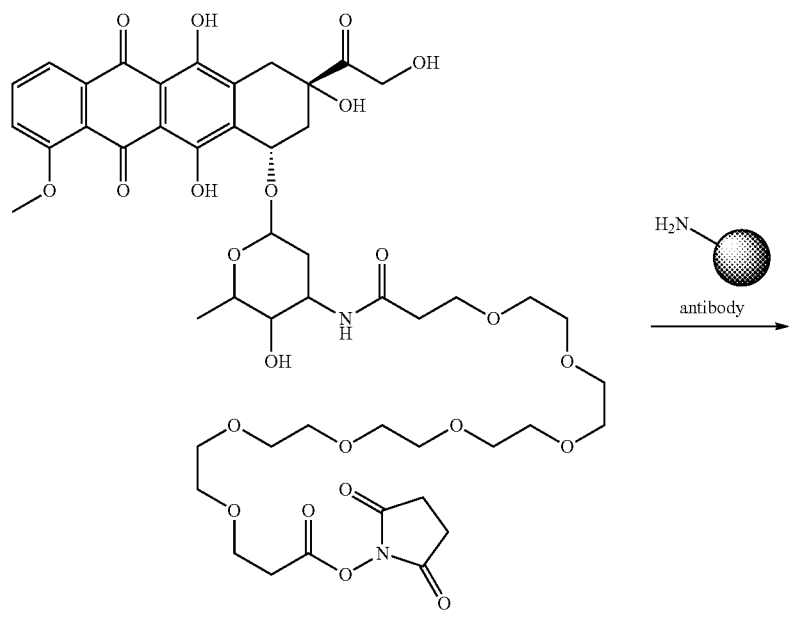
Doxorubicin-dPEG7NHS Ester (7)

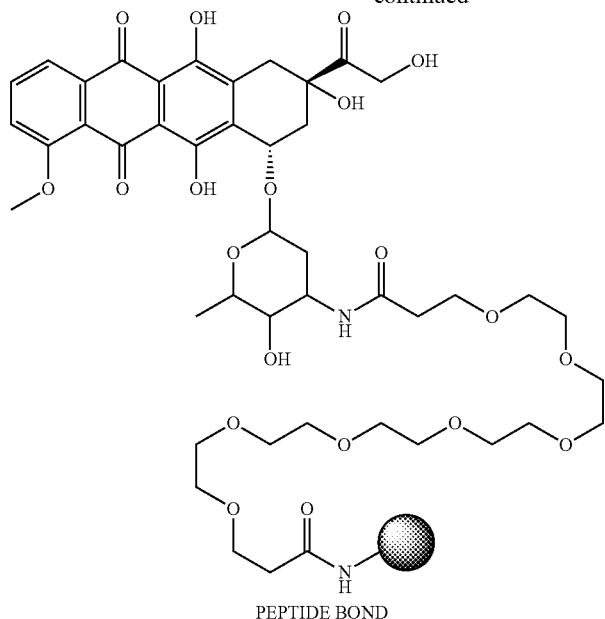
DoxorubicindPEG7-conjugate (72) via a peptide bond
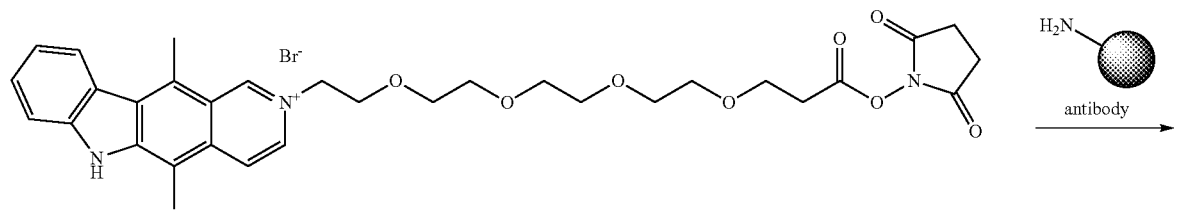
Ellipticine-PEG3-NHS (23)
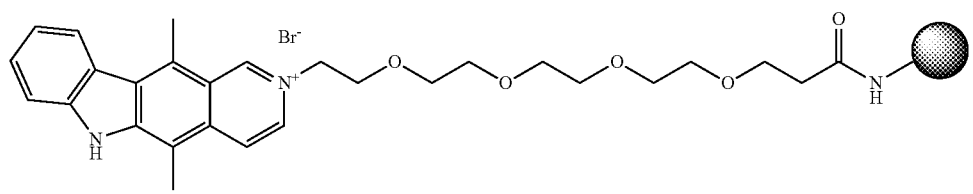
Ellipticine-PEG3-Conjugate (73)
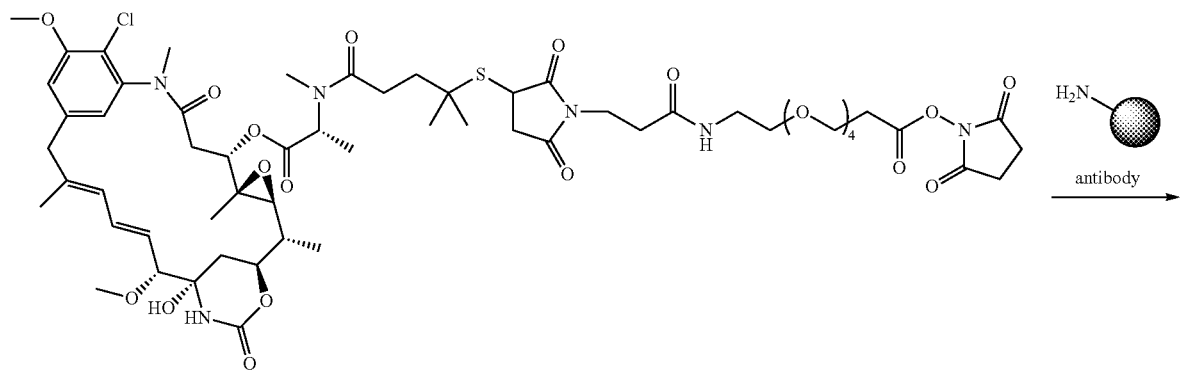
Maytansinol DM4-MaI-PEG4 NHS ester (68)

-continued
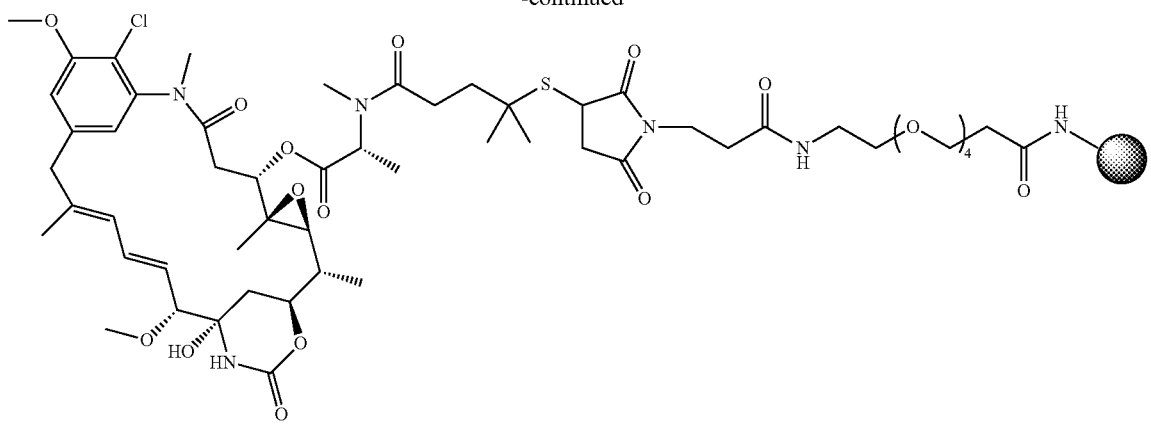
Maytansinol DM4-MaI-PEG4 Conjugate (74)
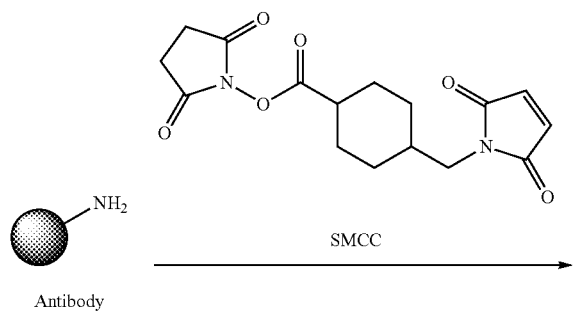
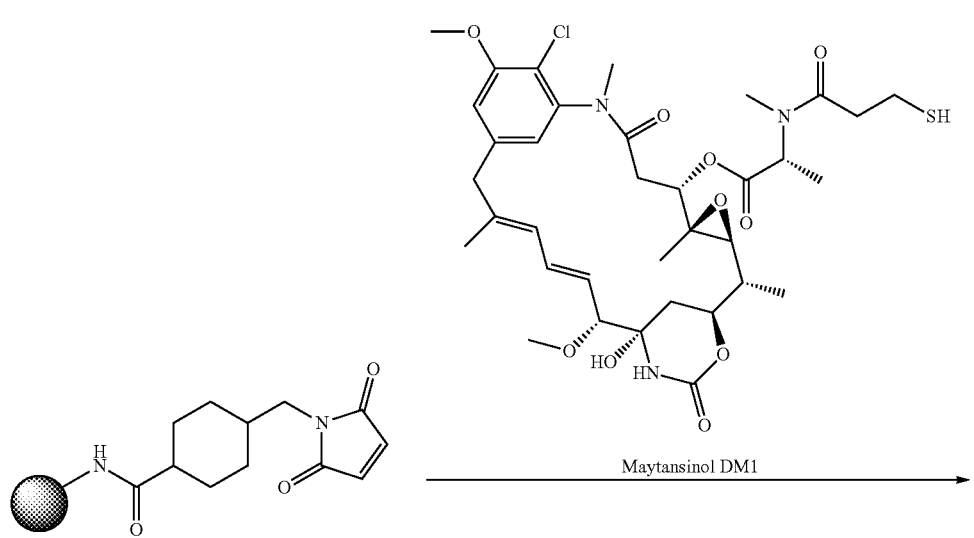

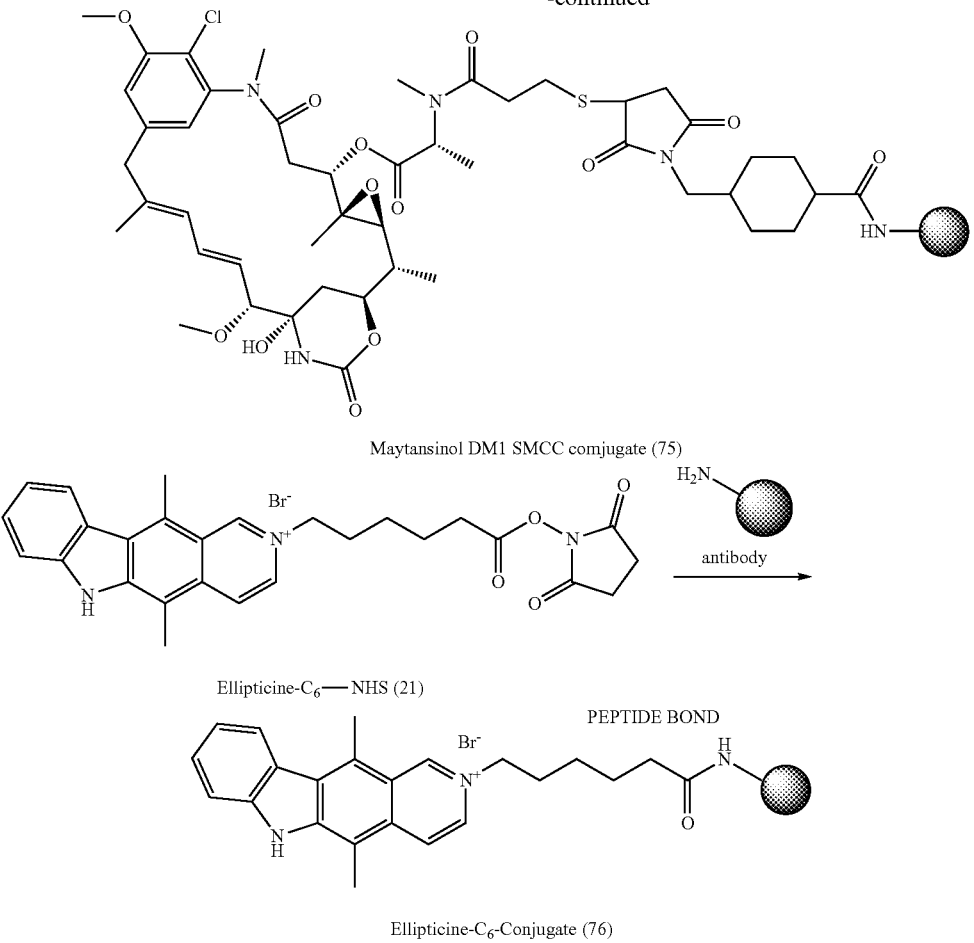

Maytansinol DM1 SMCC comjugate (75)

Ellipticine-C<sub>6</sub>—NHS (21)

Ellipticine-C<sub>6</sub>-Conjugate (76)

Example 27—Expression and Purification of a Single-Chain Fv Antibody Fragment Bearing Multiple, Well-Dispersed, Surface Lysine Residues Construction of the Anti-HER2 Cytoplasmic-Expression scFv Clone, TCT The open reading frame (ORF) of the scFv C6.5 [Adams G P et al. Cancer Res, 2001, 61:4750-55], which is known to have multiple, well-spaced, surface lysine residues, was cloned into the expression vector pET32 Xa/LIC (Novagen) carrying the ORF of thioredoxin as a fusion tag to enable the cytoplasmic expression of the protein. To facilitate the cleavage of the fusion tag at low cost and effective detection and monitoring of the resulting scFv, the following features were engineered into the vector:

a) TEV protease cleavage site, downstream of the Factor Xa cleavage site
b) Linker region between the TEV protease cleavage site and the C6.5 ORF. Without this the TEV protease fails to cleave, probably due to the fact that the structure of scFv C6.5 sterically hinders access to its cleavage site.
c) T7 tag sequence at the C-terminus of the C6.5. This Tag was chosen because it lacks lysine residues.

The resulting protein was called scFv (TCT) (Tev cleavage site, C6.5, T7 tag). The DNA sequence can be found below:

```
KEY:
Bold = Residual Ser left after TEV cleavage
Underlined = Linker region (GSGGSG)-
SEQ ID NO: 8
Unformatted = C6 sequence
Bold italics = T7 tag sequence
DNA sequence of cleaved TCT
                                    [SEQ ID NO: 1]
AGCGGTAGCGGAGGTAGCGGACAGGTGCAGCTGGTGCAGTCTGGGGCAGA

GGTGAAAAAGCCCGGGGAGTCTCTGAAGATCTCCTGTAAGGGTTCTGGAT

ACAGCTTTACCAGCTACTGGATCGCCTGGGTGCGCCAGATGCCCGGGAAA

GGCCTGGAGTACATGGGGCTCATCTATCCTGGTGACTCTGACACCAAATA

CAGCCCGTCCTTCCAAGGCCAGGTCACCATCTCAGTCGACAAGTCCGTCA

GCACTGCCTACTTGCAATGGAGCAGTCTGAAGCCCTCGGACAGCGCCGTG

TATTTTTGTGCGAGACATGACGTGGGATATTGCAGTAGTTCCAACTGCGC

AGCGTGGCCTGAATACTTCCAGCATTGGGGCCAGGGCACCCTGGTCACCG

TCTCCTCAGGTGGAGGCGGTTCAGGCGGAGGTGGCTCTGGCGGTGGCGGA

TCGCAGTCTGTGTTGACGCAGCCGCCCTCAGTGTCTGCGGCCCCAGGACA

GAAGGTCACCATCTCCTGCTCTGGAAGCAGCTCCAACATTGGGAATAATT

ATGTATCCTGGTACCAGCAGCTCCCAGGAACAGCCCCCAAACTCCTCATC
```

```
-continued
TATGGTCACACCAATCGGCCCGCAGGGGTCCCTGACCGATTCTCTGGCTC

CAAGTCTGGCACCTCAGCCTCCCTGGCCATCAGTGGGTTCCGGTCCGAGG

ATGAGGCTGATTATTACTGTGCAGCATGGGATGACAGCCTGAGTGGTTGG

GTGTTCGGCGGAGGGACCAAGCTGACCGTCCTA

ATGGCTAGCATGACTGGTGGACAGCAAATGGGT
```

Amino Acid sequence of cleaved TCT
[SEQ ID NO: 2]

```
S G S G G S G Q V Q L V Q S G A E V K K P G E S L
K I S C K G S G Y S F T S Y W I A W V R Q M P G K
G L E Y M G L I Y P G D S D T K Y S P S F Q G Q V
T I S V D K S V S T A Y L Q W S S L K P S D S A V
Y F C A R H D V G Y C S S S N C A A W P E Y F Q H
W G Q G T L V T V S S G G G G S G G G G S G G G G
S Q S V L T Q P P S V S A A P G Q K V T I S C S G
S S S N I G N N Y V S W Y Q Q L P G T A P K L L I
Y G H T N R P A G V P D R F S G S K S G T S A S L
A I S G F R S E D E A D Y Y C A A W D D S L S G W
V F G G G T K L T V L M A S M T G G Q Q M G
```

Number of Amino acids: 272

Molecular weight: 28,160 Da

Theoretical PI: 7.54

Extinction coefficient: 65 235

Bacterial Expression in 15 L Bioreactor of the Anti-HER2 Cytoplasmic-Expression scFv Clone, scFv (TCT)

TCT was produced in SHUFFLE® T7 Competent *E. coli* (NEB). Four to five single colonies of transformed cells grown overnight on selective agar plate were first inoculated in 5 ml of selective 2TY medium+1% glucose. 1 µl from the culture that was observed to be growing faster was transferred to fresh selective 5 ml cultures of 2YT+1% glucose and allowed to grow at 30° C. for about 10 hours. These steps were taken to ensure that the cell growth does enter the lag phase for too long and hence ensure the plasmid stability within growing cells.

The next day, a selective 0.5 L+1% glucose preculture was inoculated with one of two 5 ml cultures. Medium used, Supercharged Terrific Broth [12 g/l tryptone, 24 g/l yeast extract, 9 g/l Na$_2$HPO$_4$, 2.2 g/l KH$_2$PO$_4$, 2.6 g/l NH$_4$Cl, 0.7 g/l Na$_2$SO$_4$ 1 g/l NaCl, 5 g/l glycerol]. Adjust pH to 7.4, autoclave and add 2 mM MgSO$_4$ After 3.5 hrs, the preculture (OD$_{600}$ 0.8-1.2) was transferred to a 15 L Fermenter (Applikon P1000) containing 14.5 L of selective (carbenicillin 100 ug/L) Supercharged Terrific Broth+0.5% glucose and 0.05 ml/L antifoam PPG 2025. The stirrer blade speed was adjusted to between 200-500 RPM to ensure adequate dissolving of oxygen in the medium. Typically 200 RPM initially and 400-500 post-induction. The initial temperature was either 37° C. or 30° C. depending on the doubling time of the culture (typical culture doubling times (Td) 35-55 minutes).

When the culture OD$_{600}$~1.0 the culture temperature control was adjusted to 26° C. and allowed about 30 minutes to stabilise. Induction was carried out typically 3.5-5 hours after inoculation with 15 ml of 50 mM IPTG. Final IPTG culture concentration 50 uM. It is very important that the cells are well adjusted to 26° C. before induction with a low concentration of IPTG otherwise the amount of soluble protein produced decreases significantly. The fermenter was coupled with an automatic antifoam dispenser which is triggered when foam builds up.

The culture was allowed to grow for about 16 hours and harvested using Beckman JLA8.1000 for 15' @ 5KRPM. The final OD$_{600}$=35.7.

3) Protein Purification

Cells were resuspended in Lysis buffer (40 mM Tris-HCl pH 8, 750 mM NaCl, 2 mM Imidazole) and frozen in liquid nitrogen. On lysis day, the frozen cells were thoroughly thawed and the lysis buffer was adjusted to have a final concentration of 2M Urea. Urea and a high concentration of NaCl were employed to ensure better IMAC purification. The 2M Urea-treated scFv was probed with 1D NMR to ensure that the structure of scFv (TCT) was not affected.

Complete EDTA free tablets (Roche Diagnostics, 1/100 ml lysis solution) and Benzonase (Novagen >99 purity, 5 ul/100 ml lysis solution) were added. Lysis was performed with a Constant Cell Disruption Systems (model TS5) coupled to a chiller keeping the cell disruption chamber at 4° C. Cell disruption was achieved three times over at a pressure of 27 kpsi. Total volume of the lysate amounted at 2 L.

The Lysate was initially spun using an Eppendorf centrifuge 5810 R at 4000 rpm for 40 minutes to remove the bulk of cell debris and then twice using a Sorvall RC 6+, rotor F21-8×50 at 17 000 rpm for 40 minutes. The clarified supernatant was then filtered through 0.22 urn PES filter (Corning) under vacuum.

IMAC was then performed using the HisPur Ni-NTA resin from Thermo scientific under gravity flow in columns. The column was equilibrated with lysis buffer containing 2M urea. The clarified supernatant was passed through the column twice, followed by 10 bed volumes wash with the lysis buffer. The resin was then further washed with 10 bed volumes of Wash buffer 1 (40 mM Tris-HCl pH 8, 750 mM NaCl, 2M Urea, 10 mM Imidazole) and then Wash buffer 2 (40 mM Tris-HCl pH 8, 750 mM NaCl, 2M Urea, 30 mM Imidazole) until there was no significant absorbance at OD 280 nm.

The protein was then eluted ((40 mM Tris-HCl pH 8, 750 mM NaCl, 250 mM Imidazole) until there was no reading at OD 280 nm. The eluate was then dialysed extensively in TEV cleavage buffer (50 mM tris-HCl pH8, 150 mM NaCl). The protein solution was then adjusted to a concentration of about 2 mg/ml and reduced glutathione was added to a final concentration of 3 mM. In-house produced TEV protease, fused with a polyhistidine tag was added at 0.15 mg/100 mg of fusionscFv (TCT)(fTCT) and allowed the cleavage to proceed for 14-18 hours on a rolling incubator at 4° C.

The cleaved protein solution was allow to pass 3 times through Ni-NTA resin. The cleaved scFv (TCT) flowed through while the thioredoxin fusion tag, TEV protease and other proteins remain bound to the resin. A summary SDS-PAGE of the purification is shown in FIG. 2

TCT scFv was dialysed into Storage buffer (20 mM Sodium Acetate pH5, 150 mM NaCl) and then SEC was carried out to eliminate high molecular weight contaminants and scFv (TCT) soluble aggregates (FIG. 3). This buffer was selected over other buffers that do not contain amino groups because scFv (TCT) was shown to be stable in it after being subjected to multiple freeze-thaw cycles.

Example 28—Protein Engineering, Expression and Purification of a Single-Chain Fv Antibody Fragment in Order to Bear Multiple, Well-Dispersed, Surface Lysine Residues An antibody fragment that does not possess sufficient well-spaced lysine residues and demonstrates poor conjugation properties (typical DARs<5) can be modified by directed mutagenesis to bear a configuration similar to the scFv (TCT). Using general and accepted antibody and protein structural concepts from the literature [Alzari P M et al Annual Rev. Immunol. 1988. 6:555-80; Davies D R & Metzger H. Annual Rev Immuno. 1983. 1:87-117; Mariuzza R A et al. Annual Review Biophys. & Biophysical Chem, 1987, 16:139-59] in combination with 3-dimensional molecular modelling software (e.g. PyMOL, Schrodinger KK, Japan) and alignment tools such as Clustal, positions within the protein primary sequence can be identified that can be mutated to lysine residues, where lysine residues are known to be well-tolerated at that position (using databases such as IMGT or Kabat) or are known (from a solved 3D structure) or predicted (using software such as Phyre) to be at the protein surface (FIG. 1). The well-conserved structure of the immunoglobulin fold can be applied to antibodies and antibody-like domains. Modified antibody fragments with newly introduced, removed, or replaced lysine residues can be expressed and purified as described in example-27 and tested for thermostability and chemical stability as well as binding function, before accepting the modification as successful.

Example 29—Bioconjugation of Ellipticine Derivatives onto a Single-Chain Fv Antibody Fragment Bearing Multiple, Well-Dispersed, Surface Lysine Residues Ellipticine Ellipticine-$C_6$—NHS (compound 21) was conjugated to scFv-TCT in PBS at pH 8.0 in 6% MeCN with varying amounts of DMSO (either 14% or 6%) and two different sets of excess drug equivalents. The NHS was added in 5 equivalent portions for reaction 1 and in 2.7 equivalent portions for reactions 2 and 3. In more detail, Ellipticine-NHS was dissolved in anhydrous DMSO to obtain a clear yellow/orange 50 mM stock solution. A scFv (TCT) stock solution in PBS pH 8.0, stored at 4° C., was diluted in degassed PBS pH 8.0 pre-equilibrated with 6% MeCN and either 14% or 6% DMSO. The NHS was added in portions of either 5 or 2.7 equivalents every 75 min whilst mixing on a vortex at room temperature. 4 hr from completion of addition, the samples were recovered by centrifugation (2.5 min, 11 krpm). The supernatant was recovered and purified by zeba columns (Pierce) pre-equilibrated with the same buffer as the reaction mixture of each sample. The samples were then dialysed over 4000× in 6% MeCN/PBS pH 7.3 overnight at 4° C. then 8000×. The samples were recovered and analysed by SDS-PAGE (FIG. 4), UV/Vis spectroscopy (FIG. 5) and densitometry.

Conjugates became insoluble and precipitated out of solution once a certain DAR was obtained. As an example, sample 1 above contained small amounts of protein/conjugate following centrifugation and even less once purification was attempted via zeba columns, indicating that the residual soluble conjugate was very hydrophobic and adhered to the column. There was a significant amount of protein/conjugate in the pellet sample of this reaction, as seen in mainly the fluorescent gel, i.e. recovery of soluble conjugate was low. This is also supported by the UV/Vis data. Precipitation was far less pronounced for samples 2 and 3 which had 16 equivalents of drug compared to the 32 of reaction 1. The pellet samples were less intense and the soluble material more prominent both on Coomassie and fluorescence detection. There is an indication that sample 2 migrated less far on the gel than sample 3 supporting the rationale that increased amount of DMSO can lead to increased solubility of the drug, thereby increasing the efficiency of the reaction and leading to higher DARs. Overall, reaction 2 had less NHS equivalents than 1, leading to lower DARs which appear to be more soluble, but at the same time having the same number of equivalents as 3, thereby supporting the organic solvent argument.

DARs were calculated for these reactions using their UV/vis absorption spectra in buffer (FIG. 5) and the experimentally obtained extinction coefficient for Ellipticine acid. The ratio obtained spectrophotometrically was corrected using the densitometry data of the fluorescent gel (% conjugated drug vs % unreacted/non-covalently bound drug, Table 4). A drug:antibody ratio of over 5 was obtained under the best reaction conditions despite the poor solubility of the drug. The overall protein recovery was acceptable.

Quantification of Drug to Antibody Loading of an scFv-Ellipticine Conjugate

TABLE 4

Final DARs for scFv (TCT)-Ellipticine ADCs.

| No | Reaction | Final DAR |
|---|---|---|
| 1 | 32 equivalents, 14% DMSO | 5.4 |
| 2 | 16 equivalents, 14% DMSO | 5.1 |
| 3 | 16 equivalents, 6% DMSO | 3.9 |

PEG-Ellipticine

ScFv-TCT was conjugated to another Ellipticine-NHS derivative with a short PEG chain to increase water solubility (compound 23). The conjugation was carried out in parallel with Ellipticine-NHS as a control, using the best conditions for Ellipticine in order to obtain a DAR 5, which was the maximum obtained in the soluble phase. The reactions were set up as described previously, using 99% pure scFv. ScFv in PBS pH 8.0 was diluted in PBS pH 8.0 pre-equilibrated with DMSO (14%) and MeCN (6%), and then incubated for 5 min on a vortex, shaking gently at RT. The crude NHS drugs were dissolved in anhydrous DMSO to a 50 mM stock solution and were added in two portions over 15 min and incubated for a further 2 hrs at RT. The samples were recovered by centrifugation and stored at 4° C. before being purified using zeba columns pre-equilibrated with 14% DMSO/6% MeCN/PBS pH 7.3. The pellets were resuspended in buffer and gel loading buffer and all samples were analysed by SDS-PAGE (Coomassie and fluorescence, FIG. 6) and UV/Vis spectroscopy. The pellet of 2 could not be re-dissolved.

Comparing Ellipticine with PEG-Ellipticine, it is clear that under the same reaction conditions (1 and 2), the PEG derivative leads to higher recovery of soluble conjugate/protein (compound 73). The bands for 2 are very faint in comparison to 1 both in the Coomassie and the fluorescence detection. Comparing the three reaction conditions where the number of equivalents was investigated to raise the DAR, there was a shift on the gel indicating that perhaps 4 has a higher DAR than 3 and 1. Protein recovery is less for 4Z than the other two indicating that again, the maximum loading has been reached, at which point the higher DAR conjugates precipitate out of solution.

Using the UV/Vis in combination with the densitometry data (to calculate % non-covalent binding) DAR values were calculated as follows: (1): 4.1 (2): 2.0 (3): 5.1 and (4): 4.3 (Table 5). This confirmed that the PEG Ellipticine resulted in two-fold higher protein recovery and up to two-fold higher DAR compared to Ellipticine. Conjugate precipitation seems to have improved.

TABLE 5

Final DARs for scFv (TCT)-PEG-Ellipticine ADCs (compound 73)

| No | Reaction | Final DAR |
|---|---|---|
| 1 | 20 equivalents, 14% DMSO, 6% MeCN | 4.1 |
| 2 | 20 equivalents, 14% DMSO, 6% MeCN | 2.0 |
| 3 | 32 equivalents, 14% DMSO, 6% MeCN | 5.1 |
| 4 | 64 equivalents, 14% DMSO, 6% MeCN | 4.3 |

The conjugation to Ellipticine was carried out on a whole IgG as a comparison to the scFv (TCT) under identical conditions. The SDS-PAGE gels indicate at least equivalent conjugation fluorescence (FIGS. 7 and 8), hence similar DARs.

Lysosomally-Releasable Ellipticine

A cleavable dipeptide Ellipticine-NHS drug (compound 29) was conjugated to scFv (TCT) to obtain conjugates with various DARs. The reaction was controlled to obtain products with low, medium and high DARs. Initially, the hydrolysis rate of the pure isolated cleavable dipeptide Ellipticine-NHS was determined in various buffer conditions. The conditions that gave a reasonable hydrolysis rate, i.e. not too fast so that the NHS would hydrolyse to the acid before it reacted with the lysines and not too slow so that the reaction would take too long to complete. Other factors that were taken into account were the stability of the antibody in the buffer/pH/organic solvent, the stability of the drug and the concentration of the drug in the buffer. The latter is a crucial parameter; the more concentrated the drug is in the solution, the more the hydrolysis rate will decrease. Therefore, the concentration needs to be controlled to allow for an efficient rate of hydrolysis. The conditions identified and carried forward were:

Buffer—bicarbonate buffer with NaCl at pH8.8 with 20% DMSO and 30% glycerol;
Temperature—25° C.;
Mixing conditions—Thermomixer 1000 rpm;
Antibody at 1 mg/ml,
Cleavable dipeptide Ellipticine-NHS—8 equivalent addition portions; and,
NHS-drug addition rate (every 70-90 minutes).

Typically, scFv (TCT) was defrosted on the thermomixer at 4° C., then the temperature of the aliquot was slowly raised to 20° C. Any precipitate was spun down before using.

A cleavable dipeptide Ellipticine-NHS (compound 29) 100 mM stock solution was made up in anhydrous filtered DMSO. Any precipitate was collected by centrifugation. Bicarbonate buffer pH 8.8 was combined with filtered DMSO and glycerol in eppendorf microtubes and the buffer was equilibrated on the thermomixer at 4° C., then the temperature of the aliquot was raised to 20° C. whilst mixing at 1000 rpm. The antibody was added and equilibrated further (20° C., 1000 rpm) for 10 mins before the addition of the cleavable dipeptide Ellipticine-NHS was started. This was carried out by adding 8 equivalents of the NHS-drug DMSO stock and inverting to mix every 70 mins, before replacing on the thermomixer and mixing at 25° C., 1000 rpm. The total number of equivalents used depended on the required DAR. The samples were left on the thermomixer for a further 2 hrs after the last addition. The samples were then collected by centrifugation (2.5 mins, 11 krpm). The only visible precipitation was in the sample with the highest number of drug equivalents and that was very low.

All samples were initially passed through a Zeba column (Pierce) pre-equilibrated with 10% IPA/PBS before being further purified on the HPLC-SEC with 20% IPA/PBS pH7, 25° C. and analysed by SDS-PAGE, HPLC-SEC, UV/Vis spectroscopy and mass spectrometry as described above.

The unconjugated and conjugated scFv (TCT) were analysed by HPLC-size exclusion chromatography using a Tosoh TSKGel G2000WxI column. The ScFv has a retention time correlating to a MW of around 30 KDa. The conjugates all eluted earlier, indicating a larger molecular weight (due to varying drug loads), but as primarily monomeric peaks, indicating little or no aggregation.

Mass spectrometric analysis was performed by SGS M-Scan. Conjugates, as well as ScFv-TCT (control), were analysed by both MALDI-MS and then further analysed by LC-MS. All samples gave well resolved peaks.

Example 30—Bioconjugation of Doxorubicin Derivatives onto a Single-Chain Fv Antibody Fragment Bearing Multiple, Well-Dispersed, Surface Lysine Residues (a) One-Step Conjugation with Doxorubicin-NHS Derivative Doxorubicin derivatives (compounds 7, 10, 16) with an NHS reactive group were conjugated to scFv (TCT) to obtain conjugates with various DARs. The reaction was controlled to obtain products with low, medium and high DARs. Initially, the hydrolysis rate of the pure isolated Doxorubicin-NHS derivatives was determined in various buffer conditions. The conditions that gave a reasonable hydrolysis rate, i.e. not too fast so that the NHS would hydrolyse to the acid before it reacted with the lysines and not too slow so that the reaction would take too long to complete. Other factors that were taken into account were the stability of the antibody in the buffer/pH/organic solvent, the stability of the drug and the concentration of the drug in the buffer. The latter is a crucial parameter; the more concentrated the drug is in the solution, the more the hydrolysis rate will decrease. Therefore, the concentration needs to be controlled to allow for an efficient rate of hydrolysis. The conditions identified and carried forward were:

Buffer—bicarbonate buffer with NaCl at pH7.8 with 20% DMSO, 30% glycerol and 1% Tween;
Temperature—25° C.;
Mixing conditions—Thermomixer 1000 rpm;
Antibody at 1 mg/ml;
Doxorubicin-NHS derivatives—2 equivalent addition portions; and,
NHS-drug addition rate—every 70-90 minutes.

Typically, scFv (TCT) was defrosted on the thermomixer at 4° C., then the temperature of the antibody aliquot was slowly raised to 20° C. The aliquots were spun down to collect any precipitate before using.

Doxorubicin-NHS derivatives 100 mM stock solution were made up in anhydrous filtered DMSO. Any precipitate was collected by centrifugation. Bicarbonate buffer pH 8.8 was combined with filtered DMSO and glycerol in eppendorf microtubes and the buffer was equilibrated on the thermomixer at 4° C., then the temperature of the aliquot was raised to 20° C. whilst mixing at 1000 rpm. The antibody was added and equilibrated further (20° C., 1000 rpm) for 10 mins before the addition of the Doxorubicin-NHS derivatives was started.

This was carried out by adding 4 equivalents of the NHS-drug DMSO stock and inverting to mix every 70 mins, before replacing on the thermomixer and mixing at 25° C., 1000 rpm. The total number of equivalents used depended on the required DAR. The samples were left on the thermomixer for a further 2 hrs after the last addition. The samples were then collected by centrifugation (2.5 mins, 11 krpm). The only visible precipitation was in the sample with the highest number of drug equivalents and that was very low.

All samples were initially passed through a Zeba column (Pierce) pre-equilibrated with 10% IPA/PBS before being further purified on the HPLC-SEC with 20% IPA/PBS pH7, 25° C. and then analysed by SDS-PAGE, HPLC-SEC, UV/Vis spectroscopy and mass spectrometry as described above.

The unconjugated and conjugated scFv (TCT) were analysed by HPLC-size exclusion chromatography using a Tosoh TSKGel G2000WxI column. The ScFv has a retention time correlating to a MW of around 30 KDa. The conjugates all eluted earlier indicating a larger molecular weight (due to varying drug loads), but as primarily monomeric peaks, indicating little or no aggregation.

Mass spectrometric analysis was performed by SGS M-Scan. Conjugates, as well as ScFv-TCT (control), were analysed by both MALDI-MS and then further analysed by LC-MS. All samples gave well resolved peaks. The DAR was determined using the extinction coefficient for the doxorubicin drug and antibody (b) Two-Step Conjugation to a Doxorubicin-Maleimide Derivative To conjugate Doxorubicin maleimide derivatives (compounds 48, 12) onto the antibody, the antibody's native lysines were chemically converted to firstly a protected thiol which was subsequently reduced to obtain the free thiol. The free thiols could then be reacted with maleimide derivatives of Doxorubicin to obtain conjugates containing thioether bonds.

The first step of introducing the thiols onto the antibody was optimised. This involved the conjugation of the SPDP linker onto the antibody to form an amide bond between the linking group and the antibody. A lysine-optimised scFv facilitated the production of high SPDP-substituted conjugates for subsequence conjugation of a maleimide-derived drug.

Overall, SPDP conjugated well even at lower pH (7 or 8). When reduced with sufficient TCEP (115 molar excess) it gave a SH:scFv ratio of up to 12. The SPDP conjugation was carried out to introduce various ratios of SPDP linker per antibody.

The antibodies, both at 1 mg/ml, C6.5 and HMFG1 were diluted into degassed PBS pH8 containing 1 mM EDTA, 3% DMSO and 6% MeCN. A fresh colourless solution of SPDP was prepared in anhydrous DMSO and the required amount was added to the antibody solution. The samples were incubated on a roller for 3 hrs at RT and at 4° C. overnight. The samples were collected by centrifugation when minimal precipitation was observed. The excess/unconjugated SPDP linker was removed using Zeba spin columns (ThermoScientific) and buffer exchanging into degassed PBS pH8 with 1 mM EDTA. The UV/vis spectra of the samples were recorded.

For the reduction of the linker to release the free thiol on the antibody and at the same time the pyridine-2-thione, the following was carried out. TCEP was first dissolved (fresh) in water to make up a 500 mM stock solution. The SPDP linked samples were incubated with 115 equivalents of TCEP for 20 mins at 37° C. The samples were collected by centrifugation and immediately chilled on ice. The UV/vis spectra of the crude samples were recorded before removing the excess TCEP and pyridine-2-thione using zeba desalting columns using 3% DMSO/6% MeCN in degassed PBS pH7 with 1 mM EDTA as the eluent.

At this point, the efficiency of the SPDP conjugation was determined. The quantity of the released pyridine-2-thione in the crude reduced sample was determined using the spectrophotometric data. The λmax for pyridine-2-thione is 343 nm and the extinction coefficient $8080M^{-1} cm^{-1}$. The extinction coefficient at 280 nm is $5100M^{-1} cm^{-1}$ was used to correct the absorption at 280 nm. The concentration of the thione in the crude reduced solution was calculated using the A343 nm and using this concentration corrected the absorption at 280 nm to account for the thione absorption. The antibody concentration was calculated and the ratio of the SPDP:Ab was determined. The same process was repeated for the pre-reduction sample and this DAR was subtracted from the reduced sample DAR to obtain the actual SPDP:Ab ratio.

After the purification of the reduced sample, the following conjugates were obtained (Table 6) showing that up to 9 linkers could be conjugated to the scFv (TCT):

TABLE 6

Ratio of SPDP linker conjugated to a lysine-optimised scFv and a control IgG

| SPDP linker reaction ratio | C6.5 scFv | | HMFG1 IgG | |
|---|---|---|---|---|
| | Linker to Ab Ratio | Ab Recovery | Linker to Ab Ratio | Ab Recovery |
| 5 | 0.9 | 71% | 4.4 | 93% |
| 8 | 1.8 | 71% | 6.3 | 81% |
| 16 | 4 | 65% | 8.2 | 80% |
| 32 | 9 | 38% | 13 | 44% |

In another example, the above procedure was carried out similarly using 32 equivalents of SPDP and subsequently reducing the samples with 115 equivalents of TCEP. The antibody recovery in this case was much higher (92%). The reduced, purified and quantified samples were then conjugated to Doxorubicin. Doxorubicin maleimide and doxorubicin-PEG-maleimide were added to the antibody samples (in degassed PBS pH7/1 mM EDTA/3% DMSO/6% MeCN) at 2 equivalents each. The samples were incubated on a roller at RT for 3 hrs followed by 4° C. overnight. Samples were recovered by centrifugation and analysed by SDS-PAGE gel (FIG. 9) and UV/Vis spectroscopy.

The DAR for the Dox conjugates was calculated from the crude samples using UV/Vis spectroscopy and gel densitometry. From the spectroscopic data, the DAR was calculated using the Doxorubicin ε at 488 nm and 280 nm and the antibody's ε at 280 nm (Table 7).

TABLE 7

Ratio of SPDP linker conjugated to a lysine-optimised scFv and a control
IgG, followed by doxorubicine derivative conjugations

| SPDP linker reaction ratio | C6.5 scFv | | | | HMFG1 IgG | | | Dox-PEG: Ab DAR |
|---|---|---|---|---|---|---|---|---|
| | Linker to Ab Ratio | Ab Recovery | Dox: Ab DAR | Dox-PEG: Ab DAR | Linker to Ab Ratio | Ab Recovery | Dox: Ab DAR | |
| 32 | 7.5 | 92% | 3.5 | 1.6 | 6.5 | 50% | N/A | 2.5 |

The DAR was determined using the experimentally-determined molar extinction coefficient for the doxorubicin drugs (Table 7) and antibody and confirmed by mass spectrometry as described above.

Binding of High Ratio SPDP scFv Conjugates

C6.5 scFv was conjugated to SPDP as in example 30(b) with 16 equivalent excess reagent followed by reduction with 115 molar equivalents of TCEP to obtain a linker to antibody ratio of 5.4 (SPDP:scFv). This sample, as well as an unmodified control and a non-SPDP modified but reduced controls were used.

Ninety-six-well Immunosorb ELISA plates were coated with 10 µg/ml HER2-Fc in PBS, followed by the test samples, anti-myc IgG (Sigma) and anti-mouse peroxidase conjugate (Sigma). Extensive PBS washes were in between each layer and detection was with BM-Blue substrate. The plot (FIG. 10) shows that, the unmodified antibody with a $K_d$ of 25 nM showed a slightly reduced affinity for HER2 at 42 nM upon reduction but this was regained when the antibody was first conjugated with SPDP to introduce more thiols and then reduced, $K_d$=24.9 nM.

Example 31—Bioconjugation of P5 and Cemadotin Derivatives onto a Single-Chain Fv Antibody Fragment Bearing Multiple, Well-Dispersed, Surface Lysine Residues (A). ScFv (TCT)-Cemadotin Cemadotin-NHS (compound 2) was conjugated to scFv (TCT) to obtain conjugates (compound 69) with various DARs. The reaction was controlled to obtain products with low, medium, and high DARs. Initially, the hydrolysis rate of the pure, isolated Cemadotin-NHS was determined in various buffer conditions. The conditions that gave a reasonable hydrolysis rate, i.e. not too fast so that the NHS would hydrolyse to the acid before it reacted with the lysines and not too slow so that the reaction would take too long to complete. Other factors that were taken into account were the stability of the antibody in the buffer/pH/organic solvent, the stability of the drug, and the concentration of the drug in the buffer. The latter is a crucial parameter: the more concentrated the drug is in the solution, the more the hydrolysis rate will decrease. Therefore, the concentration needs to be controlled to allow for an efficient rate of hydrolysis. The conditions identified and carried forward were:

Buffer—bicarbonate buffer with NaCl at pH 8.8 with 20% DMSO;
Temperature: 20° C.;
Mixing conditions—Thermomixer 1000 rpm;
Antibody at 1 mg/ml;
Cemadotin/Cemadotin-C5 and P5C5, all NHS (16 equivalent addition portions); and,
NHS-drug addition rate (every 70-90 min).

Typically, scFv (TCT) was defrosted on the Thermomixer at 4° C., then the temperature of the aliquot was slowly raised to 20° C. Aliquots were spun down to collect any precipitate before using.

A Cemadotin-NHS 100 mM stock solution was made up in anhydrous filtered DMSO. Any precipitate was collected by centrifugation. Bicarbonate buffer pH 8.8 was combined with filtered DMSO in eppendorf microtubes and the buffer was equilibrated on a Thermomixer (with the temperature raised from 4° C. to 20° C., whilst mixing at 1000 rpm). The antibody was added and equilibrated further (20° C., 1000 rpm) for 10 min before the addition of the Cemadotin-NHS. This was carried out by adding 16 equivalents of the NHS-drug DMSO stock and inverting to mix every 70 min, before replacing on the Thermomixer and mixing at 20° C., 1000 rpm. The total number of equivalents used depended on the required DAR. The samples were left on the Thermomixer for a further 2 hrs after the last addition. The samples were then collected by centrifugation (2.5 min, 11 krpm). The only visible precipitation was in the sample with the highest number of drug equivalents and was very low.

All samples were purified from crude on the HPLC-SEC with 10% IPA/PBS pH 7, 20° C. and analysed by SDS-PAGE (FIG. 11), HPLC-SEC (FIG. 12), amino acid analysis (Table 8A-8C), mass spectrometry (FIGS. 13A-C, 14A-C, 15A-C, 16A-C, 17, 18, 19, 20, Tables 9 and 10) and binding ELISA (FIG. 21. In this example, the set up was:

Reaction 1—scFv-TCT-Cemadotin 16 equivalents;
Reaction 2—scFv-TCT-Cemadotin 48 equivalents; and
Reaction 3—scFv-TCT-Cemadotin 112 equivalents.

Figure 12A:
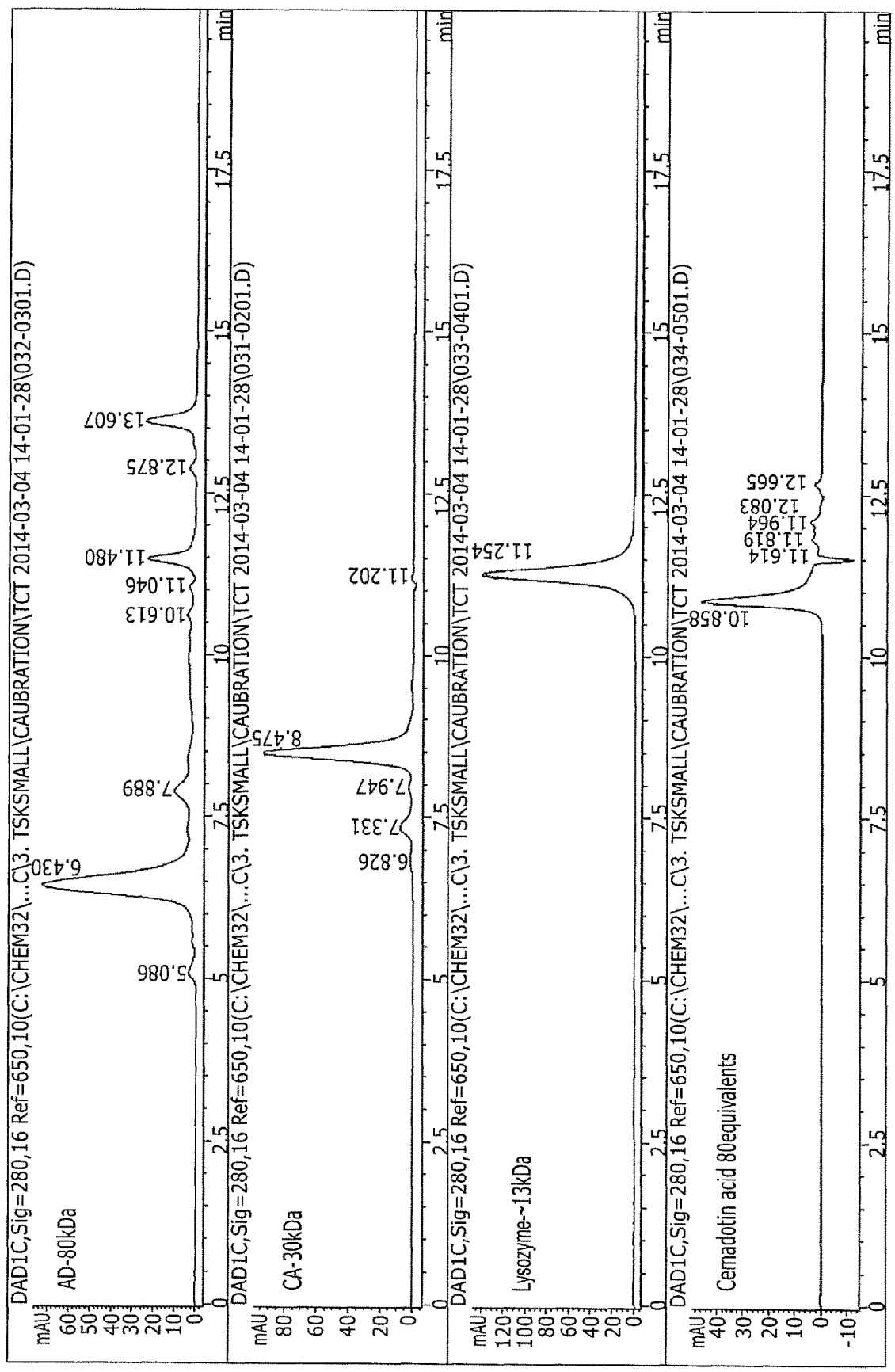
Figure 12B:
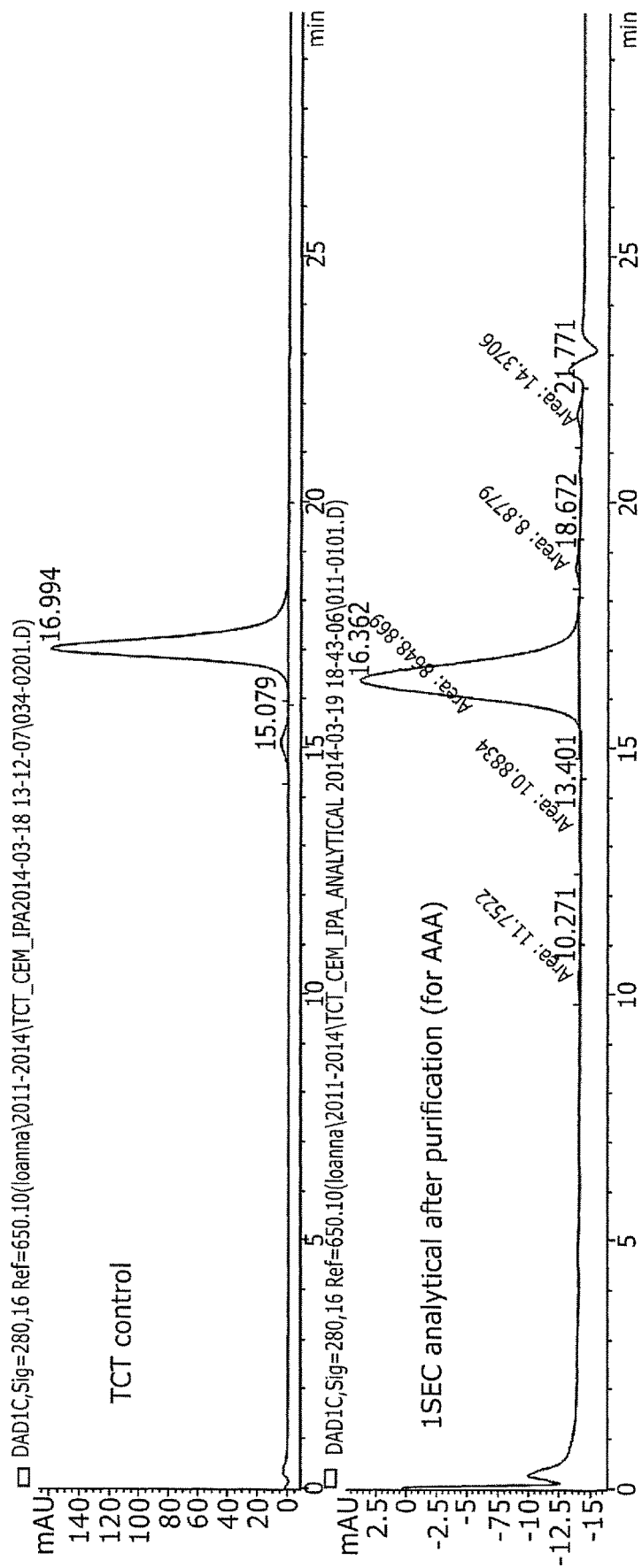
Figure 12C:
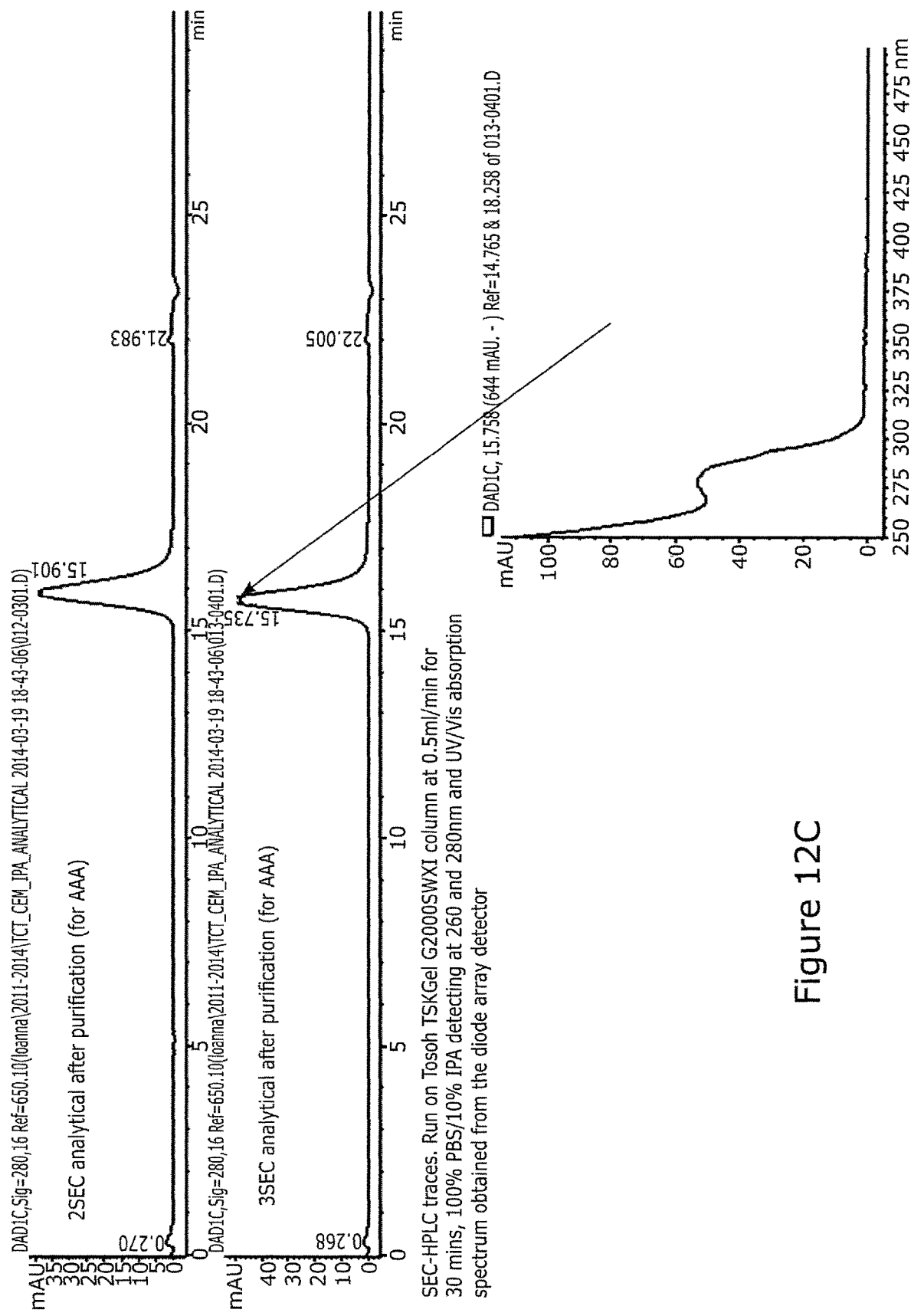

The unconjugated and conjugated scFv (TCT) were analysed by HPLCsize-exclusion chromatography using a Tosoh TSKGel G2000WxI column. The ScFv has a retention time of 15.5-16 min correlating to a MW of around 30 kDa. The three conjugates all eluted slightly and progressively earlier indicating a larger molecular weight (due to varying drug loads), but as single, sharp, monomeric peak, indicating no aggregation (FIG. 12A-C).

The DAR was accurately determined by Amino Acid Analysis (AAA) at Cambridge University's Protein and Nucleic Acid Chemistry Facility. From the AAA (Table 7A-C), the amount in mol of both the protein and the drug (due to the drug's fingerprint-release of 4-aminomethylbenzoic acid) can be derived and the DAR calculated (No mol drug/No mol protein). The concentration of the protein in the solution can be calculated by first calculating the conjugates molecular weight based on the DAR, and then subsequently converting the concentration obtained from AAA to mg/ml of protein. For example, in sample 1: scFv (TCT) is 28162 (MS), DAR is 3.9, and each Cemadotin molecule adds 667 onto the antibody. Therefore conjugate MW=28162+(3.9×

667)=30763. The concentration is 9.02 nmol/ml which is equal to 277 μg/ml of protein.

TABLE 8A

Sample: 1
Integer fit of measured mole ratios to expected values

| Amino acid | Expected value | Observed value | Closeness of fit to expected value |
|---|---|---|---|
| Cys | 6 | excluded | — |
| Asp | 15 | 15.35 | better than 5% |
| Thr | 14 | 13.67 | better than 5% |
| Ser | 46 | 44.48 | better than 5% |
| Glu | 22 | 21.72 | better than 5% |
| Gly | 44 | 43.97 | better than 5% |
| Ala | 17 | 17.21 | better than 5% |
| Val | 18 | 19.74 | within 5-10% |
| Met | 5 | excluded | — |
| Ile | 8 | 7.87 | better than 5% |
| Leu | 15 | 14.84 | better than 5% |
| Norleu std | | | — |
| Tyr | 14 | 13.42 | better than 5% |
| Phe | 7 | 6.86 | better than 5% |
| His | 3 | 2.98 | better than 5% |
| Lys | 12 | 12.72 | within 5-10% |
| Arg | 5 | 5.17 | better than 5% |
| Pro | 0 | excluded | — |
| Trp | 8 | 8.00 | (not determined) |
| Total | 259 | residues | |

| | | | Average of 2 runs |
|---|---|---|---|
| Total sample | 0.726 | nmoles | 0.72 |
| | 20.43 | ug | 20.32 |
| Concentration | 9.07 | nmoles/ml | 9.02 |
| | 255.42 | ug/ml | 254.00 |
| Cemadotin nmoles | 2.82 | 2.81 | 2.81 |
| DAR = | 3.90 | | |

TABLE 8B

Sample: 2
Integer fit of measured mole ratios to expected values

| Amino acid | Expected value | Observed value | Closeness of fit to expected value |
|---|---|---|---|
| Cys | 6 | excluded | — |
| Asp | 15 | 15.38 | better than 5% |
| Thr | 14 | 13.69 | better than 5% |
| Ser | 46 | 44.17 | better than 5% |
| Glu | 22 | 21.61 | better than 5% |
| Gly | 44 | 44.25 | better than 5% |
| Ala | 17 | 16.91 | better than 5% |
| Val | 18 | 20.00 | within 5-10% |
| Met | 5 | excluded | — |
| Ile | 8 | 8.04 | better than 5% |
| Leu | 15 | 14.93 | better than 5% |
| Norleu std | | | — |
| Tyr | 14 | 13.24 | within 5-10% |
| Phe | 7 | 7.07 | better than 5% |
| His | 3 | 3.03 | better than 5% |
| Lys | 12 | 12.62 | better than 5% |
| Arg | 5 | 5.05 | better than 5% |
| Pro | 0 | 0.00 | — |
| Trp | 8 | 8.00 | (not determined) |
| Total | 259 | residues | |

| | | | Average of 2 runs |
|---|---|---|---|
| Total sample | 0.806 | nmoles | 0.80 |
| | 22.69 | ug | 22.64 |
| Concentration | 6.20 | nmoles/ml | 6.18 |
| | 174.54 | ug/ml | 174.19 |
| Cemadotin nmoles | 6.66 | 6.54 | 6.60 |
| DAR = | 8.21 | | |

TABLE 8C

Sample: 3
Integer fit of a measured mole ratios to expected values

| Amino acid | Expected value | Observed value | Closeness of fit to expected value |
|---|---|---|---|
| Cys | 6 | excluded | — |
| Asp | 15 | 15.76 | better than 5% |
| Thr | 14 | 13.78 | better than 5% |
| Ser | 46 | 44.47 | better than 5% |
| Glu | 22 | 21.92 | better than 5% |
| Gly | 44 | 44.59 | better than 5% |
| Ala | 17 | 17.20 | better than 5% |
| Val | 18 | excluded | — |
| Met | 5 | excluded | — |
| Ile | 8 | 7.66 | better than 5% |
| Leu | 15 | 15.09 | better than 5% |
| Norleu std | | | — |
| Tyr | 14 | 13.71 | better than 5% |
| Phe | 7 | 6.81 | better than 5% |
| His | 3 | 3.06 | better than 5% |
| Lys | 12 | 12.81 | within 5-10% |
| Arg | 5 | 5.14 | better than 5% |
| Pro | 0 | 0.00 | — |
| Trp | 8 | 8.00 | (not determined) |
| Total | 259 | residues | |

| | | | Average of 2 runs |
|---|---|---|---|
| Total sample | 0.796 | nmoles | 0.79 |
| | 22.42 | ug | 22.21 |
| Concentration | 7.24 | nmoles/ml | 7.17 |
| | 203.78 | ug/ml | 201.88 |
| Cemadotin nmoles | 8.83 | 8.46 | 8.65 |
| DAR = | 10.96 | | |

Tables 8A-C. Summary of AAA results showing DARs of 3.9, 8.2 and 11 from the three conjugation reactions 1-3

Mass spectrometric analysis was performed by SGS M-Scan. Samples 1-3, as well as ScFv-TCT (control), were analysed by MALDI-MS and then further analysed by LC-MS. All samples gave well resolved peaks and these are summed up below.

Electrospray Ionisation, Mass Spectrometry (ESI-MS)

Equipment: Analyses were performed using a Waters Xevo Q-TOF (Quadrupole-Time of Flight (Q-TOF)) mass spectrometer coupled with a Dionex Ultimate 3000 MDLC system (SOPs MS900 to MS905 and HPLC012 and HPLC019).

Buffer exchange: The samples were buffer exchanged and concentrated, using Millipore Amicon Centrifugal filter units (10 kDa MWCO), into 0.05% (v/v) Formic acid.

Online ESI-MS analysis: aliquots of the TCT-Cemadotin samples were analysed using online HPLC/ES-MS analysis to provide data relating to the intact mass of the constituents as follows:

Instrument: Waters Xevo Q-ToF (Quadrupole-Time of Flight) G1 mass spectrometer equipped with a Dionex Ultimate 3000 MDLC system. Column: PLRP-S Column, Temperature: 60° C., Flow rate: 0.2 mL/minute, UV detection: 214 nm and 280 nm, Solvent A: 0.05% (v/v) Formic acid, Solvent B: 90% (aq) Acetonitrile containing 0.05% (v/v) Formic acid.

| Gradient: | |
|---|---|
| Time (mins) | % B |
| 0 | 20 |
| 5 | 55 |
| 65 | 75 |
| 73 | 75 |
| 73.1 | 98 |
| 83 | 98 |
| 83.1 | 20 |
| 111 | 20 |

The mass spectrometer was calibrated externally using Glu-Fibrinopeptide B, which was also utilised as a lockspray internal calibrant. The mass spectrometer was scanned from m/z 200 to 4000.

ESI-MS of TCT-Cemadotin 2 Samples

Figure 13A:
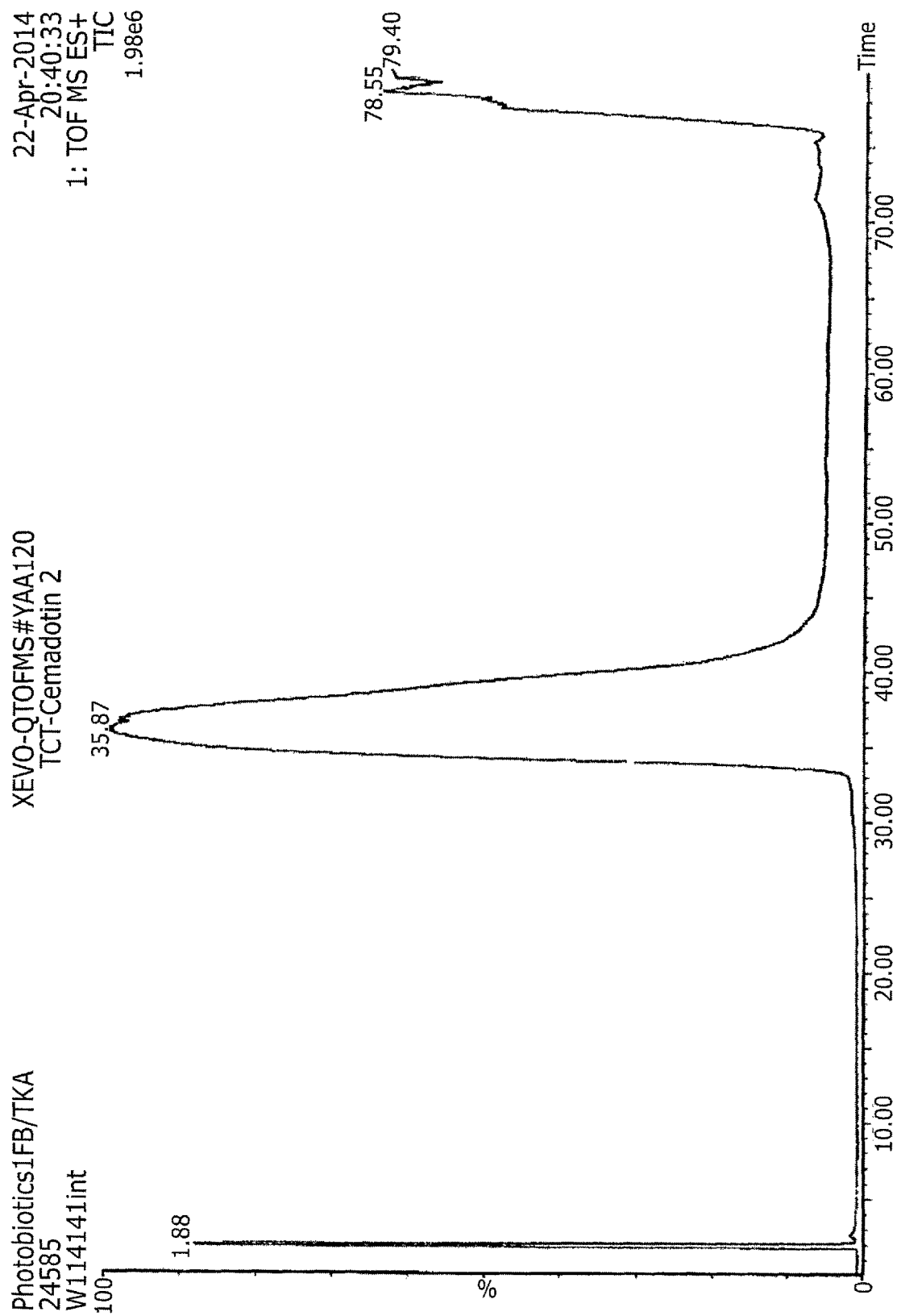
Figure 13B:
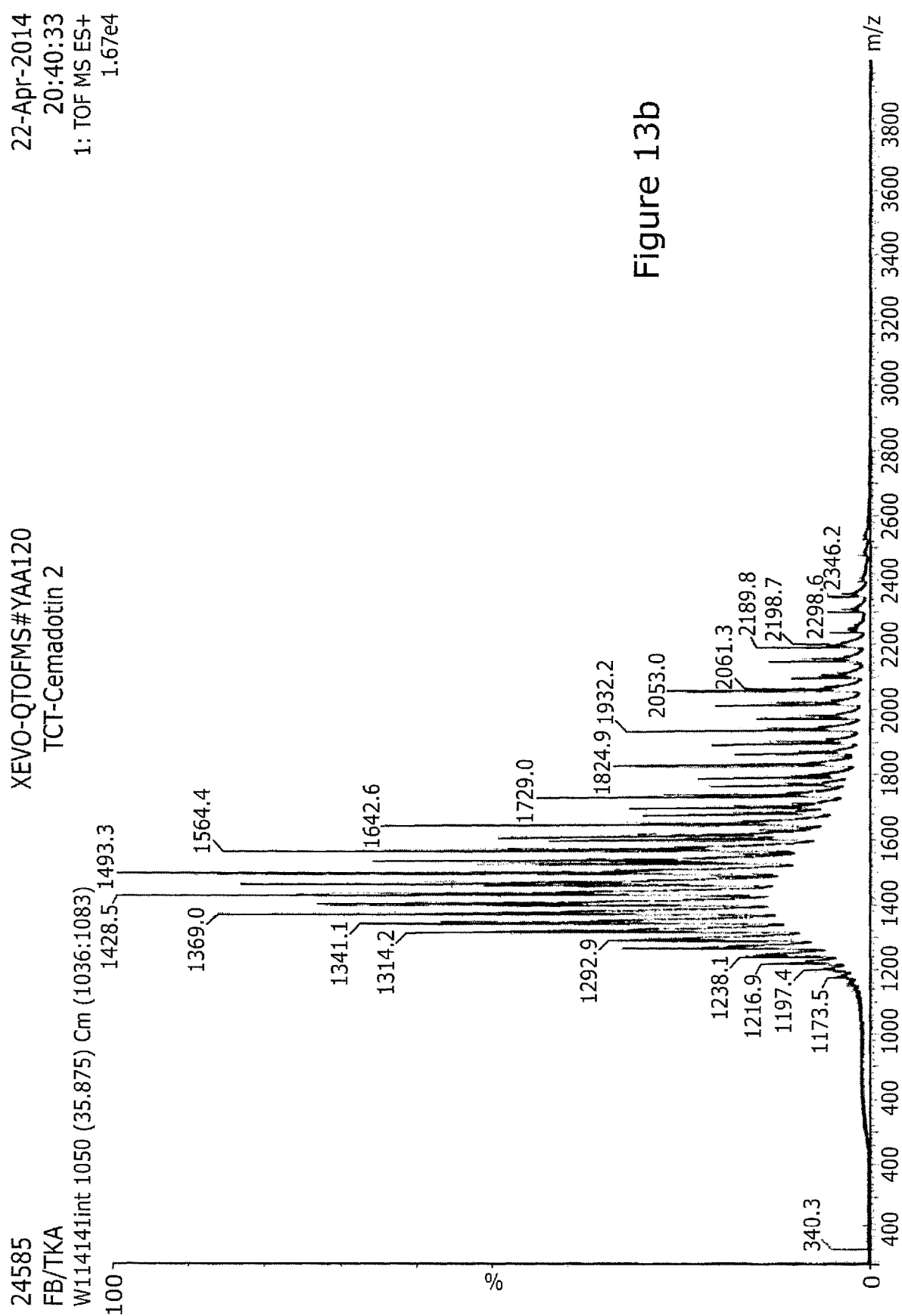
Figure 13C:
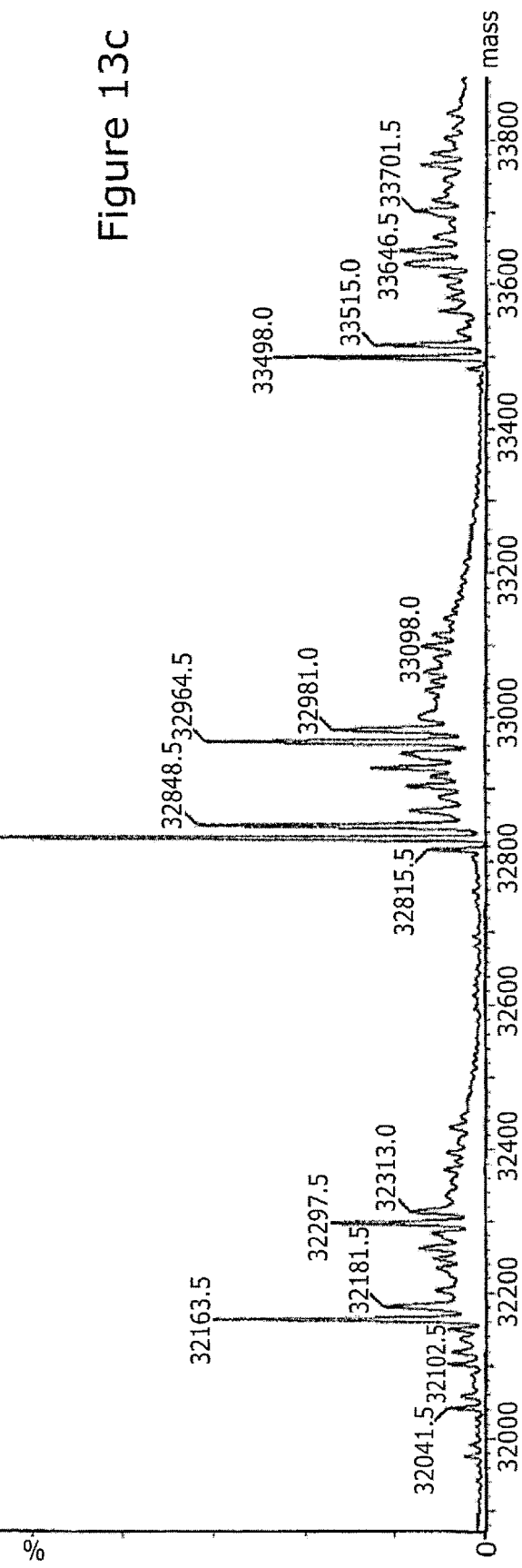

Aliquots of TCT-Cemadotin 2 samples were analysed using online HPLC/ES-MS analysis to provide data relating to the intact mass of the constituents. The Total Ion Current (TIC) chromatograms, spectra and transformed data samples TCT-Cemadotin 2 are shown below (FIG. 13A-C).

A major peak was observed in the TIC of the TCT-Cemadotin 2 sample eluting at 35.9 min. The zero-charge deconvoluted mass spectrum for this peak produced a series of major peaks at m/z 32,164, 32,831 and 33,498, which was consistent with the supplied theoretical mass of the scFv (TCT) molecule, together with 6-8 additions of the Cemadotin molecule. This correlated well with the AAA determination of the DAR of 8.21

ESI-MS of samples 1, 3 and TCT

Aliquots of samples TCT-Cemadotin 1, TCT-Cemadotin 3 and scFv (TCT) control were analysed using on-line HPLC/ES-MS analysis to provide data relating to the intact mass of the constituents. The Total Ion Current (TIC) chromatograms, spectra and transformed data samples are shown below (FIGS. 14 & 15).

Figure 16A:
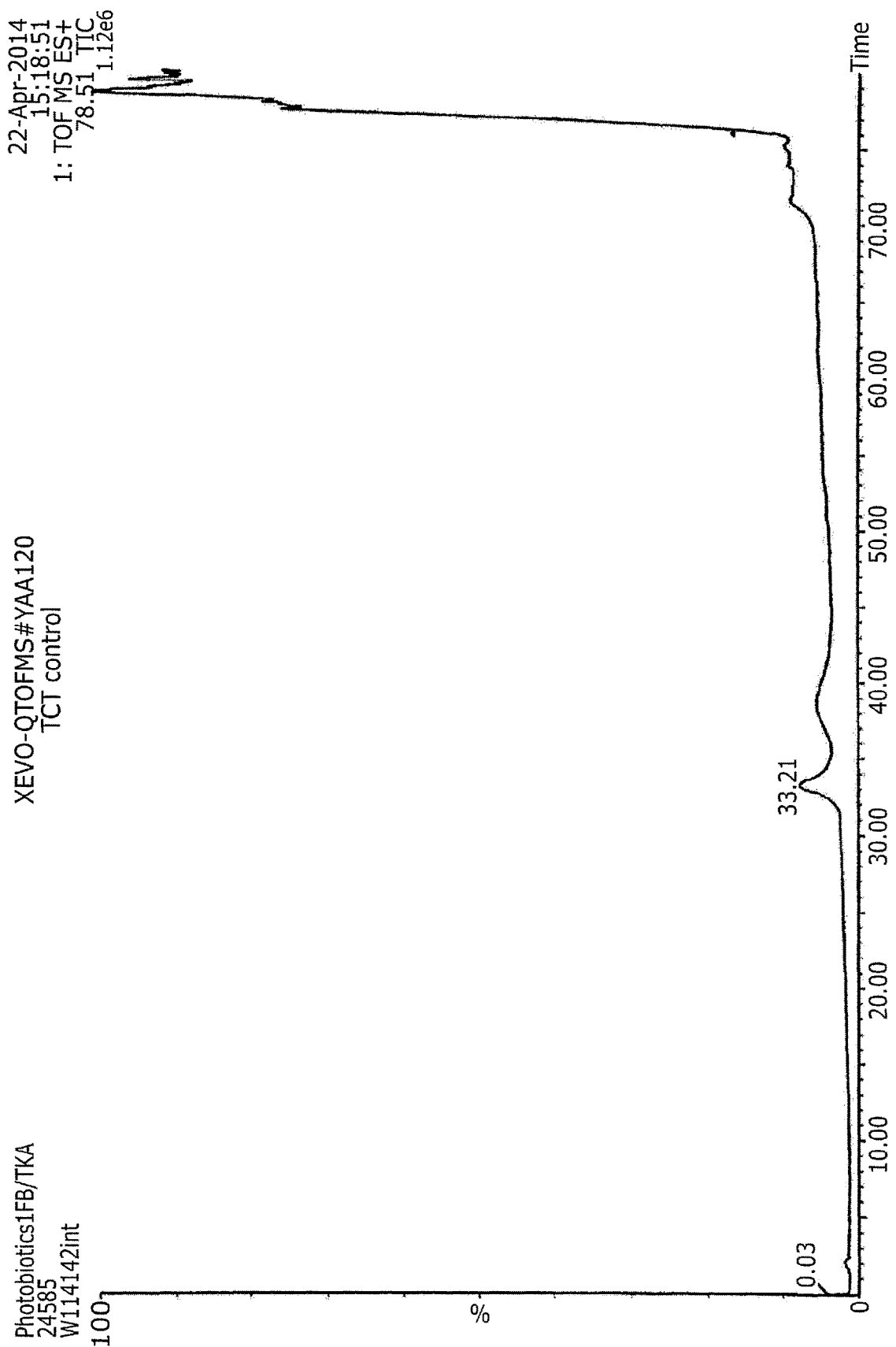
Figure 16B:
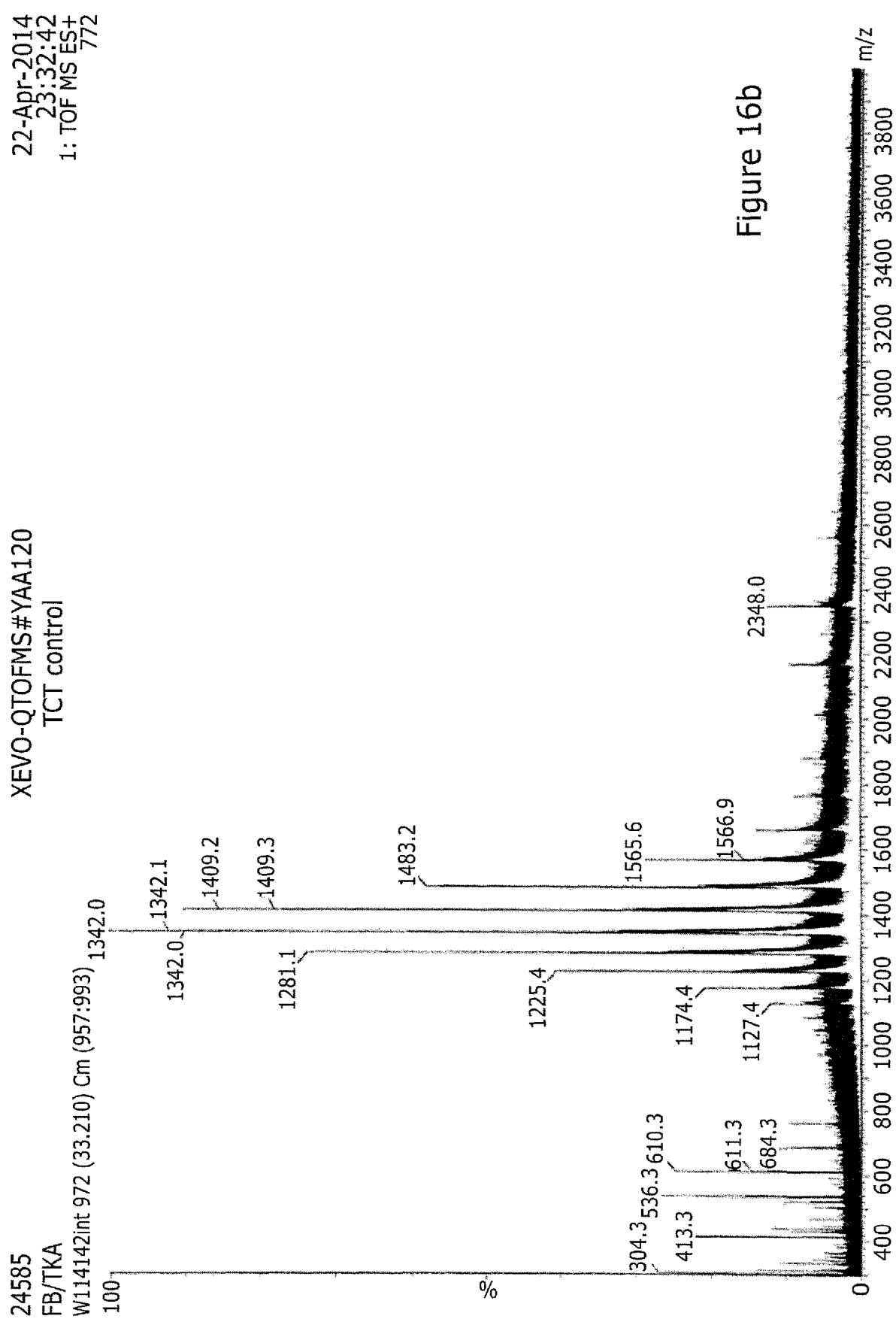
Figure 16C:
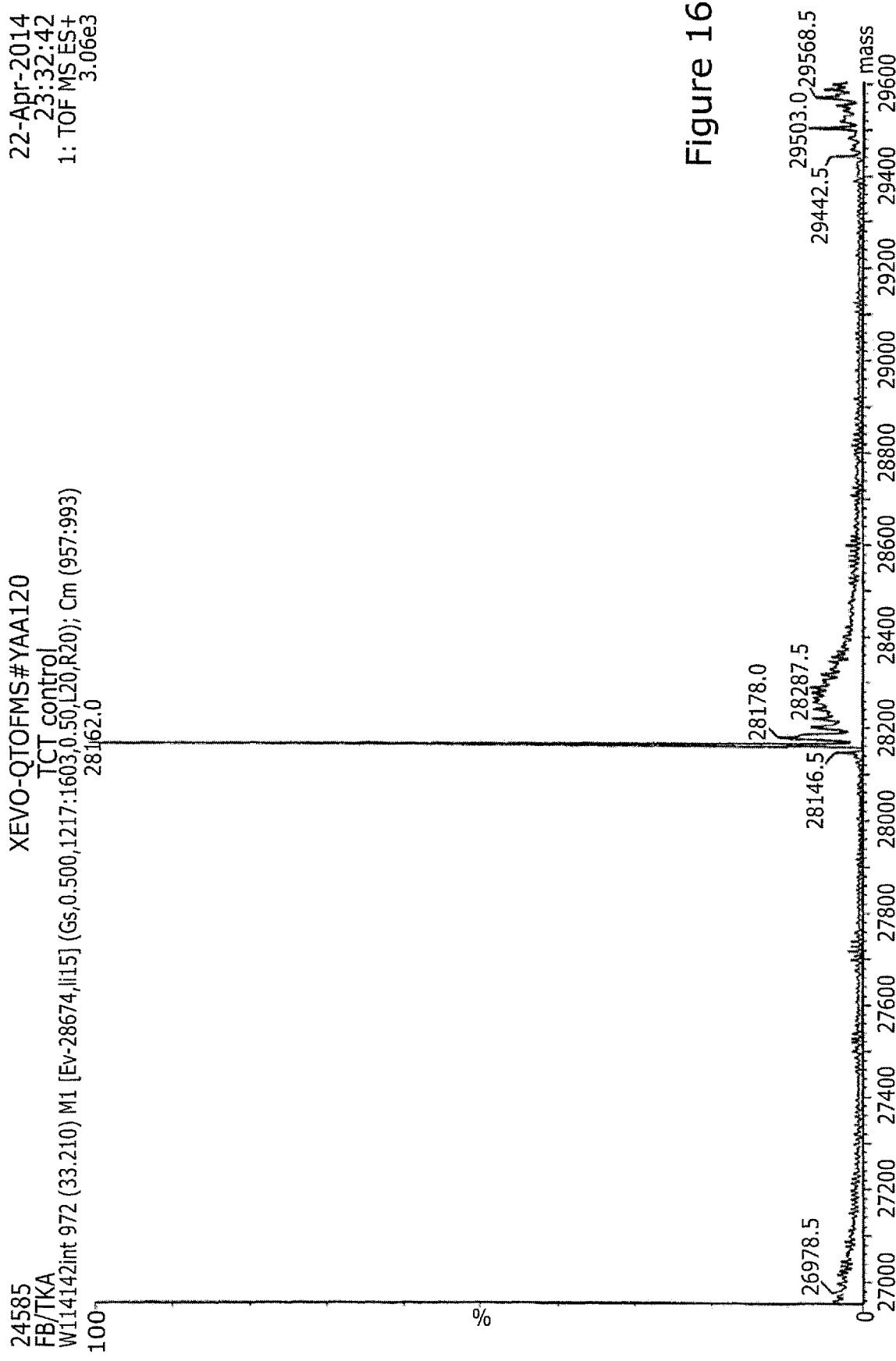

A major peak was observed in the TIC of the scFv (TCT) control sample eluting at 33.2 min. The zero-charge deconvoluted mass spectrum for this peak produces a single major component at m/z 28162 which was consistent with the theoretical mass of the scFv (TCT) molecule (FIG. 16A-C).

A major peak was observed in the TIC of the TCT-Cemadotin 1 eluting at 33.5 min. The zero-charge deconvoluted mass spectrum for this peak produces a series of major peaks at m/z 29495, 30162 and 30829, which was consistent with the supplied theoretical mass of the scFv (TCT) molecule, together with 2-4 additions of the Cemadotin molecule (FIG. 14A-C; Table 9).

A major peak was observed in the TIC of the TCT-Cemadotin 3 sample eluting at 37.1 min. The zero-charge deconvoluted mass spectrum for this peak produces a series of major peaks at m/z 33496, 34163 and 34830, which was consistent with the supplied theoretical mass of the scFv (TCT) molecule, together with 8-10 additions of the Cemadotin molecule (FIG. 15A-C; Table 9).

TABLE 9

Summary of the ESI-MS analyses of the ScFv (TCT)-Cemadotin ADCs

| Sample | Observed peak mass (m/z) | Added Mass (m/z) | Calculated DAR |
|---|---|---|---|
| ScFv (TCT) | 28162 | 0 | 0 |
| TCT-Cem ADC1 | 29495 | 1335 | 2 |
| | 30162 | 2002 | 3 |
| | 30829 | 2669 | 4 |
| TCT-Cem ADC2 | 32164 | 4004 | 6 |
| | 32831 | 4671 | 7 |
| | 33498 | 5338 | 8 |
| TCT-Cem ADC3 | 33496 | 5336 | 8 |
| | 34163 | 6303 | 9 |
| | 34830 | 6670 | 10 | scFv (TCT) molecular weight = 28160 (protein sequence) Da
Cemadotin drug molecular weight = 667 Da MALDI-Mass Spectrometry Equipment: Analyses were performed using the following equipment: Shimadzu Scientific Instruments AXIMA Performance MALDI TOF-TOF mass spectrometer.

Linear MALDI MS Analysis: a sample of myoglobin was used to calibrate the instrument externally in both positive and negative ion high mass linear mode. Samples of TCT-Cemadotin conjugate 3, TCT-Cemadotin conjugate 1, TCT-Cemadotin conjugate 2, TCT-Control were diluted 1:1 (v/v) in 50% (aq.) acetonitrile and spotted in 1 µl aliquots onto a steel 384 spot non-coated MALDI plate. Replicate spots were made for each MALDI matrix: Norharmane, 2',4',6'-Trihydroxyacetophenone monohydrate (THAP), Norharmane:THAP (4:1, v/v), and sinapinic acid matrix solutions. Spots were also made using undiluted samples, for sinapinic acid. Each spot was overlaid with 1 µL aliquots of corresponding MALDI matrix, and allowed to co-crystallise and dry under a gentle stream of air. Sinapinic acid was prepared as a saturated solution in 1:1 (v/v) 0.1% aq. Trifluoroacetic acid (TFA):acetonitrile. Norharmane was prepared as a 10 mg/mL solution in 1:1 (v/v) 0.1% aq. Trifluoroacetic acid (TFA):acetonitrile.

2',4',6'-Trihydroxyacetophenone monohydrate (THAP) was prepared as a saturated solution in 1:1 (v/v) 0.1% aq. Trifluoroacetic acid (TFA):acetonitrile. Spots containing Norharmane, 2',4',6'-Trihydroxyacetophenone monohydrate (THAP) and Norharmane:THAP (4:1, v/v) were analysed in high-mass linear mode negative ion; and spots containing sinapinic acid were analysed in high-mass linear mode positive ion. Mass spectra were collected over an appropriate mass range and the laser power was varied to achieve optimal results.

MALDI-MS of scFv (TCT) (Control Sample) in Sinapinic Acid

The MALDI-MS data obtained from the linear mode positive ion analysis of undiluted scFv (TCT). Control in sinapinic acid matrix is shown in FIG. 17. A significant peak was observed at m/z 28251, which was consistent with the expected mass of scFv (TCT) (28160 Da), within the error associated with the instrument.

MALDI-MS of TCT-Cemadotin Conjugate 1 in Sinapinic Acid

The MALDI-MS data obtained from the linear mode positive ion analysis of TCT-Cemadotin conjugate 1 in sinapinic acid matrix is shown in FIG. 18. Resolved peaks were observed at m/z 29559, 30223, 30884 and 31531, in reasonable accordance with the supplied scFv (TCT) control bearing additional conjugated masses of approximately 2, 3, 4 and 5 Cemadotin molecules respectively (using the supplied incremental mass of 667 Da) Table 10.

MALDI-MS of TCT-Cemadotin Conjugate 2 in Sinapinic Acid

The MALDI-MS data obtained from the linear mode positive ion analysis of TCT-cemadotin conjugate 2 in sinapinic acid matrix is shown in FIG. 19. Resolved peaks were observed at m/z 32293, 32948 and 33588, in reasonable accordance with the supplied scFv (TCT) control bearing additional conjugated masses of approximately 6, 7 and 8 Cemadotin molecules respectively (using the supplied incremental mass of 667 Da) Table 10.

MALDI-MS of TCT-Cemadotin Conjugate 3 in Sinapinic Acid

The MALDI-MS data obtained from the linear mode positive ion analysis of TCT-Cemadotin conjugate 3 in sinapinic acid matrix is shown in FIG. 20. Resolved peaks were observed at m/z 33809, 34415 and 35057, in reasonable accordance with the supplied scFv (TCT) control bearing additional conjugated masses of approximately 8, 9 and 10 Cemadotin molecules respectively (using the supplied incremental mass of 667 Da) Table 10.

TABLE 10

Summary of the MALDI analyses of the ScFv (TCT)-Cemadotin ADCs

| Sample | Observed peak mass (m/z) | Added Mass (m/z) | Calculated DAR |
|---|---|---|---|
| ScFv (TCT) | 28251 | 0 | 0 |
| TCT-Cem ADC1 | 29559 | 1308 | 2 |
|  | 30223 | 1972 | 3 |
|  | 30884 | 2633 | 3.9 |
|  | 31531 | 3280 | 4.9 |
| TCT-Cem ADC2 | 32293 | 4042 | 6.1 |
|  | 32948 | 4697 | 7 |
|  | 33588 | 5337 | 8 |
| TCT-Cem ADC3 | 33809 | 5558 | 8.3 |
|  | 34415 | 6164 | 9.2 |
|  | 35057 | 6806 | 10.2 |

Cemadotin drug molecular weight = 667 Da

Binding ELISA of scFv (TCT)-Cemadotin Conjugates

ScFv (TCT)-Cemadotin ADCs (compound 69) were made and characterised as described above. Their binding affinity against immobilised HER2 target antigen was determined by ELISA compared to the unmodified scFv (FIG. 21). All proteins were detected using the C-terminal T7 Tag which was not expected to be chemically modified (no lysines present). 96-well Immunosorb ELISA plates were coated with 10 µg/ml HER2-Fc in PBS, followed by the test samples, anti-T7 peroxidase conjugate. Extensive PBS washes were in between each layer and detection was with BM-Blue substrate. The plot (FIG. 21) shows that the ADC with 3.9 drugs (average DAR) loaded, substantially retained its binding affinity ($K_d$ declines slightly from 2.5 nM to 3.3 nM, the ADC with 8.2 drugs loaded, substantially retained its binding affinity ($K_d$ declines slightly from 2.5 nM to 15.5 nM). If the conjugation reaction is pushed further, conjugating to all but one of the surface lysine residues (11/12), the scFv binding is reduced but not lost ($K_d$=27.5 nM). This shows that the optimised scFv can carry a high drug load whilst retaining binding function.

Overall TCT-Cemadotin Conclusions, Biophysical Data

The conjugation conditions were optimised as detailed above. This optimisation allowed for controlled conjugation reactions with a very high yield of low, medium and high DAR conjugates. There was no precipitation of antibody/conjugate observed in any of the conjugates, therefore recovery was very high. Following SEC HPLC purification, the resulting conjugates were concentrated to ~500 µg/ml and were stable in the buffer for several weeks. Prior to using them for in vitro or in vivo testing, these conjugates were buffer exchanged into PBS and sterile filtered. Again, recovery was very high.

The products were analysed extensively by reducing SDS-PAGE, SEC-HPLC, AAA, MS and ELISA.

The techniques used for analysis are in agreement and support the argument that an optimised scFv structure, exemplified by TCT, can be loaded with multiple drugs using lysine residues on the antibody and the conjugation can be controlled to obtain monomeric conjugates (as shown by SEC-HPLC) with the desired DAR whilst retaining binding affinity. Purified conjugates with low DAR (sample 1) run closer to the control scFv (TCT) on the gel and were less polydispersed than the medium DAR (sample 2) which run slightly higher and was more polydispersed, whereas for the high DAR (sample 3) there was a clear migration shift on the gel where the sample was clearly bigger in size than the control, unmodified TCT. These observations were further supported by the HPLC where the samples had progressively shorter retention times than TCT, eluting faster from the SEC column due to their increasing size. Amino acid analysis was an extremely useful tool for further quantitative analysis and complemented the MS data. The mass spectrometry identified both high and low DAR within the same sample whereas AAA gave an average.

For sample 1, DAR was 3.9 by AAA and 3.4 and 3 by MS (ES and MALDI)

For sample 2, DAR was 8.2 by AAA and 7 and 7 by MS (ES and MALDI)

For sample 3, DAR was 10.9 by AAA and 9.2 and 9 by MS (ES and MALDI)

(B) ScFv (TCT)-P5C5

ScFv-TCT was conjugated to P5C5-NHS (compound 6) using the same method employed for Cemadotin-NHS. The HPLC purified P5C5-NHS was dissolved in filtered anhydrous DMSO to make up a 100 mM stock solution and spun down. This was stored at −20° C. when not in use. In this example, the set up was:

Reaction 1—scFv-TCT-P5C5 30 equivalents

Reaction 2—scFv-TCT-P5C5 112 equivalents

The antibody was defrosted at 4° C. and the temperature of the antibody was slowly raised to 20° C. on the Thermomixer. Any precipitate was collected by centrifugation. Bicarbonate buffer pH 8.8, was combined with anhydrous, filtered DMSO in a 1 or 5 ml eppendorf and equilibrated on the Thermomixer 20° C., 10 min, 1000 rpm before adding the antibody and equilibrating for a further 10 mins. P5C5-NHS was added in portions of 16 equivalents for reaction 2 and 10 equivalents for reaction 1 by adding the solution, inverting to mix, and replacing on the Thermomixer.

Additions were carried out every 90 min, after which point the samples were left overnight at 4° C. at 1000 rpm on the Thermomixer. Samples were recovered by centrifugation (2.5 min, 10 krpm) to obtain clear solutions. Minimal precipitation was observed for sample 2.

The samples were purified from crude on the HPLC by SEC using the Tosoh TSKGel G2000, eluting with 10% IPA/PBS pH 7.3 20° C. (same method as previously, loading ~300 µg per injection run) and analysed by SDS-PAGE (FIG. 22), HPLC-SEC (FIG. 23) and AAA (Table 11). Samples were collected, combined and concentrated on a vivaspin 20, 10 k MWCO (VS2002, 10° C., 4000 rpm). Samples were allowed to settle for 1 hr before transferring to an eppendorf microtubes, rinsing the concentrator with 200 ul of PBS. Samples were buffer exchanged into PBS pH 7.3 using a Zeba column and re-quantified using a
Nanodrop spectrometer. The readings were:
Sample 1 A280=1.46 (average of 3), 650 µg/ml
Sample 2 A280=1.32 (average of 3), 590 µg/ml The ADCs (compound 71) eluted with a faster retention time than the unmodified antibody indicating a higher molecular weight, but as soluble monomeric conjugates with no visible aggregation.

(C) scFv (TCT)-P5C5, scFv (TCT)-Cemadotin-C5, Trastuzumab-P5C5 and Trastuzumab-Cemadotin-C5

The following reactions were carried out following the same process as previously described for Cemadotin (4) and P5C5 (6) drugs. In short, the antibodies were equilibrated in buffer/DMSO through incubation at 20° C./1000 rpm, and the drug was added in 16 equivalent portions every 90 min. Samples were recovered by centrifugation and purified by SEC-HPLC (G2000SWxI for scFv (TCT) and G3000SWxI for Trastuzumab) (10% IPA/PBS isocratic). Purified fractions were then concentrated using vivaspin 20 spin concentrators 5-fold and buffer exchanged into PBS using zeba spin columns (Pierce). Samples were analysed by SDS-PAGE (FIG. 24), HPLC-SEC (FIGS. 25-27), and UV/Vis spectroscopy (FIGS. 28 & 29).

After synthesis of these conjugates, it was clear that the three P5 based derivatives behave very similarly to the cemadotin-NHS derivatives (70), leading to very soluble, monomeric, highly loaded conjugates (compound 71). These have not been quantified for DAR but when compared to previous samples (that were quantified by AAA and MS) on SDS-PAGE, and compared to the scFv (TCT) control, it is clear that low, medium and high DARs can be formed with scFv (TCT) and Cemadotin, P5C5 and Cemadotin-C5. Trastuzumab IgG was also conjugated to P5C5 and Cemadotin-C5 with shifts observed on the gel (albeit smaller than TCT). These observations were supported by the HPLC-SEC traces where the samples gave similar retention times for low, medium and high DAR conjugates with cemadotin, P5C5 and cemadotin-C5.

(D) Binding Affinity of scFv (TCT)-P5C5 ADCs

ScFv (TCT)-P5C5 ADCs were made and characterised as described in examples above. The DAR was determined by AAA as before (Table 11A & B), this time following the release of the di-proline fragment to identify and quantify the P5-based drug. Their binding affinity against immobilised HER2 target antigen was determined by ELISA compared to the unmodified scFv. All proteins were detected using the C-terminal T7 Tag which was not expected to be chemically modified (no lysines present). 96-well Immunosorb ELISA plates were coated with 104/ml HER2-Fc in PBS, followed by the test samples, anti-T7-peroxidase conjugate. Extensive PBS/tween-20 and PBS washes were in between each layer and detection was with BM-Blue substrate. The plot (FIG. 30) shows that, the ADC (scFv TCT-P5C5(1)) with 8 drugs loaded, substantially retained its binding affinity (Kd declines slightly from 7 nM to 13 nM). If the conjugation reaction is pushed to the full limit (scFv TCT-P5C5(2)), practically conjugating to all the surface lysine residues (12), the scFv binding is significantly lost due to a critical lysine residue buried in the binding site becoming drug modified. The DARs were verified by AAA (Tables 11A and 11B). This shows that the optimised scFv can carry a high drug load whilst retaining binding function.

TABLE 11A

Sample: TCT-P5C5(1)
Integer fit of measured mole ratios to expected values

| Amino acid | Expected value | Observed value | Closeness of fit to expected value |
| --- | --- | --- | --- |
| Cys | 6 | excluded | — |
| Asp | 15 | 15.76 | better than 5% |
| Thr | 14 | 13.90 | better than 5% |
| Ser | 46 | 43.51 | within 5-10% |
| Glu | 22 | 21.87 | better than 5% |
| Gly | 44 | 45.32 | better than 5% |
| Ala | 17 | 16.46 | better than 5% |
| Val | 18 | excluded | — |
| Met | 5 | 4.69 | within 5-10% |
| Ile | 8 | 8.22 | better than 5% |
| Leu | 15 | 15.79 | within 5-10% |
| Norleu std | 0 | — | — |
| Tyr | 14 | 14.64 | better than 5% |
| Phe | 7 | 6.89 | better than 5% |
| His | 3 | 3.07 | better than 5% |
| Lys | 12 | 12.00 | better than 5% |
| Arg | 5 | 4.89 | better than 5% |
| Pro | 0 | excluded | — |
| Trp | 8 | 8 | (not determined) |
| Total | 259 | residues | |

| | | | Average of 2 runs |
| --- | --- | --- | --- |
| Total sample | 0.271 | nmoles | 0.27 |
| | 7.65 | ug | 7.62 |
| Concentration | 18.10 | nmoles/ml | 18.03 |
| | 509.69 | ug/ml | 507.70 |
| P5C5 | | | |
| nmoles | 2.1980 | 2.2211 | 2.21 |
| DAR | 8.17 | | |

TABLE 11B

Sample: TCT-P5C5(2)
Integer fit of measured mole ratios to expected values

| Amino acid | Expected value | Observed value | Closeness of fit to expected value |
| --- | --- | --- | --- |
| Cys | 6 | excluded | — |
| Asp | 15 | 15.99 | within 5-10% |
| Thr | 14 | 14.20 | better than 5% |
| Ser | 46 | 43.55 | within 5-10% |
| Glu | 22 | 21.79 | better than 5% |
| Gly | 44 | 45.11 | better than 5% |
| Ala | 17 | 16.58 | better than 5% |
| Val | 18 | excluded | — |
| Met | 5 | excluded | — |
| Ile | 8 | 8.15 | better than 5% |
| Leu | 15 | 15.74 | better than 5% |
| Norleu std | 0 | — | — |
| Tyr | 14 | 14.16 | better than 5% |
| Phe | 7 | 6.74 | better than 5% |
| His | 3 | 3.20 | within 5-10% |
| Lys | 12 | 11.91 | better than 5% |
| Arg | 5 | 4.88 | better than 5% |
| Pro | 0 | 0.00 | — |
| Trp | 8 | 8 | (not determined) |
| Total | 259 | residues | |

| | | | Average of 2 runs |
| --- | --- | --- | --- |
| Total sample | 0.225 | nmoles | 0.23 |
| | 6.33 | ug | 6.54 |
| Concentration | 14.98 | nmoles/ml | 15.49 |
| | 421.82 | ug/ml | 436.14 |

TABLE 11B-continued

Sample: TCT-P5C5(2)
Integer fit of measured mole ratios to expected values

| P5C5 | | | |
|---|---|---|---|
| nmoles | 2.7742 | 2.6534 | 2.71 |
| DAR | 11.68 | | |

Table 11A & B. DAR by AAA of scFv (TCT)-P5C5 (compound 71) used in example 31 D.

(E) Cell Killing Potency of scFv (TCT)-P5C5 ADCs Compared to IgG-Based ADCs

ScFv (TCT)-P5C5 and Trastuzumab-P5C5 ADCs were made and characterised as described above (examples 31B & 31C), which had similar DARs as before. SKBr3, human breast cancer cell line, high HER2 expression levels, up to 1,000,000 receptors per cell [Lazar G A, et al Proc Natl Acad Sci USA. 2006, 103:4005-10] were grown in DMEM, at 37° C., 5% $CO_2$ in a humidified atmosphere. When confluency was 70-80%, cells were washed with PBS (2×10 ml) and incubated with trypsin for 5-7 min. Complete media was added and the cells were resuspended by pipetting. The cells were recovered by centrifugation (2 min, 2000 rpm), the supernatant was discarded, and the cells were resuspended in complete DMEM (5 ml). The cells were then counted using a haemocytometer and diluted accordingly. They were plated at 4500 cells/well (200 µl) using attachment factor and incubated overnight at 37° C., 5% $CO_2$ in a humidified atmosphere. U87 is a non-HER2 expressing glioblastoma cell line and was grown in a similar way, plated at 1000 cells/well.

The cells were exposed to the various ADCs diluted in complete media for 96 hours at 37° C., 5% $CO_2$ in a humidified atmosphere. Cell viability was measured using the Promega Aqueous Cell-titre-96™ aqueous one solution cell proliferation kit according to manufacturer's instructions. Briefly, the media was removed and 100 µl of complete phenol red free media, pre-combined with MTS reagent, was added to the cells (20 µl of reagent per 100 µl of media). The plates were read on an ELISA plate reader at 490 nm after a 2 hr incubation in the dark (5% $CO_2$, 37° C.).

The data (absorption units) were converted to % cell survival by using the untreated controls as the 100% cell survival and the Triton X-100 controls as the 100% cell death. The average absorption value for the latter was subtracted from all the rest of the data in order to get a suitable baseline. The averages were converted to survival and standard error values were obtained for each n value (as a % cell survival). The data were plotted and fitted to a dose-response sigmoidal logistic 3-parameter curve using the equation $y=y_0+a/(1+(x/x_0)b)$ where, $x_0$=IC50 and $x_0>0$ and a=100 using SigmaPlot 11.0. Experiments were repeated at least 3 times for each compound tested and a set or an average of the data was plotted and fitted to obtain a dose response curve.

The data (FIGS. 31-33, Table 12) shows that the scFv (TCT)-ADCs are specifically cytotoxic to HER2 expressing cells with mid-nM potencies. The free drug and has low potency on its own due to poor cell permeability. The higher DAR ADCs are more potent, up to the point where binding activity is lost.

TABLE 12

Summary of Cell killing potency of scFv (TCT) & Trastuzumab P5C5 ADCs (compounds 5 and 71)

| | SKBr3 Cells (HER2+++) | | U87 Cells (HER2−) | |
|---|---|---|---|---|
| Sample | IC50 µg/ml | IC50 nM | IC50 µg/ml | IC50 nM |
| scFv (TCT)-P5C5, DAR = 5 | 1.33 ± 0.1 | 47.5 ± 0.36 | — | — |
| scFv (TCT)-P5C5, DAR = 8 | 0.8 ± 0.1 | 28 ± 0.36 | — | — |
| scFv (TCT)-P5C5, DAR = 12 | 5.01 ± 1.9 | 178.6 ± 68 | 100 | 3570 |
| Trastuzumab-P5C5, DAR = 5 | 0.07 ± 0.01 | 2.5 ± 0.4 | — | — |
| Trastuzumab-P5C5, DAR = 6 | 0.02 ± 0.004 | 0.7 ± 0.14 | — | — |
| Free P5C5 (acid) drug | N/A | 2200 ± 400 | N/A | 7300 ± 900 |

Example 32—Bioconjugation of Other Payloads (Camptothecin, Paclitaxel, MMAE, Maytansine) Derivatives onto a Single-Chain Fv Antibody Fragment Bearing Multiple, Well-Dispersed, Surface Lysine Residues Camptothecin A water-soluble derivative of camptothecin-NHS ester (compound 19) was conjugated to scFv (TCT) to obtain conjugates with various DARs. The reaction was controlled to obtain products with low, medium and high DARs. Initially, the hydrolysis rate of the pure isolated camptothecin-NHS was determined in various buffer conditions. The conditions that gave a reasonable hydrolysis rate, i.e. not too fast so that the NHS would hydrolyse to the acid before it reacted with the lysines and not too slow so that the reaction would take too long to complete. Other factors that were taken into account were the stability of the antibody in the buffer/pH/organic solvent, the stability of the drug and the concentration of the drug in the buffer. The latter is a crucial parameter; the more concentrated the drug is in the solution, the more the hydrolysis rate will decrease. Therefore, the concentration needs to be controlled to allow for an efficient rate of hydrolysis. The conditions identified and carried forward were:

Buffer—bicarbonate buffer with NaCl at pH8.8 with 20% DMSO and 30% glycerol;
Temperature—25° C.)
Mixing conditions—Thermomixer 1000 rpm;
Antibody at 1 mg/ml;
Camptothecin-NHS—8 equivalent addition portions; and,
NHS-drug addition rate—every 70-90 minutes.

Typically, scFv (TCT) was defrosted on the thermomixer at 4° C., then the temperature of the antibody aliquot was slowly raised to 20° C. Aliquots were spun down to collect any precipitate before using.

A camptothecin-NHS (compound 19) 100 mM stock solution was made up in anhydrous filtered DMSO. Any precipitate was collected by centrifugation. Bicarbonate buffer pH 8.8 was combined with filtered DMSO and glycerol in eppendorf microtubes and the buffer was equilibrated on the thermomixer at 4° C., and then the temperature was raised to 20° C. whilst mixing at 1000 rpm. The antibody was added and equilibrated further (20° C., 1000 rpm) for 10 mins before the addition of the camptothecin-NHS was started.

This was carried out by adding 8 equivalents of the NHS-drug DMSO stock and inverting to mix every 70 min, before replacing on the thermomixer and mixing at 25° C., 1000 rpm. The total number of equivalents used depended on the required DAR. The samples were left on the thermomixer for a further 2 hrs after the last addition. The samples were then collected by centrifugation (2.5 mins, 11 krpm).

The only visible precipitation was in the sample with the highest number of drug equivalents and was very low.

All samples were initially passed through a Zeba column (Pierce) pre-equilibrated with 10% IPA/PBS before being further purified on the HPLC-SEC with 20% IPA/PBS pH7, 25° C., and analysed by SDS-PAGE, HPLC-SEC, UV/Vis spectroscopy and mass spectrometry as described above.

The unconjugated and conjugated scFv (TCT) were analysed by HPLC size-exclusion chromatography using a Tosoh TSKGel G2000WxI column. The ScFv has a retention time correlating to a MW of around 30 KDa. The conjugates all eluted earlier indicating a larger molecular weight (due to varying drug loads), but as primarily monomeric peaks, indicating little or no aggregation.

Mass spectrometric analysis was performed by SGS M-Scan. Conjugates, as well as ScFv-TCT (control), were analysed by both MALDI-MS, and then further analysed by LC-MS. All samples gave well resolved peaks.

Paclitaxel

A water-soluble derivative of paclitaxel-NHS ester (compound 44) was conjugated to scFv (TCT) to obtain conjugates with various DARs. The reaction was controlled to obtain products with low, medium and high DARs. Initially, the hydrolysis rate of the pure isolated paclitaxel-NHS was determined in various buffer conditions. The conditions that gave a reasonable hydrolysis rate, i.e. not too fast so that the NHS would hydrolyse to the acid before it reacted with the lysines and not too slow so that the reaction would take too long to complete. Other factors that were taken into account were the stability of the antibody in the buffer/pH/organic solvent, the stability of the drug and the concentration of the drug in the buffer. The latter is a crucial parameter; the more concentrated the drug is in the solution, the more the hydrolysis rate will decrease. Therefore, the concentration needs to be controlled to allow for an efficient rate of hydrolysis. The conditions identified and carried forward were:

Buffer—bicarbonate buffer with NaCl at pH8.8 with 20% DMSO and 30% glycerol;
Temperature—25° C.;
Mixing conditions—Thermomixer 1000 rpm;
Antibody at 1 mg/ml;
Paclitaxel-NHS—8 equivalent addition portions; and,
NHS-drug addition rate—every 70-90 minutes.

Typically, scFv (TCT) was defrosted on the thermomixer at 4° C., then the temperature of the antibody aliquot was slowly raised to 20° C. Aliquots were spun down to collect any precipitate before using.

A paclitaxel-NHS 100 mM stock solution was made up in anhydrous filtered DMSO. Any precipitate was collected by centrifugation. Bicarbonate buffer pH 8.8 was combined with filtered DMSO and glycerol in eppendorf microtubes and the buffer was equilibrated on the thermomixer at 4° C., and then the temperature was raised to 20° C. whilst mixing at 1000 rpm. The antibody was added and equilibrated further (20° C., 1000 rpm) for 10 mins before the addition of the paclitaxel-NHS was started.

This was carried out by adding 8 equivalents of the NHS-drug DMSO stock and inverting to mix every 70 min, before replacing on the thermomixer and mixing at 25° C., 1000 rpm. The total number of equivalents used depended on the required DAR. The samples were left on the thermomixer for a further 2 hrs after the last addition. The samples were then collected by centrifugation (2.5 mins, 11 krpm). The only visible precipitation was in the sample with the highest number of drug equivalents and was very low.

All samples were initially passed through a Zeba column (Pierce) pre-equilibrated with 10% IPA/PBS before being further purified on the HPLC-SEC with 20% IPA/PBS pH7, 25° C. and analysed by SDS-PAGE, HPLC-SEC, UV/Vis spectroscopy and mass spectrometry as described above.

The unconjugated and conjugated scFv (TCT) were analysed by HPLC-size exclusion chromatography using a Tosoh TSKGel G2000WxI column. The ScFv has a retention time correlating to a MW of around 30 KDa. The conjugates all eluted earlier indicating a larger molecular weight (due to varying drug loads), but as primarily monomeric peaks, indicating little or no aggregation.

Mass spectrometric analysis was performed by SGS M-Scan. Conjugates, as well as ScFv-TCT (control), were analysed by both MALDI-MS and then further analysed by LC-MS. All samples gave well resolved peaks.

MMAE

A water-soluble derivative of MMAE-NHS ester is conjugated to scFv (TCT) to obtain conjugates with various DARs. The reaction is controlled to obtain products with low, medium and high DARs. Initially, the hydrolysis rate of the pure isolated MMAE-NHS is determined in various buffer conditions. The conditions that gave a reasonable hydrolysis rate, i.e. not too fast so that the NHS would hydrolyse to the acid before it reacted with the lysines and not too slow so that the reaction would take too long to complete. Other factors that were taken into account were the stability of the antibody in the buffer/pH/organic solvent, the stability of the drug and the concentration of the drug in the buffer. The latter is a crucial parameter; the more concentrated the drug is in the solution, the more the hydrolysis rate will decrease. Therefore, the concentration needs to be controlled to allow for an efficient rate of hydrolysis. The conditions identified and carried forward were:

Buffer—bicarbonate buffer with NaCl at pH8.8 with 20% DMSO and 30% glycerol;
Temperature—25° C.;
Mixing conditions—Thermomixer 1000 rpm;
Antibody at 1 mg/ml;
MMAE-NHS—8 equivalent addition portions; and,
NHS-drug addition rate—every 70-90 minutes.

Typically, scFv (TCT) is defrosted on the thermomixer at 4° C., then the temperature of the antibody aliquot was slowly raised to 20° C. Aliquots are spun down to collect any precipitate before using.

An MMAE-NHS 100 mM stock solution is made up in anhydrous filtered DMSO. Any precipitate was collected by centrifugation. Bicarbonate buffer pH 8.8 is combined with filtered DMSO and glycerol in eppendorf microtubes and the buffer is equilibrated on the thermomixer at 4° C., and then the temperature is raised to 20° C. whilst mixing at 1000 rpm). The antibody is added and equilibrated further (20° C., 1000 rpm) for 10 mins before the addition of the MMAE-NHS is started.

This is carried out by adding 8 equivalents of the NHS-drug DMSO stock and inverting to mix every 70 min, before replacing on the thermomixer and mixing at 25° C., 1000 rpm. The total number of equivalents used depended on the required DAR. The samples are left on the thermomixer for a further 2 hrs after the last addition. The samples are then collected by centrifugation (2.5 mins, 11 krpm). The only visible precipitation is in the sample with the highest number of drug equivalents and that was very low.

All samples are initially passed through a Zeba column (Pierce) pre-equilibrated with 10% IPA/PBS before being further purified on the HPLC-SEC with 20% IPA/PBS pH7, 25° C. and analysed by SDS-PAGE, HPLC-SEC, UV/Vis spectroscopy and mass spectrometry as described above.

The unconjugated and conjugated scFv (TCT) are analysed by HPLC-size exclusion chromatography using a Tosoh TSKGel G2000WxI column. The ScFv has a retention time correlating to a MW of around 30 KDa. The conjugates all elute earlier, indicating a larger molecular weight (due to varying drug loads), but as primarily monomeric peaks, indicating little or no aggregation.

Mass spectrometric analysis are performed by SGS M-Scan. Conjugates, as well as ScFv-TCT (control), are analysed by both MALDI-MS and then further analysed by LC-MS. All samples give well resolved peaks.

Maytansine (DM4)

A water-soluble derivative of MaytansineDM4-NHS ester (compound 68) is conjugated to scFv (TCT) to obtain conjugates with various DARs (compound 74). The reaction is controlled to obtain products with low, medium and high DARs. Initially, the hydrolysis rate of the pure isolated MaytansineDM4-NHS is determined in various buffer conditions. The conditions that gave a reasonable hydrolysis rate, i.e. not too fast so that the NHS would hydrolyse to the acid before it reacted with the lysines and not too slow so that the reaction would take too long to complete. Other factors that were taken into account were the stability of the antibody in the buffer/pH/organic solvent, the stability of the drug and the concentration of the drug in the buffer. The latter is a crucial parameter; the more concentrated the drug is in the solution, the more the hydrolysis rate will decrease. Therefore, the concentration needs to be controlled to allow for an efficient rate of hydrolysis. The conditions identified and carried forward were:

Buffer (bicarbonate buffer with NaCl at pH8.8 with 20% DMSO and 30% glycerol), Temperature (25° C.), Mixing conditions (Thermomixer 1000 rpm), Antibody at 1 mg/ml, MaytansineDM4-NHS (8 equivalent addition portions), NHS-drug addition rate (every 70-90 minutes).

Typically, scFv (TCT) is defrosted on the thermomixer at 4° C., then slowly raising the temperature of the antibody aliquot to 20° C. Spun down to collect any precipitate before using.

A MaytansineDM4-NHS 100 mM stock solution is made up in anhydrous filtered DMSO. Any precipitate was collected by centrifugation. Bicarbonate buffer pH 8.8 was combined with filtered DMSO and glycerol into eppendorf microtubes and the buffer is equilibrated on the thermomixer at 4° C., and then the temperature is raised to 20° C. whilst mixing at 1000 rpm. The antibody is added and equilibrated further (20° C., 1000 rpm) for 10 mins before the addition of the MaytansineDM4-NHS was started.

This is carried out by adding 8 equivalents of the NHS-drug DMSO stock and inverting to mix every 70 min, before replacing on the thermomixer and mixing at 25° C., 1000 rpm. The total number of equivalents used depended on the required DAR. The samples are left on the thermomixer for a further 2 hrs after the last addition. The samples are then collected by centrifugation (2.5 mins, 11 krpm). The only visible precipitation is in the sample with the highest number of drug equivalents and that was very low.

All samples are initially passed through a Zeba column (Pierce) pre-equilibrated with 10% IPA/PBS before being further purified on the HPLC-SEC with 20% IPA/PBS pH7, 25° C. and analysed by SDS-PAGE, HPLC-SEC, UV/Vis spectroscopy and mass spectrometry as described above.

The unconjugated and conjugated scFv (TCT) are analysed by HPLC-size exclusion chromatography using a Tosoh TSKGel G2000WxI column. The ScFv has a retention time correlating to a MW of around 30 KDa. The conjugates all elute earlier, indicating a larger molecular weight (due to varying drug loads), but as primarily monomeric peaks, indicating little or no aggregation.

Mass spectrometric analysis are performed by SGS M-Scan. Conjugates, as well as ScFv-TCT (control), are analysed by both MALDI-MS and then further analysed by LC-MS. All samples give well resolved peaks.

Maytansine (DM1), 2-Step Method

DM1 drug is conjugated to scFv (TCT) to obtain conjugates with various DARs (compound 75). The reaction was controlled to obtain products with low, medium and high DARs. The procedure is carried out treating the scFv (TCT) with 32 equivalents of SPDP and subsequently reducing the samples with 115 equivalents of TCEP. The reduced, purified and quantified samples are then conjugated to DM1. DM1 was added to the antibody samples (in degassed PBS pH7/1 mM EDTA/20% DMSO/10% propylene glycol) at 2 equivalents each. The samples are incubated on the thermomixer (25° C., 1000 rpm) followed by 4° C. (1000 rpm) overnight. Recovered the samples by centrifugation and analysed by SDS-PAGE gel and UV/Vis spectroscopy.

All samples were initially passed through a Zeba column (Pierce) pre-equilibrated with 10% IPA/PBS before being further purified on the HPLC-SEC with 20% IPA/PBS pH7, 25° C. and analysed by SDS-PAGE, HPLC-SEC, UV/Vis spectroscopy and mass spectrometry as described above.

The unconjugated and conjugated scFv (TCT) are analysed by HPLC-size exclusion chromatography using a Tosoh TSKGel G2000WxI column. The ScFv has a retention time correlating to a MW of around 30 KDa. The conjugates all elute earlier, indicating a larger molecular weight (due to varying drug loads), but as primarily monomeric peaks, indicating little or no aggregation.

Pyrrolobenzodiazepine Conjugation, 2-Step Method

A PBD derivative, 6-maleimidocaproyl-SGD-1910 (compound 67) is conjugated to scFv (TCT) to obtain conjugates with various DARs. The reaction is controlled to obtain products with low, medium and high DARs. The procedure is carried out treating the scFv (TCT) with 32 equivalents of SPDP and subsequently reducing the samples with 115 equivalents of TCEP. The reduced, purified and quantified samples are then conjugated to 6-maleimidocaproyl-SGD-1910. 6-maleimidocaproyl-SGD-1910 was added to the antibody samples (in degassed PBS pH7/1 mM EDTA/20% DMSO/20% propylene glycol) at 2 equivalents each. The samples are incubated on the thermomixer for 3 hrs (25° C., 1000 rpm) followed by 4° C. (1000 rpm) overnight. Recovered the samples by centrifugation and analysed by SDS-PAGE gel and UV/Vis spectroscopy.

All samples were initially passed through a Zeba column (Pierce) pre-equilibrated with 10% IPA/PBS before being further purified on the HPLC-SEC with 20% IPA/PBS pH7, 25° C. and analysed by SDS-PAGE, HPLC-SEC, UV/Vis spectroscopy and mass spectrometry as described above.

The unconjugated and conjugated scFv (TCT) are analysed by HPLC-size exclusion chromatography using a Tosoh TSKGel G2000WxI column. The ScFv has a retention time correlating to a MW of around 30 KDa. The conjugates all elute earlier, indicating a larger molecular weight (due to varying drug loads), but as primarily monomeric peaks, indicating little or no aggregation.

MMAE Conjugation, 2-Step Method

An MMAE derivative, 6-maleimidocaproyl-MMAE (compound 37) is conjugated to scFv (TCT) to obtain conjugates with various DARs. The reaction is controlled to obtain products with low, medium and high DARs. The procedure was carried out treating the scFv (TCT) with 32 equivalents of SPDP and subsequently reducing the samples with 115 equivalents of TCEP. The reduced, purified and quantified samples were then conjugated to 6-maleimidocaproyl-MMAE. 6-maleimidocaproyl-MMAE is added to the antibody samples (in degassed PBS pH7/1 mM EDTA/20% DMSO) at 2 equivalents each. The samples are incubated on the thermomixer for 3 hrs (25° C., 1000 rpm) followed by 4° C. (1000 rpm) overnight. Recovered the samples by centrifugation and analysed by SDS-PAGE gel and UV/Vis spectroscopy.

All samples are initially passed through a Zeba column (Pierce) pre-equilibrated with 10% IPA/PBS before being further purified on the HPLC-SEC with 20% IPA/PBS pH7, 25° C. and analysed by SDS-PAGE, HPLC-SEC, UV/Vis spectroscopy and mass spectrometry as described above.

The unconjugated and conjugated scFv (TCT) are analysed by HPLC-size exclusion chromatography using a Tosoh TSKGel G2000WxI column. The ScFv has a retention time correlating to a MW of around 30 KDa. The conjugates all elute earlier, indicating a larger molecular weight (due to varying drug loads), but as primarily monomeric peaks, indicating little or no aggregation.

Duocarmycin Conjugates

A water-soluble derivative of seco CBI-β-Glucuronide-NHS ester (compound 65) is conjugated to scFv (TCT) to obtain conjugates with various DARs. The reaction is controlled to obtain products with low, medium and high DARs. Initially, the hydrolysis rate of the pure isolated seco CBI-β-Glucunoride-NHS ester was determined in various buffer conditions. The conditions that gave a reasonable hydrolysis rate, i.e. not too fast so that the NHS would hydrolyse to the acid before it reacted with the lysines and not too slow so that the reaction would take too long to complete. Other factors that were taken into account were the stability of the antibody in the buffer/pH/organic solvent, the stability of the drug and the concentration of the drug in the buffer. The latter is a crucial parameter; the more concentrated the drug is in the solution, the more the hydrolysis rate will decrease. Therefore, the concentration needs to be controlled to allow for an efficient rate of hydrolysis. The conditions identified and carried forward were:

Buffer (bicarbonate buffer with NaCl at pH8.8 with 20% DMSO and 30% glycerol), Temperature (25° C.), Mixing conditions (Thermomixer 1000 rpm), Antibody at 1 mg/ml, seco CBI-β-Glucuronide-NHS ester (8 equivalent addition portions), NHS-drug addition rate (every 70-90 minutes).

Typically, scFv (TCT) is defrosted on the thermomixer at 4° C., then slowly raising the temperature of the antibody aliquot to 20° C. Spun down to collect any precipitate before using.

A seco CBI-β-Glucuronide-NHS ester 100 mM stock solution is made up in anhydrous filtered DMSO. Any precipitate was collected by centrifugation.

Bicarbonate buffer pH 8.8 was combined with filtered DMSO and glycerol into eppendorf microtubes and the buffer is equilibrated on the thermomixer at 4° C., and then the temperature was raised to 20° C. whilst mixing at 1000 rpm. The antibody is added and equilibrated further (20° C., 1000 rpm) for 10 mins before the addition of the seco CBI-β-Glucuronide-NHS ester is started.

This is carried out by adding 8 equivalents of the NHS-drug DMSO stock and inverting to mix every 70 mins, before replacing on the thermomixer and mixing at 25° C., 1000 rpm. The total number of equivalents used depended on the required DAR. The samples are left on the thermomixer for a further 2 hrs after the last addition. The samples were then collected by centrifugation (2.5 mins, 11 krpm). The only visible precipitation was in the sample with the highest number of drug equivalents and was very low.

All samples are initially passed through a Zeba column (Pierce) pre-equilibrated with 10% IPA/PBS before being further purified on the HPLC-SEC with 20% IPA/PBS pH7, 25° C. and analysed by SDS-PAGE, HPLC-SEC, UV/Vis spectroscopy and mass spectrometry as described above.

The unconjugated and conjugated scFv (TCT) are analysed by HPLC-size exclusion chromatography using a Tosoh TSKGel G2000WxI column. The ScFv has a retention time correlating to a MW of around 30 KDa. The conjugates all eluted earlier, indicating a larger molecular weight (due to varying drug loads), but as primarily monomeric peaks, indicating little or no aggregation.

Example 33—Raising Anti-Cemadotin Drug Monoclonal Antibodies and Use in Detecting scFv-Cemadotin ADCs Keyhole Limpet Haemocyanin (KLH)-Cemadotin conjugate was produced by conjugating Cemadotin-NHS (compound 2) to 1 mg/ml KLH at a molar excess and purified by desalting.

Figure 34:
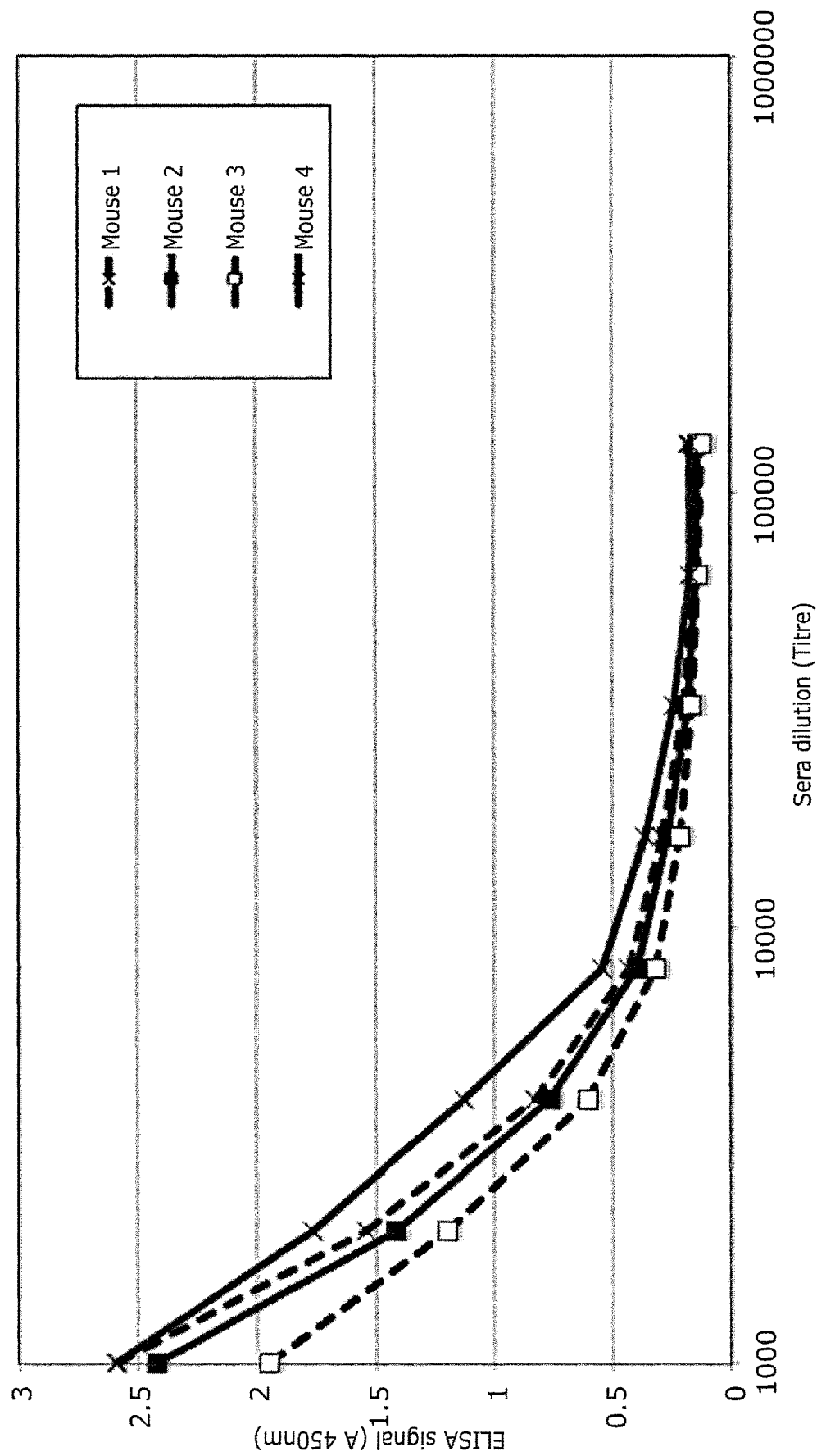

Four mice were immunized using a standard schedule [Ref: Lane Immunology book] by contract research organisation Generon Ltd. The anti-sera was tested by ELISA on scFv (TCT)-Cemadotin and unconjugated scFv (TCT) and all four responded similarly (FIG. 34).

Mouse-4 was used to create a panel of hybridomas of which, 11 clones were identified as strong binders. These 11 clones were ranked by ELISA and also tested by Western Blot for ability to bind to scFv (TCT)-Cemadotin conjugates and not the free components.

Figure 35:
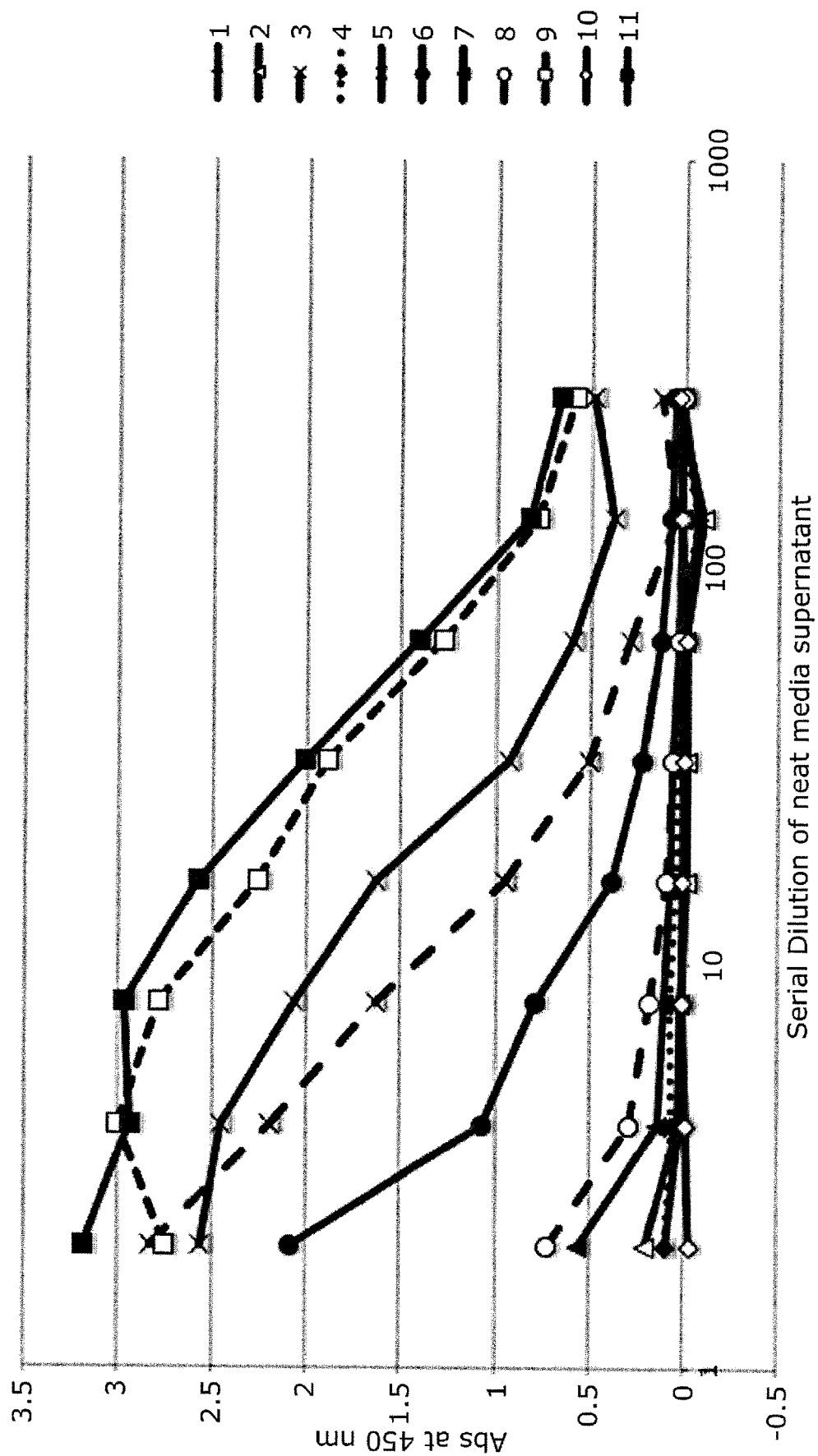

By ELISA, Clone-11 (GA6) appeared to be the best binder, while clone-9 (1E11) also performed strongly. Clones 5, 3, and 6 also showed detectable but weaker activity. Clones-7 and 8 were very weak and clones 1, 2, 4, and 10 appeared to be non-reactive (FIG. 35).

The conditioned media of the hybridomas was tested for expression levels (FIG. 36) and immunoreactivity against scFv-Cemadotin (FIG. 37) by Western Blot. Clones 3,9,11 were all good expressers whereas clones 2,4,5,6,7,10 were low/weak expressers.

Strong binding was seen in clones 5, 9 and 11, picking up higher MW species not visible by eye. Clones 3 and 6 were next strongest, picking up a possible degradation product and clones 7 & 8 were weaker. Very weak/no binding was observed for clones 1, 2, 4 and 10

Clone-9 (1E11) was selected. The hybridoma was expanded, cultured and pure Mab was prepared by protein A chromatography.

Example 34—Measurement of the Pharmacokinetic Profile and Blood Clearance of an scFv-Cemadotin Conjugate (A) Radioactive Assay An scFv, optimised for lysine conjugation was prepared as described in Example 27 or 28 and conjugated (as described in Example 31) to an NHS-derived Cemadotin drug (compound 2). The average DAR was 5 for scFv-TCT-Cem-1 and 4 for scFv-TCT-Cem-2 as determined by SDS-PAGE and IEF gels. This was radiolabelled with Iodine-125 using sodium-125-Iodide (MP Biologicals) and Iodogen™ tubes (Thermo) according to the manufacturer's instructions.

Ten micrograms of radiolabelled scFv or conjugate were injected intravenously into the tail vein of a group of 4 BALB/c female mice (Harlan UK) per time point. At each time point, blood was collected by cardiac puncture under terminal anaesthesia from 4 mice and the spleens were removed by dissection. The radioactivity from the blood and spleen tissues was measured using a gamma counter and compared to the injected dose, correcting for tissue weight. The percentage-injected dose per gram of tissue was plotted over time and pharmacokinetic parameters determined by fitting to a bi-exponential clearance model. For studying in vivo blood clearance pharmacokinetics, data values were fitted using SigmaPlot to equations that conform to the two-compartmental intravenous model of clearance, which takes into account the biexponential clearance phases, distribution phase, and elimination phase, of single intravenous doses. This is described by the exponential decay, double, four-parameter equation $y=ae^{-bx}+ce^{-dx}$, where the distribution phase clearance rate ($t_{1/2}$ alpha) can be determined by In 2/b, and the elimination clearance rate ($t_{1/2}$ beta) can be determined by In 2/d.

The scFv-drug conjugates blood clearance (FIG. 38) was similar to that of the unmodified scFv (Table 13). The spleen uptake of the scFv-drug conjugates was not significantly different to that of the unmodified scFv (FIG. 39). These data both demonstrate that the conjugation technology described here does not result in any detrimental aggregation.

TABLE 13

Pharmacokinetic parameters, blood clearance in mice of cemadotin-based conjugates (compound 69).

| Table 13 | Total Protein Level by 125-I labelling | |
|---|---|---|
| | $t_{1/2}$ (alpha) hrs | $t_{1/2}$ (beta) hrs |
| ScFv (TCT) | 0.4 | 4.3 |
| ScFv (TCT)-Cem 1 (High DAR) | 0.3 | 6.6 |

TABLE 13-continued

Pharmacokinetic parameters, blood clearance in mice of cemadotin-based conjugates (compound 69).

| Table 13 | Total Protein Level by 125-I labelling | |
|---|---|---|
| | $t_{1/2}$ (alpha) hrs | $t_{1/2}$ (beta) hrs |
| ScFv (TCT)-Cem 2 (Medium DAR) | 0.3 | 5.5 |

(B) Direct ADC/scFv Detection Assay

An anti-Cemadotin MAb was raised (Example 33) and used to follow the ADC in mouse blood, to determine the pharmacokinetic properties. Normal BALB/c mice, 6-8 weeks old were maintained in filtered cages until used. A single batch of material (scFv-TCT, scFv (TCT)-Cemadotin, DAR=5 or 8) were prepared as above (Example 31) and 0.1 mg was injected into groups of 20 mice that were sacrificed at 4 time points (5 mice analysed per time point). Around 0.5 ml of whole blood was removed by cardiac puncture into EDTA-tubes and the serum collected by centrifugation. The serum was diluted appropriately into PBS and analysed by ELISA on HER2 coated micro-titre plates (Example 11D), detecting either by anti-T7 Tag (total antibody) or anti-cemadotin (total ADC). Non-injected reference samples were used to create a calibration curve for a direct read-out of ADC/ScFv blood concentration.

The results are shown for total functional scFv (FIG. 40) and total functional ADC (FIG. 41). A comparative plot is shown in FIG. 42.

When measured directly, the free scFv demonstrated typical alpha (distribution) and beta (elimination) phases of bi-exponential blood clearance (Table 14; Constantinou A, et al (2009) Bioconjugate Chem 20:924-31), which was a rapid blood clearance due to the small size. The medium DAR ADC (5 drug payloads attached) had a slower blood clearance both in terms of tissue distribution and elimination. This suggested that the slightly larger molecular mass led to slower clearance rather than any aggregation leading to rapid clearance via the reticulo-endothelial system. This effect was even more pronounced with the higher DAR conjugate (8 drug payloads).

When the total ADC was measured, a similar pattern was seen with similar pharmacokinetic parameters (Table 14). A comparative plot illustrates this (FIG. 42). These data suggest that the scFv-based ADCs, with the high loading, have a retained or even slower blood clearance which is an indication of the low/no aggregation and favourable solubility. The residence in the blood is long enough to allow a therapeutic effect. Also, the similarities between the total scFv and total ADC content suggests that the ADC is stable and not degrading any faster than the scFv component [Lin & Tibbitts. Pharm. Res (2012) 29:2354-66; Kaur et al. Bioanalysis (2013) 5:201-226].

TABLE 14

Summary of pharmacokinetic data

| | Total Antibody Measured by Anti-HER2 binding | | ADC Levels Measured by Anti-Cemadotin drug ELISA | |
|---|---|---|---|---|
| | $t_{1/2}$ (alpha) hrs | $t_{1/2}$ (beta) hrs | $t_{1/2}$ (alpha) hrs | $t_{1/2}$ (beta) hrs |
| ScFv (TCT) | 0.4 | 5.25 | N/A | N/A |
| ScFv (TCT)-CEM (High DAR = 8) | 0.96 | 6.87 | 0.53 | 5.43 |
| ScFv (TCT)-CEM (Medium DAR = 5) | 0.55 | 6.65 | 0.51 | 3.91 |

Example 35—Measurement of the Pharmacokinetic Profile and Blood Clearance of an scFv-Ellipticine Conjugate An anti-ellipticine MAb is raised as above (e.g. example 33) and used to follow the ADC in mouse blood, to determine the pharmacokinetic properties. Normal BALB/c mice, 6-8 weeks old were maintained in filtered cages until used. A single batch of material (scFv-TCT, scFv (TCT)-ellipticine, DAR=5 or 8) is prepared as above (compound 21, Example 29) and 0.1 mg is injected into groups of 20 mice that are sacrificed at 4 time points (5 mice analysed per time point). Around 0.5 ml of whole blood is removed by cardiac puncture into EDTA-tubes and the serum collected by centrifugation. The serum is diluted appropriately into PBS and analysed by ELISA on HER2 coated micro-titre plates (Example 31D), detecting either by anti-T7 Tag (total antibody) or anti-ellipticine (total ADC). Non-injected reference samples were used to create a calibration curve for a direct read-out of ADC/ScFv blood concentration.

When measured directly, the free scFv demonstrates typical alpha (distribution) and beta (elimination) phases of bi-exponential blood clearance (Constantinou A, et al (2009) Bioconjugate Chem 20:924-31), which is a rapid blood clearance due to the small size. The medium DAR ADC (5 drug payloads attached) has a slower blood clearance both in terms of tissue distribution and elimination. This suggested that the slightly larger molecular mass led to slower clearance rather than any aggregation leading to rapid clearance via the reticulo-endothelial system. This effect is even more pronounced with the higher DAR conjugate (8 drug payloads).

Example 36—Measurement of the Pharmacokinetic Profile and Blood Clearance of an scFv-Doxorubicin Conjugate An anti-doxorubicin MAb is commercially available and used to follow the ADC in mouse blood, to determine the pharmacokinetic properties. Normal BALB/c mice, 6-8 weeks old were maintained in filtered cages until used. A single batch of material (scFv-TCT, scFv (TCT)-doxorubicin, DAR=5 or 8) is prepared as above (compound 72) and 0.1 mg is injected into groups of 20 mice that are sacrificed at 4 time points (5 mice analysed per time point). Around 0.5 ml of whole blood is removed by cardiac puncture into EDTA-tubes and the serum collected by centrifugation. The serum is diluted appropriately into PBS and analysed by ELISA on HER2 coated micro-titre plates (Example 31D), detecting either by anti-T7 Tag (total antibody) or anti-doxorubicin (total ADC). Non-injected reference samples were used to create a calibration curve for a direct read-out of ADC/ScFv blood concentration.

When measured directly, the free scFv demonstrates typical alpha (distribution) and beta (elimination) phases of bi-exponential blood clearance (Constantinou A, et al (2009) Bioconjugate Chem 20:924-31), which is a rapid blood clearance due to the small size. The medium DAR ADC (5 drug payloads attached) has a slower blood clearance both in terms of tissue distribution and elimination. This suggested that the slightly larger molecular mass led to slower clearance rather than any aggregation leading to rapid clearance via the reticulo-endothelial system. This effect is even more pronounced with the higher DAR conjugate (8 drug payloads).

Example 37—Measurement of the Pharmacokinetic Profile and Blood Clearance of an scFv-MMAE Conjugate An anti-MMAE MAb is commercially available and used to follow the ADC in mouse blood, to determine the pharmacokinetic properties. Normal BALB/c mice, 6-8 weeks old were maintained in filtered cages until used. A single batch of material (scFv-TCT, scFv (TCT)-MMAE, DAR=5 or 8) is prepared as above (Example 32) and 0.1 mg is injected into groups of 20 mice that are sacrificed at 4 time points (5 mice analysed per time point). Around 0.5 ml of whole blood is removed by cardiac puncture into EDTA-tubes and the serum collected by centrifugation. The serum is diluted appropriately into PBS and analysed by ELISA on HER2 coated micro-titre plates (Example 31 D), detecting either by anti-T7 Tag (total antibody) or anti-MMAE (total ADC). Non-injected reference samples were used to create a calibration curve for a direct read-out of ADC/ScFv blood concentration.

When measured directly, the free scFv demonstrates typical alpha (distribution) and beta (elimination) phases of bi-exponential blood clearance (Constantinou A, et al (2009) Bioconjugate Chem 20:924-31), which is a rapid blood clearance due to the small size. The medium DAR ADC (5 drug payloads attached) has a slower blood clearance both in terms of tissue distribution and elimination. This suggested that the slightly larger molecular mass led to slower clearance rather than any aggregation leading to rapid clearance via the reticulo-endothelial system. This effect is even more pronounced with the higher DAR conjugate (8 drug payloads).

Example 38—Measurement of the Tumour Uptake and Tumour to Normal Tissue Ratios of an scFv-Cemadotin Conjugate An scFv, optimised for lysine conjugation is prepared as described in Example 27 or 28 and is conjugated (as described in Example 31) to an NHS-derived Cemadotin drug (compounds 2, 69). The average DAR is between 6-10. This was radiolabelled with Iodine-125 using sodium-125-Iodide (MP Biologicals) and Lodogen™ tubes (Thermo) according to the manufacturer's instructions.

Ten micrograms of radiolabelled scFv or conjugate were injected intravenously into the tail vein of a group of 4 BALB/c nude female mice (Harlan UK) growing subcutaneous tumours of the appropriate target expression (e.g. SKOV3 for HER2 expression) per time point. At each time point, blood is collected by cardiac puncture under terminal anaesthesia from 4 mice and the tumours and normal organs are removed by dissection. The radioactivity from the blood and tissues are measured using a gamma counter and compared to the injected dose, correcting for tissue weight. The percentage-injected dose per gram of tissue is plotted over time.

Example 39—Measurement of the Tumour Uptake and Tumour to Normal Tissue Ratios of an scFv-Ellipticine Conjugate An scFv, optimised for lysine conjugation is prepared as described in Example 27 or 28 and is conjugated (as described in Example 29) to an NHS-derived ellipticine drug (compounds 23, 73). The average DAR is between 6-10. This was radiolabelled with Iodine-125 using sodium-125-Iodide (MP Biologicals) and Lodogen™ tubes (Thermo) according to the manufacturer's instructions.

Ten micrograms of radiolabelled scFv or conjugate were injected intravenously into the tail vein of a group of 4 BALB/c nude female mice (Harlan UK) growing subcutaneous tumours of the appropriate target expression (e.g. SKOV3 for HER2 expression) per time point. At each time point, blood is collected by cardiac puncture under terminal anaesthesia from 4 mice and the tumours and normal organs are removed by dissection. The radioactivity from the blood and tissues are measured using a gamma counter and compared to the injected dose, correcting for tissue weight. The percentage-injected dose per gram of tissue is plotted over time.

Example 40—Measurement of the Tumour Uptake and Tumour to Normal Tissue Ratios of an scFv-Doxorubicin Conjugate An scFv, optimised for lysine conjugation is prepared as described in Example 27 or 28 and is conjugated (as described in Example 30) to an NHS-derived doxorubicin drug (compounds 7, 72). The average DAR is between 6-8. This was radiolabelled with Iodine-125 using sodium-125-Iodide (MP Biologicals) and Lodogen™ tubes (Thermo) according to the manufacturer's instructions.

Ten micrograms of radiolabelled scFv or conjugate were injected intravenously into the tail vein of a group of 4 BALB/c nude female mice (Harlan UK) growing subcutaneous tumours of the appropriate target expression (e.g. SKOV3 for HER2 expression) per time point. At each time point, blood is collected by cardiac puncture under terminal anaesthesia from 4 mice and the tumours and normal organs are removed by dissection. The radioactivity from the blood and tissues are measured using a gamma counter and compared to the injected dose, correcting for tissue weight. The percentage-injected dose per gram of tissue is plotted over time.

Example 41—Measurement of the Tumour Uptake and Tumour to Normal Tissue Ratios of an scFv-MMAE Conjugate An scFv, optimised for lysine conjugation is prepared as described in Example 27 or 28 and is conjugated (as described in Example 32) to an NHS-derived MMAE drug. The average DAR is between 6-10. This was radiolabelled with Iodine-125 using sodium-125-Iodide (MP Biologicals) and Lodogen™ tubes (Thermo) according to the manufacturer's instructions.

Ten micrograms of radiolabelled scFv or conjugate were injected intravenously into the tail vein of a group of 4 BALB/c nude female mice (Harlan UK) growing subcutaneous tumours of the appropriate target expression (e.g. SKOV3 for HER2 expression) per time point. At each time point, blood is collected by cardiac puncture under terminal anaesthesia from 4 mice and the tumours and normal organs are removed by dissection. The radioactivity from the blood and tissues are measured using a gamma counter and compared to the injected dose, correcting for tissue weight. The percentage-injected dose per gram of tissue is plotted over time.

Example 42—Tumour Regression Studies in Nude Mice Bearing SKBr3 Tumour Xenografts Treated with Two scFv (TCT)-P5C5 ADC DARs Female nude BALB/c mice, 6-8 weeks old (Harlan UK), were used for in vivo studies. All in vivo research was carried out under a UK Home Office project license PPL 70/5833. Human tumor xenografts were set up by injecting mice subcutaneously into the left flank with 0.1 mL containing up to 5 million SKBr3 cells in 50% matrigel. Tumour growth was monitored and took 2-3 weeks to reach the required 3-5 mm diameter for subsequent testing. When tumours were about 100 mm$^3$, 10 mg/kg (0.25 mg total dose) was injected IV with a scFv (TCT)-P5C5 conjugate (as prepared in example 31, compound 71) on 5 sequential days (total ADC dose=1.25 mg per animal and the tumour sizes were monitored. The tumour volume is plotted compared to the starting volume (FIG. 43) showing about 10 days of regression until the tumour starts to grow again. This is equal to around 1 month tumour growth delay and confirms that the scFv (TCT)-ADCs have therapeutic function in a pre-clinical animal model.

Example 43—Tumour Therapy of an scFv-MMAE Conjugate

Female nude BALB/c mice, 6-8 weeks old (Harlan UK), are used for in vivo studies. All in vivo research is carried out under a UK Home Office project license. Human tumor xenografts are set up by injecting mice subcutaneously into the left flank with 0.1 mL containing up to 5 million SKOV3 cells in 50% matrigel. Tumour growth is monitored and takes 2-3 weeks to reach the required 3-5 mm diameter for subsequent testing. When tumours are about 100 mm$^3$, 10 mg/kg (0.25 mg total dose) is injected IV with a scFv (TCT)-MMAE conjugate (as prepared in example 32) on 5 sequential days (total ADC dose=1.25 mg per animal and the tumour sizes were monitored. The tumour volume is plotted compared to the starting volume.

Example 44—Pharmaceutical Formulations and Administration

A further aspect of the invention provides a pharmaceutical formulation comprising a compound according to the first aspect of the invention in admixture with a pharmaceutically or veterinarily acceptable adjuvant, diluent or carrier.

Preferably, the formulation is a unit dosage containing a daily dose or unit, daily sub-dose or an appropriate fraction thereof, of the active ingredient.

The compounds of the invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the compounds of the invention can be administered alone but will generally be administered in admixture with a suitable pharmaceutical excipient diluent or carrier selected with regard to the intended route of administration and standard pharmaceutical practice.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications. The compounds of the invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the compounds of the invention will usually be from 1 mg/kg to 30 mg/kg. Thus, for example, the tablets or capsules of the compound of the invention may contain a dose of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" delivers an appropriate dose of a compound of the invention for delivery to the patient. It will be appreciated that he overall daily dose with an aerosol will vary from patient to patient, and may be administered in a single dose or, more usually, in divided doses throughout the day.

Alternatively, the compounds of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route, particularly for treating diseases of the eye.

For ophthalmic use, the compounds of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or topical administration of the compounds of the invention is the preferred route, as they are the most convenient. In circumstances where the recipient suffers from a swallowing disorder or from impairment of drug absorption after oral administration, the drug may be administered parenterally, e.g. sublingually or buccally.

For veterinary use, a compound of the invention is administered as a suitably acceptable formulation in accordance with normal veterinary practice and the veterinary surgeon will determine the dosing regimen and route of administration which will be most appropriate for a particular animal.

Example 45—Preparation of MMAF-C$_5$—NHS Ester (78)

min: 40 to 55% B, 24 to 35 min: 55 to 85% B. compound collected at $t_R$ 16.4 min and lyophilised to give a white solid (81%). HRMS: ESI m/z Found 846.5200 [M+H]$^+$ calculated 846.5228 for $C_{44}H_{72}N_5O_{11}$ $^1$H NMR (400 MHz, DMSO-d6) δ 12.22 (s, 1H), 7.46-6.98 (m, 5H), 4.93-4.38 (m, 3H), 4.04 (dd, J=13.7, 9.9 Hz, 2H), 3.66 (dq, J=12.8, 6.4 Hz, 4H), 3.50-3.37 (m, 6H), 3.29-3.15 (m, 9H), 3.15-3.00 (m, 4H), 2.94-2.65 (m, 12H), 2.30 (t, J=7.4 Hz, 12H), 1.94 (p, J=6.6 Hz, 3H), 1.76 (p, J=7.4 Hz, 9H), 1.51-1.22 (m, 28H), 1.13 (dt, J=19.1, 6.8 Hz, 6H), 1.04-0.69 (m, 20H).

To a solution of MMAF-C$_5$ (50 mg, 0.05 mmol) in DMF (1 ml) was added DIPEA (15 μl) and TSTU (18 mg, 0.05 mmol) at room temperature. The reaction mixture was stirred under N$_2$ atmosphere for 4 h. The solvents were

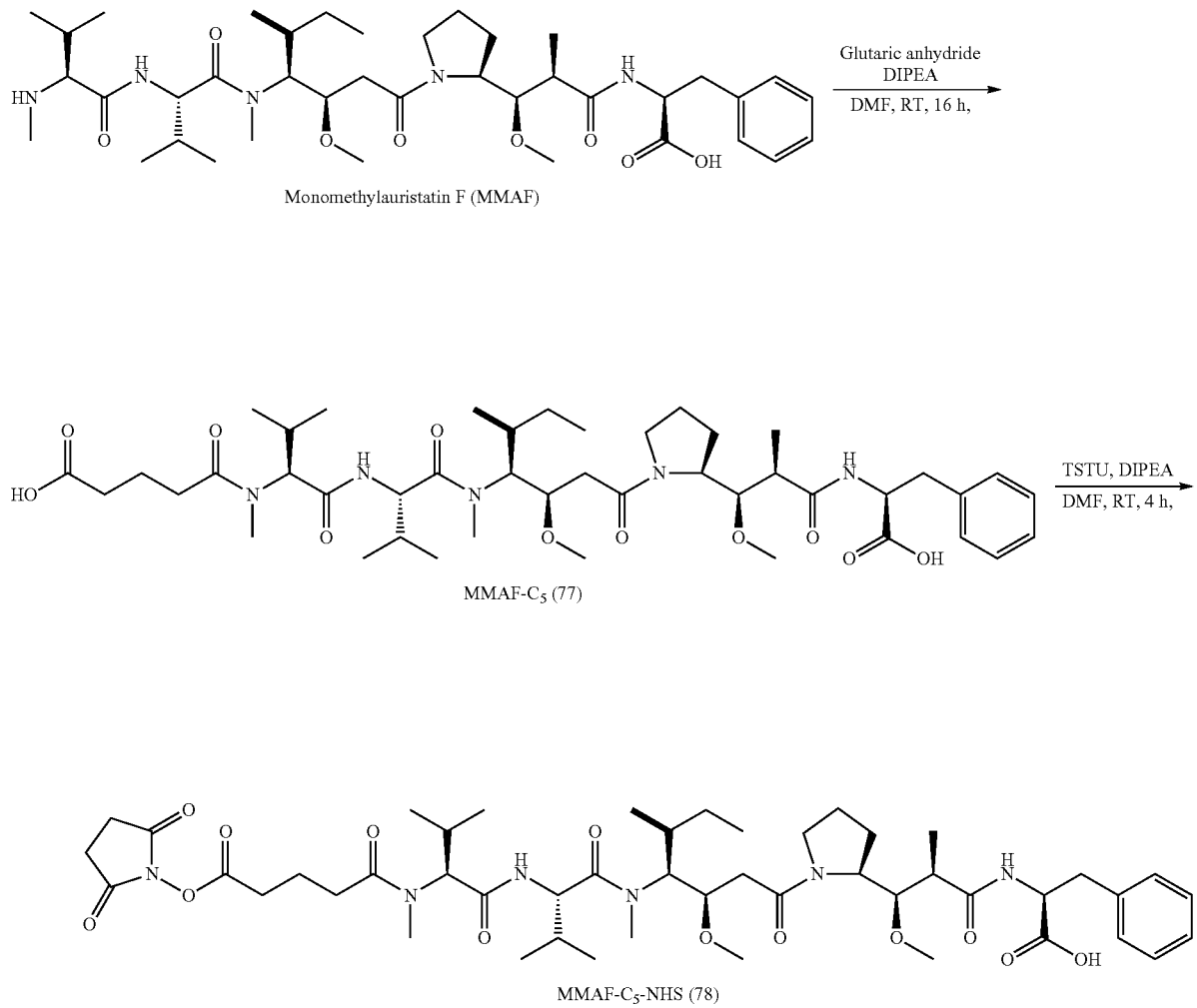

To a solution of MMAF (0.1 g, 0.177 mmol) in DMF (4 ml) was added DIPEA (0.12 ml) and glutaric anhydride (50.5 mg, 0.44 mmol) at room temperature. The reaction mixture was stirred under N$_2$ atmosphere for 16 h. The solvents were evaporated in vacuo and the obtained crude compound was purified on Prep HPLC using Phenomenex Synergi Polar-RP column (Eluents: A=0.1% TFA in Water, B=MeCN) gradient—0 to 11 Min: 15 to 40% B, 11 to 24 evaporated in vacuo and the obtained crude compound was purified on Prep HPLC using Phenomenex Synergi Polar-RP column (Eluents: A=0.1% TFA in Water, B=MeCN) gradient—0 to 11 Min: 15 to 40% B, 11 to 24 min: 40 to 55% B, 24 to 35 min: 55 to 85% B. The desired compound was collected at $t_R$ 20.4 min and lyophilised to give a white solid (22 mg, 40%). HRMS: ESI m/z Found 943.5416 [M+H]$^+$ calculated 943.5392 for $C_{48}H_{75}N_6O_{13}$ Example 46—Preparation of MMAF-C5-NHS Ester by Direct Activation

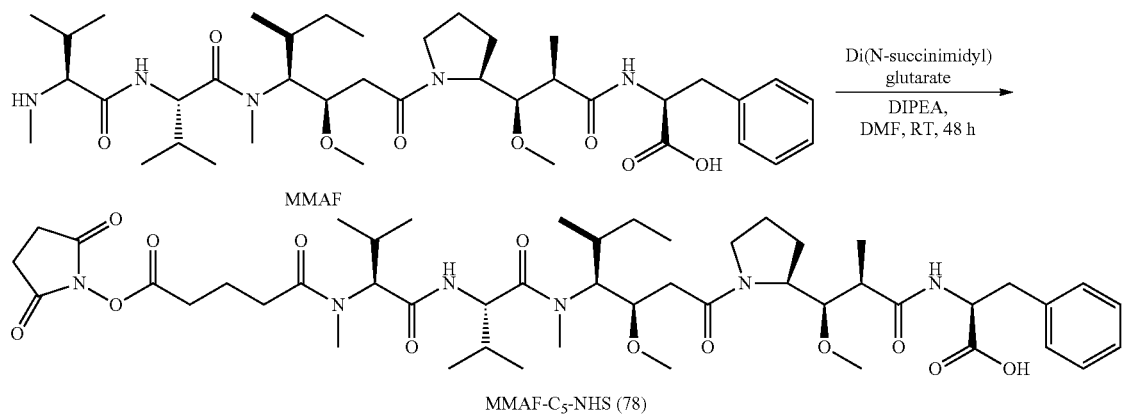

MMAF

MMAF-C₅-NHS (78)

To a solution of MMAF (50 mg, 0.06 mmol) in acetonitrile (5 ml) was added DIPEA (0.1 ml) and Di(N-succinimidyl) glutarate (193 mg, 0.6 mmol) at room temperature. The reaction mixture was stirred under $N_2$ atmosphere for 72 h. The solvents were evaporated in vacuo and the obtained crude compound was purified on Prep HPLC using Phenomenex Synergi Polar-RP column (Eluents: A=0.1% TFA in Water, B=MeCN) gradient—0 to 11 Min: 15 to 40% B, 11 to 24 min: 40 to 55% B, 24 to 35 min: 55 to 85% B. The desired compound was collected at $t_R$ 20.4 min and lyophilised to give a white solid (10 mg, 18%).

$^1$H NMR (400 MHz, DMSO-d6) δ 8.34 (t, J=7.6 Hz, 1H), 7.14-6.90 (m, 5H), 4.41 (dt, J=11.3, 4.8 Hz, 1H), 4.22 (t, J=8.1 Hz, 1H), 3.74 (dd, J=10.0, 4.4 Hz, 1H), 3.10-2.90 (m, 8H), 2.88-2.66 (m, 6H), 2.54-2.41 (m, 2H), 2.28 (p, J=1.8 Hz, 38H), 2.07-1.90 (m, 3H), 1.74-1.31 (m, 5H), 1.14 (d, J=48.5 Hz, 3H), 0.88-0.77 (m, 3H), 0.77-0.47 (m, 20H).

Example 47—Preparation of MMAE-PAB-Cit-Val-C₅—NHS (82)

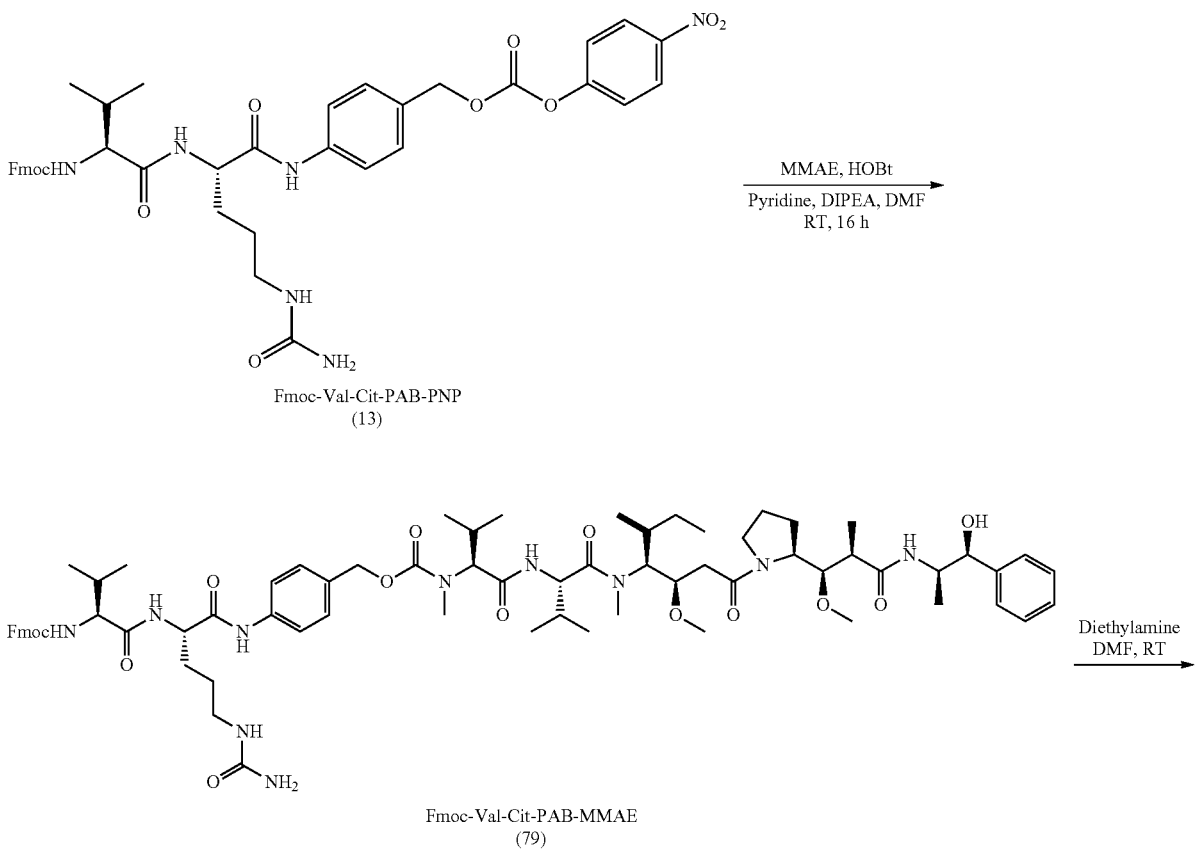

Fmoc-Val-Cit-PAB-PNP (13)

Fmoc-Val-Cit-PAB-MMAE (79)

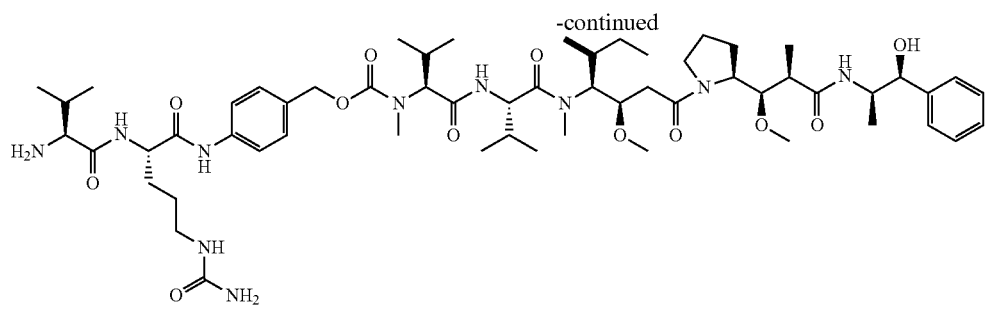

Val-Cit-PAB-MMAE
(80)

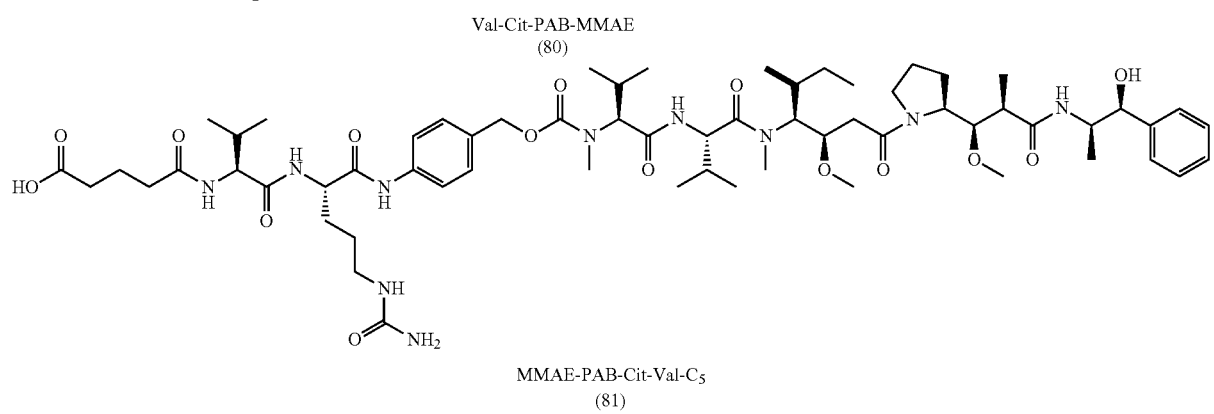

MMAE-PAB-Cit-Val-C$_5$
(81)

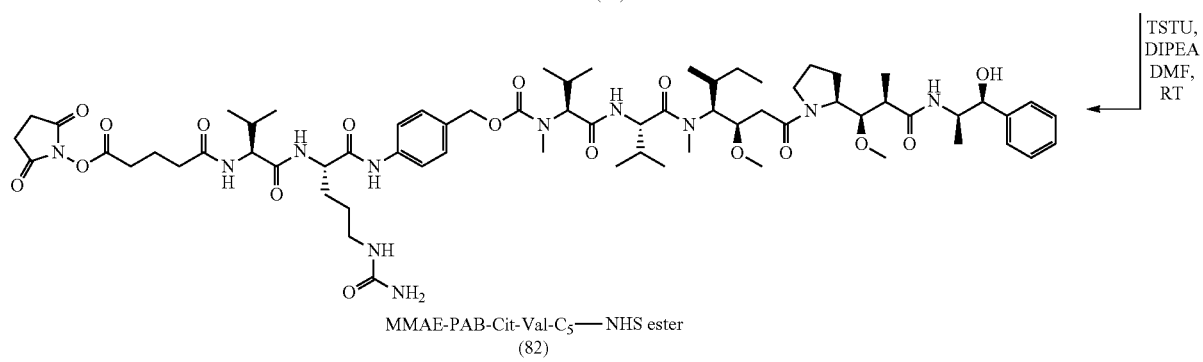

MMAE-PAB-Cit-Val-C$_5$—NHS ester
(82)

To a solution of MMAE (0.15 g, 0.18 mmol) and Fmoc-Val-Cit-PAB-PNP 13 (0.152 g, 0.19 mmol) in DMF (1.5 ml), was added HOBt (58 mg, 0.36 mmol), pyridine (0.12 ml) and DIPEA (31 µl). The reaction mixture was stirred under N$_2$ atmosphere at room temperature for 24 h. Solvents were evaporated in vacuo and the residue triturated with ethyl acetate. The resulting solid was filtered, washed with ethyl acetate, dried to give 79. LC-MS ESI m/z 1367.7 [M+Na]$^+$ This was used directly without further purification.

A solution Fmoc-Val-Cit-PAB-MMAE 79 (0.3 g, 0.22 mmol) in DMF (1.5 ml) and diethylamine (1.12 ml) was stirred for 3 hours at room temperature. The reaction mixture was then concentrated in vacuo. The product was precipitated in diethyl ether and filtered affording 0.15 g of 80 as an off white powder which was used without further purification. LC-MS ESI m/z 1145.6 [M+Na]$^+$ $^1$H NMR (400 MHz, DMSO-d6) b 10.20 (d, J=6.5 Hz, 1H), 8.70 (d, J=7.6 Hz, 1H), 8.07 (d, J=4.9 Hz, 4H), 7.61 (dd, J=26.0, 8.3 Hz, 2H), 7.45-7.21 (m, 7H), 7.18 (dd, J=8.9, 6.3 Hz, 1H), 6.04 (s, 1H), 5.48 (s, 2H), 5.21-4.88 (m, 2H), 4.63-4.37 (m, 4H), 4.26 (t, J=11.7 Hz, 1H), 3.98 (m, 3H), 3.33-3.08 (m, 12H), 3.10-2.69 (m, 8H), 2.27-1.88 (m, 5H), 1.90-1.66 (m, 5H), 1.64-1.19 (m, 7H), 1.15-0.52 (m, 36H).

To a solution of compound H-Val-Cit-PAB-MMAE 80 (0.1 g, 0.177 mmol) in DMF (4 ml) was added DIPEA (0.12 ml) and glutaric anhydride (50.5 mg, 0.44 mmol) at room temperature. The reaction mixture was stirred under N$_2$ atmosphere for 16 h. The solvents were evaporated in vacuo, the obtained crude compound 81 was washed with diethyl ether and used directly foin the next step. HRMS: ESI m/z Found 1237.7526 [M+Na]$^+$ calculated 1237.7448 for C$_{63}$H$_{101}$N$_{10}$O$_{15}$ To a solution of MMAE-PAB-Cit-Val-C$_5$ 81 (0.1 g, 0.08 mmol) in DMF (2 ml) was added DIPEA (29 µl) and TSTU (38 mg, 0.12 mmol) at room temperature and the reaction mixture was stirred under N$_2$ atmosphere for 3 h. The solvents were evaporated in vacuo and the obtained product was purified on Prep HPLC using Phenomenex Synergi Polar-RP column (Eluents: A=0.1% TFA in Water, B=MeCN) gradient—0 to 14 Min: 15 to 85% B, the desired compound was collected at t$_R$ 10.1 min and lyophilised to give a white powder (40%). HRMS: ESI m/z Found 1356.7623 [M+Na]$^+$ calculated 1356.7431 for C$_{67}$H$_{103}$N$_{11}$O$_{17}$Na $^1$H NMR (400 MHz, DMSO-d6) δ 9.79 (s, 1H), 8.05-7.79 (m, 2H), 7.68 (d, J=8.6 Hz, 2H), 7.37 (d, J=8.0 Hz, 3H), 7.25-7.00 (m, 7H), 6.96 (t, J=7.2 Hz, 1H), 4.85 (d, J=15.3 Hz, 4H), 4.55-4.09 (m, 10H), 4.00-3.56 (m, 12H), 3.13-2.85 (m, 12H), 2.75 (s, 5H), 2.67-2.58 (m, 7H), 2.54-2.36 (m, 4H), 2.28 (p, J=1.8 Hz, 88H), 2.14-1.99 (m, 4H), 1.95-1.67 (m, 5H), 1.68-1.40 (m, 8H), 1.39-0.93 (m, 7H), 0.90-0.31 (m, 40H).

Example 48—Preparation of MMAE-PAB-Cit-Val-dPEG₅-NHS Ester (84)

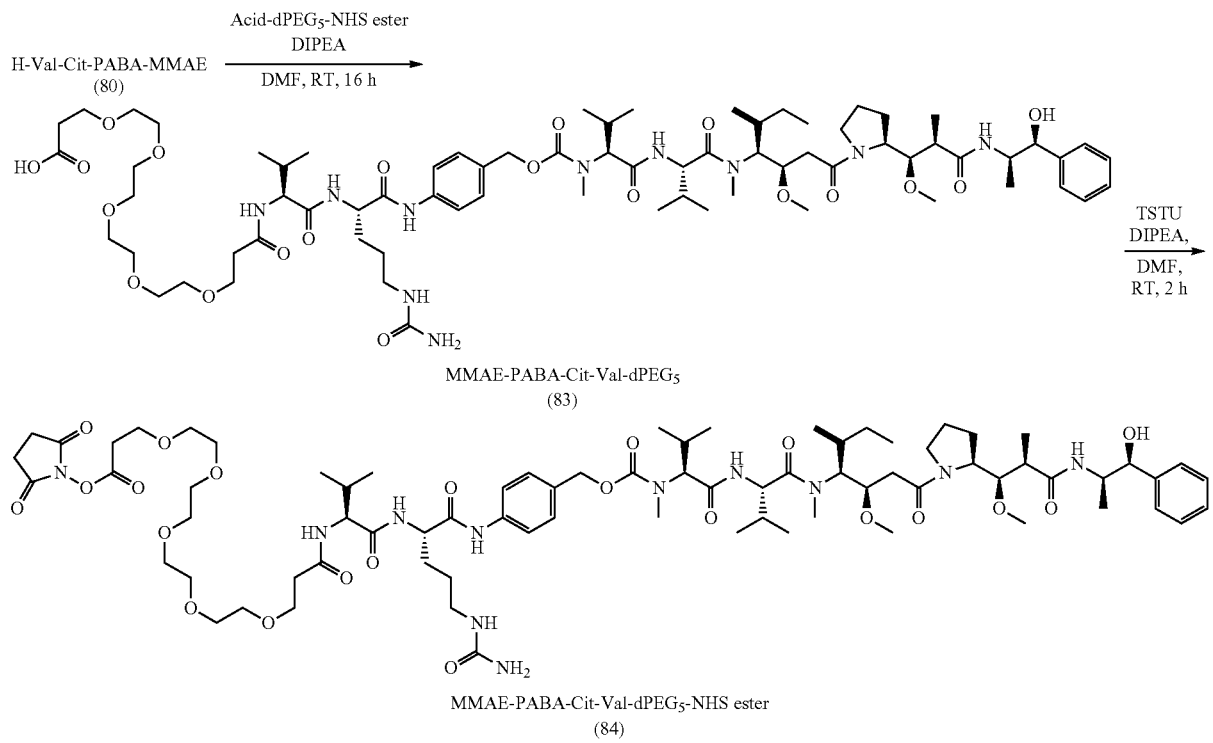

To a solution of compound H-Val-Cit-PAB-MMAE 80 (0.2 g, 0.177 mmol) in DMF (7 ml) was added DIPEA (0.1 ml) and Acid-dPEG₅-NHS (50.5 mg, 0.21 mmol) at room temperature. The reaction mixture was stirred under N₂ atmosphere for 16 h. The solvents were evaporated in vacuo, the obtained crude compound 83 was washed with diethyl ether and directly used for the next step. LC-MS ESI m/z 1466.6 [M+Na]⁺

To a solution of Acid-dPEG₅-Val-Cit-PAB-MMAE 83 (0.25 g, 0.17 mmol) in DMF (7 ml) was added DIPEA (0.15 ml) and TSTU (120 mg, 0.39 mmol) at room temperature and the reaction mixture was stirred under N₂ atmosphere for 3 h. The solvents were evaporated in vacuo and the crude product was purified on Biotage flash purification system using C18 column to yield the compound NHS-PEG₅-Val-Cit-PAB-MMAE 84 as a white solid after lyophilisation, MS: ESI m/z 1562.9 [M+Na]⁺

¹H NMR (400 MHz, DMSO-d6) δ 10.03-9.96 (m, 1H), 8.12 (dd, J=19.3, 7.8 Hz, 1H), 7.90 (t, J=8.9 Hz, 1H), 7.69-7.55 (m, 2H), 7.38-7.23 (m, 5H), 7.23-7.13 (m, 1H), 5.11-4.93 (m, 2H), 4.52-4.33 (m, 3H), 4.32-4.19 (m, 2H), 3.99 (m, 2H), 3.83-3.68 (m, 2H), 3.65-3.41 (m, 17H), 3.22 (dd, J=19.9, 8.6 Hz, 6H), 3.12 (s, 1H), 3.10-2.74 (m, 12H), 2.42 (m, 12H), 2.26 (dd, J=15.9, 9.2 Hz, 1H), 2.19-1.90 (m, 4H), 1.79-1.65 (m, 3H), 1.65-1.52 (m, 2H), 1.52-1.31 (m, 3H), 1.08-0.96 (m, 6H), 0.96-0.71 (m, 23H).

Example 49—Preparation of MMAE-PAB-Cit-Val-dPEG₉-NHS Ester (86)

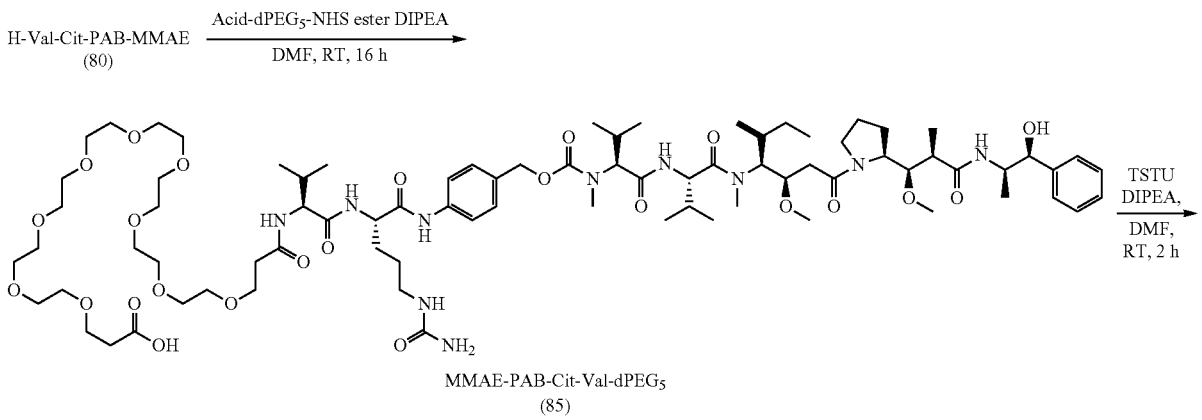

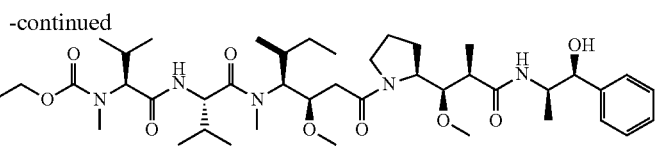
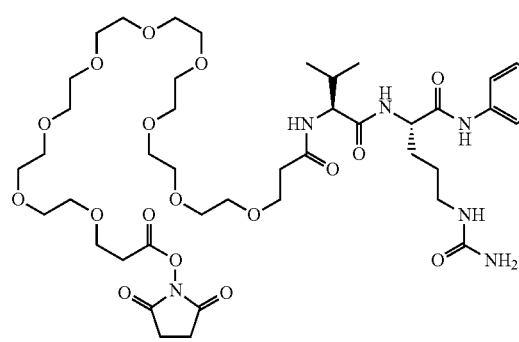

MMAE-PAB-Cit-Val-dPEG$_5$-NHS ester
(86)

MMAE-PAB-Cit-Val-dPEG$_9$-NHS ester 86 was prepared as example 47 by reacting H-Val-Cit-PAB-MMAE 80 with Acid-dPEG$_9$-NHS followed by activation with TSTU. The crude, obtained after evaporation was purified on Biotage flash purification system using C18 column to yield the compound MMAE-PAB-Cit-Val-dPEG$_9$-NHS 86 as a white solid after lyophilisation, MS: ESI m/z 1718.3093 [M+H]$^+$ Example 50—Preparation of Auristatin F-C$_5$—NHS Ester (88)

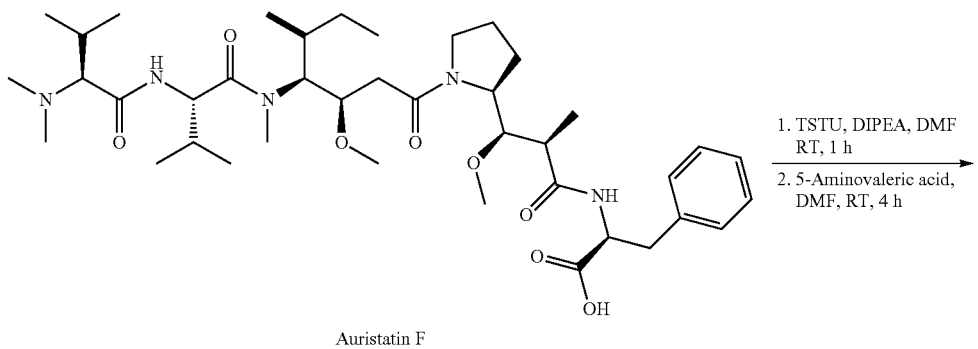

Auristatin F

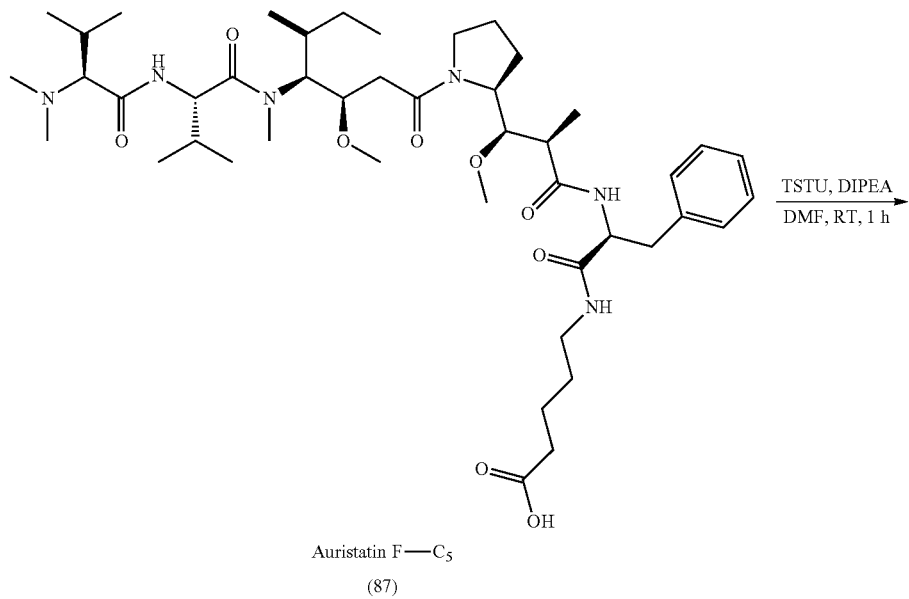

Auristatin F—C$_5$
(87)

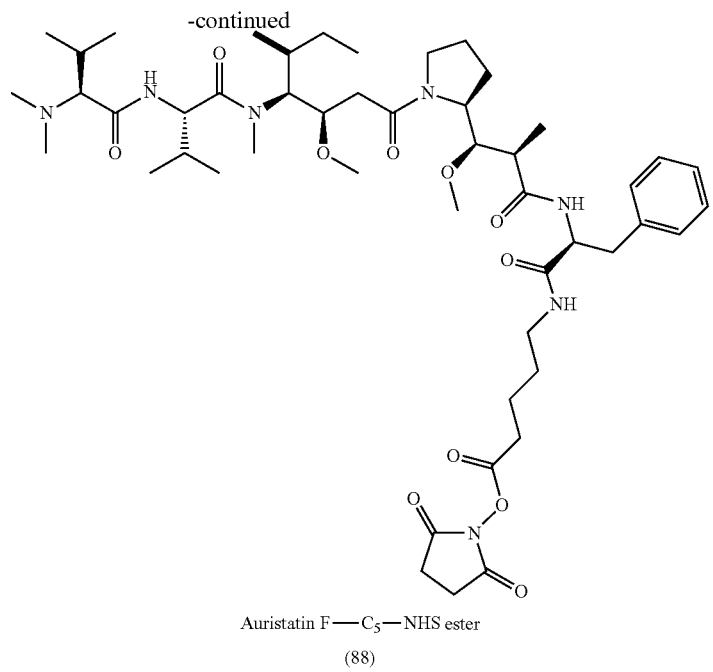

Auristatin F—C$_5$—NHS ester
(88)

Auristatin F (0.1 g, 0.116 mmol) and HATU (40 mg, 0.104 mmol) was dissolved in DMF (3 ml) and DIPEA (40 µl) was added to it. The reaction mixture was stirred at room temperature for 40 min and then added dropwise to a solution of 5-Aminovaleric acid (15 mg, 0.127 mmol) in DMF (2 ml). The reaction mixture was stirred at room temperature for 4 h and evaporated in vacuo. The crude product was purified on Biotage flash purification system using C18 column to yield the compound Auristatin F-C5 acid 87 as a white solid (85 mg, 84%). LC-MS ESI m/z 867.5 [M+Na]$^+$ To a solution of the Auristatin F-C5 acid 87 (70 mg, 0.08 mmol) in DIPEA (72 µl) and DMF (3 ml) was added TSTU (57 mg 0.19 mmol) and the reaction mixture was stirred at room temperature for 1 h. The solvents were evaporated in vacuo and the crude compound was purified on Biotage flash purification system using C18 column to yield the compound Auristatin F-C$_5$—NHS ester 88 as a white solid after lyophilisation (46 mg, 59%). LC-MS ESI m/z 964.5 [M+Na]$^+$ $^1$H NMR (400 MHz, DMSO-d6) δ 9.57 (s, 1H), 8.94 (q, J=7.9, 7.2 Hz, 1H), 8.05-7.84 (m, 1H), 7.31-7.10 (m, 5H), 4.60 (m, 2H), 3.99 (d, J=7.5 Hz, 1H), 3.84-3.73 (m, 2H), 3.70 (d, J=7.6 Hz, 1H), 3.50 (td, J=14.0, 7.5 Hz, 1H), 3.32-3.10 (m, 9H), 2.99 (m, 6H), 2.84-2.58 (m, 14H), 2.45 (dd, J=14.9, 5.0 Hz, 4H), 2.37-2.22 (m, 3H), 2.01 (dd, J=12.8, 5.7 Hz, 1H), 1.94-1.73 (m, 3H), 1.59-1.36 (m, 5H), 1.08-0.71 (m, 25H).

Example 51—Preparation of Maytansinol DM1-dPEG$_4$-NHS Ester (89)

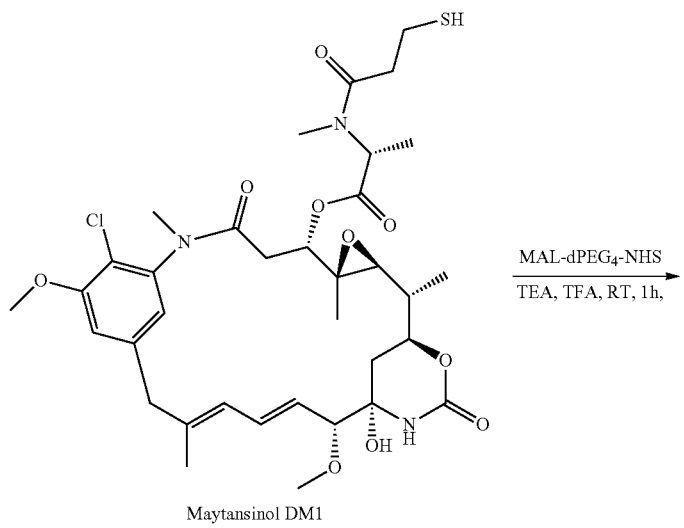

Maytansinol DM1

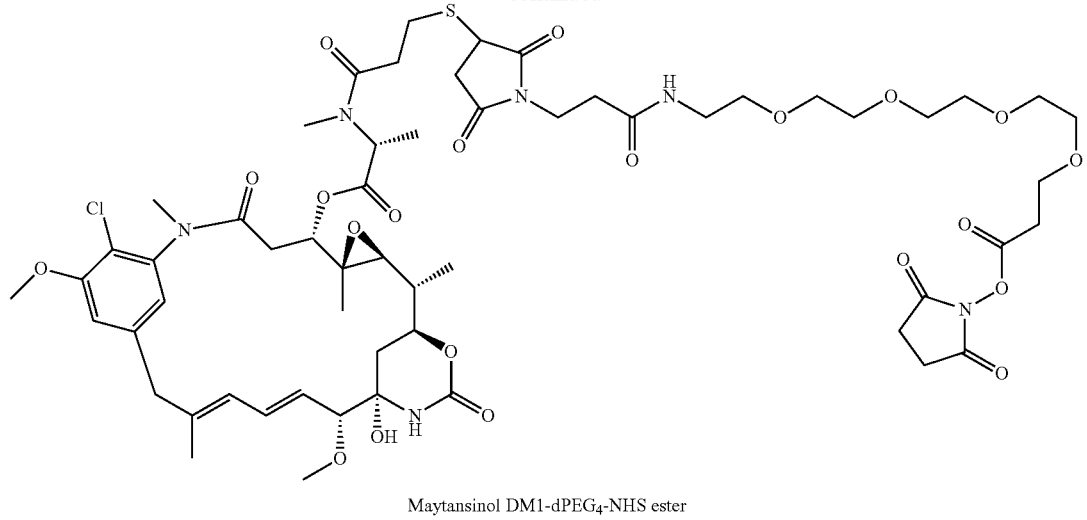

Maytansinol DM1-dPEG₄-NHS ester
(89)

To a solution of DM1 (0.1 g, 0.135 mmol) in THF was added Et3N (18.9 μl) followed by addition of the Mal-dPEG₄-NHS (77 mg, 0.15 mmol). The reaction mixture was stirred at room temperature under $N_2$ atmosphere for 1 h and the solvents were removed in vacuo. The crude product was purified on Biotage flash purification system using C1 8 column to yield the compound DM1-dPEG₅-NHS as a white solid after lyophilisation (105 mg, 75%). LC-MS ESI m/z 1274.60 [M+Na]⁺

¹H NMR (400 MHz, DMSO-d6) δ 8.01 (q, J=5.6 Hz, 1H), 7.17 (dd, J=8.1, 1.8 Hz, 1H), 6.90 (s, 1H), 6.68-6.46 (m, 3H), 5.55 (dd, J=12.8, 8.9 Hz, 1H), 5.31 (q, J=6.7 Hz, 1H), 4.52 (dd, J=12.1, 2.9 Hz, 1H), 4.07 (t, J=10.8 Hz, 2H), 3.93 (d, J=1.5 Hz, 4H), 3.85 (dd, J=9.0, 4.0 Hz, 1H), 3.71 (t, J=6.0 Hz, 2H), 3.63-3.41 (m, 18H), 3.37 (t, J=5.9 Hz, 3H), 3.32-3.07 (m, 11H), 3.07-2.86 (m, 6H), 2.79 (d, J=11.6 Hz, 7H), 2.71 (s, 4H), 2.25 (m, 4H), 2.04 (d, J=14.4 Hz, 1H), 1.59 (s, 4H), 1.55-1.34 (m, 3H), 1.33-1.03 (m, 8H), 0.78 (d, J=2.1 Hz, 3H).

Example 52—Preparation of Maytansinol DM1-dPEG₁₂-NHS Ester (90)

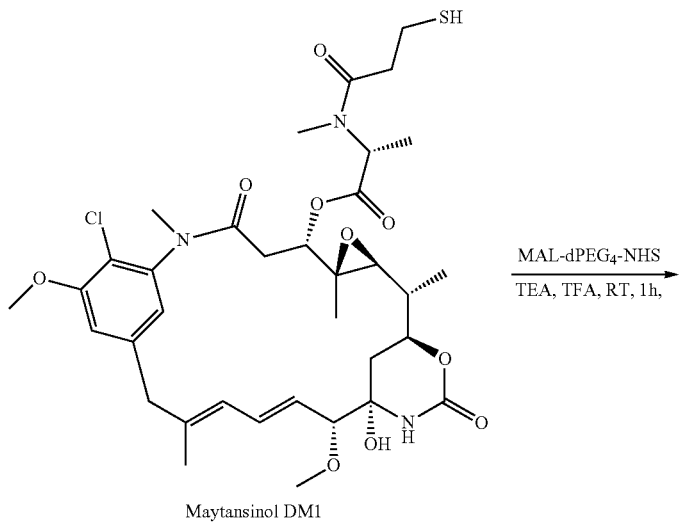

Maytansinol DM1

MAL-dPEG₄-NHS
→
TEA, TFA, RT, 1h,

-continued

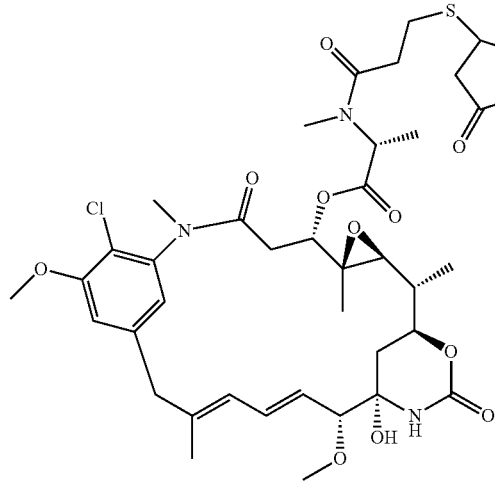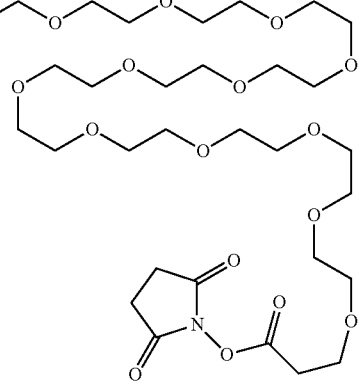

Maytansinol DM1-dPEG$_{12}$-NHS ester
(90)

To a stirred and degassed solution of DM1 (0.05 g, 0.1678 mmol) in THF (3 ml) was added Et$_3$N (9.45 µl) followed by addition of the Mal-dPEG$_9$-NHS (58.7 mg, 0.1678 mmol) dissolved in THF (4 ml). The reaction mixture was stirred at room temperature under N$_2$ atmosphere for 3 h and the solvents were removed in vacuo. The crude product was purified on Biotage flash purification system using C18 column to yield the compound DM1-dPEG$_{12}$-NHS 90 as a white solid after lyophilisation (31 mg, 28%). LC-MS ESI m/z 1625.9 [M+Na]$^+$ Example 53—Preparation of Ellipticine-(DNMEA)-PAB-Cit-Val-dPEG$_3$-NHS Ester (95)

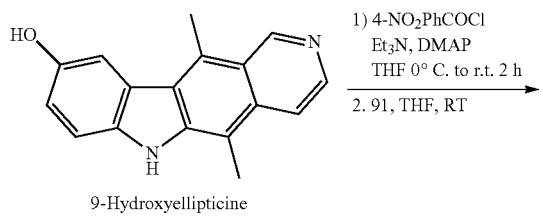

9-Hydroxyellipticine 1) 4-NO$_2$PhCOCl
Et$_3$N, DMAP
THF 0° C. to r.t. 2 h
2. 91, THF, RT

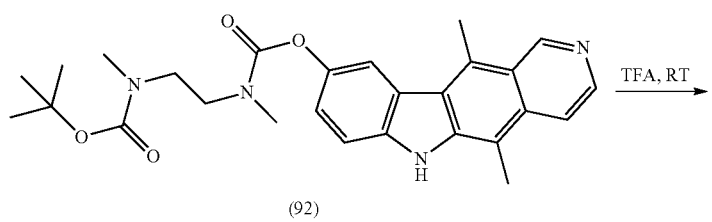

(92)

TFA, RT

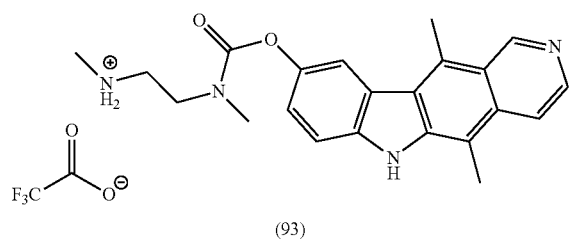

(93)

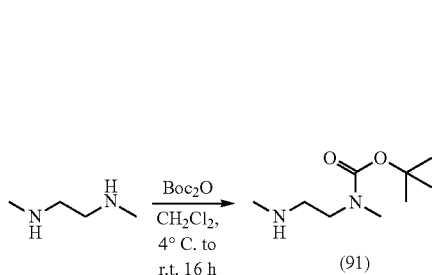
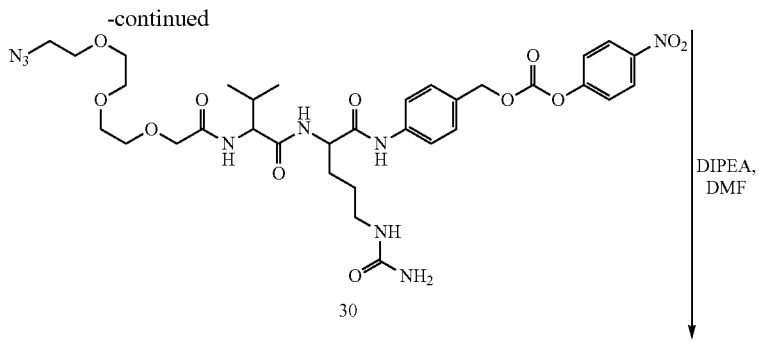
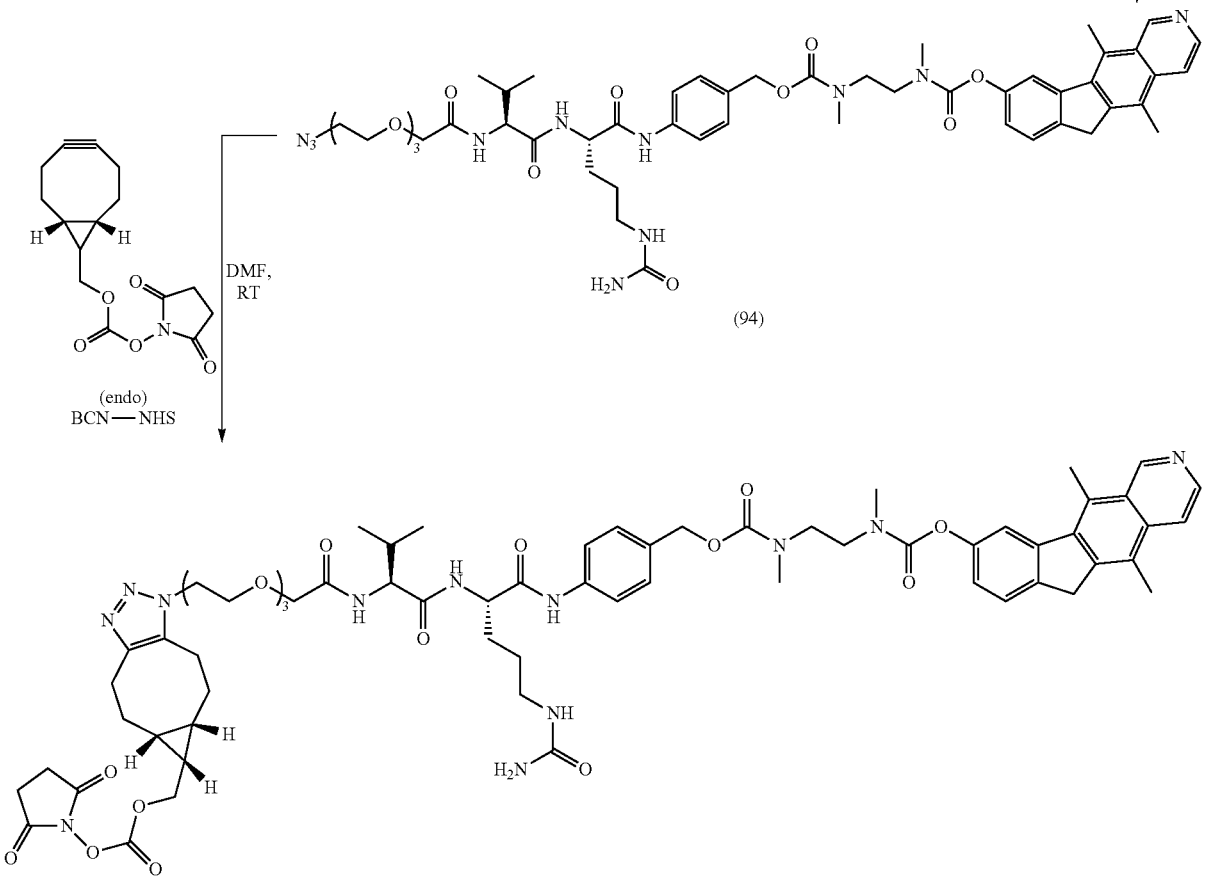

Ellipticine-(DNMEA)-PAB-Cit-Val-dPEG$_3$-NHS ester
(95)

To a stirred solution of N,N'-dimethylethylene diamine (3.66 mL, 34 mmol) in dichloromethane (40 mL) at 0° C. was added dropwise a solution of di-tert-butyl dicarbonate (2.4 g, 11 mmol) in dichloromethane (20 mL) and allowed to warm to room temperature overnight, concentrated under reduced pressure, diluted with EtOAc (100 mL), washed with water (2×100 mL), brine (100 mL), dried and concentrated under reduced pressure to give the title product 91 as a colourless oil (1.54 g, 74% yield). $^1$H NMR (400 MHz, CDCl$_3$) δ 3.26 (t, J=6.15 Hz, 2H), 2.81 (s, 3H), 2.66 (t, J=6.57 Hz, 2H), 2.38 (s, 3H), 9.28 (s, 9H) ppm.

To a stirred solution of 9-hydroxyellipticine (80 mg, 0.27 mmol), DMAP (32 mg, 0.27 mmol) and triethylamine (261 µL, 1.88 mmol) in THF (2 mL) at 0° C., was added a solution of 4-nitrophenylchloroformate (81 mg, 0.40 mmol) in THF (1.5 mL), warmed to room temperature over 2 h, to which was added a solution of BOC-diamine 91 (151 mg, 0.80 mmol) in THF (0.5 mL), stirred overnight at room temperature, concentrated under reduced pressure and chromatographed (0-20% MeOH in CH$_2$Cl$_2$) to give BOC-amine-ellipticine 92 as a yellow solid (92 mg, 72% yield). R$_f$=0.47 (10% MeOH in CH$_2$Cl$_2$), IR ν$_{max}$ 3377, 2976, 2088, 1701, 1674, 1601, 1462, 1397, 1191, 1144, 1030, 816, 790, 721 cm$^{-1}$; $^1$H NMR (400 MHz, DMSO-d6) δ 11.78 (s, 1H), 9.88-9.75 (d, J=5.4 Hz, 1H), 8.48-8.35 (d, J=6.4 Hz, 1H), 8.13 (s, 1H), 8.10 (s, 1H), 7.64-7.54 (dd, J=8.7, 3.9 Hz, 1H), 7.42-7.25 (m, 1H), 3.45 (s, 6H), 2.85-2.82 (m, 4H), 2.84 (s, 6H), 1.41 (s, 9H) ppm; $^{13}$C NMR (101 MHz, DMSO-d6) δ 226.28, 224.53, 209.31, 162.06, 142.18, 133.59, 121.52, 117.90, 116.45, 111.46, 109.63, 79.16, 55.12, 46.90, 46.13, 46.13, 28.56, 14.98, 12.47, 9.03 ppm; MS (EI$^+$) m/z 477 [M+H]$^+$; HRMS (EI$^+$) m/z calc'd for C$_{27}$H$_{33}$N$_4$O$_4$ [M+H]$^+$ 477.2502, found 477.2503.

A solution of BOC-amine-ellipticine 92 (93 mg, 0.19 mmol) in trifluoroacetic acid (2.5 mL) was stirred at room temperature for 3 h and concentrated under reduced pressure to give desired deprotected product 93 as a yellow solid (105 mg, 90% yield). $R_f$=0.14 (20% MeOH in $CH_2Cl_2$); IR $v_{max}$ 2995, 2821, 1670, 1473, 1397, 1174, 1127, 1021, 813, 795, 721 cm$^{-1}$; $^1$H NMR (400 MHz, DMSO-d6) δ 9.03-8.72 (d, J=48.5 Hz, 2H), 8.58-8.36 (m, 2H), 8.86-8.69 (m, 1H), 12.57-11.95 (d, J=2.7 Hz, 1H), 10.18-9.85 (d, J=2.2 Hz, 1H), 8.31-8.08 (dd, J=11.3, 2.2 Hz, 1H), 7.87-7.58 (d, J=8.6 Hz, 1H), 7.54-7.37 (dt, J=8.8, 2.3 Hz, 1H), 3.35-3.26 (d, J=5.1 Hz, 3H), 3.17 (s, 6H), 3.15-3.06 (qd, J=7.3, 4.7 Hz, 4H), 2.87 (s, 3H) ppm;

$^{13}$C NMR (101 MHz, DMSO-d6) δ 159.01, 158.68, 157.26, 155.79, 144.77, 134.42, 134.14, 128.46, 125.98, 122.68, 120.29, 120.07, 112.01, 110.91, 49.06, 35.16, 34.96, 33.16, 15.35, 12.48 ppm; MS (EI$^+$) m/z 377 [M]$^+$; HRMS (EI$^+$) m/z calc'd for $C_{22}H_{25}N_4O_2$ [M]$^+$ 377.1978, found 377.1974.

To a stirred solution of the activated linker 30 (60.7 mg, 0.08 mmol) in DMF (3 ml) was added at room temperature a solution of the ellipticine amine 93 (48 mg, 0.10 mmol) and DIPEA (40 μL, 0.23 mmol) in DMF (1 mL), stirred overnight, concentrated under reduced pressure and chromatographed (0-20% MeOH in $CH_2Cl_2$) to give the title product 94 (19 mg, 26% yield). $R_f$=0.30 (10% MeOH in $CH_2Cl_2$); IR $v_{max}$ 3310, 2935, 2103, 1650, 1541, 1466, 1402, 1202, 1130, 1027, 823, 800, 756, 720 cm$^{-1}$; $^1$H NMR (400 MHz, DMSO-d6) δ 11.79 (s, 1H), 10.01 (s, 1H), 9.82 (s, 1H), 8.44 (s, 2H) 8.39-8.30 (d, J=7.2 Hz, 1H), 8.23-8.16 (d, J=6.3 Hz, 1H), 8.15-8.11 (d, J=6.8 Hz, 1H), 7.63-7.54 (d, J=6.8 Hz, 2H), 2.05-1.96 (m, 1H), 7.48-7.42 (d, J=8.9 Hz, 1H), 7.32-7.27 (d, J=8.1 Hz, 3H), 5.42 (s, 2H), 5.10-5.00 (d, J=9.0 Hz, 2H), 4.46-4.28 (q, J=8.0, 7.3 Hz, 1H), 3.95 (s, 2H), 3.64-3.55 (m, 14H), 6.03 (s, 1H), 3.18-3.11 (ddd, J=10.8, 7.3, 3.7 Hz, 4H), 3.05-2.88 (m, 2H), 2.85 (s, 2H), 2.10-1.91 (dt, J=13.5, 7.2 Hz, 1H), 1.75-1.53 (m, 2H), 1.48-1.32 (m, 2H), 1.27 (s, 6H), 0.96-0.72 (ddd, J=22.7, 6.3, 3.2 Hz, 6H) ppm; $^{13}$C NMR (126 MHz, DMSO-d6) δ 171.21, 170.95, 169.44, 162.80, 159.37, 158.36, 158.12, 155.46, 147.76, 145.15, 143.25, 140.41, 139.01, 133.58, 129.03, 128.77, 124.65, 123.33, 122.68, 121.45, 119.41, 117.59, 111.50, 109.74, 70.87, 70.07, 69.90, 69.69, 57.03, 53.98, 50.51, 49.13, 47.01, 42.24, 35.24, 31.60, 29.65, 27.39, 19.64, 18.51, 17.18, 15.01, 12.88 ppm; MS (EI$^+$) m/z 1019 [M+Na]$^+$; HRMS (EI$^+$) m/z calc'd for $C_{49}H_{64}N_{12}O_{11}Na$ [M+Na]$^+$ 1019.4715, found 1019.4722.

To a stirred solution of the azide 94 (2.5 mg, 0.003 mmol) in DMF (1 mL) was added (1R,8S,9S)-bicyclo[6.1.0]non-4-yn-9-ylmethyl N-succinimidyl carbonate (0.7 mg, 0.003 mmol), stirred at room temperature for 3 h and concentrated under reduced pressure to give the title product as a yellow solid (3 mg, 93% yield). IR $v_{max}$ 3323, 2924, 1811, 1786, 1740, 1664, 1604, 1537, 1402, 1199, 1126, 828, 799, 718 cm$^{-1}$; $^1$H NMR (500 MHz, DMSO-d6) δ 12.02 (s, 1H), 10.10-9.97 (m, 1H), 9.94-9.84 (d, J=8.6 Hz, 1H), 8.49-8.41 (d, J=6.7 Hz, 2H), 8.36-8.30 (dd, J=7.2, 3.4 Hz, 1H), 7.64-7.51 (td, J=12.0, 9.0, 4.7 Hz, 1H), 7.56-7.51 (d, J=8.4 Hz, 2H), 7.45-7.40 (d, J=8.6 Hz, 1H), 7.38-7.21 (m, 3H), 6.09-5.89 (q, J=5.5, 5.0 Hz, 1H), 5.42 (s, 2H), 5.11-4.97 (m, 2H), 4.53-4.45 (t, J=8.0 Hz, 2H), 4.39-4.32 (t, J=5.4 Hz, 2H), 3.96-3.91 (d, J=3.8 Hz, 2H), 3.71-3.66 (q, J=5.7, 4.2 Hz, 2H), 3.65-3.55 (dtt, J=20.5, 9.9, 4.7 Hz, 10H), 3.51-3.43 (m, 4H), 3.18-3.08 (qd, J=7.3, 4.1 Hz, 4H), 2.91-2.87 (s, 4H), 2.86-2.85 (s, 2H), 2.292.18 (m, 2H), 2.19-2.11 (m, 2H), 2.00-1.93 (d, J=6.7 Hz, 2H), 0.90-0.70 (ddd, J=29.9, 6.9, 4.3 Hz, 6H), 2.32-1.89 (m, 6H), 2.10-2.02 (m, 2H) ppm; $^{13}$C NMR (126 MHz, DMSO-d6) δ 172.75, 170.73, 170.48, 169.94, 168.96, 162.29, 158.90, 154.87, 151.30, 144.85, 143.09, 139.99, 138.62, 133.72, 133.47, 128.53, 128.30, 122.61, 118.91, 117.16, 111.25, 109.72, 99.50, 98.90, 70.33, 70.29, 69.69, 69.65, 69.53, 69.31, 57.37, 56.55, 53.50, 53.20, 47.13, 46.54, 41.76, 40.15, 40.09, 40.00, 39.93, 39.84, 39.76, 39.67, 39.60, 39.50, 39.34, 39.17, 39.00, 38.51, 35.77, 34.82, 34.51, 31.05, 30.76, 29.17, 28.41, 26.85, 25.49, 25.34, 25.29, 25.21, 22.33, 22.04, 21.80, 21.22, 20.74, 20.69, 20.19, 19.89, 19.54, 19.15, 18.85, 18.04, 17.90, 16.92, 16.71, 16.67, 14.68, 12.41, 12.03 ppm; MS (EI$^+$) m/z 1288 [M+H]$^+$; HRMS (EI$^+$) m/z calc'd for $C_{64}H_{82}N_{13}O_{16}$ [M+H]$^+$ 1288.5995, found 1288.5625.

Example 54—Preparation of Ellipticine-(DNMEA)-PAB-Cit-Val-BCN-dPEG$_4$-NHS Ester (96)

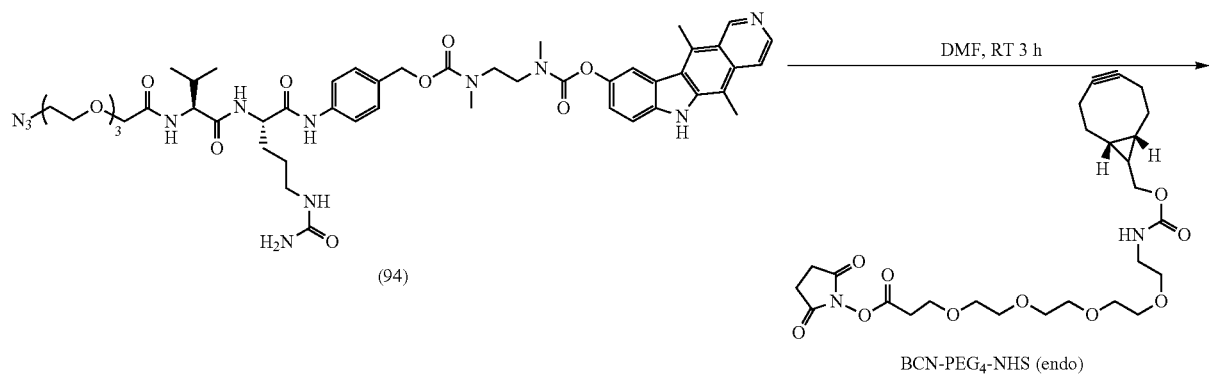

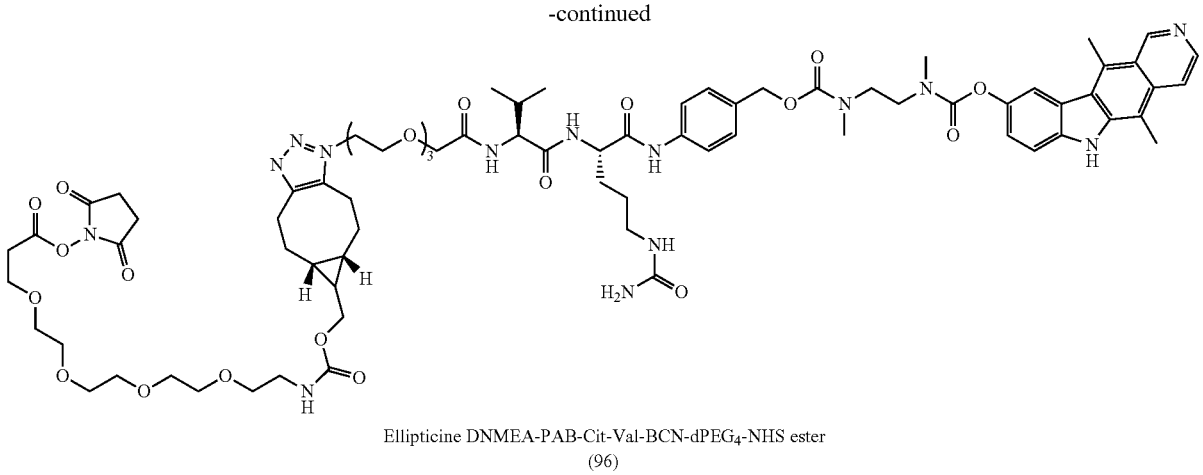

Ellipticine DNMEA-PAB-Cit-Val-BCN-dPEG$_4$-NHS ester
(96)

To a stirred solution of the azide 94 (2.5 mg, 0.003 mmol) in DMF (1 mL) was added BCN-PEG$_4$-NHS (ConjuProbe) (0.7 mg, 0.003 mmol), stirred at room temperature for 3 h and concentrated under reduced pressure to give the desired product 96 as a yellow solid (3 mg, 93% yield).

Example 55—Preparation of SN38-(DNMEA)-PAB-Cit-Val-BCN-dPEG$_4$-NHS Ester (100)

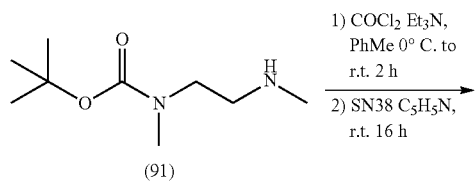

1) COCl$_2$ Et$_3$N, PhMe 0° C. to r.t. 2 h
2) SN38 C$_5$H$_5$N, r.t. 16 h (91)

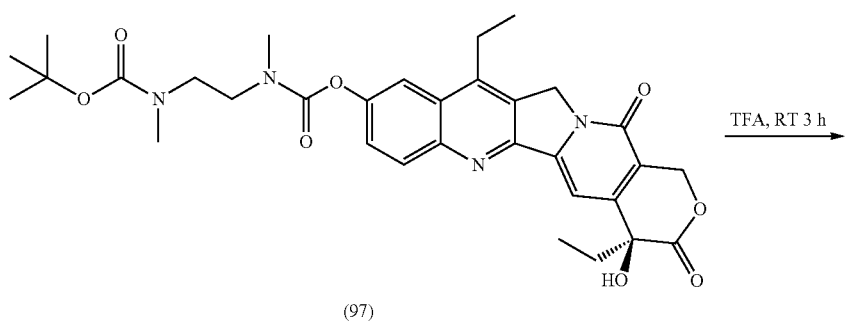

(97)

TFA, RT 3 h

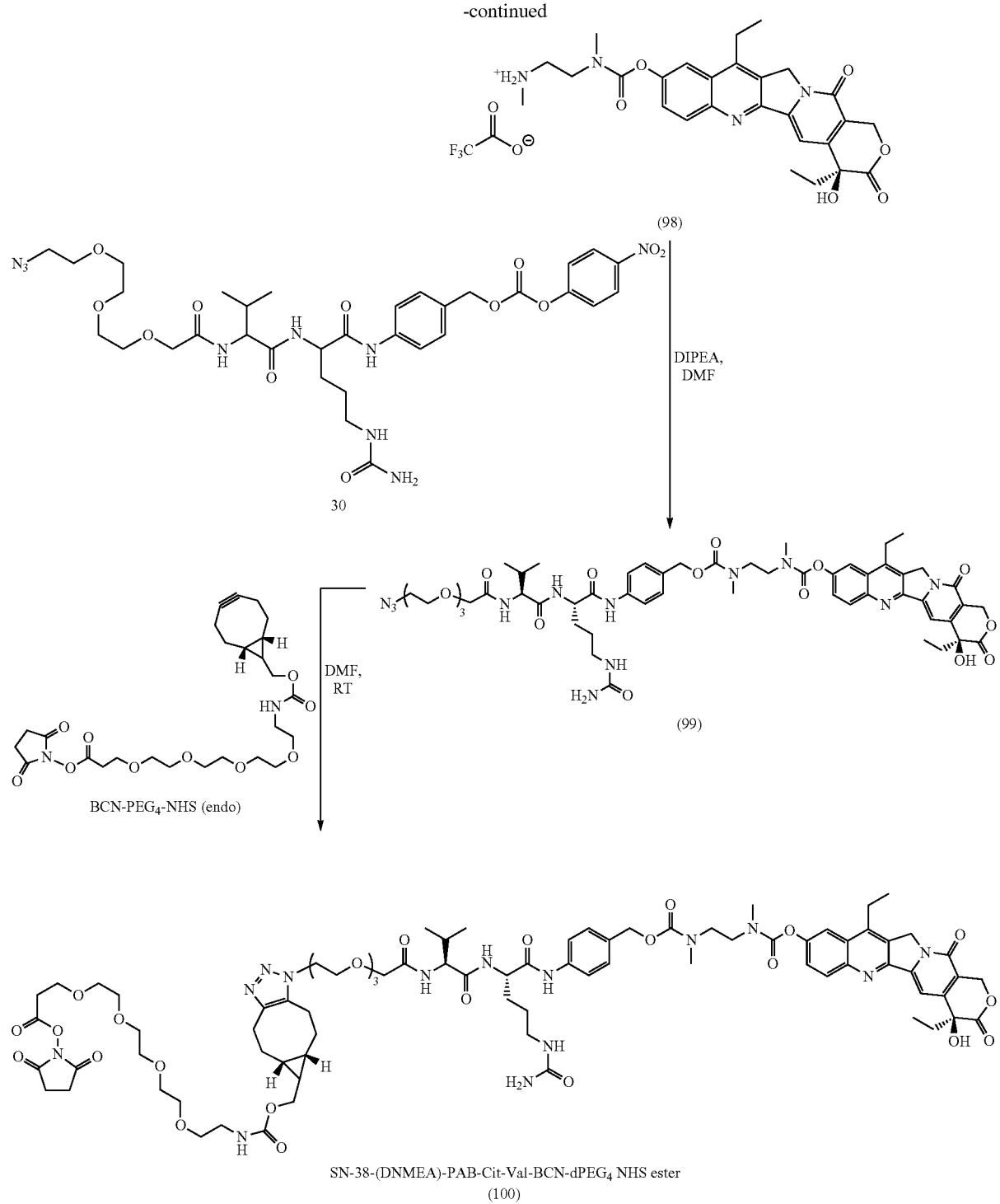

To a stirred solution of phosgene in toluene (15 wt %, 0.36 mL, 0.55 mmol) at 0° C. was added dropwise a solution of BOC-diamine 91 (94 mg, 0.50 mmol) and Et₃N (77 μL, 0.55 mmol) in toluene (1.32 mL), stirred at 0° C. for 2 h, warmed to room temperature overnight, filtered, washed with toluene (5 mL), concentrated under reduced pressure and dissolved in pyridine (2.23 mL, 27.6 mmol), to which was added SN38 (150 mg, 0.39 mmol), stirred at room temperature overnight, diluted with EtOAc (100 mL), washed with water (3×100 mL), dried, concentrated under reduced pressure and chromatographed (0-10% MeOH in CH₂Cl₂) to give the title product as a yellow solid (72 mg, 31%). $R_f$=0.57 (10% MeOH in CH₂Cl₂); ¹H NMR (400 MHz, CDCl₃) δ 8.15 (dd, J=9.3, 5.7 Hz, 1H), 7.85-7.73 (m, 1H), 7.64-7.61 (m, 1H, 7.53-7.48 (m, 1H), 5.64 (d, J=16.3 Hz, 1H), 5.22 (d, J=16.3 Hz, 1H), 5.18 (s, 2H), 3.65-2.85 (m, 6H), 2.82 (s, 6H), 1.85 (p, J=7.1 Hz, 2H), 1.40 (s, 9H), 1.34 (t, J=7.8 Hz, 3H), 0.94 (t, J=7.3 Hz, 3H) ppm; LCMS $t_R$=2.10 min m/z 607.3 [M+N]+.

Example 56—Preparation of
DM1-Mal-SO₃H—NHS (102)
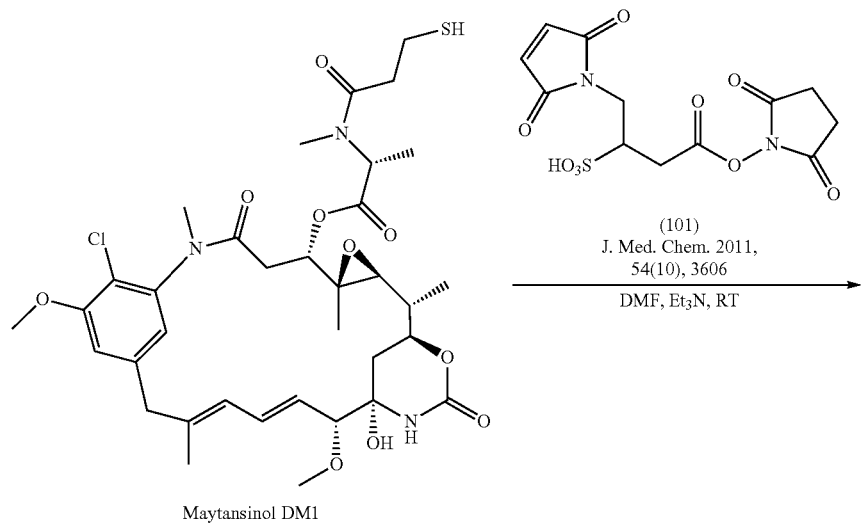
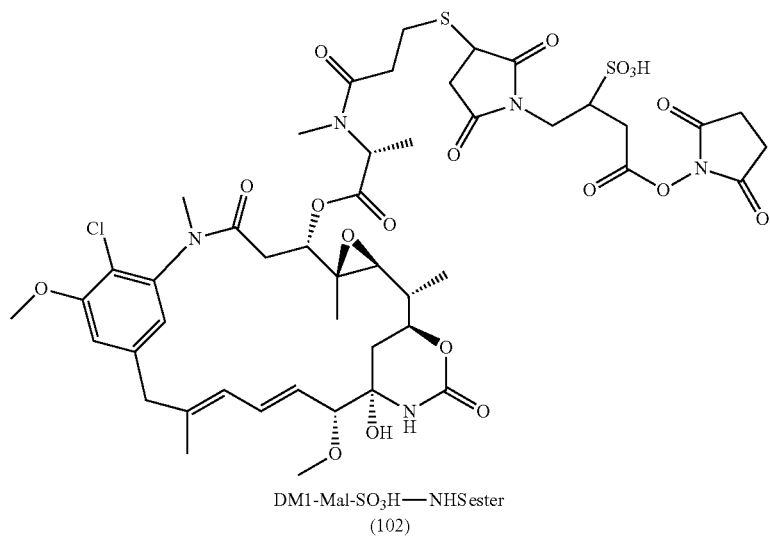
DM1-Mal-SO₃H—NHSester
(102)
Example 57—Preparation of
Maytansinol-PEG₂-Glu-BCN—NHS Ester (108)
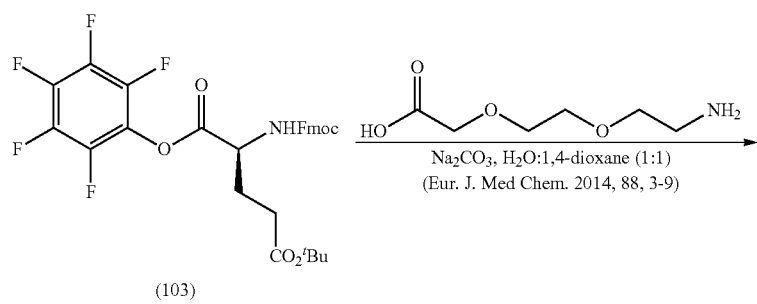

-continued
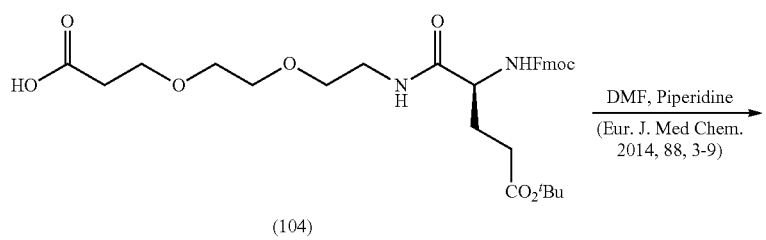
(104)
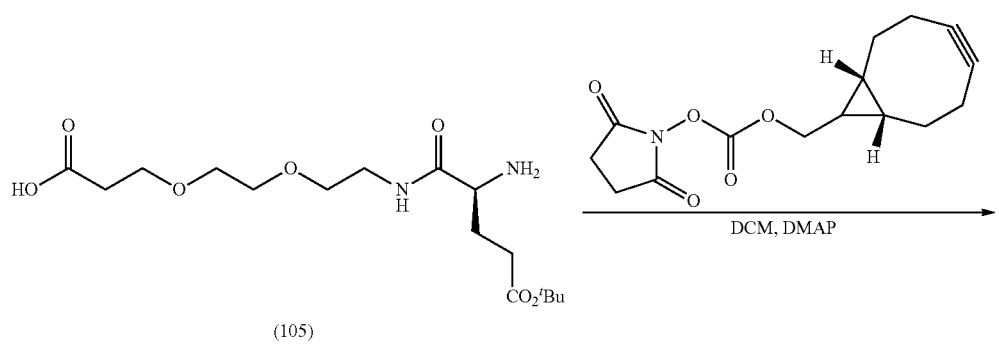
(105)
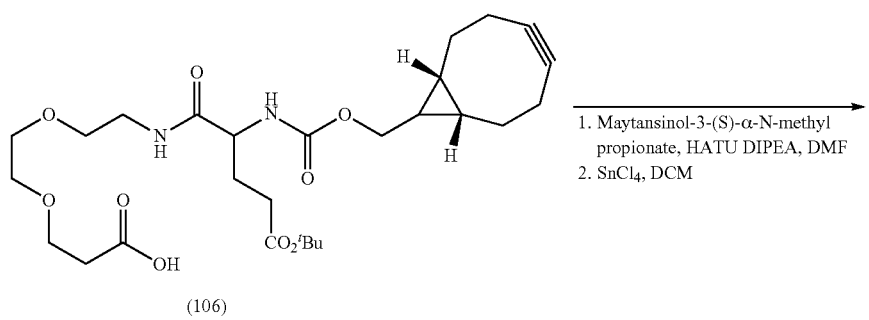
(106)
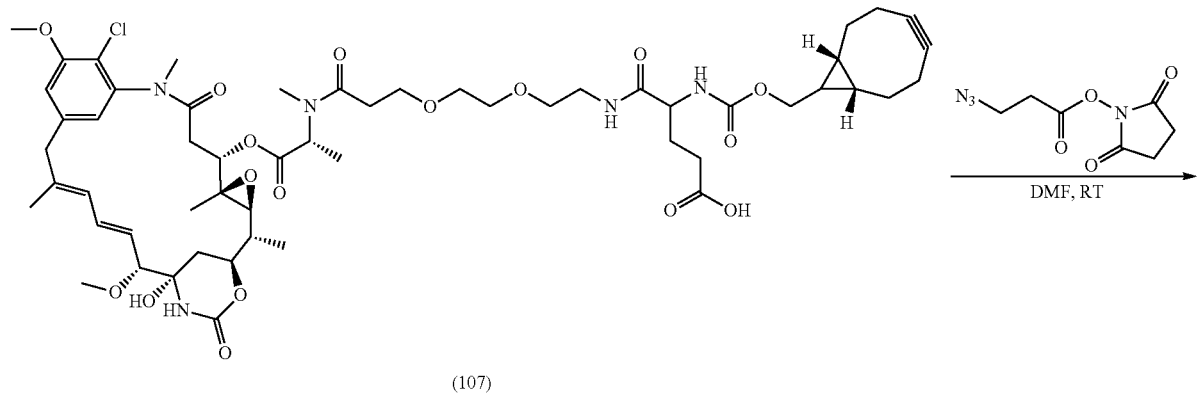
(107)

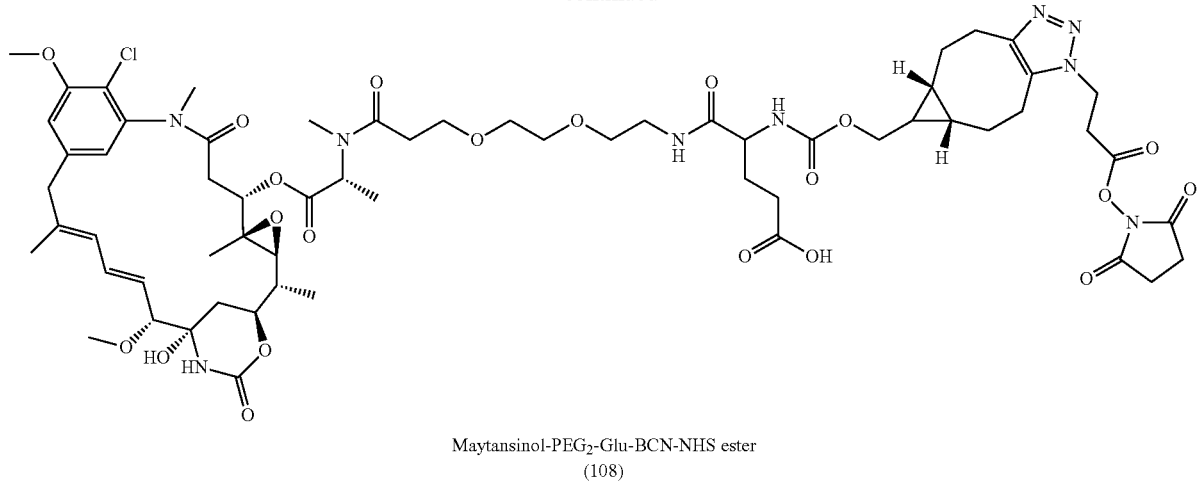 [SMILES: COc1cc2cc(c1Cl)N(C)C(=O)C[C@H](OC(=O)[C@@H](C)N(C)C(=O)CCOCCOCCNC(=O)C(CCC(=O)O)NC(=O)OCC1[C@H]3CCc4c(nnn4CCC(=O)ON4C(=O)CCC4=O)CC[C@@H]13)[C@]1(C)O[C@H]1[C@H](C)[C@@H]1C[C@@](O)(NC(=O)O1)[C@H](OC)/C=C/C=C(\C)C2]
Maytansinol-PEG₂-Glu-BCN-NHS ester
(108)
Example 58—Preparation of Maytansinol-SO₃H-BCN-dPEG₄-NHS Ester (110)
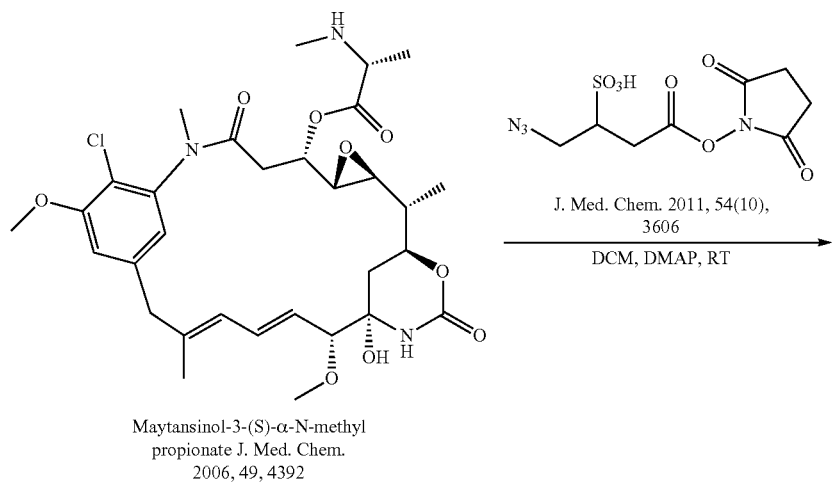
Maytansinol-3-(S)-α-N-methyl
propionate J. Med. Chem.
2006, 49, 4392
J. Med. Chem. 2011, 54(10), 3606
DCM, DMAP, RT
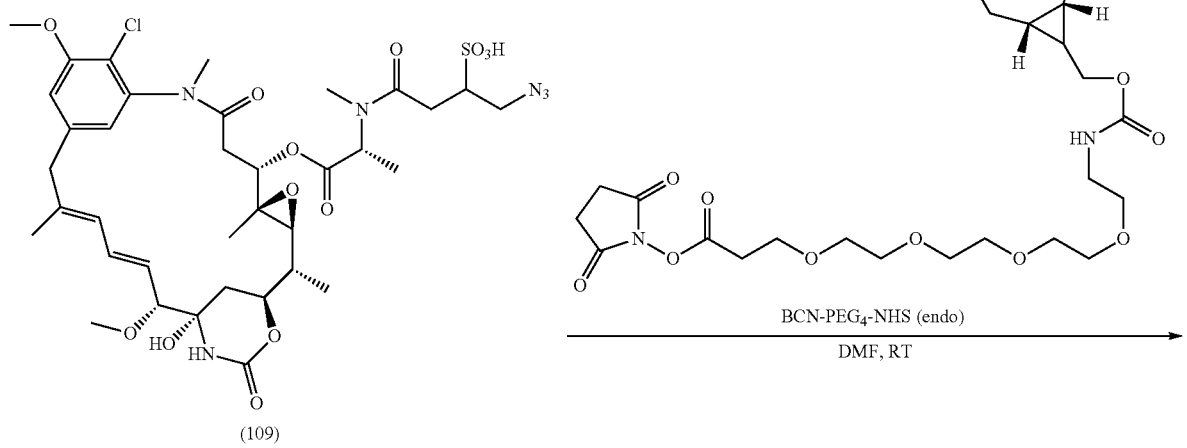
(109)
BCN-PEG₄-NHS (endo)
DMF, RT

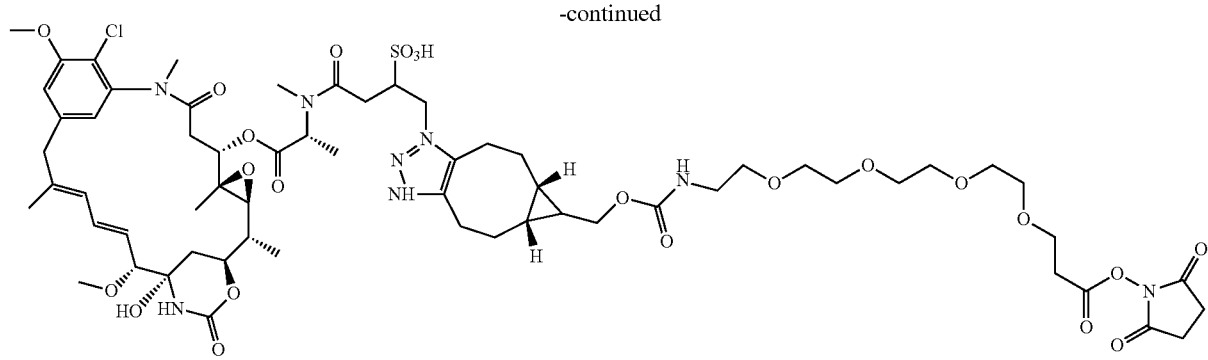
Maytansinol-SO₃H-BCN-dPEG₄-NHS ester
(110)
Example 59—Preparation of
MMAE-β-Glucuronide-C₅—NHS Ester (113)
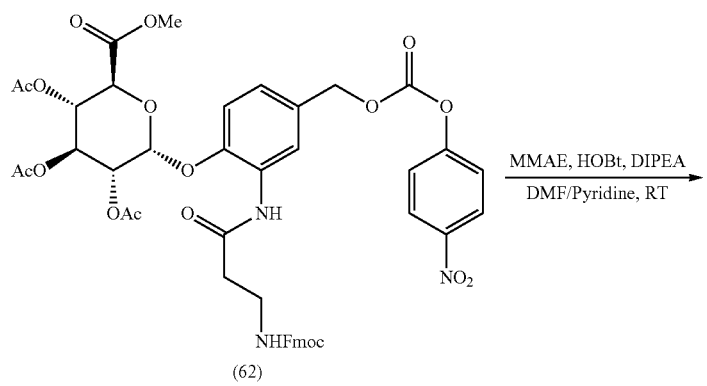
(62)
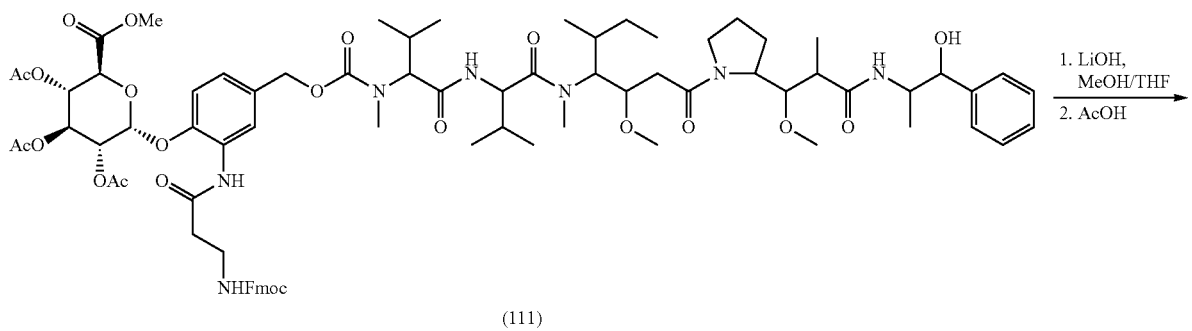
(111)
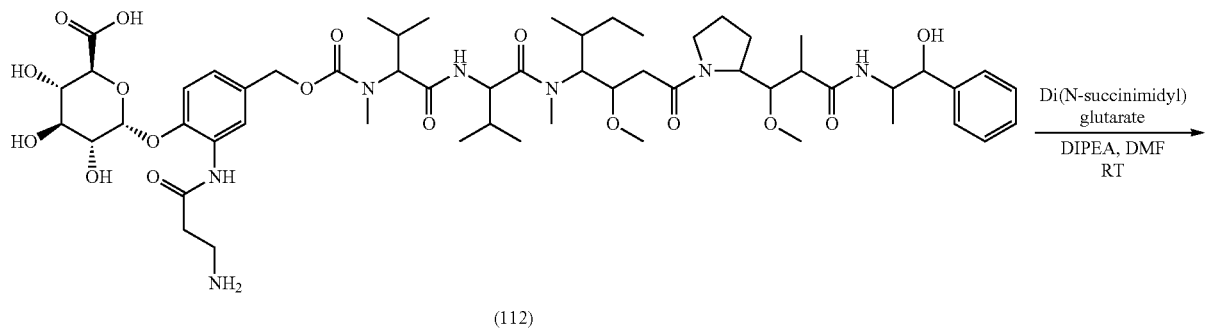
(112)

-continued
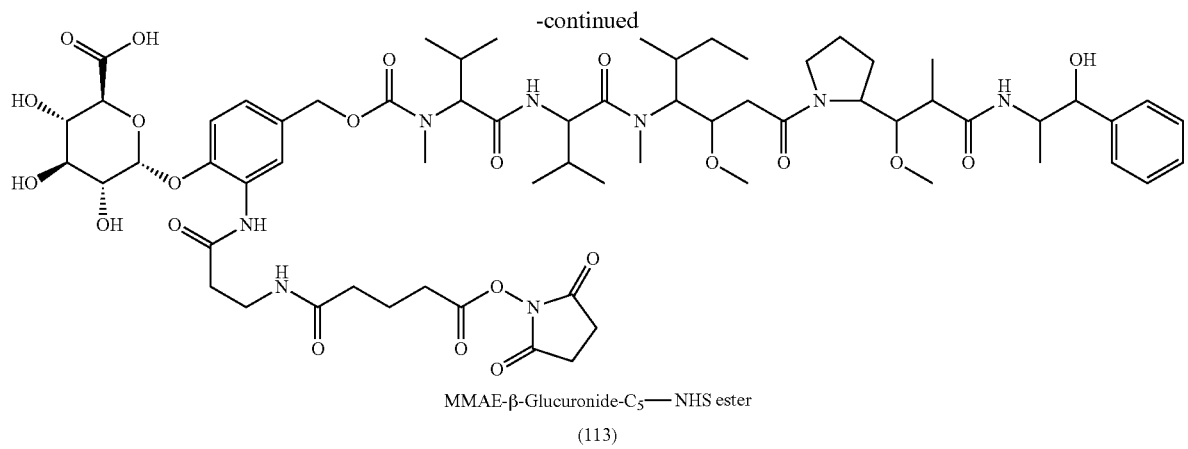
MMAE-β-Glucuronide-C₅—NHS ester
(113)
Example 60—Preparation of PBD-MMAF-Dimer-C₅—NHS Ester (116)
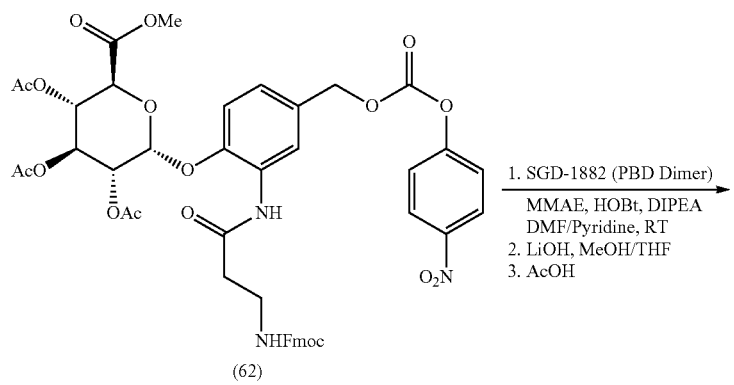
(62)
1. SGD-1882 (PBD Dimer)
MMAE, HOBt, DIPEA
DMF/Pyridine, RT
2. LiOH, MeOH/THF
3. AcOH
→
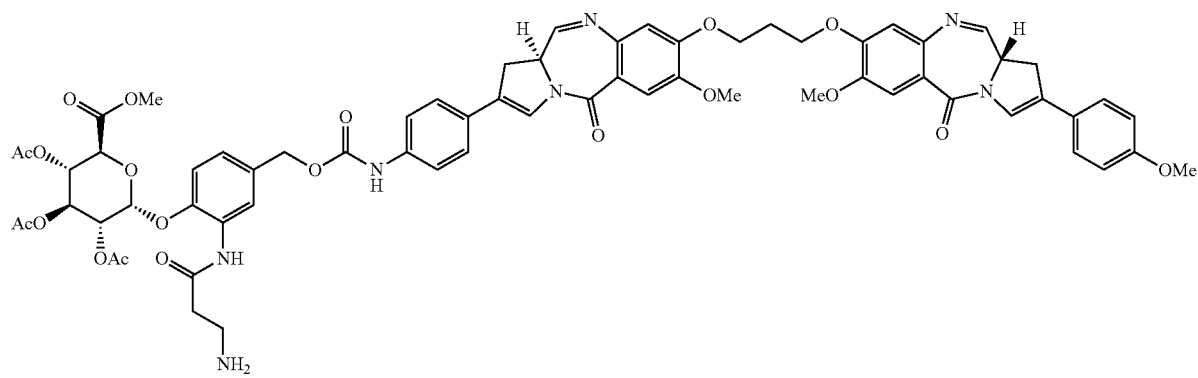
(114)

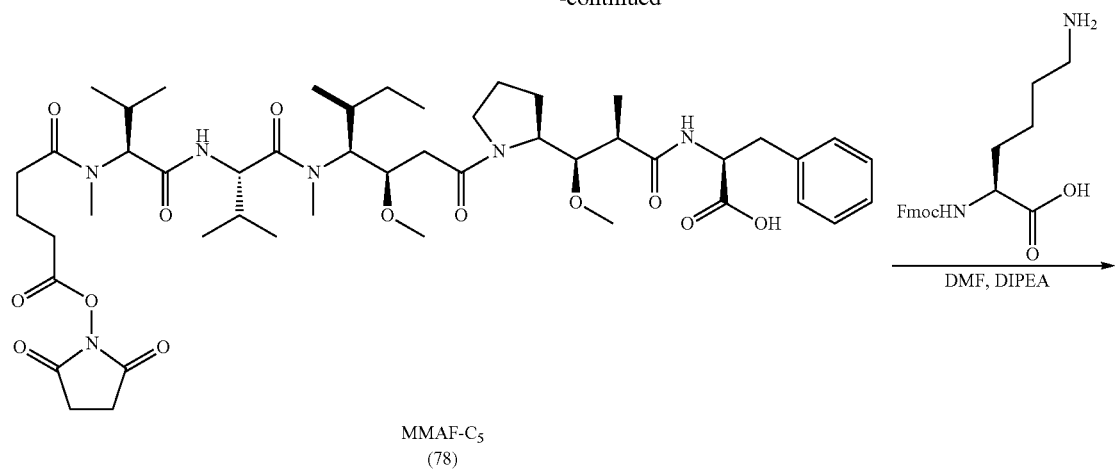
MMAF-C5
(78)
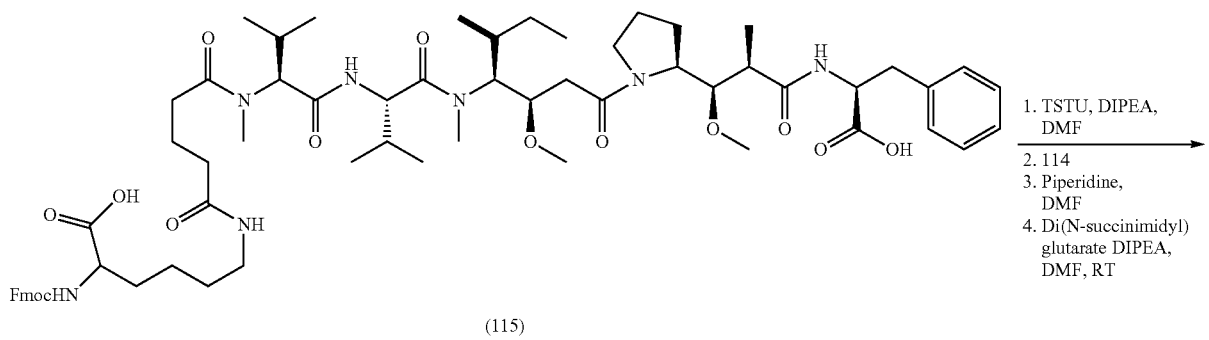
(115)
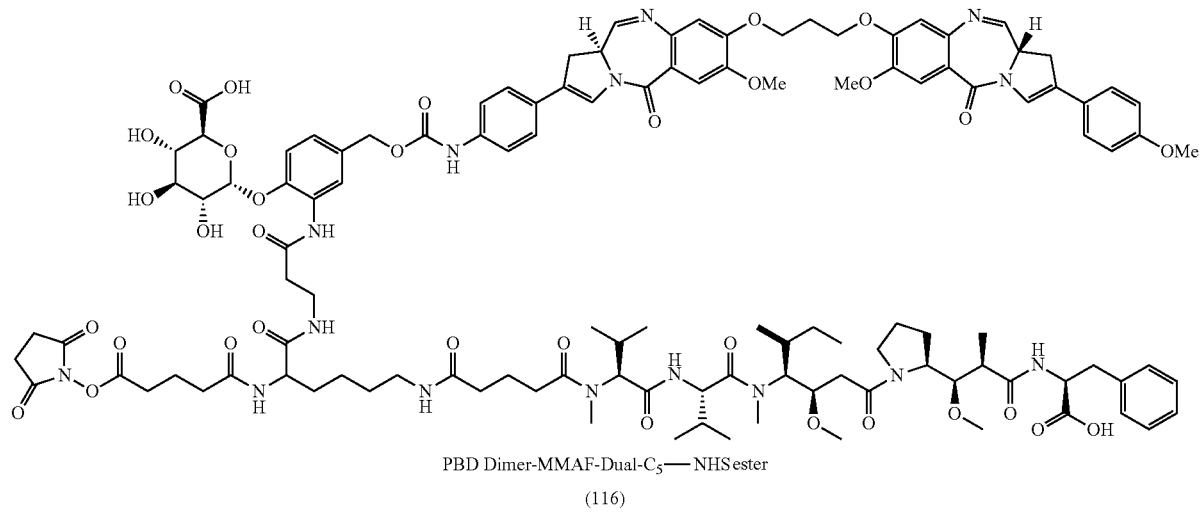
PBD Dimer-MMAF-Dual-C5—NHS ester
(116)

Example 61—Preparation of MMAF-Tetrazine
(117)
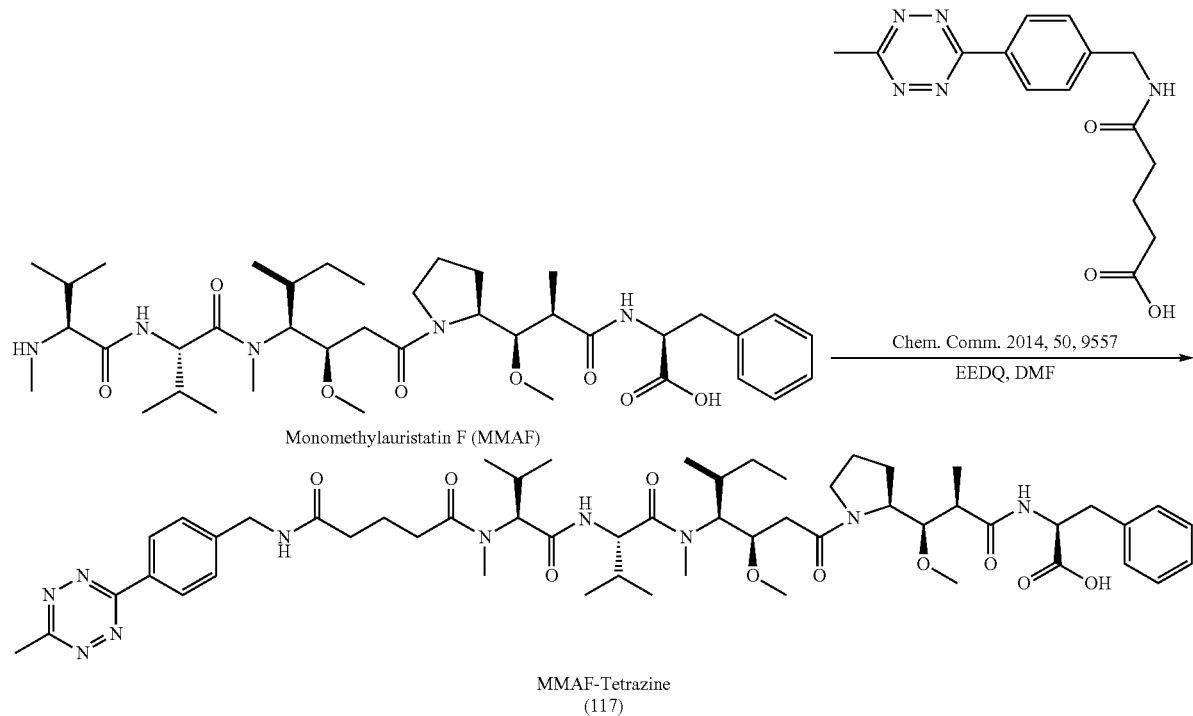
Example 62—Scheme for Conjugates
MMAF-C$_5$ Conjugate (118)

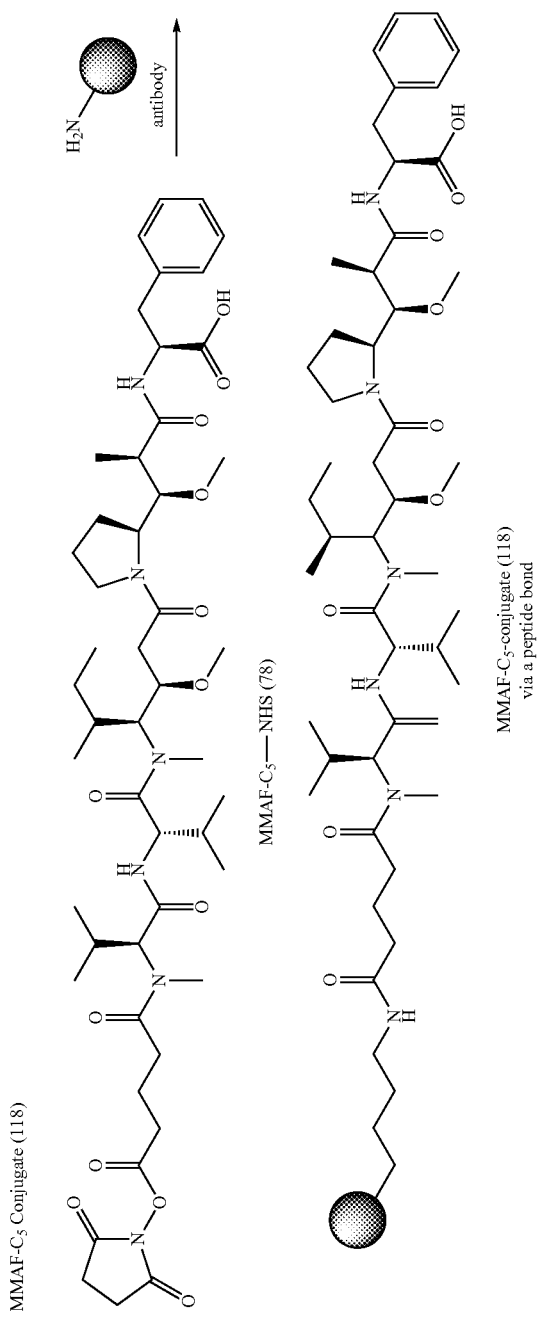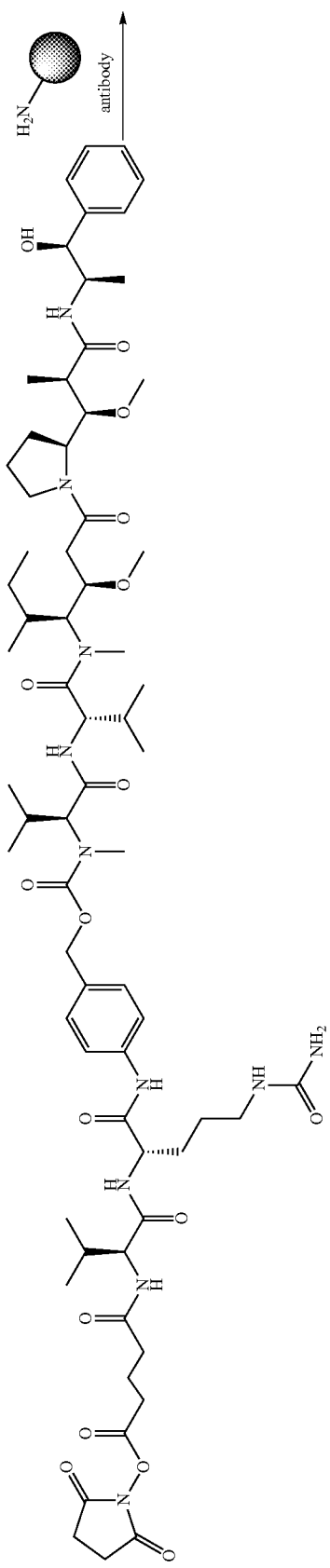

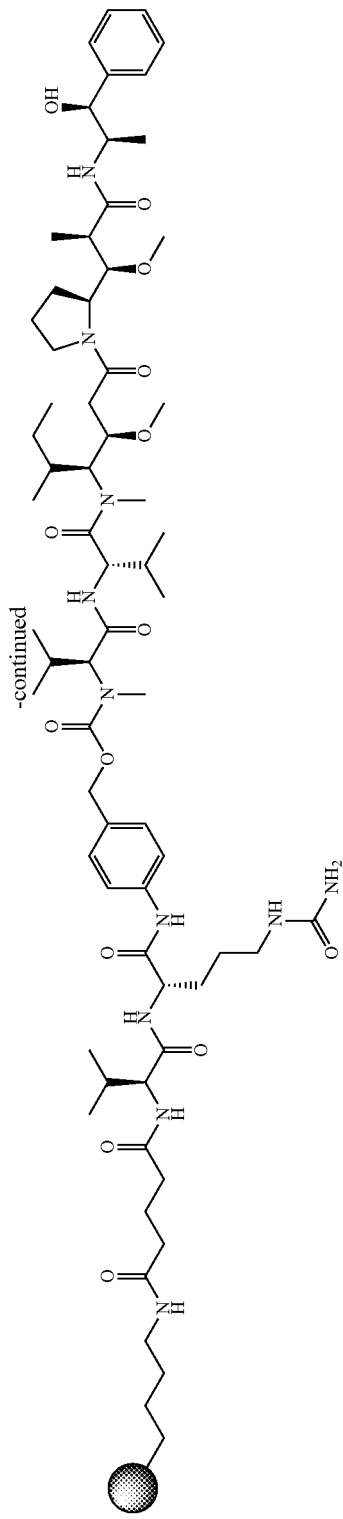
MMAE-PAB-Cit-Val-C5 conjugate (119)
via a peptide bond
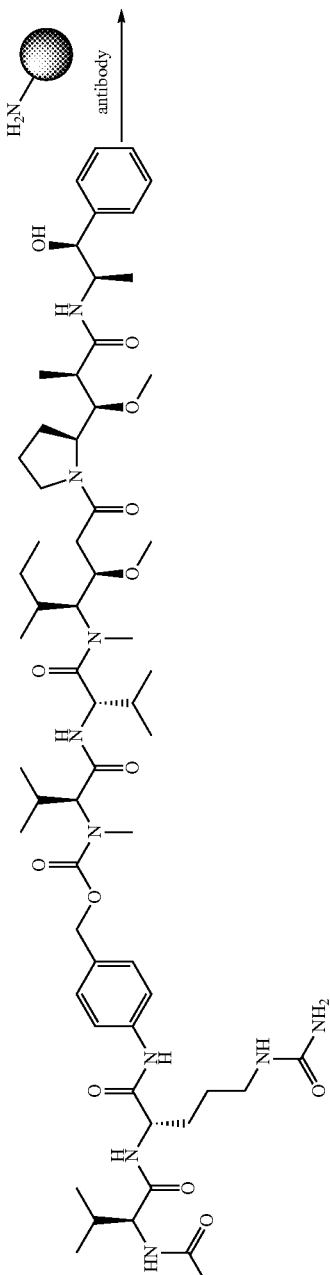
MMAE-PAB-Cit-Val-dPEG5-NHS ester (84)
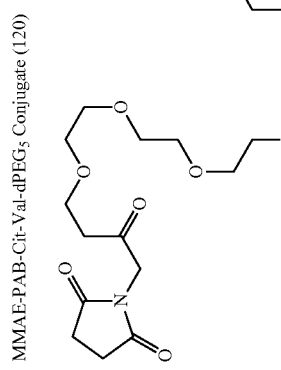
MMAE-PAB-Cit-Val-dPEG5 Conjugate (120)

-continued
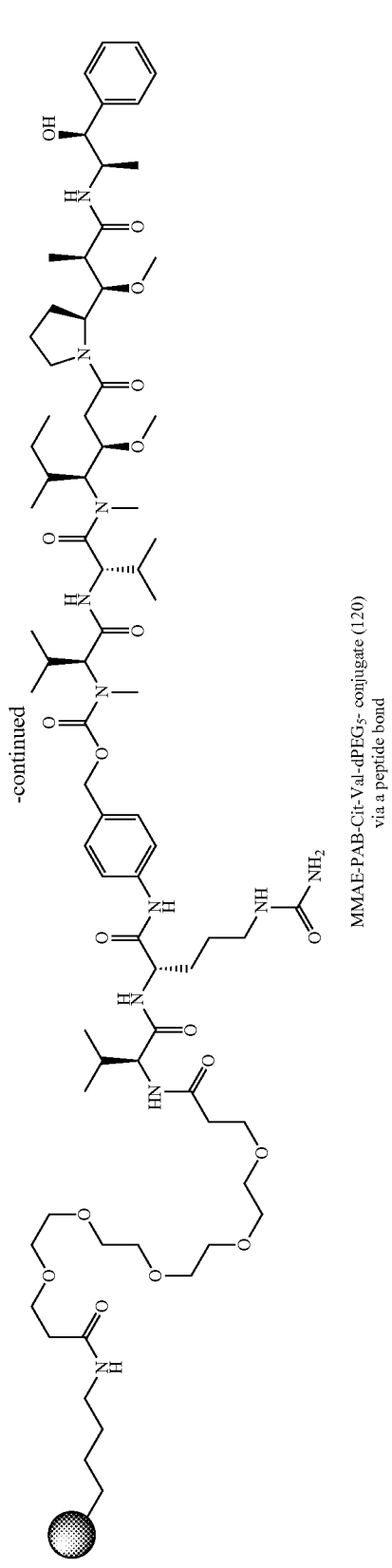
MMAE-PAB-Cit-Val-dPEG$_5$- conjugate (120)
via a peptide bond
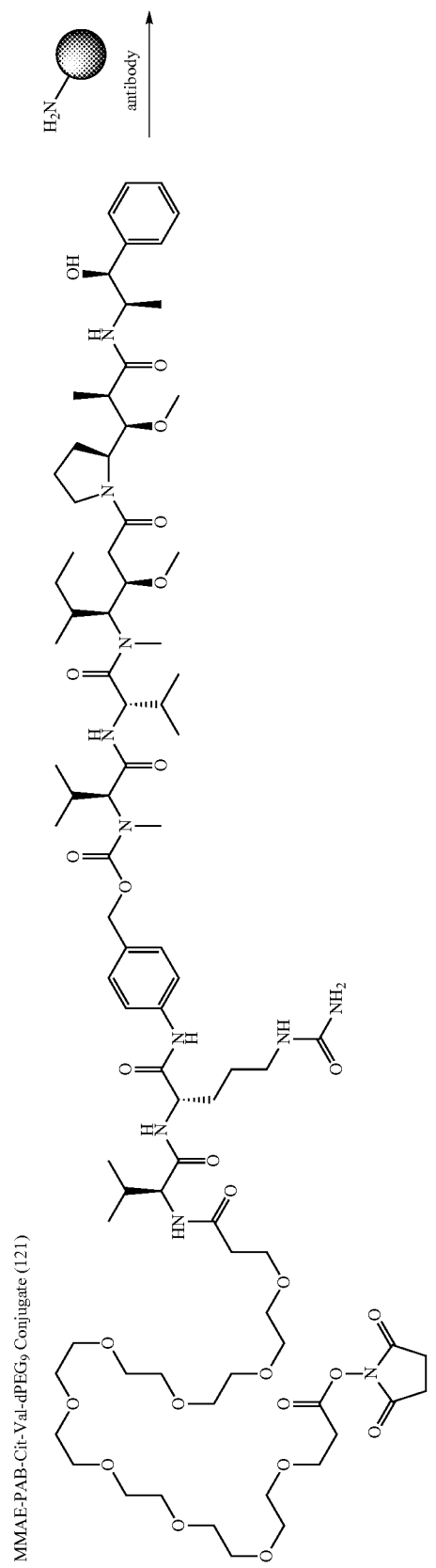
MMAE-PAB-Cit-Val-dPEG$_9$ Conjugate (121)
MMAE-PAB-Cit-Vit-dPEG$_9$-NHS ester (86)

-continued
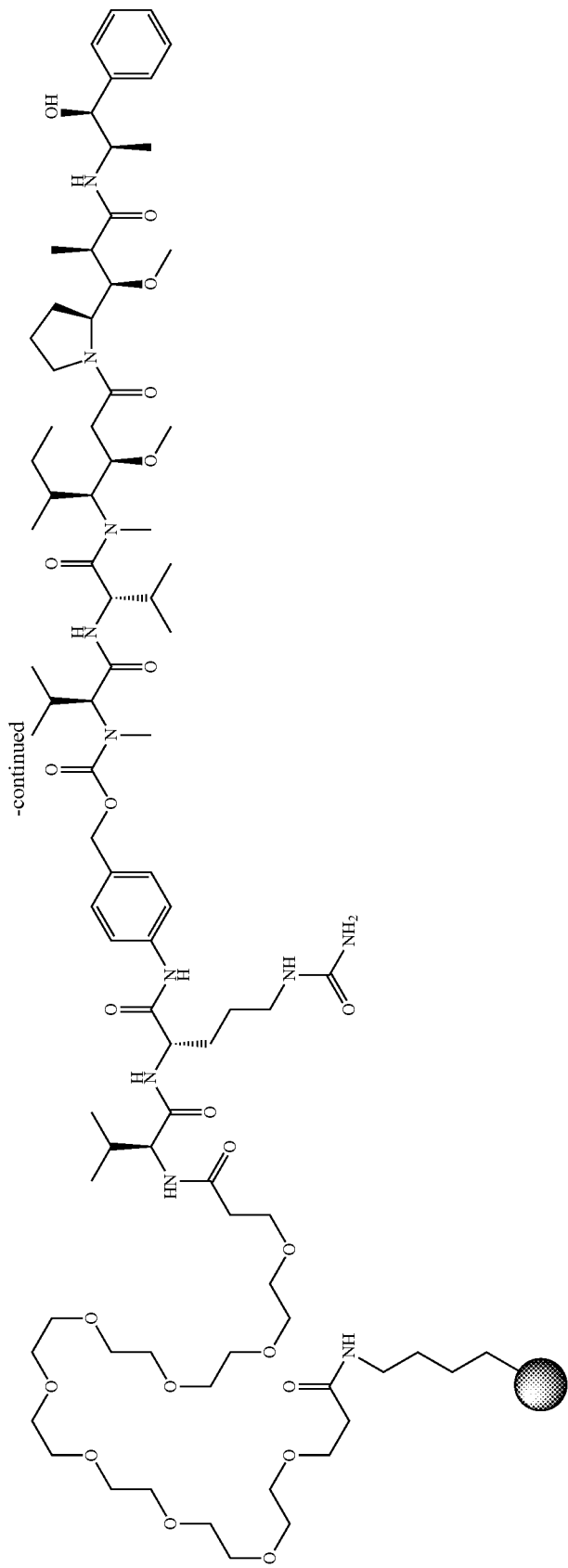
MMAE-PAB-Cit-Vit-dPEG$_9$ conjugate (121)
via a peptide

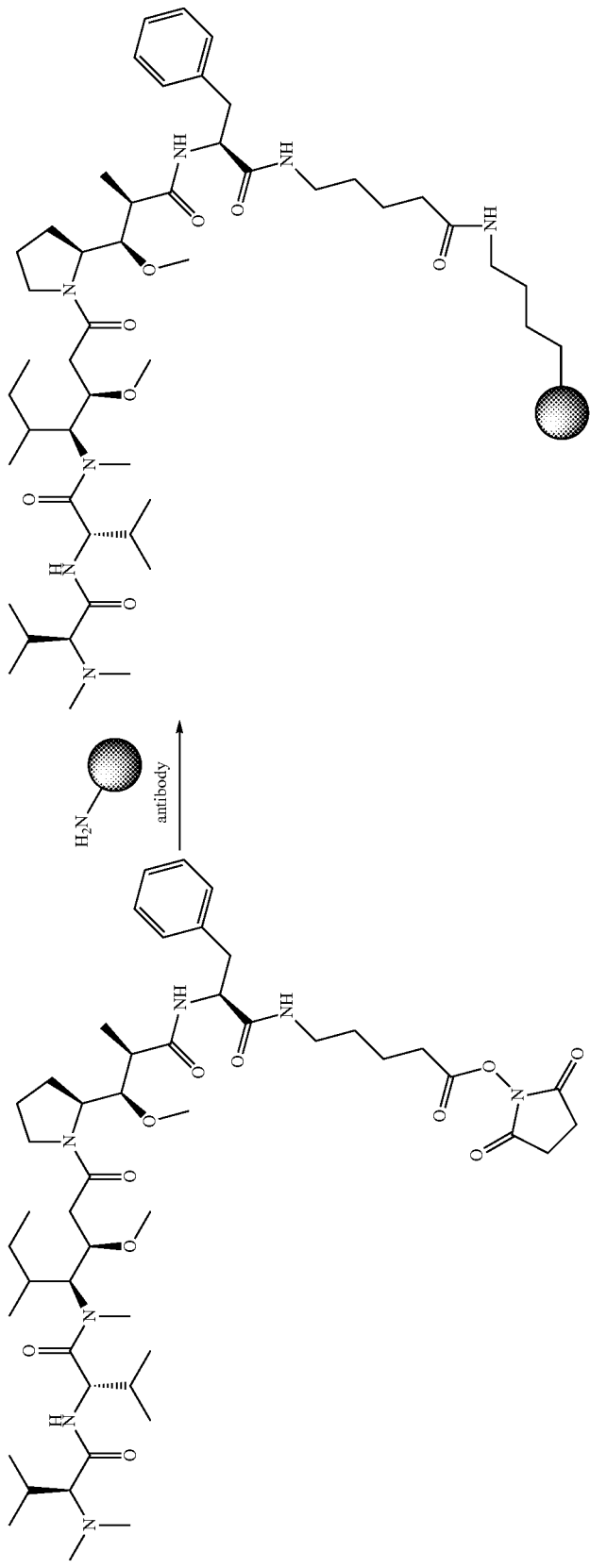

-continued
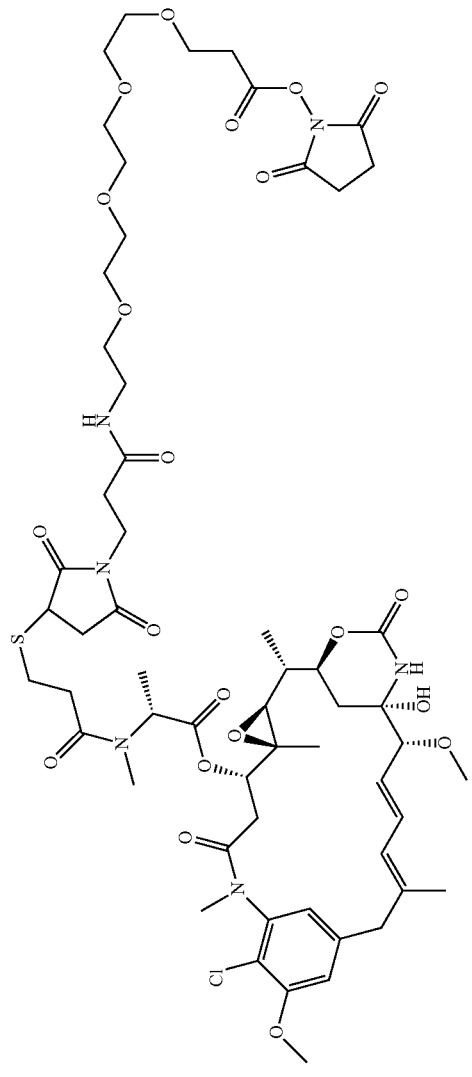
Maytansinol DM1-dPEG4 Conjugate (123)
Maytansinol DM1-dPEG4-NHS ester (89)
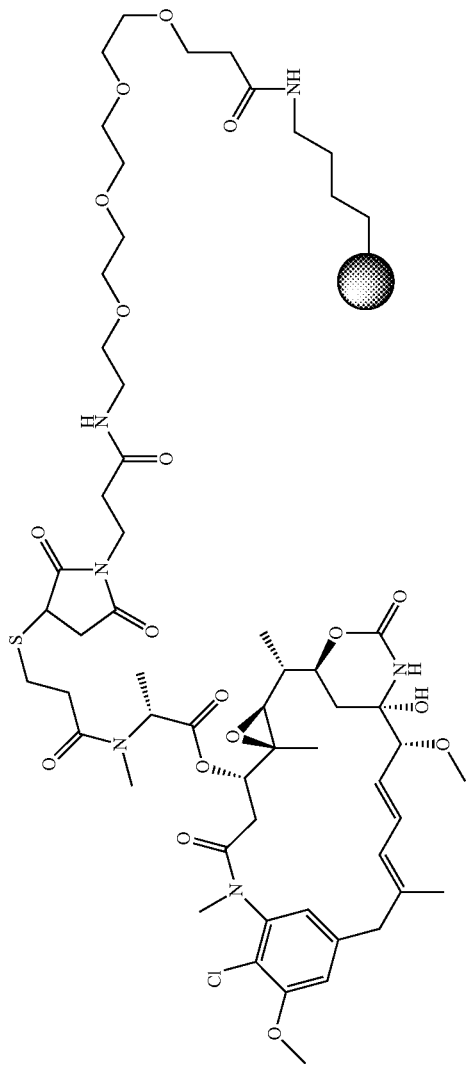
Maytansinol DM1-dPEG4 conjugate (123) via a peptide bond -continued
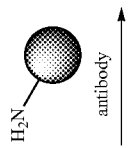
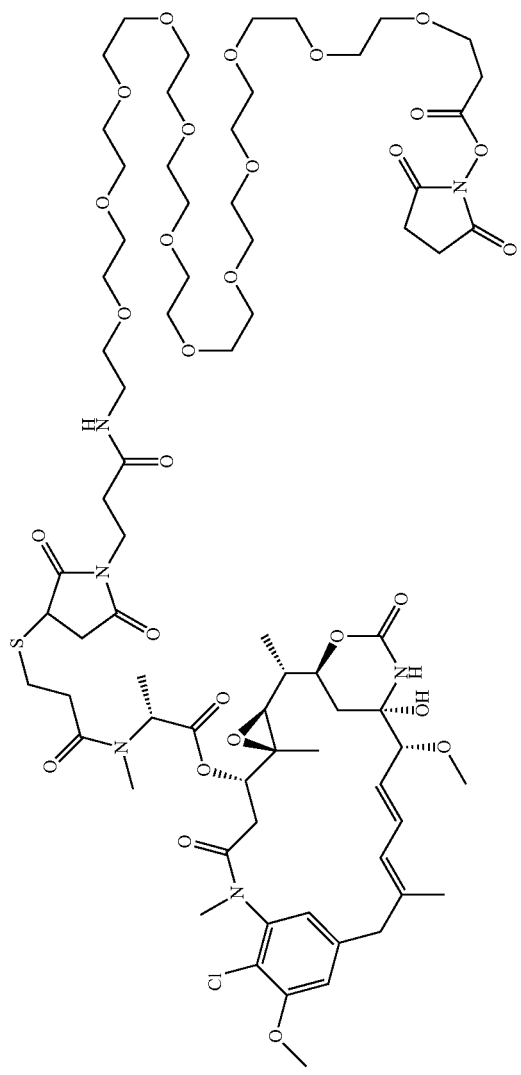
Maytansinol DM1-dPEG₁₂ Conjugate (124)
Maytansinol DM1-dPEG₉-NHS ester (90)

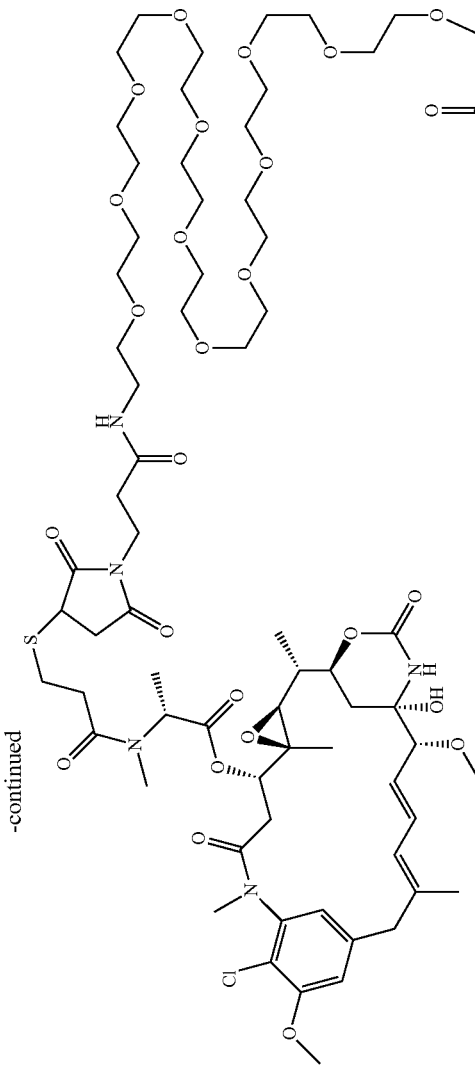
Maytansinol DM1-dPEG₁₂ conjugate (124) via a peptide bond
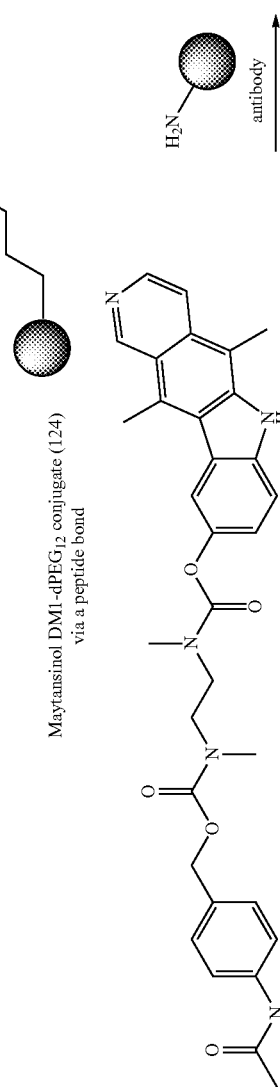
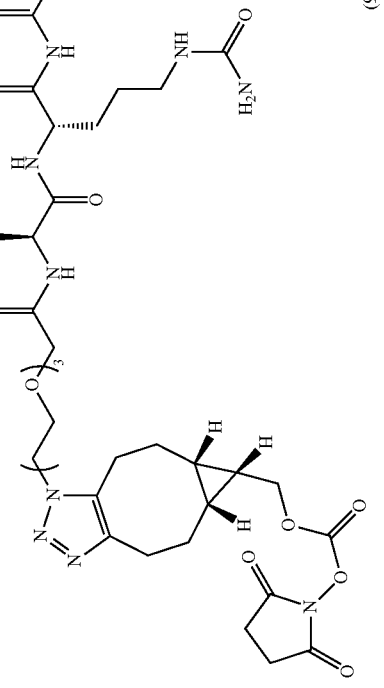
Ellipticine-(DNMEA)-PAB-Cit-Val-dPEG₃ Conjugate (125)
(95)

-continued
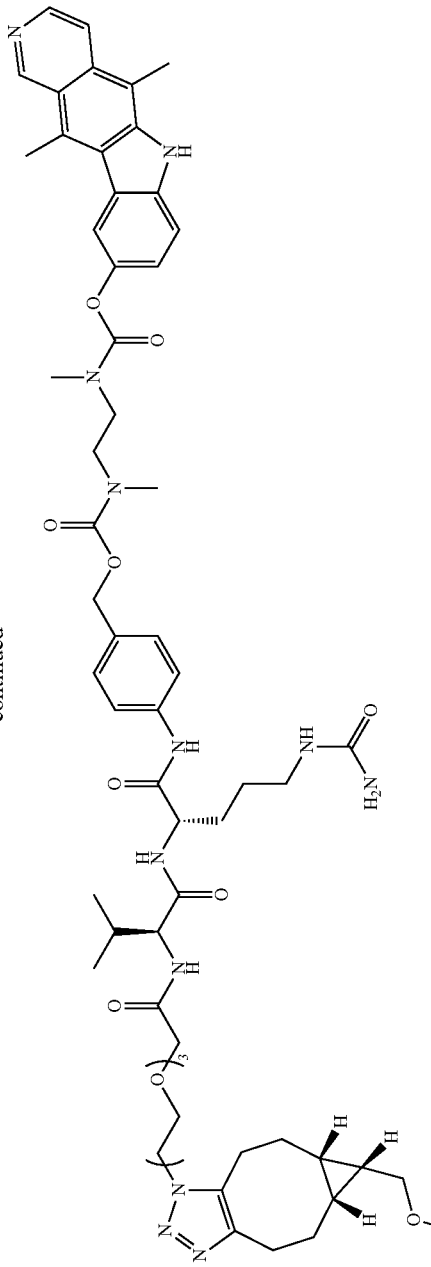
Ellipticine-(DNMEA)-PAB-Cit-Val-BCN-dPEG₄ Conjugate (126)
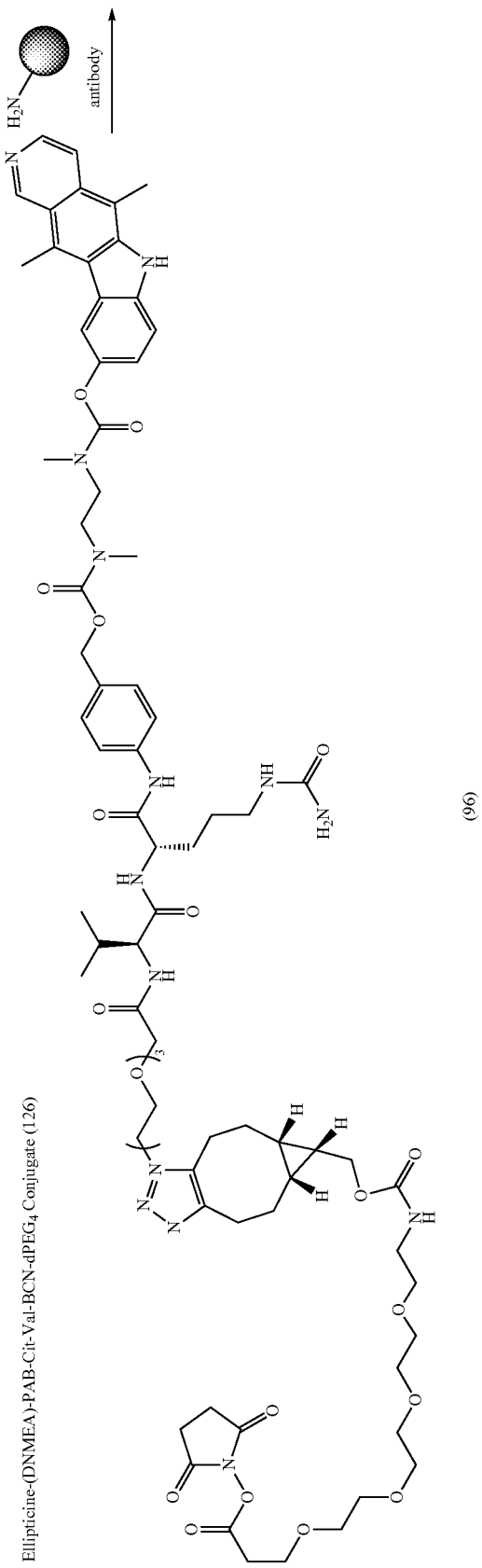
Ellipticine-(DNMEA)-PAB-Cit-Val-dPEG₃ BCN conjugate (125) via a peptide bond
(96)

-continued
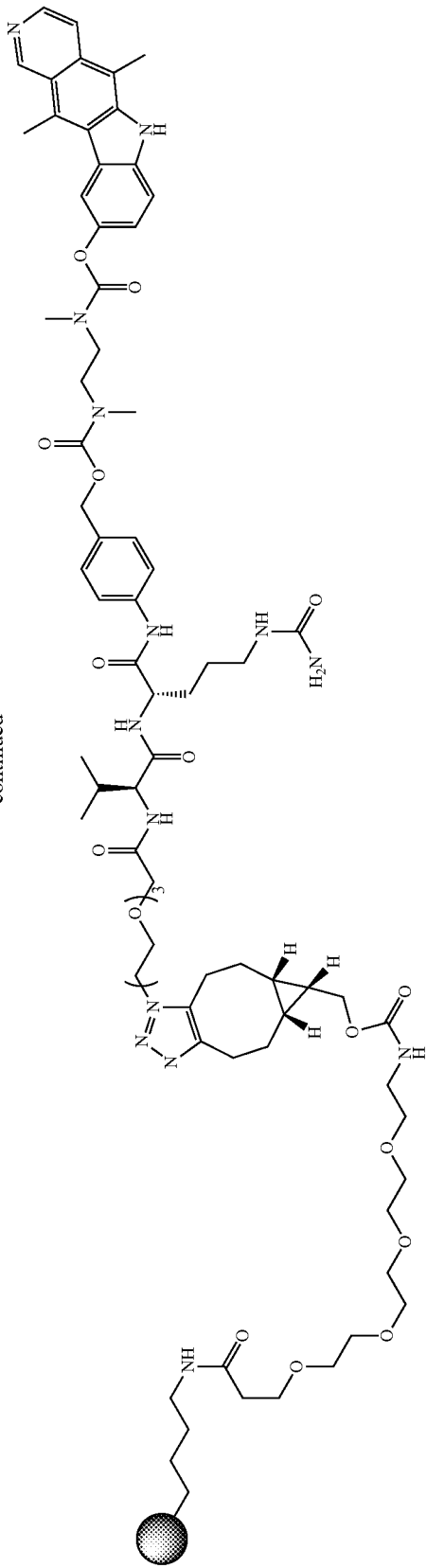
Ellipticine-(DNMEA)-PAB-Cit-Val-BCN-dPEG4 conjugate (126) via a peptide bond

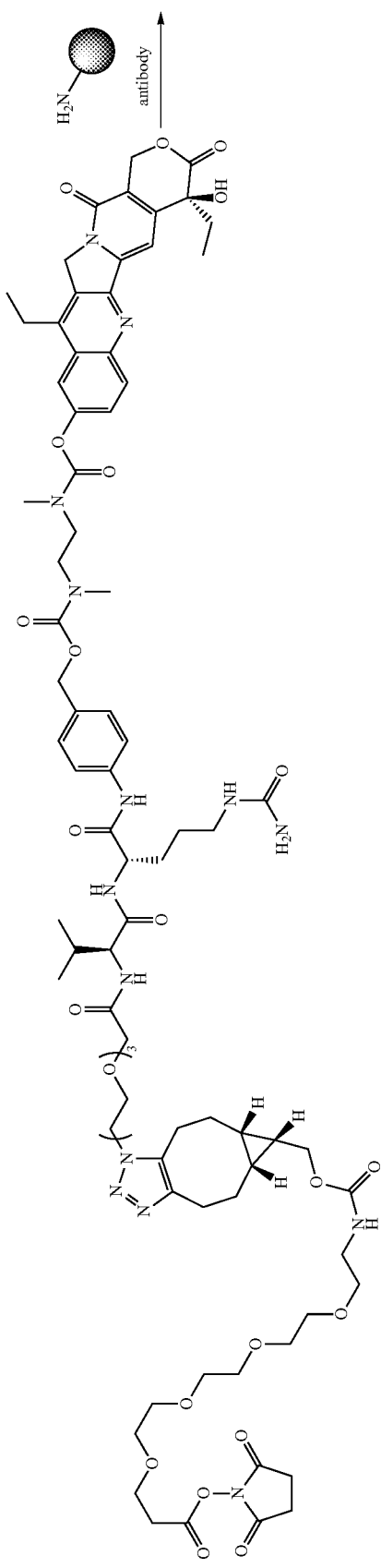
SN38-(DNMEA)-PAB-Cit-Val-BCN-dPEG4 Conjugate (127)
SN-38-(DNMEA)-PAB-Cit-Val-BCN-dPEG4 NHS ester (100)
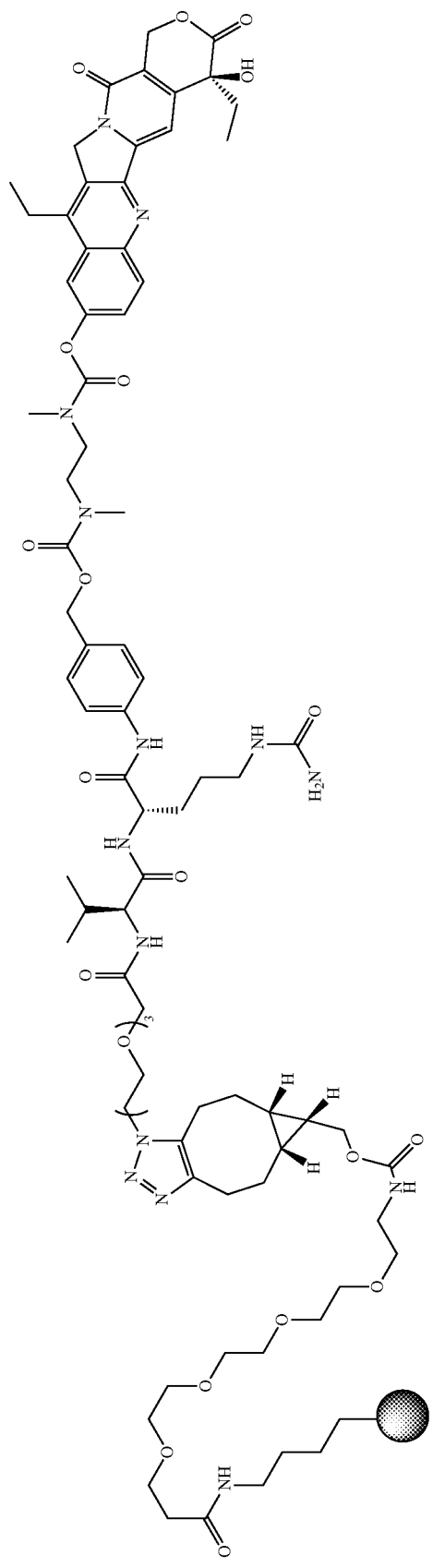
SN-38-(DNMEA)-PAB-Cit-Val-BCN-dPEG4 conjugate (127) via a peptide bond

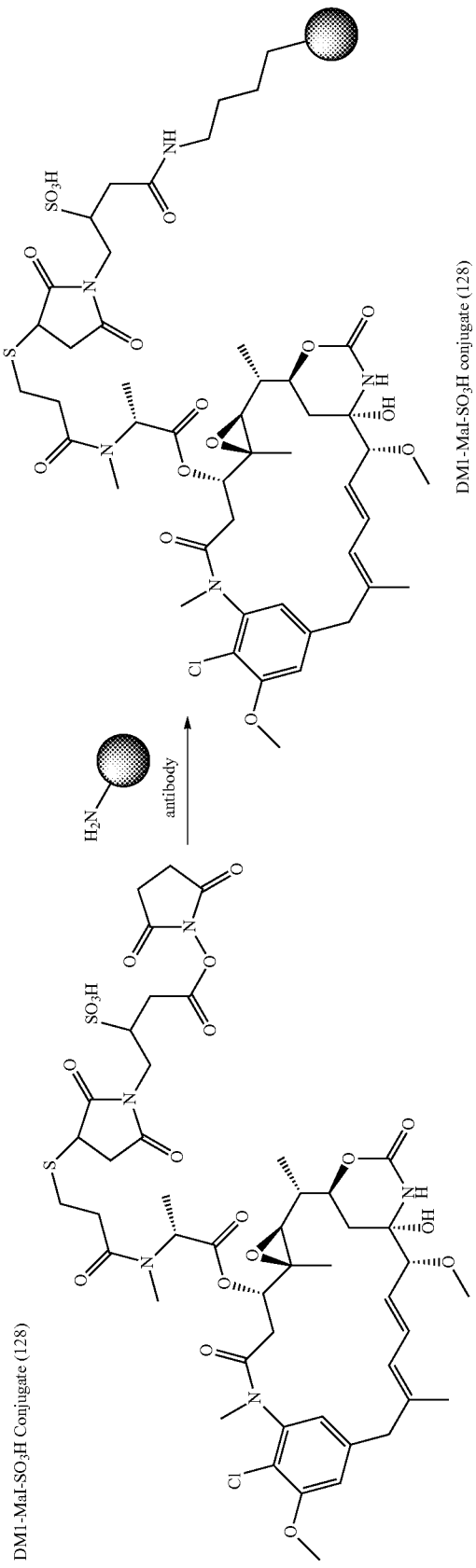
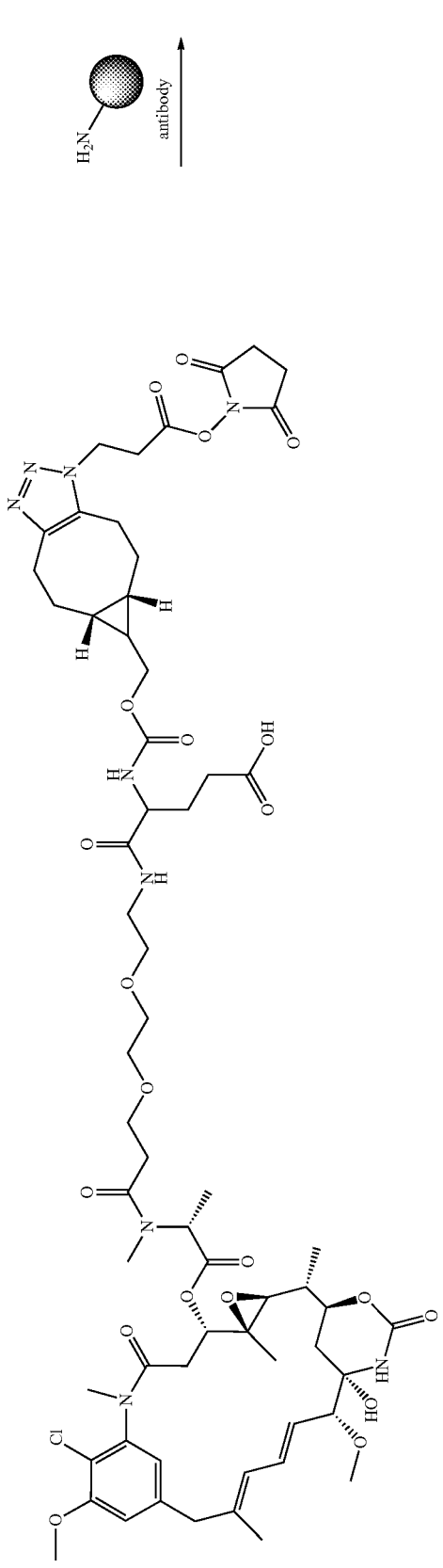

-continued
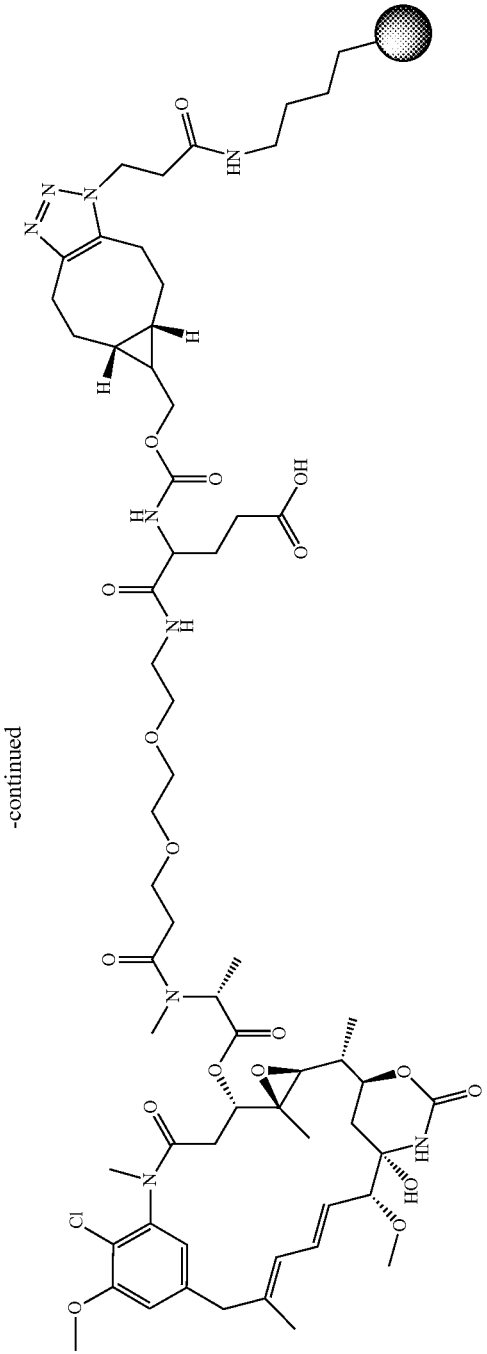
Maytansinol-PEG₂-Glu-BCN conjugate (129) via a peptide bond
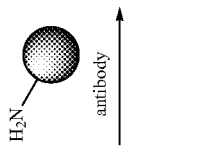
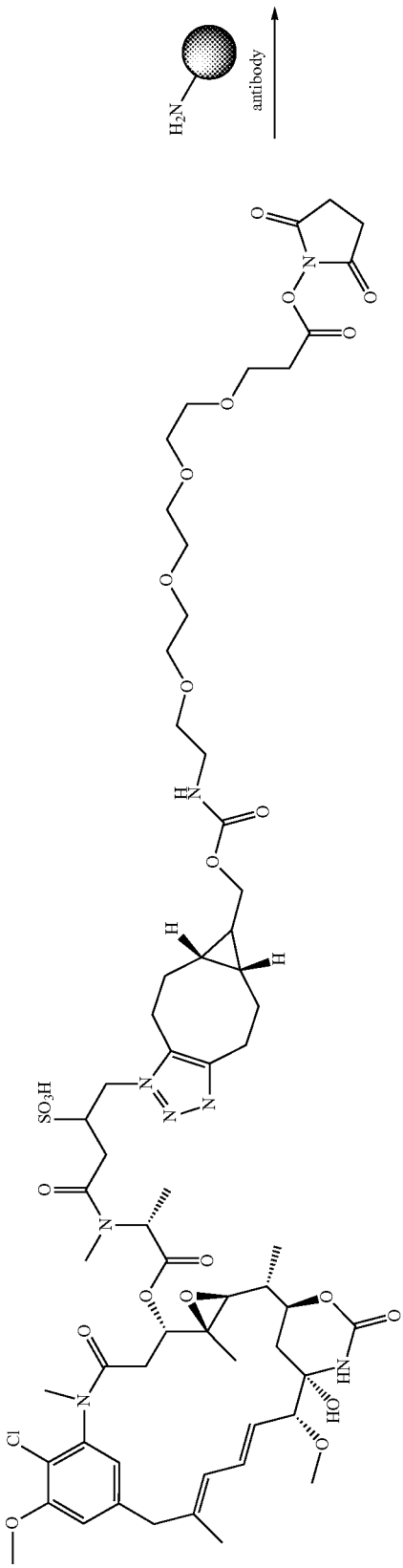
Maytansinol-SO₃H-BCN-dPEG₄-NHS ester (110)
Maytansinol-SO₃H-BCN-dPEG₄ Conjugate (130)

-continued
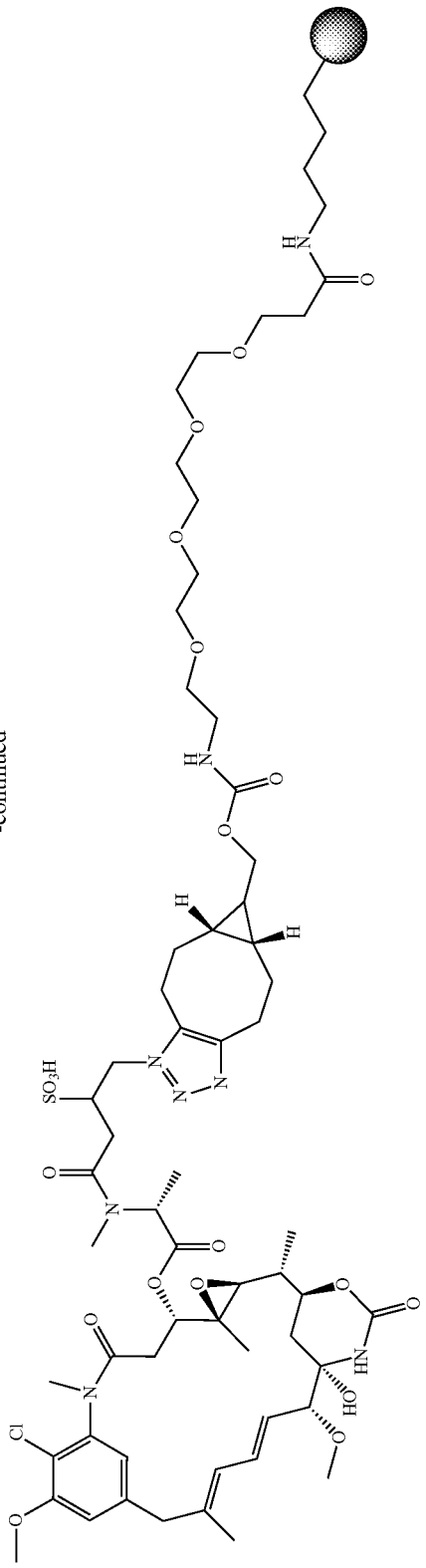
Maytansinol-SO₃H-BCN-dPEG₄ conjugate (130) via a peptide bond
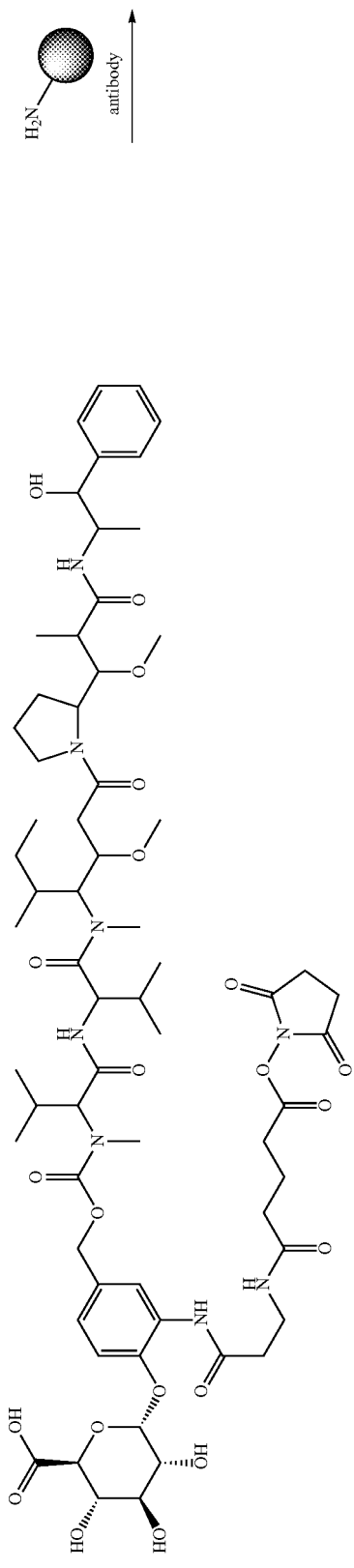
MMAE-β-Glucuronide-C₅ Conjugate (131)
MMAE-β-Glucuronide-C₅—NHS ester (113)

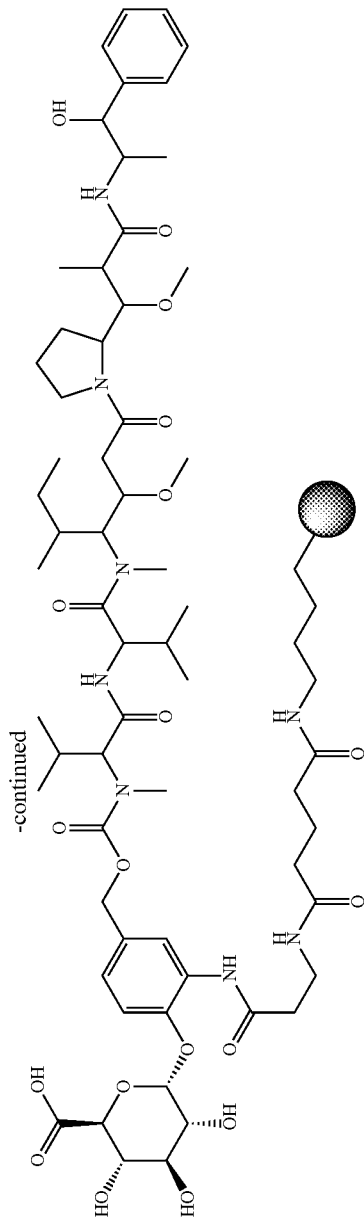
MMAE-β-Glucuronide-C5 conjugate ester (131) via a peptide bond
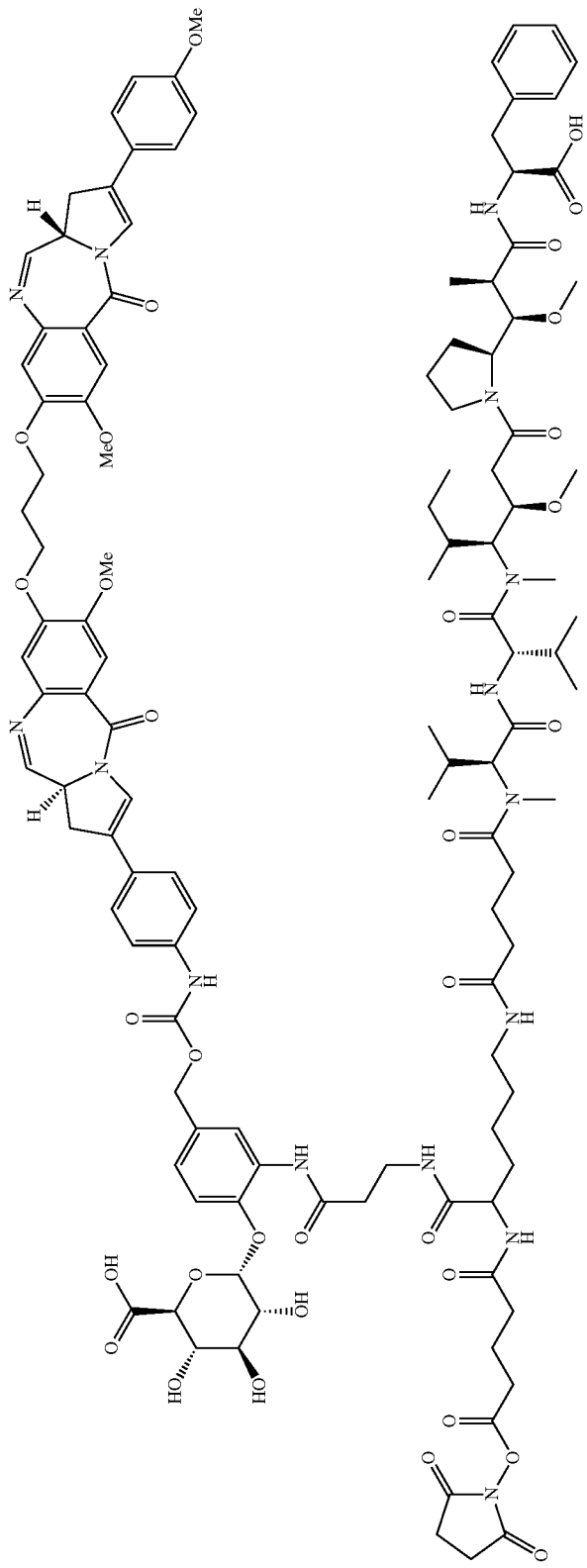
PBD Dimer-MMAF-Dual-C5 Conjugate (132)
PBD Dimer-MMAF-Dual-C5—NHS (116)

-continued
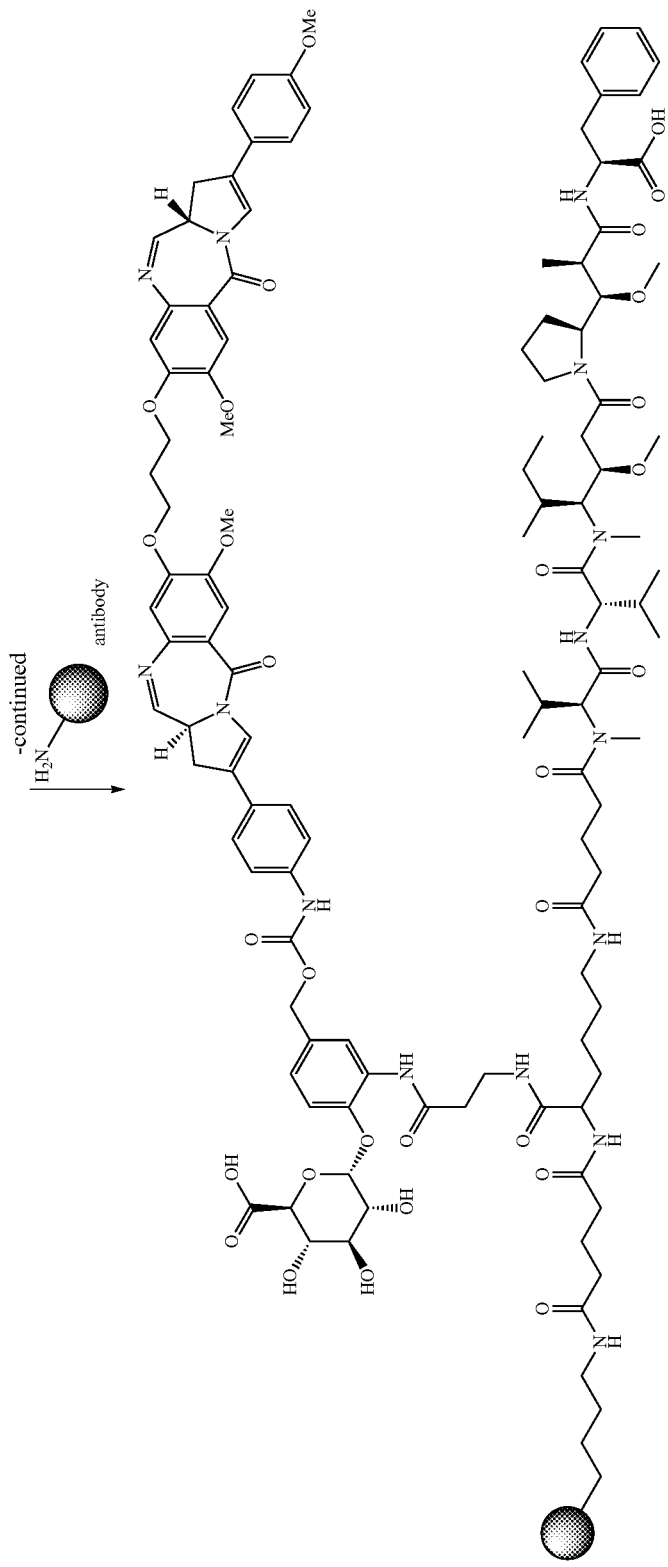
PDB Dimer-MMAF-Dual-C₅ conjugate (132)
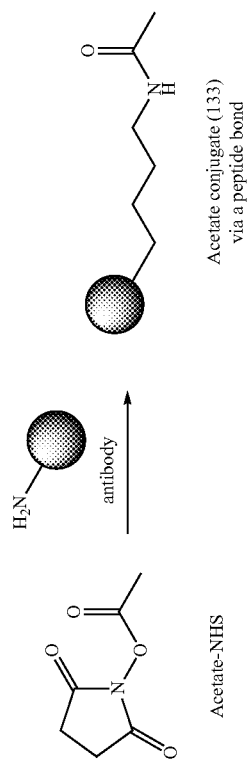
Acetate Conjugate (133) Acetate-NHS
Acetate conjugate (133) via a peptide bond -continued
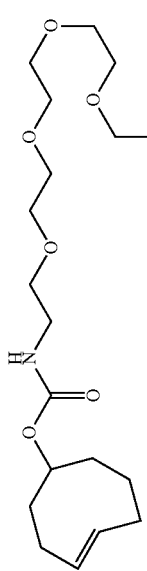
MMAF-dPEG₄-TCO Conjugate (135)
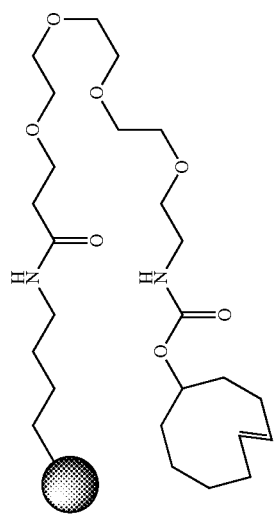
(134)
MMAF-Tetrazine (117)
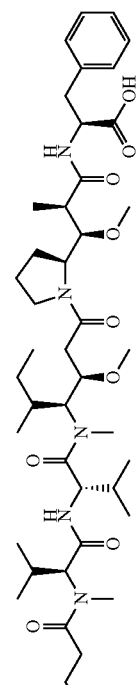
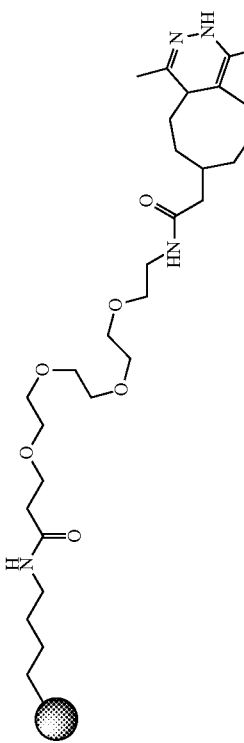
MMAF-dPEG₄-TCO conjugate (135)
via a peptide bond

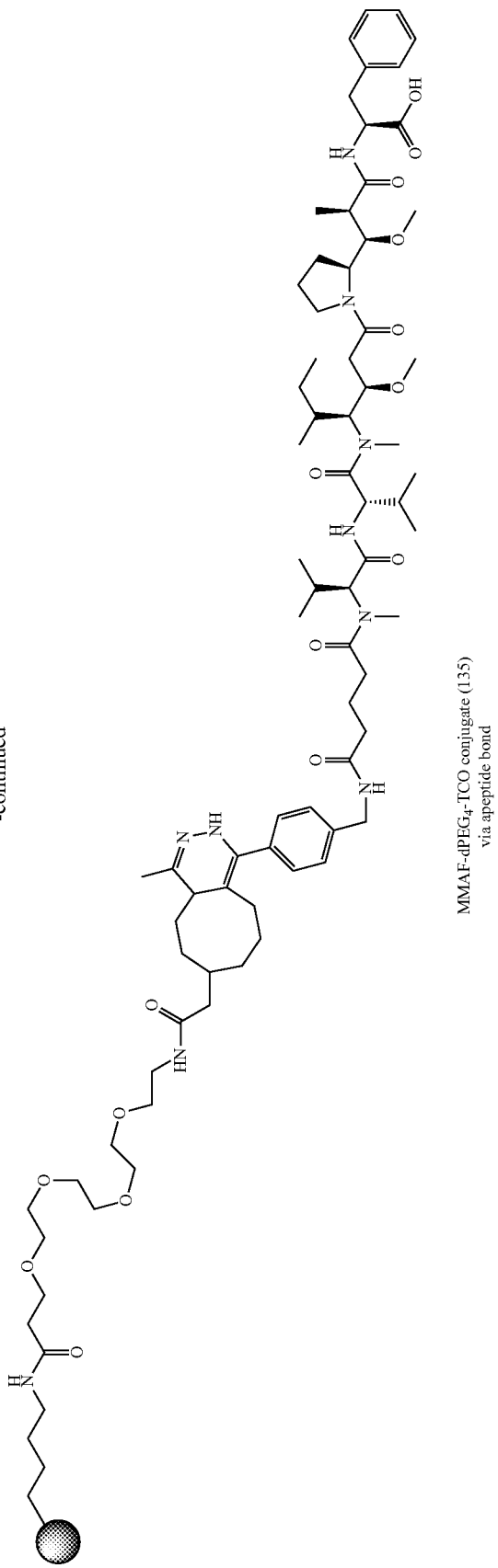
MMAF-dPEG4-TCO conjugate (135) via a peptide bond

-continued
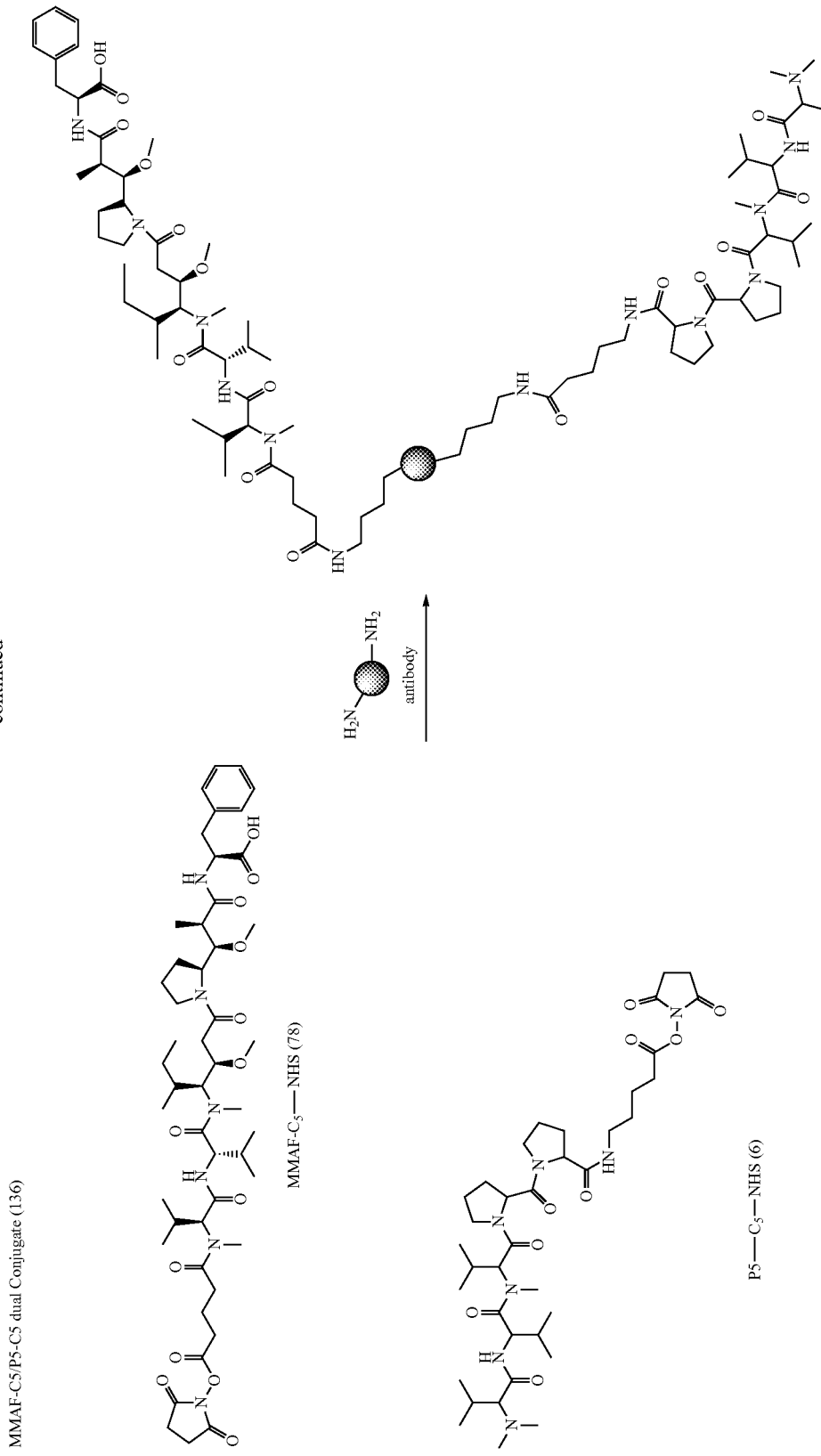

Example 63. Expression and Purification of a High Affinity Single-Chain Fv Antibody Fragment Bearing Multiple, Well-Dispersed, Surface Lysine Residues Construction of the high affinity, anti-HER2 cytoplasmic-expression scFv clone, TCT1067

The anti-HER2 scFv in Example 27 was modified by mutagenesis to increase its binding affinity by over 1000-fold [Schier R et al (1996) J. Mol. Biol 263, 551-67]. This retained the multiple, well-spaced, optimally positioned, surface lysine residues configuration and was expressed and purified as described in Example 27.

The resulting protein was called scFv (TCT1067). The DNA and protein sequences are below:

```
DNA sequence of cleaved TCT1067
                                            [SEQ ID NO: 3]
GCGGTAGCGGAGGTAGCGGACAGGTGCAGCTGGTGCAGTCTGGGGCAGA

GGTGAAAAAGCCCGGGGAGTCTCTGAAGATCTCCTGTAAGGGTTCTGGAT

ACAGCTTTACCAGCTACTGGATCGCCTGGGTGCGCCAGATGCCCGGGAAA

GGCCTGGAGTACATGGGGCTCATCTATCCTGGTGACTCTGACACCAAATA

CAGCCCGTCCTTCCAAGGCCAGGTCACCATCTCAGTCGACAAGTCCGTCA

GCACTGCCTACTTGCAATGGAGCAGTCTGAAGCCCTCGGACAGCGCCGTG

TATTTTTGTGCGAGACATGACGTGGGATATTGCACCGATCGTACCTGCGC

AGCGTGGCCTGAATGGCTGGGCGTGTGGGGCCAGGGCACCCTGGTCACCG

TCTCCTCAGGTGGAGGCGGTTCAGGCGGAGGTGGCTCTGGCGGTGGCGGA

TCGCAGTCTGTGTTGACGCAGCCGCCCTCAGTGTCTGCGGCCCAGGACA

GAAGGTCACCATCTCCTGCTCTGGAAGCAGCTCCAACATTGGGAATAATT

ATGTATCCTGGTACCAGCAGCTCCCAGGAACAGCCCCCAAACTCCTCATC

TATGGTCACACCAATCGGCCCGCAGGGGTCCCTGACCGATTCTCTGGCTC

CAAGTCTGGCACCTCAGCCTCCCTGGCCATCAGTGGGTTCCGGTCCGAGG

ATGAGGCTGATTATTACTGTGCAAGCTGGGATTATACCCTGAGTGGTTGG

GTGTTCGGCGGAGGGACCAAGCTGACCGTCCTAATGGCTAGCATGACTGG

TGGACAGCAAATGGGTTGATGAGGCTCTAACTCTCCTCT

KEY:
Bold = Residual Ser left after TEV cleavage,
Underlined = Linker region
(GSGGSG)SEQ ID NO: 8
Unformatted = scFv sequence,
Bold italics = T7 tag sequence
Amino Acid sequence of cleaved scFv (TCT1067)
                                            [SEQ ID NO: 4]
S G S G G S G Q V Q L V Q S G A E V K K P G E S L

K I S C K G S Y S F T S Y W I A W V R Q M P G K

G L E Y M G L I Y P G D S D T K Y S P S F Q G Q V

T I S V D K S V S T A Y L Q W S S L K P S D S A V

Y F C A R H D V G Y C T D R T C A A W P E W L G V

W G Q G T L V T V S S G G G G S G G G G S G G G G

S Q S V L T Q P P S V S A A P G Q K V T I S C S G

S S S N I G N N Y V S W Y Q Q L P G T A P K L L I

Y G H T N R P A G V P D R F S G S K S G T S A S L

A I S G F R S E D E A D Y Y C A S W D Y T L S G W

V F G G G T K L T V L M A S M T G G Q Q M G
```

Amino Acid Sequence of Cleaved scFv (TCT1067)
Number of Amino acids: 272, Molecular weight: 28,219 Da Theoretical PI: 8.14, Extinction coefficient: 70 735

Example 64A. Bioconjugation of a Single-Chain Fv Antibody Fragment Bearing Multiple, Well-Dispersed, Surface Lysine Residues to an NHS-Bearing Moiety Generic Method for Conjugating an scFv to a Payload-NHS Initially, the hydrolysis rate of the pure, payload-NHS was examined in selected buffer conditions in order to optimise its availability. Other factors that were taken into account were the stability of the antibody in the buffer/pH/organic solvent, the stability of the drug, and the amount and rate of the drug addition to the reaction. The conditions identified and used throughout unless otherwise specified are:

TABLE 15

| Type | Condition |
|---|---|
| Buffer | Bicarbonate buffer with 150 mM NaCl at pH 8.8 |
| Co-solvent | anhydrous filtered DMSO at a final 20% (v/v) concentration |
| Temperature | 20° C. |
| Agitation | thermomixer 1000 rpm |
| Antibody concentration | 1 mg/ml |
| Payload NHS handling | dissolved in 100% anhydrous filtered DMSO at a concentration of either 50 mM or 100 mM |
| Payload addition rate | every 70-120 mins |
| Payload addition equivalents | 10 to 16 equivalents |

The scFv was thawed at 4° C. and any precipitate formed was collected by centrifugation (10 mins, 10 krpm, 4° C.).

The stock solution of payload-NHS was made up in anhydrous filtered DMSO and any precipitate was collected by centrifugation. Bicarbonate buffer pH8.8 was combined with filtered anhydrous DMSO in protein low-bind eppendorf microtubes and the mixture was equilibrated on a Thermomixer (with the temperature raised from 4° C. to 20° C., whilst mixing at 1000 rpm). The antibody was added and equilibrated further (20° C., 1000 rpm) for 10 min before the addition of the payload-NHS. This was carried out by adding the x number of equivalents (dependent on the payload) of the NHS-drug DMSO stock and inverting to mix every 70-120 min, before replacing on the Thermomixer and mixing at 20° C., 1000 rpm. The total number of equivalents used depended on the required DAR. The samples were left on the Thermomixer for a further 2-18 hrs after the last addition. The samples were then collected by centrifugation (2.5 min, 11 krpm, 4° C.).

All samples were pH neutralised (by the addition of 0.1M NaH$_2$PO$_4$) and purified by HPLC-SEC on a Tosoh TSKGel G2000 SW$_{XL}$ column eluting with 10% IPA/PBS at pH 7, 20° C. The sample and fractions were kept cold throughout (4° C.), the relevant fractions were combined and concentrated on Vivaspin columns (HY or PES membrane) (10,000 MWCO). The IPA was removed by spin concentrating several times (at least 500 fold) using PBS, filtered through a 0.2 µm supor membrane and quantified using UV/Vis spectroscopy and amino acid analysis.

The final product was analysed by:

1. Reducing SDS-PAGE

Precast reducing SDS-PAGE gels (12%) were routinely used for analysis of samples and stained with Coomassie Blue.

2. Amino Acid Analysis

The DAR and sample concentration was accurately determined by Amino Acid Analysis (AAA) at Cambridge University's Protein and Nucleic Acid Chemistry Facility. From the AAA, the amount in mol of both the protein and the drug (due to the drug's fingerprint-release, see Table 16A for each drug) can be derived and the DAR calculated (No mol drug/No mol protein). The concentration of the protein in the solution can be calculated by first calculating the conjugate's molecular weight based on the DAR, and then subsequently converting the concentration obtained from AAA to mg/ml of protein. For example: scFv (TCT) is 28162 (MS), DAR is 'X', and each drug molecule adds 'XX' onto the antibody. Therefore conjugate MW=28162+(X×X)=X. The concentration is X nmol/ml which is equal to X µg/ml of protein.

TABLE 16A

Quantification using amino acid analyses

| Payoad | Amino acid liberated and used for quantification |
| --- | --- |
| P5C5 | 5-aminovaleric acid |
| Cemadotin | 4-aminomethylbenzoic acid |
| MMAF | no atypical ones, used calcn of excess Phenyl alanine |
| AF | 5-aminovaleric acid |
| MMAE | ornithine (from citrulline) |
| DM1 | no identifiable fragments |

3. HPLC-SEC

Samples were analysed and/or purified on a Tosoh TSK-Gel G2000SW$_{XL}$ or on a Sepax Zenix-C SEC-150, 3 µm, 7.8×300 mm, monitoring at 214 and 280 nm, flow rate 0.5 ml/min for 30 mins, 20° C., samples at 4° C. Typically, 20 µg of protein was injected for analytical runs and 300 µg for semi-preparative runs.

4. Mass Spectrometry

Sample preparation: free antibody and conjugates (payload MMAF, P5C5, AuF and MMAE) were desalted on a COSTAR® SPIN-X® (Sigma Aldrich) by centrifuging for 2 min at 10.5 g.

Typically, for free antibody, P5, AF and MMAE conjugates, 20-30 µg of protein was used. For MMAF 80 µg of protein was used.

DM1 conjugates were desalted using a 0.5 mL zeba column (thermofisher), injecting 30 µg of protein.

Liquid chromatography experiments were performed on an Agilent 1100 system connected to MSQ Plus Single Quad Detector (SQD). An XBridge column, BEH300 C4 3.5 µm 2.1×100 mm was used at 0.5 ml/min, 10 min gradient from 95% A to 50% B then holding for 5 mins at 50% B where

A: H$_2$O/0.1% FA

B: 90% CH$_3$CN/H$_2$O (0.1% FA)

Wavelength: 254 nm.

The parameters of the instruments were optimized to allow the stabilization and transmission of high molecular weight species. Scan Range: m/z=500-2000. Scan time: 1.5 s. Data obtained in continuum mode. The electrospray source of the MS was operated with a capillary voltage of 4.2 kV and a cone voltage of 50 V. Nitrogen was used as the nebulizer and desolvation gas at a total flow of 600 L/h. Ion series were generated by integration of the total ion chromatogram (TIC) over the 3.5-5.0 min range. Total mass spectra for protein samples were reconstructed from the ion series using the pre-installed ProMass software.

5. Binding Analyses by Biacore Surface Plasmon Resonance (SPR)

The binding affinity against immobilised HER2 target antigen was determined by Biacore SPR compared to the unmodified scFv on a Biacore T200. A standard amine-coupling method was used to prepare all Biacore surfaces (CM5 or CM3), as follows. Flow cells were activated individually by injecting a freshly mixed solution of 0.2M EDC in 0.05 M NHS at 30 µl/min. 12.5 µg/ml of Her2 was injected until the desired level of immobilization was reached (typically ~1500 RU). Excess NHS ester was deactivated using a 1 M ethanolamine solution. To measure the kinetics of the antibody and conjugate on the HER2 chip, a threefold serial dilution (typically at 5, 2.5, 1.25, 0.6 µg/ml or lower for free antibody and 20, 10, 5, 2.5 µg/ml for the conjugates), was injected for 160 s at 30 µl/min, allowing a 900-s dissociation phase. The dissociation time was extended to 3600 s for the highest concentration. Surfaces were regenerated with 45 s injection of MgCl$_2$ 8M.

To evaluate binding ability, manual runs were performed at 30 µl/min with a 60 s injection of the desired compound followed by 60 s waiting time and a 45 s of regeneration at 10 µl/min using MgCl$_2$ 8M. All data was analysed using the software, BIAEvaluation.

Method for Scaling Up Conjugations for In Vivo Sample Preparation

Freshly filtered bioconjugation buffer was combined with freshly filtered anhydrous DMSO in a 50 ml falcon tube and equilibrated on a Thermomixer (12 mins at 4° C. at 800 rpm, 6 mins, 20° C., 500 rpm). The scFv was thawed at 4° C. and any precipitate formed was collected by centrifugation (10 mins, 10 krpm, 4° C.). A stock solution of the payload-NHS was dissolved in anhydrous filtered DMSO and any precipitate formed was collected by centrifugation. The antibody was added to the buffer mixture and allowed to equilibrate on the thermomixer for 10 mins at 20° C., 350 rpm before the addition of the payload-NHS. This was carried out by adding the required equivalents of the payload-NHS DMSO stock, before replacing on the Thermomixer and mixing at 20° C., 350 rpm. The samples were left on the Thermomixer for a further 2 hrs/18 hrs after the last addition. The samples were then collected by centrifugation (20 min, 4 krpm, 4° C.) and purified by SEC on an AKTA Avant system using a Superdex 75, 26/600 column eluting with 10% IPA/PBS unless otherwise stated. A maximum flow rate for the column was used at 2.6 ml/min, detecting wavelengths 214 and 280 nm. The crude sample and fractions were kept cold throughout the purification process. Fractions were combined and concentrated using Vivacell 100 10 kMWCO (PES membrane) (Sartorius) before buffer exchanging into PBS using the same process. The concentrated and buffer exchanged samples were quantified by UV/Vis spectroscopy filtered through a sterile 0.2 µm supor membrane, re-quantified, diluted accordingly and analysed as before by SDS-PAGE, HPLC-SEC, Amino acid analysis, mass spectrometry and binding analyses by Biacore SPR.

Trastuzumab-payload conjugates were synthesised as control samples. These reactions were carried out as described above for the scFv, noting the changes in the protein concentration and the payload NHS addition:

TABLE 16B

Reaction conditions for trastuzumab bioconjugations

| Type | Condition |
| --- | --- |
| Buffer | Bicarbonate buffer with 150 mM Nacl at pH 8.8 |
| Co-solvent | anhydrous filtered DMSO at a final 20% (v/v) concentration |
| Temperature | 20° C. |
| Agitation | thermomixer 1000 rpm |
| Antibody concentration | 5 mg/ml |
| Payload-NHS handling | 100 mM or 50 mM (as per the scFv) solution in 100% anhydrous filtered DMSO |
| Payload-NHS addition rate | N/A |
| Payload-NHS addition portions | all added in one portion |

The following trastuzumab conjugates were made using the following reaction conditions:

Trastuzumab-P5-C5; 6 equivalents, Trastuzumab-MMAF-C5; 7 equivalents,

Trastuzumab-AF-C5; 5.5 equivalents, Trastuzumab-MMAE-PAB-Cit-Val-dPEG$_9$; 6 equivalents.

The conjugates were processed as per the scFv using the appropriate HPLC-SEC columns, Tosoh TSKGel G3000SW$_{XL}$ and on the AKTA Avant a Superdex 200, 26/600.

Example 64B. Bioconjugation of Single-Chain Fv Antibody Fragments Bearing Multiple, Well-Dispersed, Surface Lysine Residues to Small NHS-Bearing Moieties Demonstrates Full OptiLinked Conjugation Capacity A small molecule Acetate-NHS (CH3-CO—NHS) was conjugated to scFv (TCT and TCT1067) to obtain conjugates (compound 133) with a high DAR (where "drug"=small molecule acetate payload). The conditions identified and carried forward for the conjugations were:

TABLE 17

Reaction conditions for acetate-NHS bioconjugations

| Type | Condition |
| --- | --- |
| Buffer | Bicarbonate buffer with 150 mM NaCl at pH 8.8 |
| Co-solvent | Anhydrous filtered DMSO at a final 20% (v/v) concentration |
| Temperature | 20° C. |
| Agitation | Thermomixer 1000 rpm |
| Antibody concentration | 1 mg/ml |
| Acetate-NHS handling | 100 mM solution in 100% anhydrous filtered DMSO |
| Acetate-NHS addition rate | Every 90 min |
| Acetate-NHS addition portions | 16 equivalents |

The reactions were carried out as per Example 64A.
In this example, the set up was:
Reaction 1—scFv (TCT): Ac—NHS, 110 equivalents;
Reaction 2—scFv (TCT1067): Ac—NHS, 110 equivalents The unconjugated and conjugated scFvs (TCT and TCT1067) were analysed by HPLC size-exclusion chromatography. The scFv (TCT1067) has a retention time of 7.53 min correlating to a MW of around 30 kDa. Its conjugate eluted earlier at 7.23 min indicating a larger molecular weight, but as a single, sharp, monomeric peak, indicating no aggregation (FIG. 44). The ScFv (TCT) had a retention time of 7.36 min correlating to a MW of around 30 kDa. Its conjugate eluted earlier at 7.15 min indicating a larger molecular weight (due to varying small molecule loads), but as a single, sharp, monomeric peak, indicating no aggregation (FIG. 44).

LC-MS Method and Data Acquisition (Denaturing, Non-Covalent Conditions)

The LCMS, Total Ion Current (TIC) chromatograms and spectra and the deconvoluted data of scFv (TCT and TCT1067)-Acetate are shown in FIGS. 45 and 46 and a summary in Table 18.

A single major peak was observed in the TIC of the scFv (TCT and TCT1067)-Acetate samples. TCT-acetate eluting at 10.1 min and TCT1067-acetate eluting at 10.3 min. The zero-charge deconvoluted mass spectrum for this peak produced a major peaks at m/z 28792 for TCT-acetate and 28891 for TCT1067-acetate, which was consistent with the supplied theoretical mass of the scFv (TCT and TCT1067) molecule, together with 15 and 16 additions of the small molecule respectively.

TABLE 18

Summary of the LC-MS analyses of the scFv-Acetate conjugates (133)

| Sample | Retention time (min) | Observed peak mass (m/z) | Added mass (m/z) | Calculated DAR |
| --- | --- | --- | --- | --- |
| scFv (TCT) | 8.27 | 28160 | 0 | 0 |
| TCT-acetate conjugate 1 | 12.1 | 28792 | 632 | 15 |
| scFv (TCT1067) | 8.35 | 28215 | 0 | 0 |
| TCT1067-acetate conjugate 2 | 10.72 | 28891 | 672 | 16 |

Binding Activity of scFv (TCT and TCT1067)-Acetate Conjugates

ScFv (TCT and TCT1067)-Acetate conjugates were made and characterised as described above. Their binding affinities against immobilised HER2 target antigen was determined by Biacore SPR compared to the unmodified scFv.

The scFv (TCT)-Acetate DAR 15 had an association rate of $5.93 \times 10^6$ $M^{-1}$ $s^{-1}$ and a dissociation rate of $1.71 \times 10^{-2}$ $s^{-1}$, giving an overall binding Kd of 2.9 nM. This was very similar to the unmodified scFv (TCT) which had an association rate of $2.8 \times 10^6$ $M^{-1}$ $s^{-1}$ and a dissociation rate of $4.17 \times 10^{-3}$ $s^{-1}$, with an overall binding Kd of 1.49 nM, indicating no loss of binding function.

The scFv (TCT1067)-Acetate DAR 16 had an association rate of $3.63 \times 10^6$ $M^{-1}$ $s^{-1}$ and a dissociation rate of $7.64 \times 10^{-5}$ $s^{-1}$, giving an overall binding Kd of 21 pM. This was very similar to the unmodified scFv (TCT1067) which had an association rate of $3.9 \times 10^6$ $M^{-1}$ $s^{-1}$ and a dissociation rate of $3.7 \times 10^{-5}$ $s^{-1}$, with an overall binding Kd of 9.5 pM, indicating no loss of binding.

Overall Small Molecule (Acetate) Conclusions, Biophysical Data

The conjugation conditions were optimised as detailed above. This optimisation allowed for controlled conjugation reactions with a very high yield of low, medium and high DAR conjugates. There was no precipitation of antibody/conjugate observed in any of the conjugates and recovery was overall very high. Following SEC HPLC purification, the resulting conjugates were concentrated to H mg/ml.

The orthogonal techniques used for analysis are in agreement and support that an optimised scFv structure, exemplified by scFv (TCT or TCT1067), can be fully loaded with multiple molecules using lysine residues on the antibody and the conjugation can be controlled to obtain monomeric conjugates (as shown by SEC-HPLC) with the desired DAR whilst retaining binding function and affinity. The LCMS data supported by the HPLC SEC traces indicate that both antibodies can be effectively conjugated to full lysine occupancy to obtain monomeric conjugates. The conjugates showed shorter SEC retention times than the respective antibody controls in both cases. The LCMS indicates that the conjugates in both cases have a higher DAR than the total number of lysines of each antibody. When carrying out reactions at a highly alkaline pH with a large excess of a small NHS activated molecule it is possible that secondary amino acids will start to conjugate. In this case, we speculate that 12 Lysines, 1 terminal amine are predominantly modified.

Example 65. Bioconjugation of MMAF Derivatives with a Short Linker onto Two Single-Chain Fv Antibody Fragment Bearing Multiple, Well-Dispersed, Surface Lysine Residues

Example 65A. ScFv (TCT)-MMAF with a $C_5$ Linker

MMAF-C5-NHS (compound 78) was conjugated to scFv (TCT) to obtain conjugates (compound 118) with various DARs. The reaction was controlled to obtain products with medium and high DARs. The conditions identified and carried forward for the conjugations were:

TABLE 19

Reaction conditions for MMAFC5-NHS bioconjugations

| Type | Condition |
| --- | --- |
| Buffer | Bicarbonate buffer with 150 mM NaCl at pH 8.8 |
| Co-solvent | Anhydrous filtered DMSO at a final 20% (v/v) concentration |
| Temperature | 20° C. |
| Agitation | Thermomixer 1000 rpm |
| Antibody concentration | 1 mg/ml |
| MMAF-C5-NHS handling | 50 mM solution in 100% anhydrous filtered DMSO |
| MMAF-C5 addition rate | Every 90 min |
| MMAF-C5-NHS addition portions | 10 equivalents |

The reactions were carried out as per Example 64A noting that some minor aggregation was observed in the crude sample which resolved once the sample was purified. Recovery was ~50%. This reaction was scalable.

In this example, the set up was:
Reaction 1—scFv-TCT: MMAF-C5-NHS, 60 equivalents and
Reaction 2—scFv-TCT: MMAF-C5-NHS, 100 equivalents The unconjugated and conjugated scFv (TCT) were analysed by HPLC size-exclusion chromatography. The scFv has a retention time of 17.9 min correlating to a MW of around 30 kDa. The two conjugates eluted progressively earlier at 16.4 mins for ADC 1 and 16.1 mins for ADC 2 indicating a larger molecular weight (due to varying drug loads), but as a single, sharp, monomeric peak, indicating no aggregation (FIG. 47). Conjugation reaction 2 showed some aggregation at 17% that could be removed. An SDS-PAGE gel of reaction 2 showed complete conjugation and higher molecular weight (FIG. 48).

The DAR was determined by Amino Acid Analysis (AAA) at Cambridge University's Protein and Nucleic Acid Chemistry Facility to obtain the results shown in Tables 20-21.

TABLE 20

Summary of AAA results showing DARs of 6.6 for reaction 1
Reaction: 1 TCT-MMAF-C5
Integer fit of measured mole ratios to expected values

| Amino acid | Expected value | Observed value | Closeness of fit to expected value |
| --- | --- | --- | --- |
| Cys | 6 | not determined | — |
| Asp | 15 | 16.20 | within 5-10% |
| Thr | 14 | 14.12 | better than 5% |
| Ser | 46 | 43.97 | better than 5% |
| Glu | 22 | 21.57 | better than 5% |
| Gly | 44 | 43.19 | better than 5% |
| Ala | 17 | 16.46 | better than 5% |
| Val | 0 | excluded | — |
| Met | 5 | 5.15 | better than 5% |
| Ile | 8 | 8.27 | better than 5% |
| Leu | 15 | 15.75 | better than 5% |
| Norleu std | | | |
| Tyr | 14 | 14.62 | better than 5% |
| Phe | 0 | excluded | — |
| His | 3 | 3.22 | within 5-10% |
| Lys | 12 | 12.69 | within 5-10% |
| Arg | 5 | 4.79 | better than 5% |
| Pro | 0 | excluded | — |
| Trp | 8 | | (not determined) |
| Total (used) | 220 | residues | |

| | | | Average |
| --- | --- | --- | --- |
| Total sample | 0.169 | nmoles | 0.166 |
| | 4.76 | ug | 4.68 |
| Concentration | 27.28 | nmoles/ml | 26.80 |
| | 768.28 | ug/ml | 754.91 |
| MMAF Total sample | 1.13 | nmoles | |
| DAR | | | 6.64 |

TABLE 21

Summary of AAA results showing DARs of 8 for reactions 2
Reaction: 2 TCT-MMAF-C5
Integer fit of measured mole ratios to expected values

| Amino acid | Expected value | Observed value | Closeness of fit to expected value |
| --- | --- | --- | --- |
| Cys | 6 | not determined | — |
| Asp | 15 | 15.39 | better than 5% |
| Thr | 14 | 13.53 | better than 5% |
| Ser | 46 | 42.72 | within 5-10% |
| Glu | 22 | 22.56 | better than 5% |
| Gly | 44 | 47.69 | within 5-10% |
| Ala | 17 | 16.62 | better than 5% |
| Val | 0 | excluded | — |

TABLE 21-continued

Summary of AAA results showing DARs of 8 for reactions 2
Reaction: 2 TCT-MMAF-C5
Integer fit of measured mole ratios to expected values

| | Expected value | Observed value | Closeness of fit to expected value |
|---|---|---|---|
| Met | 5 | 4.69 | within 5-10% |
| Ile | 8 | 7.89 | better than 5% |
| Leu | 15 | 14.96 | better than 5% |
| Norleu std | | | |
| Tyr | 14 | 13.87 | better than 5% |
| Phe | 0 | excluded | — |
| His | 3 | 3.10 | better than 5% |
| Lys | 12 | 12.20 | better than 5% |
| Arg | 5 | 4.78 | better than 5% |
| Pro | 0 | excluded | — |
| Trp | 8 | | (not determined) |
| Total (used) | 220 | residues | |

| | | | Average |
|---|---|---|---|
| Total sample | 0.058 | nmoles | 0.050 |
| | 1.64 | ug | 1.40 |
| Concentration | 5.25 | nmoles/ml | 4.49 |
| | 147.91 | ug/ml | 126.42 |
| MMAF Total sample | 0.476 | | |
| DAR | | | 7.96 |

LC-MS analysis was performed as described in Example 64A.

The LCMS, Total Ion Current (TIC) chromatograms and spectra and the deconvoluted data of scFv (TCT)-C5-MMAF 1 and 2 are shown in FIGS. 49 and 50 and a summary in Table 22.

A major peak was observed in the TIC of the scFv (TCT)-C5-MMAF 1 sample eluting at 10.2 min. The zero-charge deconvoluted mass spectrum for this peak produced a series of major peaks at m/z 30645, 31473, 32301 and 33129 which was consistent with the supplied theoretical mass of the scFv (TCT) molecule, together with 3-6 additions of the MMAF-C5 molecule. For sample 2, a major peak was observed in the TIC at 9.9-11.4 min corresponding to the zero-charge deconvoluted mass at m/z 31474, 32302, 33130 and 33958 which was consistent with the supplied theoretical mass of the scFv (TCT) together with 4-7 additions of MMAF-C5.

TABLE 22

Summary of the LC-MS analyses of the scFv (TCT)-MMAF C5 conjugates (118)

| Sample | Retention time (min) | Observed peak mass (m/z) | Added mass (m/z) | Calculated DAR | Average DAR |
|---|---|---|---|---|---|
| scFv (TCT) | 8.27 | 28160 | 0 | 0 | 0 |
| TCT-MMAF-C5 ADC 1 | 10.2 | 30645 | 2485 | 3 | 4.5 |
| | | 31473 | 3313 | 4 | |
| | | 32301 | 4141 | 5 | |
| | | 33129 | 4969 | 6 | |
| TCT-MMAF-C5 ADC 2 | 9.9 | 31474 | 3314 | 4 | 5.5 |
| | 10.4 | 32302 | 4142 | 5 | |
| | 10.9 | 33130 | 4970 | 6 | |
| | 11.4 | 33958 | 5798 | 7 | |

Therefore, for:

Reaction 1, DAR was 6.64 by AAA and 4.5 by MS, with an average of 5.6

Reaction 2, DAR was 8.0 by AAA and 5.5 by MS, with an average of 6.8.

Binding Activity of scFv (TCT)-MMAF-C5 Conjugates

ScFv (TCT)-MMAF-C5 (compound 118) were made and characterised as described above. Their binding affinities against immobilised HER2 target antigen was determined by Biacore SPR compared to the unmodified scFv as in Example 64A.

The scFv (TCT)-MMAF-C5 1 DAR 5.6 had an association rate of $7.7 \times_{10}^5$ $M^{-1}$ $s^{-1}$ and a dissociation rate of $4.2 \times 10^{-3}$ $s^{-1}$, giving an overall binding Kd of 5.4 nM. The scFv (TCT)-MMAF-C5 DAR 6.8 had an association rate of $1.2 \times 10^6$ $M^{-1}$ $s^{-1}$ and a dissociation rate of $4.2 \times 10^{-3}$ giving an overall binding Kd of 3.6 nM. This was essentially unchanged compared to the unmodified scFv (TCT) which had an association rate of $2.8 \times 10^6$ $M^{-1}$ $s^{-1}$ and a dissociation rate of $4.17 \times 10^{-3}$ $s^{-1}$, with an overall binding Kd of 1.49 nM, indicating no loss of binding function.

Overall TCT-MMAF-C5 Conclusions, Biophysical Data

The conjugation conditions were optimised as detailed above. This optimisation allowed for controlled conjugation reactions to obtain medium and high DAR conjugates. There was minimal precipitation of antibody/conjugate observed during the synthesis. Following SEC HPLC purification, the resulting conjugates were concentrated to ~1.5 mg/ml and were stable in the buffer for several months.

The orthogonal techniques used for analysis are in agreement and support that an optimised scFv structure, exemplified by scFv (TCT), can be loaded with multiple drugs using lysine residues on the antibody and the conjugation can be controlled to obtain monomeric conjugates (as shown by SEC-HPLC with the desired DAR whilst retaining binding function and affinity. On the HPLC the samples had progressively shorter retention times than the scFv (TCT), eluting faster from the SEC column due to their increasing size. Amino acid analysis was an extremely useful tool for further quantitative analysis and complemented the MS data.

Example 65B. ScFv (TCT1067)-MMAF with a $C_5$ Linker

MMAF-C5-NHS (compound 78) was conjugated to scFv (TCT) to obtain conjugates (compound 118) with various DARs. The conditions identified and carried forward were:

TABLE 23

Reaction conditions for MMAF-C5-NHS bioconjugations

| Type | Condition |
|---|---|
| Buffer | Bicarbonate buffer with 150 mM NaCl at pH 8.8 |
| Co-solvent | Anhydrous filtered DMSO at a final 20% (v/v) concentration |
| Temperature | 20° C. |
| Agitation | Thermomixer 1000 rpm |
| Antibody concentration | 1 mg/ml |
| MMAF-C5-NHS handling | 50 mM solution in 100% anhydrous filtered DMSO |
| MMAF-C5 addition rate | Every 90 min |
| MMAF-C5-NHS addition portions | 10 equivalents |

The reactions were carried out as per Example 64A noting that some minor aggregation was observed in the crude sample which resolved once the sample was purified. Total recovery was ~50-60%. These reactions were scalable. In this example, the set up was:

Reaction 1—scFv-TCT1067: MMAF-C5-NHS, 60 equivalents and

Reaction 2—scFv-TCT1067: MMAF-C5-NHS, 100 equivalents.

The unconjugated and conjugated scFv (TCT1067) were analysed by HPLC size-exclusion chromatography. The ScFv has a retention time of 18.1 min correlating to a MW of around 30 kDa. The two conjugates all eluted slightly and progressively earlier indicating a larger molecular weight (due to varying drug loads), but as a single, sharp, monomeric peak, indicating no aggregation (FIG. 51).

The DAR was accurately determined by Amino Acid Analysis (AAA) at Cambridge University's Protein and Nucleic Acid Chemistry Facility as shown in Table 24 and

TABLE 24

Summary of AAA results showing DARs of 6.4 for reaction 1
Reaction: 1 TCT1067-MMAF-C5
Integer fit of measured mole ratios to expected values

| Amino acid | Expected value | Observed value | Closeness of fit to expected value |
|---|---|---|---|
| Cys | 6 | not determined | — |
| Asp | 14 | 15.11 | within 5-10% |
| Thr | 17 | 16.77 | better than 5% |
| Ser | 44 | 41.02 | within 5-10% |
| Glu | 21 | 20.99 | better than 5% |
| Gly | 45 | 44.44 | better than 5% |
| Ala | 16 | 15.65 | better than 5% |
| Val | 0 | excluded | — |
| Met | 5 | 4.84 | better than 5% |
| Ile | 8 | 8.22 | better than 5% |
| Leu Norleu std | 16 | 17.15 | within 5-10% |
| Tyr | 14 | 14.49 | better than 5% |
| Phe | 0 | excluded | — |
| His | 2 | 2.11 | within 5-10% |
| Lys | 12 | 12.93 | within 5-10% |
| Arg | 6 | 6.30 | better than 5% |
| Pro | 0 | excluded | — |
| Trp | 9 | | (not determined) |
| Total (used) | 220 | residues | |

| | | | Average |
|---|---|---|---|
| Total sample | 0.17 | nmoles | 0.16 |
| | 4.83 | ug | 4.49 |
| Concentration | 38.80 | nmoles/ml | 36.01 |
| | 1098.2738 | ug/ml | 1019.373151 |
| MMAF Total sample | 1.109 | | |
| DAR | | | 6.36 |

TABLE 25

Summary of AAA results showing DARs of 8.6 for reaction 2
Reaction: 2 TCT1067-MMAF-05
Integer fit of measured mole ratios to expected values

| Amino acid | Expected value | Observed value | Closeness of fit to expected value |
|---|---|---|---|
| Cys | 6 | not determined | — |
| Asp | 14 | 14.83 | within 5-10% |
| Thr | 17 | 17.62 | better than 5% |
| Ser | 44 | 41.77 | within 5-10% |
| Glu | 21 | 20.66 | better than 5% |
| Gly | 45 | 48.17 | within 5-10% |
| Ala | 16 | 15.11 | within 5-10% |
| Val | 0 | excluded | — |

TABLE 25-continued

Summary of AAA results showing DARs of 8.6 for reaction 2
Reaction: 2 TCT1067-MMAF-05
Integer fit of measured mole ratios to expected values

| | Expected value | Observed value | Closeness of fit to expected value |
|---|---|---|---|
| Met | 5 | 4.92 | better than 5% |
| Ile | 8 | 8.07 | better than 5% |
| Leu Norleu std | 16 | 14.99 | within 5-10% |
| Tyr | 14 | 13.72 | better than 5% |
| Phe | 0 | excluded | — |
| His | 2 | 2.04 | better than 5% |
| Lys | 12 | 12.05 | better than 5% |
| Arg | 6 | 6.06 | better than 5% |
| Pro | 0 | excluded | — |
| Trp | 9 | | (not determined) |
| Total (used) | 220 | residues | |

| | | | Average |
|---|---|---|---|
| Total sample | 0.071 | nmoles | 0.078 |
| | 2.00 | ug | 2.20 |
| Concentration | 6.47 | nmoles/ml | 7.12 |
| | 183.28 | ug/ml | 201.43 |
| MMAF Total sample | 0.635 | | |
| DAR | | | 8.61 |

LC-MS analysis was performed as described in Example 64A.

The LCMS, Total Ion Current (TIC) chromatograms and spectra and the deconvoluted data of scFv (TCT1067)-C5-MMAF 1 and 2 are shown in FIG. 52 and a summary in Table 26.

A major peak was observed in the TIC of the scFv (TCT1067)-C5-MMAF 1 sample eluting at 10.1 min. The zero-charge deconvoluted mass spectrum for this peak produced a series of major peaks at m/z 29874, 30702, 31530, 32358 and 33186, which was consistent with the supplied theoretical mass of the scFv (TCT1067) molecule, together with 2-6 additions of the MMAF molecule. For sample 2, the TIC had the main peaks eluting at 9.3-12 min. The zero-charge deconvoluted mass spectrum for this peak produced a series of major peaks at m/z 30703, 31531, 32358, 33186, 34015 and 34843 which was consistent with the supplied theoretical mass of the scFv (TCT1067) molecule, together with 3-8 additions of the MMAF molecule.

TABLE 26

Summary of the LC-MS analyses of the scFV(TCT1067)-MMAF-C5 conjugates (118)

| Sample | Retention time (min) | Observed peak mass (m/z) | Added mass (m/z) | Calculated DAR | Average DAR |
|---|---|---|---|---|---|
| scFv(TCT1067) | 8.35 | 28215 | 0 | 0 | 0 |
| TCT1067-MMAF-C5 ADC 1 | 10.1 | 29874 | 1659 | 2 | 4.0 |
| | | 30702 | 2487 | 3 | |
| | | 31530 | 3315 | 4 | |
| | | 32358 | 4143 | 5 | |
| | | 33186 | 4971 | 6 | |
| TCT1067-MMAF-C5 ADC 2 | 9.9-12.0 | 30703 | 2484 | 3 | 5.5 |
| | | 31531 | 3312 | 4 | |
| | | 32358 | 4139 | 5 | |
| | | 33186 | 4967 | 6 | |
| | | 34015 | 5796 | 7 | |
| | | 34843 | 6624 | 8 | |

Therefore,

For sample 1, DAR was 6.4 by AAA and 4.0 by MS with an average of 5.2

For sample 2, DAR was 8.6 by AAA and 5.5 by MS with an average of 7.1.

Binding Activity of scFv (TCT1067)-MMAF-C5 Conjugates

ScFv (TCT1067)-MMAF-C5 (compound 118) were made and characterised as described above. Their binding affinities against immobilised HER2 target antigen was determined by Biacore SPR compared to the unmodified scFv as described in Example 64A.

The scFv (TCT1067)-MMAF-C5 DAR 5.2 had an association rate of $1.8 \times 10^6$ $M^{-1}$ $s^{-1}$ and a dissociation rate of $3.4 \times 10^{-5}$ $s^{-1}$, giving an overall binding Kd of 19.6 pM. The scFv (TCT)-MMAF-C5 DAR 7.1 had an association rate of $4.6 \times 10^6$ $M^{-1}$ $s^{-1}$ and a dissociation rate of $1.7 \times 10^{-5}$ $s^{-1}$, giving an overall binding Kd of 3.8 pM. This was essentially unchanged compared to the unmodified scFv (TCT1067) which had an association rate of $3.9 \times 10^6$ $M^{-1}$ $s^{-1}$ and a dissociation rate of $3.7 \times 10^{-5}$ $s^{-1}$, with an overall binding Kd of 9.5 pM, indicating no loss of binding function.

Overall scFv (TCT1067)-MMAF-C5 Conclusions, Biophysical Data

The conjugation conditions were optimised as detailed above. This optimisation allowed for controlled conjugation reactions to obtain medium and high DAR conjugates. There was very little precipitation of antibody/conjugate observed in the high DAR conjugates (none observed for the medium DAR) which resolved upon purification. Following SEC HPLC purification, the resulting conjugates were concentrated to ~1-3 mg/ml and were stable in buffer for several months.

The orthogonal techniques used for analysis are in agreement and support that an optimised scFv structure, exemplified by scFv (TCT1067), can be loaded with multiple drugs using lysine residues on the antibody and the conjugation can be controlled to obtain monomeric conjugates (as shown by SEC-HPLC) with the desired DAR whilst retaining binding function and affinity. On the SDS gel (FIG. 53), purified conjugates with medium DAR (sample 1) run slightly higher and was more polydispersed, whereas for the high DAR (sample 2) there was a clear migration shift on the gel where the sample was clearly bigger in size than the control, unmodified scFv (TCT1067). These observations were further supported by the HPLC where the samples had progressively shorter retention times than TCT1067, eluting faster from the SEC column due to their increasing size. Amino acid analysis was an extremely useful tool for further quantitative analysis and complemented the MS data. The mass spectrometry identified both high and low DAR within the same sample whereas AAA gave an average.

Example 66. Bioconjugation of P5-C5 Derivatives onto a High Affinity Single-Chain Fv Antibody Fragment Bearing Multiple, Well-Dispersed, Surface Lysine Residues P5-C5-NHS (compound 6) was conjugated to scFv (TCT1067) to obtain conjugates (compound 71) with various DARs. The reaction was controlled to obtain products with high DARs. The conditions identified and carried forward for the conjugations were:

TABLE 27

Reaction conditions for P5-C5-NHS bioconjugations

| Type | Condition |
|---|---|
| Buffer | Bicarbonate buffer with 150 mM NaCl at pH 8.8 |
| Co-solvent | Anhydrous filtered DMSO at a final 20% (v/v) concentration |
| Temperature | 20° C. |
| Agitation | Thermomixer 1000 rpm |
| Antibody concentration | 1 mg/ml |
| P5C5-NHS handling | 100 mM solution in 100% anhydrous filtered DMSO |
| P5C5-NHS addition rate | Every 80 min |
| P5C5-NHS addition portions | 10 equivalents |

The reaction was carried out as detailed in Example 64A.

In this example, the set up was:

Reaction 1—scFv (TCT1067): P5-C5-NHS, 60 equivalents;

The unconjugated and conjugated scFv (TCT1067) were analysed by HPLC size-exclusion chromatography. The scFv has a retention time of 18.1 min correlating to a MW of around 30 kDa. The conjugate eluted slightly and earlier at 16.5 mins indicating a larger molecular weight (due to varying drug loads), but as a single, sharp, monomeric peak, indicating no aggregation (FIG. 54). An SDS-PAGE gel (FIG. 55) showed a clean, conjugate of low dispersity and larger molecular weight compared to the scFv. This reaction was scalable.

The DAR was also determined by Amino Acid Analysis (AAA) at Cambridge University's Protein and Nucleic Acid Chemistry Facility and the results are shown in Table 28.

TABLE 28

Summary of AAA results showing DAR of 10.4
Reaction: 1 scFv (TCT1067)-P5C5
Integer fit of measured mole ratios to expected values

| Amino acid | Expected value | Observed value | Closeness of fit to expected value |
|---|---|---|---|
| Cys | 6 | not determined | — |
| Asp | 14 | 14.62 | better than 5% |
| Thr | 17 | 18.20 | within 5-10% |
| Ser | 44 | 43.22 | better than 5% |
| Glu | 21 | 19.72 | within 5-10% |
| Gly | 45 | 43.95 | better than 5% |
| Ala | 16 | 15.25 | better than 5% |
| Val | 19 | 20.20 | within 5-10% |
| Met | 0 | excluded | — |
| Ile | 8 | 8.63 | within 5-10% |
| Leu | 16 | 16.17 | better than 5% |
| Norleu std | | | |
| Tyr | 0 | excluded | — |
| Phe | 0 | excluded | — |
| His | 2 | 1.87 | within 5-10% |
| Lys | 12 | 12.63 | within 5-10% |
| Arg | 6 | 5.53 | within 5-10% |
| Pro | 0 | excluded | — |
| Trp | 9 | | (not determined) |
| Total (used) | 220 | residues | |

| | | | Average |
|---|---|---|---|
| Total sample | 0.274 | nmoles | 0.299 |
| | 7.77 | ug | 8.47 |

TABLE 28-continued

Summary of AAA results showing DAR of 10.4
Reaction: 1 scFv (TCT1067)-P5C5
Integer fit of measured mole ratios to expected values

| | Expected value | Observed value | Closeness of fit to expected value |
|---|---|---|---|
| Concentration | 68.62 | nmoles/ml | 74.85 |
| | 1942.45 | ug/ml | 2118.70 |
| DAR | | 10.4 | |

Mass spectrometric analysis was performed as described in Example 64A.

The LCMS, Total Ion Current (TIC) chromatograms and spectra and the deconvoluted data of scFv (TCT1067)-P5-C5 are shown in FIG. 56.

A major peak was observed in the TIC of the scFv (TCT1067)-P5-C5 sample eluting at 7.8 min. The zero-charge deconvoluted mass spectrum for this peak produced a series of major peaks as shown in Table 29 which was consistent with the supplied theoretical mass of the scFv (TCT1067) molecule, together with 10-14 additions of the P5-C5 molecule giving an average DAR 11.7. This correlated well with the AAA determination of the DAR of 10.4.

TABLE 29

Summary of the LC-MS of scFv (TCT1067)-P5-C5 (compounds 71)

| Sample | Retention time (min) | Observed peak mass (m/z) | Added mass (m/z) | Calculated DAR | Weighed Average DAR |
|---|---|---|---|---|---|
| scFv (TCT1067) | 8.35 | 28215 | 0 | 0 | 0 |
| TCT1067-P5C5 ADC 1 | 8.2 | 34553 | 6334 | 10 | 11.7 |
| | | 35186 | 6967 | 11 | |
| | | 35819 | 7600 | 12 | |
| | | 36452 | 8233 | 13 | |
| | | 37085 | 8866 | 14 | |

Overall, for scFv (TCT1067)-P5-C5, DAR was 10.4 by AAA and 11.7 by MS with an overall average 10.9.

Binding Activity of scFv (TCT1067)-P5-C5 Conjugates

ScFv (TCT1067)-P5-C5 (compound 71) was made and characterised as described above. Its binding affinity against immobilised HER2 target antigen was determined by Biacore SPR compared to the unmodified scFv as described in Example 64A.

The scFv (TCT1067)-P5-C5 DAR 10.9 had an association rate of $2.36 \times 10^5 M^{-1} s^1$ and a dissociation rate of $7.13 \times 10^{-5}$ $s^{-1}$, giving an overall binding Kd of 302 pM. There was a moderate reduction in the association rate (due to reversible steric hindrance of the antibody binding site by the high number of attached payloads), but once bound, there was insignificant effect on the dissociation rate compared to the unmodified scFv (TCT1067) which had an association rate of $3.9 \times 10^6 M^{-1} s^{-1}$ and a dissociation rate of $3.7 \times 10^{-5} s^{-1}$, with an overall binding Kd of 9.5 pM.

Overall scFv (TCT1067)-P5-C5 Conclusions, Biophysical Data

The conjugation conditions were optimised as detailed above. This optimisation allowed for controlled conjugation reactions with a high yield of high DAR conjugates. There was no precipitation of antibody/conjugate observed in any of the conjugates and overall recovery was very high ~60%.

Following SEC HPLC purification, the resulting conjugates were concentrated to ~3 mg/ml and were stable in the buffer for several months.

The orthogonal techniques used for analysis are in agreement and support that an optimised scFv structure, exemplified by scFv (TCT1067), can be loaded with multiple drugs using lysine residues on the antibody and the conjugation can be controlled to obtain monomeric conjugates (as shown by SEC-HPLC) with the desired DAR whilst retaining binding affinity. The LCMS, SEC and AAA data support that a monomeric conjugate with a high DAR was made. In conjunction with the Biacore data, this conjugate retained binding to HER2. The mass spectrometry identified both high and lower DAR within the same sample whereas AAA gave an average.

Example 67. Bioconjugation of Auristatin F Derivatives with a Short Linker onto two single-chain Fv antibody fragment bearing multiple, well-dispersed, surface lysine residues

Example 67A. ScFv (TCT)-Auristatin F with a $C_5$ Linker

Auristatin-F-C5-NHS (compound 88) was conjugated to scFv (TCT) to obtain conjugates (compound 122) with various DARs. The reaction was controlled to obtain products with a high DAR. The conditions identified and carried forward were:

TABLE 30

Reaction conditions for Auristatin F-C5-NHS bioconjugations

| Type | Condition |
|---|---|
| Buffer | Bicarbonate buffer with 150 mM NaCl at pH 8.8 |
| Co-solvent | Anhydrous filtered DMSO at a final 20% (v/v) concentration |
| Temperature | 20° C. |
| Agitation | Thermomixer 1000 rpm |
| Antibody concentration | 1 mg/ml |
| AF-C5-NHS handling | 50 mM solution in 100% anhydrous filtered DMSO |
| AF-C5-NHS addition rate | Every 120 mins |
| AF-C5-NHS addition portions | 10 equivalents |

The reaction was carried out as detailed in Example 64A. In this example, the set up was:

Reaction 1—scFv-TCT-Auristatin-F-C5-NHS, 30 Equivalents;

The unconjugated and conjugated scFv (TCT) were analysed by HPLC size-exclusion chromatography. The scFv has a retention time of 7.4 min correlating to a MW of around 30 kDa. The conjugate eluted slightly earlier at 7.2 min indicating a larger molecular weight (due to varying drug loads), but as a single, sharp, monomeric peak, indicating no aggregation (FIG. 57). These reactions were scalable.

LC-MS analysis was performed as described in Example 64A.

The LCMS, Total Ion Current (TIC) chromatograms and spectra and the deconvoluted data of scFv (TCT)-Auristatin F-C5 are shown in FIG. 58 and a summary in Table 31.

A major peak was observed in the TIC of the scFv (TCT)-Auristatin F-C5 sample eluting at 9.5 min. The zero-charge deconvoluted mass spectrum for this peak produced a series of major peaks at m/z 33125, 33953, 34780, 35607, 36435 and 37261 which was consistent with the supplied theoretical mass of the scFv (TCT) molecule, together with 6-11 additions of the MMAF molecule.

TABLE 31

Summary of the LC-MS of scFv (TCT)-Auristatin-F-C5 conjugates (122)

| Sample | Retention time (min) | Observed peak mass (m/z) | Added mass (m/z) | Calculated DAR | Average DAR |
|---|---|---|---|---|---|
| scFv(TCT) | | 28160 | 0 | 0 | 0 |
| TCT-AF-C5 ADC 1 | 9.51 | 33125 | 4965 | 6 | 8.5 |
| | | 33953 | 5793 | 7 | |
| | | 34780 | 6620 | 8 | |
| | | 35607 | 7447 | 9 | |
| | | 36435 | 8275 | 10 | |
| | | 37261 | 9101 | 11 | |

Binding activity of scFv (TCT)-C5-Auristatin-F conjugates ScFv (TCT)-Auristatin F-C5 (compound 122) were made and characterised as described above. Their binding function against immobilised HER2 target antigen was verified compared to the unmodified scFv as described in Example 64A.

Overall scFv (TCT)-Auristatin F-C5 Conclusions, Biophysical Data

The conjugation conditions were optimised as detailed above. This optimisation allowed for controlled conjugation reactions with a high yield of high DAR conjugates. Following SEC HPLC purification, the resulting conjugates were concentrated to ~600 µg/ml and were stable in the buffer for several weeks. Again, recovery was high at ~50%.

The techniques used for analysis support that an optimised scFv structure, exemplified by TCT, can be loaded with multiple drugs using lysine residues on the antibody and the conjugation can be controlled to obtain monomeric conjugates (as shown by SEC-HPLC) with the desired DAR whilst retaining binding affinity. The LCMS data was further supported by the HPLC-SEC where the sample had a shorter retention time than TCT, eluting faster from the SEC column due to its increasing size.

Example 67B. ScFv (TCT1067)-Auristatin with a $C_5$ Linker

Auristatin F-C5-NHS (compound 88) was conjugated to scFv (TCT1067) to obtain conjugates (compound 122) with various DARs. The reaction was controlled to obtain products with medium and high DARs. The conditions identified and carried forward were:

TABLE 32

Reaction conditions for Auristatin F-C5-NHS bioconjugations

| Type | Condition |
|---|---|
| Buffer | Bicarbonate buffer with 150 mM NaCl at pH 8.8 |
| Co-solvent | anhydrous filtered DMSO at a final 20% (v/v) concentration |
| Temperature | 20° C. |
| Agitation | thermomixer 1000 rpm |
| Antibody concentration | 1 mg/ml |
| AF-C5-NHS handling | 50 mM solution in 100% anhydrous filtered DMSO |

TABLE 32-continued

Reaction conditions for Auristatin F-C5-NHS bioconjugations

| Type | Condition |
|---|---|
| AF-C5-NHS addition rate | every 120 mins |
| AF-C5-NHS addition portions | 1 × 5 equivalents (reaction 1); 2 × 10 equivalents (reaction 2); 3 × 8.3 equivalents (reaction 3) |

The reactions were carried out as per Example 64A noting that the only minor visible precipitation was in the sample with the highest number of drug equivalents. This was resolved with centrifugation and subsequent purification.

In this example, the set up was:

Reaction 1—scFv (TCT1067)-Auristatin-F-C5-NHS, 5 equivalents;

Reaction 2—scFv (TCT1067)-Auristatin-F-C5-NHS, 10 equivalents;

Reaction 3—scFv (TCT1067)-Auristatin-F-C5-NHS, 25 equivalents

The DAR was also determined by Amino Acid Analysis (AAA) at Cambridge University's Protein and Nucleic Acid Chemistry Facility and the results are shown in Tables 33-35.

TABLE 33

Summary of AAA results showing DARs of 3.64
Reaction: 1 scFv (TCT1067)-Auristatin-F-C5
Integer fit of measured mole ratios to expected values

| | Expected value | Observed value | Closeness of fit to expected value |
|---|---|---|---|
| Amino acid | | | |
| Cys | 6 | not determined | — |
| Asp | 14 | 14.7 | better than 5% |
| Thr | 17 | 16.64 | better than 5% |
| Ser | 44 | 40.77 | within 5-10% |
| Glu | 21 | 20.87 | better than 5% |
| Gly | 45 | 46.35 | better than 5% |
| Ala | 16 | 16.19 | better than 5% |
| Val | 0 | excluded | — |
| Met | 5 | 4.79 | better than 5% |
| Ile | 8 | 8.08 | better than 5% |
| Leu | 16 | 16.58 | better than 5% |
| Norleu std | | | |
| Tyr | 14 | 14.47 | better than 5% |
| Phe | 0 | excluded | — |
| His | 2 | 2.02 | better than 5% |
| Lys | 12 | 12.49 | better than 5% |
| Arg | 6 | 6.07 | better than 5% |
| Pro | 0 | excluded | — |
| Trp | 9 | | (not determined) |
| Total (used) | 220 | residues | |

| | | | Average |
|---|---|---|---|
| Total sample | 0.159 | nmoles | 0.16 |
| | 4.49 | ug | 4.54 |
| Concentration | 22.66 | nmoles/ml | 22.92 |
| | 641.34 | ug/ml | 648.88 |
| | | corrected ug/ml | 705.16 |
| | | DAR AAA | 3.64 |

TABLE 34

Summary of AAA results showing DARs of 6.31
Reaction: 2 scFv (TCT1067)-Auristatin-F-C5
Integer fit of measured mole ratios to expected values

| Amino acid | Expected value | Observed value | Closeness of fit to expected value |
|---|---|---|---|
| Cys | 6 | not determined | — |
| Asp | 14 | 14.46 | better than 5% |
| Thr | 17 | 16.46 | better than 5% |
| Ser | 44 | 41.20 | within 5-10% |
| Glu | 21 | 20.84 | better than 5% |
| Gly | 45 | 46.24 | better than 5% |
| Ala | 16 | 15.89 | better than 5% |
| Val | 0 | excluded | — |
| Met | 5 | 4.58 | within 5-10% |
| Ile | 8 | 7.88 | better than 5% |
| Leu | 16 | 17.15 | within 5-10% |
| Norleu std | | | |
| Tyr | 14 | 14.32 | better than 5% |
| Phe | 0 | excluded | — |
| His | 2 | 2.17 | within 5-10% |
| Lys | 12 | 12.63 | within 5-10% |
| Arg | 6 | 6.19 | better than 5% |
| Pro | 0 | excluded | — |
| Trp | 9 | | (not determined) |
| Total (used) | 220 | residues | |

| | | | Average |
|---|---|---|---|
| Total sample | 0.163 | nmoles | 0.168 |
| | 4.60 | ug | 4.74 |
| Concentration | 20.84 | nmoles/ml | 21.49 |
| | 589.78 | ug/ml | 608.28 |
| | | corrected ug/ml | 661.03 |
| | | DAR AAA | 6.31 |

TABLE 35

Summary of AAA results showing DARs of 13.4
Sample: 3 scFv (TCT1067)-Auristatin-F-C5
Integer fit of measured mole ratios to expected values

| Amino acid | Expected value | Observed value | Closeness of fit to expected value |
|---|---|---|---|
| Cys | 6 | not determined | — |
| Asp | 14 | 14.60 | better than 5% |
| Thr | 17 | 16.66 | better than 5% |
| Ser | 44 | 40.55 | within 5-10% |
| Glu | 21 | 21.23 | better than 5% |
| Gly | 45 | 46.74 | better than 5% |
| Ala | 16 | 16.06 | better than 5% |
| Val | 0 | excluded | — |
| Met | 0 | excluded | — |
| Ile | 8 | 7.74 | better than 5% |
| Leu | 16 | 16.23 | better than 5% |
| Norleu std | | | |
| Tyr | 14 | 14.31 | better than 5% |
| Phe | 0 | excluded | — |
| His | 2 | 2.17 | within 5-10% |
| Lys | 12 | 12.68 | within 5-10% |
| Arg | 6 | 6.04 | better than 5% |
| Pro | 0 | excluded | — |
| Trp | 9 | | (not determined) |
| Total (used) | 215 | residues | |

TABLE 35-continued

Summary of AAA results showing DARs of 13.4
Sample: 3 scFv (TCT1067)-Auristatin-F-C5
Integer fit of measured mole ratios to expected values

| | Expected value | Observed value | Closeness of fit to expected value |
|---|---|---|---|
| | | | Average |
| Total sample | 0.169 | nmoles | 0.170 |
| | 4.80 | ug | 4.80 |
| Concentration | 18.83 | nmoles/ml | 18.84 |
| | 532.94 | ug/ml | 533.27 |
| | | corrected ug/ml | 579.52 |
| | | DAR AAA | 13.40 |

The unconjugated and conjugated scFv (TCT1067) were analysed by HPLC size-exclusion chromatography. The scFv has a retention time of 18.1 min correlating to a MW of around 30 kDa. The three conjugates all eluted slightly and progressively earlier (at 17.9 min, 17.92 min and 17.87 min) indicating a larger molecular weight (due to varying drug loads), but as a single, sharp, monomeric peak, indicating no aggregation (FIG. 59).

LC-MS analysis was performed as described in Example 64A.

The LCMS, Total Ion Current (TIC) chromatograms and spectra and the deconvoluted data of scFv (TCT1067)-C5-Auristatin-F are shown in FIG. 60 and summarised in Table 36.

A major peak was observed in the TIC of the scFv (TCT1067)-C5-Auristatin-F reaction 1 eluting at 8.19 min. The zero-charge deconvoluted mass spectrum for this peak produced a series of major peaks at m/z 29037, 29865, 30692, 31519 and 32345 which was consistent with the supplied theoretical mass of the scFv (TCT1067) molecule, together with 1-5 additions of the Auristatin F molecule with an average DAR of 2.9.

A major peak was observed in the TIC of the scFv (TCT1067)-C5-Auristatin-F reaction 2 eluting at 9.47 min. The zero-charge deconvoluted mass spectrum for this peak produced a series of major peaks at m/z 29866, 30692, 31519, 32347, 33174 and 34001 which was consistent with the supplied theoretical mass of the scFv (TCT1067) molecule, together with 2-7 additions of the Auristatin F molecule with an average DAR of 4.98.

A major peak was observed in the TIC of the scFv (TCT1067)-C5-Auristatin-F reaction 3 eluting at 9.97 min. The zero-charge deconvoluted mass spectrum for this peak produced a series of major peaks at m/z 34826, 35653, 36480, 37307, 38134 and 38960 which was consistent with the supplied theoretical mass of the scFv (TCT1067) molecule, together with 8-13 additions of the Auristatin F molecule with an average DAR of 10.3.

TABLE 36

Summary of the LC-MS of scFv (TCT1067)-Auristatin F-C5 (122)

| Sample | Retention time (min) | Observed peak mass (m/z) | Added mass (m/z) | Calculated DAR | Weighed Average DAR |
|---|---|---|---|---|---|
| scFv (TCT1067) | 8.35 | 28215 | 0 | 0 | 0.00 |
| TCT1067-AF-C5 ADC 1 | 8.11 | 29037 | 818 | 1 | 2.90 |
| | | 29865 | 1646 | 2 | |
| | | 30692 | 2473 | 3 | |

TABLE 36-continued

Summary of the LC-MS of scFv (TCT1067)-Auristatin F-C5 (122)

| Sample | Retention time (min) | Observed peak mass (m/z) | Added mass (m/z) | Calculated DAR | Weighed Average DAR |
|---|---|---|---|---|---|
| | | 31519 | 3300 | 4 | |
| | | 32345 | 4126 | 5 | |
| TCT1067-AF-C5 ADC2 | 9.47 | 29866 | 1647 | 2 | 4.98 |
| | | 30692 | 2473 | 3 | |
| | | 31519 | 3300 | 4 | |
| | | 32347 | 4128 | 5 | |
| | | 33174 | 4955 | 6 | |
| | | 34001 | 5782 | 7 | |
| TCT1067-AF-C5 ADC 3 | 9.97 | 34826 | 6607 | 8 | 10.30 |
| | | 35653 | 7434 | 9 | |
| | | 36480 | 8261 | 10 | |
| | | 37307 | 9088 | 11 | |
| | | 38134 | 9915 | 12 | |
| | | 38960 | 10741 | 13 | |

Therefore, overall,

For reaction 1, DAR was 3.64 by AAA and 2.9 by MS with an average DAR of 3.3

For reaction 2, DAR was 6.31 by AAA and 4.98 by MS with an average DAR of 5.65.

For reaction 3, DAR was 13.4 by AAA and 10.4 by MS with an average DAR of 11.9.

An SDS-PAGE was run (FIG. 61) that shows the increased molecular weights of the conjugates but notably, the high homogeneity of the high DAR species from reaction sample 3.

Binding Activity of scFv (TCT1067)-AF-C5 Conjugates

ScFv (TCT1067)-Auristatin-F-C5 conjugates (compound 122) were made and characterised as described above. Their binding affinities against immobilised HER2 target antigen was determined by Biacore SPR compared to the unmodified scFv as described in Example 64A.

The scFv (TCT1067)-Auristatin-F-C5 DAR 3.3 had an association rate of $5.56 \times 10^5$ $M^{-1}$ $s^{-1}$ and a dissociation rate of $1.82 \times 10^{-5}$ $s^{-1}$, giving an overall binding Kd of 32.8 pM.

The scFv (TCT1067)-Auristatin-F-C5 DAR 5.65 had an association rate of $3.36 \times 10^5$ $M^{-1}$ $s^{-1}$ and a dissociation rate of $1.35 \times 10^{-5}$ $s^{-1}$, giving an overall binding Kd of 40.3 pM.

The scFv (TCT1067)-Auristatin-F-C5 DAR 11.9 had an association rate of $2.17 \times 10^4$ $M^{-1}$ $s^{-1}$ and a dissociation rate of $1.76 \times 10^{-5}$ $s^{-1}$, giving an overall binding Kd of 810 pM.

The low and medium DAR samples had affinities that were very similar to the unmodified scFv (TCT1067) which had an association rate of $3.9 \times 10^6$ $M^{-1}$ $s^{-1}$ and a dissociation rate of $3.7 \times 10^{-5}$ $s^{-1}$, with an overall binding Kd of 9.5 pM, indicating no loss of binding function. The high DAR sample had a moderately reduced association rate (due to reversible steric hindrance of the antibody binding site by the high number of attached payloads), but once bound, there was insignificant effect on the dissociation rate compared to the unmodified scFv.

Overall scFv (TCT1067)-Auristatin F-C5 Conclusions, Biophysical Data

The conjugation conditions were optimised as detailed above. This optimisation allowed for controlled conjugation reactions with a high yield of low, medium and high DAR conjugates. Following purification and processing, the conjugates were concentrated to ~9 mg/ml and were stable in the buffer for several months.

The orthogonal techniques used for analysis are in agreement and support that an optimised scFv structure, exemplified by scFv (TCT1067), can be loaded with multiple drugs using lysine residues on the antibody and the conjugation can be controlled to obtain monomeric conjugates (as shown by SEC-HPLC) with the desired DAR whilst retaining function and binding affinity. Purified conjugates with low DAR (reaction 1) run closer to the control scFv (TCT) on the gel and were less polydispersed than the medium DAR (reaction 2) which run slightly higher and was more polydispersed, whereas for the high DAR (reaction 3) there was a clear migration shift on the gel where the sample was clearly bigger in size than the control, unmodified scFv (TCT1067). These observations were further supported by the HPLC SEC where the samples had progressively shorter retention times than TCT, eluting faster due to their increasing size. Amino acid analysis was an extremely useful tool for further quantitative analysis and supported the LC-MS data.

Example 68. Bioconjugation of a MMAE Derivative with a Protease Cleavable Linker onto a High Affinity Single-Chain Fv Antibody Fragment Bearing Multiple, Well-Dispersed, Surface Lysine Residues The cytotoxic drug MMAE-PAB-Cit-Val-dPEG$_9$ NHS (compound 86) was conjugated to scFv (TCT1067) to obtain conjugates (compound 121) with a high DAR. The conditions identified and carried forward were:

TABLE 37

Reaction conditions for MMAE-PAB-Cit-Val-dPEG$_9$ NHS bioconjugations

| Type | Condition |
|---|---|
| Buffer | Bicarbonate buffer with 20 mM NaCl at pH 8.8 |
| Co-solvent | Anhydrous filtered DMSO at a final 20% (v/v) concentration |
| Temperature | 20° C. |
| Agitation | Thermomixer 1000 rpm |
| Antibody concentration | 1 mg/ml |
| MMAE-PABA-vc-PEG9-NHS handling | 50 mM solution in 100% anhydrous filtered DMSO |
| MMAE-PABA-vc-PEG9-NHS addition rate | Every 120 mins |
| MMAE-PABA-vc-PEG9-NHS addition equivalents | 10 equivalents |

The reaction was carried out as detailed in Example 64A noting that the MMAE-PABA-vc-PEG$_9$-NHS required repeated vortexing to fully solubilise in DMSO. The reaction was carried out in a low salt buffer. The crude conjugate had no visible precipitation and was purified by SEC on an AKTA Avant system using a Superdex 75, 26/600 column eluting with 10% IPA/20 mM NaCl phosphate buffer pH7. Fractions were combined and concentrated using Vivacell 100 10 kMWCO (PES membrane) (Sartorius) before buffer exchanging into 20 mM NaCl phosphate buffer pH7 using the same process. An HPLC-SEC run (FIG. 62) showed a single monomeric peak with very low aggregation. This reaction was scalable.

Reaction 1—scFv-TCT1067: MMAE-PAB-Cit-Val-dPEG$_9$ 30 equivalents;

The DAR was also determined by Amino Acid Analysis (AAA) at Cambridge University's Protein and Nucleic Acid Chemistry Facility and the results are shown in Table 38.

TABLE 38

Summary of AAA results showing DAR of 9.6 for reaction 1
Reaction: 1 scFv (TCT1067)-MMAE-PAB-Cit-Val-dPEG$_9$
Integer fit of measured mole ratios to expected values

|  | Expected value | Observed value | Closeness of fit to expected value |
|---|---|---|---|
| Amino acid | | | |
| Cys | 6 | not determined | — |
| Asp | 14 | 13.96 | better than 5% |
| Thr | 17 | 17.56 | better than 5% |
| Ser | 44 | 40.04 | within 5-10% |
| Glu | 0 | excluded | — |
| Gly | 45 | 45.75 | better than 5% |
| Ala | 16 | 17.43 | within 5-10% |
| Val | 0 | excluded | — |
| Met | 0 | excluded | — |
| Ile | 8 | 8.34 | better than 5% |
| Leu | 16 | 16.28 | better than 5% |
| Norleu std | | | |
| Tyr | 0 | excluded | — |
| Phe | 0 | excluded | — |
| His | 2 | 2.05 | better than 5% |
| Lys | 12 | 12.39 | better than 5% |
| Arg | 6 | 5.86 | better than 5% |
| Pro | 13 | 13.35 | better than 5% |
| Trp | 9 |  | (not determined) |
| Total (used) | 193 | residues | |

|  |  |  | Average |
|---|---|---|---|
| Total sample | 0.142 | nmoles | 0.151 |
|  | 4.01 | ug | 4.28 |
| Concentration | 2.18 | nmoles/ml | 2.32 |
|  | 61.69 | ug/ml | 65.77 |

| Total sample | Ornithine |
|---|---|
| i | 1.540 |
| ii | 1.370 |
| average | 1.46 |
| DAR | 9.6 |

Mass spectrometric analysis was performed as described in Example 64A. The LCMS, Total Ion Current (TIC) chromatograms and spectra and the deconvoluted data of scFv (TCT1067)-MMAE-PAB-Cit-Val-dPEG$_9$ are shown in FIG. 63 and a summary in Table 39.

Several peaks corresponding to the various DAR species were observed in the UV/TIC of the sample eluting at between 10 and 12 min. The zero-charge deconvoluted mass spectrum for each peak corresponded to a series of major peaks at m/z 37837, 39439, 41042 and 42644 which was consistent with the supplied theoretical mass of the scFv (TCT1067) molecule with 6-9 additions of the MMAE moiety.

TABLE 39

Summary of the LC-MS of scFv (TCT1067)-MMAE-PAB-Cit-Val-dPEG$_9$ (121)

| Sample | Retention time (min) | Observed peak mass (m/z) | Added mass (m/z) | Calculated DAR | Average DAR |
|---|---|---|---|---|---|
| scFv(TCT1067) | 8.35 | 28215 | 0 | 0 | 0 |
| TCT1067- | 10.7 | 37837 | 9618 | 6 | 7.5 |
| MMAE ADC1 | 11.1 | 39439 | 11220 | 7 | |
|  | 11.4 | 41042 | 12823 | 8 | |
|  | 11.9 | 42644 | 14425 | 9 | |

Therefore, overall,

For scFv (TCT1067)-MMAE-PAB-Cit-Val-dPEG$_9$ reaction 1, DAR was 9.6 by AAA and 7.5 by LC-MS with an average DAR of 8.6.

An SDS-PAGE was run (FIG. 64) that shows the increased molecular weight of the conjugate but notably, the high homogeneity of the high DAR species from reaction sample 1.

Binding Activity of scFv (TCT1067)-MMAE-PAB-Cit-Val-dPEG$_9$ Conjugates

TCT(1067)-MMAE-PABA-vc-PEG$_9$ (compound 121) were made and characterised as described above. Its binding affinity against immobilised HER2 target antigen was determined by Biacore SPR compared to the unmodified scFv as described in Example 64A.

The scFv (TCT1067)-MMAE-PAB-Cit-Val-dPEG$_9$ conjugate, DAR 8.6 had an association rate of $2.21 \times 10^4$ M$^{-1}$ s$^{-1}$ and a dissociation rate of $2.23 \times 10^{-5}$ s$^{-1}$, giving an overall binding Kd of 1 nM. There was a reduction in the association rate (due to reversible steric hindrance of the antibody binding site by the high number of attached payloads), but once bound, there was insignificant effect on the dissociation rate compared to the unmodified scFv (TCT1067) which had an association rate of $3.88 \times 10^6$ M$^{-1}$ s$^{-1}$ and a dissociation rate of $3.69 \times 10^{-5}$ s$^{-1}$, with an overall binding Kd of 9.5 pM.

Overall scFv (TCT1067)-MMAE-PAB-Cit-Val-dPEG$_9$ Conclusions

The conjugation conditions were optimised as detailed above obtaining a conjugate with a high DAR. Following purification, concentration and filtration, the resulting conjugates appeared stable in the buffer for several weeks.

The orthogonal techniques used for analysis are in agreement and support that an optimised scFv structure, exemplified by TCT(1067), can be loaded with multiple drugs using lysine residues on the antibody and the conjugation can be controlled to obtain monomeric conjugates (as shown by SEC-HPLC) with the desired DAR whilst retaining binding affinity. The purified conjugate with high DAR (reaction 1) showed a clear migration shift on the gel where the sample was bigger in size than the control, unmodified TCT1067. These observations were further supported by the HPLC SEC where the sample had a significantly shorter retention time eluting at 15.1 mins than the control eluting at 18.1 mins, eluting faster from the SEC column due to its increasing size. Amino acid analysis was an extremely useful tool for further quantitative analysis and supported the LC-MS data.

Example 69. Bioconjugation of Two Different Payload Types onto a scFv Antibody Fragment Bearing Multiple, Well-Dispersed, Surface Lysine Residues The cytotoxic drugs P5-C5-NHS (compound 6) and MMAF-C5-NHS (compound 78) were conjugated to scFv (TCT1067) to obtain conjugates (compound 135) with a high DAR. The conditions identified and carried forward for the conjugations were:

TABLE 40

Reaction conditions for MMAF/P5C5 dual payload bioconjugations

| Type | Condition |
|---|---|
| Buffer | Bicarbonate buffer with 150 mM NaCl at pH 8.8 |

TABLE 40-continued

Reaction conditions for MMAF/P5C5 dual payload bioconjugations

| Type | Condition |
|---|---|
| Co-solvent | Anhydrous filtered DMSO at a final 20% (v/v) concentration |
| Temperature | 20° C. |
| Agitation | Thermomixer 1000 rpm |
| Antibody concentration | 1 mg/ml |
| MMAF-C5-NHS and P5-C5-NHS handling | 100 mM solution in 100% anhydrous filtered DMSO |
| MMAF-C5-NHS and P5-C5-NHS addition rate | Every 90 min |
| MMAF-C5-NHS and P5-C5 NHS addition portions | 11 equivalents |

The reaction was carried out as per Example 64A noting that the MMAF-C5-NHS was added during the first addition and the subsequent two additions were carried out adding P5-C5-NHS. All other handling and purification processes were as Example 64A.

Reaction 1—scFv-TCT1067: MMAF-C5-P5-C5; 11 equivalents MMAF-C5 NHS and 21 equivalents of P5-C5 NHS;

The unconjugated and conjugated scFv (TCT1067) were analysed by HPLC size-exclusion chromatography. The scFv has a retention time of 18.1 min correlating to a MW of around 30 kDa. The conjugate eluted slightly earlier at 17.8 min indicating a larger molecular weight (due to varying drug loads), but as a single, sharp, monomeric peak, indicating no aggregation (FIG. 65).

The DAR was also determined by Amino Acid Analysis (AAA) at Cambridge University's Protein and Nucleic Acid Chemistry Facility and the results are shown in Table 41.

TABLE 41

Summary of AAA results showing dual payload DARs
Reaction: 1 scFv (TCT1067)-MMAF-C5/P5-C5
Integer fit of measured mole ratios to expected values

| Amino acid | Expected value | Observed value | Closeness of fit to expected value |
|---|---|---|---|
| Cys | 6 | not determined | — |
| Asp | 14 | 14.80 | within 5-10% |
| Thr | 17 | 17.10 | better than 5% |
| Ser | 44 | 41.29 | within 5-10% |
| Glu | 21 | 21.54 | better than 5% |
| Gly | 45 | 47.85 | within 5-10% |
| Ala | 16 | 16.20 | better than 5% |
| Val | 0 | excluded | — |
| Met | 5 | 4.95 | better than 5% |
| Ile | 8 | 7.66 | better than 5% |
| Leu | 16 | 15.79 | better than 5% |
| Norleu std | | | |
| Tyr | 14 | 13.82 | better than 5% |
| Phe | 0 | excluded | — |
| His | 2 | 1.81 | within 5-10% |
| Lys | 12 | 11.48 | better than 5% |
| Arg | 6 | 5.70 | within 5-10% |
| Pro | 0 | excluded | — |
| Trp | 9 | | (not determined) |
| Total (used) | 220 | residues | |
| | | | Average |
| Total sample | 0.223 | nmoles | 0.217 |
| | 6.32 | ug | 6.15 |

TABLE 41-continued

Summary of AAA results showing dual payload DARs
Reaction: 1 scFv (TCT1067)-MMAF-C5/P5-C5
Integer fit of measured mole ratios to expected values

| | Expected value | Observed value | Closeness of fit to expected value |
|---|---|---|---|
| Concentration | 55.85 | nmoles/ml | 54.33 |
| | 1580.85 | ug/ml | 1537.79 |
| Total | | DAR | |
| MMAF (Phe) | 0.137 | 0.61 | 0.7 |
| P5C5 (Ava) | 1.028 | 4.60 | 4.6 |

LC-MS analysis was performed as described in Example 64A.

The LCMS, Total Ion Current (TIC) chromatograms and spectra and the deconvoluted data of scFv (TCT1067)-MMAF-C5/P5-C5 are shown in FIG. 66 and a summary in table 42.

A major peak was observed in the TIC of the scFv (TCT1067)-MMAF-C5/P5-C5 sample eluting at 8.7-10.5 min. The zero-charge deconvoluted mass spectrum for this peak produced a series of major peaks at m/z 31332, 31964, 32597, 33230, 33963, 31135, 31769, 32499, 30307, 30940, 31673, 32306, 30113, 30746, 31478, 32109.

These were consistent with the supplied theoretical mass of the scFv (TCT1067) molecule, together with several combinations of MMAF-C5 and P5-C5 as indicated in Table 42.

TABLE 42

Summary of LCMS of scFv (TCT1067)-MMAF-C5/P5-C5 dual payload (135)

| Sample | Retention time (min) | Observed peak mass (m/z) | Added mass (m/z) | Estimated DAR MMAF-C5 | Estimated DAR P5-C5 |
|---|---|---|---|---|---|
| scFv (TCT1067) | 8.35 | 28215 | 0 | 0 | 0 |
| TCT1067-MMAF/C5-P5-C5 ADC | 9.7 | 31332 | 3113 | 3 | 1 |
| | | 31964 | 3745 | 3 | 2 |
| | | 32597 | 4378 | 3 | 3 |
| | | 33230 | 5011 | 3 | 4 |
| | 9.4 | 31135 | 2916 | 2 | 2 |
| | | 31769 | 3550 | 2 | 3 |
| | | 32499 | 4280 | 2 | 4 |
| | | 33135 | 4916 | 2 | 5 |
| | 8.9 | 30307 | 2088 | 1 | 2 |
| | | 30940 | 2721 | 1 | 3 |
| | | 31673 | 3454 | 2 | 3 |
| | | 32306 | 4087 | 1 | 5 |
| | 8.7 | 30114 | 1895 | 0 | 3 |
| | | 30747 | 2528 | 0 | 4 |
| | | 31479 | 3260 | 0 | 5 |
| | | 32109 | 3890 | 0 | 6 |

Overall scFv (TCT1067)-MMAF-C5/P5-C5 Conclusions, Biophysical Data

The conjugation conditions were optimised as detailed above. This optimisation allowed for controlled conjugation reactions with a high yield of high DAR conjugates. The resulting conjugates were concentrated to ~1.5 g/ml and were stable in buffer for several weeks.

Example 70. Bioconjugation of a Maytansine-DM1 Derivative with a Linker onto a High Affinity Single-Chain Fv Antibody Fragment Bearing Multiple, Well-Dispersed, Surface Lysine Residues Maytansine DM1-dPEG$_{12}$-NHS (compound 90) was conjugated to scFv (TCT1067) to obtain conjugates (compound 124) with various DARs. The conditions identified and carried forward were:

TABLE 43

Reaction conditions for DM1-dPEG$_{12}$-NHS - bioconjugations

| Type | Condition |
|---|---|
| Buffer | PBS buffer at pH 8.0 and 0.1% Polysorbate-20 |
| Co-solvent | Anhydrous filtered DMSO at a final 20% (v/v) concentration |
| Temperature | 20° C. |
| Agitation | Thermomixer 1000 rpm |
| Antibody concentration | 1 mg/ml |
| Maytansine DM1-PEG(12)-NHS handling | 100 mM solution in 100% anhydrous filtered DMSO |
| Maytansine DM1-PEG(12)-NHS addition rate | Every 120 min |
| Maytansine DM1-PEG(12)-NHS addition portions | 8 equivalents |

The reactions were set up as per Table 37 and Example 64A noting that, prior to adding the drug stock to the reaction, the total amount needed was diluted in 25% of the total volume of the DMSO required for the reaction. The drug addition was carried out by adding 16 equivalents of the NHS-drug DMSO form this new stock solution. Precipitation was visible at the completion of the reactions and that increased with increasing number of equivalents.

In this example, the set up was:
Reaction 1—scFv-TCT1067: DM1-dPEG$_{12}$ NHS, 16 equivalents;
Reaction 2—scFv-TCT1067: DM1-dPEG$_{12}$ NHS, 32 equivalents The unconjugated and conjugated scFv (TCT1067) were analysed by HPLC size-exclusion chromatography (FIG. 67). The scFv has a retention time of 19 min correlating to a MW of around 30 kDa. The two conjugates all eluted slightly and progressively earlier indicating a larger molecular weight (due to varying drug loads), with some aggregation observed, as follows:

| | |
|---|---|
| Reaction 1 | 1% aggregates |
| Reaction 2 | 4% aggregates |

LC-MS analysis was performed as described in Example 64A.

The LCMS, Total Ion Current (TIC) chromatograms and spectra and the deconvoluted data of scFv (TCT1067)-DM1-dPEG$_{12}$ are shown in FIG. 68 and a summary in Table 44.

In sample 1, a major peak was observed in the TIC of the scFv (TCT1067)-DM1-dPEG$_{12}$ sample eluting at 11 min. The zero-charge deconvoluted mass spectrum for this peak produced a series of major peaks at m/z 37144, 38631 and 40079, which was consistent with the supplied theoretical mass of the scFv (TCT1067) molecule, together with 6, 7 and 8 additions of the Maytansine DM1 molecule. In sample 2, the conjugate eluted at 11.5 mins and the deconvoluted mass gave a peak at m/z 40123 which corresponds to the scFv (TCT1067) together with 8 additions of Maytansine DM1.

TABLE 44

Summary of the LC-MS of scFv (TCT1067)-DM1-dPEG$_{12}$ (124)

| Sample | Retention time (min) | Observed peak mass (m/z) | Added mass (m/z) | Calculated DAR | Average DAR |
|---|---|---|---|---|---|
| scFv (TCT1067) | 8.35 | 28215 | 0 | 0 | |
| TCT1067-Maytansine-PEG(12) DM1 ADC 1 | 10.6 | 37144 | 9024 | 6 | 7 |
| | 10.9 | 38631 | 10528 | 7 | |
| | 11-11.5 | 40079 | 12032 | 8 | |
| TCT1067-Maytansine-PEG(12) DM1 ADC 2 | 11.5-12.0 | 40123 | 12032 | 8 | 8 |

An SDS-PAGE was run (FIG. 69) that shows the increased molecular weight of the conjugates reaction samples 1 and 2.

Binding Activity of scFv (TCT1067)-DM1-dPEG$_{12}$

ScFv (TCT1067)-DM1-dPEG$_{12}$ (compound 124) was made and characterised as described above. Their binding affinities against immobilised HER2 target antigen was determined by Biacore SPR compared to the unmodified scFv as described in Example 64A.

The scFv (TCT1067)-DM1-dPEG$_{12}$ DAR 8 had an association rate of $1.32 \times 10^4$ M$^{-1}$ s$^{-1}$ and a dissociation rate of $3.28 \times 10^{-5}$ s$^{-1}$, giving an overall binding Kd of 2.48 nM. The scFv (TCT1067)-DM1-dPEG$_{12}$ DAR 7 had an association rate of $1.95 \times 10^4$ M$^{-1}$ s$^{-1}$ and a dissociation rate of $2.7 \times 10^{-5}$ s$^{-1}$, giving an overall binding Kd of 1.39 nM. Both conjugates had a moderately reduced association rate (due to reversible steric hindrance of the antibody binding site by the high number of attached payloads), but once bound, there was insignificant effect on the dissociation rate compared to the unmodified scFv (TCT1067) which had an association rate of $3.9 \times 10^6$ M$^{-1}$ s$^{-1}$ and a dissociation rate of $3.7 \times 10^{-5}$ s$^{-1}$, with an overall binding Kd of 9.5 pM.

Overall scFv (TCT1067)-DM1-dPEG$_{12}$ Conclusions, Biophysical Data

The conjugation conditions were optimised as detailed above. This optimisation allowed for controlled conjugation reactions to obtain conjugates with medium and high DAR. The purified conjugates were concentrated to ~500 µg/ml in buffer.

The orthogonal techniques used for analysis are in agreement and support that an optimised scFv structure, exemplified by scFv (TCT1067), can be loaded with multiple drugs using lysine residues on the antibody and the conjugation can be controlled to obtain monomeric conjugates (as shown by SEC-HPLC) with the desired DAR whilst retaining binding affinity. On an SDS gel, the purified conjugates with a medium DAR (sample 1) run slightly higher and was more polydispersed, whereas for the high DAR (sample 2) there was a clear migration shift on the gel where the sample was clearly bigger in size than the control, unmodified scFv (TCT1067). These observations were further supported by the HPLC where the samples had progressively shorter retention times than TCT, eluting faster from the SEC column due to their increasing size.

Example 71. Bioconjugation of Auristatin F to an scFv which has a High Lysine Content which is not Optimally-Dispersed ('Non-OptiLinked') Leads to Aggregation and Lower than Desired Drug:Antibody Ratios An scFv based on the panitumumab monoclonal antibody [SEQ ID 5] has a high affinity [U.S. Pat. No. 8,227,580B2] and possesses 8 Lysine residues that are predicted to be surface exposed, but are not in an optimal spatial configuration and are not in preferred locations compared to the example of scFv (TCT1067) with only 4 similar positions (see below). This panitumumab scFv (scFv (Pan)) was constructed, expressed and purified using established methodology [Bhatti M et al (2008) 122: 1155] and used in bioconjugation reactions under identical conditions to scFv (TCT1067) using the payload Auristatin F. The conditions used were:

TABLE 44A

Reaction conditions for AF-C5-NHS bioconjugations

| Type | Condition |
|---|---|
| Buffer | Bicarbonate buffer with 150 mM NaCl at pH 8.8 |
| Co-solvent | anhydrous filtered DMSO at a final 20% (v/v) concentration |
| Temperature | 20° C. |
| Agitation | thermomixer 1000 rpm |
| Antibody concentration | 0.83 mg/ml |
| AF-C5-NHS handling | 50 mM solution in 100% anhydrous filtered DMSO |
| AF-C5-NHS addition rate | every 120 min |
| AF-C5-NHS addition portions | 5 equivalents |

Amino Acid Sequence of Panitumumab Single Chain Fv

[SEQ ID NO. 5]
QVQLQESGPGLVKPSETLSLTCTVSGGSVSSGDYYWTWIRQSPGKGLEWI

GHIYYSGNTNYNPSLKSRLTISIDTSKTQFSLKLSSVTAADTAIYYCVRD

RVTGAFDIWGQGTMVTVSSGGGGSGGGGSGGGGSDIQMTQSPSSLSASVG

DRTVITCQASQDISNYLNWYQQKPGKAPKLLIYDASNLETGVPSRFSGSG

SGTDFTFTISSLQPEDIATYFCQHFDHLPLAFGGGTKVEIQNGSEQKLIS

EEDLAAA

Amino acid sequence alignment of scFv (TCT1067), T against scFv (panitumumab), P. Lysine residues are in bold and commonly-positioned lysine residues are underlined. Panitumumab has 8 lysines that are in a significantly different configuration to the 12 that are present in the scFv (TCT1067).

T   QVQLVQSGAEVKKPGESLKISCKGSGYS--FTSYWIAWVRQMPG
    KGLEYMGLIYPGDSDT

P   QVQLQESGPGLVKPSETLSLTCTVSGGSVSSGDYYWTWIRQSPG
    KGLEWIGHIYYS-GNT

T   KYSPSFQGQVTISVDKSVSTAYLQWSSLKPSDSAVYFCARHDVG
    YCTDRTCAAWPEWLGV

P   NYNPSLKSRLTISIDTSKTQFSLKLSSVTAADTAIYYCVRDRVT
    -----------GAFDI

T   WGQGTLVTVSSGGGGSGGGGSGGGGSQSVLTQPP-SVSAAPGQK
    VTISCSGSSSNIGNNY

P   WGQGTMVTVSSGGGGSGGGGSGGGGSDIQMTQSPSSLSASVGDR
    TVITCQASQ--DISNY

T   VSWYQQLPGTAPKLLIYGHTNRPAGVPDRFSGSKSGTSASLAIS
    GFRSEDEADYYCASWD

P   LNWYQQKPGKAPKLLIYDASNLETGVPSRFSGSGSGTDFTFTIS
    SLQPEDIATYFCQHFD

T   YTLSGWVFGGGTKLTVL

P   HLP--LAFGGGTKVEIQ
[T = SEQ ID NO. 6; P = SEQ ID NO. 7]

Low, medium and high DAR conjugation reaction conditions were set up as described in Example 67B and the conjugates analysed by SDS-PAGE (FIG. 70), HPLC-SEC (FIG. 71), Biacore SPR binding analysis and LC-MS (FIG. 72). The results are summarised in Table 45. In each case, a significantly higher fraction of the scFv (Pan) was found to be aggregated and observed to precipitate. Under similar reaction conditions that were used for the scFv (TCT1067), only low DARs were observed with panitumumab scFv and attempts to obtain a maximum DAR of 9 led to insoluble precipitate. The soluble conjugates retained their binding function. The scFv (TCT1067) retained its binding function as also shown in Auristatin F (Example 67). Table 45 shows that a higher average DAR can be obtained with an OptiLinked scFv under similar conjugation conditions (DAR 3.5 vs DAR 5 and no conjugate vs DAR 9) with higher yields. There are no observable aggregates in the OptiLinked scFv conjugates, unlike the non-OptiLinked scFv (FIG. 71, Table 45). This demonstrates that structure, optimal spacing, and preferred locations are key factors for effective bioconjugation and that high lysine content is not enough.

TABLE 45

Comparison of a 'non-OptiLinked' scFv (panitumumab) vs an 'OptiLinked scFv' (TCT1067)

| Reaction | scFv | Molar equivalents of Auristatin F-C5 NHS used | DAR distribution by LC-MS and (mean DAR) | Yield | % aggregate by HPLC-SEC (FIG. 71) |
|---|---|---|---|---|---|
| 1 | Panitumumab | 5 | 0, 1, 2, 3, 4 (3) | 44% | 37% |
| 2 | Panitumumab | 10 | 0, 1, 2, 3, 4, 5 (3.4) | 26% | 42% |

TABLE 45-continued

Comparison of a 'non-OptiLinked' scFv (panitumumab) vs an 'OptiLinked scFv' (TCT1067)

| Reaction | scFv | Molar equivalents of Auristatin F-C5 NHS used | DAR distribution by LC-MS and (mean DAR) | Yield | % aggregate by HPLC-SEC (FIG. 71) |
|---|---|---|---|---|---|
| 3 | Panitumumab | 25 | None | 0%* | 95% |
| 4 | TCT1067 | 5 | 0, 1, 2, 3 (2) | 65% | 0% |
| 5 | TCT1067 | 10 | 2, 3, 4, 5, 6, 7 (5) | 70% | 0% |
| 6 | TCT1067 | 25 | 7, 8, 9, 10, 11(9) | 46% | 0% |

*observed precipitation

Example 72. Cell Killing Potency and Specificity of a Medium and High Affinity scFv Conjugated to Medium and High DAR Payloads

Example 72A. scFv (TCT)-MMAF-C5, scFv (TCT1067)-MMAF-C5 and Trastuzumab-MMAF-C5 Conjugates (117), DAR 6.5

ScFv (TCT)-MMAF-C5, ScFv (TCT1067)-MMAF-C5 and Trastuzumab-MMAF-C5 conjugates (118) were made and characterised as described above (Examples 65 which had similar DARs as before. SKBr3, human breast cancer cell line, high HER2 expression levels, up to 1,000,000 receptors per cell [Lazar G A, et al Proc Natl Acad Sci USA. 2006, 103:4005-10] were grown in McCoy's 5A/10% FCS (complete media) at 37° C., 5% $CO_2$ in a humidified atmosphere. When confluency was 70-80%, cells were washed with PBS (2×10 ml) and incubated with trypsin for 5-7 min. Complete McCoy's 5A was added and the cells were resuspended by pipetting. The cells were recovered by centrifugation (2 min, 2000 rpm), the supernatant was discarded, and the cells were resuspended in complete McCoy's 5A (5 ml). The cells were then counted using a haemocytometer and diluted accordingly. They were plated at 5000 cells/well (200 µl) using attachment factor and incubated overnight at 37° C., 5% $CO_2$ in a humidified atmosphere. U87 is a non-HER2 expressing glioblastoma cell line [Zitron I M et al (2013) BMC Cancer 13:83] and was grown in a similar way, plated at 1000 cells/well (using DMEM media). BT474 is a HER2 expressing breast cancer cell line [Brockhoff G et al (2007) Cell Prolif 40:488-507] and was grown in a similar way, plated at 7500 cells/well (using RPMI media). NCI-N87 is a HER2 expressing gastric cancer cell line [Yamashita-Kashima Y et al (2013) Oncol. Rep 30:1087-93] and was grown in a similar way, plated at 7500 cells/well (using RPMI media).

The cells were exposed to the various ADCs diluted in complete media for 96 hours at 37° C., 5% $CO_2$ in a humidified atmosphere. Cell viability was measured using the Promega Aqueous Cell-titre-96™ aqueous one solution cell proliferation kit (MTS reagent) according to manufacturer's instructions. Briefly, the media was removed and 100 µl of complete phenol red free media, pre-combined with MTS reagent, was added to the cells (20 µl of reagent per 100 µl of media). The plates were read on an ELISA plate reader at 490 nm after a 2 hr incubation in the dark (5% $CO_2$, 37° C.).

The data (absorption units) were converted to % cell survival by using the untreated controls as the 100% cell survival and the Triton X-100 controls as the 100% cell death. The average absorption value for the latter was subtracted from all the rest of the data in order to get a suitable baseline. The averages were converted to survival and standard error values were obtained for each n value (as a % cell survival). The data were plotted and fitted to a dose-response sigmoidal logistic 3-parameter curve using the equation $y = y_0 + a/(1+(x/x_0)b)$ where, $x_0 = IC50$ and $x_0 > 0$ and $a = 100$ using Graph Pad Prism. Experiments were repeated at least 3 times for each compound tested and a set or an average of the data was plotted and fitted to obtain a dose-response curve.

The data (FIGS. 73-76, Table 46) shows that the scFv (TCT or TCT1067)-ADCs are specifically cytotoxic to HER2 expressing cells with nM to pM potencies. The high DAR leads to a high cell-killing potency. The free drug has low potency and poor specificity on its own (FIG. 73 Table 46) due to the poor cellular uptake and the unconjugated antibodies have no to low potency on their own (FIG. 74-75, Table 46)

TABLE 46

Summary of Cell killing potency of scFv (TCT & TCT1067) & Trastuzumab MMAF-C5 conjugates (compounds 118)
NC = No cytotoxicity

| Sample | SKBr3 Cells (HER2+++) IC50 µg/ml | SKBr3 Cells (HER2+++) IC50 pM | BT474 Cells (HER2++) IC50 µg/ml | BT474 Cells (HER2++) IC50 pM | U87 Cells (HER2−) IC50 µg/ml | U87 Cells (HER2−) IC50 pM |
|---|---|---|---|---|---|---|
| scFv (TCT)-MMAF-C5, DAR 6.6 | 0.087 | 3.1 | 0.2 | 7.14 | >5 | NC |
| scFv (TCT1067)-MMAF-C5, DAR 6.4 | 0.007 | 250 | 0.008 | 286 | >5 | NC |
| Trastuzumab-MMAF-C5, DAR 4 | 0.004 | 26 | 0.01 | 67 | >5 | NC |
| Free drug MMAF | NC | NC | — | >10,000 | NC | NC |
| Unconjugated scFv | NC | NC | NC | NC | NC | NC |
| Unconjugated trastuzumab | 0.6 | 4000 | NC | NC | NC | NC |

Example 72B. scFv (TCT)-MMAF-C5, scFv (TCT1067)-MMAF-C5 and Trastuzumab-MMAF-C5 Conjugates (118), DAR 8

Cell killing assays were set up as described in Example 72A

The data (FIGS. 73-75 & 77, Table 47) shows that the scFv (TCT or TCT1067) conjugates are specifically cytotoxic to HER2 expressing cells with nM to pM potencies. The high DAR leads to a high cell-killing potency. The free drug has low potency and poor specificity on its own (FIG. 73, Table 47) due to poor cellular uptake and the unconjugated antibodies have no to low potency on their own (FIG. 74-75, Table 47).

TABLE 47

Summary of Cell killing potency of scFv (TCT & TCT1067) & Trastuzumab MMAF-C5 conjugates (compounds 118)
NC = No cytotoxicity

| Sample | SKBr3 Cells (HER2+++) | | BT474 Cells (HER2++) | | U87 Cells (HER2−) | |
|---|---|---|---|---|---|---|
| | IC50 µg/ml | IC50 pM | IC50 µg/ml | IC50 pM | IC50 µg/ml | IC50 pM |
| scFv (TCT)-MMAF DAR 8 | 0.0053 | 189 | 0.02 | 714 | NC | NC |
| scFv (TCT1067)-MMAF DAR 8.7 | 0.00091 | 32.5 | 0.001 | 35.7 | NC | NC |
| Trastuzumab-MMAF, DAR 6 | 0.0051 | 34 | 0.05 | 336 | NC | NC |
| Free drug MMAF | NC | NC | NC | NC | NC | NC |
| Unconjugated scFv | NC | NC | NC | NC | NC | NC |
| Unconjugated trastuzumab | 0.6 | 4000 | NC | NC | NC | NC |

Example 72C. scFv (TCT1067)-P5C5 and Trastuzumab-P5C5 Conjugates (71), DAR 10.6 and 12.5

Cell killing assays were set up as described in Example 72A.

The data (FIG. 78-80, Table 48) shows that the scFv (TCT or TCT1067) conjugates are specifically cytotoxic to HER2 expressing cells with nM to pM potencies. The high DAR leads to a high cell-killing potency. The free drug has low potency and poor specificity on its own (FIG. 78-80, Table 48) due to poor cellular uptake and the unconjugated antibodies have no to low potency on their own (FIG. 74-75, Table 48).

TABLE 48

Summary of Cell killing potency of scFv (TCT1067) & Trastuzumab P5C5 ADCs (compounds 71)
NC = No cytotoxicity, ND = Not determined

| Sample | SKBr3 Cells (HER2+++) | | BT474 Cells (HER2++) | | U87 Cells (HER2−) | |
|---|---|---|---|---|---|---|
| | IC50 µg/ml | IC50 nM | IC50 µg/ml | IC50 nM | IC50 µg/ml | IC50 nM |
| scFv (TCT1067)-P5C5 DAR 12.5 | 0.04 | 1.42 | 0.3 | 10.7 | NC | NC |
| scFv (TCT1067)-P5C5 DAR 10.6 | ND | ND | 0.5 | 17.85 | NC | NC |
| Trastuzumab-P5C5, DAR 6 | ND | ND | 0.2 | 1.33 | NC | NC |
| Free drug P5C5 | — | >33,000 | — | >3300 | — | 100,000 |
| Unconjugated scFv | NC | NC | NC | NC | NC | NC |
| Unconjugated trastuzumab | 0.6 | 4 | NC | NC | NC | NC |

Example 72D. scFv (TCT1067)-Auristatin F-C5 at Low, Medium and High DARs and Trastuzumab-Auristatin F-C5 Conjugates (122)

Cell killing assays were set up as described in Example 72A

The data (FIGS. 74-75, 81-82, Table 49) shows that the scFv (TCT1067)-ADCs were specifically cytotoxic to HER2 expressing cells with nM to pM potencies. The high DAR leads to a high cell-killing potency. The free drug has some potency but poor specificity on its own (FIG. 81, Table 49) due to non-specific cellular uptake and the unconjugated antibodies have no to low potency on their own (FIG. 74-75, Table 49).

TABLE 49

Summary of Cell killing potency of scFv (TCT1067)-Auristatin F-C5 & Trastuzumab Auristatin F-C5 ADCs (compounds 122)
NC = No cytotoxicity, ND = Not determined

| Sample | SKBr3 Cells (HER2+++) | | BT474 Cells (HER2++) | | NCI-N874 Cells (HER2++) | | U87 Cells (HER2−) | |
|---|---|---|---|---|---|---|---|---|
| | IC50 µg/ml | IC50 pM | IC50 µg/ml | IC50 pM | IC50 µg/ml | IC50 pM | IC50 µg/ml | IC50 pM |
| scFv (TCT1067)-Auristatin F-C5, DAR 2.7 | 0.00089 | 31.7 | 0.00115 | 39.2 | 0.00087 | 31.05 | NC | NC |
| scFv (TCT1067)-Auristatin F-C5, DAR 6.2 | 0.00101 | 36.1 | 0.00112 | 39.9 | 0.00036 | 12.85 | NC | NC |
| scFv (TCT1067)-Auristatin F-C5, DAR 11.8 | 0.00844 | 299 | 0.01082 | 386 | 0.0087 | 310 | NC | NC |
| Trastuzumab-Auristatin F-C5, DAR 4.8 | 0.003171 | 21 | 0.008193 | 54.6 | 0.0018 | 6.7 | NC | NC |
| Free drug Auristatin F | | >5500 | | >2500 | | ND | | >12,500 |
| Unconjugated scFv | NC | NC | NC | NC | NC | NC | NC | NC |
| Unconjugated trastuzumab | 0.6 | 4000 | NC | NC | NC | NC | NC | NC |

Example 72E. ScFv (TCT1067)-DM1-(dPEG$_{12}$) and Trastuzumab-DM1-(dPEG$_{12}$) Conjugates (124) Low, Medium and High DAR Cell killing assays were set up as described in Example 72A The data (FIGS. 74-75, 83-84, Table 50) shows that the scFv (TCT or TCT1067) conjugates are specifically cytotoxic to HER2 expressing cells with nM to pM potencies. The high DAR leads to a high cell-killing potency. The free drug has some potency but poor specificity on its own (FIG. 83, Table 50) due to non-specific cellular uptake and the unconjugated antibodies have no to low potency on their own (FIG. 74-75, Table 50).

TABLE 50

Summary of Cell killing potency of scFv (TCT1067)-DM1-(dPEG$_{12}$) & Trastuzumab-DM19(dPEG$_{12}$) ADCs (compounds 124)
NC = No cytotoxicity

| Sample | SKBr3 Cells (HER2 +++) | | U87 Cells (HER2−) | |
|---|---|---|---|---|
| | IC50 µg/ml | IC50 nM | IC50 µg/ml | IC50 nM |
| scFv (TCT1067)-DM1 DAR 3.5 | 0.0417 | 1.49 | 0.641 | 22.9 |
| scFv (TCT1067)-DM1 DAR 5.5 | 0.0078 | 0.0278 | 0.419 | 14.94 |
| scFv (TC11067)-DM1 DAR 8 | 0.07606 | 2.7 | 0.355 | 12.66 |
| Free drug DM1 | — | 47.63 | — | 50.7 |
| Unconjugated scFv | NC | NC | NC | NC |

Example 72F. ScFv (TCT1067)-MMAE-PAB-Cit-Val-dPEG$_9$ and Trastuzumab-MMAE-PAB-Cit-Val-dPEG$_9$ Conjugates, DAR9 (121)

Cell killing assays were set up as described in Example 72A.

The data (FIGS. 74-75, 85-86, Table 51) shows that the scFv (TCT or TCT1067)-ADCs are specifically cytotoxic to HER2 expressing cells with nM to pM potencies. The high DAR leads to a high cell-killing potency. The high DAR leads to a high cell-killing potency. The free drug has low potency but poor specificity on its own (FIG. 85, Table 50) due to non-specific cellular uptake and the unconjugated antibodies have no to low potency on their own (FIG. 74-75, Table 51).

TABLE 51

Summary of Cell killing potency of scFv (TCT1067)-MMAE-PAB-Cit-Val-dPEG$_9$ & Trastuzumab-MMAE-PAB-Cit-Val-dPEG$_9$ ADCs (compounds 120)
NC = No cytotoxicity

| Sample | SKBr3 Cells (HER2+++) | | U87 Cells (HER2−) | | NCI-N87 Cells (HER2++) | |
|---|---|---|---|---|---|---|
| | IC50 µg/ml | IC50 nM | IC50 µg/ml | IC50 nM | IC50 µg/ml | IC50 nM |
| scFv (TCT1067)-MMAE-PAB-Cit-Val-dPEG$_9$, DAR 9 | 0.04476 | 1.59 | 0.1 | 3.57 | 0.195 | 6.947 |
| Trastuzumab-MMAE-PAB-Cit-Val-dPEG$_9$, DAR 4 | 0.0052 | 0.035 | NC | NC | 0.067 | 0.45 |
| Free drug MMAE | NC | NC | NC | NC | ND | ND |
| Unconjugated scFv | NC | NC | NC | NC | NC | NC |
| Unconjugated trastuzumab | 0.6 | 4 | NC | NC | NC | NC |

Example 73. Demonstration that Antibody Fragment ADCs are Highly Potent at Lower Incubation Times Cell killing assays were set up as described in Example 72A but the incubation time was shortened to 4 hours to mimic the reduced exposure time expected in vivo of antibody fragment-based ADCs. Two similar DAR (around 5) conjugates were compared (1) high affinity scFv (TCT1067)-AF-C5 conjugate, DAR 5.3 (2) Trastuzumab-AF-C5 conjugate, DAR 4.8. The results are shown in FIG. 87-88 and Table 52. A 24-fold reduction in exposure time for the scFv (TCT1067)-AF-C5 conjugate led to a 2.2-fold reduction in potency, whereas a 24-fold reduction in exposure time for the Trastuzumab-AF-C5 conjugate led to a more dramatic reduction in potency of 4.8-fold. This suggests that the high DAR in a smaller sized protein leads to an ADC that maintains its potency under shorter tumour cell contact conditions.

TABLE 52

Cell killing potency of scFv (TCT1067)-AF-C5 conjugates, DAR 5.3 (compounds 122) for short and long incubations
NC = No cytotoxicity

| | SKBr3 Cells (HER2 +++) | |
|---|---|---|
| Sample | IC50 µg/ml | IC50 pM |
| Free Auristatin 4 hours | 0.00181 | >100,000 |
| Free Auristatin, 96 hours | 0.00081 | >10,000 |
| ScFv (TCT1067)-AF-C5 DAR 5.3, 4 hours | 0.00181 | 64.4 |
| ScFv (TCT1067)-AF-C5 DAR 5.3, 96 hours | 0.00081 | 28.8 |
| Trastuzumab-AF-C5 DAR 4.8, 4 hours | 0.0144 | 93.4 |
| Trastuzumab-AF-C5 DAR 4.8, 96 hours | 0.0029 | 19.3 |

Example 74. Demonstration that OptiLinked scFv-Drug Conjugates Penetrate into Human Tumour Xenografts More Rapidly than the Whole Immunoglobulin-Drug Conjugate with Equivalent Payloads Mice. Female severe combined immunodeficient mice (Fox Chase SCID®, CB-17/Icr-Prkdcscid/IcrIcoCrl, Charles River Laboratories) were twelve weeks old with a body weight (BW) range of 15.3 to 18.4 grams on Day 1 of the study. The animals were fed ad libitum water (reverse osmosis, 1 ppm Cl), and NIH 31 Modified and Irradiated Lab Diet® consisting of 18.0% crude protein, 5.0% crude fat, and 5.0% crude fiber. The mice were housed on irradiated Enrich-o'cobs™ Laboratory Animal Bedding in static microisolators on a 12-hour light cycle at 20-22° C. (68-72° F.) and 40-60% humidity. Charles River Discovery Services North Carolina (CR Discovery Services, who carried out this contracted R&D) specifically complies with the recommendations of the Guide for Care and Use of Laboratory Animals with respect to restraint, husbandry, surgical procedures, feed and fluid regulation, and veterinary care. The animal care and use program at CR Discovery Services is accredited by the Association for Assessment and Accreditation of Laboratory Animal Care International (AAALAC), which assures compliance with accepted standards for the care and use of laboratory animals.

In Vivo Implantation and Tumor Growth. Xenografts were initiated with BT474 human breast carcinomas maintained at CR Discovery Services by serial subcutaneous transplantation in SCID mice. On the day of tumor implant, each test mouse received a 1 mm³ BT474 fragment implanted subcutaneously in the right flank, and tumor growth was monitored as the average size approached the target range of 400 to 600 mm³. Fifty days after tumor implantation, designated as Day 1 of the study, the animals were re-sorted into groups each consisting of two mice with individual tumor volumes of 405 to 600 mm³ and group mean tumor volumes of 466 to 503 mm³. Tumors were measured in two dimensions using calipers, and volume was calculated using the formula:

$$\text{Tumor Volume (mm}^3\text{)} = w^2 \times l/2$$

where w=width and l=length, in mm, of the tumor. Tumor weight may be estimated with the assumption that 1 mg is equivalent to 1 mm³ of tumor volume.

Therapeutic (test) Agents. All test agents were prepared as ready-to-dose dosing solutions at concentrations of 0.625 mg/mL. All dosing solutions were stored at 4° C. until dosed. All treatments were administered in a dosing volume of 8 mL/kg scaled to the body weights of the individual animals resulting in a dose of 5 mg/kg. Treatment. On Day 1 of the study, female SCID mice bearing established BT474 xenografts were dosed according to the treatment plan summarized in Table 53. All agents were administered intravenously (i.v.) via tail vein injection in a single dose on Day 1.

TABLE 53

Treatment plan for tumour uptake study using scFv-P5C5 conjugates (71)

| Group | Agent | Dose (mg/kg) | Number of doses | Tumours excised after (hours) |
|---|---|---|---|---|
| 1 | Trastuzumab-P5C5 | 5 | 1 | 2 |
| 2 | scFv (TCT)-P5C5 | 5 | 1 | 2 |
| 3 | scFv (TCT1067)-P5C5 | 5 | 1 | 2 |

Endpoint. The study endpoint occurred on Day 1, two hours post dose.

Treatment-Related Side Effects. Test animals were weighed Day 1. Animals were observed frequently for overt signs of any adverse, treatment-related side effects. Individual body weight loss was monitored every other day and any animal whose weight exceeded the limits for acceptable body weight loss was euthanized. Group mean body weight loss also was monitored as per protocol. Acceptable toxicity for the maximum tolerated dose (MTD) was defined as a group mean body weight loss of less than 20% during the test.

Sampling. Samples were collected two hours post dose in the study for further analysis. Blood (full blood volume) was collected from all animals via terminal cardiac puncture under isoflurane anesthesia. Once collected, blood samples were processed for plasma using lithium heparin as the anticoagulant. Each plasma sample was then frozen and stored at −80° C. for analysis. Immediately following the collection of blood, tumors were collected. Tumors were place in formalin for approximately 24 hours at room temperature and then transferred to 70% ethanol. Tumors were then embedded in paraffin wax blocks and multiple slides of serial sections of each tumor were made.

Immunohistochemical analyses. Slides containing tumour sections were deparafinized by incubating in xylene for 2×5 minutes, rehydrated by incubating in 100% ethanol for 4×2 minutes and distilled water for 2×5 minutes. The slides were drained briefly by standing on absorbent tissue and hydrophobic pen (a 'PAP' pen) was used to draw a circle around each section, taking care not to touch the section. Each section was covered with 100-400 μl of blocking solution (1% BSA in TBS) and incubated for 1 hr in a humidified chamber. The blocking solution was flicked off and 100-400 μl of primary antibody (mouse anti-cemadotin monoclonal antibody, Example 33, 5 μg/ml) in the blocking buffer was applied and incubated overnight at 4° C. in a humidified chamber. Next, the antibody solution was removed and the sections were washed three times in TBS buffer for 5 mins each, then the secondary antibody (goat anti-mouse FITC conjugate, Thermo-Fisher 62-6511, 1:50 or anti-human FITC conjugate Thermo-Fisher 054211, 1:20) solution (in the blocking buffer) was added and incubated for 60 mins at room temperature in the dark. The antibody solution was removed and the sections washed three times in TBS buffer for 5 mins each. The sections were mounted with coverslips using a mounting medium. The mounting medium was allowed to set and the slides viewed under a fluorescent microscope, with digital images captured.

FIG. 89 shows representative images of tumour sections at 2 hrs post-dosing. A medium affinity scFv (TCT)-P5C5 and high affinity scFv (TCT1067)-P5C5 conjugates can be clearly seen to localise throughout the tumour with some peri-vascular staining evident in the high affinity sample. Very little trastuzumab ADC is seen in the tumour at 2 hrs as seen from the low fluorescence. This demonstrates faster tumour uptake of a fragment-based ADC, when detecting the payload component (total ADC).

Example 75A. Demonstration that OptiLinked scFv-Drug Conjugates have a Slower Plasma Pharmacokinetic Profile than that of the Unmodified scFv in Rodent Animal Models Mice. Female BALB/c mice (BALB/cAnNCrl, Charles River) were eight weeks old with body weights ranging from 15.9 to 21.9 grams at the beginning of the study. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated Enrich-o'cobs™ Laboratory Animal Bedding in static microisolators on a 12-hour light cycle at 20-22° C. (68-72° F.) and at 40-60% humidity. Charles River Discovery Services North Carolina (CR Discovery Services, who carried out this contracted R&D) specifically complies with the recommendations of the Guide for Care and Use of Laboratory Animals with respect to restraint, husbandry, surgical procedures, feed and fluid regulation, and veterinary care. The Animal Care and Use program at CR Discovery Services is accredited by the Association for Assessment and Accreditation of Laboratory Animal Care International, which assures compliance with accepted standards for the care and use of laboratory animals.

Rats. Male Sprague-Dawley rats (sourced from Charles River, UK) were group housed in a temperature and light controlled facility on a 12 hour light/dark cycle with food and water available ad libitum. Rats selected for study inclusion were individually housed until completion of the study. All animals were subjected to health monitoring in accordance with the guidelines by the onsite home office registered veterinarian. All animal experimentation was covered under the UK Animals (Scientific Procedures) Act (1986) and EU directive 86/609/EEC. All such work was monitored by regular inspections of procedures and facilities by the on-site Veterinarian and UK Home Office inspectors. The study design required the surgical implantation of catheters into the jugular of male Sprague-Dawley rats.

Rats were anaesthetised using the inhalation anaesthetic isoflurane and placed in dorsal recumbency. The right jugular vein was exposed and a loose ligature was placed caudally and the cranial end of vein was ligated. A small incision was made between the ligatures into which the catheter (polyethylene 50 tubing) was inserted. The catheter was secured in place by tying the loose ligature around the catheterised vessel. A small incision was made in the scapular region to serve as the exit site of the catheter. The catheter was subcutaneously tunneled and exteriorised through the scapular incision. Patency of the catheter was tested, and the catheter was filled with a locking solution (heparinised saline) and sealed with a stainless steel pin. Post-operative monitoring of animals was performed according to Home Office good practice guidelines. Intravenous dosing was via the tail vein.

Therapeutic (test) Agents. All test agents were supplied as ready-to-dose dosing solutions. All dosing solutions were stored at 4° C. until dosed. All treatments were administered in a dosing volume scaled to the body weights of the individual animals to obtain the dosing concentration described in the treatment tables.

Treatment (mice). On Day 1 of the study, mice were divided into groups each consisting of eighteen mice (per test agent being evaluated), and dosing was initiated according to the treatment plan summarized in the treatment tables. All doses were administered intravenously (i.v.) by tail vein injection as described in the tables below.

Treatment (rats). On Day 1 of the study, rats were divided into groups of three animals (per test agent being evaluated), and dosing was initiated according to the treatment plan summarized in the tables below Endpoint. The study endpoint occurred after the last sampling point, typically on Day 2 or 4, twenty-four or seventy-two hours post dose.

Treatment-Related Side Effects. Test animals were weighed twice on Day 1. Animals were observed frequently for overt signs of any adverse, treatment-related side effects. Individual body weight loss was monitored every other day and any animal whose weight exceeded the limits for acceptable body weight loss was euthanized. Group mean body weight loss also was monitored. Acceptable toxicity for the maximum tolerated dose (MTD) was defined as a group mean body weight loss of less than 20% during the test.

Sampling (mice). Blood (full blood volume) was collected from three animals per treatment group per timepoint. Samples were collected from all animals via terminal cardiac puncture under isoflurane anesthesia. Once collected, blood samples were collected into collection tubes containing lithium heparin or K2EDTA as anticoagulants and were processed for plasma at each timepoint. Each plasma sample was stored at −80° C. until used for analysis.

Sampling (rats). Serial venous blood samples (approx. 0.1-0.2 ml) were collected via the exteriorised jugular vein catheter at specified time points (0.5 to 72 hrs post dosing) and placed in heparinised containers. Prior to taking the blood samples the catheter was evacuated of heparinised saline to prevent dilution of the blood sample. Following each blood sample the volume of blood removed is replaced with an equal volume of heparinised saline via the catheter and sealed. Blood samples were centrifuged (5 minutes, 16,100 g, 4° C.) to separate the plasma. Plasma samples were transferred to fresh containers and promptly frozen and stored at −20° C. until used for analysis.

Quantification of test agents in plasma. An ELISA was carried out as described in Example 31 The detecting antibodies were (a) Anti-T7 tag to detect the scFv (total antibody), (b) Anti-Human Fab-specific to detect trastuzumab (total antibody), (c) Anti-MMAF (Concortis), Anti-MMAE (Concortis), anti-DM1

(Concortis) and anti-cemadotin (in-house mouse monoclonal antibody, Example 33 that also recognised P5C5 and AuristatinF), total ADC. The reference test agents were used to construct a calibration curve for which the plasma samples were compared to, in order to quantify the amount present. The concentration was plotted against time (average of three animals with standard error) and fitted to a 2-phase decay curve using GraphPad Prism to derive kinetic parameters.

Example 75B. Pharmacokinetic Analyses of ScFv (TCT)-MMAF-C5, Trastuzumab-MMAF-C5 Conjugates (118) and Unconjugated Antibodies in Mice Mice were prepared, treated and plasma analysed as described in Example 75A. The dosing and sampling schedule is shown in Table 54.

TABLE 54

Pharmacokinetic dosing and analyses of scFv (TCT)-MMAF-C5, Trastuzumab-MMAF-C5 conjugates (compounds 118) and unconjugated antibodies in mice

| Test agent | Administered dose | Sampling times (hrs) | Analysis |
| --- | --- | --- | --- |
| scFv (TCT)-MMAF-C5 | 1 × 5 mg/kg | 0.5, 1, 2, 4, 8, 24 | ELISA anti-payload ELISA anti-T7 Tag |
| Trastuzumab-MMAF-C5 | 1 × 5 mg/kg | 1, 2, 6, 24, 48, 72 | ELISA anti-Human IgG ELISA anti-payload |
| scFv (TCT) | 1 × 5 mg/kg | 2, 4, 6, 24 | ELISA anti-T7 Tag |

The pharmacokinetic plot is shown in FIG. 90 and the derived pharmacokinetic parameters are shown in Table 55. The scFv (TCT) clears rapidly from the circulation whereas the trastuzumab IgG ADC clears much more slowly, both as expected. Unexpectedly, the scFv (TCT)-MMAF-C5 conjugate clears more slowly than the unmodified fragment despite the high payload loading indicating that the high DAR enabled by the OptiLink conjugation does not lead to aggregation in vivo and does not lead to rapid clearance via the reticulo-endothelial system. The slower clearance of the scFv (TCT)-MMAF-C5 conjugate leads to a significant blood exposure (as illustrated by the area under the clearance curve, (AUC)), which in turn leads to a significant and effective tumour exposure. The MMAF conjugates also had a lower volume of distribution compared to the unmodified scFv which led to a 14-fold higher bioavailability. The scFv (TCT)-MMAF-C5 conjugates were detected in the plasma via its T7 tag (detecting total antibody) and via the payload (detecting total ADC). The trastuzumab-MMAF-C5 conjugates were detected in the plasma using anti-human Fab (detecting total antibody) and via the payload (detecting total ADC). The clearance lines for the scFv (TCT)-MMAF conjugates were very similar suggesting that the scFv (TCT)-MMAF-C5 conjugates were stable in plasma and insignificant de-conjugation was occurring.

TABLE 55

Pharmacokinetic parameters of scFv (TCT)-MMAF-C5, Trastuzumab-MMAF-C5 conjugates (compounds 117) and unconjugated antibodies in mice

| | Elimination half-life (hrs) | | |
| --- | --- | --- | --- |
| Test agent | Total antibody | Total ADC | Bioavailability (blood exposure, AUC, 24 hrs)* |
| scFv (TCT)-MMAF-C5 | 2.84 | 2.78 | 40.88 |
| Trastuzumab-MMAF-C5 | 20.11 | 24.93 | 1890 |
| scFv (TCT) | 2.78 | — | 2.9 |

*Calculated from mean AUC in anti-payload and anti-protein detection (µghr/ml)

Example 75C. Pharmacokinetic Analyses of scFv (TCT1067)-MMAF-C5, Trastuzumab-MMAF-C5 Conjugates (118) and Unconjugated Antibodies in Mice Mice were prepared, treated and plasma analysed as described in Example 75A. The dosing and sampling schedule is shown in Table 56.

TABLE 56

Pharmacokinetic dosing and analyses of scFv (TCT)-MMAF-C5, Trastuzumab-MMAF-C5 conjugates (compounds 118) and unconjugated antibodies in mice

| Test agent | Administered dose | Sampling times (hrs) | Analysis |
|---|---|---|---|
| scFv (TCT1067)-MMAF-C5 | 1 × 5 mg/kg | 0.5, 1, 2, 4, 8, 24 | ELISA anti-payload ELISA anti-T7 Tag |
| Trastuzumab-MMAF-C5 | 1 × 5 mg/kg | 1, 2, 6, 24, 48, 72 | ELISA anti-Human IgG ELISA anti-payload |
| scFv (TCT1067) | 1 × 5 mg/kg | 0.5, 1, 2, 4, 8, 24 | ELISA anti-T7 Tag |

The pharmacokinetic plot is shown in FIG. 91 and the derived pharmacokinetic parameters are shown in Table 57. The scFv (TCT1067) clears rapidly from the circulation whereas the trastuzumab IgG ADC clears much more slowly, both as expected. Unexpectedly, the scFv (TCT1067)-MMAF-C5 conjugate clears more slowly than the unmodified fragment despite the high payload loading indicating that the high DAR enabled by the OPTILINK™ conjugation does not lead to aggregation in vivo and does not lead to rapid clearance via the reticulo-endothelial system. The slower clearance of the scFv (TCT1067)-MMAF-C5 conjugate leads to a significant blood exposure (as illustrated by the area under the clearance curve, (AUC)), showing a 15.5-fold increase in bioavailability, which in turn leads to a significant and effective tumour exposure. The MMAF-C5 conjugates also had a lower volume of distribution compared to the unmodified scFv which led to a higher bioavailability. The scFv (TCT1067)-MMAF-C5 conjugates were detected in the plasma via its T7 tag (detecting total antibody) and via the payload (detecting total ADC). The trastuzumab-MMAF-C5 conjugates were detected in the plasma using anti-human Fab (detecting total antibody) and via the payload (detecting total ADC). The clearance lines for the scFv (TCT1067)-MMAF-C5 conjugates were very similar suggesting that the scFv (TCT1067)-MMAF-C5 conjugates were stable in plasma and insignificant de-conjugation was occurring.

TABLE 57

Pharmacokinetic parameters of scFv (TCT)-MMAF-C5, Trastuzumab-MMAF-C5 conjugates (compounds 118) and unconjugated antibodies in mice

| | Elimination half-life (hrs) | | |
|---|---|---|---|
| Test agent | Total Antibody | Total ADC | Bioavailability (blood exposure, AUC, 24 hrs)* |
| scFv (TCT1067)-MMAF-C5 | 3.34 | 2.62 | 126 |
| Trastuzumab-MMAF-C5 | 20.11 | 24.93 | 1890 |
| scFv (TCT1067) | 1.05 | — | 8.12 |

*Calculated from mean AUC in anti-payload and anti-protein detection (µghr/ml)

Example 75D. Pharmacokinetic Analyses of scFv (TCT)-P5C5, Trastuzumab-P5C5 Conjugates (71) and Unconjugated Antibodies in Mice Mice were prepared, treated and plasma analysed as described in Example 75A The dosing and sampling schedule is shown in Table 58.

TABLE 58

Pharmacokinetic dosing and analyses of scFv (TCT)-P5C5, Trastuzumab-P5C5 conjugates (compounds 71) and unconjugated antibodies in mice

| Test agent | Administered dose | Sampling times (hrs) | Analysis |
|---|---|---|---|
| scFv (TCT)-P5C5 | 1 × 5 mg/kg | 0.5, 1, 2, 4, 8, 24 | ELISA anti-payload ELISA anti-T7 Tag |
| Trastuzumab-P5C5 | 1 × 5 mg/kg | 1, 2, 6, 24, 48, 72 | ELISA anti-Human IgG ELISA anti-payload |
| scFv (TCT) | 1 × 5 mg/kg | 2, 4, 6, 24 | ELISA anti-T7 Tag |

The pharmacokinetic plot is shown in FIG. 92 and the derived pharmacokinetic parameters are shown in Table 59. The scFv (TCT) clears rapidly from the circulation whereas the trastuzumab IgG ADC clears much more slowly, both as expected. Unexpectedly, the scFv (TCT)-P5C5 conjugate clears more slowly than the unmodified fragment despite the high payload loading indicating that the high DAR enabled by the OptiLink conjugation does not lead to aggregation in vivo and does not lead to rapid clearance via the reticulo-endothelial system. The slower clearance of the scFv (TCT)-P5C5 conjugate leads to a significant blood exposure (as illustrated by the 74-fold increase in the area under the clearance curve, (AUC)), which in turn leads to a significant and effective tumour exposure. The P5C5 conjugates also had a lower volume of distribution compared to the unmodified scFv which led to a higher bioavailability. The scFv (TCT)-P5C5 conjugates were detected in the plasma via its T7 tag (detecting total antibody) and via the payload (detecting total ADC). The trastuzumab-P5C5 conjugates were detected in the plasma using anti-human Fab (detecting total antibody) and via the payload (detecting total ADC). The clearance lines for the scFv (TCT)-P5C5 conjugates were very similar suggesting that the scFv (TCT)-P5C5 conjugates were stable in plasma and insignificant de-conjugation was occurring.

TABLE 59

Pharmacokinetic parameters of scFv (TCT1067)-P5C5, Trastuzumab-P5C5 conjugates (compounds 71) and unconjugated antibodies in mice

| | Elimination half-life (hrs) | | |
|---|---|---|---|
| Test agent | Total Antibody | Total ADC | Bioavailability (blood exposure, AUC, 24 hrs)* |
| scFv (TCT)-P5C5 | 4.69 | 4.99 | 215.35 |
| Trastuzumab-P5C5 | 17.3 | ND | >150 |
| scFv (TCT) | 2.78 | | 2.91 |

*Calculated from mean AUC in anti-payload and anti-protein detection (µghr/ml)

Example 75E. ScFv (TCT1067)-Auristatin F-C5, Trastuzumab-Auristatin F-C5 Conjugates (122) and Unconjugated Antibodies in Mice Mice were prepared, treated and plasma analysed as described in Example 75A The dosing and sampling schedule is shown in Table 60.

TABLE 60

Pharmacokinetic dosing and analyses of scFv (TCT1067)-AF-C5, Trastuzumab-AF-C5 conjugates (compounds 122) and unconjugated antibodies in mice

| Test agent | Administered dose | Sampling times (hrs) | Analysis |
|---|---|---|---|
| scFv (TCT1067)-AF-C5 | 1 × 2 mg/kg | 0.5, 1, 2, 4, 8, 24 | ELISA anti-payload ELISA anti-T7 Tag |
| scFv (TCT1067) | 1 × 2 mg/kg | 0.5, 1, 2, 4, 8, 24 | ELISA anti-T7 Tag |

The pharmacokinetic plot is shown in FIG. 93 and the derived pharmacokinetic parameters are shown in Table 61. The scFv (TCT1067) clears rapidly from the circulation. Unexpectedly, the scFv (TCT1067)-AF-C5 conjugate clears more slowly than the unmodified fragment despite the high payload loading indicating that the high DAR enabled by the OptiLink conjugation does not lead to aggregation in vivo and does not lead to rapid clearance via the reticulo-endothelial system. The slower clearance of the scFv (TCT1067)-AF-C5 conjugate leads to a significant blood exposure (as illustrated by the area under the clearance curve, (AUC)), showing a 3.5-fold higher bioavailability, which in turn leads to a significant and effective tumour exposure. The AuristatinF conjugates also had a lower volume of distribution compared to the unmodified scFv which led to a higher bioavailability. The scFv (TCT1067)-AF-C5 conjugates were detected in the plasma via its T7 tag (detecting total antibody) and via the payload (detecting total ADC). The clearance lines for the scFv (TCT1067)-AF-C5 conjugates were very similar suggesting that the scFv (TCT1067)-AF-C5 conjugates were stable in plasma and insignificant de-conjugation was occurring.

TABLE 61

Pharmacokinetic parameters of scFv (TCT1067)-AF-C5, Trastuzumab-AF-C5 conjugates (compounds 122) and unconjugated antibodies in mice

| Test agent | Elimination half-life (hrs) Total Antibody | Total ADC | Bioavailability (blood exposure, AUC, 24 hrs)* |
|---|---|---|---|
| scFv (TCT1067)-AF-C5 | 0.92 | 0.85 | 27.6 |
| scFv (TCT1067) | 1.05 | | 8.13 |

ND = not determined
*Calculated from mean AUC in anti-payload and anti-protein detection (µghr/ml)

Example 75F. ScFv (TCT1067)-DM1(PEG$_{12}$), Trastuzumab-DM1(PEG$_{12}$) Conjugates (124) and Unconjugated Antibodies in Mice Mice were prepared, treated and plasma analysed as described in Example 75A The dosing and sampling schedule is shown in Table 61.

TABLE 61

Pharmacokinetic and dosing analyses of scFv (TCT1067)-DM1(dPEG$_{12}$) (compound 124) and unconjugated scFv in mice

| Test agent | Administered dose | Sampling times (hrs) | Analysis |
|---|---|---|---|
| scFv (TCT1067)-DM1 (dPEG$_{12}$) | 1 × 2 mg/kg | 0.5, 1, 2, 4, 8, 24 | ELISA anti-payload ELISA anti-T7 Tag |
| scFv (TCT1067) | 1 × 2 mg/kg | 0.5, 1, 2, 4, 8, 24 | ELISA anti-T7 Tag |

The pharmacokinetic plot is shown in FIG. 94 and the derived pharmacokinetic parameters are shown in Table 62. The scFv (TCT1067) clears rapidly from the circulation. Unexpectedly, the scFv (TCT1067)-DM1(dPEG$_{12}$)conjugate clears more slowly than the unmodified fragment despite the high payload loading indicating that the high DAR enabled by the OptiLink conjugation does not lead to aggregation in vivo and does not lead to rapid clearance via the reticulo-endothelial system. The slower clearance of the scFv (TCT1067)-DM1(dPEG$_{12}$) conjugate leads to a significant blood exposure (as illustrated by the area under the clearance curve, (AUC)), showing a 3-fold higher bioavailability, which in turn leads to a significant and effective tumour exposure. The DM1(dPEG$_{12}$) conjugate also had a lower volume of distribution compared to the unmodified scFv which led to a higher bioavailability. The scFv (TCT1067)-DM1(dPEG$_{12}$) conjugates were detected in the plasma via its T7 tag (detecting total antibody) and via the payload (detecting total ADC). The clearance lines for the scFv (TCT1067)-DM1(dPEG$_{12}$) conjugates were very similar suggesting that the scFv (TCT1067)-DM1(dPEG$_{12}$) conjugates were stable in plasma and insignificant de-conjugation was occurring.

TABLE 62

Pharmacokinetic parameters of scFv (TCT1067)-DM1(dPEG$_{12}$), Trastuzumab-DM1(dPEG$_{12}$) (compounds 124) conjugates and unconjugated antibodies in mice

| Test agent | Elimination half-life (hrs) Total Antibody | Total ADC | Bioavailability (blood exposure, AUC 24 hrs)* |
|---|---|---|---|
| scFv (TCT1067)-DM1 (dPEG$_{12}$) | 0.92 | 1.53 | 22.15 |
| scFv (TCT1067) | 1.05 | — | 8.13 |

*Calculated from mean AUC in anti-payload and anti-protein detection (µghr/ml)

Example 75G. ScFv (TCT1067)-P5C5 Conjugate (71) and Unconjugated Antibody in Rats Rats were prepared, treated and plasma analysed as described in Example 75A The dosing and sampling schedule is shown in Table 63.

TABLE 63

Pharmacokinetic and dosing analyses of scFv (TCT1067)-P5C5 (compound 71) and unconjugated antibody in rats

| Test agent | Administered dose | Sampling times (hrs) | Analysis |
|---|---|---|---|
| scFv (TCT1067)-P5C5 | 1 × 4 mg/kg | 0.5, 1, 2, 4, 8, 24 | ELISA anti-payload ELISA anti-T7 Tag |
| scFv (TCT1067) | 1 × 4 mg/kg | 0.5, 1, 2, 4, 8, 24 | ELISA anti-T7 Tag |

The pharmacokinetic plot is shown in FIG. 95 and the derived pharmacokinetic parameters are shown in Table 64. The scFv (TCT1067) clears rapidly from the circulation whereas the trastuzumab IgG ADC clears much more slowly, both as expected. Unexpectedly, the scFv (TCT1067)-P5C5) conjugate clears more slowly than the unmodified fragment despite the high payload loading indicating that the high DAR enabled by the OptiLink conjugation does not lead to aggregation in vivo and does not lead to rapid clearance via the reticulo-endothelial system. The slower clearance of the scFv (TCT1067)-P5C5 conjugate leads to a significant blood exposure (as illustrated by the area under the clearance curve, (AUC)), showing a 4.5-fold higher bioavailability, which in turn leads to a significant and effective tumour exposure. The P5C5 conjugate also had a lower volume of distribution compared to the unmodified scFv which led to a higher bioavailability. The scFv (TCT1067)-P5C5 conjugate were detected in the plasma via its T7 tag (detecting total antibody) and via the payload (detecting total ADC). The clearance lines for the scFv (TCT1067)-P5C5 conjugates were very similar suggesting that the scFv (TCT1067)-P5C5 conjugates were stable in plasma and insignificant de-conjugation was occurring. The urine from the treated animals was collected over 24 hours, concentrated 10-fold in a spin concentrator (MWCO-10 kDa) and dialysed against PBS. These samples, from three rats per group, were analysed on a Biacore SPR chip. The data showed (FIGS. 95B and C) that there was comparable binding activity in the free scFv samples compared to the scFv-P5C5 conjugate samples suggesting that the scFv and conjugates clear, to some extent through the kidneys which leaves proteins and their conjugates intact.

TABLE 64

Pharmacokinetic parameters of scFv (TCT1067)-P5C5 conjugate (compound 71) and unconjugated antibody in rats

| Test agent | Elimination half-life (hrs) | | Bioavailability (blood exposure, AUC 24 hrs)* |
|---|---|---|---|
| | Total Antibody | Total ADC | |
| scFv (TCT1067)-P5C5 | 0.512 | 2.2085 | 90.1 |
| scFv (TCT1067) | 0.8 | | 20.46 |

*Calculated from mean AUC in anti-payload and anti-protein detection (µghr/ml)

Example 76. OptiLinked scFv-Drug Conjugates Tumour Regression or Eradication Studies in Human Tumour Xenografts Models Compared to Equivalent Payload-Bearing Whole Immunoglobulin-Drug Conjugates and Controls Mice. Female severe combined immunodeficient mice (Fox Chase SCID®, CB-17/Icr-Prkdcscid/IcrIcoCrl Charles River Laboratories) were Twelve weeks old with a body weight (BW) range of 15.3 to 18.4 grams on Day 1 of the study. The animals were fed ad libitum water (reverse osmosis, 1 ppm Cl), and NIH 31 Modified and Irradiated Lab Diet® consisting of 18.0% crude protein, 5.0% crude fat, and 5.0% crude fiber. The mice were housed on irradiated Enrich-o'cobs™ Laboratory Animal Bedding in static microisolators on a 12-hour light cycle at 20-22° C. (68-72° F.) and 40-60% humidity. Charles River Discovery Services North Carolina (CR Discovery Services, who carried out this contracted R&D) specifically complies with the recommendations of the Guide for Care and Use of Laboratory Animals with respect to restraint, husbandry, surgical procedures, feed and fluid regulation, and veterinary care. The Animal Care and Use program at CR Discovery Services is accredited by the Association for Assessment and Accreditation of Laboratory Animal Care International (AAALAC), which assures compliance with accepted standards for the care and use of laboratory animals.

In Vivo Implantation and Tumor Growth. Xenografts were initiated with (a) BT474 human breast carcinomas maintained at CR Discovery Services by serial subcutaneous transplantation in SCID mice. On the day of tumor implant, each test mouse received a 1 mm3 BT474 fragment implanted subcutaneously in the right flank, and tumor growth was monitored as the average size approached the target range of 110 to 144 mm$^3$. Fifty days after tumor implantation, designated as Day 1 of the study, the animals were re-sorted into six groups each consisting of two mice with individual tumor volumes of 110 to 144 mm$^3$ and group mean tumor volumes of 115 to 118 mm$^3$. (b) Xenografts were initiated with a cell suspension of NCI-N87 tumour cells implanted subcutaneously in the right flank, and tumor growth was monitored as the average size approached the target range of 110 to 144 mm$^3$. Tumors were measured in two dimensions using calipers, and volume was calculated using the formula:

Tumor Volume (mm$^3$)=width$^2$×length/2 where width and length of the tumor was in mm. Tumor weight may be estimated with the assumption that 1 mg is equivalent to 1 mm$^3$ of tumor volume.

Therapeutic Agents and treatment. All test agents were supplied as ready-to-dose dosing solutions and stored at 4° C. until used. All treatments were administered in a dosing volume scaled to the body weights of the individual animals to achieve the dosing concentration described in the respective treatment tables. All agents were administered intravenously (i.v.) via tail vein injection.

Endpoint. The study continued for up to 90 days or until the tumours reached a maximum size of 1000 mm$^3$.

Treatment-Related Side Effects. Test animals were weighed Day 1. Animals were observed frequently for overt signs of any adverse, treatment-related side effects. Individual body weight loss was monitored every other day and any animal whose weight exceeded the limits for acceptable body weight loss was euthanized. Group mean body weight loss also was monitored as per protocol. Acceptable toxicity for the maximum tolerated dose (MTD) was defined as a group mean body weight loss of less than 20% during the test.

Example 76A. Tumour Growth Inhibition or Eradication in a BT474 Xenograft Model with scFv (TCT1067)-MMAF-C5, Trastuzumab-MMAF-C5 Conjugates (117) and Free MMAF Therapeutic Agents BT474 tumours were set up as described in Example 76. The treatment plan for this experiment is described in Table 65

TABLE 65

Treatment plan for scFv (TCT1067)-MMAF-C5 (compound 118) compared to trastuzumab-MMAF-C5 benchmark

| No | Therapeutic agent or control | Dose administered (mg/kg) | Schedule | Number of doses |
|---|---|---|---|---|
| 1 | Vehicle (saline) | 8 ml vol | Every other day | 12 |
| 2 | Free MMAF | 1 | Every other day | 12 |
| 3 | scFv (TCT1067)-MMAF-C5 | 0.05 | Every other day | 12 |
| 4 | scFv (TCT1067)-MMAF-C5 | 0.5 | Every other day | 12 |
| 5 | scFv (TCT1067)-MMAF-C5 | 2 | Every other day | 12 |
| 6 | Trastuzumab-MMAF-C5 | 5 | Once per week | 4 |
| 7 | Trastuzumab-MMAF-C5 | 1 | Once per week | 4 |

Tumour volume (mm³) was plotted against time (FIG. 96) and animal body weight change (%) was plotted against time (FIG. 96). The benchmark control (trastuzumab-MMAF-C5) was dosed at 5 mg/kg as well as the lower dose of 1 mg/kg, at weekly intervals. A very similar ADC was previously shown to be highly efficacious [Zimmerman E S et al (2014) Bioconj. Chem 25:351-61]. The high affinity scFv (1067)-MMAF-C5 conjugates were dosed more frequently to account for the more rapid pharmacokinetic clearance at three doses.

The results show that there is a clear dose-response relationship with all of the ADCs with the scFv (TCT1067)-MMAF-C5 2 mg/kg dosing regimen leading to complete (100%) cures (durable to almost 90 days) by day 30. The scFv (TCT1067)-MMAF-C5 0.5 mg/kg dosing regimen also led to complete (100%) cures (reached by 90 day) A similar response was seen, as expected with the Trastuzumab-MMAF-C5 5 mg/kg dosing regimen. However, the ability to give more payload with the scFv (TCT1067)-MMAF-C5 ADC, more frequently resulted in the tumours shrinking more rapidly, approximately twice as fast as the trastuzumab-MMAF-C5 ADC. The saline (vehicle) and free payload treated animal group tumours grew rapidly. The scFv (TCT1067)-MMAF-C5 treatment seemed to be better tolerated as seen from the increasing body weights with the antibody fragment ADC group of mice being up to 15% heavier than the IgG-MMAF-C5 ADC group of mice. An estimation of the therapeutic index for the scFv (TCT1067)-MMAF-C5 is at least 40 (at least 2 mg/kg, maximum tolerated dose/0.05 mg/kg minimum efficacious dose), compared to an approximate value of around 5 for the trastuzumab ADC.

Example 76B. Tumour Growth Inhibition or Eradication in a BT474 Xenograft Model with scFv (TCT)-MMAF-C5, Trastuzumab-MMAF-C5 Conjugates (Compounds 118) and Free MMAF Therapeutic Agents BT474 tumours were set up as described in Example 76. The treatment plan for this experiment is described in Table 66.

TABLE 66

Treatment plan for scFv (TCT)-MMAF-C5 (118) compared to trastuzumab-MMAF-C5 benchmark

| No | Therapeutic agent or control | Dose administered (mg/kg) | Schedule | Number of doses |
|---|---|---|---|---|
| 1 | Vehicle (saline) | 8 ml vol | Every other day | 12 |
| 2 | Free MMAF | 1 | Every other day | 12 |
| 3 | scFv (TCT)-MMAF-C5 | 0.5 | Every other day | 12 |
| 4 | scFv (TCT)-MMAF-C5 | 2 | Every other day | 12 |
| 5 | Trastuzumab-MMAF-C5 | 1 | Once per week | 4 |
| 6 | Trastuzumab-MMAF-C5 | 5 | Once per week | 4 |

Tumour volume (mm³) was plotted against time (FIG. 97) and animal body weight change (%) was plotted against time (FIG. 97). The benchmark control (trastuzumab-MMAF-C5) was dosed at 5 mg/kg which has previously been shown to be highly efficacious as well as the lower dose of 1 mg/kg, at weekly intervals. The medium affinity scFv (TCT)-MMAF-C5 conjugates were dosed more frequently to account for the more rapid pharmacokinetic clearance at three lower doses. The data from example 74A is included as a comparison.

The results show that there is a clear dose-response relationship with all of the ADCs with the scFv (TCT)-MMAF-C5 2 mg/kg dosing regimen leading to complete (100%) cures (durable to almost 90 days) by day 30. A similar response was seen, as expected with the Trastuzumab-MMAF-C5 5 mg/kg dosing regimen. However, the ability to give more payload with the scFv (TCT)-MMAF-C5 ADC, more frequently resulted in the tumours shrinking more rapidly. The saline (vehicle) and free payload treated animal group tumours grew rapidly. The scFv (TCT)-MMAF-C5 treatment seemed to be better tolerated as seen from the increasing body weights with the antibody fragment ADC group of mice being up to 20% heavier than the trastuzumab-MMAF-C5 ADC group of mice. Despite the 1000-fold difference in binding affinity (Example 63) between the two antibody fragment ADCs, the 2 mg/kg dosing regimens led to similar and rapid responses suggesting that binding affinity is not a critical factor (although there must be a minimum affinity) but the high payload loading and rapid penetration lead to high efficacy. At the lower dose of 0.5 mg/kg scFv (TCT)-MMAF-C5 the responses are inferior to the higher affinity scFv where the tumours start to regrow at day 40 with a cure rate of 50%

Example 76C. Tumour Growth Inhibition or Eradication in BT474 Xenograft Model with scFv (TCT1067)-P5C5 and Trastuzumab-P5C5 Conjugates (Compounds 71)

BT474 tumours were set up as described in Example 76. The treatment plan for this experiment is described in Table 67.

TABLE 67

Treatment plan for scFv (TCT1067)-P5C5 compared to trastuzumab-P5C5 benchmark (compounds 71)

| No | Therapeutic agent or control | Dose administered (mg/kg) | Schedule | Number of doses |
|---|---|---|---|---|
| 1 | Vehicle (saline) | 8 ml vol | Every other day | 12 |
| 2 | scFv (TCT1067)-P5C5 | 5 | Every other day | 12 |
| 3 | Trastuzumab-P5C5 | 5 | Once per week | 4 |

Tumour volume (mm$^3$) was plotted against time (FIG. 98) and animal body weight change (%) was plotted against time (FIG. 98). The benchmark control (trastuzumab-P5C5) was dosed at 5 mg/kg which has previously been shown to be highly efficacious as well as the lower dose of 1 mg/kg, at weekly intervals. The high affinity scFv (TCT1067)-P5-C5 conjugates were dosed more frequently to account for the more rapid pharmacokinetic clearance at three lower doses.

The scFv (TCT1067)-MMAF 2 mg/kg dosing regimen which led to complete (100%) cures is also shown for comparison. The scFv (TCT1067)-P5C5 5 mg/kg dosing regimen led to an approximate 20-day tumour growth delay, however the Trastuzumab-P5C5 5 mg/kg dosing regimen led to a marginal, insignificant growth delay. Therefore the ability to give more payload with the scFv (TCT1067)-P5C5 ADC, more frequently resulted in the tumours shrinking more effectively than the trastuzumab-P5C5 ADC. The saline (vehicle) and free payload treated animal group tumours grew rapidly. The scFv (TCT1067)-P5C5 treatment seemed to be better tolerated as seen from the increasing body weights with the antibody fragment ADC group of mice being up to 20% heavier than the trastuzumab-P5-C5 ADC group of mice.

Example 76D. Tumour Growth Inhibition or Eradication in a BT474 Human Breast Cancer Xenograft Model with scFv (TCT1067) Conjugates at Two Different DARs BT474 tumours were set up as described in Example 76. The treatment plan for this experiment is described in Table 68.

TABLE 68

Treatment plan for scFv (TCT1067)-Auristatin F-C5 conjugates (compounds 122) at two DARs

| No | Therapeutic agent or control | Dose administered (mg/kg) | Schedule | Number of doses |
|---|---|---|---|---|
| 1 | Vehicle (saline) | 8 ml | Every 4 days | 4 |
| 2 | scFv (TCT1067)-AF-C5 (L) | 5 | Every 4 days | 4 |
| 3 | scFv (TCT1067)-AF-C5 (M) | 5 | Every 4 days | 4 |

Tumour volume (mm$^3$) was plotted against time (FIG. 99) and animal body weight change (%) was plotted against time (FIG. 99). The high affinity scFv (1067)-AF-C5 conjugates at a low (L) DAR (2.7) and medium (M) DAR (5.7) were given 4 doses. The scFv (TCT1067)-AF 5 mg/kg dosing regimen led to complete (100%) cures by day 45, at a less frequent dosing regimen and fewer doses compared to Examples 76A and 76B. The higher DAR conjugate was more effective. The saline (vehicle) treated animal group tumours grew rapidly. Both conjugates seemed to be well tolerated as seen from the increasing body weights.

Example 76E. Tumour Growth Inhibition or Eradication in a BT474 Human Breast Cancer Xenograft Model with scFv (TCT1067)-AF-C5 Conjugates at Three Different DARs BT474 tumours were set up as described in Example 76. The treatment plan for this experiment is described in Table 69.

TABLE 69

Treatment plan for scFv (TCT1067)-Auristatin F-C5 conjugates (compounds 122) at three DARs

| No | Therapeutic agent or control | Dose administered (mg/kg) | Schedule | Number of doses |
|---|---|---|---|---|
| 1 | Vehicle (saline) | 8 ml | Every 4 days | 2 |
| 2 | scFv (TCT1067)-AF-C5 (L) | 5 | Every 4 days | 2 |
| 3 | scFv (TCT1067)-AF-C5 (M) | 5 | Every 4 days | 2 |
| 3 | scFv (TCT1067)-AF-C5 (H) | 5 | Every 4 days | 2 |

Tumour volume (mm$^3$) was plotted against time (FIG. 100). The high affinity scFv (1067)-AF conjugates at a low (L) DAR (2.7), medium (M) DAR (5.7) and high (H) DAR (11) were given 2 doses. At the time of this application, the higher DAR conjugate was more effective at eliciting tumour regression.

Example 76F. ScFv (TCT1067)-MMAE-PAB-Cit-Val-dPEG$_9$, Trastuzumab-MMAE-PAB-Cit-Val-dPEG$_9$ Conjugates (121) and Free MMAE in a NCI-N87 Human Gastric Cancer Xenograft Model NCI-N87 tumours are set up as described in Example 76. The treatment plan for this experiment is described in Table 64.

TABLE 70

Treatment plan for scFv (TCT1067)-MMAE-PAB-Cit-Val-dPEG$_9$ compared to trastuzumab-MMAE-PAB-Cit-Val-dPEG$_9$ benchmark (compounds 121)

| No | Therapeutic agent or control | Dose administered (mg/kg) | Schedule | Number of doses |
|---|---|---|---|---|
| 1 | Vehicle (saline) | 8 ml | Every 4 days | 8 |
| 2 | scFv (TCT1067)-MMAE-PAB-Cit-Val-dPEG$_9$ | 5 | Every 4 days | 8 |
| 3 | Trastuzumab-MMAE-PAB-Cit-Val-dPEG$_9$ | 5 | Once per week | 4 |

Example 77 Bioconjugation of a TCO Derivative onto a High Affinity Single-Chain Fv Antibody Fragment Bearing Multiple, Well-Dispersed, Surface Lysine Residues for a 2-Step Tetrazine Click Reaction TCO-PEG$_4$-NHS (purchased from Jena Biosciences) was conjugated to scFv (TCT) to obtain 1 conjugate (compound 134) with medium DARs. The conditions identified and carried forward were:

| Type | Condition |
|---|---|
| Buffer | Bicarbonate buffer with 150 mM NaCl at pH 8.8 |
| Co-solvent | anhydrous filtered DMSO at a final 20% (v/v) concentration |
| Temperature | 20° C. |
| Agitation | thermomixer 1000 rpm |
| Antibody concentration | 1 mg/ml |
| TCO-PEG4-NHS handling | 100 mM solution in 100% anhydrous filtered DMSO |
| TCO-PEG4-NHS addition rate | every 120 min |
| TCO-PEG4-NHS addition portions | 8 equivalents |

The reactions were carried out as per Example 64A.

In this example, the set up was:

Reaction 1—scFv (TCT): TCO-PEG$_4$-NHS, 16 equivalents.

No visible precipitates were noticeable and the sample recovery was high. The sample was analysed by SDS-PAGE (FIG. 101) and LCMS (FIG. 102).

The LCMS, Total Ion Current (TIC) chromatograms and spectra and the deconvoluted data are shown in FIG. 102.

A major peak was observed in the TIC of the scFv (TCT)-TCO-PEG$_4$ sample eluting at 12.3 mins. The zero-charge deconvoluted mass spectrum for this peak produced peaks at m/z 30956 and 31372 corresponding to the theoretical mass of the scFv together with 7 and 8 additions of the TCO-PEG$_4$ molecule. Therefore, the conjugate (compound 134) had an average DAR of 7.5.

A tetrazine-terminated linker-payload, such as the MMAF (117), can subsequently be conjugated in a second step to form an antibody drug conjugate (135).

Example 78—Preparation of SN38-(DNMEA)-PAB-Cit-Val-dPEG$_5$-NHS ester (140)

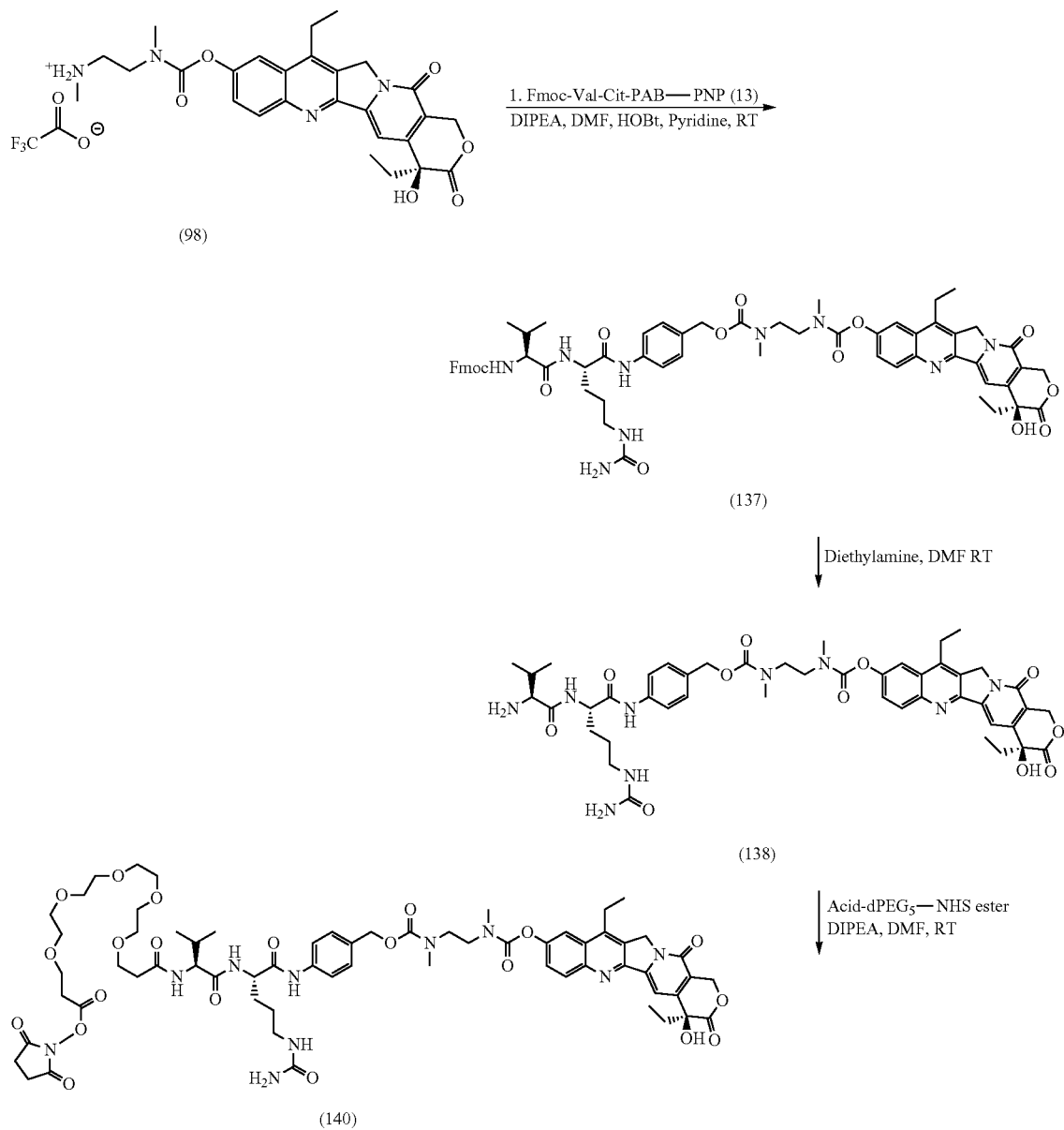

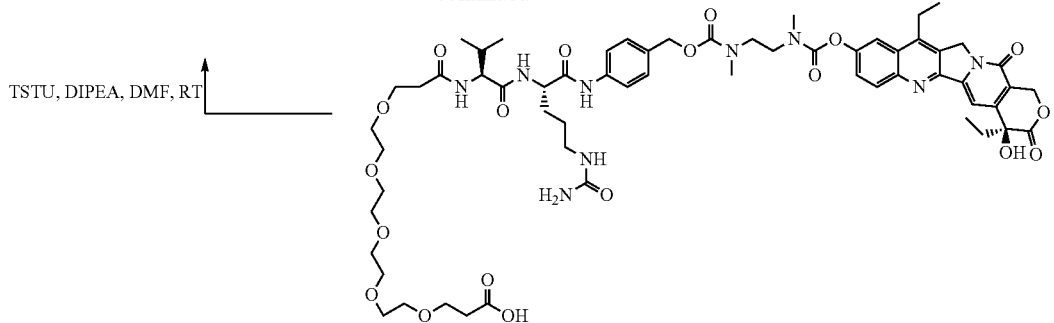

(139)

To a stirred solution of DNMEA-SN38 98 (80 mg, 0.13 mmol) and Fmoc-Val-Cit-PAB-PNP 13 (0.14 g, 0.19 mmol) in DMF (2 ml), was added HOBt (34 mg, 0.25 mmol), pyridine (52 µl) and DIPEA (22 µl). The reaction mixture was stirred under $N_2$ atmosphere at room temperature for 24 h. Solvents were evaporated in vacuo and the resulting residue was directly used for the next step. HRMS: ESI m/z Found 1135.0803 [M+H]$^+$ calculated 1135.2650 for $C_{61}H_{68}N_9O_{13}$.

A solution of Fmoc-Val-Cit-PAB-DNMEA-SN38 137 (90 mg, 0.08 mmol) in DMF (1.5 ml) and diethylamine (0.4 ml) was stirred for 3 hours at room temperature. The reaction mixture was then concentrated in vacuo and was directly used without further purification. HRMS: ESI m/z Found 913.0200 [M+H]$^+$ calculated 913.0220 for $C_{46}H_{58}N_9O_{11}$.

To a solution of H-Val-Cit-PAB-DNMEA-SN38 138 (70 mg, 0.08 mmol) in DMF (3 ml) was added DIPEA (40 µl) and Acid-dPEG$_5$-NHS (40 mg, 0.09 mmol) at room temperature. The reaction mixture was stirred under $N_2$ atmosphere for 16 h. The solvents were evaporated in vacuo, the obtained crude compound was used directly for the next step. HRMS: ESI m/z Found 1233.2537 [M+H]$^+$ calculated 1233.3600 for $C_{60}H_82N_9O_{19}$.

To a solution of Acid-dPEG$_5$-Val-Cit-PAB-DNMEA-SN38 (90 mg, 0.07 mmol) in DMF (3 ml) was added DIPEA (63 µl) and TSTU (44 mg, 0.14 mmol) at room temperature and the reaction mixture was stirred under $N_2$ atmosphere for 3 h. The solvents were evaporated in vacuo and the crude product was purified on Biotage flash purification system using C18 column to give the desired compound NHS-dPEG$_5$-Val-Cit-PAB-DNMEA-SN38 140 HRMS: ESI m/z Found 1330.3479 [M+H]$^+$ calculated 1330.4300 for $C_{64}H_{85}N_{10}O_2$, Example 79 Bioconjugation of an SN-38 Derivative with a Protease Cleavable Linker onto a High Affinity Single-Chain Fv Antibody Fragment Bearing Multiple, Well-Dispersed, Surface Lysine Residues

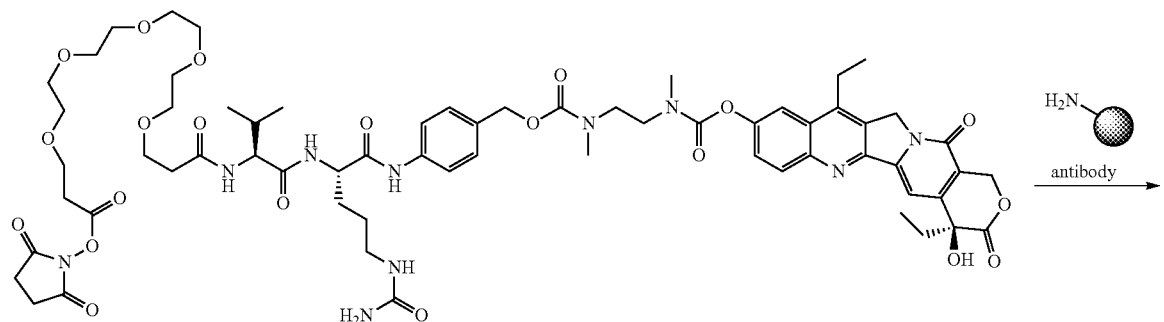

(140)

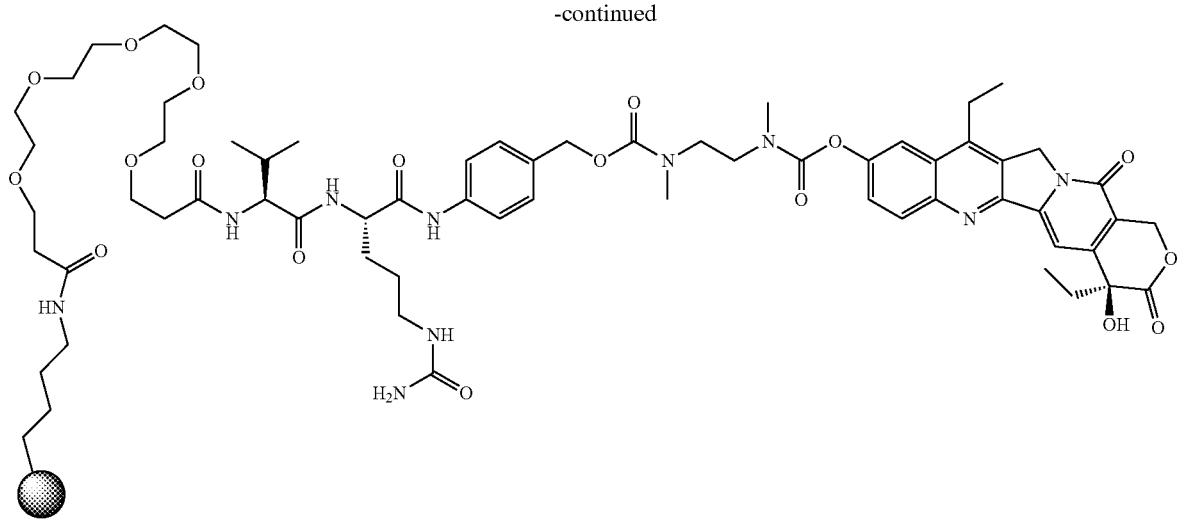

SN38-(DNMEA)—PAB-Cit-Val-dPEG$_5$ conjugate (141)
via a peptide bond

SN38-(DNMEA)-PAB-Cit-Val-dPEG$_5$-NHS Ester (140) was Conjugated to scFv (TCT1067) to Obtain Conjugates (141) of Various DARs.

The conditions used for the conjugations were:

| Type | Condition |
| --- | --- |
| Buffer | Bicarbonate buffer with 150 mM NaCl at pH 8.8 |
| Co-solvent | anhydrous filtered DMSO at a final 20% (v/v) concentration |
| Temperature | 20° C. |
| Agitation | thermomixer 1000 rpm |
| Antibody concentration | 1 mg/ml |
| SN38-(DNMEA)-PAB-Cit-Val-dPEG$_5$-NHS handling | 50 mM solution in 100% anhydrous filtered DMSO |
| SN38-(DNMEA)-PAB-Cit-Val-dPEG$_5$-NHS addition rate | every 90 min |
| SN38-(DNMEA)-PAB-Cit-Val-dPEG$_5$-NHS addition portions | 5 equivalents for reaction 1; 10 equivalents for reaction 2; 12.5 equivalents for reaction 3 and 4. |

The reactions were carried out as detailed in Example 64A.

In this example, the set up was:

Reaction 1—scFv (TCT1067): SN38-(DNMEA)-PAB-Cit-Val-dPEG$_5$-NHS, 5 equivalents

Figure 104:
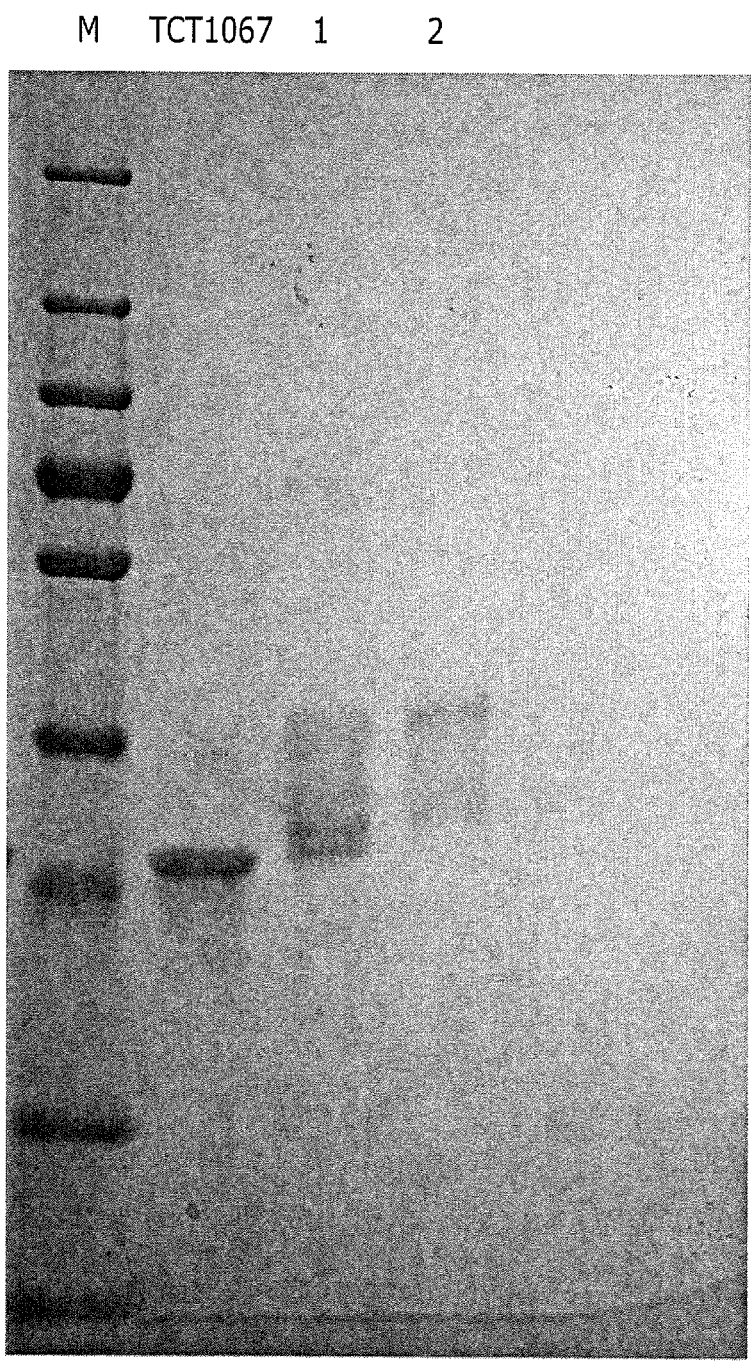

Reaction 2—scFv (TCT1067): SN38-(DNMEA)-PAB-Cit-Val-dPEG$_5$-NHS, 10 equivalents Reaction 3—scFv (TCT1067): SN38-(DNMEA)-PAB-Cit-Val-dPEG$_5$-NHS, 25 equivalents Reaction 4—scFv (TCT1067): SN38-(DNMEA)-PAB-Cit-Val-dPEG$_5$-NHS, 35 equivalents The unconjugated and conjugated scFv (TCT1067) were analysed by HPLC size exclusion chromatography (FIG. 103) and SDS PAGE (FIG. 104). The scFv has a retention time of 18.4 mins correlating to a MW of around 30 kDa. The conjugates eluted slightly earlier at 18.1 mins for reaction 1, 17.8 mins for reaction 2, 16.9 mins for reaction 3 and 16.8 mins for reaction 4 indicating a higher molecular weight (due to varying drug loads). The conjugates also showed (at the same retention time) significant absorption at 360 nm, a characteristic absorption peak of the drug which is absent from the unconjugated scFv control. Any aggregates formed can be removed. The DARs of the purified samples were calculated by UV/Vis absorption spectroscopy, using the extinction coefficient for the drug at 370 nm (17000 M$^{-1}$ cm$^{-1}$) and 280 nm (4700 M$^{-1}$ cm$^{-1}$) and for the antibody at 280 nm (70735 M$^{-1}$ cm$^{-1}$). The calculated DARs were 2.9, 4.6 and 6.4 for samples 1, 2 and 3 respectively. For samples 1 and 2, the SDS PAGE gel showed a polydispersed band at a higher molecular weight to the scFv.

Example 80 Bioconjugation of Auristatin-C5-NHS onto a High Affinity Diabody Fragment Bearing Multiple, Well-Dispersed, Surface Lysine Residues AF-C5-NHS Ester (88) was Conjugated to Diabody (TCT) and as a Control to scFv (TCT) to Obtain Conjugates (Compound 122) of Various DARs.

The reaction conditions used were as follows:

| Type | Condition |
| --- | --- |
| Buffer | Bicarbonate buffer with 150 mM NaCl at pH 8.8 |
| Co-solvent | anhydrous filtered DMSO at a final 20% (v/v) concentration |
| Temperature | 20° C. |
| Agitation | thermomixer 1000 rpm |
| Antibody concentration | 0.71 mg/ml |
| AF-C5-NHS handling | 50 mM solution in 100% anhydrous filtered DMSO |
| AF-C5-NHS addition rate | every 90 min |
| AF-C5-NHS addition portions | 7.5 equivalents |

The reactions were carried out as detailed in Example 64A.

In this example, the set up was:

Reaction 1: diabody (TCT): AF-C5-NHS, 30 equivalents;
Reaction 2: scFv (TCT): AF-C5-NHS, 15 equivalents;

The SDS PAGE gel in FIG. 105 which is run under reducing conditions, shows the unconjugated diabody and unconjugated scFv running at the same molecular weight as expected. The conjugates, 1 and 2 run slightly higher than the unconjugated antibodies. The two conjugates run at the same molecular weight indicating that the two antibodies have conjugated equally well.

The invention claimed is:

1. A compound comprising at least five of the same therapeutic agents coupled to a carrier molecule, with a minimum coupling ratio of 5:1 and a maximum coupling ratio of 13:1;
   wherein the carrier molecule is an antibody fragment selected from the group consisting of scFv, Fv, dsFv, bs-scFv, di-scFvs (also known as bi-scFvs), and diabodies; and
   wherein the therapeutic agents are each directly coupled or indirectly coupled onto a separate surface lysine amino acid residue;
   and further wherein the therapeutic agent is a non-photosensitising agent selected from the group consisting of a DNA-binding drug, a microtubule destabilizing agent, and a topoisomerase inhibitor;
   and wherein the coupled lysine amino acids of the carrier molecule are not adjacent in the primary sequence, and are not within 3 angstroms in the three-dimensional structure of the carrier molecule; and wherein the therapeutic agents, when coupled onto the carrier molecule at a lysine amino acid, are separated by a distance from 3.5 to 25 angstroms.

2. A compound according to claim 1 wherein the binding affinity of the carrier molecule is qualitatively substantially unaltered in the coupled form in comparison to the binding affinity when in an uncoupled form when measured by Enzyme-Linked Immunosorbent Assay (ELISA) or Surface Plasmon Resonance (SPR).

3. A compound according to claim 1 wherein the compound has (a) an IC50 of 100 nM to 0.1 pM and/or (b) an IC50 of at least 10-fold lower than the therapeutic agent when uncoupled.

4. A compound according to claim 1 wherein the compound has (a) a serum half-life of at least 2 hours, optionally the serum half-life of at least 2 hours is measured in mice or in humans, and/or (b) an in vivo serum half-life of at least 50% of that of the uncoupled antibody fragment.

5. A compound according to claim 1 wherein the compound has (a) a solubility of at least 1 mg/ml in phosphate-buffered saline at room temperature, and/or (b) a solubility of at least 1 mg/ml in phosphate-buffered saline at room temperature in the presence of an excipient.

6. A compound according to claim 5 wherein the excipient is up to 0.5% polysorbate, 1% glycerol, 0.5% glycine, 0.1% histidine, 0.5% chlorobutanol, 5% propylene glycol, 2% benzyl alcohol, 0.05% octanoic acid and/or 0.1% Nacetyl tryptophan.

7. A compound according to claim 1 wherein the compound has an aggregation level of up to 5% in phosphate-buffered saline at room temperature.

8. A compound according to claim 1 wherein the therapeutic agents are directly coupled onto the carrier molecule at a lysine amino acid, optionally wherein the direct coupling to the amino acid is via an N-hydroxy-succinmide ester.

9. A compound according to claim 1 wherein the therapeutic agents are indirectly coupled onto the carrier molecule at a lysine amino acid, optionally wherein the indirect coupling to the amino acid is via a thiol or maleimide.

10. A compound according to claim 1 wherein the carrier molecule binds selectively to a target, optionally wherein the target is a target cell or an extracellular target molecule.

11. A compound according to claim 10 wherein the carrier molecule, on binding the target cell, is internalized into the cell.

12. A compound according to claim 1 wherein the carrier molecule is humanized or human.

13. A compound according to claim 1 wherein the carrier molecule binds specifically to HER2, EGFR, HER3, MUC1, EpCAM, CEA, Fibronectin-EDB, CD19, CD20, CD22, LeY, CD30, CD33, CD79b, GPNMB, PSMA, CD56, CD37, Folate receptor, CA6, CD27 L, MUC16, CD66e, CD74, Trop-2 or guanylate cyclase.

14. A compound according to claim 1 wherein the scFv binds specifically to HER2, optionally wherein the scFv has the amino acid sequence of SEQ ID NO. 2, SEQ ID NO. 4 or SEQ ID NO. 5.

15. A pharmaceutical composition comprising the compound of claim 1 and a pharmaceutically-acceptable carrier, excipient or diluent.

16. A compound according to claim 1 wherein the DNA-binding drug is selected from the group consisting of ellipticine or a derivative or analogue thereof and an anthracycline or a derivative or analogue thereof.

17. A compound according to claim 16 wherein the anthracycline or a derivative or analogue thereof is doxorubicin.

18. A compound according to claim 1 wherein the microtubule destabilizing agent is selected from the group consisting of a maytansinoid or a derivative or analogue thereof, a dolostatin or a derivative or analogue thereof, cemadotin or a derivative or analogue thereof, and an aurastatin or a derivative or analogue thereof.

19. A compound according to claim 18 wherein the cemadotin derivative or analogue is P5 or P5-C5.

20. A compound according to claim 18 wherein the aurastatin or a derivative or analogue thereof is MMAE or MMAF.

21. A compound according to claim 1 wherein topoisomerase inhibitor is a camptothecin or a derivative or analogue thereof.

22. A compound according to claim 21 wherein the camptothecin derivative or analogue is SN-38.

* * * * *

SEQUENCE LISTING

```
<160> NUMBER OF SEQ ID NOS: 8

<210> SEQ ID NO 1
<211> LENGTH: 816
<212> TYPE: DNA
<213> ORGANISM: Artificial Sequence
<220> FEATURE:
<221> NAME/KEY: source
<222> LOCATION: 1..816
<223> OTHER INFORMATION: /mol_type="unassigned DNA"
      /note="DNA sequence of cleaved TCT"
      /organism="Artificial Sequence"

<400> SEQUENCE: 1
agcggtagcg gaggtagcgg acaggtgcag ctggtgcagt ctggggcaga ggtgaaaaag      60
cccggggagt ctctgaagat ctcctgtaag ggttctggat acagctttac cagctactgg     120
atcgcctggg tgcgccagat gcccgggaaa ggcctggagt acatggggct catctatcct     180
ggtgactctg acaccaaata cagcccgtcc ttccaaggcc aggtcaccat ctcagtcgac     240
aagtccgtca gcactgccta cttgcaatgg agcagtctga agcccgga cagcgccgtg       300 tattttgtg cgagacatga cgtgggatat tgcagtagtt ccaactgcgc agcgtggcct      360
gaatacttcc agcattgggg ccagggcacc ctggtcaccg tctcctcagg tggaggcggt     420
tcaggcggag gtggctctgg cggtggcgga tcgcagtctg tgttgacgca gccgccctca     480
gtgtctgcgg ccccaggaca gaaggtcacc atctcctgct ctggaagcag ctccaacatt    540
gggaataatt atgtatcctg gtaccagcag ctcccaggaa cagcccccaa actcctcatc    600
tatggtcaca ccaatcggcc cgcaggggtc cctgaccgat tctctggctc caagtctggc    660
acctcagcct ccctggccat cagtgggttc cggtccgagg atgaggctga ttattactgt     720
gcagcatggg atgacagcct gagtggttgg gtgttcggcg agggaccaa gctgaccgtc     780 ctaatggcta gcatgactgg tggacagcaa atgggt                              816

<210> SEQ ID NO 2
<211> LENGTH: 272
<212> TYPE: PRT
<213> ORGANISM: Artificial Sequence
<220> FEATURE:
<223> OTHER INFORMATION: Amino Acid sequence of cleaved TCT

<400> SEQUENCE: 2

Ser Gly Ser Gly Gly Ser Gly Gln Val Gln Leu Val Gln Ser Gly Ala
1               5                   10                  15

Glu Val Lys Lys Pro Gly Glu Ser Leu Lys Ile Ser Cys Lys Gly Ser
            20                  25                  30

Gly Tyr Ser Phe Thr Ser Tyr Trp Ile Ala Trp Val Arg Gln Met Pro
        35                  40                  45

Gly Lys Gly Leu Glu Tyr Met Gly Leu Ile Tyr Pro Gly Asp Ser Asp
    50                  55                  60

Thr Lys Tyr Ser Pro Ser Phe Gln Gly Gln Val Thr Ile Ser Val Asp
65                  70                  75                  80

Lys Ser Val Ser Thr Ala Tyr Leu Gln Trp Ser Ser Leu Lys Pro Ser
                85                  90                  95

Asp Ser Ala Val Tyr Phe Cys Ala Arg His Asp Val Gly Tyr Cys Ser
```

```
              100             105                 110
Ser Ser Asn Cys Ala Ala Trp Pro Glu Tyr Phe Gln His Trp Gly Gln
            115                 120             125

Gly Thr Leu Val Thr Val Ser Gly Gly Gly Ser Gly Gly Gly
    130             135             140

Gly Ser Gly Gly Gly Ser Gln Ser Val Leu Thr Gln Pro Pro Ser
145             150             155             160

Val Ser Ala Ala Pro Gly Gln Lys Val Thr Ile Ser Cys Ser Gly Ser
            165             170             175

Ser Ser Asn Ile Gly Asn Asn Tyr Val Ser Trp Tyr Gln Gln Leu Pro
            180             185             190

Gly Thr Ala Pro Lys Leu Leu Ile Tyr Gly His Thr Asn Arg Pro Ala
            195             200             205

Gly Val Pro Asp Arg Phe Ser Gly Ser Lys Ser Gly Thr Ser Ala Ser
            210             215             220

Leu Ala Ile Ser Gly Phe Arg Ser Glu Asp Glu Ala Asp Tyr Tyr Cys
225             230             235             240

Ala Ala Trp Asp Asp Ser Leu Ser Gly Trp Val Phe Gly Gly Gly Thr
            245             250             255

Lys Leu Thr Val Leu Met Ala Ser Met Thr Gly Gly Gln Gln Met Gly
            260             265             270

<210> SEQ ID NO 3
<211> LENGTH: 838
<212> TYPE: DNA
<213> ORGANISM: Artificial Sequence
<220> FEATURE:
<221> NAME/KEY: source
<222> LOCATION: 1..838
<223> OTHER INFORMATION: /mol_type="unassigned DNA"
      /note="DNA sequence of cleaved TCT1067 "
      /organism="Artificial Sequence"

<400> SEQUENCE: 3
gcggtagcgg aggtagcgga caggtgcagc tggtgcagtc tggggcagag gtgaaaaagc     60
ccggggagtc tctgaagatc tcctgtaagg gttctggata cagctttacc agctactgga    120
tcgcctgggt gcgccagatg cccgggaaag gcctggagta catggggctc atctatcctg    180
gtgactctga caccaaatac agcccgtcct tccaaggcca ggtcaccatc tcagtcgaca    240
agtccgtcag cactgcctac ttgcaatgga gcagtctgaa gccctcggac agcgccgtgt    300 attttgtgc gagacatgac gtgggatatt gcaccgatcg tacctgcgca gcgtggcctg    360
aatggctggg cgtgtggggc cagggcaccc tggtcaccgt ctcctcaggt ggaggcggtt    420
caggcggagg tggctctggc ggtggcggat cgcagtctgt gttgacgcag ccgccctcag    480
tgtctgcggc cccaggacag aaggtcacca tctcctgctc tggaagcagc tccaacattg    540
ggaataatta tgtatcctgg taccagcagc tcccaggaac agcccccaaa ctcctcatct    600
atggtcacac caatcggccc gcaggggtcc ctgaccgatt ctctggctcc aagtctggca    660
cctcagcctc cctggccatc agtgggttcc ggtccgagga tgaggctgat tattactgtg    720
caagctggga ttatccctg agtggttggg tgttcggcgg agggaccaag ctgaccgtcc    780
taatggctag catgactggt ggacagcaaa tgggttgatg aggctctaac tctcctct     838

<210> SEQ ID NO 4
<211> LENGTH: 272
<212> TYPE: PRT
<213> ORGANISM: Artificial Sequence
```

-continued

```
<220> FEATURE:
<223> OTHER INFORMATION: Amino Acid sequence of cleaved scFv (TCT1067)

<400> SEQUENCE: 4

Ser Gly Ser Gly Gly Ser Gly Gln Val Gln Leu Val Gln Ser Gly Ala
1               5                   10                  15

Glu Val Lys Lys Pro Gly Glu Ser Leu Lys Ile Ser Cys Lys Gly Ser
            20                  25                  30

Gly Tyr Ser Phe Thr Ser Tyr Trp Ile Ala Trp Val Arg Gln Met Pro
        35                  40                  45

Gly Lys Gly Leu Glu Tyr Met Gly Leu Ile Tyr Pro Gly Asp Ser Asp
    50                  55                  60

Thr Lys Tyr Ser Pro Ser Phe Gln Gly Gln Val Thr Ile Ser Val Asp
65                  70                  75                  80

Lys Ser Val Ser Thr Ala Tyr Leu Gln Trp Ser Ser Leu Lys Pro Ser
                85                  90                  95

Asp Ser Ala Val Tyr Phe Cys Ala Arg His Asp Val Gly Tyr Cys Thr
            100                 105                 110

Asp Arg Thr Cys Ala Ala Trp Pro Glu Trp Leu Gly Val Trp Gly Gln
        115                 120                 125

Gly Thr Leu Val Thr Val Ser Ser Gly Gly Gly Ser Gly Gly Gly
    130                 135                 140

Gly Ser Gly Gly Gly Ser Gln Ser Val Leu Thr Gln Pro Pro Ser
145                 150                 155                 160

Val Ser Ala Ala Pro Gly Gln Lys Val Thr Ile Ser Cys Ser Gly Ser
                165                 170                 175

Ser Ser Asn Ile Gly Asn Asn Tyr Val Ser Trp Tyr Gln Gln Leu Pro
            180                 185                 190

Gly Thr Ala Pro Lys Leu Leu Ile Tyr Gly His Thr Asn Arg Pro Ala
        195                 200                 205

Gly Val Pro Asp Arg Phe Ser Gly Ser Lys Ser Gly Thr Ser Ala Ser
    210                 215                 220

Leu Ala Ile Ser Gly Phe Arg Ser Glu Asp Glu Ala Asp Tyr Tyr Cys
225                 230                 235                 240

Ala Ser Trp Asp Tyr Thr Leu Ser Gly Trp Val Phe Gly Gly Gly Thr
                245                 250                 255

Lys Leu Thr Val Leu Met Ala Ser Met Thr Gly Gly Gln Met Gly
            260                 265                 270

<210> SEQ ID NO 5
<211> LENGTH: 257
<212> TYPE: PRT
<213> ORGANISM: Artificial Sequence
<220> FEATURE:
<223> OTHER INFORMATION: Amino acid sequence of panitumumab single chain
      Fv

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60
```

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Gly Gly Gly Ser Gly Gly Gly Gly
            115                 120                 125

Ser Gly Gly Gly Gly Ser Asp Ile Gln Met Thr Gln Ser Pro Ser Ser
    130                 135                 140

Leu Ser Ala Ser Val Gly Asp Arg Thr Val Ile Thr Cys Gln Ala Ser
145                 150                 155                 160

Gln Asp Ile Ser Asn Tyr Leu Asn Trp Tyr Gln Gln Lys Pro Gly Lys
                165                 170                 175

Ala Pro Lys Leu Leu Ile Tyr Asp Ala Ser Asn Leu Glu Thr Gly Val
            180                 185                 190

Pro Ser Arg Phe Ser Gly Ser Gly Ser Gly Thr Asp Phe Thr Phe Thr
        195                 200                 205

Ile Ser Ser Leu Gln Pro Glu Asp Ile Ala Thr Tyr Phe Cys Gln His
    210                 215                 220

Phe Asp His Leu Pro Leu Ala Phe Gly Gly Gly Thr Lys Val Glu Ile
225                 230                 235                 240

Gln Asn Gly Ser Glu Gln Lys Leu Ile Ser Glu Glu Asp Leu Ala Ala
                245                 250                 255

Ala

<210> SEQ ID NO 6
<211> LENGTH: 254
<212> TYPE: PRT
<213> ORGANISM: Artificial Sequence
<220> FEATURE:
<223> OTHER INFORMATION: Amino acid sequence of scFv (TCT1067)

<400> SEQUENCE: 6

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ala Trp Val Arg Gln Met Pro Gly Lys Gly Leu Glu Tyr Met
            35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Thr Asp Arg Thr Cys Ala Ala Trp
            100                 105                 110

Pro Glu Trp Leu Gly Val Trp Gly Gln Gly Thr Leu Val Thr Val Ser
        115                 120                 125

Ser Gly Gly Gly Gly Ser Gly Gly Gly Gly Ser Gly Gly Gly Gly Ser
    130                 135                 140

Gln Ser Val Leu Thr Gln Pro Pro Ser Val Ser Ala Ala Pro Gly Gln
145                 150                 155                 160

Lys Val Thr Ile Ser Cys Ser Gly Ser Ser Ser Asn Ile Gly Asn Asn

```
                        165                 170                 175
Tyr Val Ser Trp Tyr Gln Gln Leu Pro Gly Thr Ala Pro Lys Leu Leu
            180                 185                 190

Ile Tyr Gly His Thr Asn Arg Pro Ala Gly Val Pro Asp Arg Phe Ser
        195                 200                 205

Gly Ser Lys Ser Gly Thr Ser Ala Ser Leu Ala Ile Ser Gly Phe Arg
    210                 215                 220

Ser Glu Asp Glu Ala Asp Tyr Tyr Cys Ala Ser Trp Asp Tyr Thr Leu
225                 230                 235                 240

Ser Gly Trp Val Phe Gly Gly Gly Thr Lys Leu Thr Val Leu
                245                 250

<210> SEQ ID NO 7
<211> LENGTH: 241
<212> TYPE: PRT
<213> ORGANISM: Artificial Sequence
<220> FEATURE:
<223> OTHER INFORMATION: Amino acid sequence of scFv (panitumumab)

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Thr Val Ile Thr Cys Gln Ala Ser
145                 150                 155                 160

Gln Asp Ile Ser Asn Tyr Leu Asn Trp Tyr Gln Gln Lys Pro Gly Lys
                165                 170                 175

Ala Pro Lys Leu Leu Ile Tyr Asp Ala Ser Asn Leu Glu Thr Gly Val
            180                 185                 190

Pro Ser Arg Phe Ser Gly Ser Gly Ser Gly Thr Asp Phe Thr Phe Thr
        195                 200                 205

Ile Ser Ser Leu Gln Pro Glu Asp Ile Ala Thr Tyr Phe Cys Gln His
    210                 215                 220

Phe Asp His Leu Pro Leu Ala Phe Gly Gly Gly Thr Lys Val Glu Ile
225                 230                 235                 240

Gln

<210> SEQ ID NO 8
<211> LENGTH: 6
<212> TYPE: PRT
<213> ORGANISM: Artificial Sequence
```

```
<220> FEATURE:
<223> OTHER INFORMATION: Linker region

<400> SEQUENCE: 8

Gly Ser Gly Gly Ser Gly
1               5
```